(12) United States Patent
Boitano et al.

(10) Patent No.: US 12,171,839 B2
(45) Date of Patent: *Dec. 24, 2024

(54) ANTIBODY DRUG CONJUGATES FOR ABLATING HEMATOPOIETIC STEM CELLS

(71) Applicant: Novartis AG, Basel (CH)

(72) Inventors: Anthony Edward Boitano, Waban, MA (US); Matthew Burger, Belmont, MA (US); Susan E. Cellitti, San Diego, CA (US); Michael P. Cooke, Boston, MA (US); Catrin Finner, Neuried (DE); Bernhard Hubert Geierstanger, Solano Beach, CA (US); Yunho Jin, San Diego, CA (US); Si Tuen Lee-Hoeflich, Lexington, MA (US); HongNgoc Thi Pham, San Mateo, CA (US); Siew Ho Schleyer, El Cerrito, CA (US); Kathrin Tissot, Neuried (DE); Tetsuo Uno, San Diego, CA (US); Ben Wen, Encinitas, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/833,077

(22) Filed: Jun. 6, 2022

(65) Prior Publication Data

US 2022/0305134 A1 Sep. 29, 2022

Related U.S. Application Data

(63) Continuation of application No. 16/470,897, filed as application No. PCT/IB2017/058159 on Dec. 19, 2017, now Pat. No. 11,357,864.

(60) Provisional application No. 62/437,622, filed on Dec. 21, 2016, provisional application No. 62/520,854, filed on Jun. 16, 2017.

(51) Int. Cl.
| | | |
|---|---|---|
| *C07K 16/00* | (2006.01) |
| *A61K 38/07* | (2006.01) |
| *A61K 38/12* | (2006.01) |
| *A61K 47/68* | (2017.01) |
| *C07K 16/28* | (2006.01) |
| *C07K 16/46* | (2006.01) |

(52) U.S. Cl.
CPC .......... *A61K 47/6849* (2017.08); *A61K 38/07* (2013.01); *A61K 38/12* (2013.01); *A61K 47/68031* (2023.08); *A61K 47/68033* (2023.08); *A61K 47/6831* (2017.08); *C07K 16/2803* (2013.01); *C07K 2317/21* (2013.01); *C07K 2317/55* (2013.01); *C07K 2317/92* (2013.01)

(58) Field of Classification Search
None
See application file for complete search history.

(56) References Cited

U.S. PATENT DOCUMENTS

| | | |
|---|---|---|
| 9,498,543 B2 | 11/2016 | Abrams et al. |
| 9,789,203 B2 | 10/2017 | Abrams et al. |
| 10,117,953 B2 | 11/2018 | Abrams et al. |
| 10,786,578 B2 | 9/2020 | Abrams et al. |
| 2010/0226927 A1 | 9/2010 | Weissman et al. |
| 2014/0271688 A1 | 9/2014 | Abrams et al. |
| 2015/0320880 A1 | 11/2015 | Abrams et al. |
| 2017/0021033 A1* | 1/2017 | Geierstanger ...... A61K 47/6855 |

FOREIGN PATENT DOCUMENTS

| | | |
|---|---|---|
| EA | 201591801 A1 | 3/2016 |
| EA | 023665 B1 | 6/2016 |
| JP | 2006500904 T2 | 1/2006 |
| WO | 03068821 A2 | 8/2003 |
| WO | 2004002425 A2 | 1/2004 |
| WO | 2004085476 A2 | 10/2004 |
| WO | 2007127317 A2 | 11/2007 |
| WO | 2008067115 A2 | 6/2008 |
| WO | 2008067225 A2 | 6/2008 |
| WO | 2012103165 A2 | 8/2012 |
| WO | 2014018625 A1 | 1/2014 |
| WO | 2014150937 A1 | 9/2014 |
| WO | 2015138615 A2 | 9/2015 |
| WO | 2015189791 A1 | 12/2015 |
| WO | 2016020791 A1 | 2/2016 |
| WO | 2016071856 A1 | 5/2016 |
| WO | 2016164502 A1 | 10/2016 |
| WO | WO-2016203432 A1 * | 12/2016 ............ A61K 38/07 |
| WO | 2017219029 A2 | 12/2017 |

OTHER PUBLICATIONS

Anonymous, "Phase 1 Study of LOP628 in Adult Patients with CKit-positive Solid Tumors and Acute Myeloid Leukemia Sponsor: Novartis Pharmaceuticals", Aug. 20, 2014, pp. 1-8, XP055772686, URL:https://clinicaltrials.gov/cts/show/NCT02221505.

Chhabra et al., Hematopoietic stem cell transplantation in immunocompetent hosts without radiation or chemotherapy, Science Translational Medicine, Aug. 10, 2016, 1-10., 8(351).

Czechowicz et al., Selective hematopoietic stem cell ablation using CD117-antibody-drug-conjugates enables safe and effective transplantation with immunity preservation, Nature Communications, Jan. 12, 2019, 10:617.

Doronina, et al., Development of potent monoclonal antibody auristatin conjugates for cancer therapy, Nature Biotechnology, Jul. 2003, 778-784, 21(7).

(Continued)

*Primary Examiner* — Maher M Haddad
(74) *Attorney, Agent, or Firm* — K&L Gates LLP

(57) ABSTRACT

The present invention provides antibody drug conjugates, wherein an antibody or antibody fragment that specifically binds to human cKIT is linked to a drug moiety, optionally through a linker. The present invention further provides pharmaceutical compositions comprising the antibody drug conjugates; and methods of making and using such pharmaceutical compositions for ablating hematopoietic stem cells in a patient in need thereof.

11 Claims, 13 Drawing Sheets

Specification includes a Sequence Listing.

(56) References Cited

OTHER PUBLICATIONS

Edling et al., c-Kit—A hematopoietic cell essential receptor tyrosine kinase, The International Journal of Biochemistry & Cell Biology, Jan. 20, 2007, 1995-1998, 39(11).
Froelich et al., Targeted Gene Delivery to CD117-Expressing Cells In Vivo With Lentiviral Vectors Co-Displaying Stem Cell Factor and a Fusogenic Molecule, Biotechnology and Bioengineering, Apr. 17, 2009, 206-215, 104(1).
Hamilton, Antibody-drug conjugates for cancer therapy: The technological and regulatory challenges of developing drug-biologic hybrids, Biologicals, 2015, 318-332, 43(5).
Hong et al., Abstract 5325: A c-Kit targeting antibody-drug conjugate is efficiently metabolized and activated inside cancer cell lines and xenograft tumors, Cancer Research, Aug. 2015, URL:http://cancerres.aacrjournals.org/content/75/15_supplement/5325.
Jain et al., Current ADS Linker Chemistry, Pharm Res, Mar. 11, 2015, 3526-3540, 32.
Kraft et al., Effect and Kinetics of Depleting ACK-2 Anti C-Kit Monoclonal Antobody on Hematopoeisis and Hematopoetic Progenitors and Ability to Condition for Bone Marrow Transplantation, Blood, 2004, 322B, 104(11).
Kurosawa et al., Immobilized Anti-KIT Monoclonal Antibody Induces Ligand-Independent Dimerization and Activation of Steel Factor Receptor: Biologic Similarity With Membrane-Bound Form of Steel Factor Rather Than Its Soluble Form, Blood, Mar. 15, 1996, 2235-2243, 87(6).
L'Italien et al., Mechanistic Insights of an immunological Adverse Event Induced by an Anti-KIT Antibody Drug Conjugate and Mitigation Strategies, Clinical Cancer Research, Jul. 15, 2018, 3465-3474., 24(14).
Lee-Hoeflich, LOP628 (cKit ADC): From the clinic back to the bench Mechanistic insight into clinical hypersensitivity reactions to enable clinical decision making, Presentation, 2016, 28 slides.
Maderna et al., Recent Advances in the Development of New Auristatins: Structural Modifications and Application in Antibody Drug Conjugates, Molecular Pharmaceutics, Feb. 19, 2015, 1798-1812, 12.
Palchaudhuri et al., Non-genotoxic conditioning for hematopoietic stem cell transplantation using a hematopoietic-cell-specific internalizing immunotoxin, Nature Biotechnology, Jul. 2016, 738-747., 34(7).
Pearse et al., CD117-Amanitin Antibody Drug Conjugates Effectively Deplete Human and Non-HUman Primate HSCs: Proof of Concept As a Targeted Strategy for Conditioning Patients for Bone Marrow Transplant, Blood, Nov. 29, 2018, 3314, 132(Supplement 1).
Storz, Antibody-drug conjugates: Intellectual property considerations, mAbs, Nov./Dec. 2015, 989-1009, 7(6).
Tetsuo Uno, Drug Attachment Options and Designed Cleavable Linker Elements, ADC Worl Summit San Diego Workshop F, Oct. 10, 2016, 35 slides.
Xue et al., Antibody targeting KIT as petransplantation conditioning in immunocompetent mice, Blood, Dec. 9, 2010, 5419-5422., 116(24).
Yoshida et al., Therapeutic Efficacy of C-Kit-Targeted Radioimmunotherapy Using 90Y-Labeled Anti-C-Kit Antibodies in a Mouse Model of Small Cell Lung Cancer, PLOS, Mar. 14, 2013, e59248, 1-8, 8(3).
Stahl et al., "Targeting KIT on innate immune cells to enhance the antitumor activity of checkpoint inhibitors," Immunotherapy (2016) vol. 8, No. 7, pp. 767-774.

* cited by examiner

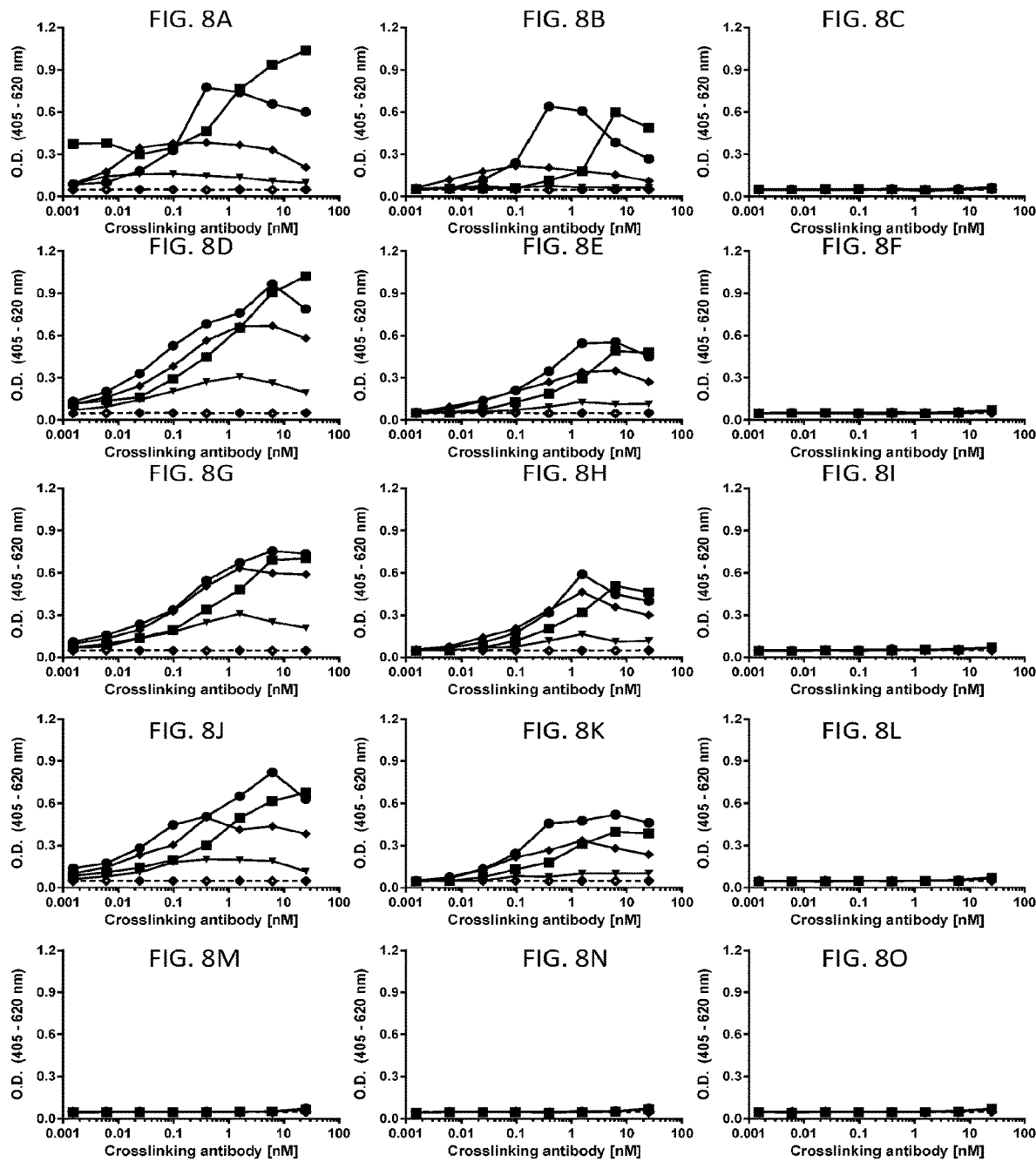

ANTIBODY DRUG CONJUGATES FOR ABLATING HEMATOPOIETIC STEM CELLS

CROSS-REFERENCE TO RELATED APPLICATIONS

This application is a continuation of U.S. patent application Ser. No. 16/470,897, now U.S. Pat. No. 11,357,864, which is a National Stage Entry of International Application No. PCT/IB2017/058159 filed on Dec. 19, 2017, which claims the benefit of U.S. Provisional Application No. 62/437,622 filed Dec. 21, 2016, and U.S. Provisional Application No. 62/520,854 filed Jun. 16, 2017, the contents of which are hereby incorporated by reference in their entireties.

FIELD OF THE INVENTION

The present disclosure is directed to anti-cKIT antibody drug conjugates, and their uses for ablating hematopoietic stem cells in a patient in need thereof, e.g., a hematopoietic stem cell transplantation recipient.

SEQUENCE LISTING

The instant application contains a Sequence Listing which has been submitted electronically in ASCII format and is hereby incorporated by reference in its entirety. Said ASCII copy, created on Dec. 14, 2017, is named PAT057400-US-CNT_SL.txt and is 209,938 bytes in size.

BACKGROUND OF THE INVENTION cKIT (CD117) is a single transmembrane receptor tyrosine kinase that binds the ligand Stem Cell Factor (SCF). SCF induces homodimerization of cKIT which activates its tyrosine kinase activity and signals through both the PI3-AKT and MAPK pathways (Kindblom et al., Am J. Path. 1998 152(5):1259). cKIT was initially discovered as an oncogene as a truncated form expressed by a feline retrovirus (Besmer et al., Nature 1986 320:415-421). Cloning of the corresponding human gene demonstrated that cKIT is a member of the type III class of receptor tyrosine kinases, which count among the family members, FLT3, CSF-1 receptor and PDGF receptor. cKIT is required for the development of hematopoietic cells, germ cells, mast cells and melanocytes. Hematopoietic progenitor cells, e.g., hematopoietic stem cells (HSC), in the bone marrow, express high level of cKIT on cell surface. In addition, mast cells, melanocytes in the skin, and interstitial cells of Cajal in the digestive tract express cKIT.

Hematopoietic stem cells (HSCs) are capable of regenerating all blood and immune cells in a transplant recipient and therefore have great therapeutic potential. Hematopoietic stem cell transplantation is widely used as therapies for leukemia, lymphoma, and other life-threatening diseases. Many risks, however, are associated with such transplantation, including poor engraftment, immunological rejection, graft-versus-host disease (GVHD), or infection. Allogeneic hematopoietic stem cell transplantation generally requires conditioning of the recipient through cyto-reductive treatments to prevent immunological rejection of the graft. Current conditioning regimens are often so toxic to the host that they are contra-indicated for large groups of transplantation patients and/or cannot be provided in sufficient amounts to prevent graft-versus-host disease. Thus, there is a need for improving the conditioning and transplantation methods and decreasing the risks associated with hematopoietic stem cell transplantation and increasing its effectiveness for various disorders.

SUMMARY OF THE INVENTION

The present disclosure provides antibody drug conjugates, wherein an antibody or antibody fragment (e.g., Fab or Fab') that specifically binds to human cKIT is linked to a drug moiety (e.g., a cytotoxic agent), optionally through a linker. Those antibody drug conjugates can selectively deliver a cytotoxic agent to cells expressing cKIT, e.g., hematopoietic stem cells, thereby selectively ablate those cells in a patient, e.g., a hematopoietic stem cell transplantation recipient. Preferably, the cKIT antibody drug conjugates have pharmacokinetic properties such that it will not be present and/or active in a patient's circulation for an extended time, so they can be used for conditioning hematopoietic stem cell transplant recipients prior to hematopoietic stem cell transplantation. In some embodiments, provided herein are conjugates comprising an antibody fragment (e.g., Fab or Fab') that specifically binds to cKIT, linked to a drug moiety (e.g., a cytotoxic agent), optionally through a linker. Surprisingly, the present inventors found that the full length anti-cKIT antibodies (e.g., full-length IgGs), F(ab')$_2$ fragments, and toxin conjugates thereof cause mast cell degranulation, but the anti-cKIT Fab' or Fab-toxin conjugates do not cause mast cell degranulation, even when crosslinked and/or multimerized into larger complexes as could be observed if a patient developed or had pre-existing anti-drug antibodies recognizing Fab fragments. The present disclosure further provides pharmaceutical compositions comprising the antibody drug conjugates, and methods of making and using such pharmaceutical compositions for ablating hematopoietic stem cells in a patient in need thereof, e.g., a hematopoietic stem cell transplantation recipient.

In one aspect, the present disclosure is directed to a conjugate of Formula (I):

$$A\text{-}(L_B\text{-}(D)_n)_y \qquad \text{Formula (I)};$$

wherein:
  A is an antibody fragment that specifically binds to human cKIT;
  $L_B$ is a linker;
  D is a cytotoxic agent;
  n is an integer from 1 to 10, and y is an integer from 1 to 10.

In one aspect, the present disclosure is directed to a conjugate of having the structure of Formula (C):

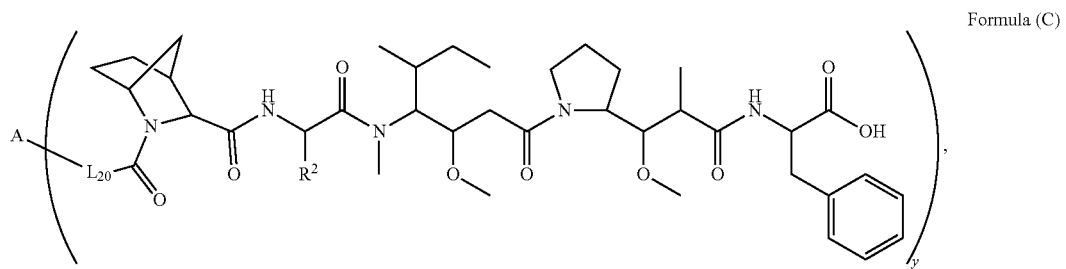

Formula (C)

wherein A, $L_{20}$, y and $R^2$, are as defined herein.

In one aspect, the present disclosure is directed to a conjugate of having the structure of Formula (D):

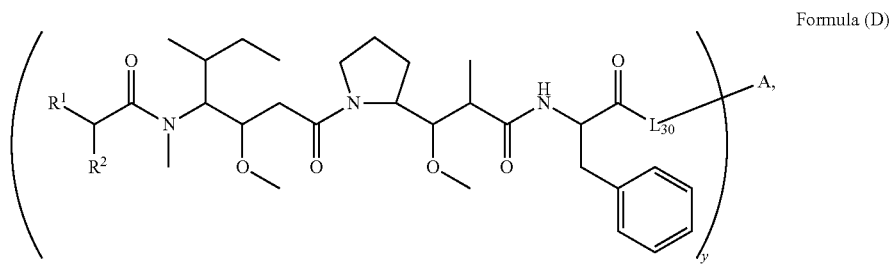

Formula (D)

wherein A, $L_{30}$, y, $R^1$ and $R^2$, are as defined herein.

In one aspect, the present disclosure is directed to a conjugate of having the structure of Formula (E):

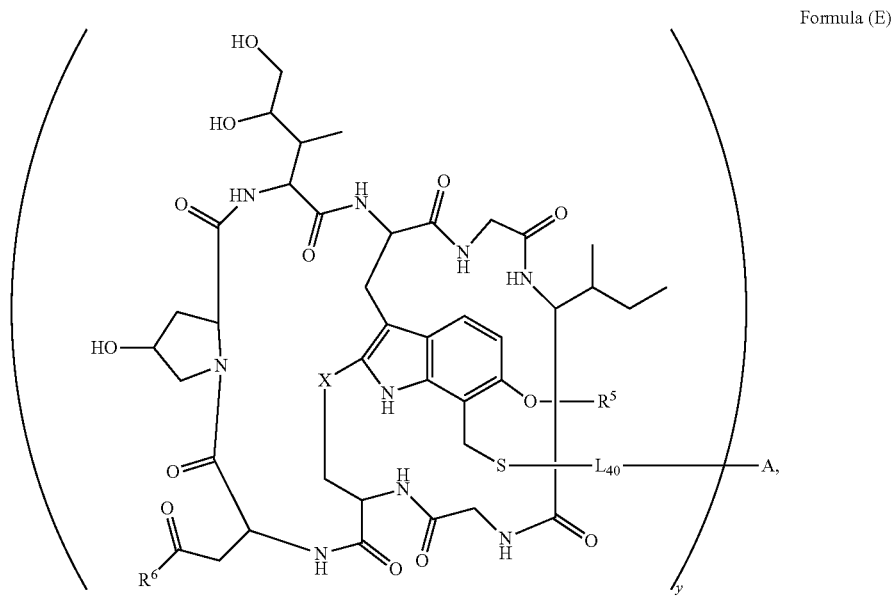

Formula (E)

wherein A, $L_{40}$, y, X, $R^5$ and $R^6$, are as defined herein.

In another aspect, provided herein are antibodies and antibody fragments (e.g., Fab or Fab') that specifically bind to human cKIT. Such anti-cKIT antibodies and antibody fragments (e.g., Fab or Fab') can be used in any of the conjugates described herein.

In some embodiments, the antibody or antibody fragment (e.g., Fab or Fab') that specifically binds to human cKIT is an antibody or antibody fragment (e.g., Fab or Fab') that specifically binds to the extracellular domain of human cKIT (SEQ ID NO: 112).

In some embodiments, the antibody or antibody fragment (e.g., Fab or Fab') that specifically binds to human cKIT is an antibody or antibody fragment (e.g., Fab or Fab') that specifically binds to an epitope in domains 1-3 of human cKIT (SEQ ID NO: 113).

In some embodiments, the antibody or antibody fragment (e.g., Fab or Fab') that specifically binds to human cKIT is an antibody or antibody fragment (e.g., Fab or Fab') described in Table 1.

In some embodiments, the antibody or antibody fragment (e.g., Fab or Fab') that specifically binds to human cKIT comprises a HCDR1 of SEQ ID NO: 1, a HCDR2 of SEQ ID NO: 2; a HCDR3 of SEQ ID NO: 3; a LCDR1 of SEQ ID NO: 16; a LCDR2 of SEQ ID NO: 17; and a LCDR3 of SEQ ID NO: 18.

In some embodiments, the antibody or antibody fragment (e.g., Fab or Fab') that specifically binds to human cKIT comprises a HCDR1 of SEQ ID NO: 4, a HCDR2 of SEQ ID NO: 5; a HCDR3 of SEQ ID NO: 3; a LCDR1 of SEQ ID NO:19; a LCDR2 of SEQ ID NO: 20; and a LCDR3 of SEQ ID NO: 21.

In some embodiments, the antibody or antibody fragment (e.g., Fab or Fab') that specifically binds to human cKIT comprises a HCDR1 of SEQ ID NO: 6, a HCDR2 of SEQ ID NO: 2; a HCDR3 of SEQ ID NO: 3; a LCDR1 of SEQ ID NO:16; a LCDR2 of SEQ ID NO: 17; and a LCDR3 of SEQ ID NO: 18.

In some embodiments, the antibody or antibody fragment (e.g., Fab or Fab') that specifically binds to human cKIT comprises a HCDR1 of SEQ ID NO: 7, a HCDR2 of SEQ ID NO: 8; a HCDR3 of SEQ ID NO: 9; a LCDR1 of SEQ ID NO: 22; a LCDR2 of SEQ ID NO: 20; and a LCDR3 of SEQ ID NO: 18.

In some embodiments, the antibody or antibody fragment (e.g., Fab or Fab') that specifically binds to human cKIT comprises a HCDR1 of SEQ ID NO: 27, a HCDR2 of SEQ ID NO: 28; a HCDR3 of SEQ ID NO: 29; a LCDR1 of SEQ ID NO: 42; a LCDR2 of SEQ ID NO: 17; and a LCDR3 of SEQ ID NO: 43.

In some embodiments, the antibody or antibody fragment (e.g., Fab or Fab') that specifically binds to human cKIT comprises a HCDR1 of SEQ ID NO: 30, a HCDR2 of SEQ ID NO: 31; a HCDR3 of SEQ ID NO: 29; a LCDR1 of SEQ ID NO: 44; a LCDR2 of SEQ ID NO: 20; and a LCDR3 of SEQ ID NO: 45.

In some embodiments, the antibody or antibody fragment (e.g., Fab or Fab') that specifically binds to human cKIT comprises a HCDR1 of SEQ ID NO: 32, a HCDR2 of SEQ ID NO: 28; a HCDR3 of SEQ ID NO: 29; a LCDR1 of SEQ ID NO: 42; a LCDR2 of SEQ ID NO: 17; and a LCDR3 of SEQ ID NO: 43.

In some embodiments, the antibody or antibody fragment (e.g., Fab or Fab') that specifically binds to human cKIT comprises a HCDR1 of SEQ ID NO: 33, a HCDR2 of SEQ ID NO: 34; a HCDR3 of SEQ ID NO: 35; a LCDR1 of SEQ ID NO: 46; a LCDR2 of SEQ ID NO: 20; and a LCDR3 of SEQ ID NO: 43.

In some embodiments, the antibody or antibody fragment (e.g., Fab or Fab') that specifically binds to human cKIT comprises a HCDR1 of SEQ ID NO: 1, a HCDR2 of SEQ ID NO: 51; a HCDR3 of SEQ ID NO: 3; a LCDR1 of SEQ ID NO:16; a LCDR2 of SEQ ID NO: 17; and a LCDR3 of SEQ ID NO: 18.

In some embodiments, the antibody or antibody fragment (e.g., Fab or Fab') that specifically binds to human cKIT comprises a HCDR1 of SEQ ID NO: 4, a HCDR2 of SEQ ID NO: 52; a HCDR3 of SEQ ID NO: 3; a LCDR1 of SEQ ID NO:19; a LCDR2 of SEQ ID NO: 20; and a LCDR3 of SEQ ID NO: 21.

In some embodiments, the antibody or antibody fragment (e.g., Fab or Fab') that specifically binds to human cKIT comprises a HCDR1 of SEQ ID NO: 6, a HCDR2 of SEQ ID NO: 51; a HCDR3 of SEQ ID NO: 3; a LCDR1 of SEQ ID NO:16; a LCDR2 of SEQ ID NO: 17; and a LCDR3 of SEQ ID NO: 18.

In some embodiments, the antibody or antibody fragment (e.g., Fab or Fab') that specifically binds to human cKIT comprises a HCDR1 of SEQ ID NO: 7, a HCDR2 of SEQ ID NO: 53; a HCDR3 of SEQ ID NO: 9; a LCDR1 of SEQ ID NO: 22; a LCDR2 of SEQ ID NO: 20; and a LCDR3 of SEQ ID NO: 18.

In some embodiments, the antibody or antibody fragment (e.g., Fab or Fab') that specifically binds to human cKIT comprises a HCDR1 of SEQ ID NO: 60, a HCDR2 of SEQ ID NO: 61; a HCDR3 of SEQ ID NO: 62; a LCDR1 of SEQ ID NO: 75; a LCDR2 of SEQ ID NO: 76; and a LCDR3 of SEQ ID NO: 77.

In some embodiments, the antibody or antibody fragment (e.g., Fab or Fab') that specifically binds to human cKIT comprises a HCDR1 of SEQ ID NO: 63, a HCDR2 of SEQ ID NO: 64; a HCDR3 of SEQ ID NO: 62; a LCDR1 of SEQ ID NO: 78; a LCDR2 of SEQ ID NO: 79; and a LCDR3 of SEQ ID NO: 80.

In some embodiments, the antibody or antibody fragment (e.g., Fab or Fab') that specifically binds to human cKIT comprises a HCDR1 of SEQ ID NO: 65, a HCDR2 of SEQ ID NO: 61; a HCDR3 of SEQ ID NO: 62; a LCDR1 of SEQ ID NO:75; a LCDR2 of SEQ ID NO: 76; and a LCDR3 of SEQ ID NO: 77.

In some embodiments, the antibody or antibody fragment (e.g., Fab or Fab') that specifically binds to human cKIT comprises a HCDR1 of SEQ ID NO: 66, a HCDR2 of SEQ ID NO: 67; a HCDR3 of SEQ ID NO: 68; a LCDR1 of SEQ ID NO: 81; a LCDR2 of SEQ ID NO: 79; and a LCDR3 of SEQ ID NO: 77.

In some embodiments, the antibody or antibody fragment (e.g., Fab or Fab') that specifically binds to human cKIT comprises a HCDR1 of SEQ ID NO: 86, a HCDR2 of SEQ ID NO: 87; a HCDR3 of SEQ ID NO: 88; a LCDR1 of SEQ ID NO: 101; a LCDR2 of SEQ ID NO: 102; and a LCDR3 of SEQ ID NO: 103.

In some embodiments, the antibody or antibody fragment (e.g., Fab or Fab') that specifically binds to human cKIT comprises a HCDR1 of SEQ ID NO: 89, a HCDR2 of SEQ ID NO: 90; a HCDR3 of SEQ ID NO: 88; a LCDR1 of SEQ ID NO: 104; a LCDR2 of SEQ ID NO: 105; and a LCDR3 of SEQ ID NO: 106.

In some embodiments, the antibody or antibody fragment (e.g., Fab or Fab') that specifically binds to human cKIT comprises a HCDR1 of SEQ ID NO: 91, a HCDR2 of SEQ ID NO: 87; a HCDR3 of SEQ ID NO: 88; a LCDR1 of SEQ ID NO: 101; a LCDR2 of SEQ ID NO: 102; and a LCDR3 of SEQ ID NO: 103.

In some embodiments, the antibody or antibody fragment (e.g., Fab or Fab') that specifically binds to human cKIT comprises a HCDR1 of SEQ ID NO: 92, a HCDR2 of SEQ ID NO: 93; a HCDR3 of SEQ ID NO: 94; a LCDR1 of SEQ ID NO: 107; a LCDR2 of SEQ ID NO: 105; and a LCDR3 of SEQ ID NO: 103.

In some embodiments, the antibody or antibody fragment (e.g., Fab or Fab') that specifically binds to human cKIT comprises a heavy chain variable region (VH) comprising the amino acid sequence of SEQ ID NO: 10, and a light chain variable region (VL) comprising the amino acid sequence of SEQ ID NO: 23.

In some embodiments, the antibody or antibody fragment (e.g., Fab or Fab') that specifically binds to human cKIT comprises a VH comprising the amino acid sequence of SEQ ID NO: 36, and a VL comprising the amino acid sequence of SEQ ID NO: 47.

In some embodiments, the antibody or antibody fragment (e.g., Fab or Fab') that specifically binds to human cKIT comprises a VH comprising the amino acid sequence of SEQ ID NO: 54, and a VL comprising the amino acid sequence of SEQ ID NO: 23.

In some embodiments, the antibody or antibody fragment (e.g., Fab or Fab') that specifically binds to human cKIT comprises a VH comprising the amino acid sequence of SEQ ID NO: 69, and a VL comprising the amino acid sequence of SEQ ID NO: 82.

In some embodiments, the antibody or antibody fragment (e.g., Fab or Fab') that specifically binds to human cKIT comprises a VH comprising the amino acid sequence of SEQ ID NO: 95, and a VL comprising the amino acid sequence of SEQ ID NO: 108.

In some embodiments, the antibody fragment (e.g., Fab') that specifically binds to human cKIT comprises a heavy chain comprising the amino acid sequence of SEQ ID NO: 14, and a light chain comprising the amino acid sequence of SEQ ID NO: 25.

In some embodiments, the antibody fragment (e.g., Fab') that specifically binds to human cKIT comprises a heavy chain comprising the amino acid sequence of SEQ ID NO: 40, and a light chain comprising the amino acid sequence of SEQ ID NO: 49.

In some embodiments, the antibody fragment (e.g., Fab') that specifically binds to human cKIT comprises a heavy chain comprising the amino acid sequence of SEQ ID NO: 58, and a light chain comprising the amino acid sequence of SEQ ID NO: 25.

In some embodiments, the antibody fragment (e.g., Fab') that specifically binds to human cKIT comprises a heavy chain comprising the amino acid sequence of SEQ ID NO: 73, and a light chain comprising the amino acid sequence of SEQ ID NO: 84.

In some embodiments, the antibody fragment (e.g., Fab') that specifically binds to human cKIT comprises a heavy chain comprising the amino acid sequence of SEQ ID NO: 99, and a light chain comprising the amino acid sequence of SEQ ID NO: 110.

In some embodiments, the antibody fragment (e.g., Fab) that specifically binds to human cKIT comprises a heavy chain comprising the amino acid sequence of SEQ ID NO: 118, and a light chain comprising the amino acid sequence of SEQ ID NO: 122.

In some embodiments, the antibody fragment (e.g., Fab) that specifically binds to human cKIT comprises a heavy chain comprising the amino acid sequence of SEQ ID NO: 118, and a light chain comprising the amino acid sequence of SEQ ID NO: 123.

In some embodiments, the antibody fragment (e.g., Fab) that specifically binds to human cKIT comprises a heavy chain comprising the amino acid sequence of SEQ ID NO: 124, and a light chain comprising the amino acid sequence of SEQ ID NO: 128.

In some embodiments, the antibody fragment (e.g., Fab) that specifically binds to human cKIT comprises a heavy chain comprising the amino acid sequence of SEQ ID NO: 124, and a light chain comprising the amino acid sequence of SEQ ID NO: 129.

In some embodiments, the antibody fragment (e.g., Fab) that specifically binds to human cKIT comprises a heavy chain comprising the amino acid sequence of SEQ ID NO: 130, and a light chain comprising the amino acid sequence of SEQ ID NO: 134.

In some embodiments, the antibody fragment (e.g., Fab) that specifically binds to human cKIT comprises a heavy chain comprising the amino acid sequence of SEQ ID NO: 130, and a light chain comprising the amino acid sequence of SEQ ID NO: 135.

In some embodiments, the antibody fragment (e.g., Fab) that specifically binds to human cKIT comprises a heavy chain comprising the amino acid sequence of SEQ ID NO: 136, and a light chain comprising the amino acid sequence of SEQ ID NO: 140.

In some embodiments, the antibody fragment (e.g., Fab) that specifically binds to human cKIT comprises a heavy chain comprising the amino acid sequence of SEQ ID NO: 141, and a light chain comprising the amino acid sequence of SEQ ID NO: 145.

In some embodiments, the antibody fragment (e.g., Fab') that specifically binds to human cKIT comprises a heavy chain comprising an amino acid sequence selected from SEQ ID NO: 119, 120 or 121, and a light chain comprising the amino acid sequence of SEQ ID NO: 25.

In some embodiments, the antibody fragment (e.g., Fab') that specifically binds to human cKIT comprises a heavy chain comprising an amino acid sequence selected from SEQ ID NO: 125, 126, or 127, and a light chain comprising the amino acid sequence of SEQ ID NO: 49.

In some embodiments, the antibody fragment (e.g., Fab') that specifically binds to human cKIT comprises a heavy chain comprising an amino acid sequence selected from SEQ ID NO: 131, 132, or 133, and a light chain comprising the amino acid sequence of SEQ ID NO: 25.

In some embodiments, the antibody fragment (e.g., Fab') that specifically binds to human cKIT comprises a heavy chain comprising an amino acid sequence selected from SEQ ID NO: 137, 138, or 139, and a light chain comprising the amino acid sequence of SEQ ID NO: 84.

In some embodiments, the antibody fragment (e.g., Fab') that specifically binds to human cKIT comprises a heavy chain comprising an amino acid sequence selected from SEQ ID NO: 142, 143, or 144, and a light chain comprising the amino acid sequence of SEQ ID NO: 110.

In some embodiments, the antibody that specifically binds to human cKIT comprises a heavy chain comprising the amino acid sequence of SEQ ID NO: 12, and a light chain comprising the amino acid sequence of SEQ ID NO: 25.

In some embodiments, the antibody that specifically binds to human cKIT comprises a heavy chain comprising the amino acid sequence of SEQ ID NO: 38, and a light chain comprising the amino acid sequence of SEQ ID NO: 49.

In some embodiments, the antibody that specifically binds to human cKIT comprises a heavy chain comprising the amino acid sequence of SEQ ID NO: 56, and a light chain comprising the amino acid sequence of SEQ ID NO: 25.

In some embodiments, the antibody that specifically binds to human cKIT comprises a heavy chain comprising the amino acid sequence of SEQ ID NO: 71, and a light chain comprising the amino acid sequence of SEQ ID NO: 84.

In some embodiments, the antibody that specifically binds to human cKIT comprises a heavy chain comprising the amino acid sequence of SEQ ID NO: 97, and a light chain comprising the amino acid sequence of SEQ ID NO: 110.

In some embodiments, provided herein are conjugates comprising an antibody fragment (e.g., Fab or Fab') that specifically binds to cKIT (anti-cKIT Fab or Fab'), linked to a drug moiety (e.g., a cytotoxic agent), optionally through a linker. The anti-cKIT Fab or Fab' can be any of the Fab or Fab' described herein, e.g., any of the Fab or Fab' in Table 1. As described herein, such anti-cKIT Fab' or Fab-toxin conjugates are able to ablate human HSC cells in vitro and in vivo, but do not cause mast cell degranulation even when crosslinked and/or multimerized into larger complexes.

BRIEF DESCRIPTION OF THE DRAWINGS

FIG. 3A is a line graph showing titration of either anti-cKIT Fab'-(1) DAR4 conjugates (closed symbols, solid lines) or full length anti-cKIT antibodies (open symbols, dashed lines) for various anti-cKIT clones: anti-cKIT Ab4/Fab'4 (circles), anti-cKIT Ab3/Fab'3 (squares), anti-cKIT Ab2/Fab'2 (up triangles), anti-cKIT Ab1/Fab'1 (down triangles), and control anti-Her2 Ab/Fab' (diamonds). FIG. 3B is a line graph showing titration of anti-IgE as a positive control for mast cell degranulation. Mast cell degranulation was observed for all concentrations of anti-IgE tested. FIGS. 3C-3J are line graphs showing mast cell degranulation level triggered by anti-cKIT Fab'-(1) DAR4 conjugates (described in Table 2) or full length IgG anti-cKIT Ab controls (described in Table 8) at various concentrations: absent (open diamonds and dashed lines); 0.006 nM (triangles); 0.098 nM (diamonds); 1.56 nM (circles); and 25 nM (squares), when the test agents were cross-linked using an antibody specific for the Fab portion on the antibody test agents (titrated on x-axis). FIGS. 3C and 3D show no mast cell degranulation was triggered by J4 conjugate at all tested concentrations (FIG. 3C), whereas full length anti-cKIT Ab4, when cross-linked, caused mast cell degranulation (FIG. 3D). FIGS. 3E and 3F show no mast cell degranulation was triggered by J1 conjugate at all tested concentrations (FIG. 3E), whereas full length anti-cKIT Ab1, when cross-linked, caused mast cell degranulation (FIG. 3F). FIGS. 3G and 3H show no mast cell degranulation was triggered by J2 conjugate at all tested concentrations (FIG. 3G), whereas full length anti-cKIT Ab2, when cross-linked, caused mast cell degranulation (FIG. 3H). FIGS. 3I and 3J show no mast cell degranulation was triggered by J3 conjugate at all tested concentrations (FIG. 3I), whereas full length anti-cKIT Ab3, when cross-linked, caused mast cell degranulation (FIG. 3J). FIGS. 3K and 3L are line graphs showing no mast cell degranulation caused by control conjugate J6 (FIG. 3K) or full length anti-Her2 antibody (FIG. 3L) when cross-linked.

FIGS. 7A-7C show that full length anti-cKIT Ab4 (HC-E152C-S375C) (FIG. 7A) and anti-cKIT F(ab'4)$_2$ (HC-E152C) fragment conjugated with compound (4) (FIG. 7B) caused mast cell degranulation when cross-linked, while no mast cell degranulation was triggered by Fab4 (HC-E152C) fragment at all tested concentrations (FIG. 7C). FIGS. 7D-7F show that full length anti-cKIT Ab3 (HC-E152C-S375C) (FIG. 7D) and F(ab'3)$_2$ (HC-E152C) fragment conjugated to compound (5) (FIG. 7E) caused mast cell degranulation when cross-linked, while no mast cell degranulation was triggered by Fab3 (E152C) fragment conjugated to compound (4) at all tested concentrations (FIG. 7F). FIGS. 7G-7I are line graphs showing no mast cell degranulation caused by anti-Her2 antibody (HC-E152C-S375C) (FIG. 7G), anti-Her2-F(ab')$_2$ (HC-E152C) fragment conjugated to compound (4) (FIG. 7H), or anti-Her2-Fab (HC-E152C) fragment conjugated to compound (7) (FIG. 7I) when cross-linked.

FIGS. 8A-8O are line graphs showing representative results of in vitro human mast cell degranulation assays, which used human peripheral blood HSC-derived mast cells and beta-hexosaminidase release as the readout (assessed by absorbance at 405 nm with baseline subtraction based on reference absorbance at 620 nm). Data shown here were collected in the absence of SCF. The line graphs show mast cell degranulation level triggered by antibodies or antibody fragments at various concentrations: 0.006 nM (triangles); 0.098 nM (diamonds); 1.6 nM (circles); and 25 nM (squares), when the test agents were cross-linked using an antibody specific for the Fab portion on the antibody test agents (titrated on x-axis). For reference, the cross-linker antibody alone is plotted on each graph (open diamonds, dashed line). FIGS. 8A-8C show that full length anti-cKIT Ab4 (FIG. 8A) and anti-cKIT F(ab'4)$_2$ fragment (FIG. 8B) caused mast cell degranulation when cross-linked, while no mast cell degranulation was triggered by anti-cKIT Fab4 (HC-E152C) fragment at all tested concentrations (FIG. 8C). FIGS. 8D-8F show that full length anti-cKIT Ab1 (FIG. 8D) and anti-cKIT F(ab'1)$_2$ fragment (FIG. 8E) caused mast cell degranulation when cross-linked, while no mast cell degranulation was triggered by anti-cKIT Fab1 (HC-E152C) fragment at all tested concentrations (FIG. 8F). FIGS. 8G-8I show that full length anti-cKIT Ab2 (FIG. 8G) and anti-cKIT F(ab'2)$_2$ fragment (FIG. 8H) caused mast cell degranulation when cross-linked, while no mast cell degranulation was triggered by anti-cKIT Fab2 (HC-E152C) fragment at all tested concentrations (FIG. 8I). FIGS. 8J-8L show that full length anti-cKIT Ab3 (FIG. 8J) and anti-cKIT F(ab'3)$_2$ fragment (FIG. 8K) caused mast cell degranulation when cross-linked, while no mast cell degranulation was triggered by anti-cKIT Fab3 (HC-E152C) fragment at all tested concentrations (FIG. 8L). FIGS. 8M-8O are line graphs showing no mast cell degranulation caused by anti-Her2 antibody (FIG. 8M), anti-Her2-F(ab')$_2$ fragment (FIG. 8N), or anti-Her2-Fab (HC-E152C) fragment (FIG. 8O) when cross-linked.

DETAILED DESCRIPTION

Figure 1:
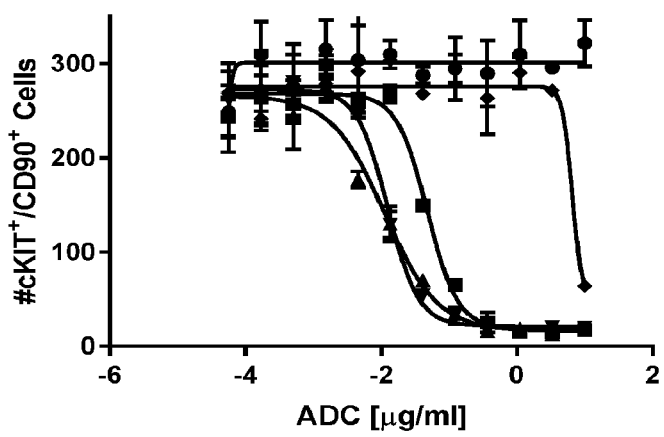
FIG. 1 is a line graph showing all tested anti-cKIT Fab'-(1) DAR4 conjugates (see Table 2 for conjugate details) killed human stem and progenitor cells (cKIT$^+$/CD90$^+$ cells) in vitro with approximately equal potency: J3 (squares); J2 (up triangles); J1 (down triangles). A control ADC, J6 (diamonds), did not kill human HSCs as compared to PBS control (circles).

The present disclosure provides antibody drug conjugates, wherein an antibody or antibody fragment (e.g., Fab or Fab') that specifically binds to human cKIT is linked to a drug moiety (e.g., a cytotoxic agent), optionally through a linker. Those antibody drug conjugates can selectively deliver a cytotoxic agent to cells expressing cKIT, e.g., hematopoietic stem cells, thereby selectively ablate those cells in a patient, e.g., a hematopoietic stem cell transplantation recipient. Preferably, the cKIT antibody drug conjugates have pharmacokinetic properties such that it will not be present and/or active in a patient's circulation for an extended time, so they can be used for conditioning hematopoietic stem cell transplant recipients prior to hematopoietic stem cell transplantation. In some embodiments, provided herein are conjugates comprising an antibody fragment (e.g., Fab or Fab') that specifically binds to cKIT, linked to a drug moiety (e.g., a cytotoxic agent), optionally through a linker. Surprisingly, the present inventors found that the full length anti-cKIT antibodies (e.g., full-length IgGs), F(ab')$_2$ fragments, and toxin conjugates thereof cause mast cell degranulation, but the anti-cKIT Fab' or Fab-toxin conjugates do not cause mast cell degranulation, even when crosslinked and/or multimerized into larger complexes as could be observed if a patient developed or had pre-existing anti-drug antibodies recognizing Fab fragments. The present disclosure further provides pharmaceutical compositions comprising the antibody drug conjugates, and methods of making and using such pharmaceutical compositions for ablating hematopoietic stem cells in a patient in need thereof, e.g., a hematopoietic stem cell transplantation recipient.

Definitions

Unless stated otherwise, the following terms and phrases as used herein are intended to have the following meanings:

The term "alkyl" refers to a monovalent saturated hydrocarbon chain having the specified number of carbon atoms. For example, $C_{1-6}$alkyl refers to an alkyl group having from 1 to 6 carbon atoms. Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

The term "antibody," as used herein, refers to a protein, or polypeptide sequence derived from an immunoglobulin molecule that specifically binds to an antigen. Antibodies can be polyclonal or monoclonal, multiple or single chain, or intact immunoglobulins, and may be derived from natural sources or from recombinant sources. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An antibody can be a monoclonal antibody, human antibody, humanized antibody, camelid antibody, or chimeric antibody. The antibodies can be of any isotype (e.g., IgG, IgE, IgM, IgD, IgA and IgY), class (e.g., IgG1, IgG2, IgG3, IgG4, IgA1 and IgA2) or subclass.

"Complementarity-determining domains" or "complementary-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. CDRs can be referred to by their region and order. For example, "VHCDR1" or "HCDR1" both refer to the first CDR of the heavy chain variable region. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme) and ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (CDR1), 51-57 (CDR2) and 93-102 (CDR3), and the CDR amino acid residues in the VL are numbered approximately 27-32 (CDR1), 50-52 (CDR2), and 89-97 (CDR3) (numbering according to "Kabat"). Under IMGT, the CDR regions of an antibody can be determined using the program IMGT/DomainGap Align.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3, and in some cases, CH4) confer important biological properties such as secretion, transplacental mobility, Fc receptor binding, complement binding, FcRn receptor binding, half-life, pharmacokinetics and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antibody fragment" or "antigen binding fragment", as used herein, refers to one or more portions of an antibody that retain the ability to specifically interact with (e.g., by binding, steric hindrance, stabilizing/destabilizing, spatial distribution) an epitope of an antigen (e.g., cKIT). Examples of antibody fragments include, but are not limited to, a Fab fragment, which is a monovalent fragment consisting of the VL, VH, CL and CH1 domains; a Fab' fragment, which is a monovalent fragment consisting of the VL, VH, CL, CH1 domains, and the hinge region; a F(ab')2 fragment, which is a bivalent fragment comprising two Fab fragments linked by a disulfide bridge at the hinge region; a half antibody, which includes a single heavy chain and a single light chain linked by a disulfide bridge; a one-arm antibody, which includes a Fab fragment linked to an Fc region; a CH2 domain-deleted antibody, which includes two Fab fragments linked to the CH3 domain dimers (see Glaser, J Biol Chem. 2005; 280(50):41494-503); a single-chain Fv (scFv); a disulfide-linked Fv (sdFv); a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody. For example, a Fab fragment can include amino acid residues 1-222 (EU numbering) of the heavy chain of an antibody; whereas a Fab' fragment can include amino acid residues 1-236 (EU numbering) of the heavy chain of an antibody. The Fab or Fab' fragment of an antibody can be generated recombinantly or by enzymatic digestion of a parent antibody. Recombinantly generated Fab or Fab' may be engineered to introduce amino acids for site-specific conjugation such as cysteines (Junutula, J. R.; et al., Nature biotechnology 2008, 26, 925), pyrroline-carboxy-lysines (Ou, W. et al., Proc Natl Acad Sci USA 2011; 108(26):10437-42) or unnatural amino acids (for example Tian, F. et al., Proc Natl Acad Sci USA 2014, 111, 1766, Axup, J. Y. et al., Proc Natl Acad Sci USA. 2012, 109, 16101. Similarly, mutations or peptide tags can be added to facilitate conjugation through phosphopantetheine transferases (Grunewald, J. et al., Bioconjugate chemistry 2015, 26, 2554); formyl glycine forming enzyme (Drake, P. M. et al., Bioconjugate chemistry 2014, 25, 1331), transglutaminase (Strop, P. et al., *Chemistry & biology* 2013, 20, 161), sortase (Beerli, R. R.; Hell, T.; Merkel, A. S.; Grawunder, U. *PloS one* 2015, 10, e0131177) or other enzymatic conjugation strategies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antibody fragments or antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antibody fragments or antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000.

The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the disclosure specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)). A "paratope" is the part of the antibody which recognizes the epitope of the antigen.

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one aspect, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some aspects, antibodies or antibody fragments are selected that cross-react with certain desired molecules.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91%, 92%, 93%, 94%, 95%, 96%, 97%, 98%, 99%, or 100% sequence identity with the reference variable region nucleic acid or amino acid sequence.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least 10 to 100 times over the background.

The term "equilibrium dissociation constant (KD [M])" refers to the dissociation rate constant (kd $[s^{-1}]$) divided by the association rate constant (ka $[s^{-1}, M^{-1}]$). Equilibrium dissociation constants can be measured using any known method in the art. The antibodies of the present disclosure generally will have an equilibrium dissociation constant of less than about $10^{-7}$ or $10^{-8}$ M, for example, less than about $10^{-9}$ M or $10^{-10}$ M, in some aspects, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than an antibody drug conjugate of the present disclosure. In some aspects, the phrase "consisting essentially of" expressly excludes the inclusion of one or more additional active agents other than an antibody drug conjugate of the present disclosure and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a Pichia cell, a fungal cell, a Trichoderma cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17, (1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453, (1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "conjugate" or "antibody drug conjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the conjugate. Additionally, the conjugate can be provided in the form of a fusion protein that may be expressed from a polynucleotide encoding the conjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "toxin", "cytotoxin" or "cytotoxic agent" as used herein, refers to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein refers to a chemical moiety that is conjugated to an antibody or antigen binding fragment, and can include any therapeutic or diagnostic agent, for example, an anti-cancer, anti-inflammatory, anti-infective (e.g., anti-fungal, antibacterial, anti-parasitic, anti-viral), or an anesthetic agent. In certain aspects, a drug moiety is selected from an Eg5 inhibitor, a V-ATPase inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder, an RNA polymerase inhibitor, an amanitin, a spliceosome inhibitor, a topoisomerase inhibitor and a DHFR inhibitor. Methods for attaching each of these to a linker compatible with the antibodies and method of the present disclosure are known in the art. See, e.g., Singh et al., (2009) Therapeutic Antibodies: Methods and Protocols, vol. 525, 445-457. In addition, a payload can be a biophysical probe, a fluorophore, a spin label, an infrared probe, an affinity probe, a chelator, a spectroscopic probe, a radioactive probe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

The term "cKIT" (also known as KIT, PBT, SCFR, C-Kit, CD117) refers to a tyrosine kinase receptor that is a member of the receptor tyrosine kinase III family. The nucleic acid and amino acid sequences of human cKIT isoforms are known, and have been published in GenBank with the following Accession Nos:

NM_000222.2→NP_000213.1 Mast/stem cell growth factor receptor Kit isoform 1 precursor;

NM_001093772.1→NP_001087241.1 Mast/stem cell growth factor receptor Kit isoform 2 precursor.

Structurally, cKIT receptor is a type I transmembrane protein and contains a signal peptide, 5 Ig-like C2 domains in the extracellular domain and has a protein kinase domain in its intracellular domain. As used herein, the term "cKIT" is used to refer collectively to all naturally occurring isoforms of cKIT protein, or a variant thereof.

The term "variant" refers to a polypeptide that has a substantially identical amino acid sequence to a reference polypeptide, or is encoded by a substantially identical nucleotide sequence, and is capable of having one or more activities of the reference polypeptide. For example, a variant can have about 85%, 90%, 91%, 92%, 93%, 94%, 95%, 96%, 97%, 98%, 99% or higher sequence identity to a reference polypeptide, while retain one or more activities of the reference polypeptide.

As used herein, the terms "treat", "treating," or "treatment" of any disease or disorder refer in one aspect, to ameliorating the disease or disorder (i.e., slowing or arresting or reducing the development of the disease or at least one of the clinical symptoms thereof). In another aspect, "treat", "treating," or "treatment" refers to alleviating or ameliorating at least one physical parameter including those which may not be discernible by the patient. In yet another aspect, "treat", "treating," or "treatment" refers to modulating the disease or disorder, either physically, (e.g., stabilization of a discernible symptom), physiologically, (e.g., stabilization of a physical parameter), or both. In yet another aspect, "treat", "treating," or "treatment" refers to preventing or delaying the onset or development or progression of the disease or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some aspects, a therapeutically acceptable amount does not induce or cause undesirable side effects. A therapeutically acceptable amount can be determined by first administering a low dose, and then incrementally increasing that dose until the desired effect is achieved. A "therapeutically effective dosage," of the molecules of the present disclosure can prevent the onset of, or result in a decrease in severity of, respectively, disease symptoms, including symptoms associated with cancer.

The term "co-administer" refers to the simultaneous presence of two active agents in the blood of an individual. Active agents that are co-administered can be concurrently or sequentially delivered.

The term 'thiol-maleimide' as used herein refers to a group formed by reaction of a thiol with maleimide, having this general formula:

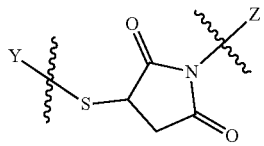

where Y and Z are groups to be connected via the thiol-maleimide linkage and can comprise linker components, antibodies or payloads. The thiol-maleimide may form the following ring opened structures

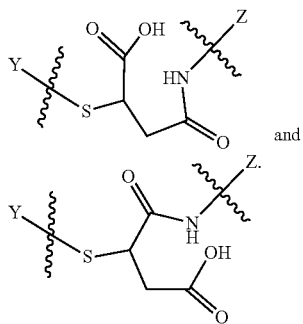

"Cleavable" as used herein refers to a linking group or linker component that connects two moieties by covalent connections, but breaks down to sever the covalent connection between the moieties under physiologically relevant conditions, typically a cleavable linking group is severed in vivo more rapidly in an intracellular environment than when outside a cell, causing release of the payload to preferentially occur inside a targeted cell. Cleavage may be enzymatic or non-enzymatic, but generally releases a payload from an antibody without degrading the antibody. Cleavage may leave some portion of a linking group or linker component attached to the payload, or it may release the payload without any residue of the linking group.

"Non-cleavable" as used herein refers to a linking group or linker component that is not especially susceptible to breaking down under physiological conditions, e.g., it is at least as stable as the antibody or antigen binding fragment portion of the conjugate. Such linking groups are sometimes referred to as 'stable', meaning they are sufficiently resistant to degradation to keep the payload connected to antibody or antigen binding fragment until the antibody or antigen binding fragment is itself at least partially degraded, i.e., the degradation of the antibody or antigen binding fragment precedes cleavage of the linking group in vivo. Degradation of the antibody portion of an ADC having a stable or non-cleavable linking group may leave some or all of the linking group, e.g., one or more amino acid groups from an antibody, attached to the payload or drug moiety that is delivered in vivo.

Linker-Drug Moiety ($L_B$-$(D)_n$)

In one aspect, the Linker-Drug moiety of the invention comprises one or more cytotoxins covalently attached to a linker ($L_B$), wherein the one or more cytotoxins are independently selected from an auristatin, an amanitin, a maytansinoid and a saporin.

In another aspect, the Linker-Drug moiety of the invention comprises one or more cytotoxins covalently attached to a linker ($L_B$), wherein the one or more cytotoxins are independently selected from an auristatin and an amanitin.

In one aspect, the Linker-Drug moiety of the invention comprises one or more cytotoxins covalently attached to a linker ($L_B$), wherein the linker ($L_B$) is a cleavable linker and the one or more cytotoxins are independently selected from an auristatin, an amanitin, a maytansinoid and a saporin.

In another aspect, the Linker-Drug moiety of the invention comprises one or more cytotoxins covalently attached to a linker ($L_B$), wherein the linker ($L_B$) is a cleavable linker and the one or more cytotoxins are independently selected from an auristatin and an amanitin.

In one aspect, the Linker-Drug moiety of the invention comprises one or more cytotoxins covalently attached to a linker ($L_B$), wherein the linker ($L_B$) is a non-cleavable linker and the one or more cytotoxins are independently selected from an auristatin, an amanitin, a maytansinoid and a saporin.

In another aspect, the Drug moiety (D) is a protein toxin selected from saporin, pokeweed antiviral protein (PAP), bryodin 1, bouganin, gelonin, ricin, abrin, mistletoe lectin, modeccin, volkensin, asparin, momordin, ebulin, viscumin, Shiga toxin, diphtheria toxin (DT), or Pseudomonas exotoxin (PE). Such protein toxins are capable of killing cells by inactivating ribosome or inhibiting protein synthesis by interfering with elongation factor 2 (EF2) function (see Kreitman et al., Immunotoxins for targeted cancer therapy, The AAPS Journal 2006; 8 (3) Article 63; Gadadhar and Karande, Targeted Cancer Therapy: History and Development of Immunotoxins, Chapter 1 of Resistance to Immunotoxins in Cancer Therapy, pp 1-31). In some embodiments, the protein toxin is saporin. Such protein toxin can be covalently attached to a cleavable or noncleavable linker ($L_B$).

In another aspect, the Linker-Drug moiety of the invention comprises one or more cytotoxins covalently attached to a linker ($L_B$), wherein the linker ($L_B$) is a non-cleavable linker and the one or more cytotoxins are independently selected from an auristatin or an amanitin.

In one aspect the Linker-Drug moiety of the invention is a compound having the structure of Formula (A), or stereoisomers or pharmaceutically acceptable salts thereof, Formula (A)

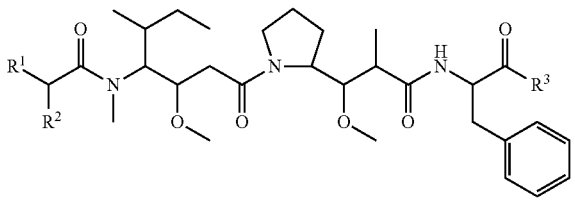

wherein:
$R^1$ is

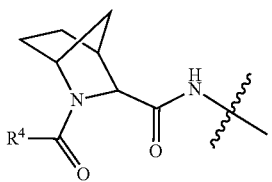

and $R^3$ is —OH;
or
$R^1$ is

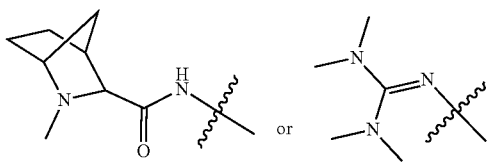

and $R^3$ is $-L_5R^{14}$;
$R^2$ is $C_1$-$C_6$alkyl;
$R^4$ is $-L_1R^{14}$, $-L_2R^{24}$, $-L_2R^{34}$ or $-L_3R^{44}$;
$L_1$ is —((CH$_2$)$_m$O)$_p$(CH$_2$)$_m$X$_1$L$_4$-, —((CH$_2$)$_m$O)$_p$(CH$_2$)$_m$X$_2$L$_4$-, —((CH$_2$)$_m$O)$_p$(CH$_2$)$_m$—, —(CH$_2$)$_m$—, —(CH$_2$)$_m$X$_1$(CH$_2$)$_m$—, —(CH$_2$)$_m$NHC(=O)(CH$_2$)$_m$—, —(CH$_2$)$_m$NHC(=O)(CH$_2$)$_m$C(=O)NH(CH$_2$)$_m$—, —((CH$_2$)$_m$O)$_p$(CH$_2$)$_m$NHC(=O)(CH$_2$)$_m$, —((CH$_2$)$_m$O)$_p$CH$_2$)$_m$C(=O)NH(CH$_2$)$_m$—, —X$_3$X$_4$C(=O)((CH$_2$)$_m$O)$_p$(CH$_2$)$_m$—, —X$_3$X$_4$C(=O)(CH$_2$)$_m$—, —X$_3$C(=O)(CH$_2$)$_m$NHC(=O)(CH$_2$)$_m$—, —X$_3$C(=O)(CH$_2$)$_m$NHC(=O)((CH$_2$)$_m$O)$_p$(CH$_2$)$_m$—, —(CH$_2$)$_m$C(R$_7$)$_2$—, —(CH$_2$)$_m$C(R$_7$)$_2$SS(CH$_2$)$_m$NHC(=O)(CH$_2$)$_m$— or —(CH$_2$)$_m$X$_3$C(=O)(CH$_2$)$_m$NHC(=O)((CH$_2$)$_m$O)$_p$(CH$_2$)$_m$—;
$L_2$ is —((CH$_2$)$_m$O)$_p$(CH$_2$)$_m$—, —(CH$_2$)$_m$X$_1$(CH$_2$)$_m$—, —(CH$_2$)$_m$NHC(=O)(CH$_2$)$_m$—, —(CH$_2$)$_m$NHC(=O)(CH$_2$)$_m$C(=O)NH(CH$_2$)$_m$—, —((CH$_2$)$_m$O)$_p$(CH$_2$)$_m$NHC(=O)(CH$_2$)$_m$, —((CH$_2$)$_m$O)$_p$CH$_2$)$_m$C(=O)NH(CH$_2$)$_m$—, —X$_3$X$_4$C(=O)((CH$_2$)$_m$O)$_p$(CH$_2$)$_m$—, —X$_3$X$_4$C(=O)(CH$_2$)$_m$—, —X$_3$C(=O)(CH$_2$)$_m$NHC(=O)(CH$_2$)$_m$—, —X$_3$C(=O)(CH$_2$)$_m$NHC(=O)((CH$_2$)$_m$O)$_p$(CH$_2$)$_m$—, —(CH$_2$)$_m$C(R$_7$)$_2$—, —(CH$_2$)$_m$C(R$_7$)$_2$SS(CH$_2$)$_m$NHC(=O)(CH$_2$)$_m$— or —(CH$_2$)$_m$X$_3$C(=O)(CH$_2$)$_m$NHC(=O)((CH$_2$)$_m$O)$_p$(CH$_2$)$_m$—;

$L_3$ is —((CH$_2$)$_m$O)$_p$(CH$_2$)$_m$X$_1$L$_4$-, —((CH$_2$)$_m$O)$_p$(CH$_2$)$_m$X$_2$L$_4$-, —((CH$_2$)$_m$O)$_p$(CH$_2$)$_m$—, —(CH$_2$)$_m$—, —(CH$_2$)$_m$X$_1$(CH$_2$)$_m$—, —(CH$_2$)$_m$NHC(=O)(CH$_2$)$_m$—, —(CH$_2$)$_m$NHC(=O)(CH$_2$)$_m$C(=O)NH(CH$_2$)$_m$—, —((CH$_2$)$_m$O)$_p$(CH$_2$)$_m$NHC(=O)(CH$_2$)$_m$, —((CH$_2$)$_m$O)$_p$CH$_2$)$_m$C(=O)NH(CH$_2$)$_m$—, —X$_3$X$_4$C(=O)((CH$_2$)$_m$O)$_p$(CH$_2$)$_m$—, —X$_3$X$_4$C(=O)(CH$_2$)$_m$—, —X$_3$C(=O)(CH$_2$)$_m$NHC(=O)(CH$_2$)$_m$—, —X$_3$C(=O)(CH$_2$)$_m$NHC(=O)((CH$_2$)$_m$O)$_p$(CH$_2$)$_m$—, —(CH$_2$)$_m$C(R$_7$)$_2$—, —(CH$_2$)$_m$C(R$_7$)$_2$SS(CH$_2$)$_m$NHC(=O)(CH$_2$)$_m$— or —(CH$_2$)$_m$X$_3$C(=O)(CH$_2$)$_m$NHC(=O)((CH$_2$)$_m$O)$_p$(CH$_2$)$_m$—;
$L_4$ is —(CH$_2$)$_m$—;
$L_5$ is —NHS(=O)$_2$(CH$_2$)$_m$X$_1$L$_4$-, —NH((CH$_2$)$_m$O)$_p$(CH$_2$)$_m$X$_1$L$_4$-, —NH((CH$_2$)$_m$O)$_p$(CH$_2$)$_m$X$_2$L$_4$-, —NH((CH$_2$)$_m$O)$_p$(CH$_2$)$_m$—, —NH(CH$_2$)$_m$—, —NH(CH$_2$)$_m$X$_1$(CH$_2$)$_m$—, —NH(CH$_2$)$_m$NHC(=O)(CH$_2$)$_m$—, —NH(CH$_2$)$_m$NHC(=O)(CH$_2$)$_m$C(=O)NH(CH$_2$)$_m$—, —NH((CH$_2$)$_m$O)$_p$(CH$_2$)$_m$NHC(=O)(CH$_2$)$_m$, —NH((CH$_2$)$_m$O)$_p$CH$_2$)$_m$C(=O)NH(CH$_2$)$_m$—, —NH(CH$_2$)$_n$C(R$_7$)$_2$—, —NH(CH$_2$)$_m$C(R$_7$)$_2$SS(CH$_2$)$_m$NHC(=O)(CH$_2$)$_m$— or —NH(CH$_2$)$_m$X$_3$C(=O)(CH$_2$)$_m$NHC(=O)((CH$_2$)$_m$O)$_p$(CH$_2$)$_m$—
$X_1$ is

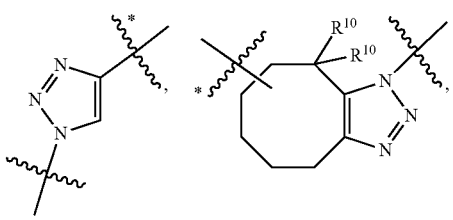

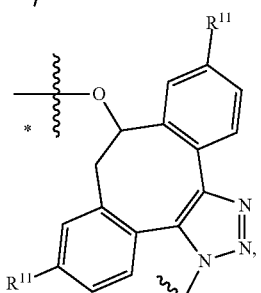

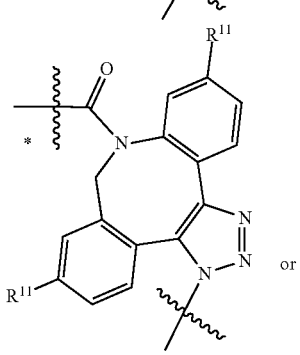

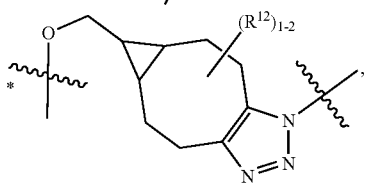

where the * indicates attachment point to $L_4$;

$X_2$ is
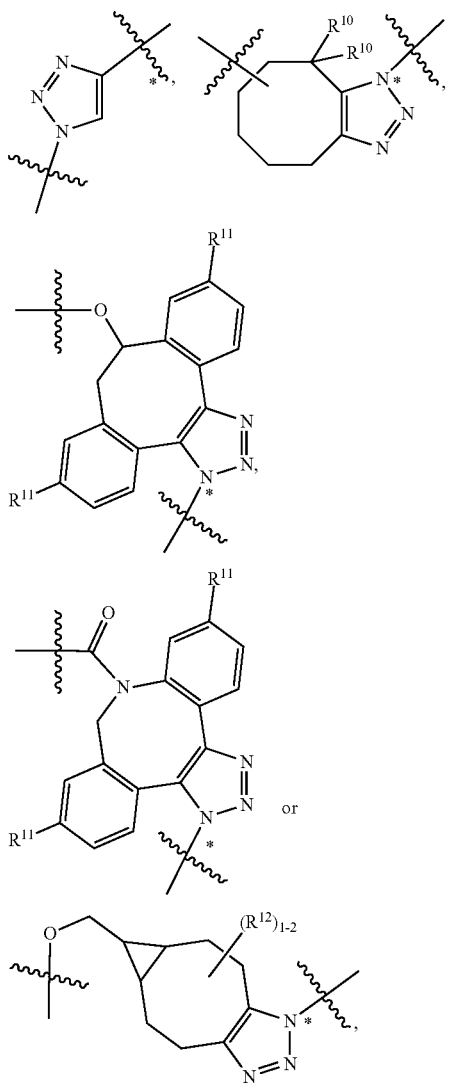
where the * indicates attachment point to $L_4$;
$X_3$ is
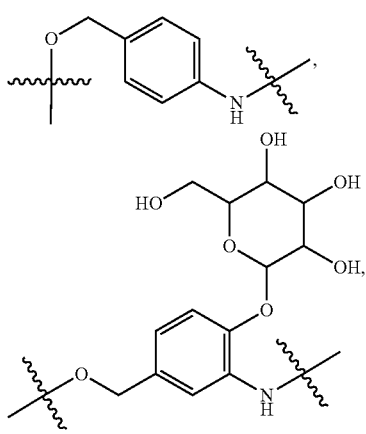
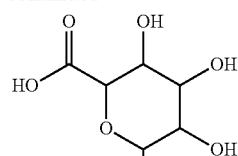
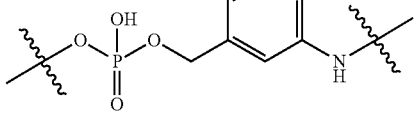 or
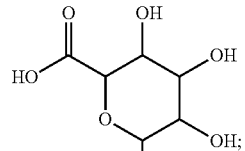
$X_4$ is
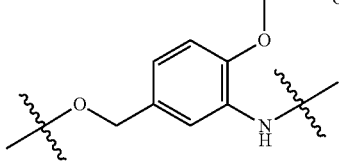
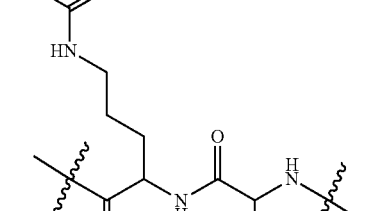,
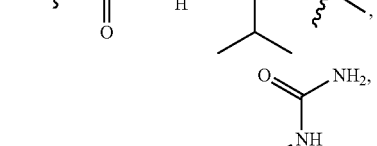

-continued
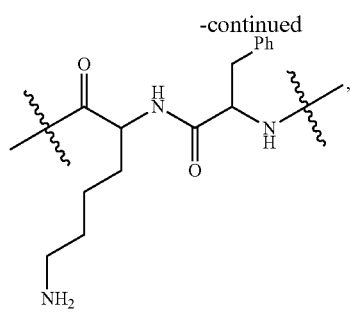
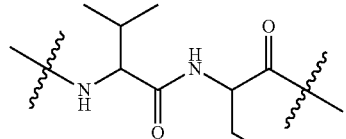
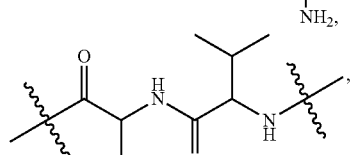
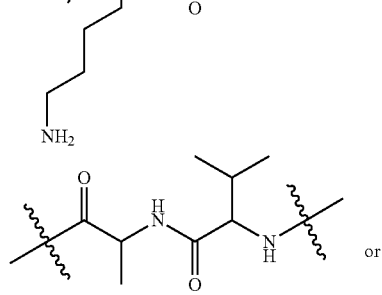 or
-continued
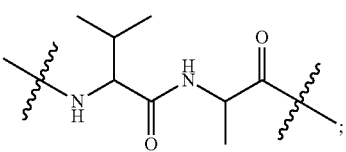
R$^{14}$ is
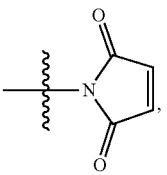
—N$_3$, —ONH$_2$, —NR$^7$C(=O)CH=CH$_2$, SH, —SSR$^{13}$, —S(=O)$_2$(CH=CH$_2$), —NR$^7$S(=O)$_2$(CH=CH$_2$), —NR$^7$C(=O)CH$_2$Br, —NR$^7$C(=O)CH$_2$I, —NHC(=O)CH$_2$Br, —NHC(=O)CH$_2$I, —C(=O)NHNH$_2$,
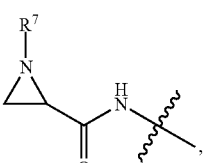
—CO$_2$H, —NH$_2$,
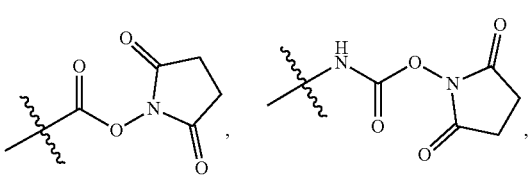
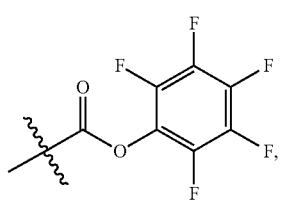 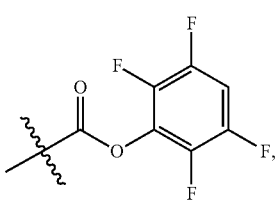 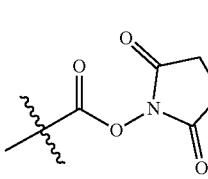
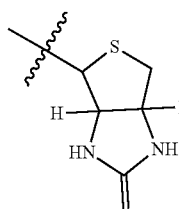 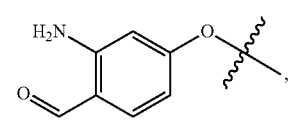 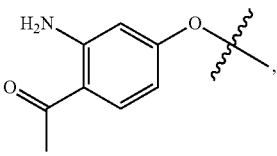
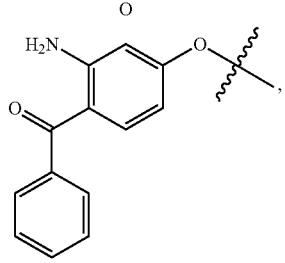 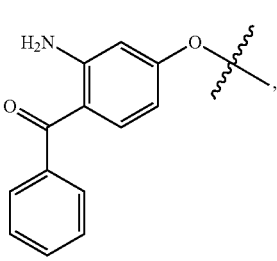

-continued
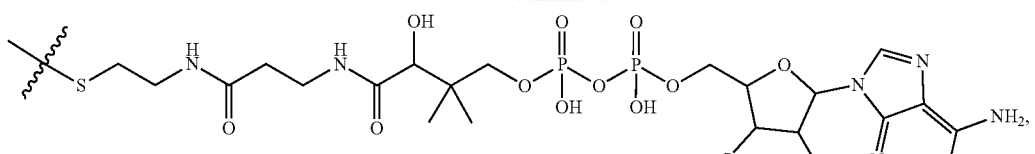
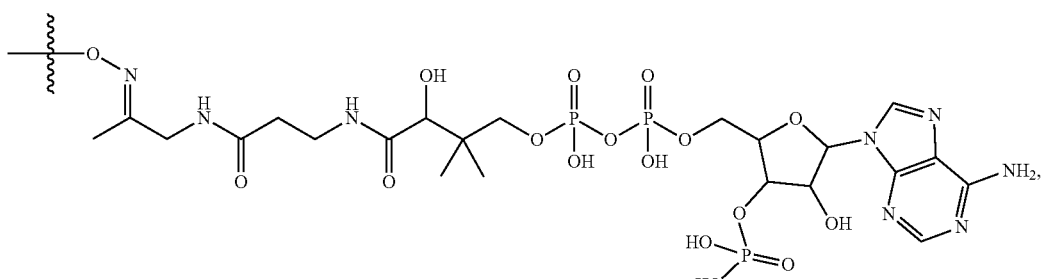
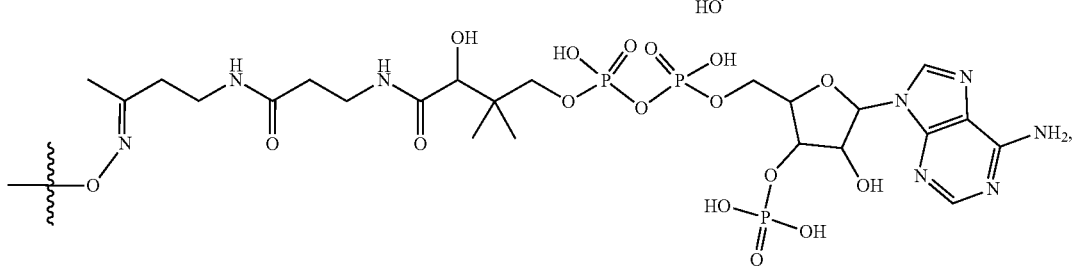
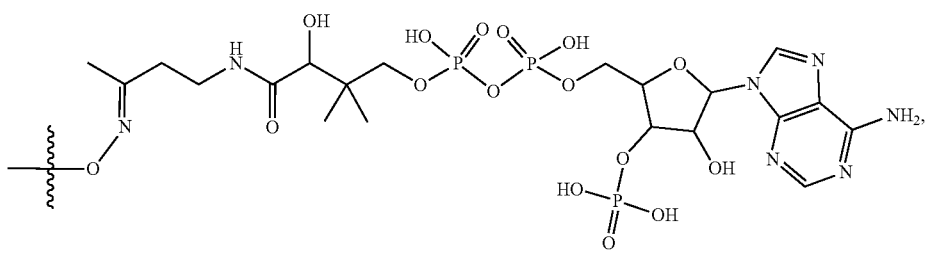
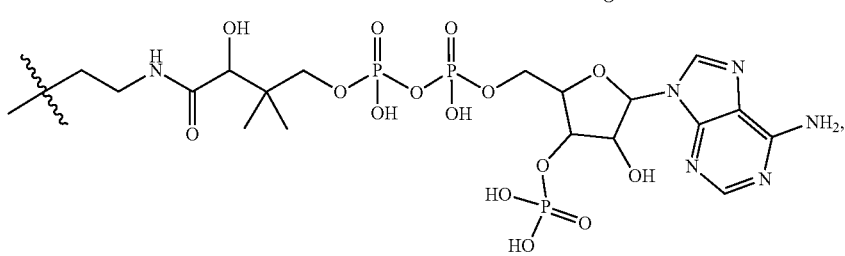
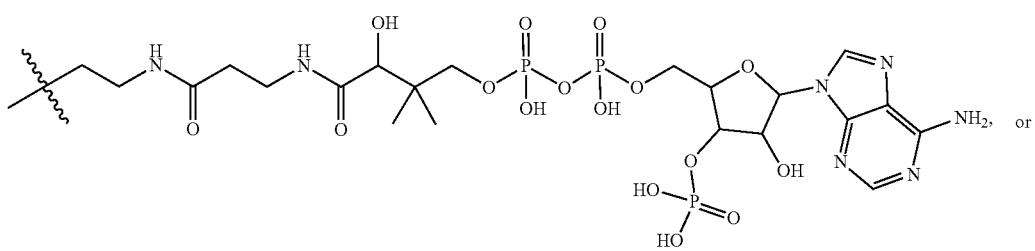

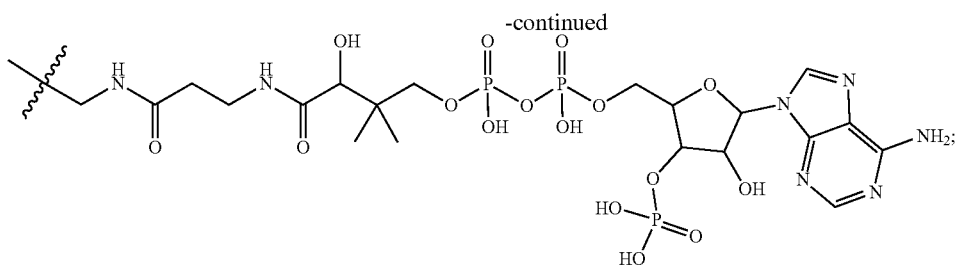

R²⁴ is

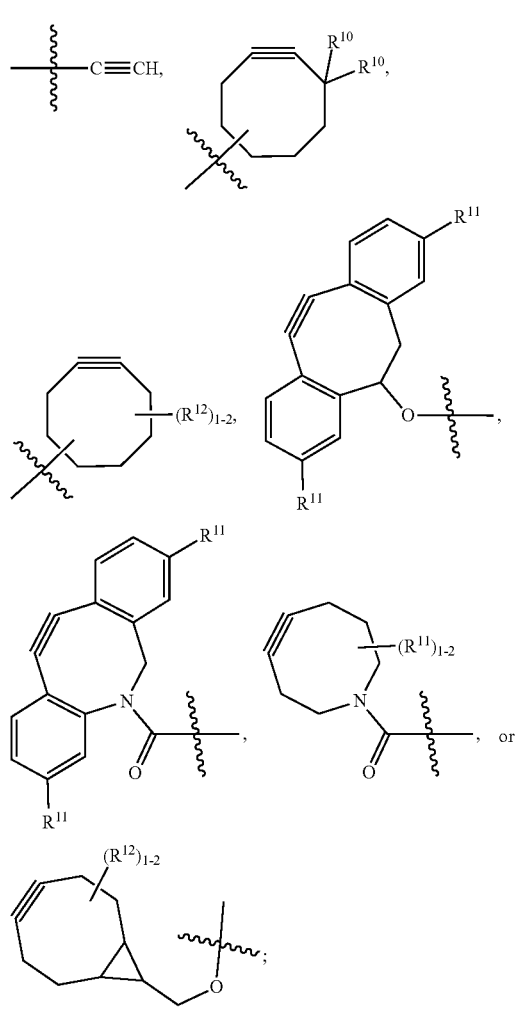

R³⁴ is, —N₃, —ONH₂, —NR⁷C(=O)CH=CH₂, —C(=O)NHNH₂, —CO₂H, —NH₂,

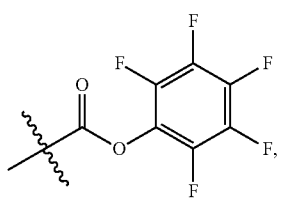

or —NR⁷C(=O)CH₂R⁸;
each R⁷ is independently selected from H and $C_1$-$C_6$alkyl;
R⁸ is —S(CH₂)$_n$CHR⁹NH₂;
R⁹ is —C(=O)OR⁷;
each R¹⁰ is independently selected from H, $C_1$-$C_6$alkyl, F, Cl, and —OH;
each R¹¹ is independently selected from H, $C_1$-$C_6$alkyl, F, Cl, —NH₂, —OCH₃, —OCH₂CH₃, —N(CH₃)₂, —CN, —NO₂ and —OH;
each R¹² is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

$R^{13}$ is 2-pyridyl or 4-pyridyl;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

In another aspect the Linker-Drug moiety of the invention is a compound having the structure of Formula (B), or stereoisomers or pharmaceutically acceptable salts thereof, Formula (B)

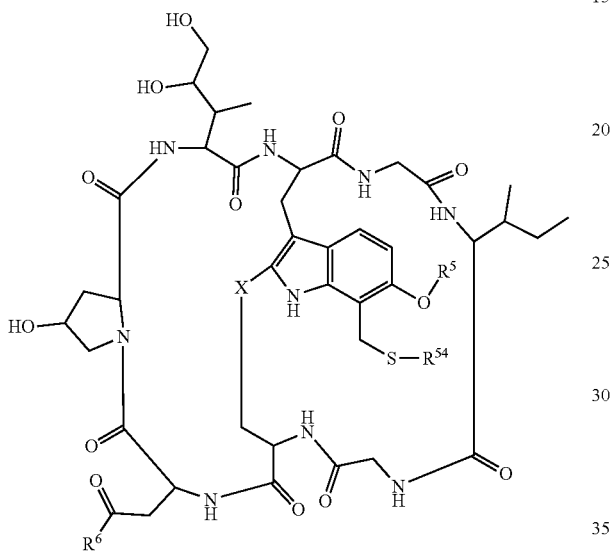

wherein:
$R^{54}$ is -$L_6R^{14}$, -$L_7R^{24}$, -$L_7R^{34}$ or -$L_8R^{44}$;
X is S(=O), S(=O)$_2$ or S;
$R^5$ is H, —CH$_3$ or —CD$_3$;
$R^6$ is —NH$_2$ or —OH;
$L_6$ is —((CH$_2$)$_m$O)$_p$(CH$_2$)$_m$X$_1$L$_4$-, —((CH$_2$)$_m$O)$_p$(CH$_2$)$_m$X$_2$L$_4$-, -L$_4$NHC(=O)NH((CH$_2$)$_m$O)$_p$(CH$_2$)$_m$X$_1$L$_4$-, -L$_4$NHC(=O)NH ((CH$_2$)$_m$O)$_p$(CH$_2$)$_m$X$_2$L$_4$-, —((CH$_2$)$_m$O)$_p$(CH$_2$)$_m$—, —(CH$_2$)$_m$—, —(CH$_2$)$_m$X$_1$(CH$_2$)$_m$—, —(CH$_2$)$_m$NHC(=O) (CH$_2$)$_m$—, —(CH$_2$)$_m$NHC(=O)(CH$_2$)$_m$C(=O)NH (CH$_2$)$_m$—, —((CH$_2$)$_m$O)$_p$(CH$_2$)$_m$NHC(=O)(CH$_2$)$_m$, —((CH$_2$)$_m$O)$_p$CH$_2$)$_m$C(=O)NH(CH$_2$)$_m$—, —(CH$_2$)$_m$C(R$_7$)$_2$— or —(CH$_2$)$_m$C(R$_7$)$_2$SS(CH$_2$)$_m$NHC(=O)(CH$_2$)$_m$—;

$L_7$ is —((CH$_2$)$_m$O)$_p$(CH$_2$)$_m$—, —(CH$_2$)$_m$X$_1$(CH$_2$)$_m$—, -L$_4$NHC(=O)NH((CH$_2$)$_m$O)$_p$(CH$_2$)$_m$—, -L$_4$NHC(=O)NH ((CH$_2$)$_m$O)$_p$(CH$_2$)$_m$—, —(CH$_2$)$_m$NHC(=O) (CH$_2$)$_m$—, —(CH$_2$)$_m$NHC(=O)(CH$_2$)$_m$C(=O)NH (CH$_2$)$_m$—, —((CH$_2$)$_m$O)$_p$(CH$_2$)$_m$NHC(=O)(CH$_2$)$_m$, —((CH$_2$)$_m$O)$_p$CH$_2$)$_m$C(=O)NH(CH$_2$)$_m$—, —(CH$_2$)$_m$C(R$_7$)$_2$—, or —(CH$_2$)$_m$C(R$_7$)$_2$SS(CH$_2$)$_m$NHC(=O)(CH$_2$)$_m$—;

$L_6$ is —((CH$_2$)$_m$O)$_p$(CH$_2$)$_m$X$_1$L$_4$-, —((CH$_2$)$_m$O)$_p$(CH$_2$)$_m$X$_2$L$_4$-, -L$_4$NHC(=O)NH((CH$_2$)$_m$O)$_p$(CH$_2$)$_m$X$_1$L$_4$-, -L$_4$NHC(=O)NH ((CH$_2$)$_m$O)$_p$(CH$_2$)$_m$X$_2$L$_4$-, —((CH$_2$)$_m$O)$_p$(CH$_2$)$_m$—, —(CH$_2$)$_m$—, —(CH$_2$)$_m$X$_1$(CH$_2$)$_m$—, —(CH$_2$)$_m$NHC(=O) (CH$_2$)$_m$—, —(CH$_2$)$_m$NHC(=O)(CH$_2$)$_m$C(=O)NH (CH$_2$)$_m$—, —((CH$_2$)$_m$O)$_p$(CH$_2$)$_m$NHC(=O)(CH$_2$)$_m$, —((CH$_2$)$_m$O)$_p$CH$_2$)$_m$C(=O)NH(CH$_2$)$_m$—, —(CH$_2$)$_m$C(R$_7$)$_2$— or —(CH$_2$)$_m$C(R$_7$)$_2$SS(CH$_2$)$_m$NHC(=O)(CH$_2$)$_m$—;

$L_4$ is —(CH$_2$)$_m$—;

$X_1$ is

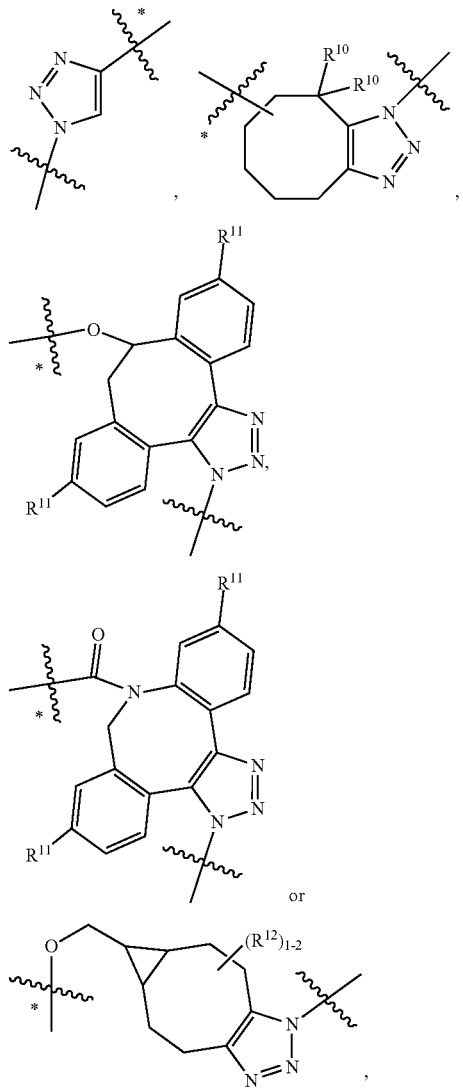

where the * indicates attachment point to $L_4$;

$X_2$ is

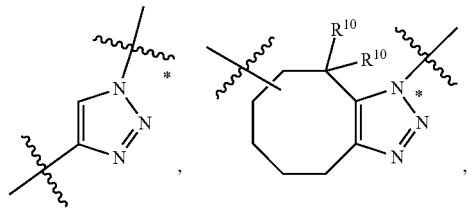

-continued
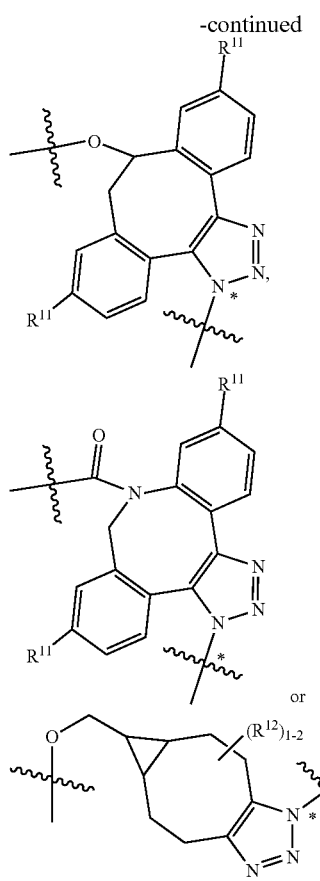
where the * indicates attachment point to $L_4$;
$R^{14}$ is
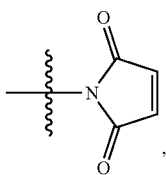 [SMILES: *N1C(=O)C=CC1=O]
$-N_3$, $-ONH_2$, $-NR^7C(=O)CH=CH_2$, SH, $-SSR^{13}$, $-S(=O)_2(CH=CH_2)$, $-NR^7S(=O)_2(CH=CH_2)$, $-NR^7C(=O)CH_2Br$, $-NR^7C(=O)CH_2I$, $-NHC(=O)CH_2Br$, $-NHC(=O)CH_2I$, $-C(=O)NHNH_2$,
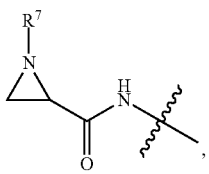
$-CO_2H$, $-NH_2$,
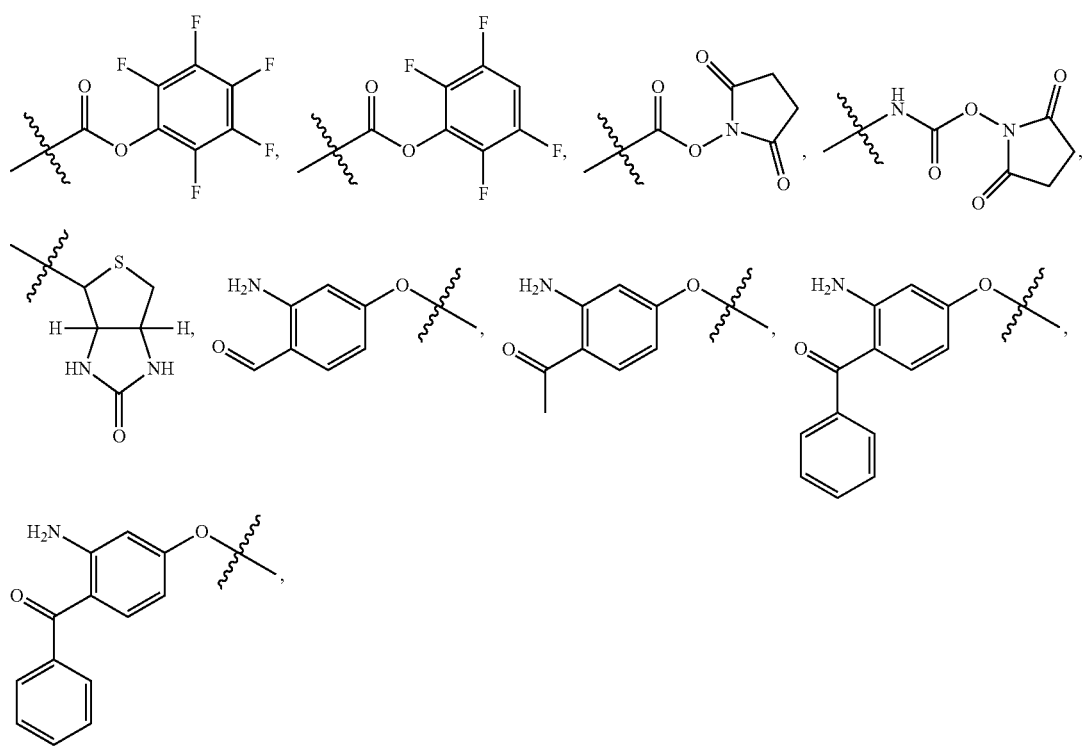

-continued
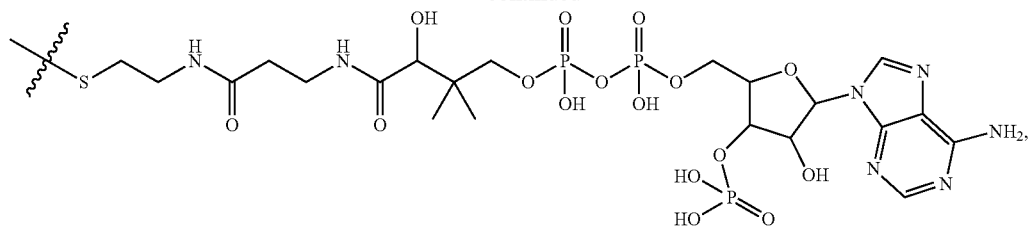
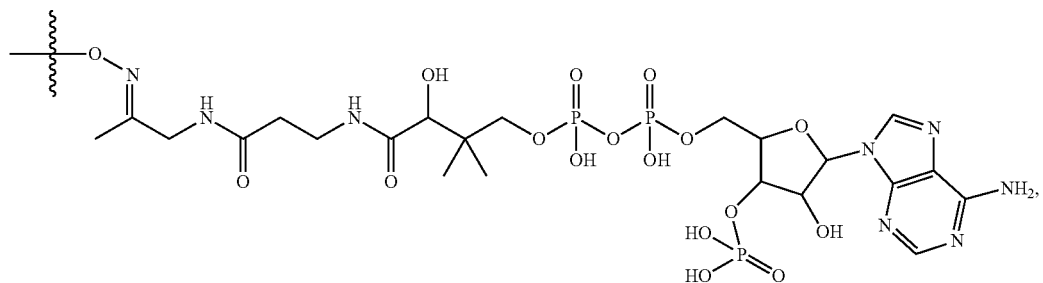
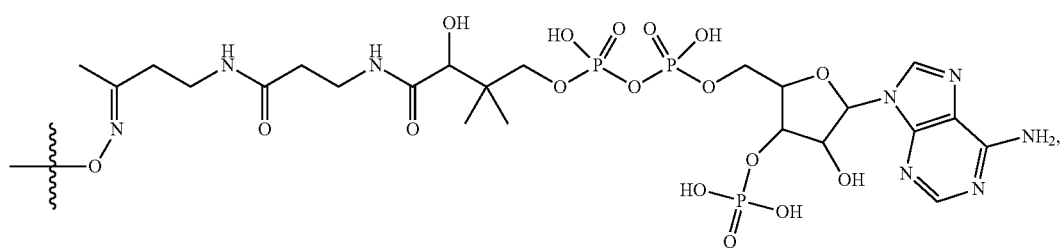
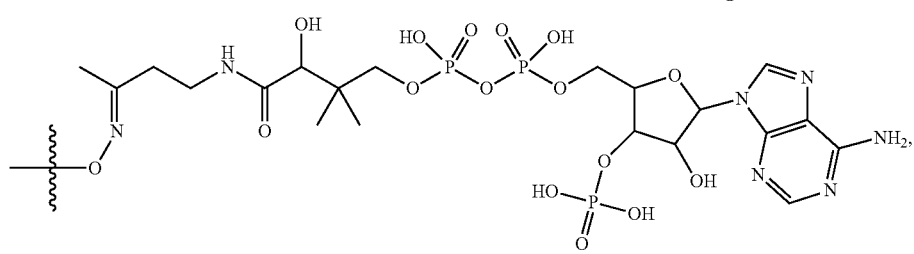
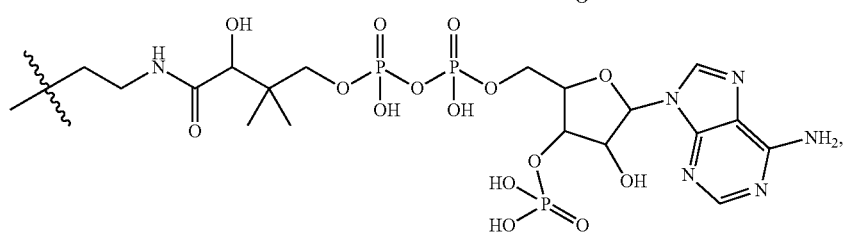
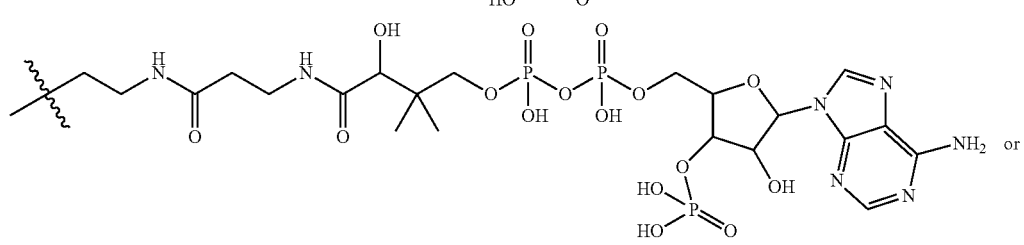 or
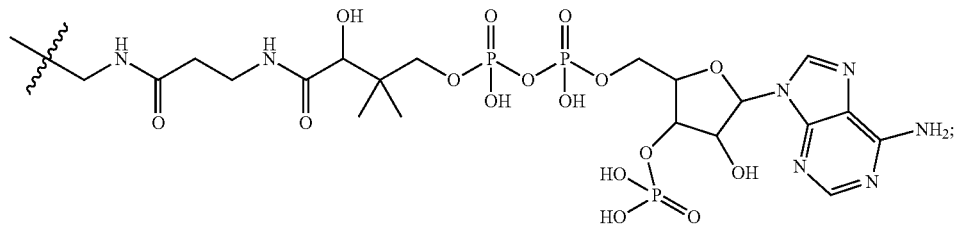

$R^{24}$ is

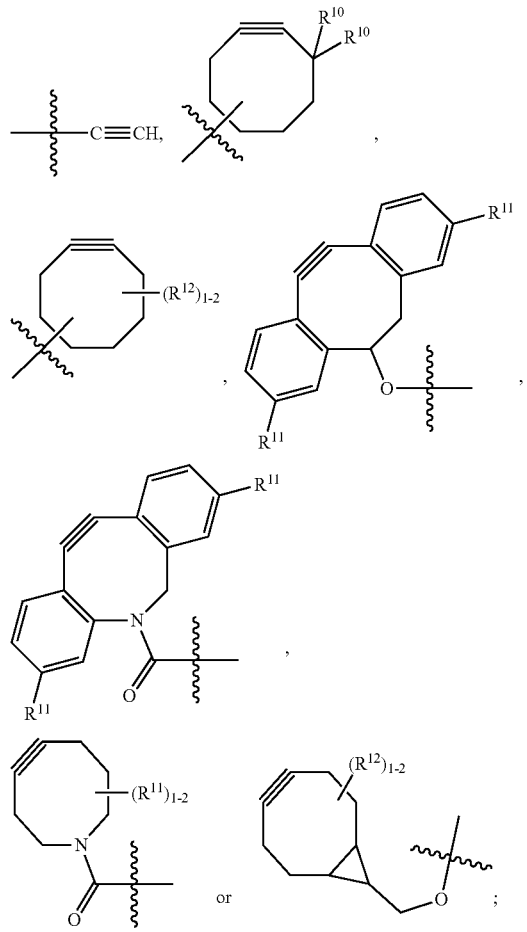

$R^{34}$ is, —$N_3$, —$ONH_2$, —$NR^7C(=O)CH=CH_2$, —$C(=O)NHNH_2$, —$CO_2H$, —$NH_2$,

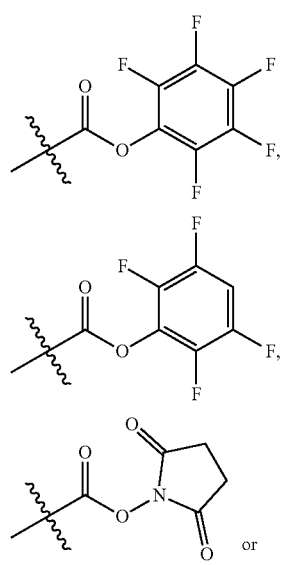

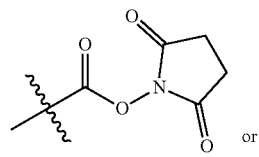

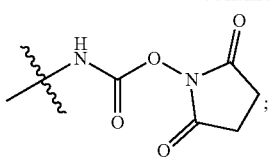

$R^{44}$ is

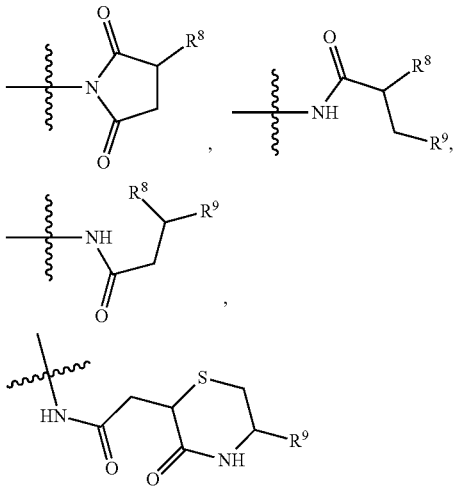

or —$NR^7C(=O)CH_2R^8$;

each $R^7$ is independently selected from H and $C_1$-$C_6$alkyl;

$R^8$ is —$S(CH_2)_n CHR^9 NH_2$;

$R^9$ is —$C(=O)OR^7$;

each $R^{10}$ is independently selected from H, $C_1$-$C_6$alkyl, F, Cl, and —OH;

each $R^{11}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

$R^{13}$ is 2-pyridyl or 4-pyridyl;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

Certain aspects and examples of the Linker-Drug moiety of the invention are provided in the following listing of additional, enumerated embodiments. It will be recognized that features specified in each embodiment may be combined with other specified features to provide further embodiments of the present invention.

Embodiment 1. The compound of Formula (A), or a pharmaceutically acceptable salt thereof, having the structure of Formula (A-1), or a pharmaceutically acceptable salt thereof:

Formula (A-1)

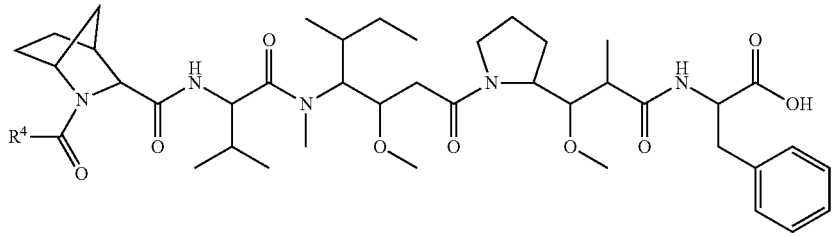

wherein: R⁴ is as defined above.

Embodiment 2. The compound of Formula (A), or a pharmaceutically acceptable salt thereof, having the structure of Formula (A-2) or Formula (A-3), or a pharmaceutically acceptable salt thereof:

Formula (A-2)

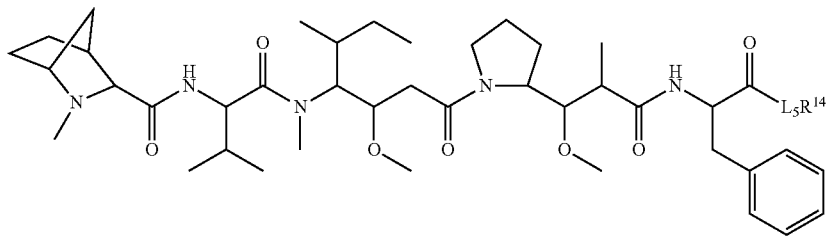

Formula (A-3)

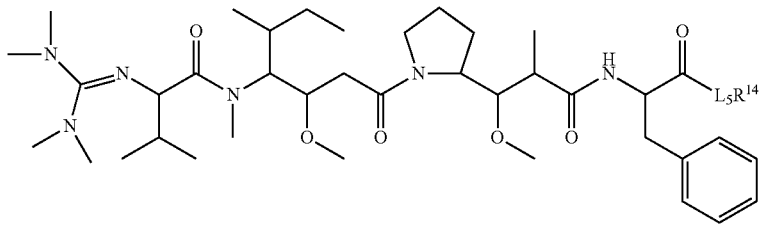

wherein: $L_5$ and $R^{14}$ are as defined above.

Embodiment 3. The compound of Formula (A), or a pharmaceutically acceptable salt thereof, having the structure of Formula (A-1a), or a pharmaceutically acceptable salt thereof:

Formula (A-1a)

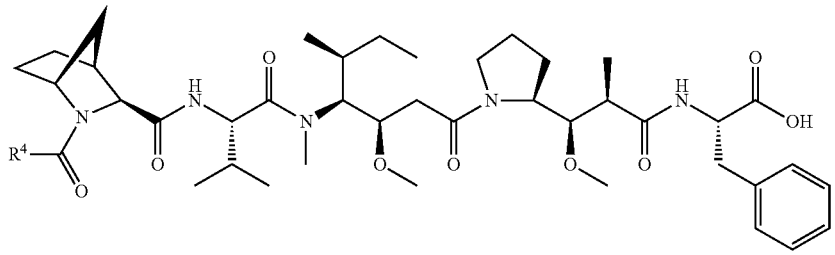

wherein: R⁴ is as defined above.

Embodiment 4. The compound of Formula (A), or a pharmaceutically acceptable salt thereof, having the structure of Formula (A-2a) or Formula (A-3a), or a pharmaceutically acceptable salt thereof:

Formula (A-2a)

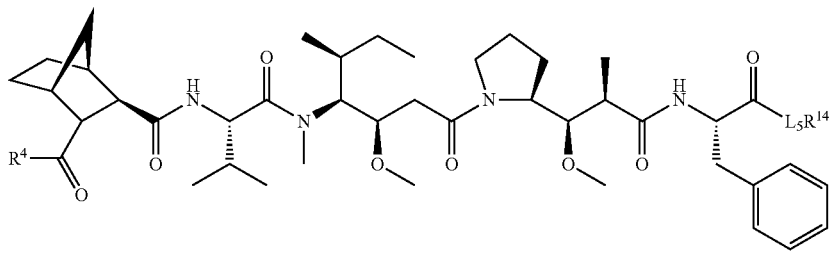

Formula (A-3a)

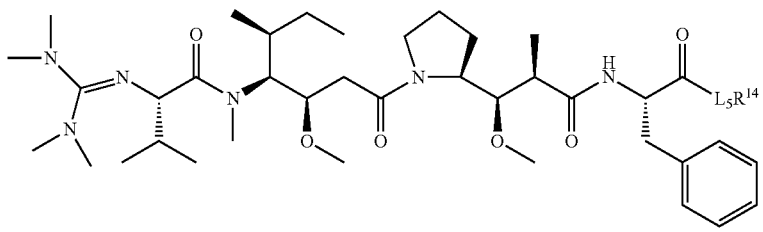

wherein: $L_5$ and $R^{14}$ are as defined above.

Embodiment 5. The compound of Formula (A), Formula (A-1) or Formula (A-1a), or a pharmaceutically acceptable salt thereof, wherein:

$R^4$ is $-L_1R^{14}$, $-L_2R^{24}$, $-L_2R^{34}$ or $-L_3R^{44}$;

$L_1$ is $-((CH_2)_mO)_p(CH_2)_mX_1L_4-$, $-((CH_2)_mO)_p(CH_2)_mX_2L_4-$, $-((CH_2)_mO)_p(CH_2)_m-$, $-(CH_2)_m-$, $-X_3X_4C(=O)((CH_2)_mO)_p(CH_2)_m-$, $-X_3X_4C(=O)(CH_2)_m-$, $-X_3C(=O)(CH_2)_mNHC(=O)(CH_2)_m-$, $-X_3C(=O)(CH_2)_mNHC(=O)((CH_2)_mO)_p(CH_2)_m-$;

$L_2$ is $-((CH_2)_mO)_p(CH_2)_m-$;

$L_3$ is $-((CH_2)_mO)_p(CH_2)_mX_1L_4-$, $-((CH_2)_mO)_p(CH_2)_mX_2L_4-$, $-((CH_2)_mO)_p(CH_2)_m-$, $-(CH_2)_m-$, $X_3X_4C(=O)((CH_2)_mO)_p(CH_2)_m-$, $-X_3X_4C(=O)(CH_2)_m-$, $-X_3C(=O)(CH_2)_mNHC(=O)(CH_2)_m-$, $-X_3C(=O)(CH_2)_mNHC(=O)((CH_2)_mO)_p(CH_2)_m-$;

$L_4$ is $-(CH_2)_m-$ $X_1$ is

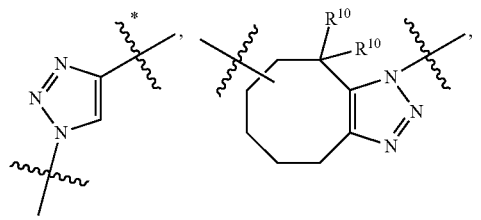

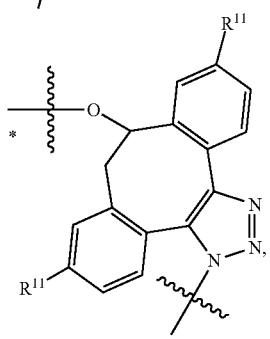

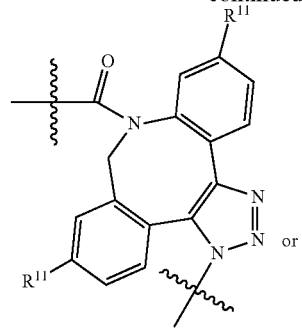

-continued

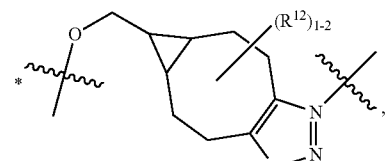

or where the * indicates attachment point to $L_4$;

$X_2$ is

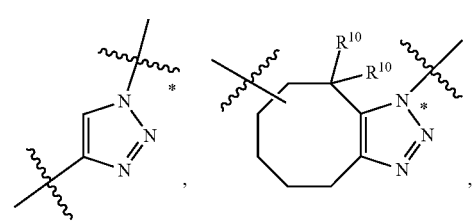

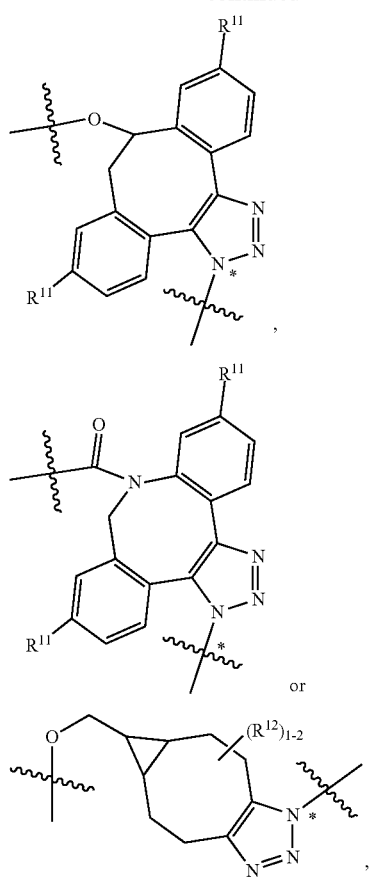
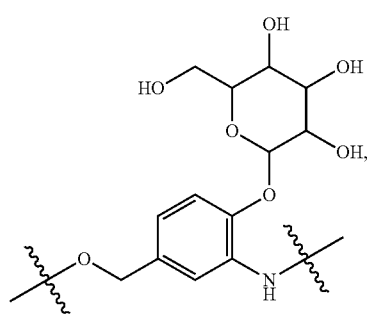
where the * indicates attachment point to $L_4$;
$X_3$ is
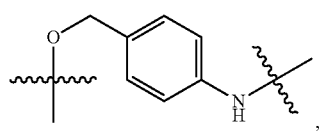
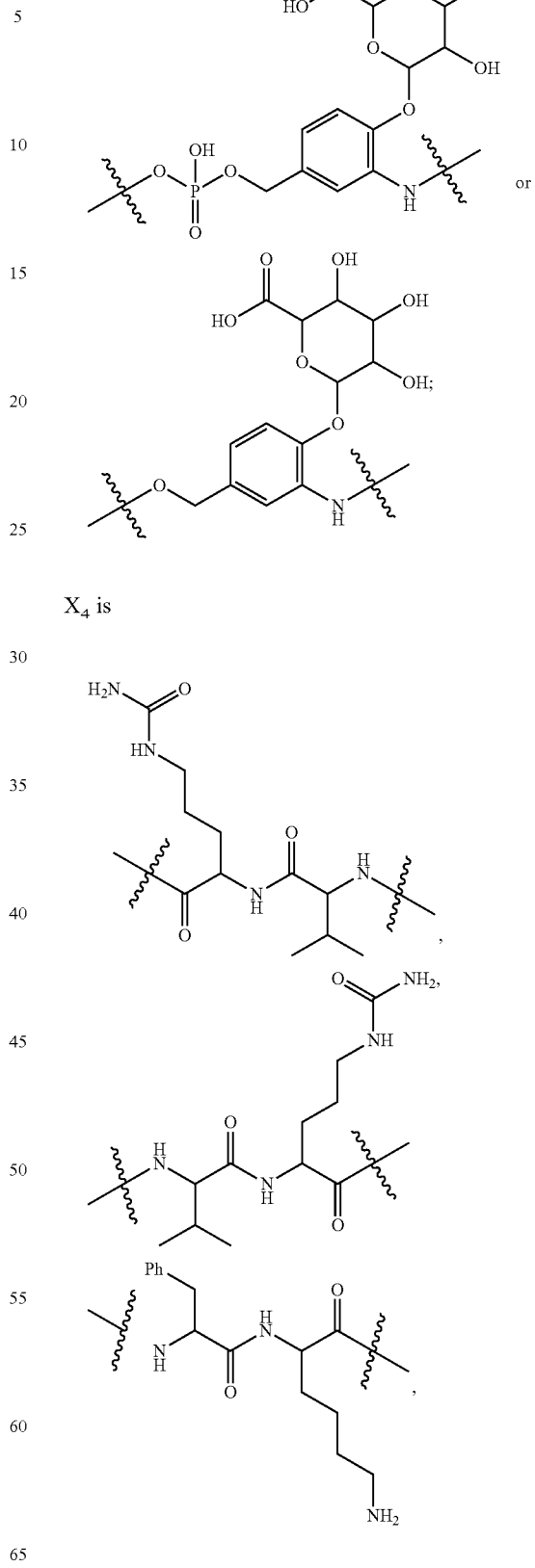
$X_4$ is 49
-continued
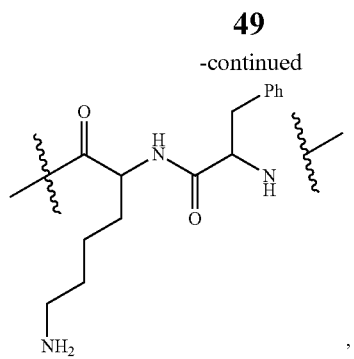
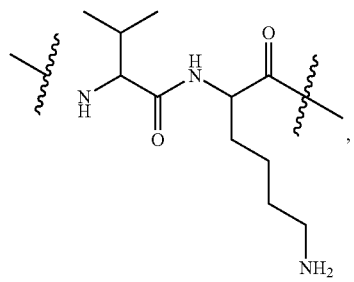
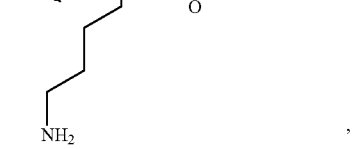
50
-continued
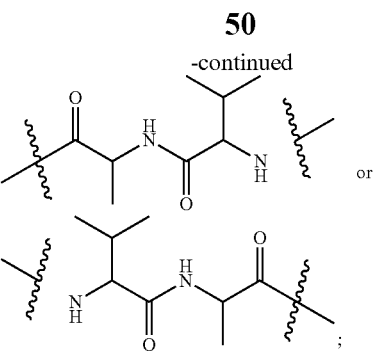
$R^{14}$ is
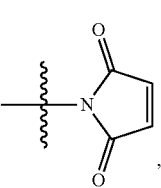 [SMILES: *N1C(=O)C=CC1=O]
—$N_3$, —$ONH_2$, —$NR^7C(=O)CH=CH_2$, SH, —$S(=O)_2(CH=CH_2)$, —$NR^7S(=O)_2(CH=CH_2)$, —$NR^7C(=O)CH_2Br$, —$NR^7C(=O)CH_2I$, —$NHC(=O)CH_2Br$, —$NHC(=O)CH_2I$, —$C(O)NHNH_2$,
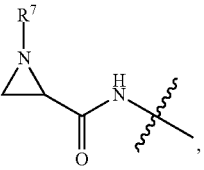
—$CO_2H$, —$NH_2$,
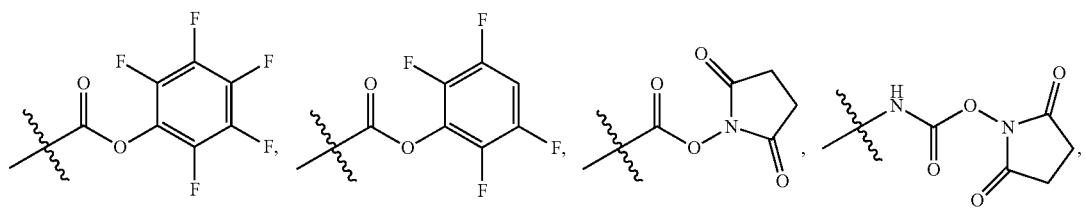
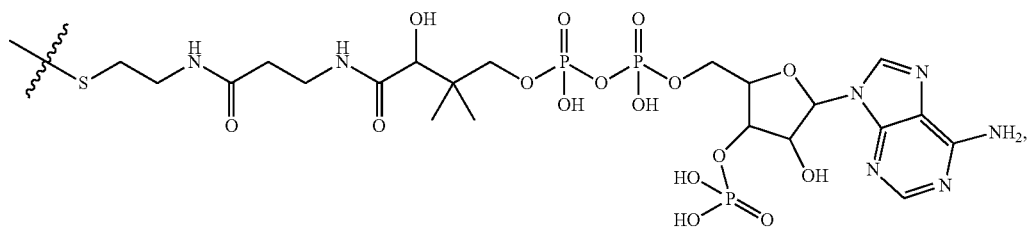

-continued
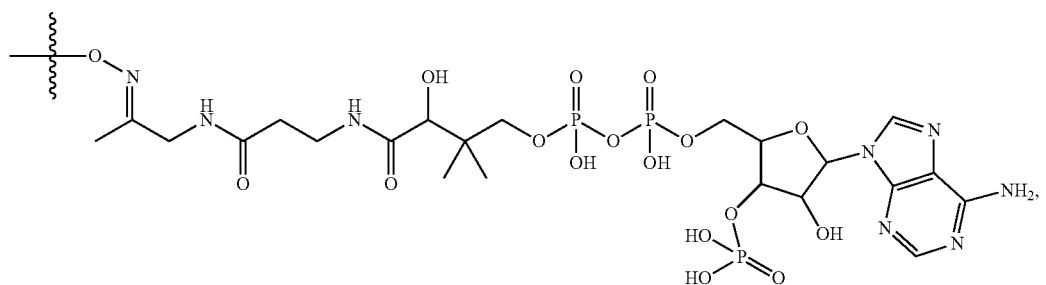
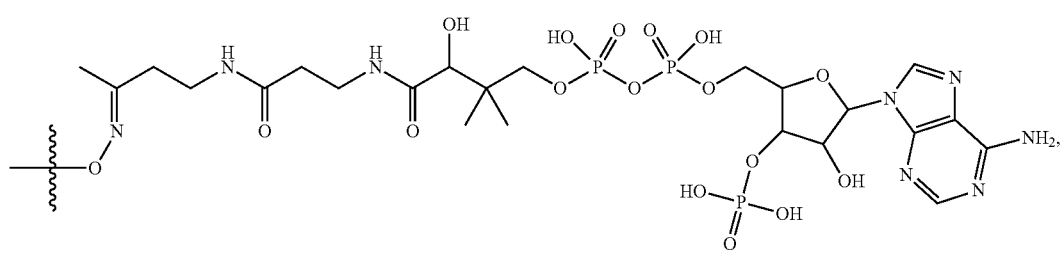
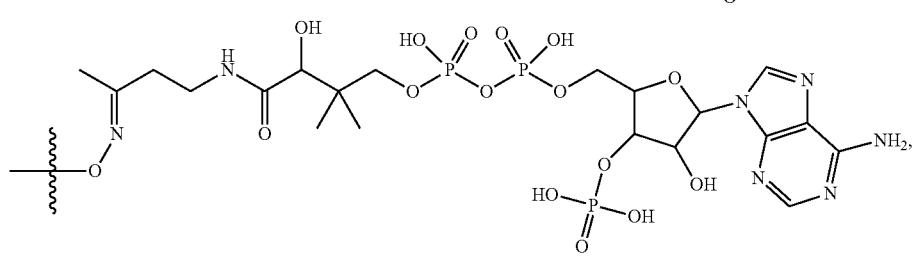
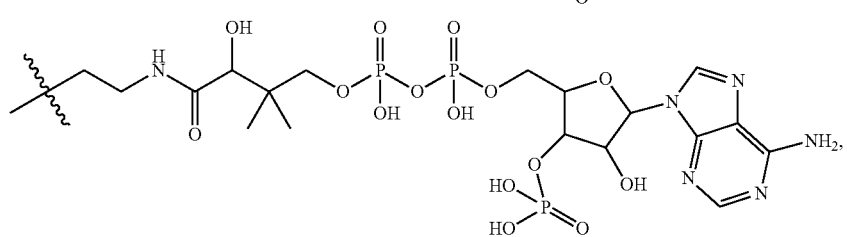
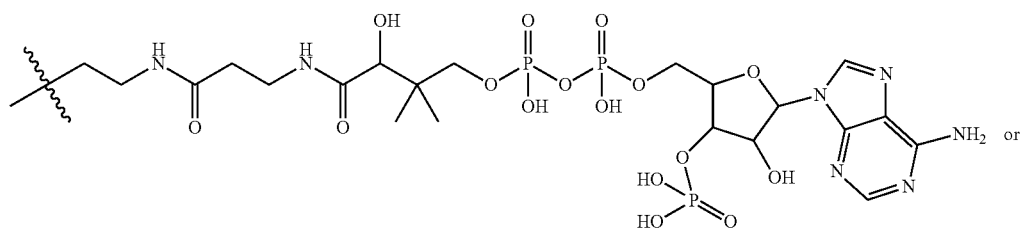 or
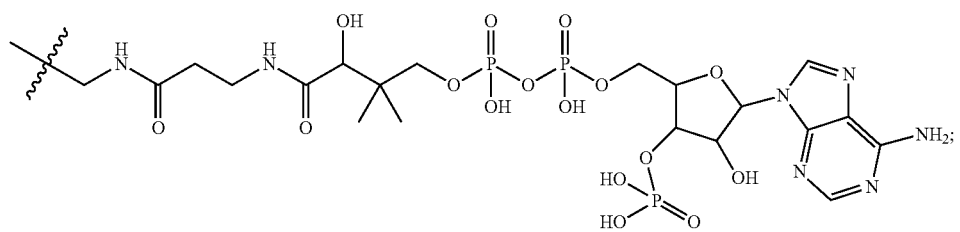

$R^{24}$ is

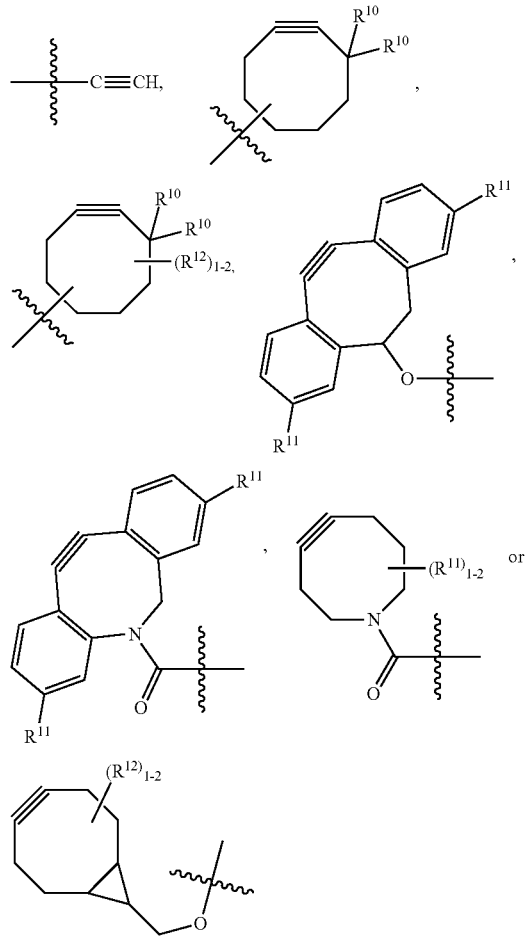

$R^{34}$ is, $-N_3$, $-ONH_2$, $-NR^7C(=O)CH=CH_2$, $-C(O)NHNH_2$, $-CO_2H$, $-NH_2$,

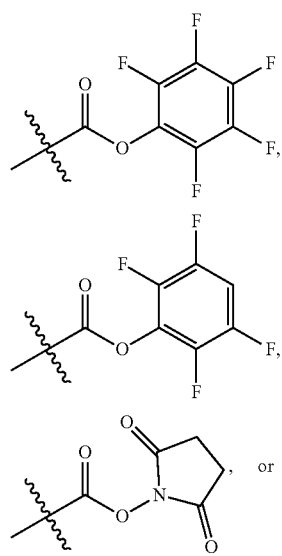

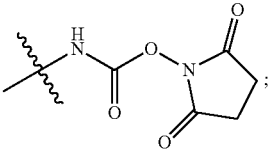

$R^{44}$ is

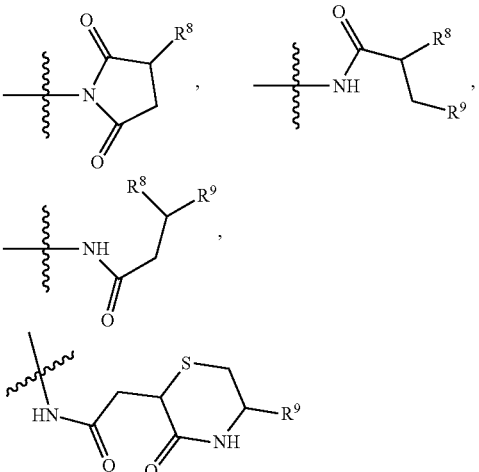

or $-NR^7C(=O)CH_2R^8$;

each $R^7$ is independently selected from H and $C_1$-$C_8$alkyl;

$R^8$ is $-S(CH_2)_nCHR^9NH_2$ $R^9$ is $-C(=O)OR^7$;

each $R^{10}$ is independently selected from H, $C_1$-$C_6$alkyl, F, Cl, and $-OH$;

each $R^{11}$ is independently selected from H, $C_1$-$C_6$alkyl, F, Cl, $-NH_2$, $-OCH_3$, $-OCH_2CH_3$, $-N(CH_3)_2$, $-ON$, $-NO_2$ and $-OH$;

each $R^{12}$ is independently selected from H, $C_{1-6}$alkyl, fluoro, benzyloxy substituted with $-C(=O)OH$, benzyl substituted with $-C(=O)OH$, $C_{1-4}$alkoxy substituted with $-C(=O)OH$ and $C_{1-4}$alkyl substituted with $-C(=O)OH$;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

Embodiment 6. The compound of Formula (A), Formula (A-2), Formula (A-3), Formula (A-2a) or Formula (A-3a), or a pharmaceutically acceptable salt thereof, wherein:

$L_4$ is $-(CH_2)_m-$;

$L_5$ is $-NHS(=O)_2(CH_2)_mX_1L_4-$, $-NH((CH_2)_mO)_p(CH_2)_mX_1L_4-$, $-NH((CH_2)_mO)_p(CH_2)_mX_2L_4-$, $-NH((CH_2)_mO)_p(CH_2)_m-$ or $-NH(CH_2)_m-$;

$X_1$ is

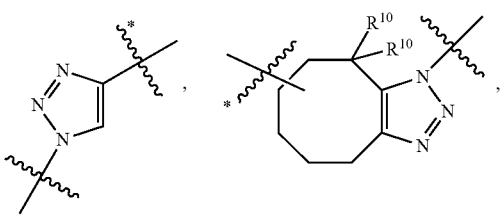

-continued
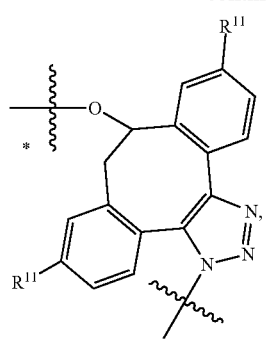
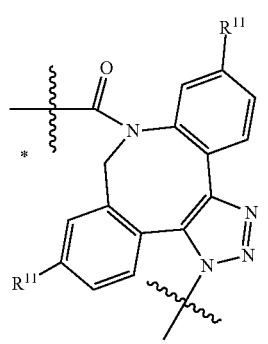
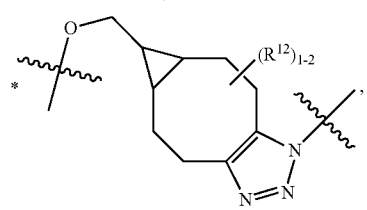
where the * indicates attachment point to L₄;
X₂ is
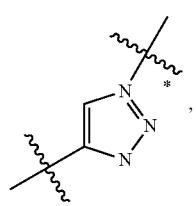, 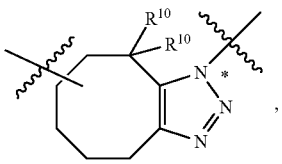,
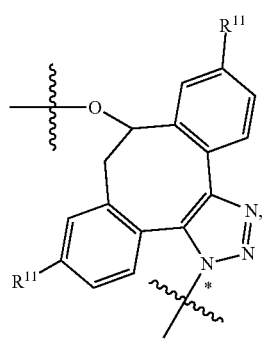
-continued
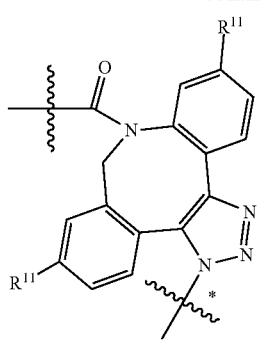
or
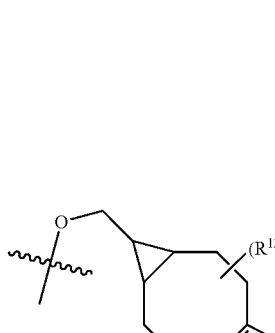
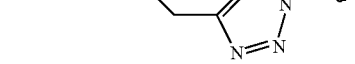
where the * indicates attachment point to L₄;
R¹⁴ is
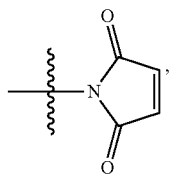,
—N₃, —ONH₂, —NR⁷C(=O)CH=CH₂, SH, —S(=O)₂(CH=CH₂), —NR⁷S(=O)₂(CH=CH₂), —NR⁷C(=O)CH₂Br, —NR⁷C(=O)CH₂I, —NHC(=O)CH₂Br, —NHC(=O)CH₂I, —C(O)NHNH₂,
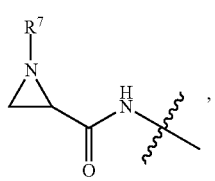,
—CO₂H, —NH₂,

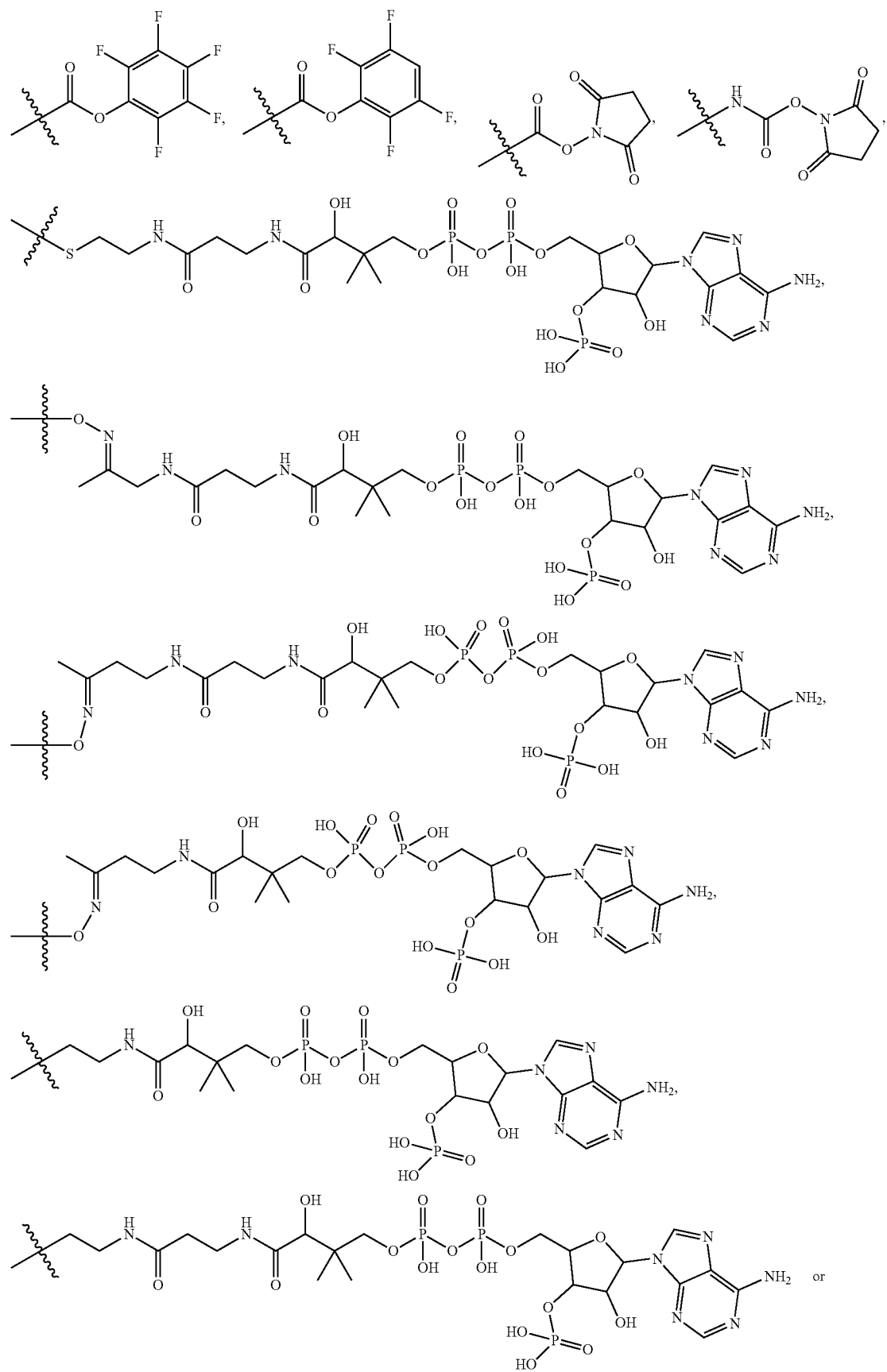

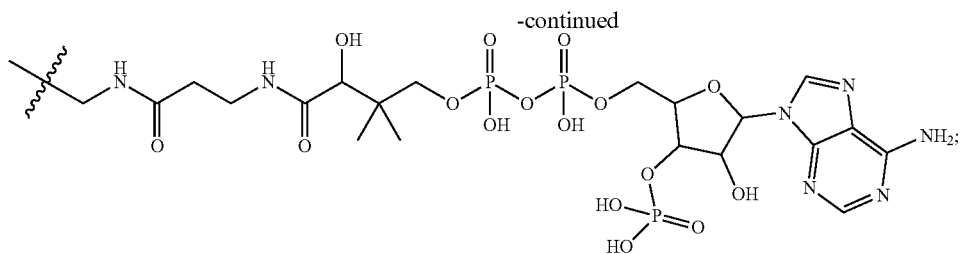

each $R^7$ is independently selected from H and $C_1$-$C_6$alkyl;

each $R^{10}$ is independently selected from H, $C_1$-$C_6$alkyl, F, Cl, and —OH;

each $R^{11}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

Embodiment 7. The compound of Formula (A), Formula (A-1) or Formula (A-1a), or a pharmaceutically acceptable salt thereof, wherein:

$R^4$ is -$L_1R^{14}$;

$L_1$ is —$((CH_2)_mO)_p(CH_2)_mX_1L_4$-, —$((CH_2)_mO)_p(CH_2)_m$— or —$(CH_2)_m$—;

$L_4$ is —$(CH_2)_m$—

$L_5$ is —NHS(=O)$_2$($CH_2)_mX_1L_4$;

$X_1$ is

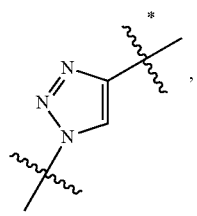 [SMILES: *c1cn(*)nn1]

where the * indicates attachment point to $L_4$;

$R^{14}$ is

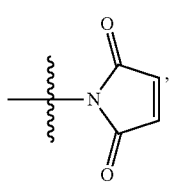 [SMILES: *N1C(=O)C=CC1=O]

—$ONH_2$,

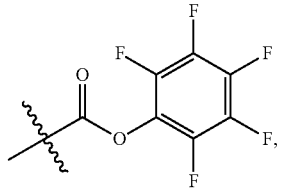

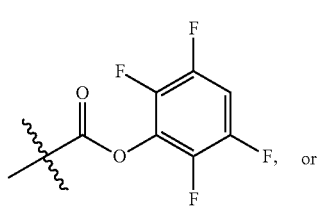, or

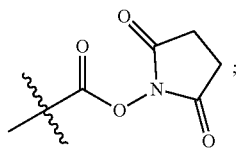

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

Embodiment 8. The compound of Formula (A), Formula (A-2), Formula (A-3), Formula (A-2a) or Formula (A-3a), or a pharmaceutically acceptable salt thereof, wherein:

$L_4$ is —$(CH_2)_m$—

$L_5$ is —NHS(=O)$_2$($CH_2)_mX_1L_4$;

$X_1$ is

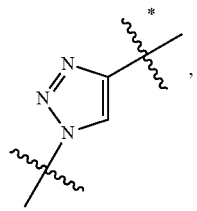 [SMILES: *c1cn(*)nn1]

where the * indicates attachment point to $L_4$;

$R^{14}$ is
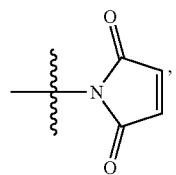 [SMILES: *N1C(=O)C=CC1=O]
—ONH₂,
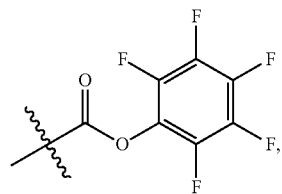
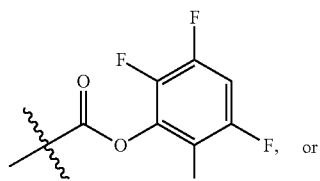, or
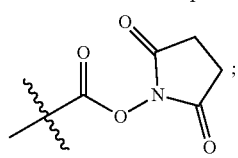
each m is independently selected from 1, 2, 3, 4, 5, 6, 7, 8, 9 and 10, and
each p is independently selected from 1, 2, 3, 4, 5, 6, 7, 8, 9, 10, 11, 12, 13 and 14.
Embodiment 9. The compound of Formula (A) selected from:
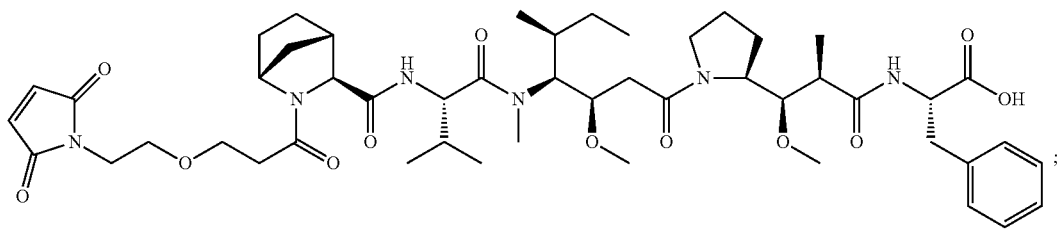
(1)
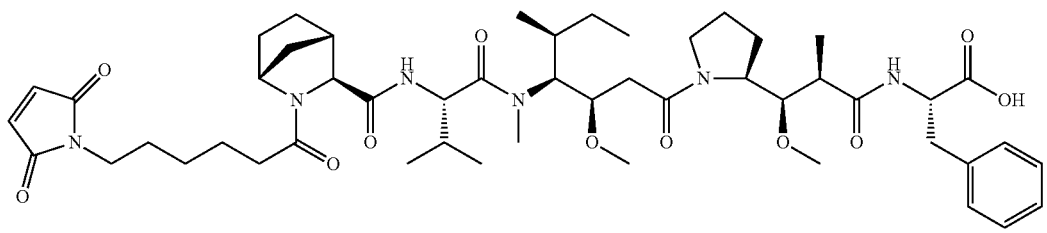
(2)
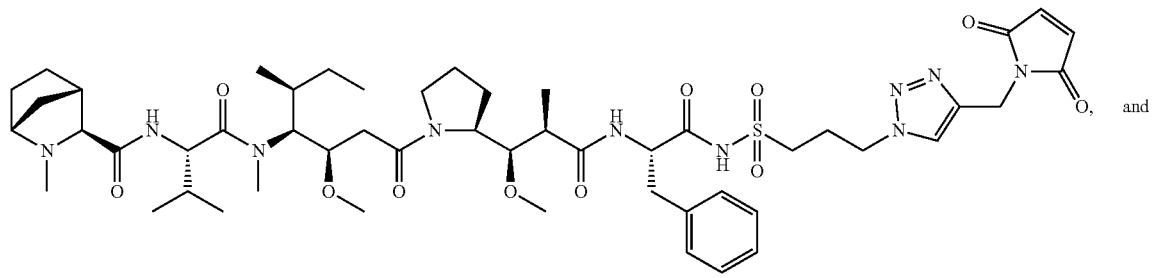
(3) and

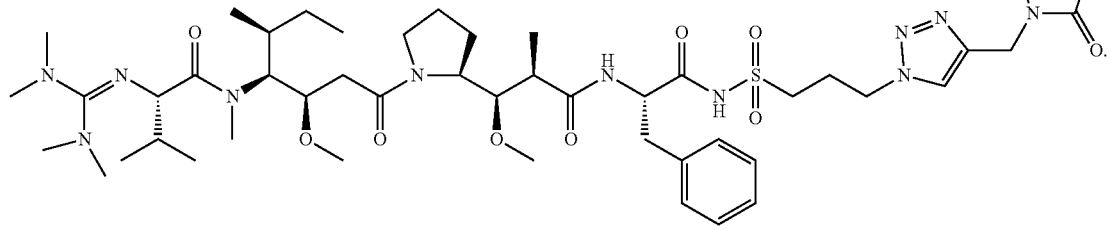

(4)

Embodiment 10. The compound of Formula (B), or a pharmaceutically acceptable salt thereof, having the structure of Formula (B-1), or a pharmaceutically acceptable salt thereof:

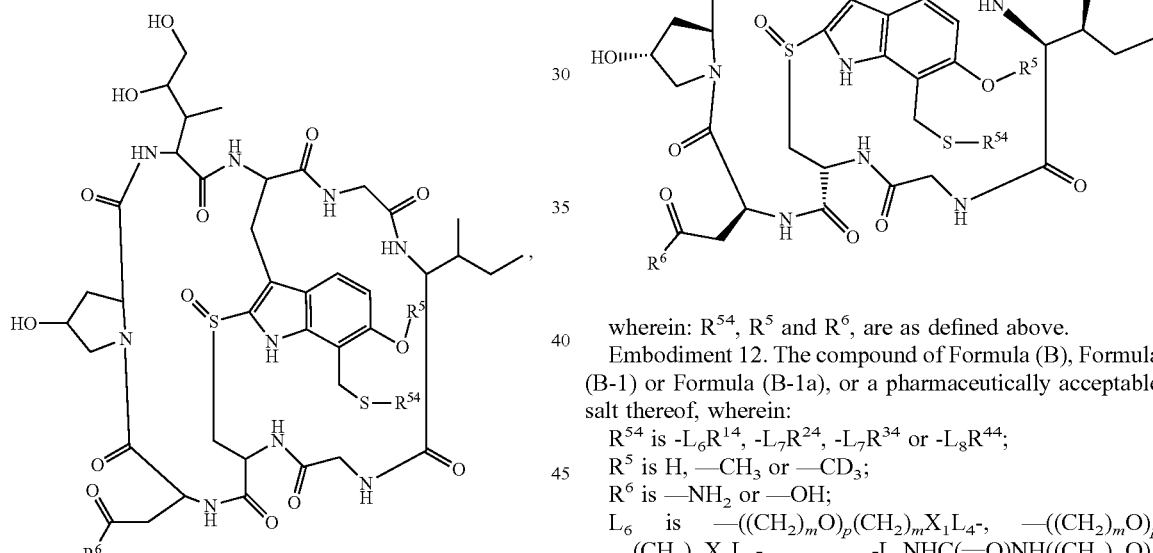

Formula (B-1)

wherein: $R^{54}$, $R^5$ and $R^6$, are as defined above.

Embodiment 11. The compound of Formula (B), or a pharmaceutically acceptable salt thereof, having the structure of Formula (B-1a), or a pharmaceutically acceptable salt thereof:

Formula (B-1a)

wherein: $R^{54}$, $R^5$ and $R^6$, are as defined above.

Embodiment 12. The compound of Formula (B), Formula (B-1) or Formula (B-1a), or a pharmaceutically acceptable salt thereof, wherein:

$R^{54}$ is $-L_6R^{14}$, $-L_7R^{24}$, $-L_7R^{34}$ or $-L_8R^{44}$;

$R^5$ is H, —$CH_3$ or —$CD_3$;

$R^6$ is —$NH_2$ or —OH;

$L_6$ is —$((CH_2)_mO)_p(CH_2)_mX_1L_4$-, —$((CH_2)_mO)_p(CH_2)_mX_2L_4$-, $-L_4NHC(=O)NH((CH_2)_mO)_p(CH_2)_mX_1L_4$-, $-L_4NHC(=O)NH((CH_2)_mO)_p(CH_2)_mX_2L_4$-, —$((CH_2)_mO)_p(CH_2)_m$— or —$(CH_2)_m$—;

$L_7$ is —$((CH_2)_mO)_p(CH_2)_m$—

$L_6$ is —$((CH_2)_mO)_p(CH_2)_mX_1L_4$-, —$((CH_2)_mO)_p(CH_2)_mX_2L_4$-, —$((CH_2)_mO)_p(CH_2)_m$—, —$(CH_2)_m$—;

$L_4$ is —$(CH_2)_m$—;

$X_1$ is

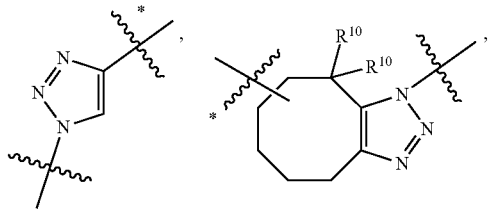

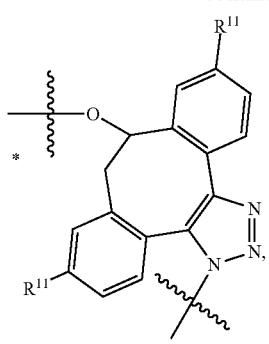
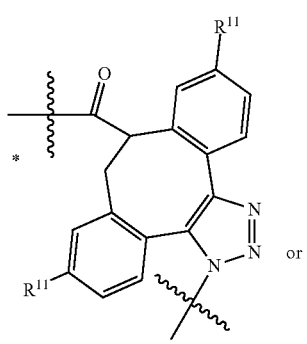
where the * indicates attachment point to $L_4$;
$X_2$ is
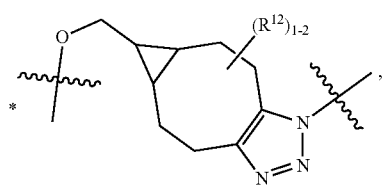
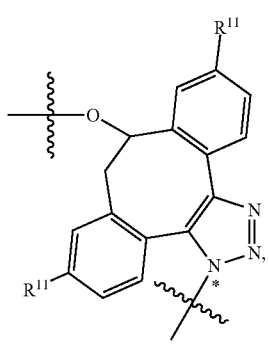
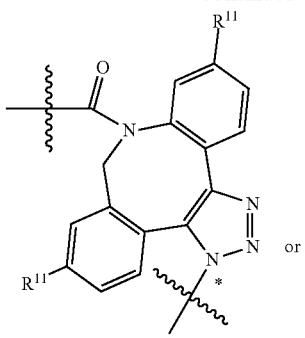 or
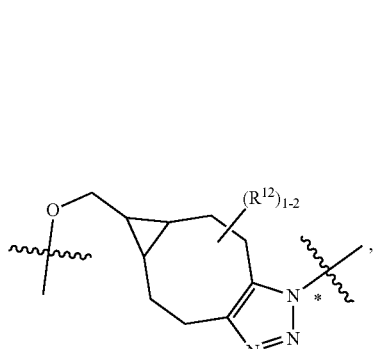
where the * indicates attachment point to $L_4$;
$R^{14}$ is
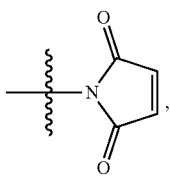
—$N_3$,  —$ONH_2$,  —$NR^7C(=O)CH=CH_2$,  SH, —$S(=O)_2(CH=CH_2)$,  —$NR^7S(=O)_2(CH=CH_2)$, —$NR^7C(=O)CH_2Br$,  —$NR^7C(=O)CH_2I$,  —NHC$(=O)CH_2Br$, —$NHC(=O)CH_2I$, —$C(O)NHNH_2$,
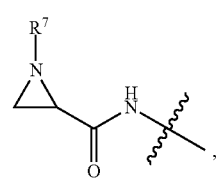
—$CO_2H$, —$NH_2$,

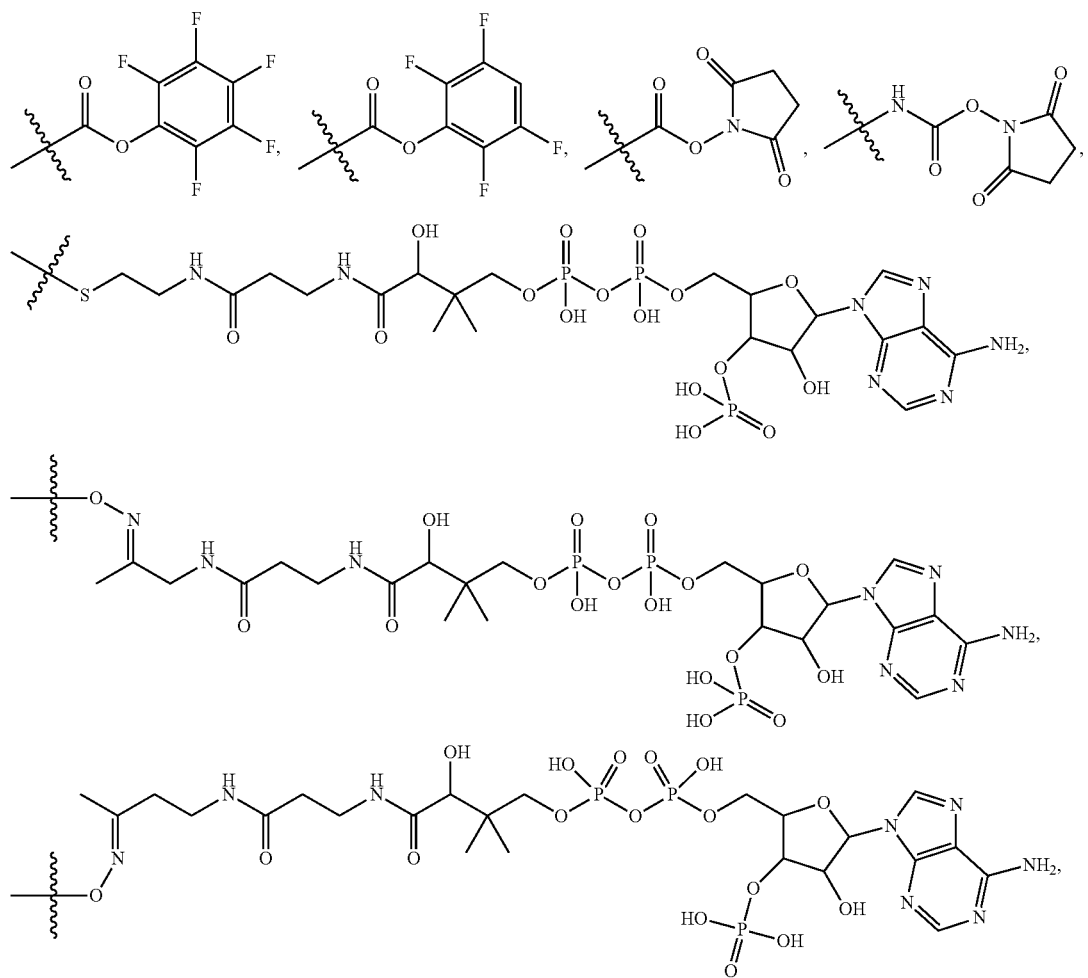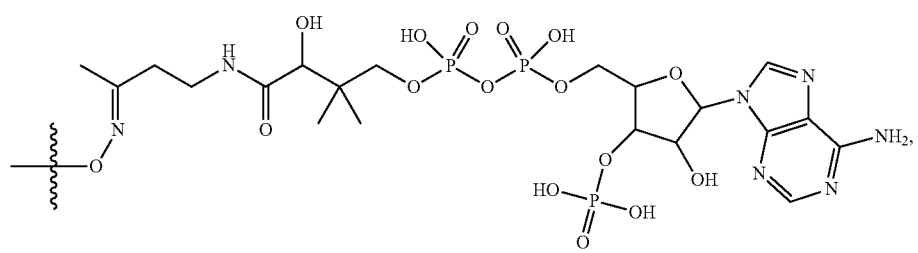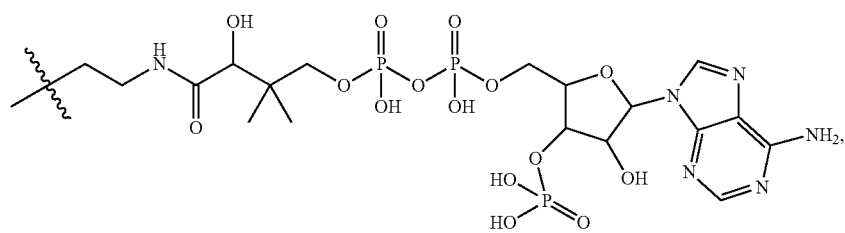

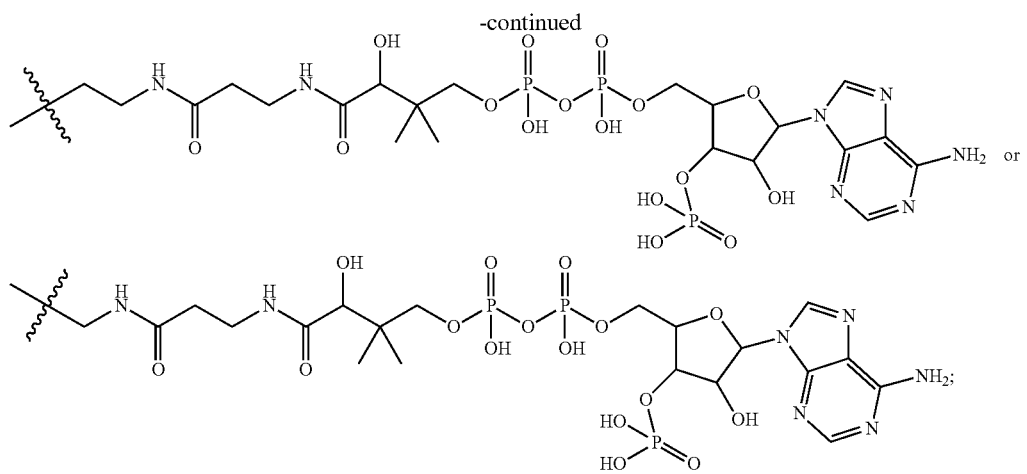
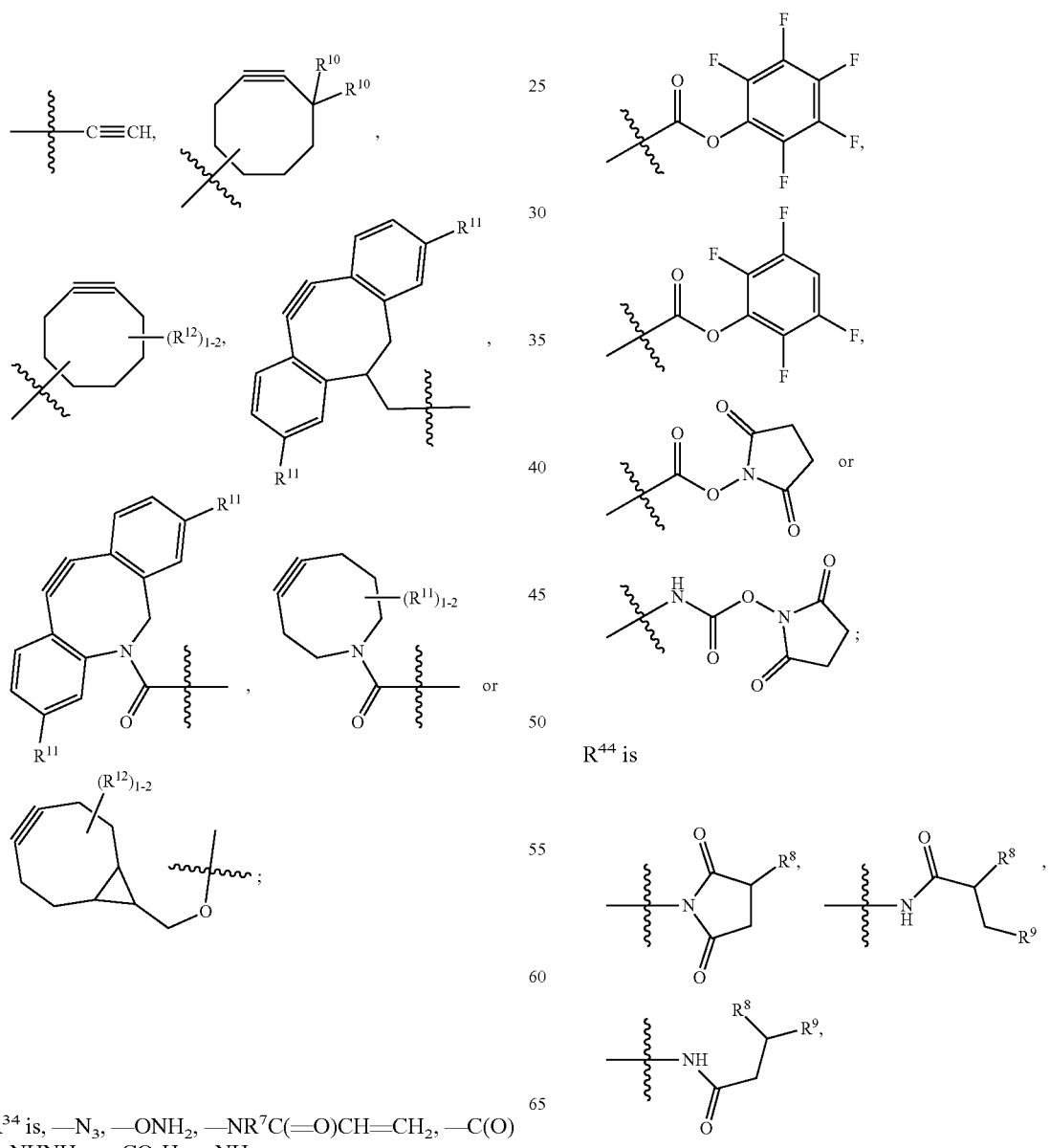
$R^{34}$ is, —$N_3$, —$ONH_2$, —$NR^7C(=O)CH=CH_2$, —$C(O)NHNH_2$, —$CO_2H$, —$NH_2$, -continued

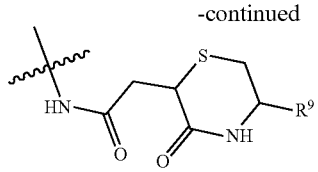

or —NR$^7$C(=O)CH$_2$R$^8$;

each R$^7$ is independently selected from H and C$_1$-C$_6$alkyl;

R$^8$ is —S(CH$_2$)$_n$CHR$^9$NH$_2$;

R$^9$ is —C(=O)OR$^7$;

each R$^{10}$ is independently selected from H, C$_1$-C$_6$alkyl, F, Cl, and —OH;

each R$^{11}$ is independently selected from H, C$_1$-C$_6$alkyl, F, Cl, —NH$_2$, —OCH$_3$, —OCH$_2$CH$_3$, —N(CH$_3$)$_2$, —CN, —NO$_2$ and —OH;

each R$^{12}$ is independently selected from H, C$_{1-6}$alkyl, fluoro, benzyloxy substituted with —C(=O)OH, benzyl substituted with —C(=O)OH, C$_{1-4}$alkoxy substituted with —C(=O)OH and C$_{1-4}$alkyl substituted with —C(=O)OH;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

Embodiment 13. The compound of Formula (B), Formula (B-1) or Formula (B-1a), or a pharmaceutically acceptable salt thereof, wherein:

R$^{54}$ is -L$_6$R$^{14}$;

R$^5$ is —CH$_3$;

R$^6$ is —NH$_2$;

L$_6$ is —((CH$_2$)$_m$O)$_p$(CH$_2$)$_m$X$_1$L$_4$-, —((CH$_2$)$_m$O)$_p$(CH$_2$)$_m$—, -L$_4$NHC(=O)NH((CH$_2$)$_m$O)$_p$(CH$_2$)$_m$X$_1$L$_4$-, -L$_4$NHC(=O)NH ((CH$_2$)$_m$O)$_p$(CH$_2$)$_m$X$_2$L$_4$-; or —(CH$_2$)$_m$—;

L$_4$ is —(CH$_2$)$_m$—

X$_1$ is

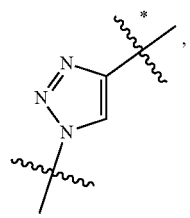

where the * indicates attachment point to L$_4$;

R$^{14}$ is

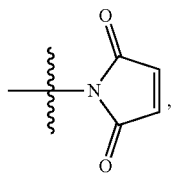

—ONH$_2$,

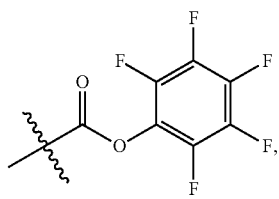

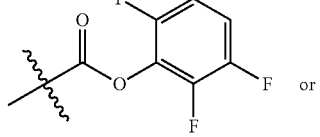 or

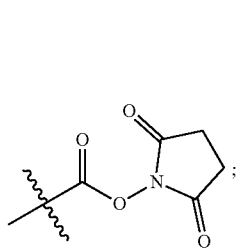

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

Embodiment 14. The compound of Formula (B) selected from:

(5)
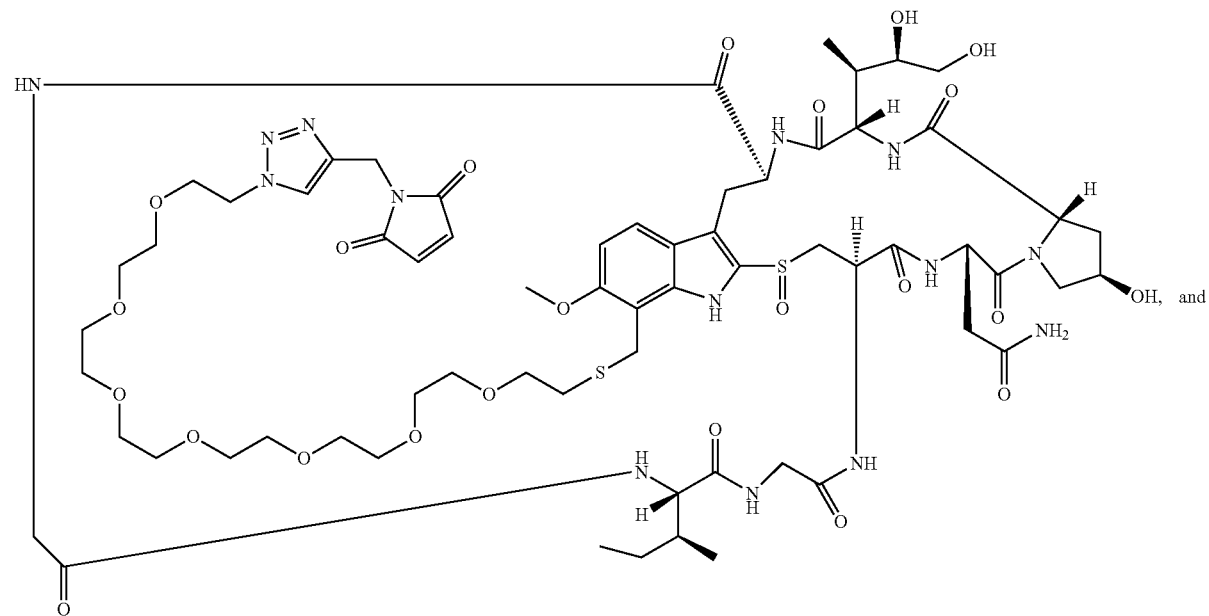
(6)
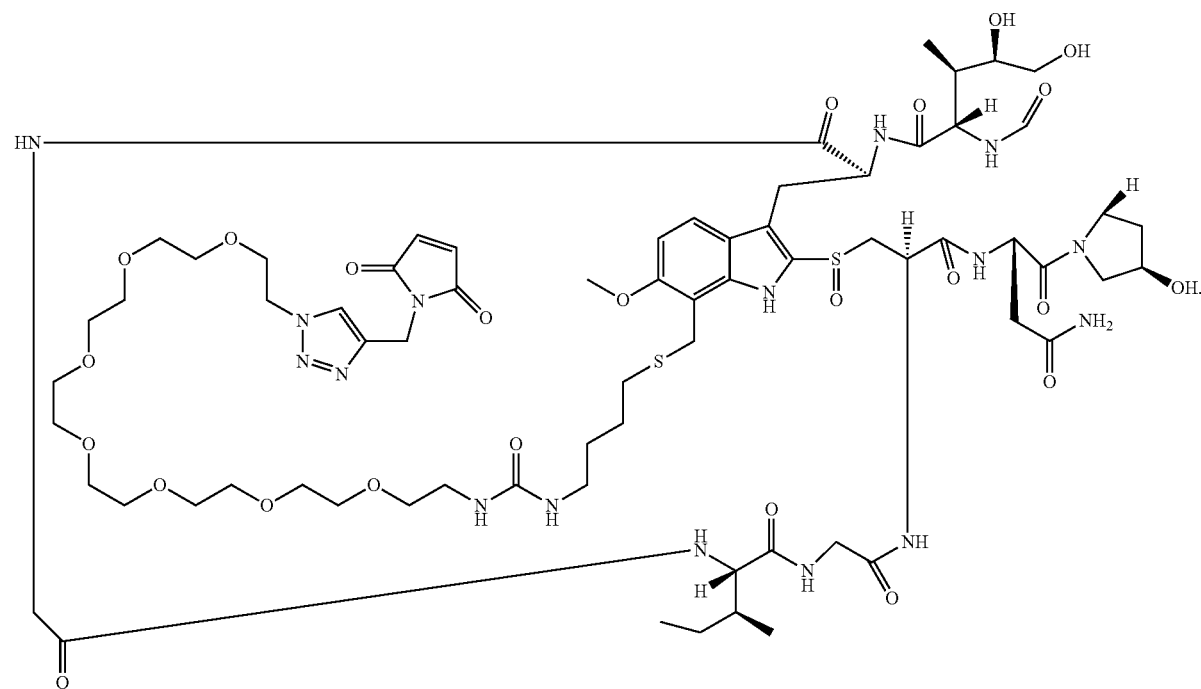
In another aspect the Linker-Drug moiety of the invention is selected from:

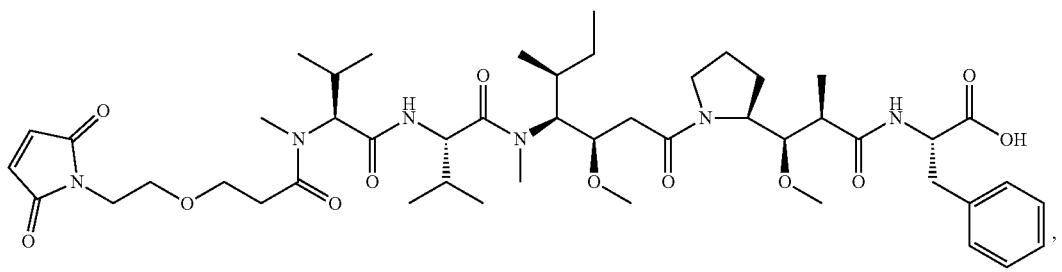
,
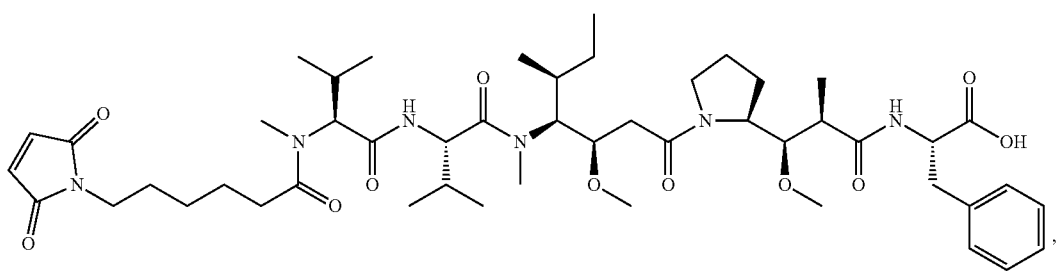
,
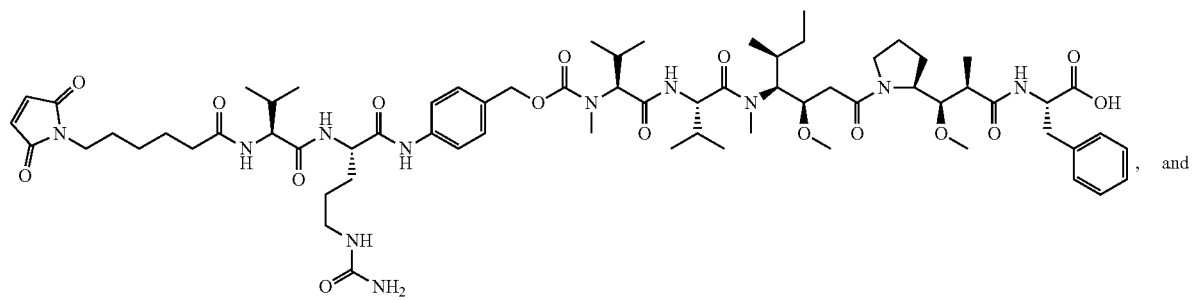
, and
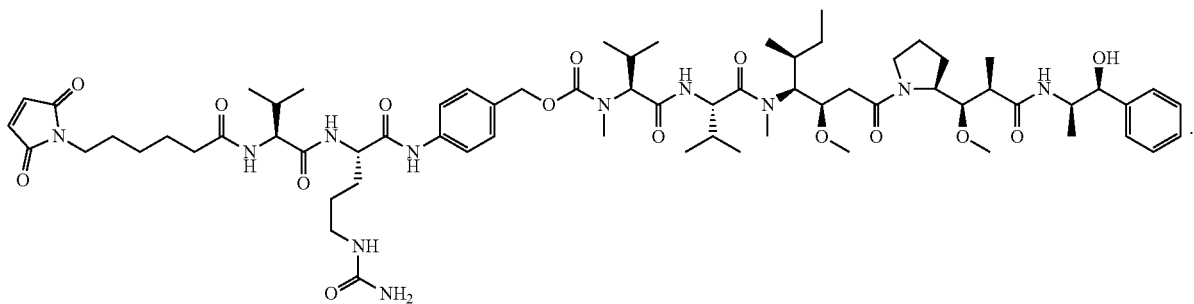
.
In another aspect the Linker-Drug moiety of the invention is selected from:

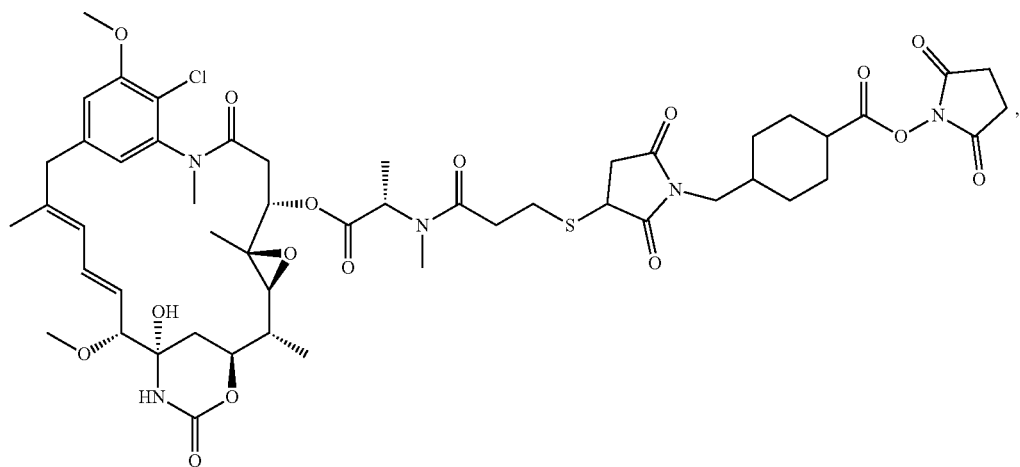
(SMCC-DM1)
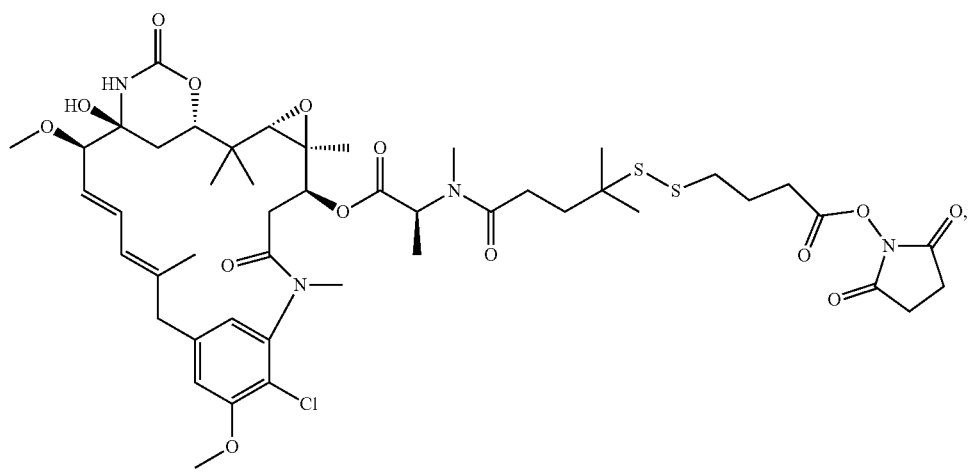
(SPDB-DM4)
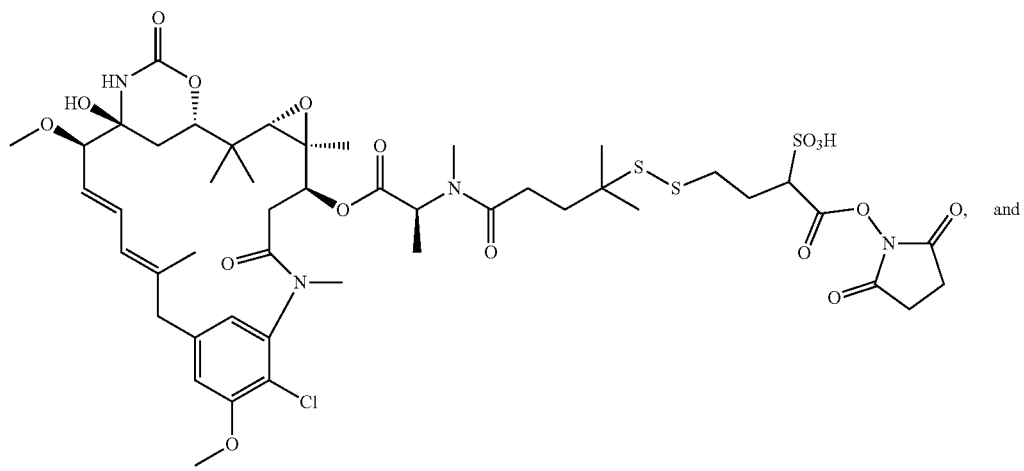
(sulfo-SPDB-DM4)

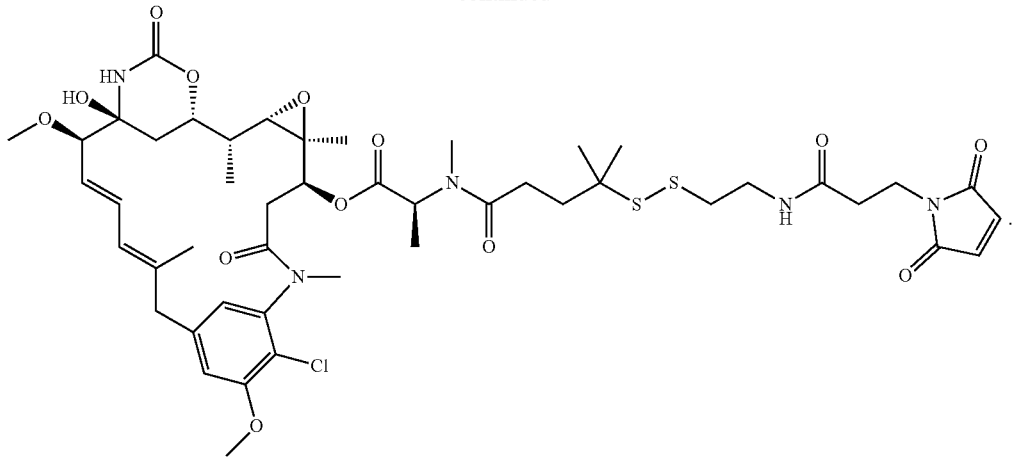

(MPET-DM4)

Antibody Drug Conjugates

The present disclosure provides antibody drug conjugates, wherein an antibody or antibody fragment (e.g., Fab or Fab') that specifically binds to cKIT is linked to a drug moiety (e.g., a cytotoxic agent), optionally through a linker. In one aspect, the antibody or antibody fragment (e.g., Fab or Fab') is linked, via covalent attachment by a linker, to a drug moiety that is a cytotoxic agent.

The antibody drug conjugates can selectively deliver a cytotoxic agent to cells expressing cKIT, e.g., hematopoietic stem cells, thereby selectively ablate those cells in a patient, e.g., a hematopoietic stem cell transplantation recipient. Preferably, the cKIT antibody drug conjugates have short half-life and will be cleared from a patient's circulation so they can be used for conditioning hematopoietic stem cell transplant recipients prior to hematopoietic stem cell transplantation.

In some embodiments, the cKIT antibody drug conjugates disclosed herein are modified to have reduced ability to induce mast cell degranulation, even when cross-linked and/or multimerized into larger complexes. For example, the cKIT antibody drug conjugates disclosed herein are modified to have a reduced ability to induce mast cell degranulation that is, is about, or is at least 10%, 20%, 30%, 40%, 50%, 60%, 70%, 80%, 90%, 95%, 99% reduced in comparison to a full-length cKIT antibody, an F(ab')$_2$ or an F(ab)$_2$ fragment, or conjugate thereof, even when cross-linked and/or multimerized into larger complexes. In some embodiments, the cKIT antibody drug conjugates disclosed herein may comprise an anti-cKIT Fab or Fab' fragment. In some embodiments, the anti-cKIT antibody drug conjugates disclosed herein may have minimal activity to induce mast cell degranulation, e.g., a baseline corrected O.D. readout of less than 0.25, e.g., less than 0.2, less than 0.15, or less than 0.1, in a beta-hexosaminidase release assay, even when cross-linked and/or multimerized into larger complexes.

In some embodiments, provided herein are conjugates comprising an antibody fragment (e.g., Fab or Fab') that specifically binds to cKIT (anti-cKIT Fab or Fab'), linked to a drug moiety (e.g., a cytotoxic agent), optionally through a linker. As described herein, such anti-cKIT Fab' or Fab-toxin conjugates are able to ablate human HSC cells in vitro and in vivo, but do not cause mast cell degranulation even when crosslinked and/or multimerized into larger complexes.

In one aspect, the disclosure provides for an conjugate of Formula (I):

Formula (I);

wherein:
A is an antibody fragment (e.g., Fab or Fab') that specifically binds to human cKIT;
$L_B$ is a linker;
D is a cytotoxic agent;
n is an integer from 1 to 10, and
y is an integer from 1 to 10,
where the Linker-Drug moiety ($L_B$-(D)$_n$) is covalently attached to the antibody fragment (A).

In one aspect, the present disclosure is directed to a conjugate of Formula (II):

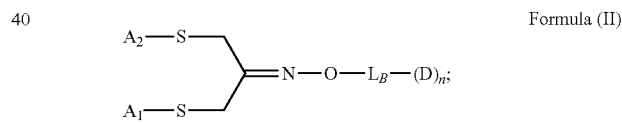
Formula (II)

$A_1$ is an antibody fragment (e.g., Fab or Fab') or chain (e.g. HC or LC) that specifically binds to human cKIT;
$A_2$ is an antibody fragment (e.g., Fab or Fab') or chain (e.g. HC or LC) that specifically binds to human cKIT;
$L_B$ is a linker;
D is a cytotoxic agent, and
n is an integer from 1 to 10,
where the Linker-Drug moiety ($L_B$-(D)$_n$) covalently couples the antibody fragments $A_1$ and $A_2$.

In one aspect, the one of more drug moieties, D, in the conjugates of Formula (I) and Formula (II) are independently selected from an auristatin, an amanitin, a maytansinoid and a saporin.

In another aspect, the one of more drug moieties, D, in the conjugates of Formula (I) are independently selected from an auristatin and an amanitin.

In the conjugates of Formula (I), one or more Linker-Drug moiety ($L_B$-(D)$_n$) can be covalently attached to the antibody fragment, A (e.g. Fab or Fab'), thereby covalently attaching one or more drug moieties, D, to the antibody fragment, A (e.g. Fab or Fab'), through linker, $L_B$. $L_B$ is any chemical moiety that is capable of linking the antibody fragment, A (e.g. Fab or Fab') to one or more drug moieties, D. The conjugates of Formula (I), wherein one or more drug moieties, D, are covalently linked to an antibody fragment, A (e.g. Fab or Fab'), can be formed using a bifunctional or multifunctional linker reagent having one or more reactive functional groups that are the same or different. One of the reactive functional groups of the bifunctional or multifunctional linker reagent is used to react with a group on the antibody fragment, A, by way of example, a thiol or an amine (e.g. a cysteine, an N-terminus or amino acid side chain such as lysine) to form a covalent linkage with one end of the linker $L_B$. Such reactive functional groups of the bifunctional or multifunctional linker reagent include, but are not limited to, a maleimide, a thiol and an NHS ester. The other reactive functional group or groups of the bifunctional or multifunctional linker reagent are used to covalently attached one or more drug moieties, D, to linker $L_B$.

In the conjugates of Formula (II), a ketone bridge is formed by reaction of pendent thiols on antibody fragments $A_1$ and $A_2$ and a 1,3-dihaloacetone, such as 1,3-dichloroacetone, 1,3-dibromoacetone, 1,3-diiodoacetone, and bis-sulfonate esters of 1, 3-dihydroxyacetone, which thereby covalently couples the antibody fragments $A_1$ and $A_2$. This ketone bridge moiety is used to covalently attach one or more drug moieties, D, to the antibody fragments $A_1$ and $A_2$ through a linker $L_B$. $L_B$ is any chemical moiety that is capable of linking the antibody fragment, $A_1$ and $A_2$ to one or more drug moieties, D. The conjugates of Formula (II), wherein one or more drug moieties, D, are covalently linked to antibody fragments $A_1$ and $A_2$, can be formed using a bifunctional or multifunctional linker reagent having one or more reactive functional groups that are the same or different. In an embodiment, one the reactive functional groups of the bifunctional or multifunctional linker reagent is an alkoxyamine which is used to react with the ketone bridge to form an oxime linkage with one end of the linker $L_B$, and the other reactive functional group or groups of the bifunctional or multifunctional linker reagent are used to covalently attached one or more drug moieties, D, to linker $L_B$. In another embodiment, one the reactive functional groups of the bifunctional or multifunctional linker reagent is an hydrazine which is used to react with the ketone bridge to form a hydrazone linkage with one end of the linker $L_B$, and the other reactive functional group or groups of the bifunctional or multifunctional linker reagent are used to covalently attached one or more drug moieties, D, to linker $L_B$.

In one aspect, $L_B$ is a cleavable linker. In another aspect, $L_B$ is a non-cleavable linker. In some aspects, $L_B$ is an acid-labile linker, photo-labile linker, peptidase cleavable linker, esterase cleavable linker, glycosidase cleavable linker, phosphodiesterase cleavable linker, a disulfide bond reducible linker, a hydrophilic linker, or a dicarboxylic acid based linker.

In another aspect, the drug moiety (D) is a protein toxin selected from saporin, pokeweed antiviral protein (PAP), bryodin 1, bouganin, gelonin, ricin, abrin, mistletoe lectin, modeccin, volkensin, asparin, momordin, ebulin, viscumin, Shiga toxin, diphtheria toxin (DT), or Pseudomonas exotoxin (PE). Such protein toxins are capable of killing cells by inactivating ribosome or inhibiting protein synthesis by interfering with elongation factor 2 (EF2) function (see Kreitman et al., Immunotoxins for targeted cancer therapy, The AAPS Journal 2006; 8 (3) Article 63; Gadadhar and Karande, Targeted Cancer Therapy: History and Development of Immunotoxins, Chapter 1 of Resistance to Immunotoxins in Cancer Therapy, pp 1-31). In some embodiments, the protein toxin is saporin. The protein toxin can be attached to the anti-cKIT antibody fragment (A) covalently through a cleavable or noncleavable linker ($L_B$). In some embodiments, the protein toxin is linked to the anti-cKIT antibody fragment through a disulfide or thioether linkage.

While the drug to antibody ratio has an exact integer value for a specific conjugate molecule (e.g., the product of n and y in Formula (I) and "n" in Formula (II)), it is understood that the value will often be an average value when used to describe a sample containing many molecules, due to some degree of inhomogeneity, typically associated with the conjugation step. The average loading for a sample of a conjugate is referred to herein as the drug to antibody (or Fab') ratio, or "DAR." In some aspects, the DAR is between about 1 and about 5, and typically is about 1, 2, 3, or 4. In some aspects, at least 50% of a sample by weight is compound having the average DAR plus or minus 2, and preferably at least 50% of the sample is a conjugate that contains the average DAR plus or minus 1. Other aspects include conjugates wherein the DAR is about 2. In some aspects, a DAR of 'about y' means the measured value for DAR is within 20% of the product of n and y in Formula (I). In some aspects, a DAR of 'about n' means the measured value for DAR is within 20% of n in Formula (II).

In one aspect, the average molar ratio of the drug to the antibody fragment (Fab or Fab') in the conjugates of Formula (I) (i.e., average value of the product of n and y, also known as drug to antibody ratio (DAR)) is about 1 to about 10, about 1 to about 6 (e.g., 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0), about 1 to about 5, about 1.5 to about 4.5, or about 2 to about 4.

In one aspect, the average molar ratio of the drug to the antibody fragments $A_1$ and $A_2$ in the conjugates of Formula (II) (i.e., average value of n, also known as drug to antibody ratio (DAR)) is about 1 to about 10, about 1 to about 6 (e.g., 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0), about 1 to about 5, about 1.5 to about 4.5, or about 2 to about 4.

In one aspect provided by the disclosure, the conjugate has substantially high purity and has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free drug (e.g., auristatin, amanitin, maytansinoid or saporin) level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total cytotoxic agent).

In one aspect the conjugates of the invention have the structure of Formula (C):

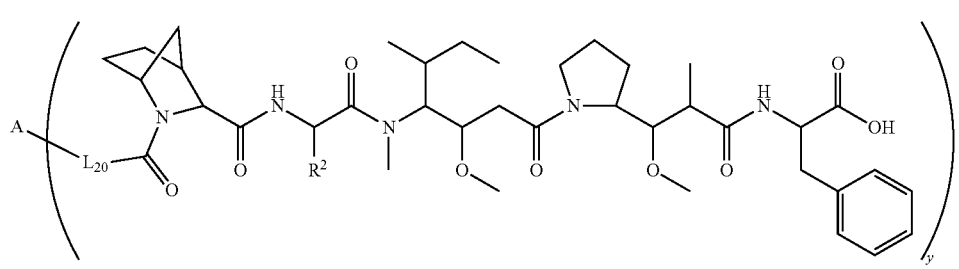

Formula (C)

wherein:
A represents an antibody fragment (e.g., Fab or Fab') that specifically binds to human cKIT;
y is an integer from 1 to 10;
$R^2$ is $C_1$-$C_6$alkyl;
$L_{20}$ is -$L_1R^{40}$;
$L_1$ is —$((CH_2)_mO)_p(CH_2)_mX_1L_4$-, —$((CH_2)_mO)_p(CH_2)_mX_2L_4$-, —$((CH_2)_mO)_p(CH_2)_m$—, —$(CH_2)_m$—, —$(CH_2)_mX_1(CH_2)_m$—, —$(CH_2)_mNHC(=O)(CH_2)_m$—, —$(CH_2)_mNHC(=O)(CH_2)_mC(=O)NH(CH_2)_m$—, —$((CH_2)_mO)_p(CH_2)_mNHC(=O)(CH_2)_m$—, —$((CH_2)_mO)_pCH_2)_mC(=O)NH(CH_2)_m$—, $X_3X_4C(=O)((CH_2)_mO)_p(CH_2)_m$—, —$X_3X_4C(=O)(CH_2)_m$—, —$X_3C(=O)(CH_2)_nNHC(=O)(CH_2)_m$—, —$X_3C(=O)(CH_2)_mNHC(=O)((CH_2)_mO)_p(CH_2)_m$—, —$(CH_2)_mC(R_7)_2$—, —$(CH_2)_mC(R_7)_2SS(CH_2)_mNHC(=O)(CH_2)_m$— or —$(CH_2)_mX_3C(=O)(CH_2)_mNHC(=O)((CH_2)_mO)_p(CH_2)_m$—

$L_4$ is —$((CH_2)_m$;
$X_1$ is

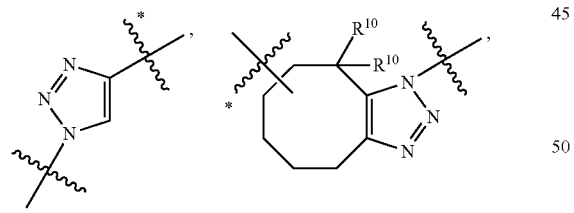

$X_2$ is

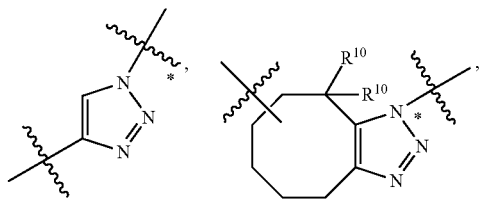

-continued

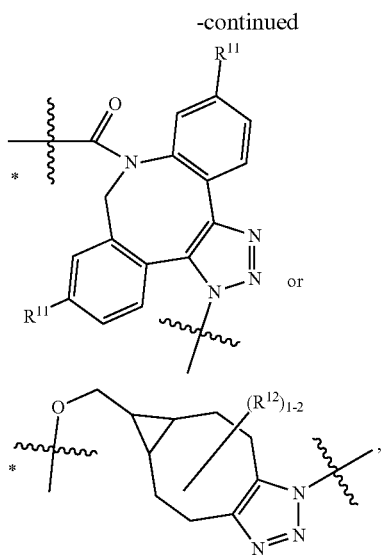

where the * indicates attachment point to $L_4$;

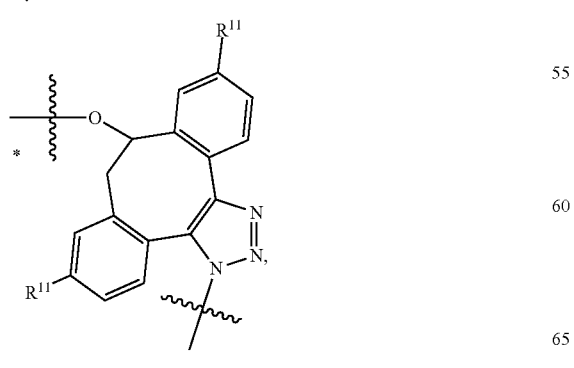

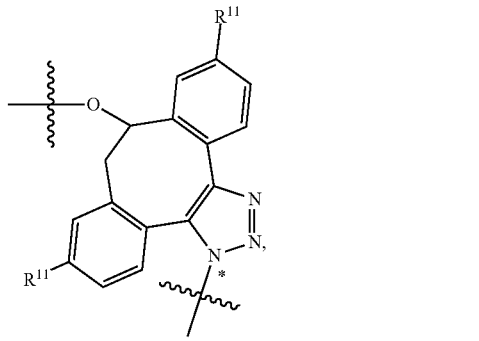

-continued
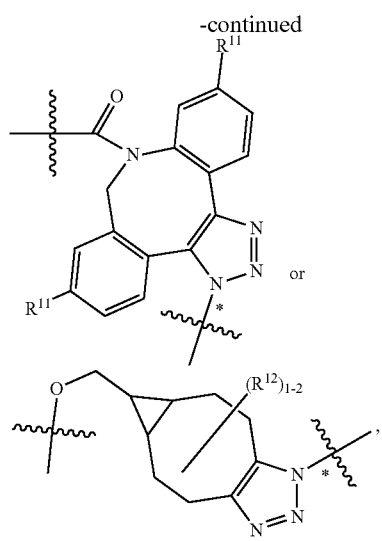
or
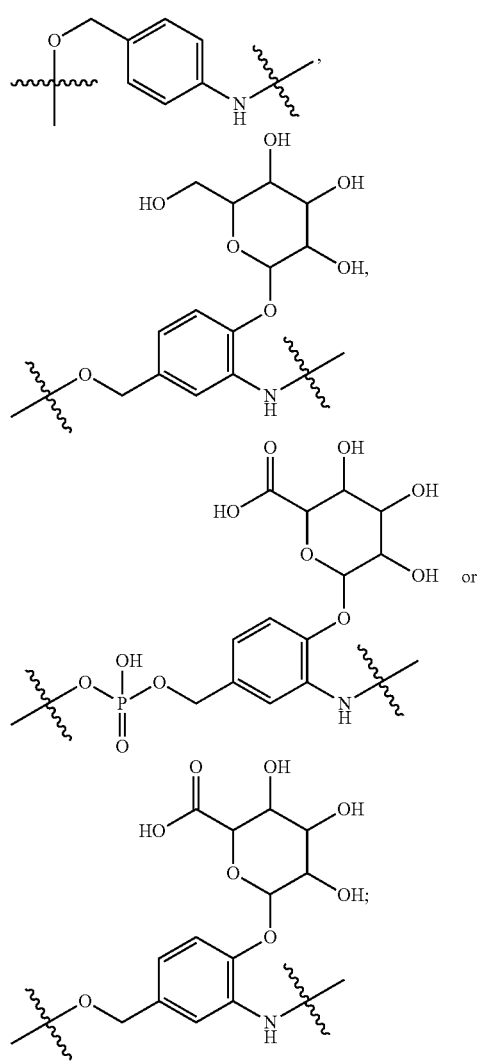
where the * indicates attachment point to $L_4$;
$X_3$ is
$X_4$ is
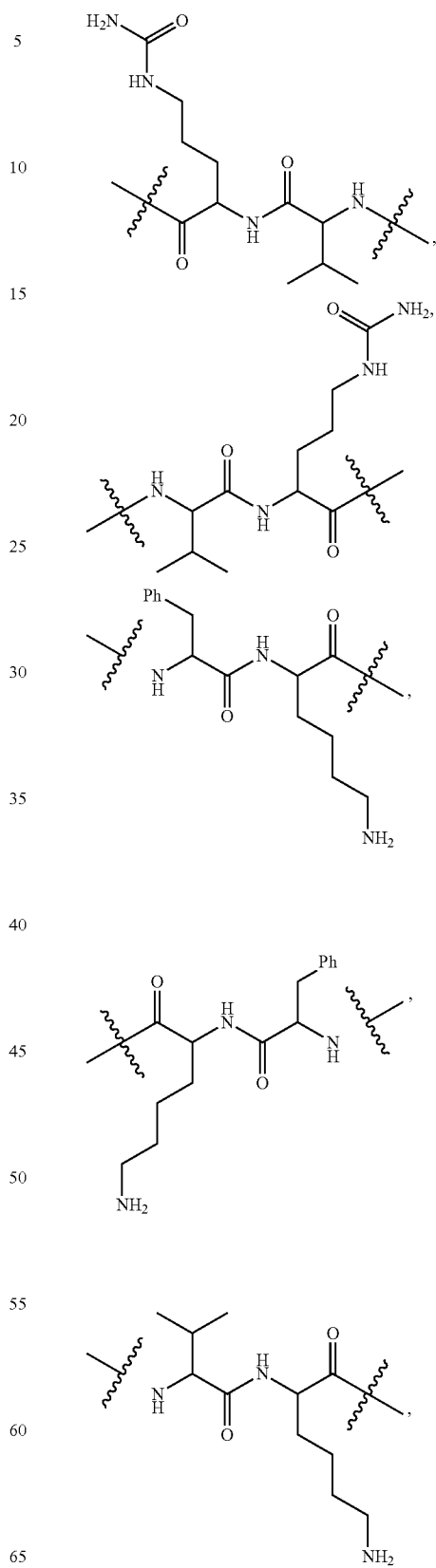

-continued
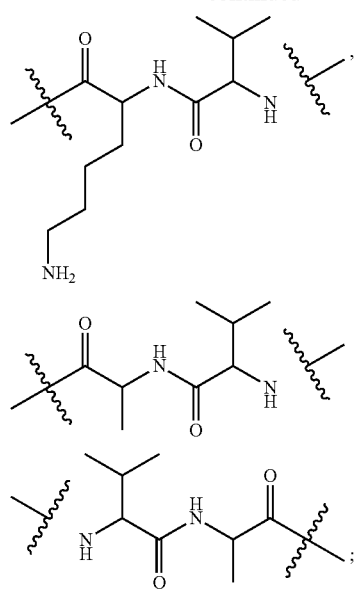
R⁴⁰ is
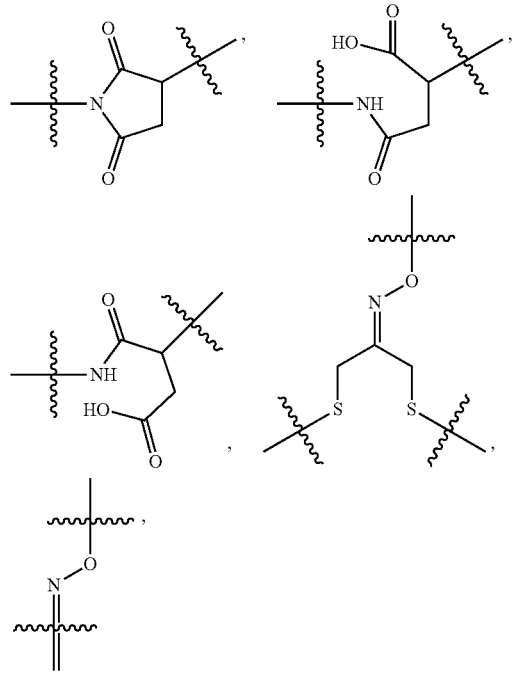
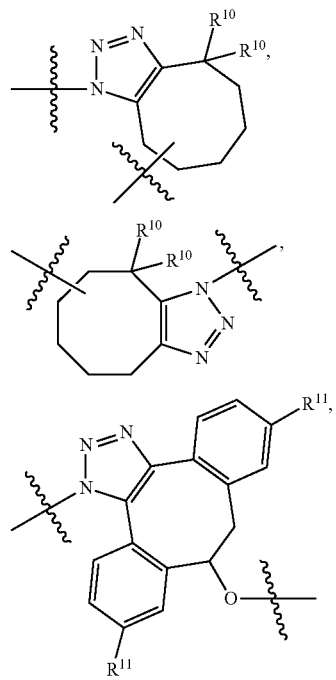
—NR⁷C(=O)CH₂—, —NHC(=O)CH₂—, —S(=O)₂CH₂CH₂—, —(CH₂)₂S(=O)₂CH₂CH₂—, —NR⁷S(=O)₂CH₂CH₂, —NR⁷C(=O)CH₂CH₂, —NH—, —C(=O)—, —NHC(=O)—, —CH₂NHCH₂CH₂—, —NHCH₂CH₂—, —S—,

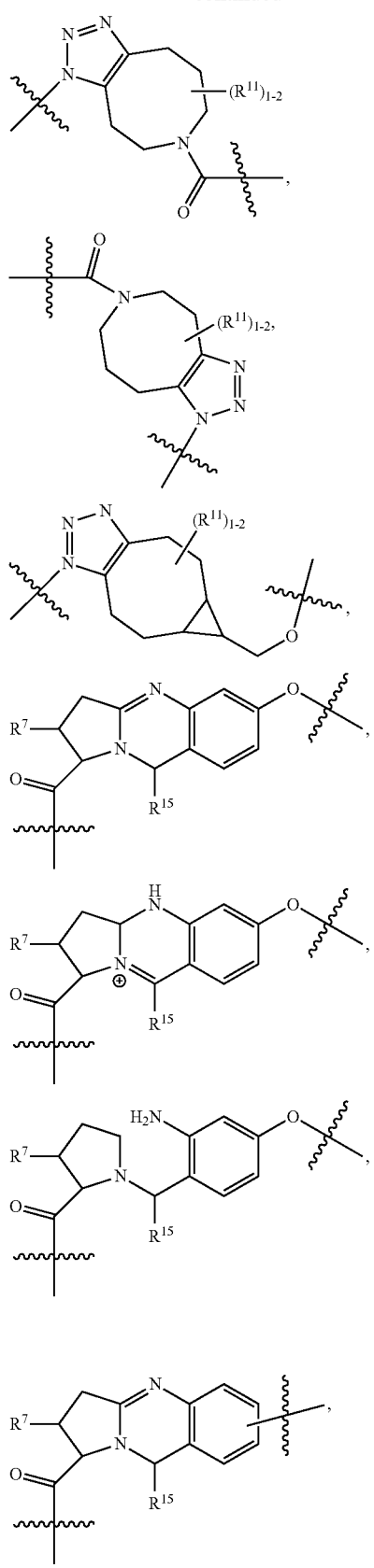
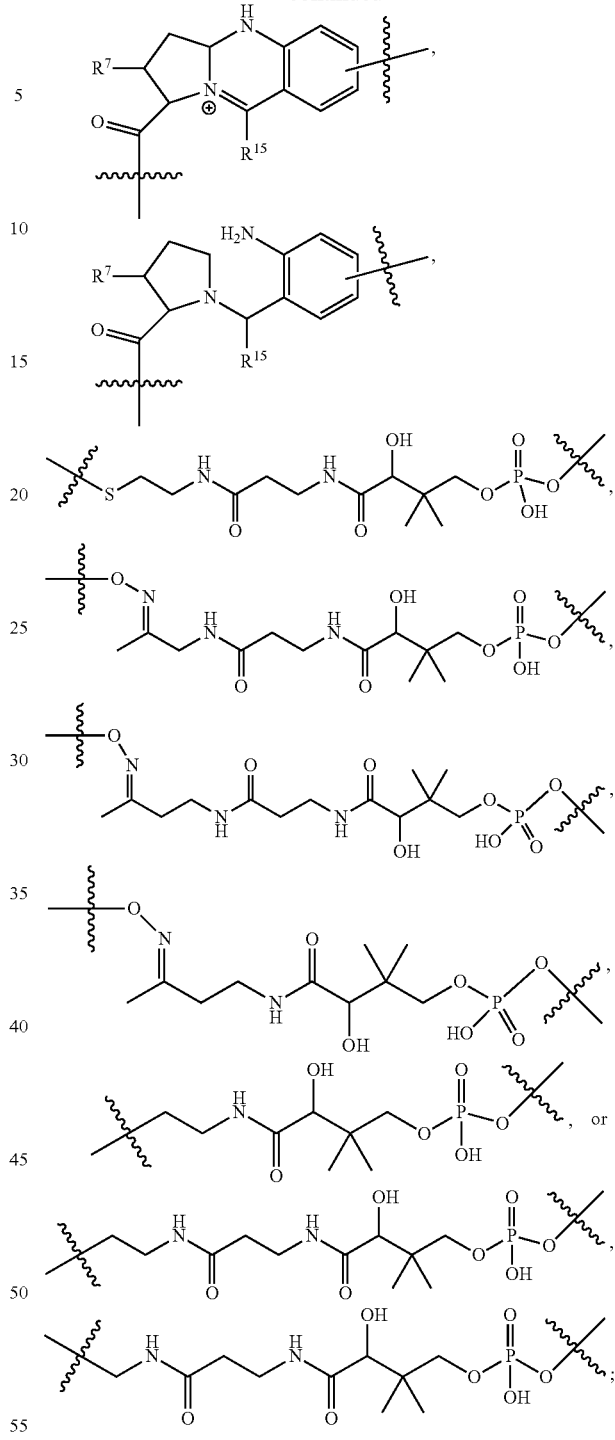

each R[7] is independently selected from H and $C_1$-$C_6$alkyl;
each R[10] is independently selected from H, $C_1$-$C_6$alkyl, F, Cl, and —OH;
each R[11] is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;
each R[12] is independently selected from H, $C_{1-6}$alkyl, fluoro, benzyloxy substituted with —C(═O)OH, benzyl substituted with —C(═O)OH, $C_{1-4}$alkoxy substituted with —C(═O)OH and $C_{1-4}$alkyl substituted with —C(═O)OH;

each $R^{15}$ is independently selected from H, —$CH_3$ and phenyl;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

In another aspect the conjugates of the invention have the structure of Formula (D):

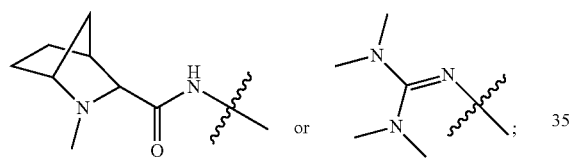

Formula (D)

wherein:

A represents an antibody fragment (e.g., Fab or Fab') that specifically binds to human cKIT;

y is an integer from 1 to 10;

$R^1$ is

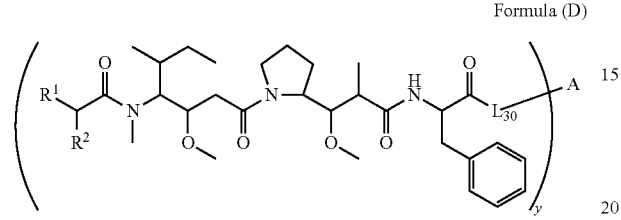

$R^2$ is $C_1$-$C_6$alkyl;

$L_{30}$ is -$L_5R^{40}$;

$L_4$ is —$((CH_2)_m$;

$L_5$ is —NHS(=O)$_2$(CH$_2$)$_m$X$_1$L$_4$-, —NH((CH$_2$)$_m$O)$_p$ (CH$_2$)$_m$X$_1$L$_4$-, —NH((CH$_2$)$_m$O)$_p$(CH$_2$)$_m$X$_2$L$_4$-, —NH ((CH$_2$)$_m$O)$_p$(CH$_2$)$_m$—, —NH(CH$_2$)$_m$—, —NH(CH$_2$)$_m$X$_1$(CH$_2$)$_m$—, —NH(CH$_2$)$_m$NHC(=O) (CH$_2$)$_m$—, —NH(CH$_2$)$_m$NHC(=O)(CH$_2$)$_m$C(=O)NH (CH$_2$)$_m$—, —NH((CH$_2$)$_m$O)$_p$(CH$_2$)$_m$NHC(=O) (CH$_2$)$_m$, —NH((CH$_2$)$_m$O)$_p$CH$_2$)$_n$C(=O) NH(CH$_2$)$_m$—, —NH(CH$_2$)$_n$C(R$_7$)$_2$—, —NH(CH$_2$)$_m$C (R$_7$)$_2$SS(CH$_2$)$_m$NHC(=O)(CH$_2$)$_m$— or —NH(CH$_2$)$_m$ X$_3$C(=O)(CH$_2$)$_m$NHC(=O)((CH$_2$)$_m$O)$_p$(CH$_2$)$_m$—;

$X_1$ is

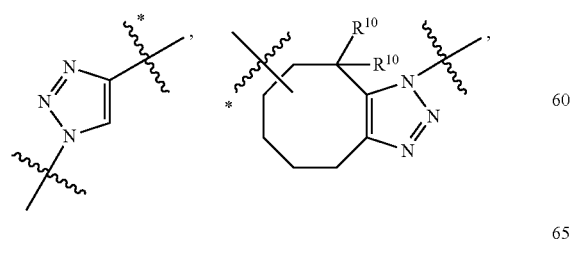

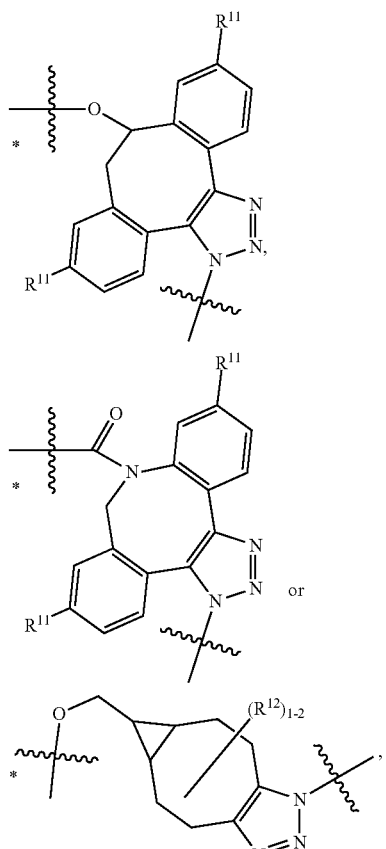

where the * indicates attachment point to $L_4$;

$X_2$ is

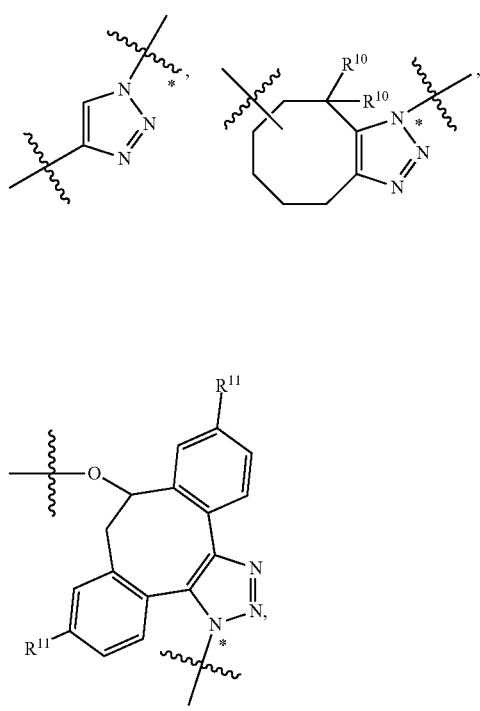

-continued
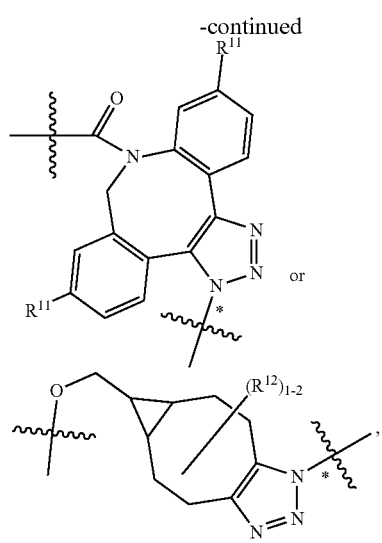
or
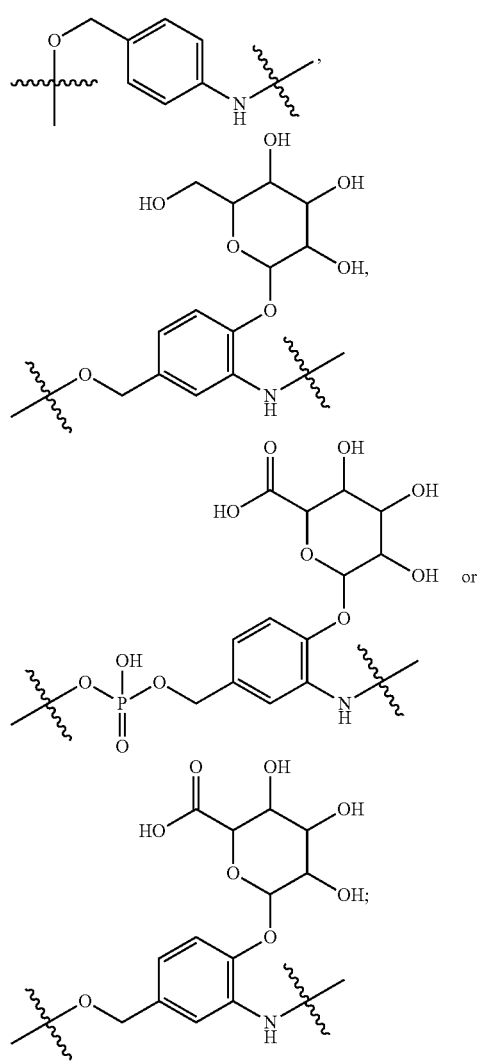
where the * indicates attachment point to L$_4$;
X$_3$ is
X$_4$ is
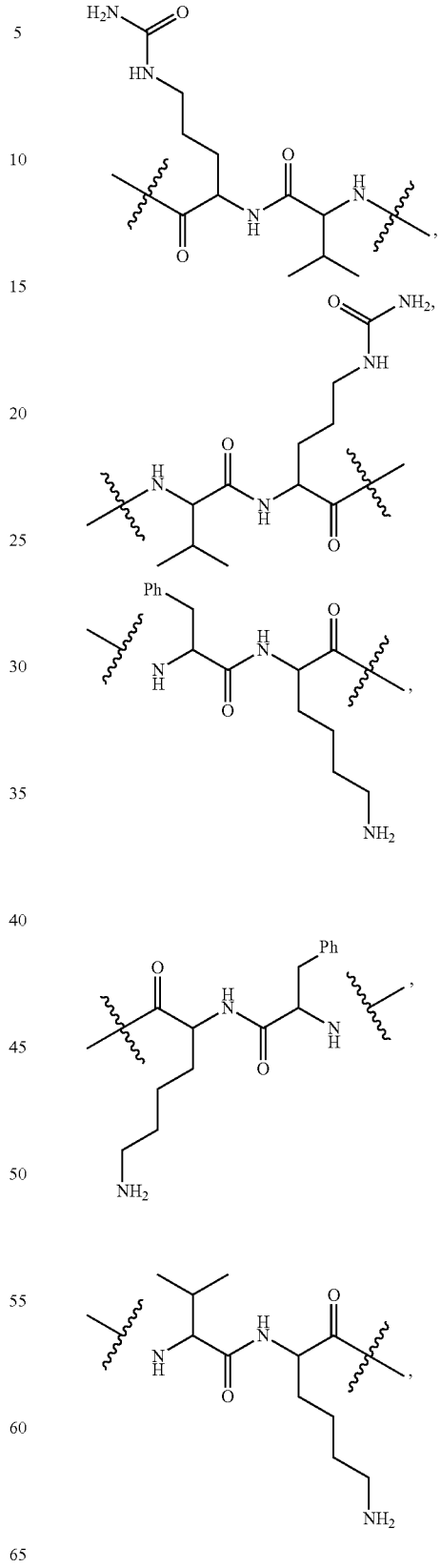

-continued
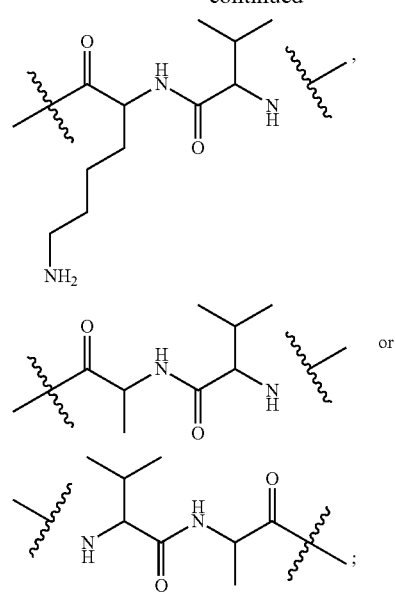
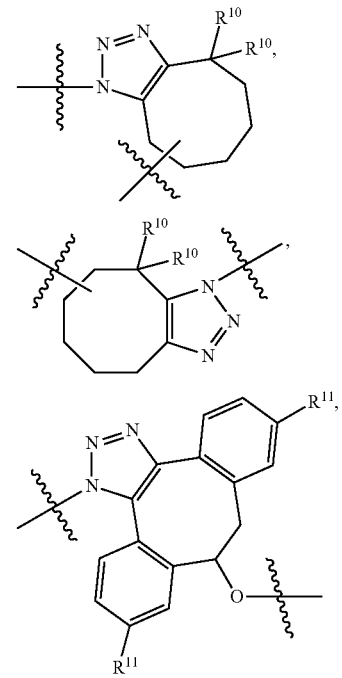
$R^{40}$ is
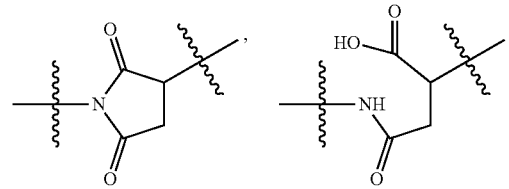
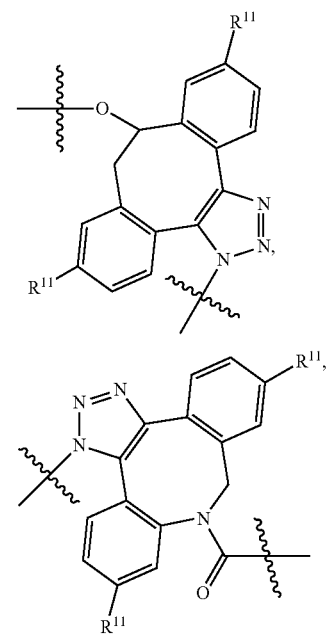
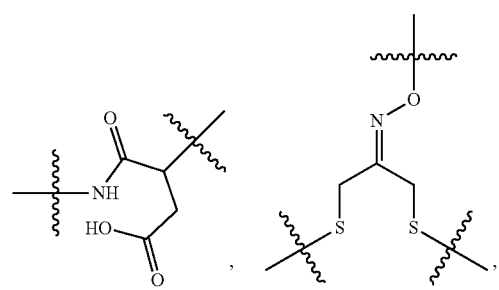
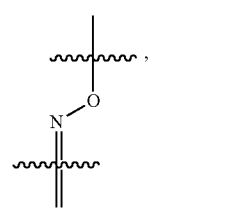,
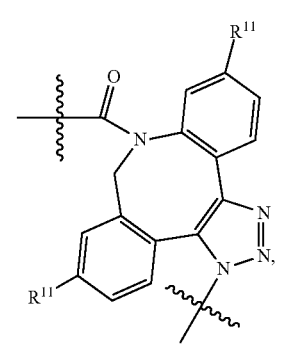
—NR$^7$C(=O)CH$_2$—, —NHC(=O)CH$_2$—,
—S(=O)$_2$CH$_2$CH$_2$—, —(CH$_2$)$_2$S(=O)$_2$CH$_2$CH$_2$—,
—NR$^7$S(=O)$_2$CH$_2$CH$_2$, —NR$^7$C(=O)CH$_2$CH$_2$,
—NH—, —C(=O)—, —NHC(=O)—,
—CH$_2$NHCH$_2$CH$_2$—, —NHCH$_2$CH$_2$—, —S—, 97
-continued

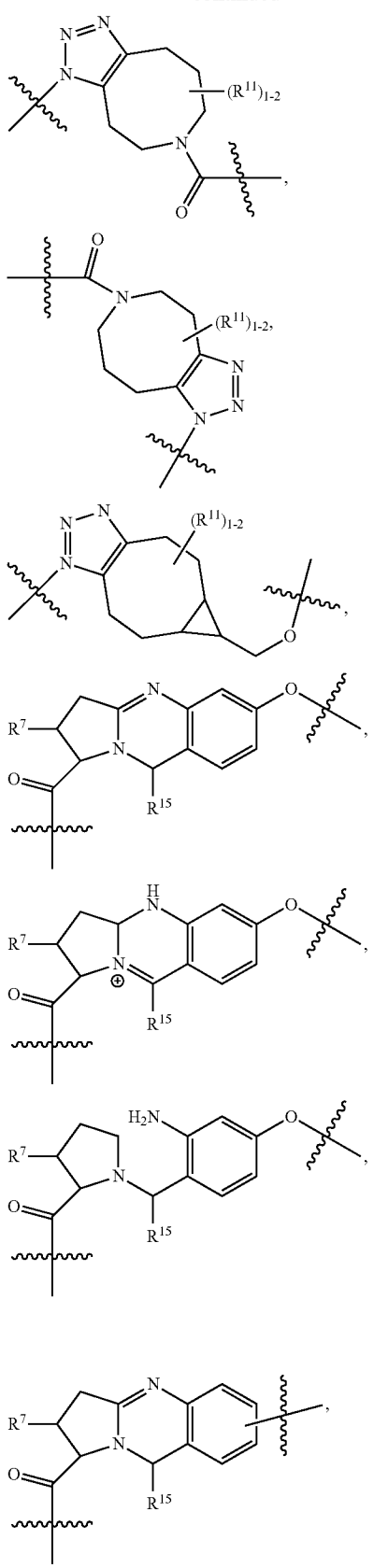

98
-continued

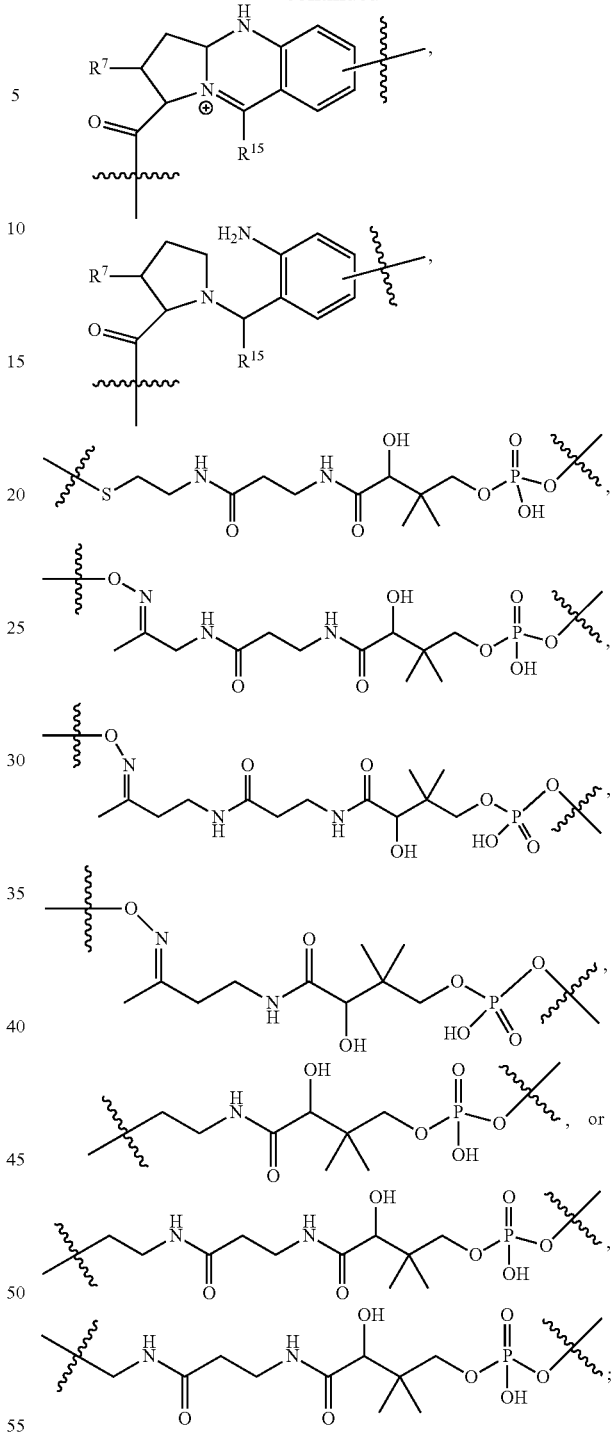

each $R^7$ is independently selected from H and $C_{1-6}$alkyl;
each $R^{10}$ is independently selected from H, $C_1$-$C_6$alkyl, F, Cl, and —OH;
each $R^{11}$ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;
each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{15}$ is independently selected from H, —$CH_3$ and phenyl;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

In another aspect the conjugates of the invention have the structure of Formula (E):

Formula (E)

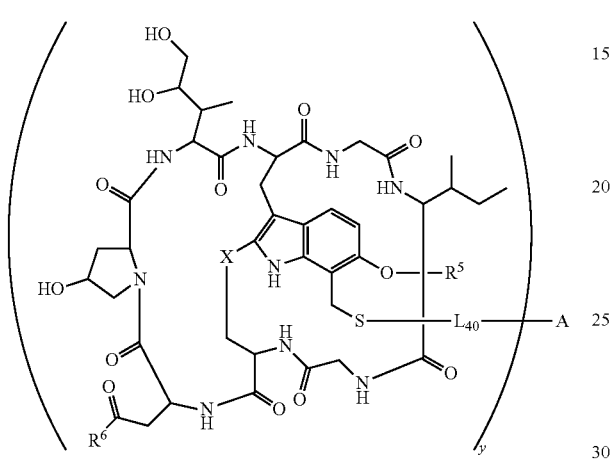

wherein:

A represents an antibody fragment (e.g., Fab or Fab') that specifically binds to human cKIT;

y is an integer from 1 to 10;

X is S(=O), S(=O)$_2$ or S;

$R^5$ is H, —$CH_3$ or —$CD_3$;

$R^6$ is —$NH_2$ or —OH;

$L_{40}$ is -$L_6R^{40}$;

$L_6$ is —$((CH_2)_mO)_p(CH_2)_mX_1L_4$-, —$((CH_2)_mO)_p(CH_2)_mX_2L_4$-, -$L_4NHC(=O)NH((CH_2)_mO)_p(CH_2)_mX_1L_4$-, -$L_4NHC(=O)NH((CH_2)_mO)_p(CH_2)_mX_2L_4$-, —$((CH_2)_mO)_p(CH_2)_m$—, —$(CH_2)_m$—, —$(CH_2)_mX_1(CH_2)_m$—, —$(CH_2)_mNHC(=O)(CH_2)_m$—, —$(CH_2)_mNHC(=O)(CH_2)_mC(=O)NH(CH_2)_m$—, —$((CH_2)_mO)_p(CH_2)_mNHC(=O)(CH_2)_m$—, —$((CH_2)_mO)_pCH_2)_mC(=O)NH(CH_2)_m$—, —$(CH_2)_mC(R_7)_2$— or —$(CH_2)_mC(R_7)_2SS(CH_2)_mNHC(=O)(CH_2)_m$—

$L_4$ is —$((CH_2)_m$;

$X_1$ is

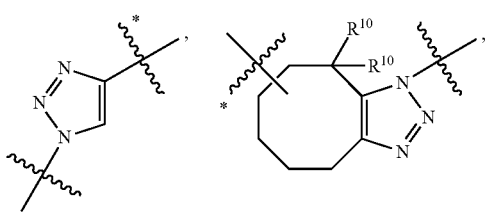

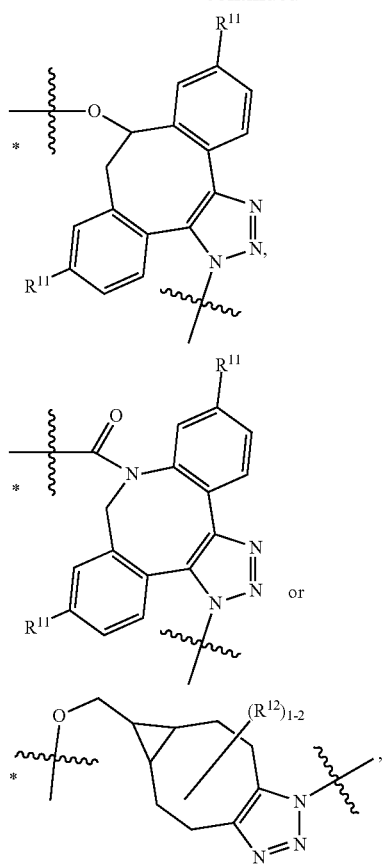

where the * indicates attachment point to $L_4$;

$X_2$ is

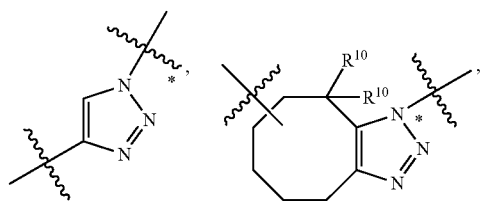

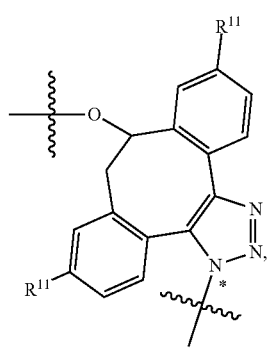

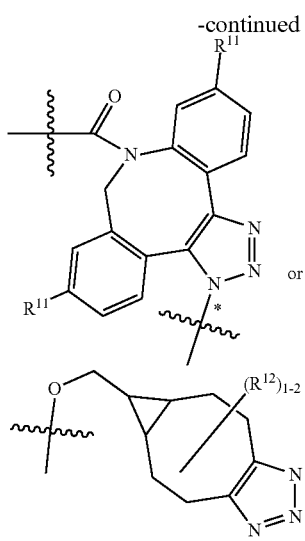
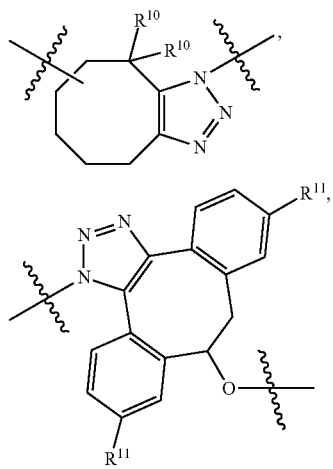
where the * indicates attachment point to $L_4$;
$R^{40}$ is
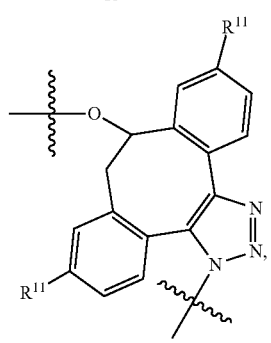
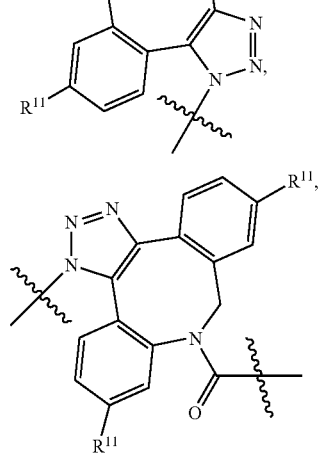
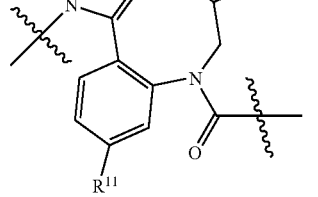
$-NR^7C(=O)CH_2-$, $-NHC(=O)CH_2-$,
$-S(=O)_2CH_2CH_2-$, $-(CH_2)_2S(=O)_2CH_2CH_2-$,
$-NR^7S(=O)_2CH_2CH_2$, $-NR^7C(=O)CH_2CH_2-$,
$-NH-$, $-C(=O)-$, $-NHC(=O)-$,
$-CH_2NHCH_2CH_2-$, $-NHCH_2CH_2-$, $-S-$,
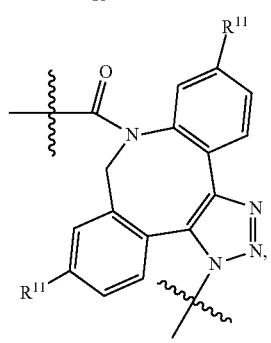
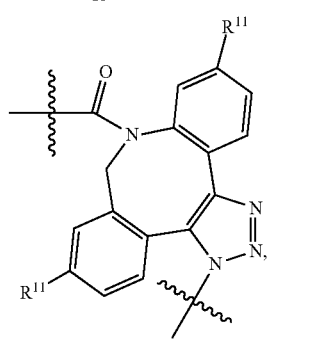
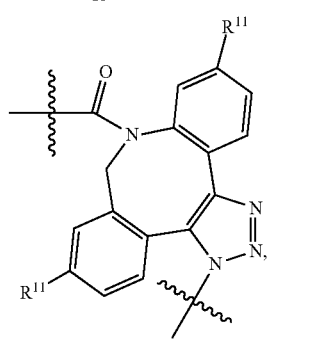
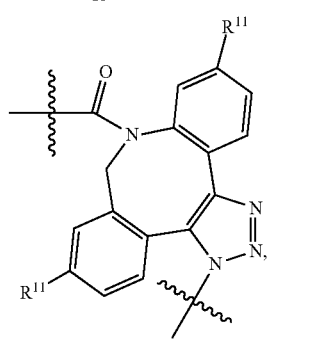
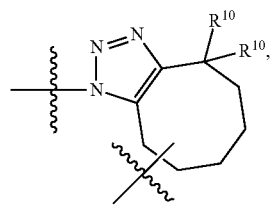
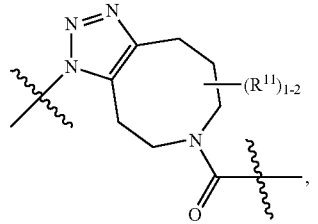

-continued

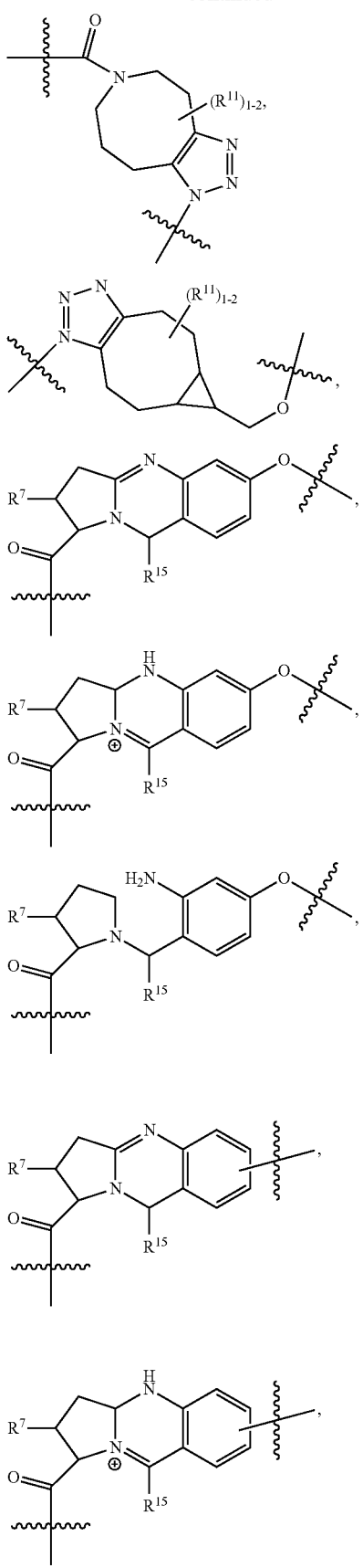

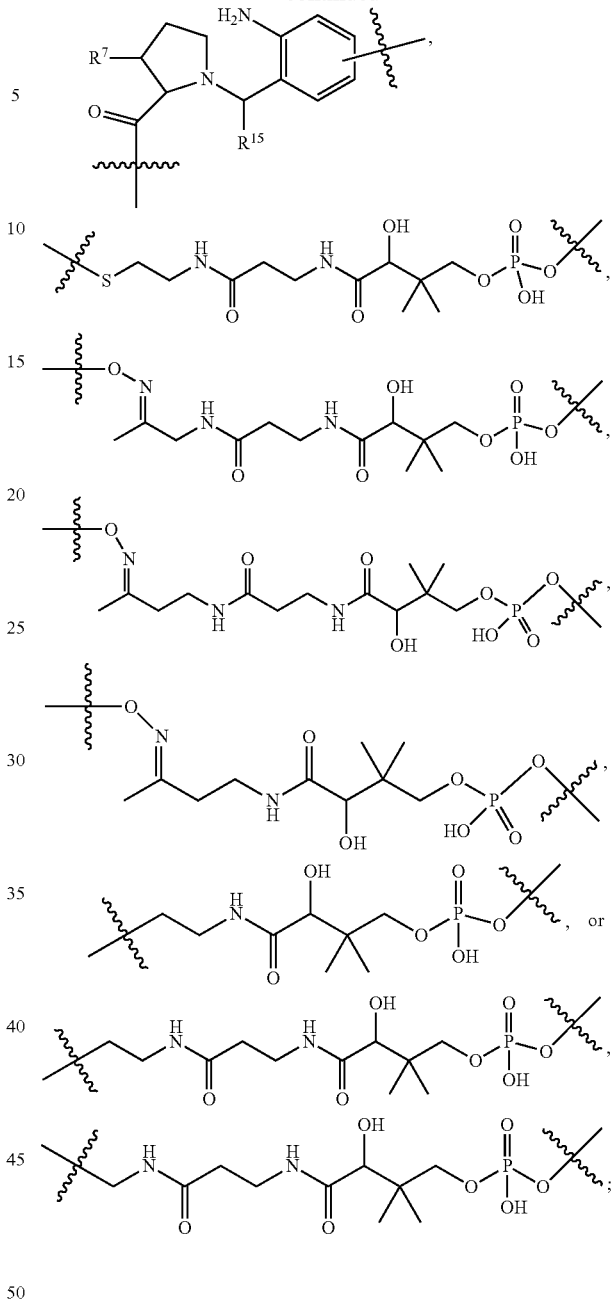

each R[7] is independently selected from H and $C_1$-$C_6$alkyl;

each R[10] is independently selected from H, $C_1$-$C_6$alkyl, F, Cl, and —OH;

each R[11] is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;

each R[12] is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each R[15] is independently selected from H, —$CH_3$ and phenyl;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

Certain aspects and examples of the conjugates of the invention are provided in the following listing of additional, enumerated embodiments. It will be recognized that features specified in each embodiment may be combined with other specified features to provide further embodiments of the present invention.

Embodiment 15. The conjugate having the structure of Formula (C) is a conjugate having has the structure of Formula (C-1):

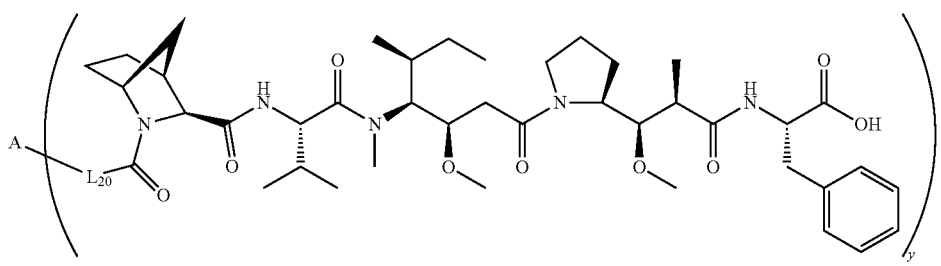

Formula (C-1)

wherein: A, y, and $L_{20}$ are as defined above.

Embodiment 16. The conjugate having the structure of Formula (C) or Formula (C-1) wherein:

A represents an antibody fragment (e.g., Fab or Fab') that specifically binds to human cKIT;

y is an integer from 1 to 10;

$L_{20}$ is $-L_1R^{40}$;

$L_1$ is $-((CH_2)_mO)_p(CH_2)_mX_1L_4-$, $-((CH_2)_mO)_p(CH_2)_mX_2L_4-$, $-((CH_2)_mO)_p(CH_2)_m-$, $-(CH_2)_m-$, $-X_3X_4C(=O)((CH_2)_mO)_p(CH_2)_m-$, $-X_3X_4C(=O)(CH_2)_m-$, $-X_3C(=O)(CH_2)_mNHC(=O)(CH_2)_m-$, $-X_3C(=O)(CH_2)_mNHC(=O)((CH_2)_mO)_p(CH_2)_m-$;

$L_4$ is $-((CH_2)_m$;

$X_1$ is

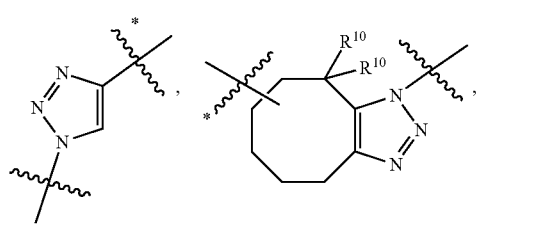

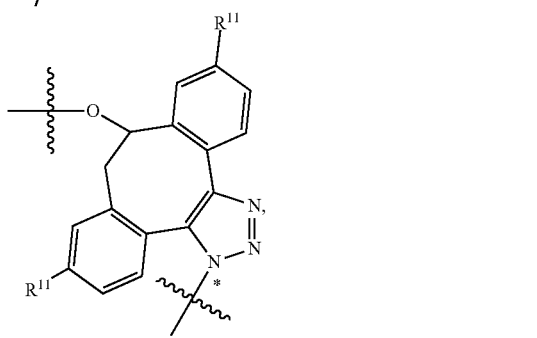

-continued

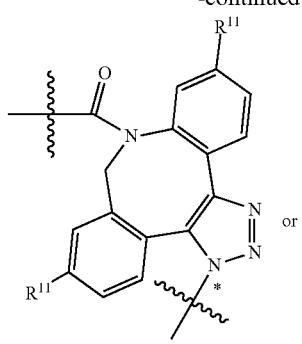

or

-continued

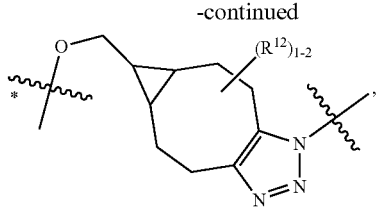

where the * indicates attachment point to $L_4$;

$X_2$ is

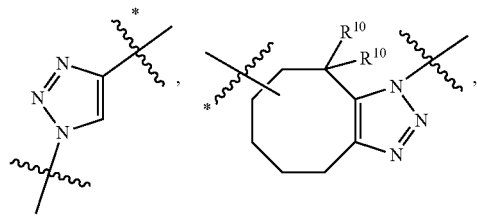

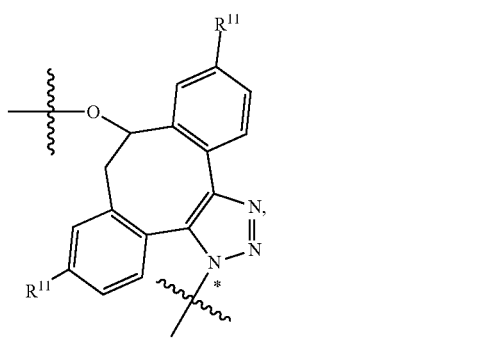

107
-continued
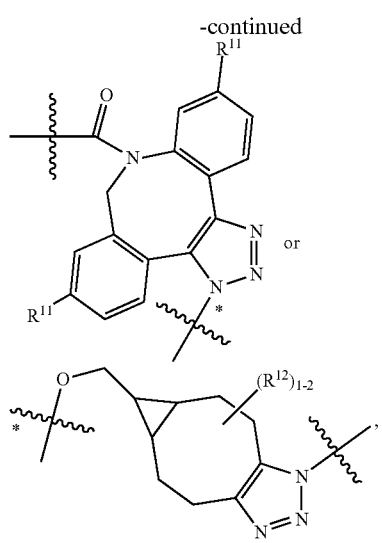
where the * indicates attachment point to L$_4$;
X$_3$ is
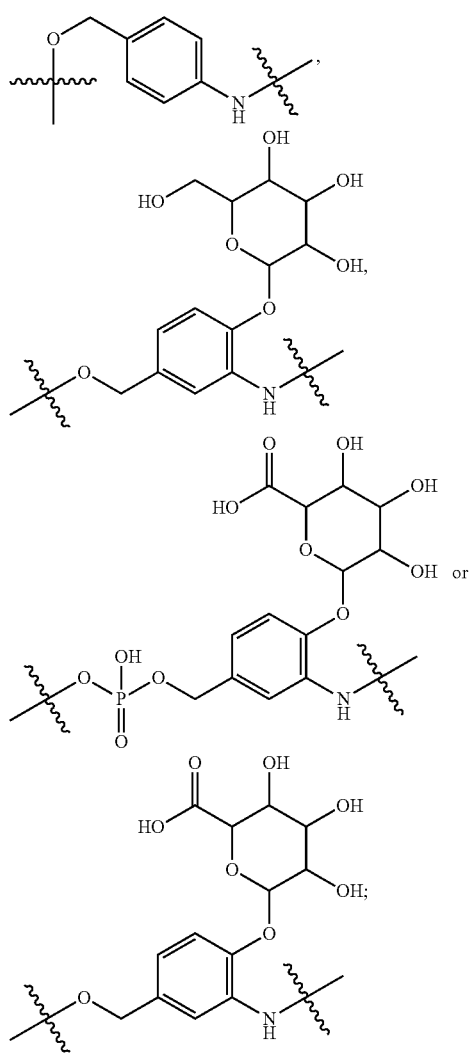
108
X$_4$ is
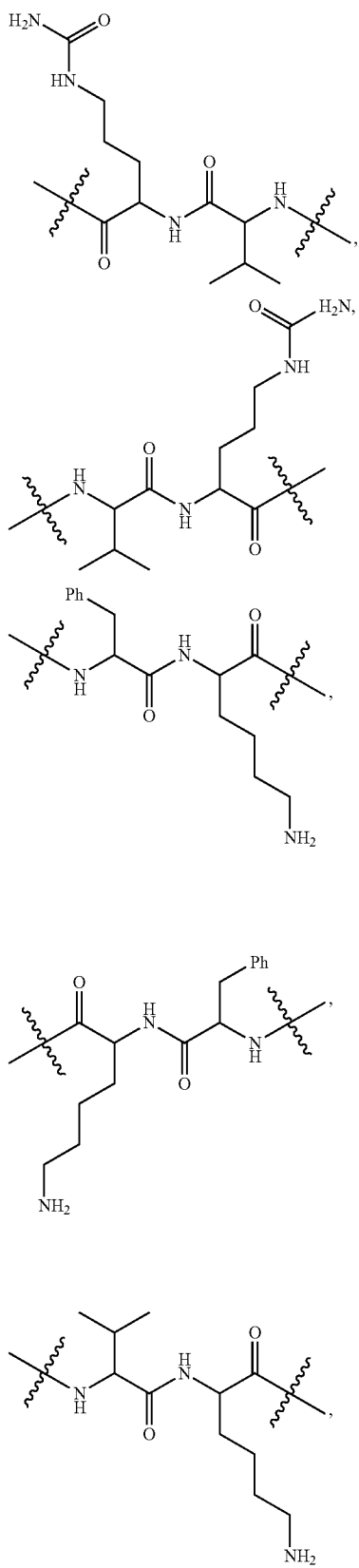

-continued
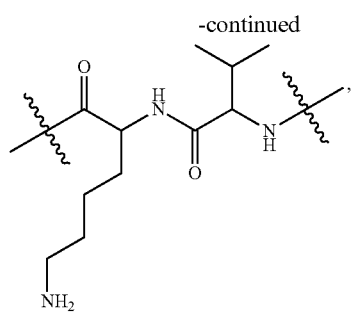
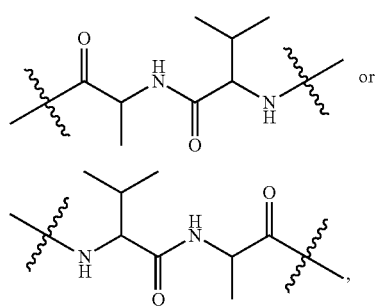
or
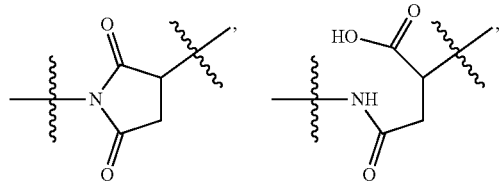
R⁴⁰ is
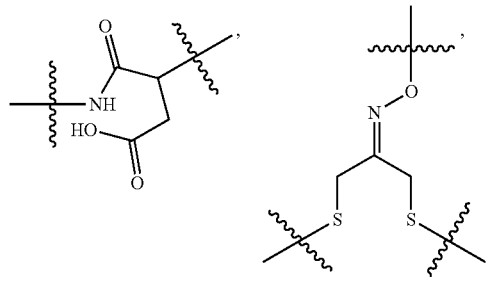
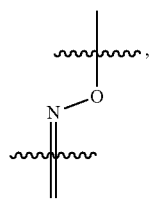
—NR⁷C(=O)CH₂—,     —NHC(=O)CH₂—,
—S(=O)₂CH₂CH₂—,    —(CH₂)₂S(=O)₂CH₂CH₂—,
—NR⁷S(=O)₂CH₂CH₂,  —NR⁷C(=O)CH₂CH₂—,
—NH—,              —C(=O)—,          —NHC(=O)—,
—CH₂NHCH₂CH₂—,     —NHCH₂CH₂—,       —S—,
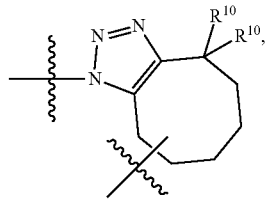
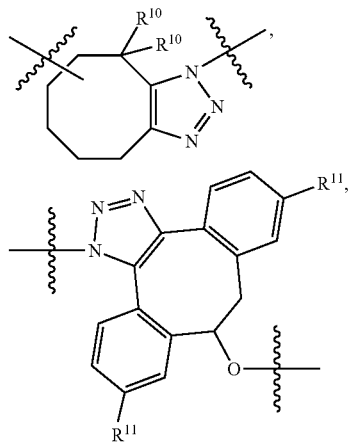
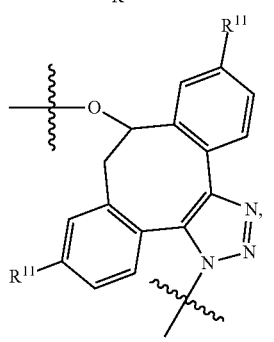
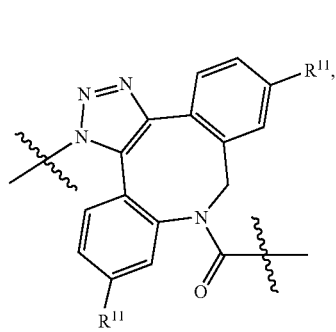
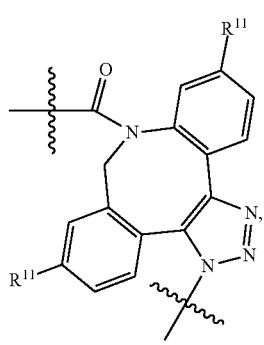

-continued

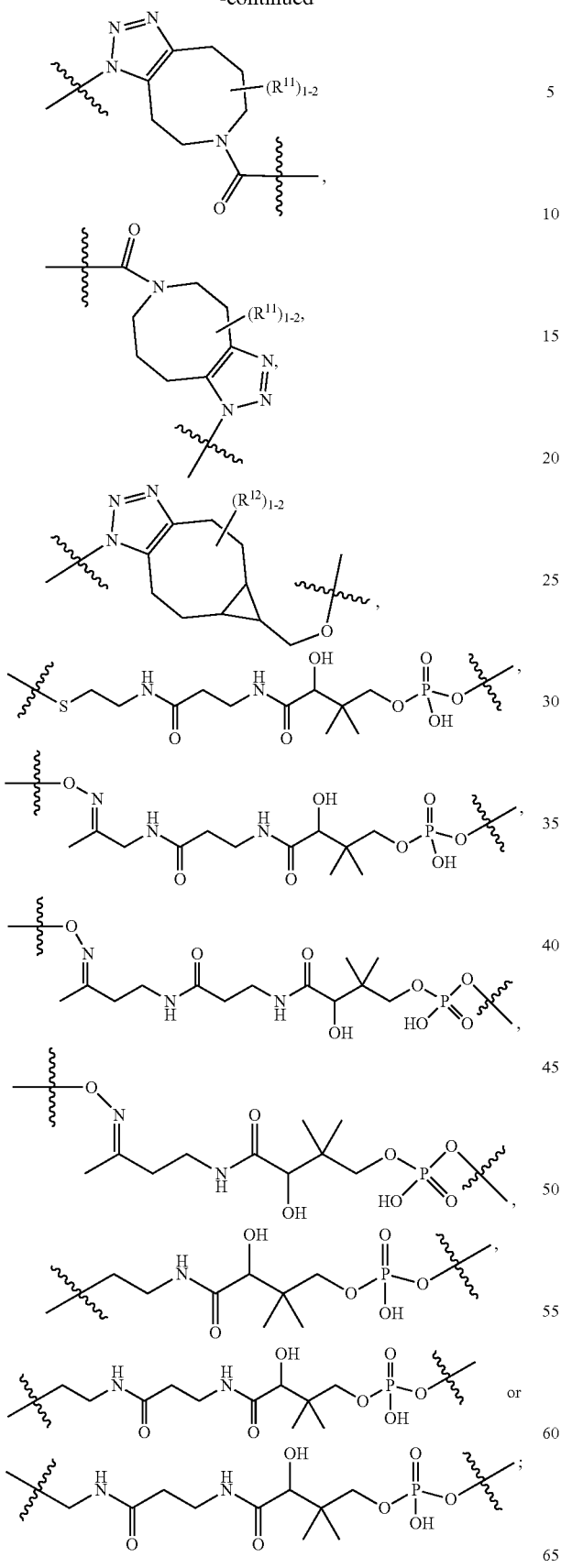

each $R^7$ is independently selected from H and $C_1$-$C_6$alkyl;
each $R^{10}$ is independently selected from H, $C_1$-$C_6$alkyl, F, Cl, and —OH;
each $R^{11}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;
each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
each m is independently selected from 1, 2, 3, 4, 5, 6, 7, 8, 9 and 10, and
each p is independently selected from 1, 2, 3, 4, 5, 6, 7, 8, 9, 10, 11, 12, 13 and 14.

Embodiment 17. The conjugate having the structure of Formula (C) or Formula (C-1), wherein:
A represents an antibody fragment (e.g., Fab or Fab') that specifically binds to human cKIT;
y is an integer from 1 to 10;
$L_{20}$ is -$L_1R^{40}$;
$L_1$ is —$((CH_2)_mO)_p(CH_2)_mX_1L_4$-, —$((CH_2)_mO)_p(CH_2)_mX_2L_4$-, —$((CH_2)_mO)_p(CH_2)_m$— or —$(CH_2)_m$—;
$L_4$ is —$((CH_2)_m$;
$X_1$ is

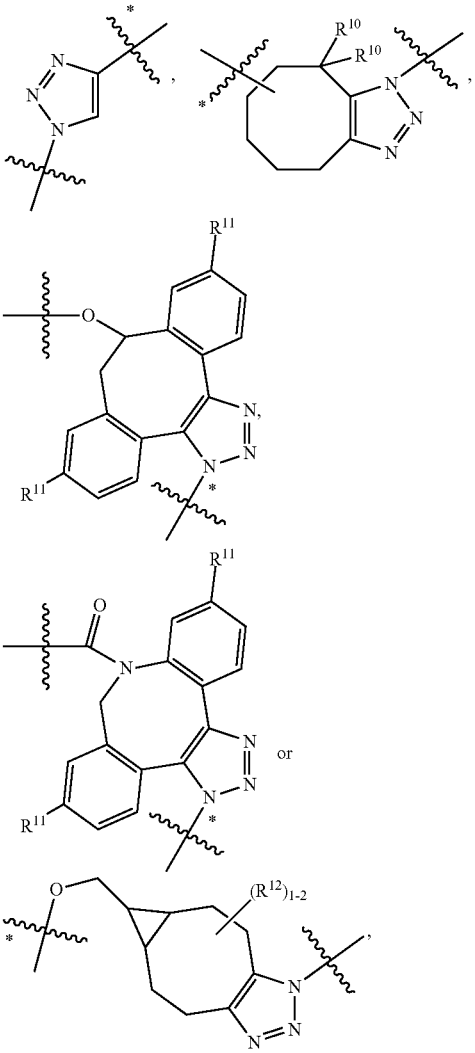

where the * indicates attachment point to $L_4$;

$X_2$ is
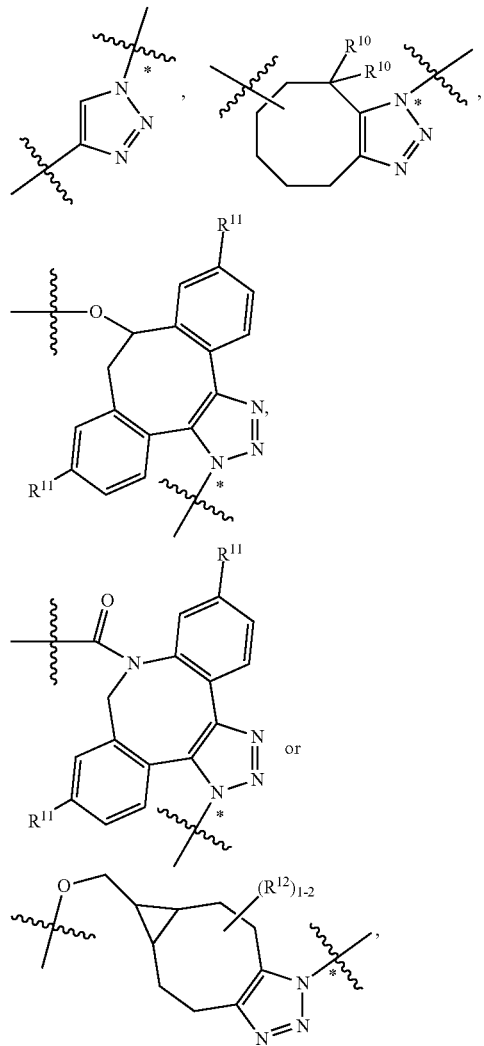
where the * indicates attachment point to $L_4$;
$R^{40}$ is
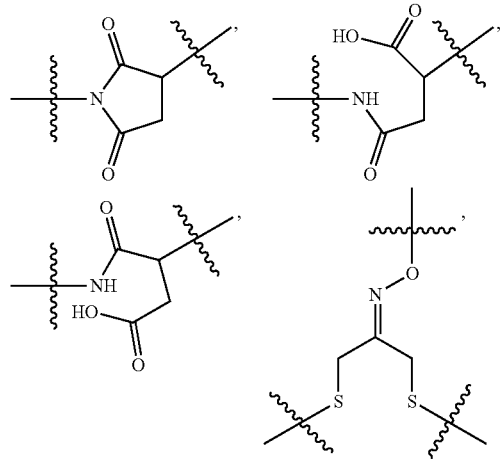
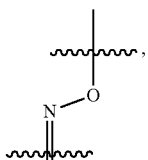
—$NR^7C(=O)CH_2$—, —$NHC(=O)CH_2$—,
—$S(=O)_2CH_2CH_2$—, —$(CH_2)_2S(=O)_2CH_2CH_2$—,
—$NR^7S(=O)_2CH_2CH_2$, —$NR^7C(=O)CH_2CH_2$—,
—$NH$—, —$C(=O)$—, —$NHC(=O)$—,
—$CH_2NHCH_2CH_2$—, —$NHCH_2CH_2$—, —$S$—,
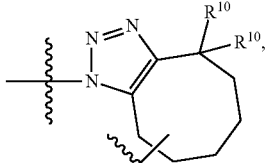
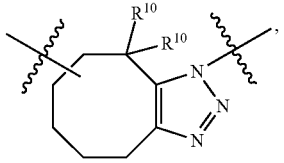
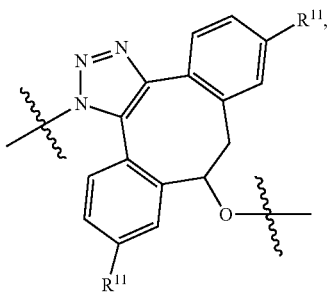
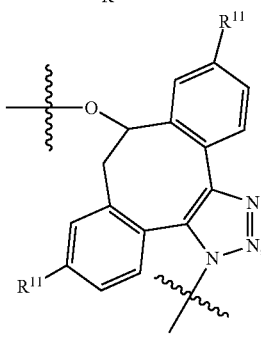
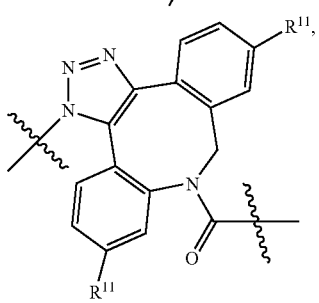

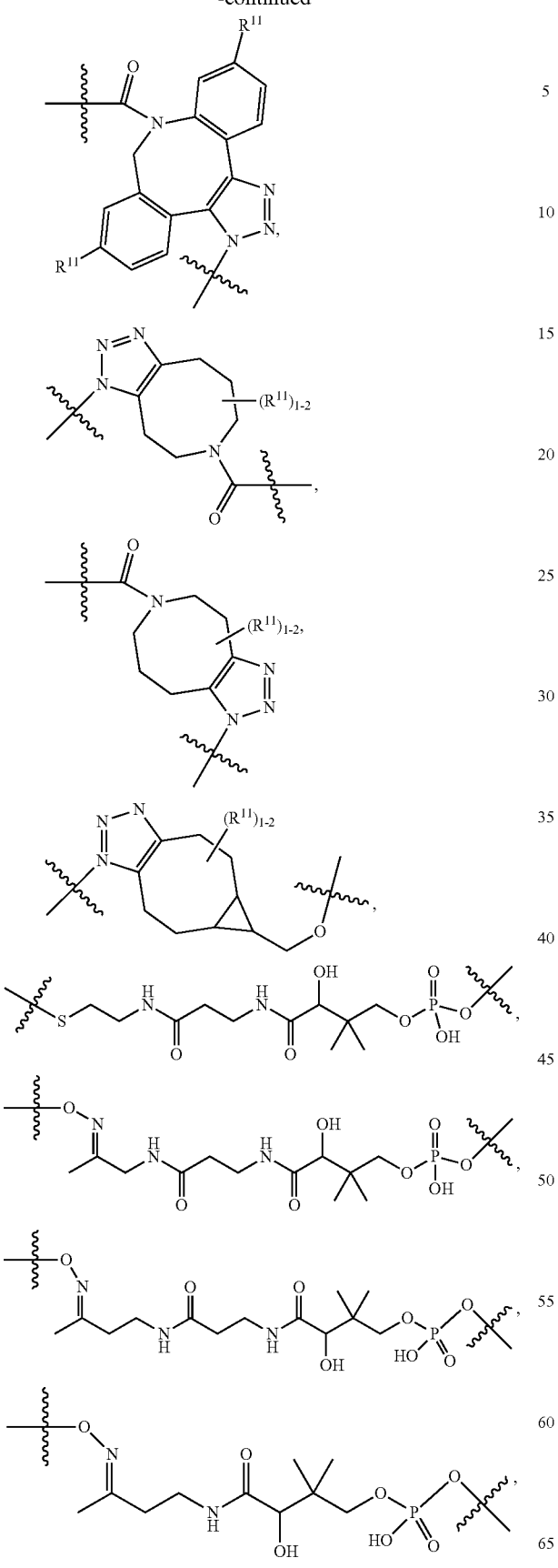

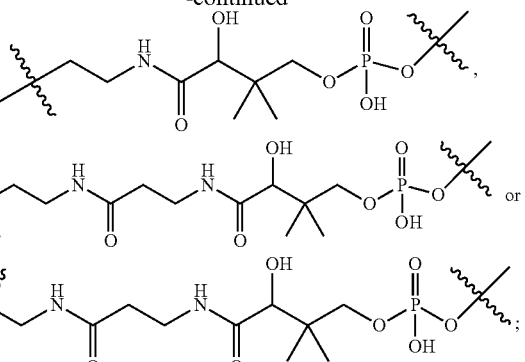

each $R^7$ is independently selected from H and $C_1$-$C_6$alkyl;
each $R^{10}$ is independently selected from H, $C_1$-$C_6$alkyl, F, Cl, and —OH;
each $R^{11}$ is independently selected from H, $C_1$-$C_6$alkyl, F, Cl, —$NH_2$, —$OCH_3$, —$OCH_2CH_3$, —$N(CH_3)_2$, —CN, —$NO_2$ and —OH;
each $R^{12}$ is independently selected from H, $C_{1-6}$alkyl, fluoro, benzyloxy substituted with —C(═O)OH, benzyl substituted with —C(═O)OH, $C_{1-4}$alkoxy substituted with —C(═O)OH and $C_{1-4}$alkyl substituted with —C(═O)OH;
each m is independently selected from 1, 2, 3, 4, 5, 6, 7, 8, 9 and 10, and
each p is independently selected from 1, 2, 3, 4, 5, 6, 7, 8, 9, 10, 11, 12, 13 and 14.

Embodiment 18. The conjugate having the structure of Formula (C) or Formula (C-1), wherein:
A represents an antibody fragment (e.g., Fab or Fab') that specifically binds to human cKIT;
y is an integer from 1 to 10;
$L_{20}$ is -$L_1R^{40}$;
$L_1$ is —$((CH_2)_mO)_p(CH_2)_mX_1L_4$-, —$((CH_2)_mO)_p(CH_2)_m$— or —$(CH_2)_m$—;
$L_4$ is —$((CH_2)_m$;
$X_1$ is

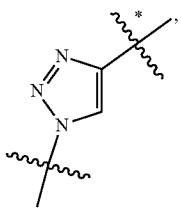

where the * indicates attachment point to $L_4$;
$R^{40}$ is

117
-continued
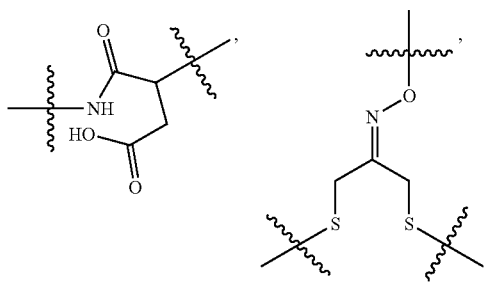 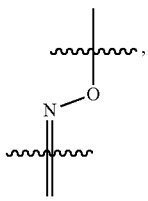
118
-continued
each m is independently selected from 1, 2, 3, 4, 5, 6, 7, 8, 9 and 10, and
each p is independently selected from 1, 2, 3, 4, 5, 6, 7, 8, 9, 10, 11, 12, 13 and 14.
Embodiment 19. The conjugate having the structure of Formula (C) or Formula (C-1) selected from:
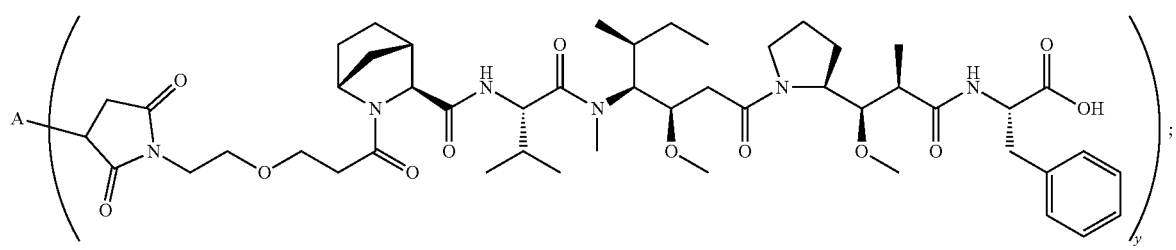
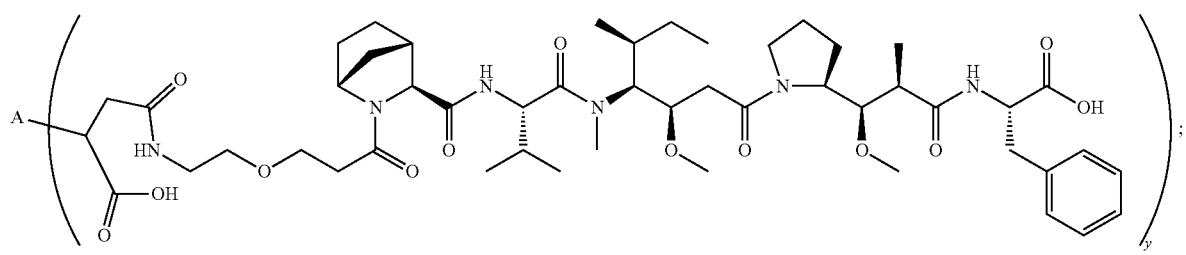
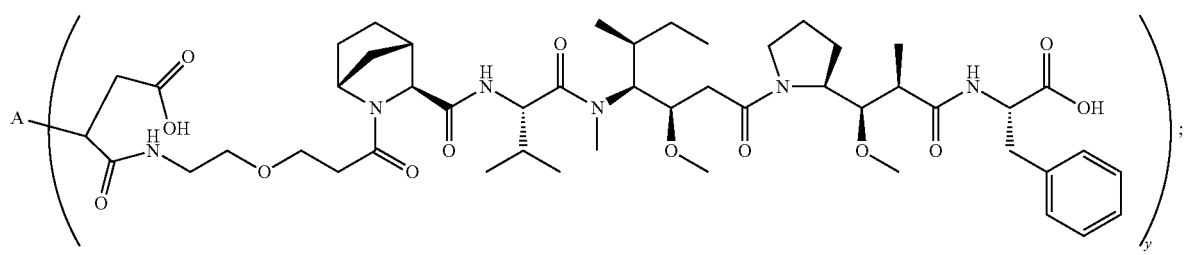
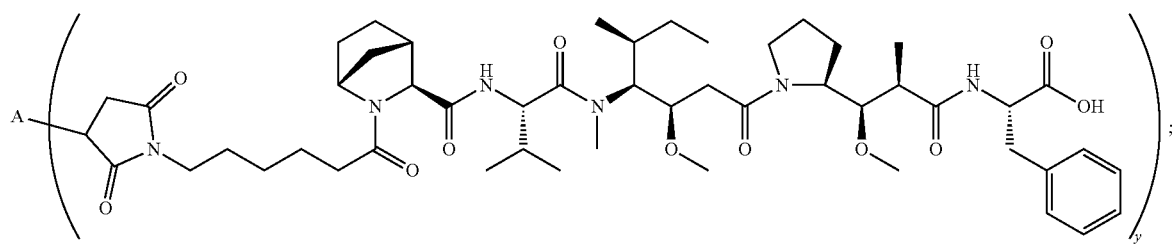

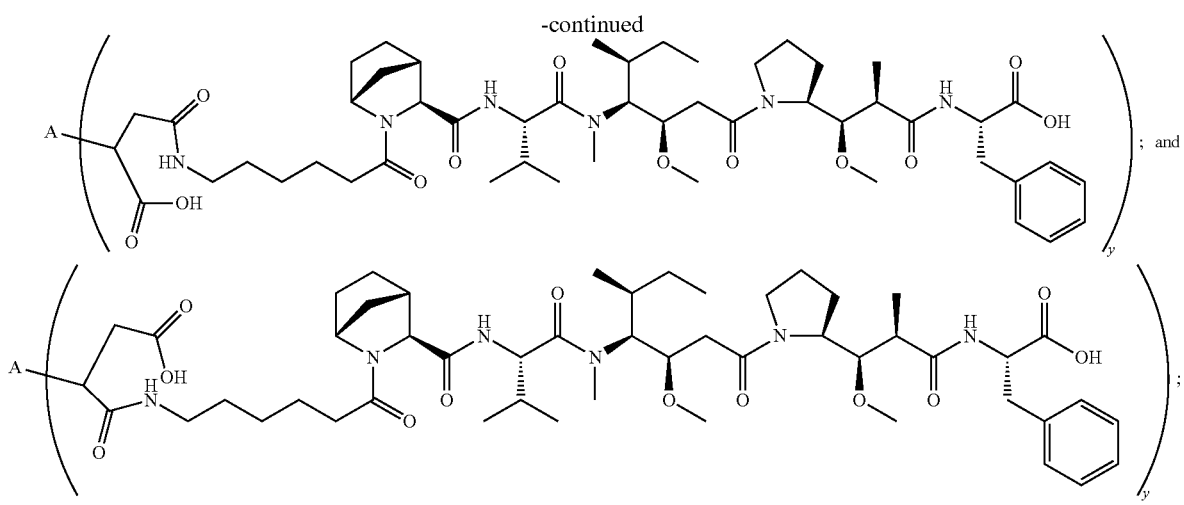
; and
;
Embodiment 20. The conjugate having the structure of Formula (D) is a conjugate having has the structure of Formula (D-1) or Formula (D-2):
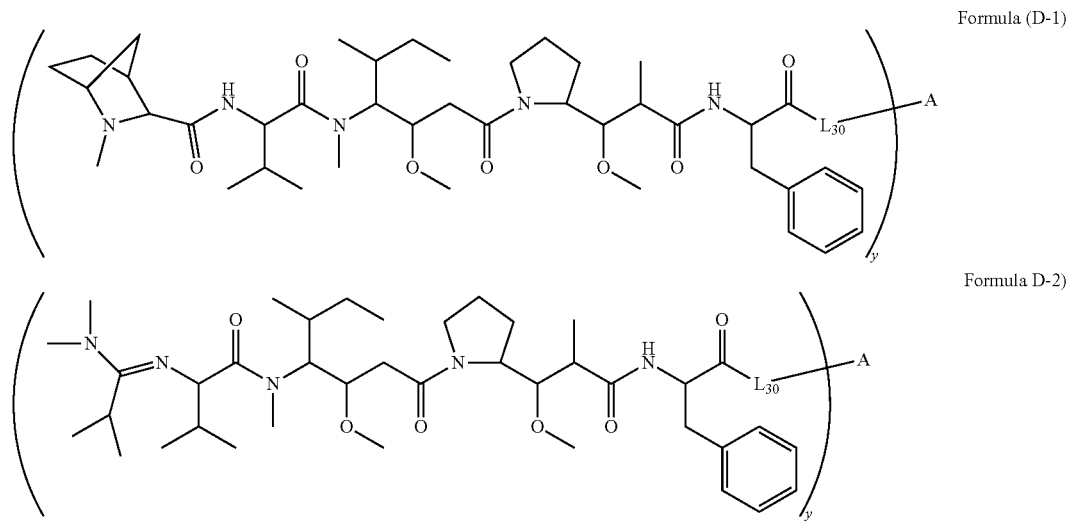
Formula (D-1)
Formula D-2)
wherein: A, y and $L_{30}$ are as defined above.
Embodiment 21. The conjugate having the structure of Formula (D) is a conjugate having has the structure of Formula (D-1a) or Formula (D-2a):
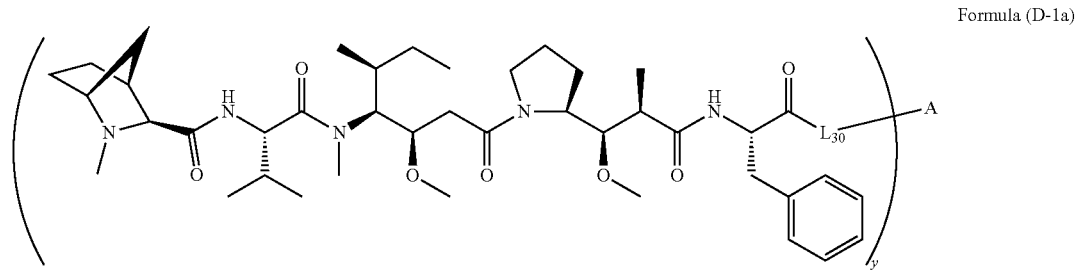
Formula (D-1a)

Formula D-2a)

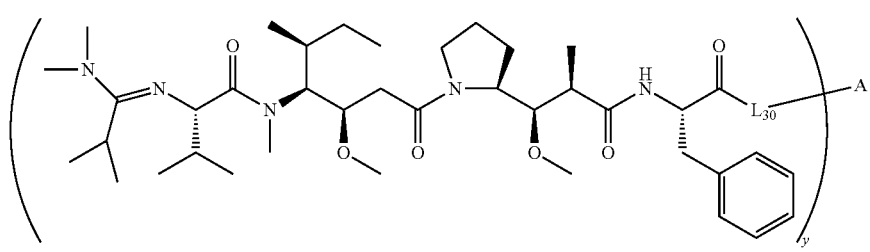

wherein: A, y and $L_{30}$ are as defined above.

Embodiment 22. The conjugate having the structure of Formula (D), Formula (D-1), Formula (D-2), Formula (D-1a) or Formula (D-2a), wherein:

A represents an antibody fragment (e.g., Fab or Fab') that specifically binds to human cKIT;

y is an integer from 1 to 10;

$L_{30}$ is -$L_5R^{40}$;

$L_4$ is —$((CH_2)_m$;

$L_5$ is —$NHS(=O)_2(CH_2)_mX_1L_4$-, —$NH((CH_2)_mO)_p(CH_2)_mX_1L_4$-, —$NH((CH_2)_mO)_p(CH_2)_mX_2L_4$-, —$NH((CH_2)_mO)_p(CH_2)_m$— or —$NH(CH_2)_m$—;

$X_1$ is

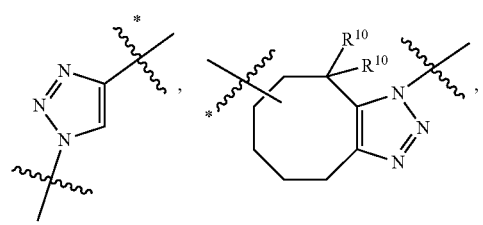

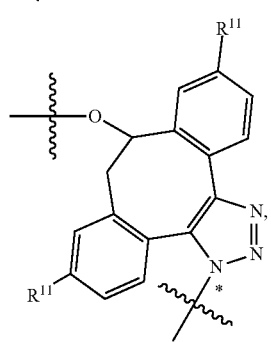

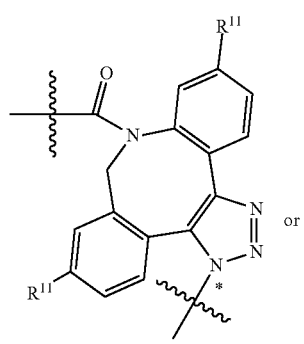

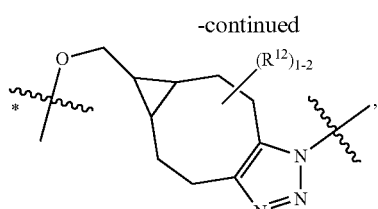

where the * indicates attachment point to $L_4$;

$X_2$ is

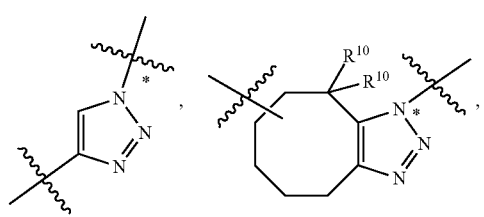

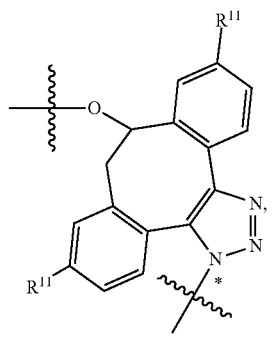

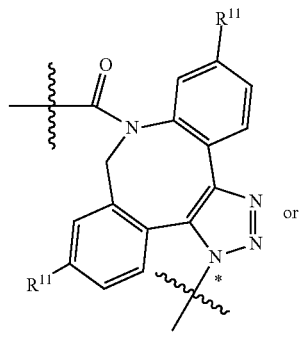

123
-continued
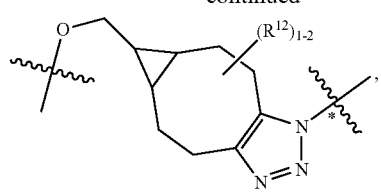
where the * indicates attachment point to $L_4$;
$R^{40}$ is
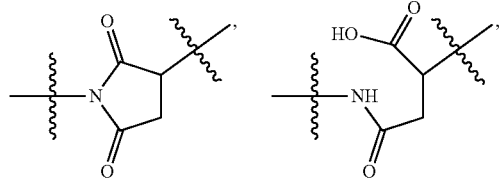
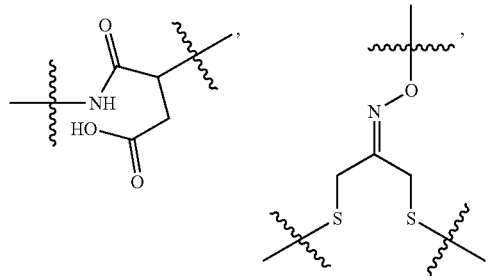
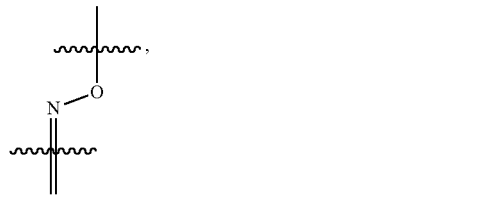
—$NR^7C(=O)CH_2$—, —$NHC(=O)CH_2$—,
—$S(=O)_2CH_2CH_2$—, —$(CH_2)_2S(=O)_2CH_2CH_2$—,
—$NR^7S(=O)_2CH_2CH_2$, —$NR^7C(=O)CH_2CH_2$—,
—$NH$—, —$C(=O)$—, —$NHC(=O)$—,
—$CH_2NHCH_2CH_2$—, —$NHCH_2CH_2$—, —$S$—,
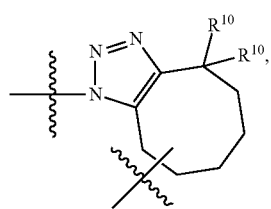
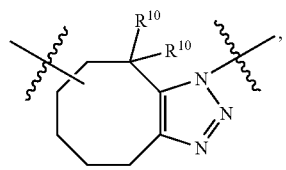
124
-continued
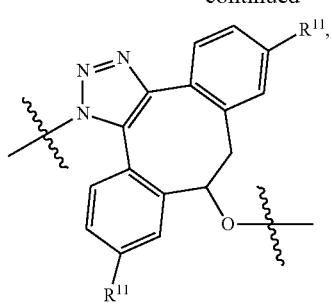
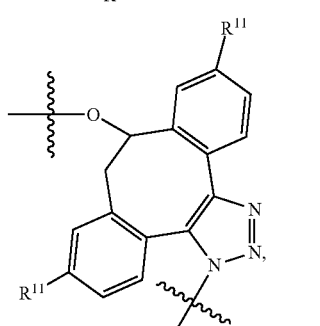
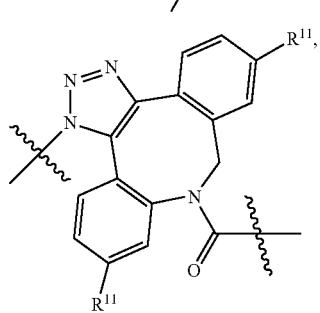
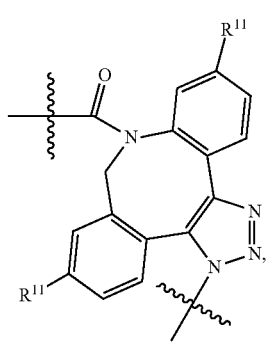
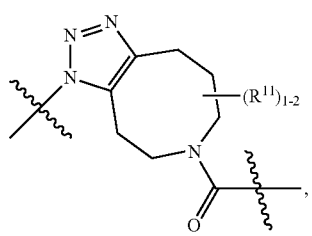

-continued

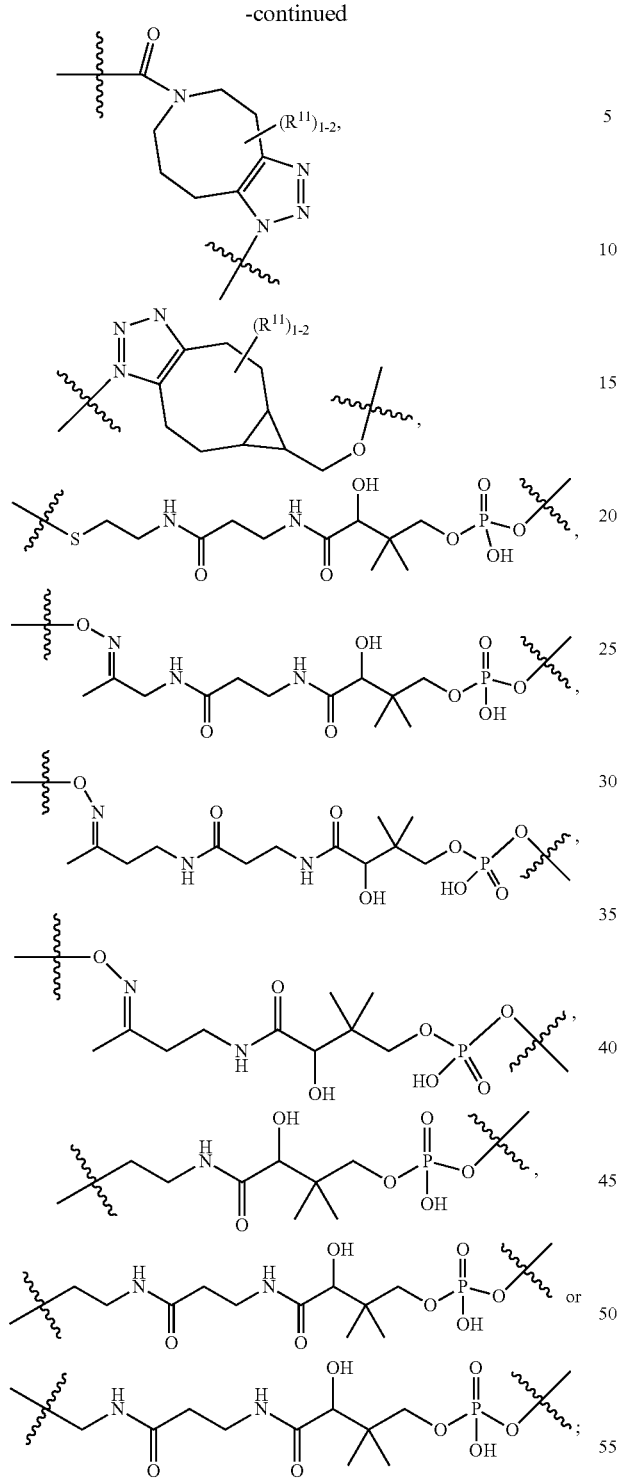

each $R^7$ is independently selected from H and $C_1$-$C_6$alkyl;

each $R^{10}$ is independently selected from H, $C_1$-$C_6$alkyl, F, Cl, and —OH;

each $R^{11}$ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;

each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

Embodiment 23. The conjugate having the structure of Formula (D), Formula (D-1), Formula (D-2), Formula (D-1a) or Formula (D-2a):

wherein:

A represents an antibody fragment (e.g., Fab or Fab') that specifically binds to human cKIT;

y is an integer from 1 to 10;

$L_{30}$ is -$L_5R^{40}$;

$L_4$ is —((CH$_2$)$_m$;

$L_5$ is —NHS(=O)$_2$(CH$_2$)$_m$X$_1$L$_4$-, —NH((CH$_2$)$_m$O)$_p$(CH$_2$)$_m$X$_1$L$_4$-, —NH((CH$_2$)$_m$O)$_p$(CH$_2$)$_m$X$_2$L$_4$-, —NH((CH$_2$)$_m$O)$_p$(CH$_2$)$_m$— or —NH(CH$_2$)$_m$—;

$X_1$ is

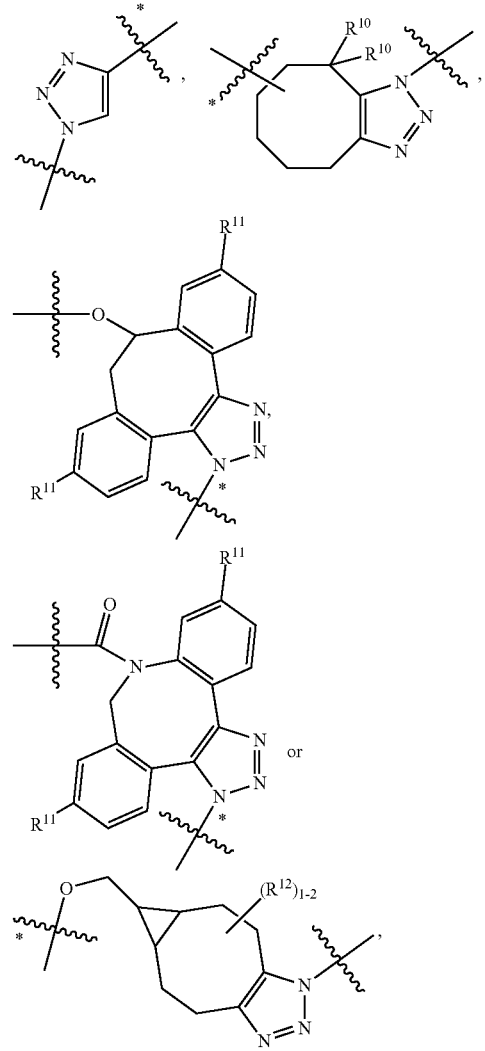

where the * indicates attachment point to $L_4$;

$X_2$ is
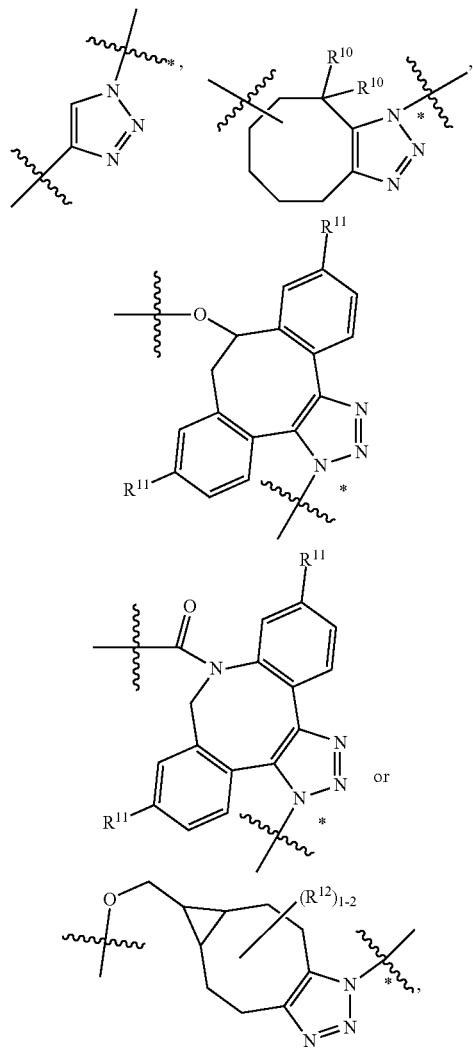
where the * indicates attachment point to $L_4$;
$R_{40}$ is
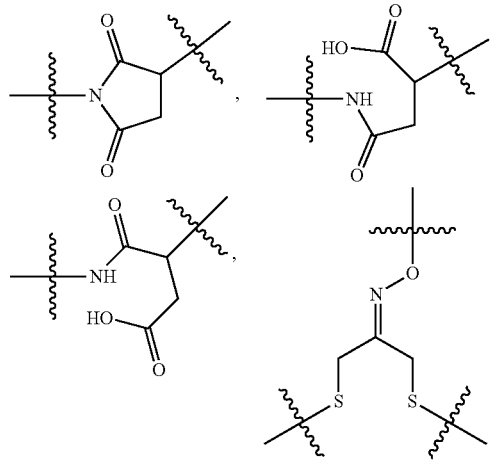
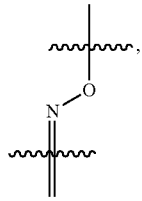
—NR$^7$C(=O)CH$_2$—, —NHC(=O)CH$_2$—,
—S(=O)$_2$CH$_2$CH$_2$—, —(CH$_2$)$_2$S(=O)$_2$CH$_2$CH$_2$—,
—NR$^7$S(=O)$_2$CH$_2$CH$_2$, —NR$^7$C(=O)CH$_2$CH$_2$—,
—NH—, —C(=O)—, —NHC(=O)—,
—CH$_2$NHCH$_2$CH$_2$—, —NHCH$_2$CH$_2$—, —S—,
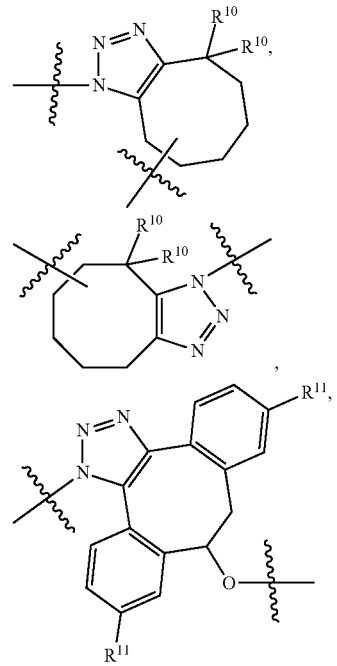
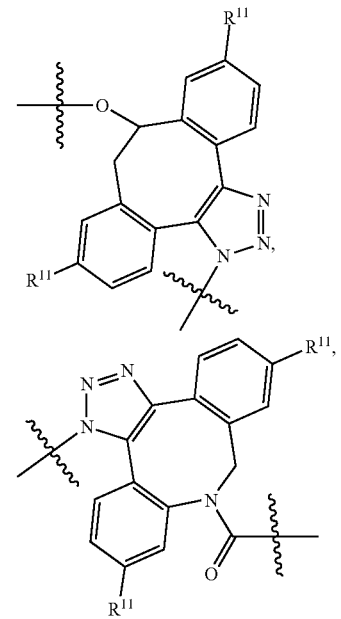

-continued

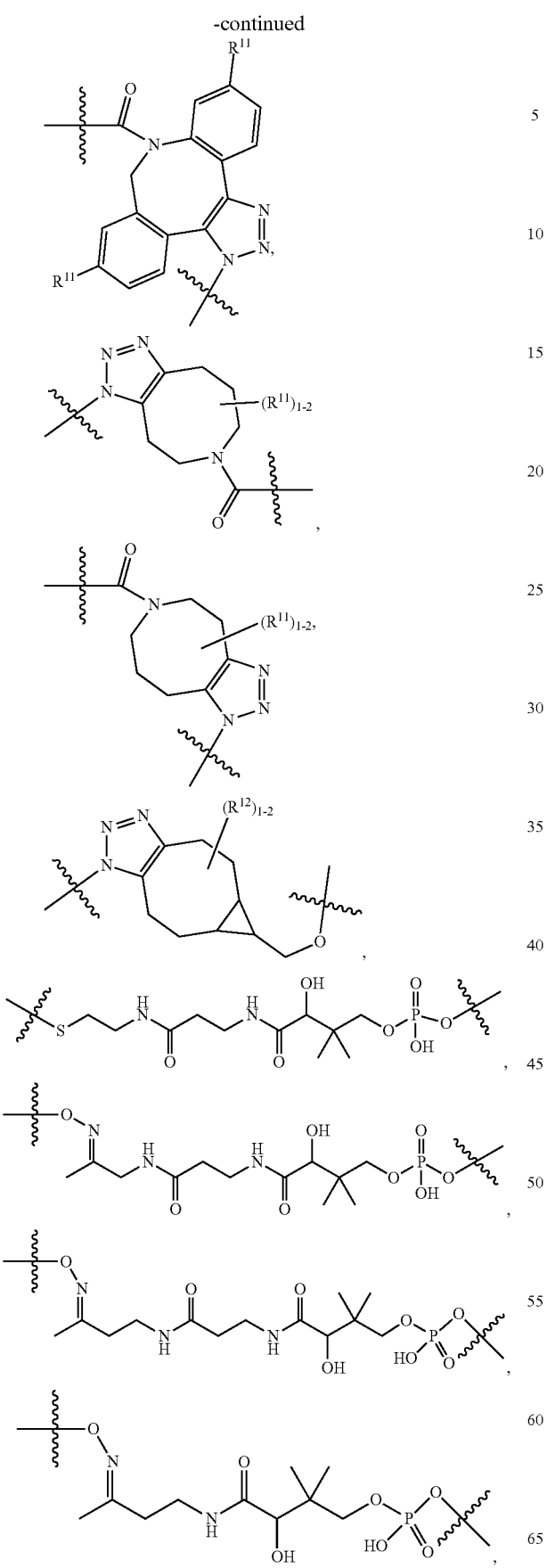

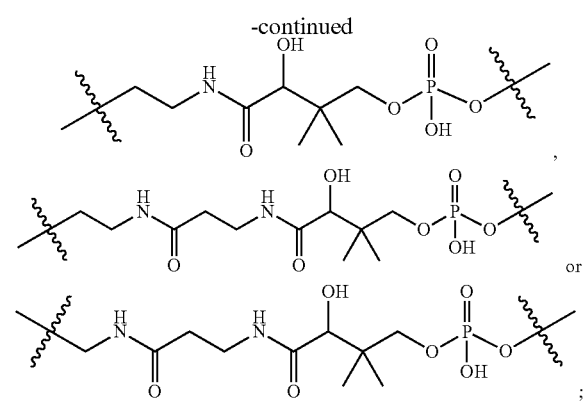

each $R^7$ is independently selected from H and $C_1$-$C_6$alkyl;
each $R^{10}$ is independently selected from H, $C_1$-$C_6$alkyl, F, Cl, and —OH;
each $R^{11}$ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;
each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
each m is independently selected from 1, 2, 3, 4, 5, 6, 7, 8, 9 and 10, and
each p is independently selected from 1, 2, 3, 4, 5, 6, 7, 8, 9, 10, 11, 12, 13 and 14.

Embodiment 24. The conjugate having the structure of Formula (D), Formula (D-1), Formula (D-2), Formula (D-1a) or Formula (D-2a), wherein:
A represents an antibody fragment (e.g., Fab or Fab') that specifically binds to human cKIT;
y is an integer from 1 to 10;
$L_{30}$ is -$L_5R^{40}$;
$L_4$ is —((CH$_2$)$_m$;
$L_5$ is —NHS(=O)$_2$(CH$_2$)$_m$X$_1$L$_4$;
$X_1$ is

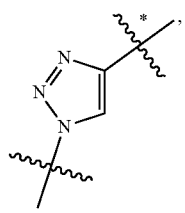 [SMILES: *c1cn(*)nn1]

where the * indicates attachment point to $L_4$;
$R^{40}$ is

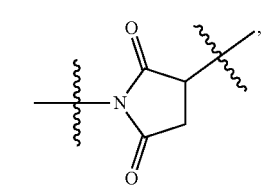

131
-continued
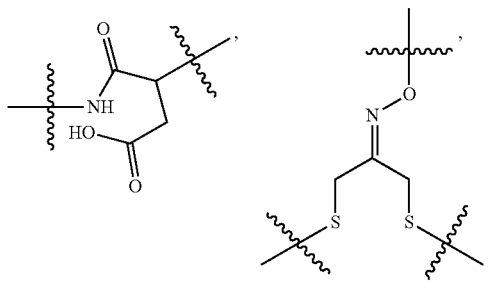
132
-continued
each m is independently selected from 1, 2, 3, 4, 5, 6, 7, 8, 9 and 10, and
each p is independently selected from 1, 2, 3, 4, 5, 6, 7, 8, 9, 10, 11, 12, 13 and 14.
Embodiment 25. The conjugate having the structure of Formula (D), Formula (D-1), Formula (D-2), Formula (D-1a) or Formula (D-2a) selected from:
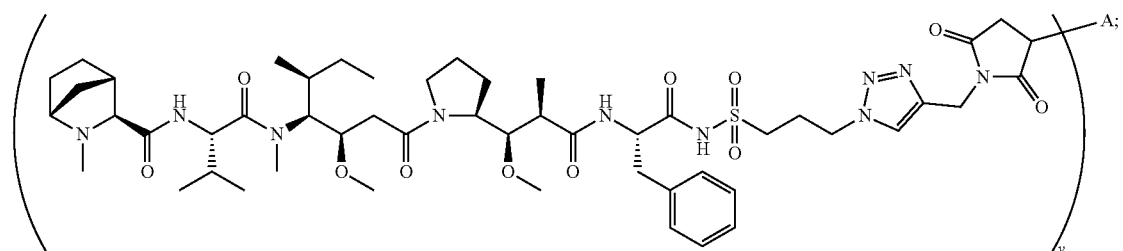
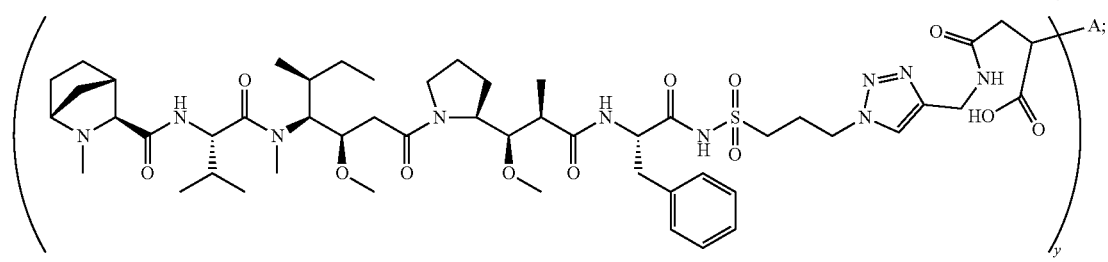
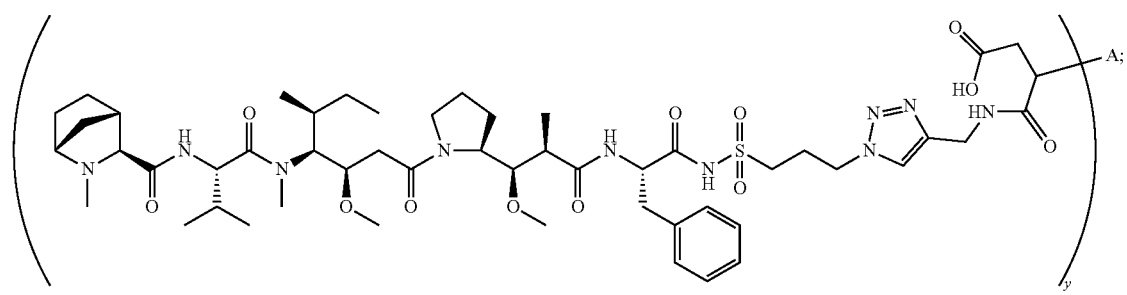
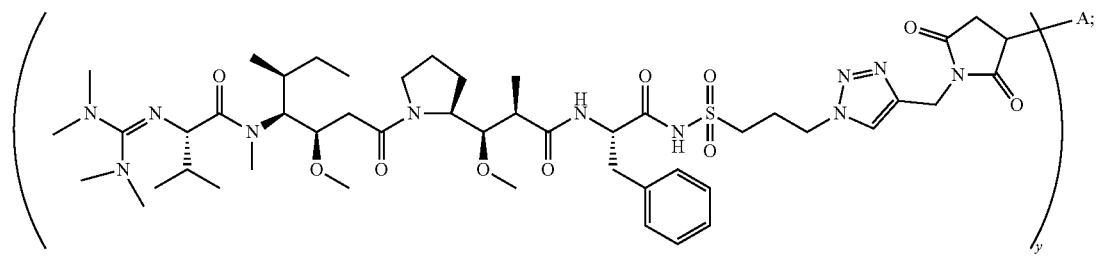

-continued
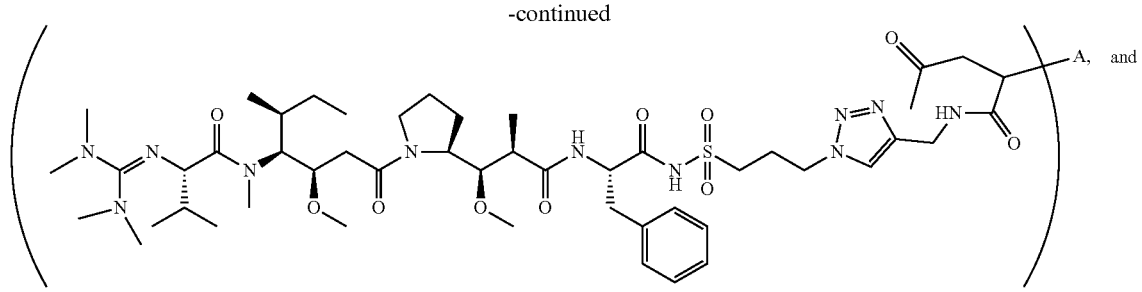
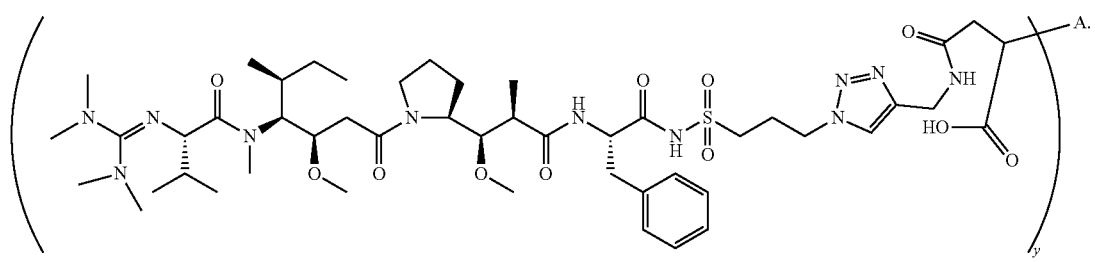
Embodiment 26. The conjugate having the structure of Formula (E) is a conjugate having has the structure of Formula (E-1):
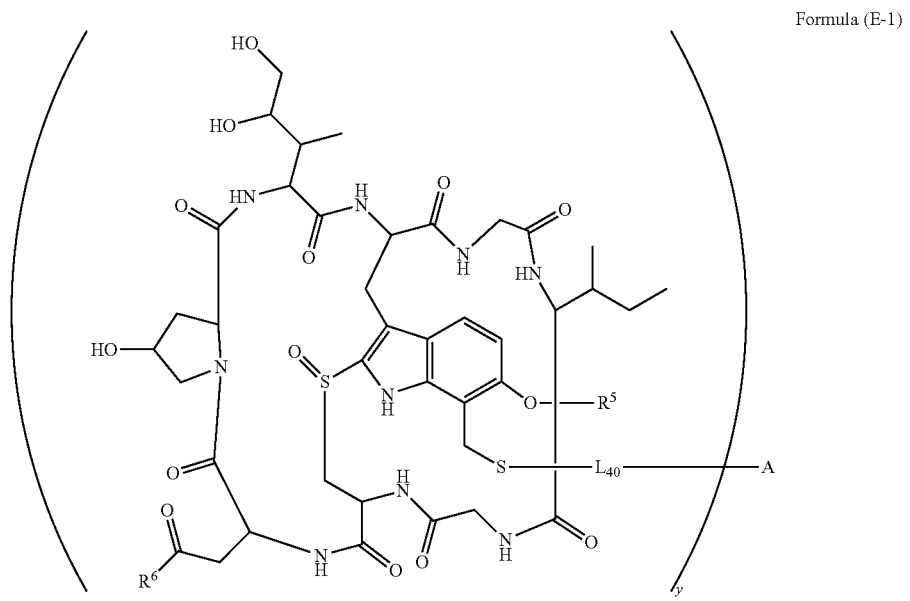
Formula (E-1)
wherein: A, y, $R^5$, $R^6$ and $L_{40}$ are as defined above.
Embodiment 27. The conjugate having the structure of Formula (E) is a conjugate having has the structure of Formula (E-1a):

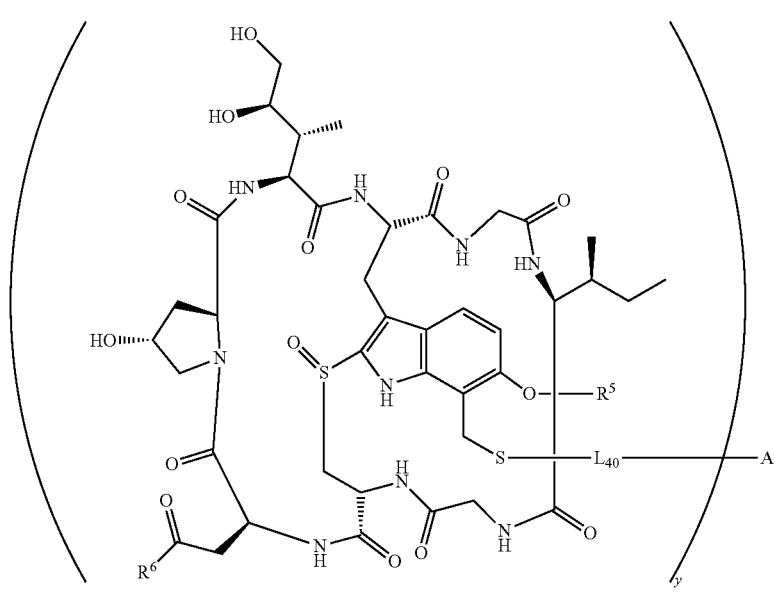

Formula (E-1a)

wherein: A, y, $R^5$, $R^6$ and $L_{40}$ are as defined above.

Embodiment 28. The conjugate having the structure of Formula (E), Formula (E-1) or Formula (E-1a), wherein:

A represents an antibody fragment (e.g., Fab or Fab') that specifically binds to human cKIT;

y is an integer from 1 to 10;

$R^5$ is H, —$CH_3$ or —$CD_3$;

$R^6$ is —$NH_2$ or —OH;

$L_{40}$ is -$L_6R^{40}$;

$L_6$ is —$((CH_2)_mO)_p(CH_2)_mX_1L_4$-, —$((CH_2)_mO)_p(CH_2)_mX_2L_4$-, -$L_4$NHC(=O)NH$((CH_2)_mO)_p(CH_2)_mX_1L_4$-, -$L_4$NHC(=O)NH $((CH_2)_mO)_p(CH_2)_mX_2L_4$-, —$((CH_2)_mO)_p(CH_2)_m$— or —$(CH_2)_m$—;

$L_4$ is —$((CH_2)_m$;

$X_1$ is where the * indicates attachment point to $L_4$;

$X_2$ is

-continued
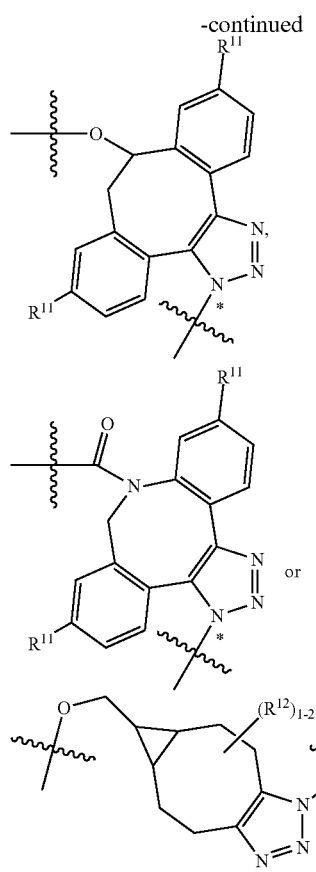
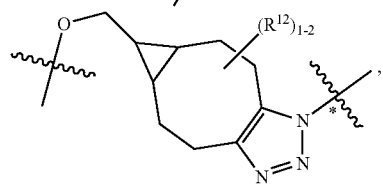
where the * indicates attachment point to $L_4$;
$R^{40}$ is
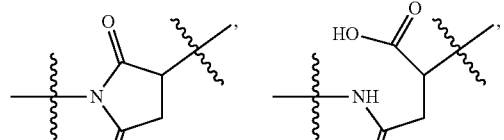
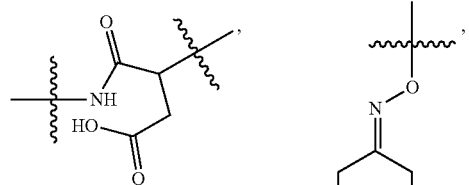
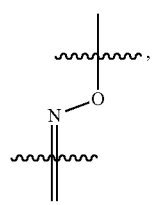
—NR$^7$C(=O)CH$_2$—, —NHC(=O)CH$_2$—,
—S(=O)$_2$CH$_2$CH$_2$—, —(CH$_2$)$_2$S(=O)$_2$CH$_2$CH$_2$—,
—NR$^7$S(=O)$_2$CH$_2$CH$_2$, —NR$^7$C(=O)CH$_2$CH$_2$—,
—NH—, —C(=O)—, —NHC(=O)—,
—CH$_2$NHCH$_2$CH$_2$—, —NHCH$_2$CH$_2$—, —S—,
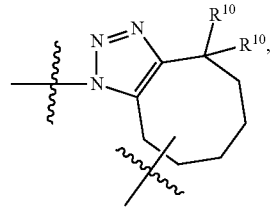
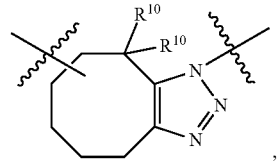
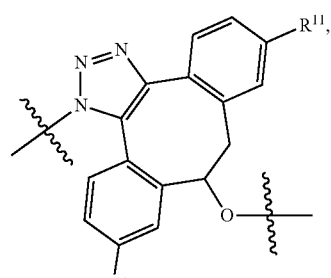
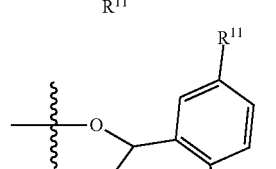
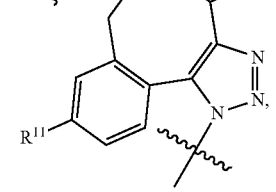
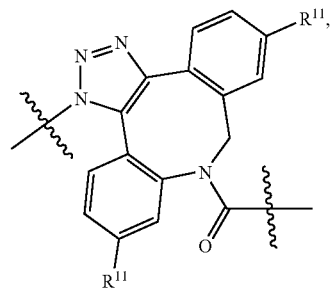
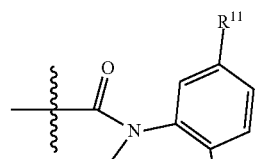
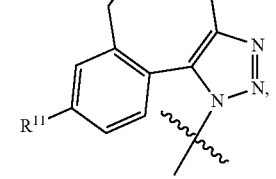

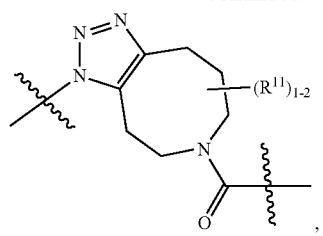,
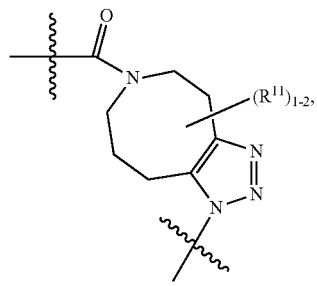,
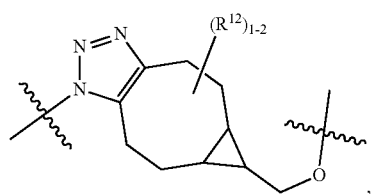,
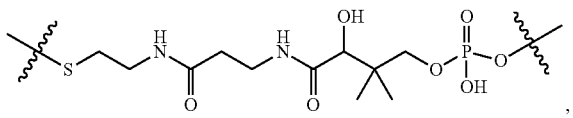,
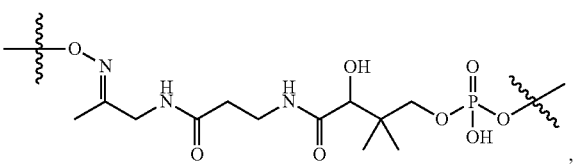,
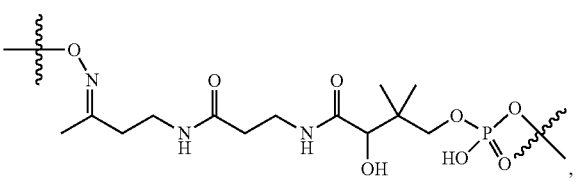,
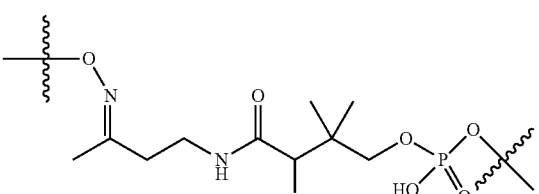,
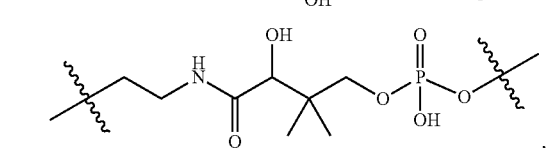,
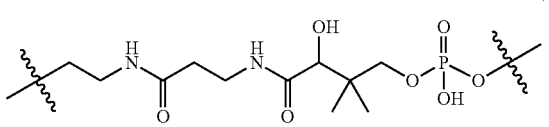 or

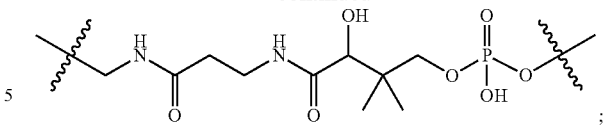;

each $R^7$ is independently selected from H and $C_1$-$C_6$alkyl;

each $R^{10}$ is independently selected from H, $C_1$-$C_6$alkyl, F, Cl, and —OH;

each $R^{11}$ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;

each $R^{12}$ is independently selected from H, $C_{1\text{-}6}$alkyl, fluoro, benzyloxy substituted with —C(=O)OH, benzyl substituted with —C(=O)OH, $C_{1\text{-}4}$alkoxy substituted with —C(=O)OH and $C_{1\text{-}4}$alkyl substituted with —C(=O)OH;

each m is independently selected from 1, 2, 3, 4, 5, 6, 7, 8, 9 and 10, and each p is independently selected from 1, 2, 3, 4, 5, 6, 7, 8, 9, 10, 11, 12, 13 and 14.

Embodiment 29. The conjugate having the structure of Formula (E), Formula (E-1) or Formula (E-1a), wherein:

A represents an antibody fragment (e.g., Fab or Fab') that specifically binds to human cKIT;

y is an integer from 1 to 10;

$R^5$ is H, —CH$_3$ or —CD$_3$;

$R^6$ is —NH$_2$ or —OH;

$L_{40}$ is -$L_6R^{40}$;

$L_6$ is —((CH$_2$)$_m$O)$_p$(CH$_2$)$_m$X$_1$L$_4$-, —((CH$_2$)$_m$O)$_p$(CH$_2$)$_m$X$_2$L$_4$-, -L$_4$NHC(=O)NH((CH$_2$)$_m$O)$_p$(CH$_2$)$_m$X$_1$L$_4$-, -L$_4$NHC(=O)NH((CH$_2$)$_m$O)$_p$(CH$_2$)$_m$X$_2$L$_4$-, —((CH$_2$)$_m$O)$_p$(CH$_2$)$_m$— or —(CH$_2$)$_m$—;

$L_4$ is —((CH$_2$)$_m$;

$X_1$ is

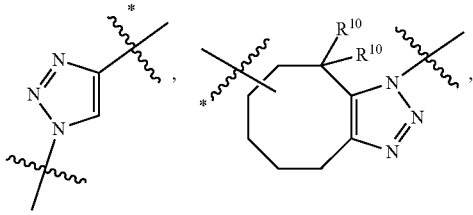

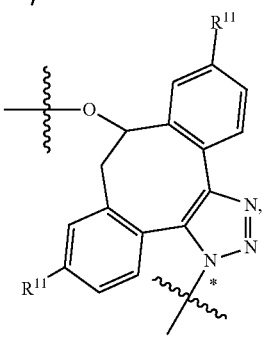

-continued
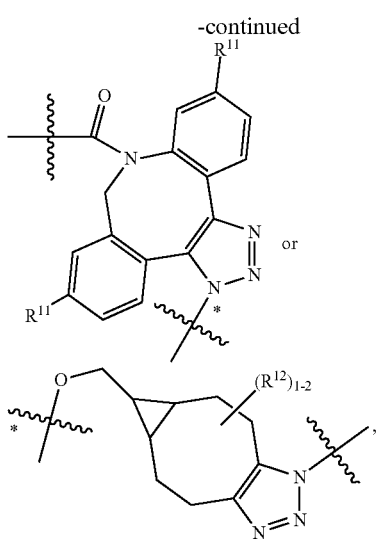
or
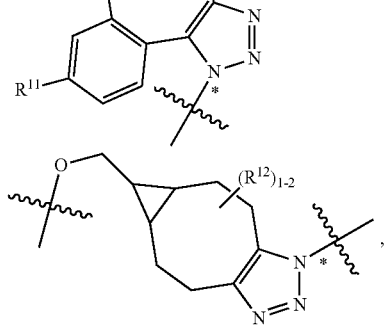
where the * indicates attachment point to $L_4$;
$X_2$ is
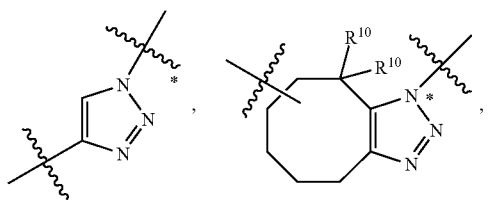
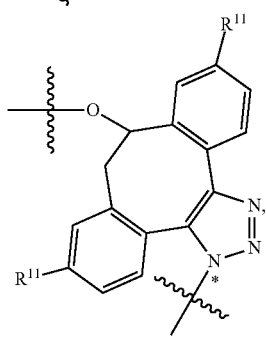
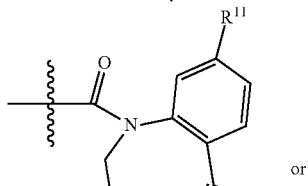
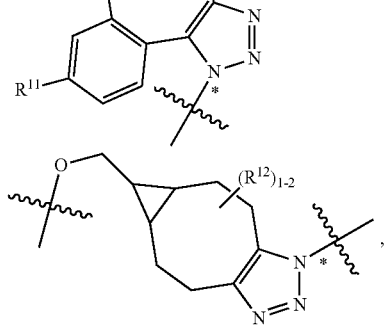
where the * indicates attachment point to $L_4$;
$R^{40}$ is
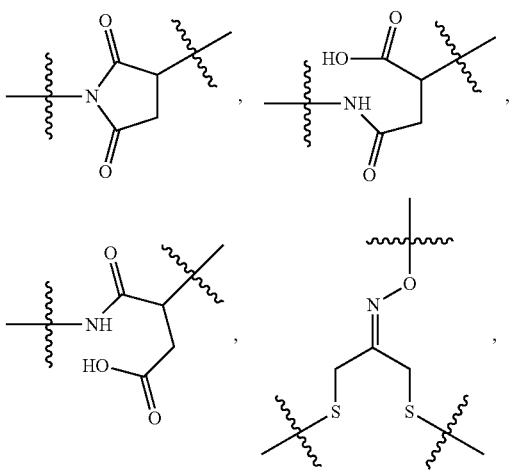
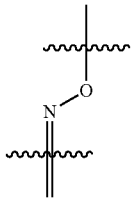
—NR$^7$C(=O)CH$_2$—, —NHC(=O)CH$_2$—,
—S(=O)$_2$CH$_2$CH$_2$—, —(CH$_2$)$_2$S(=O)$_2$CH$_2$CH$_2$—,
—NR$^7$S(=O)$_2$CH$_2$CH$_2$, —NR$^7$C(=O)CH$_2$CH$_2$—,
—NH—, —C(=O)—, —NHC(=O)—,
—CH$_2$NHCH$_2$CH$_2$—, —NHCH$_2$CH$_2$—, —S—,
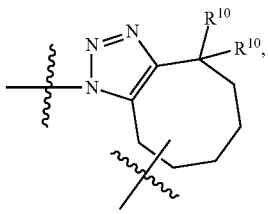
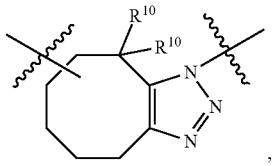
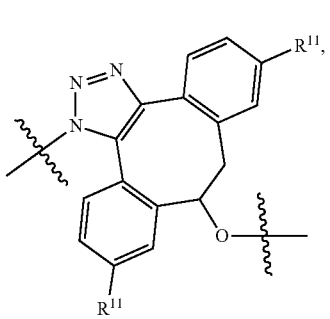

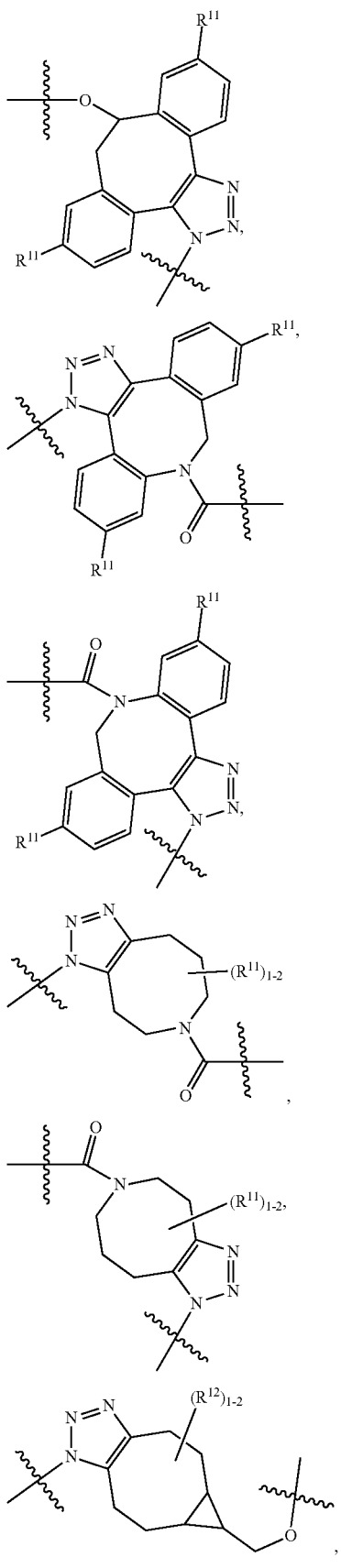

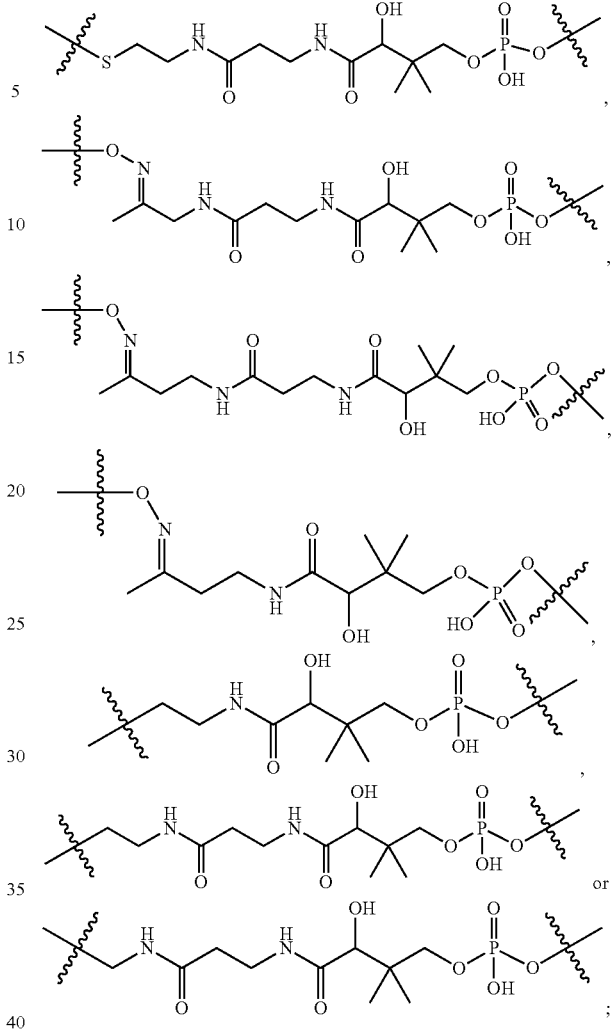

each $R^7$ is independently selected from H and $C_1$-$C_6$alkyl;
each $R^{10}$ is independently selected from H, $C_1$-$C_6$alkyl, F, Cl, and —OH;
each $R^{11}$ is independently selected from H, $C_1$-$C_6$alkyl, F, Cl, —NH$_2$, —OCH$_3$, —OCH$_2$CH$_3$, —N(CH$_3$)$_2$, —CN, —NO$_2$ and —OH;
each $R^{12}$ is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;
each m is independently selected from 1, 2, 3, 4, 5, 6, 7, 8, 9 and 10, and
each p is independently selected from 1, 2, 3, 4, 5, 6, 7, 8, 9, 10, 11, 12, 13 and 14.

Embodiment 30. The conjugate having the structure of Formula (E), Formula (E-1) or Formula (E-1a), wherein:
A represents an antibody fragment (e.g., Fab or Fab') that specifically binds to human cKIT;
y is an integer from 1 to 10;
$R^5$ is —CH$_3$;
$R^6$ is —NH$_2$;
$L_{40}$ is -$L_6R^{40}$;
$L_6$ is —((CH$_2$)$_m$O)$_p$(CH$_2$)$_m$X$_1$L$_4$-, —((CH$_2$)$_m$O)$_p$(CH$_2$)$_m$—, -L$_4$NHC(=O)NH((CH$_2$)$_m$O)$_p$(CH$_2$)$_m$X$_1$L$_4$-, -L$_4$NHC(=O)NH ((CH$_2$)$_m$O)$_p$(CH$_2$)$_m$X$_2$L$_4$-, or —(CH$_2$)$_m$—

$L_4$ is $-((CH_2)_m$;
$X_1$ is
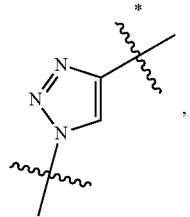 [SMILES: *c1cn(*)nn1]
where the * indicates attachment point to $L_4$;
$R^{40}$ is
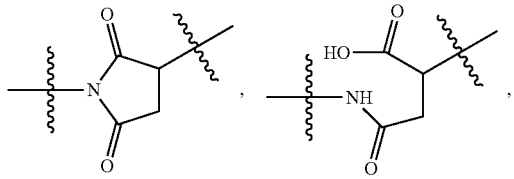
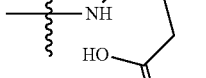
each m is independently selected from 1, 2, 3, 4, 5, 6, 7, 8, 9 and 10, and
each p is independently selected from 1, 2, 3, 4, 5, 6, 7, 8, 9, 10, 11, 12, 13 and 14.
Embodiment 31. The conjugate having the structure of Formula (E), Formula (E-1) or Formula (E-1a) selected from:
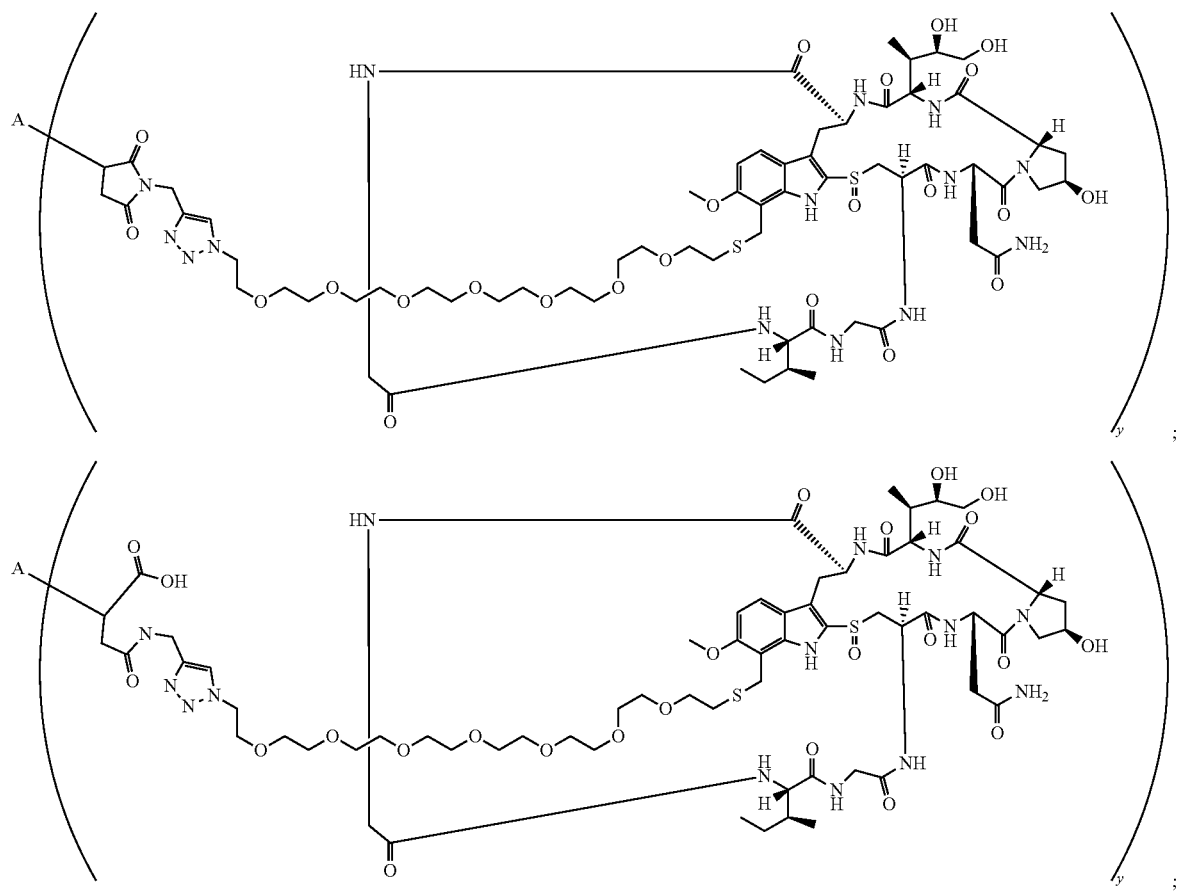

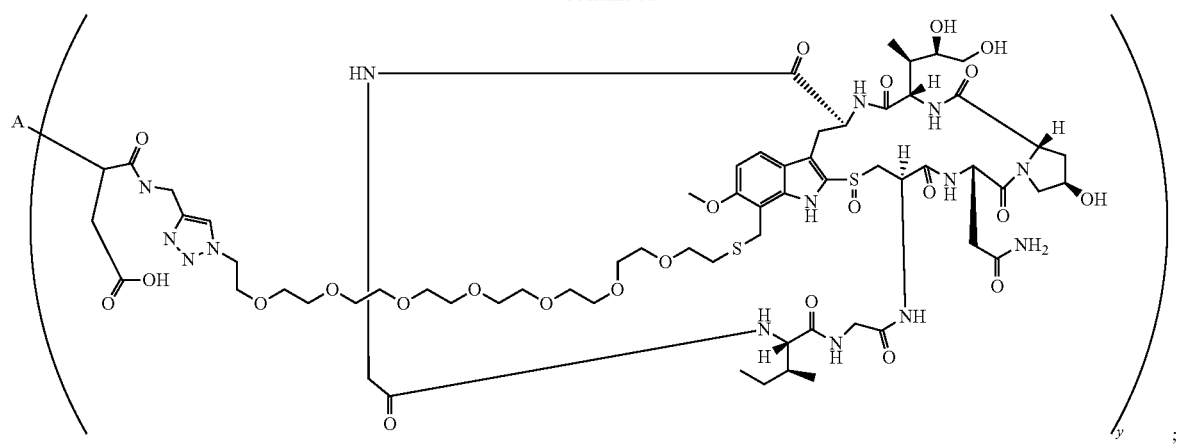
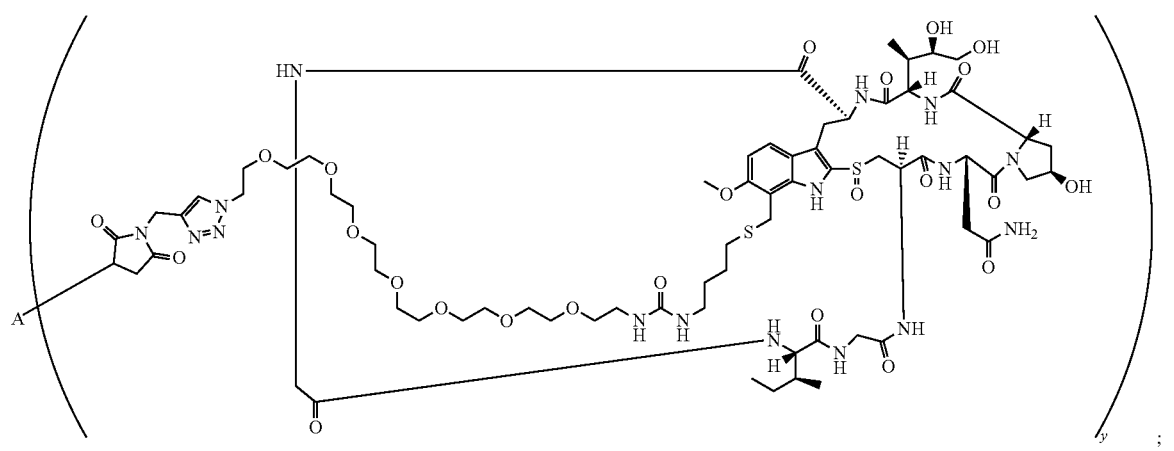
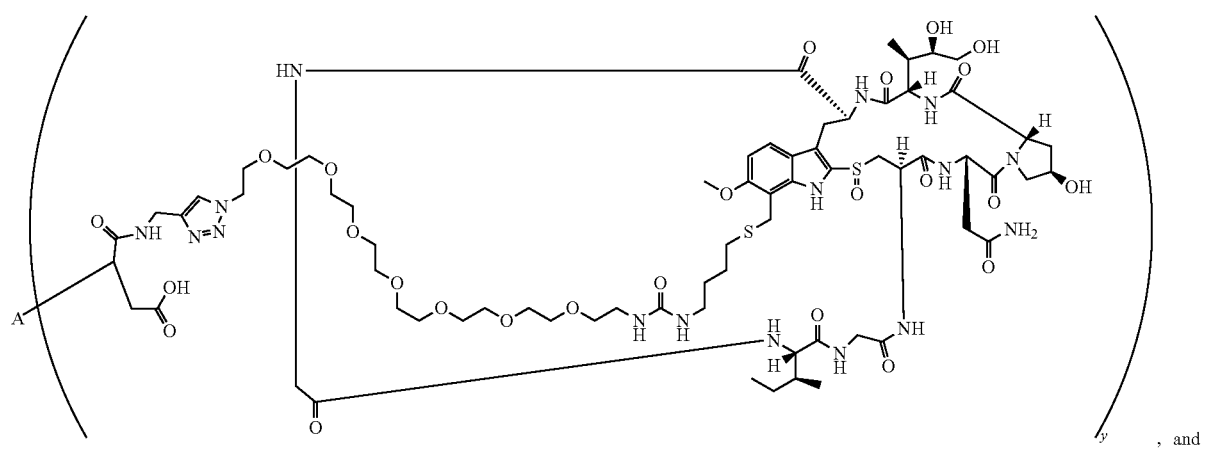

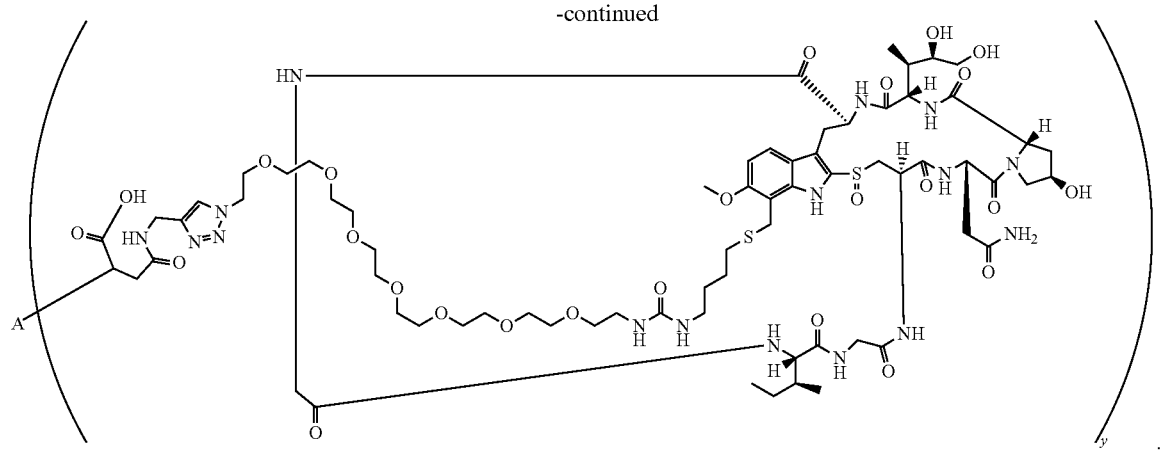
In another aspect of the antibody drug conjugate of the invention is selected from:
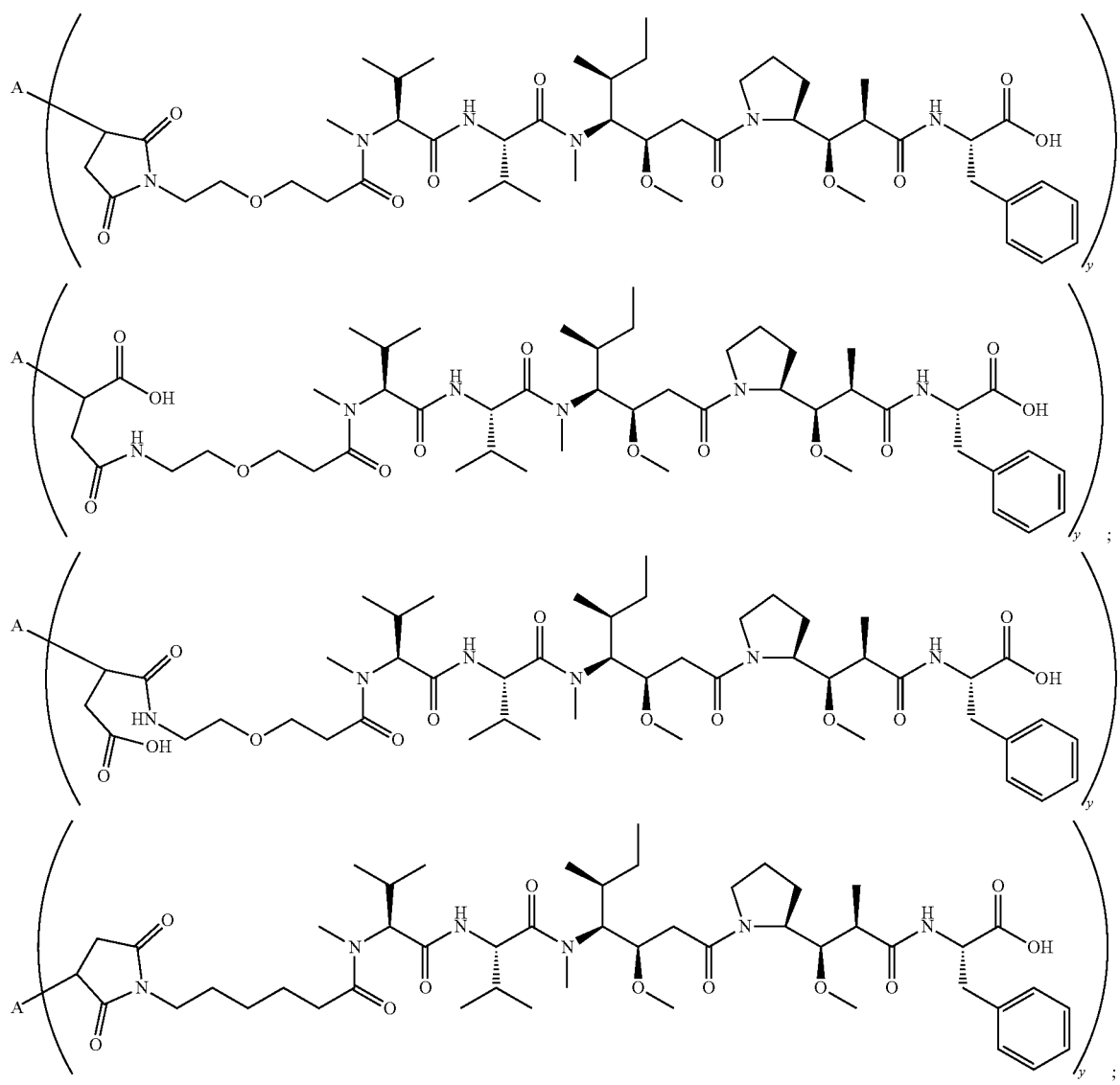

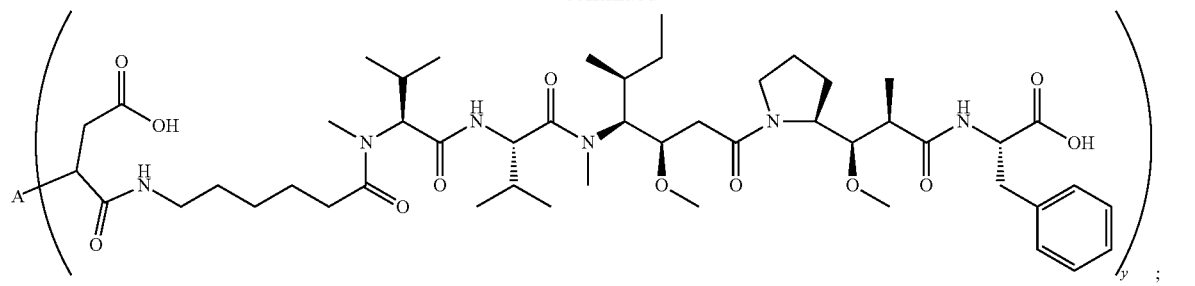
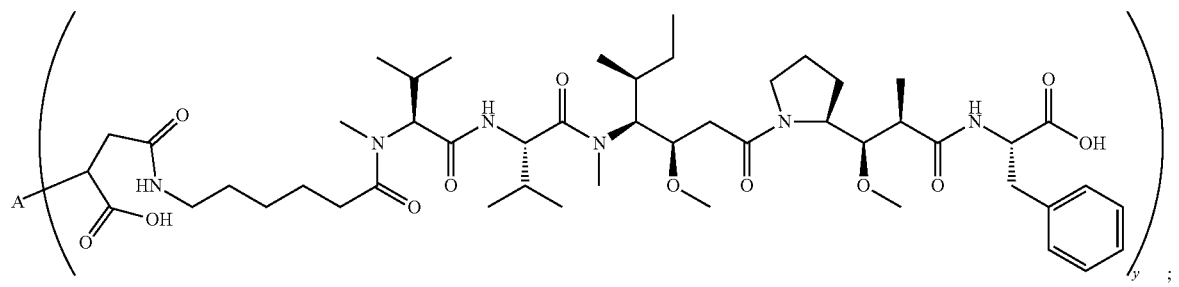
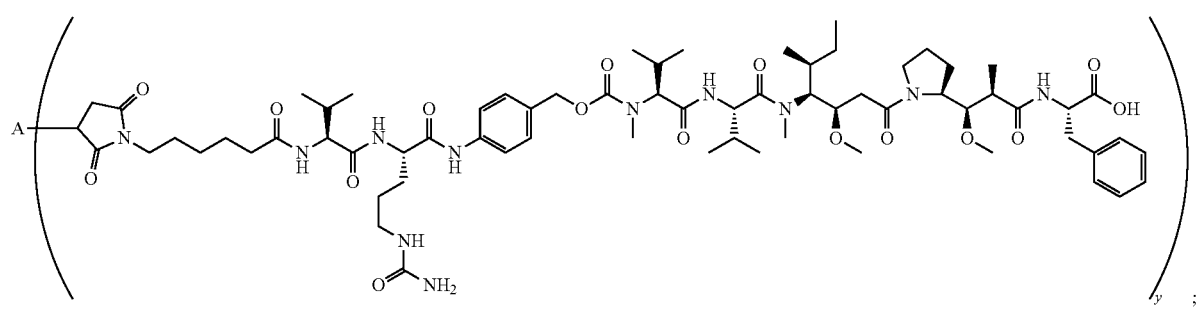
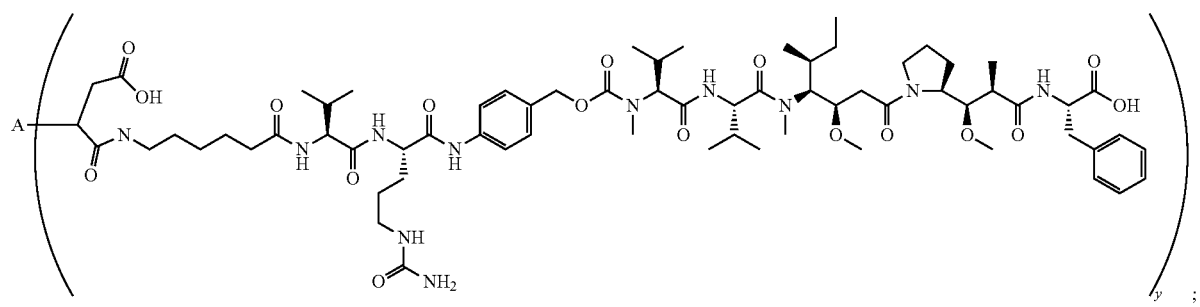
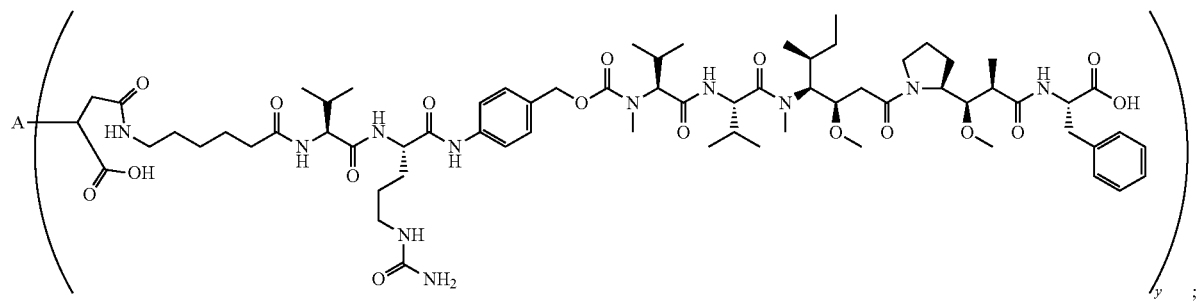

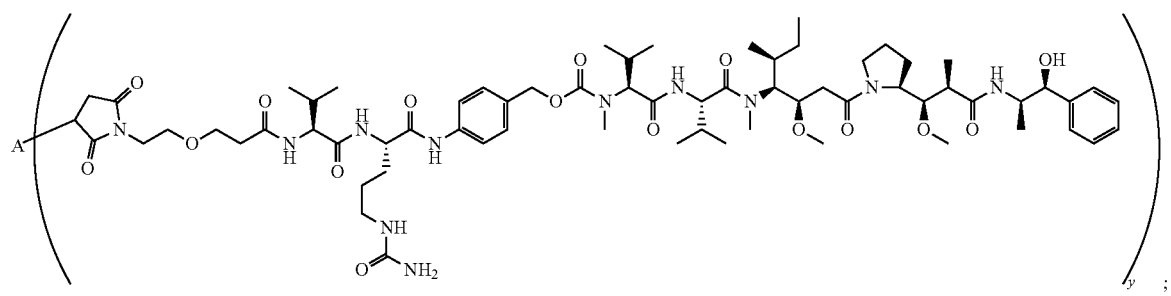;
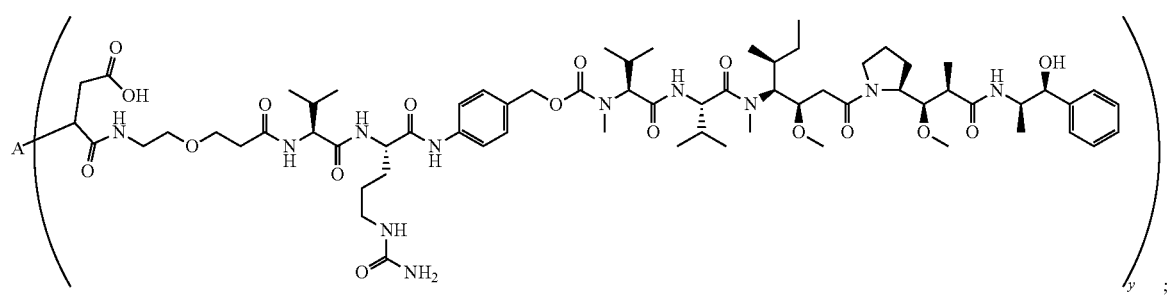;
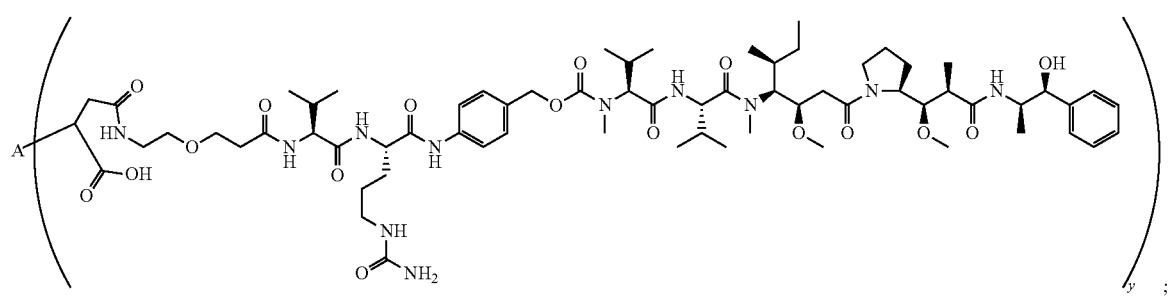;
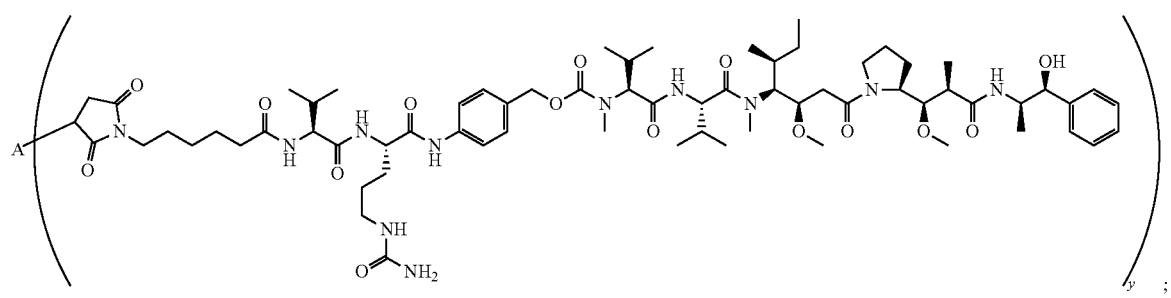;
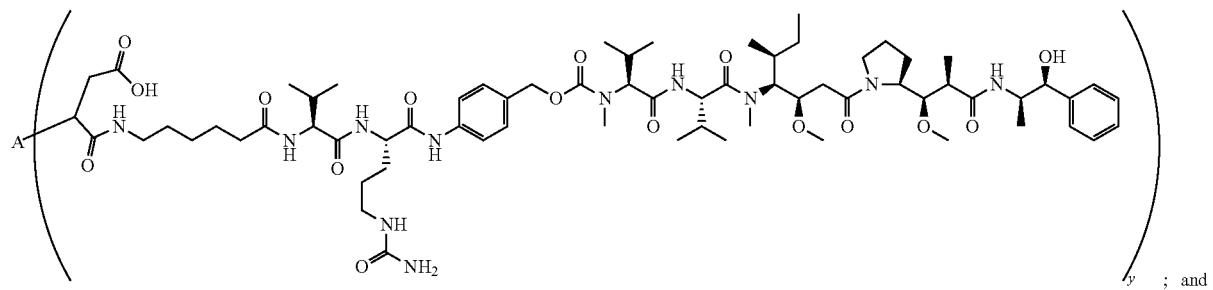; and

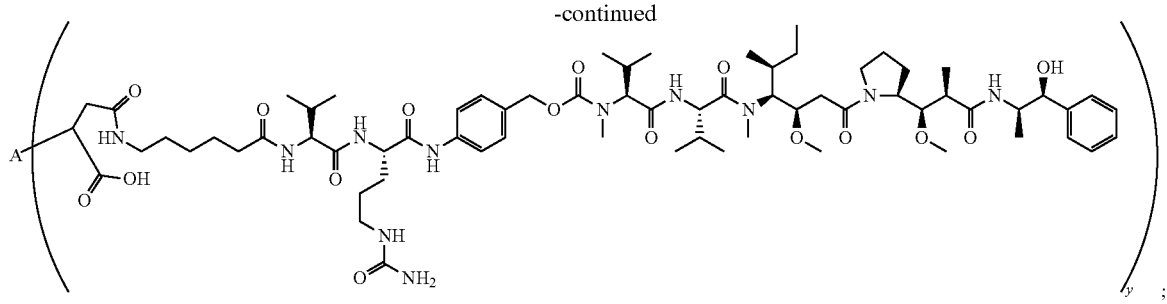
wherein A represents an antibody fragment (e.g., Fab or Fab') that specifically binds to human cKIT, and y is an integer from 1 to 10.
In another aspect of the antibody drug conjugate of the invention is selected from:
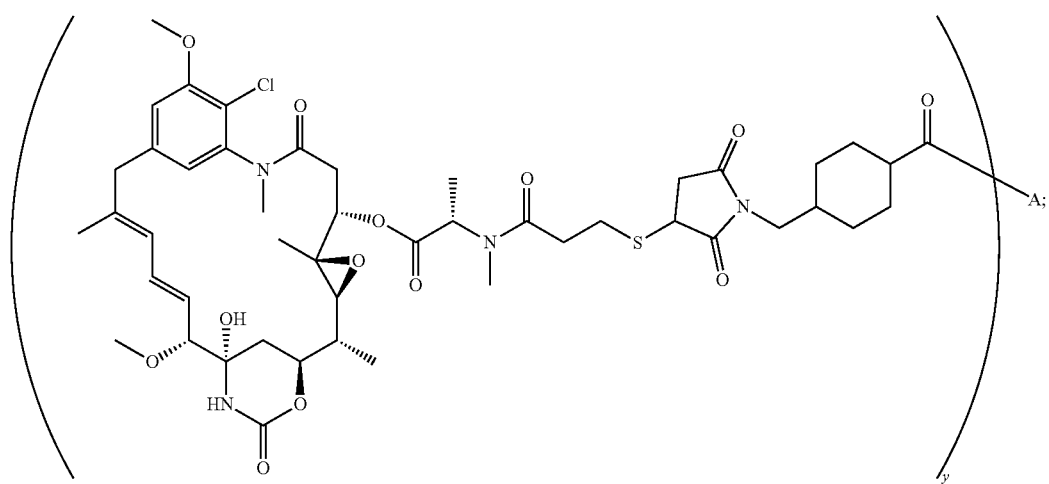
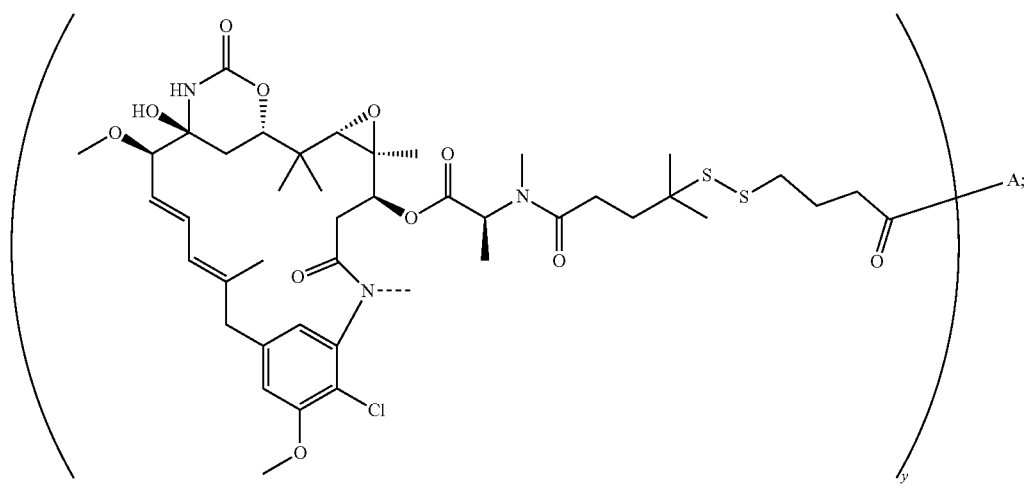

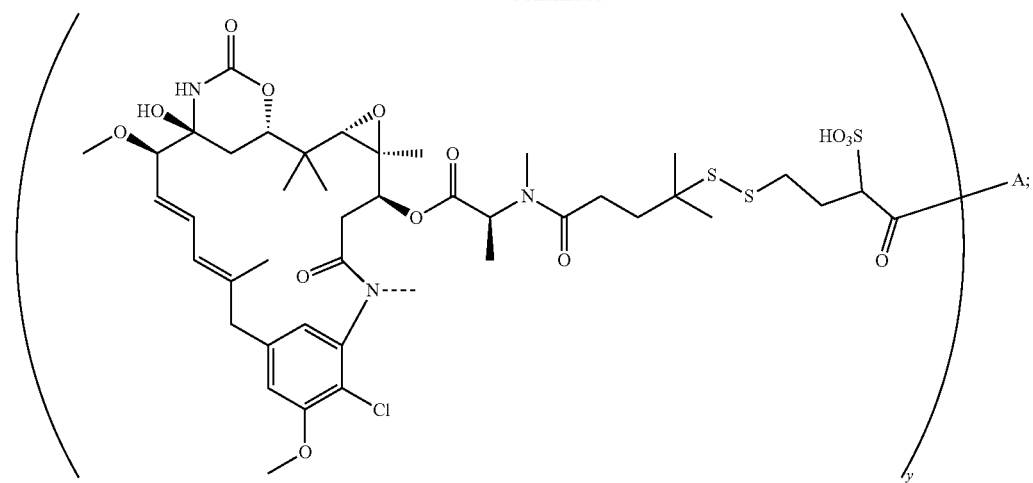
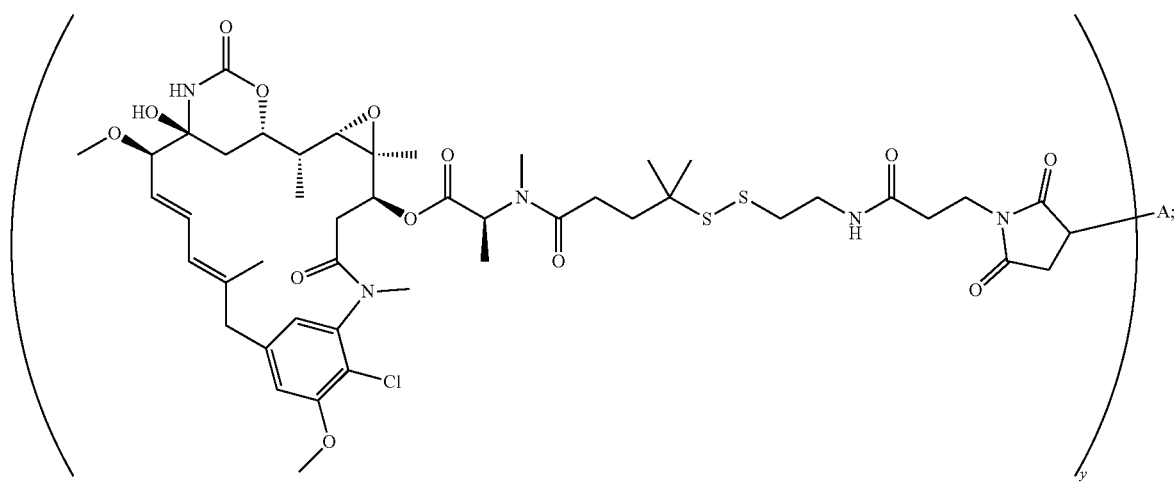
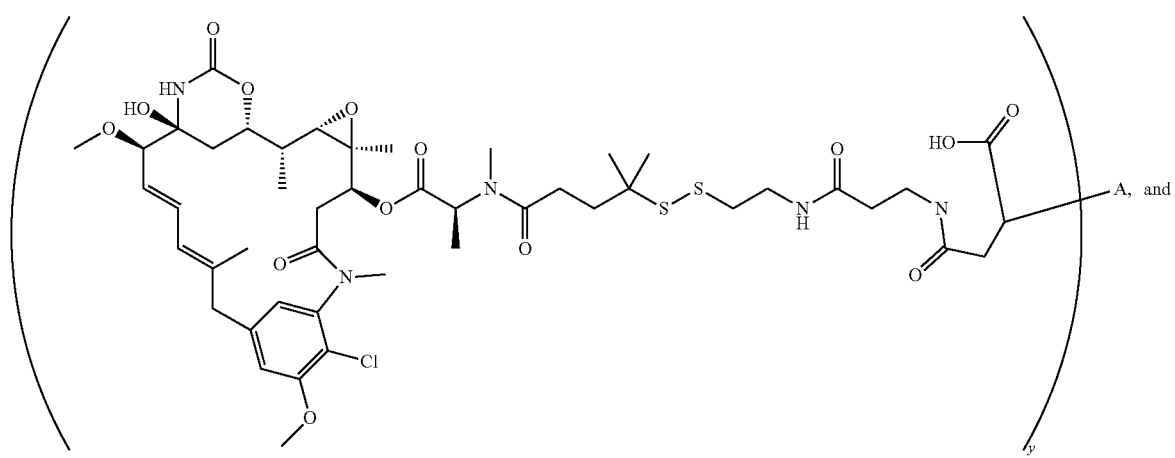

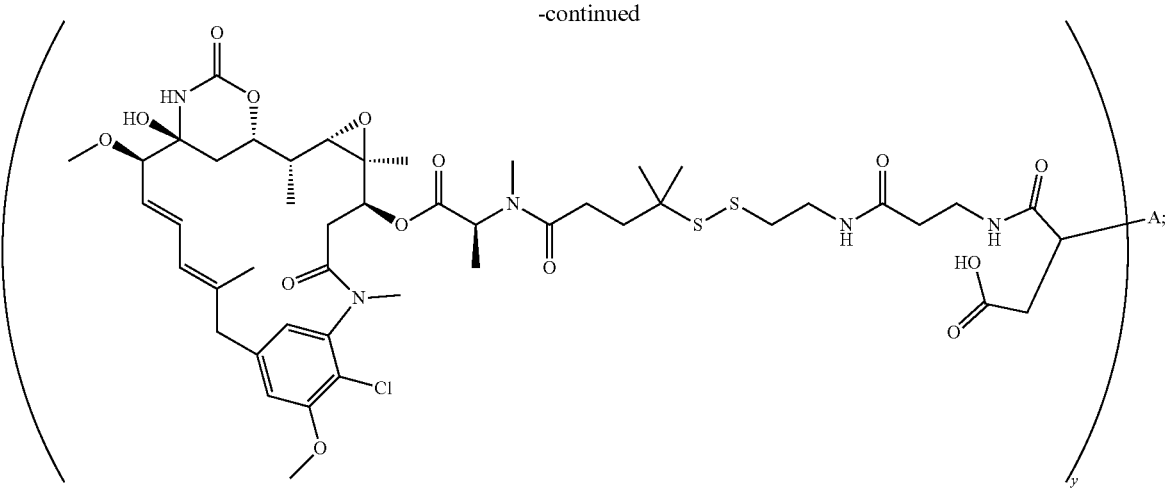

wherein A represents an antibody fragment (e.g., Fab or Fab') that specifically binds to human cKIT, and y is an integer from 1 to 10.

Synthesis of Exemplary Linker-Drug Compounds

Example 1: Synthesis of (S)-2-((2R,3R)-3-((S)-1-((3R,4S,5S)-4-((S)-2-((1R,3S,4S)-2-(3-(2-(2,5-Dioxo-2,5-dihydro-1H-pyrrol-1-yl)ethoxy)propanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (C1)

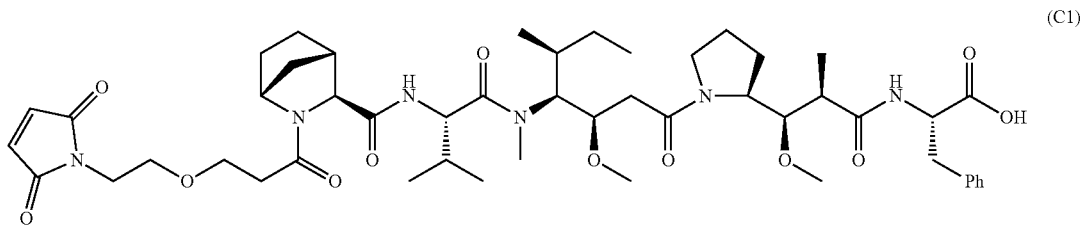 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H]1[C@H]2CC[C@H](C2)N1C(=O)CCOCCN1C(=O)C=CC1=O)C(C)C]

(C1)

Step 1: To a solution of BocVal-Dil-Dap-OH (1.00 g, 1.75 mmol) in N,N-dimethylformamide (DMF, 20.0 mL) at 0° C. were added N,N-diisopropyl ethylamine (DIEA, 0.677 g, 5.25 mmol) and 1-[bis(dimethylamino)methylene]-1H-1,2,3-triazolo[4,5-b]pyridinium 3-oxid hexafluorophosphate (HATU)(0.731 g, 1.93 mmol). The resulting solution was then stirred for 5 minutes and added to a solution of L-phenylalanine methyl ester HCl salt (0.377 g, 1.75 mmol) and DIEA (0.226 g, 1.75 mmol) in DMF (5.0 mL) at 0° C. The reaction mixture was warmed to room temperature, stirred for an additional 30 minutes and then concentrated. The residue was purified by reverse phase HPLC using the ISCO system, C18 column, eluted with 20-90% acetonitrile-water to obtain BocVal-Dil-Dap-PheOMe: MS m/z 733.4 (M+1); retention time 1.47 minutes.

Step 2: To a solution of BocVal-Dil-Dap-PheOMe (0.683 g, 0.932 mmol) obtained in step 1 in methanol (20 mL) was added HCl (4N in 1, 4-dioxane, 16 mL). The reaction mixture was stirred at room temperature for 7 hours and concentrated. The residue was dissolved in dioxane and lyophilized to obtain Val-Dil-Dap-PheOMe HCl salt: MS m/z 633.4 (M+1); retention time 0.96 minutes.

Step 3: (1R,3S,4S)—N-Boc-2-azabicyclo[2.2.1]heptane-3-carboxylic acid (12.6 mg, 0.052 mmol) was dissolved in DMF (1 mL) in a 15 ml round bottom flask. DIEA (12.3 mg, 0.095 mmol) and HATU (19 mg, 0.050 mmol) were added. The reaction mixture was stirred for 10 minutes and Val-Dil-Dap-PheOMe HCl salt (30 mg, 0.090 mmol) in DMF (1.0 mL) was added. The reaction mixture was stirred for 1 hour. LCMS analysis indicated the reaction was complete and the resulting mixture was purified by reverse phase HPLC using C18 column, eluted with 20-90% acetonitrile-H₂O containing 0.05% trifluoroacetic acid (TFA). The fractions containing the desired product were pooled and concentrated to obtain (1R,3S,4S)-tert-butyl 3-(((S)-1-(((3R,4S,5S)-3-methoxy-1-((S)-2-((1R,2R)-1-methoxy-3-(((S)-1-methoxy-1-oxo-3-phenylpropan-2-yl)amino)-2-methyl-3-oxopropyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate: MS m/z 856.6 (M+1); retention time 1.67 minutes.

Step 4: The product obtained in step 3 was dissolved in dichloromethane (DCM) (2.0 mL) and treated with TFA (0.5 mL). The reaction mixture was stirred at room temperature for 1 hour. LCMS analysis showed the reaction was complete. The reaction mixture was concentrated by rotary evaporator to give (S)-Methyl 2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate as a TFA salt: MS m/z 756.6 (M+1); retention time 1.22 minutes.

Step 5: In a 25 mL round bottom flask were added (S)-methyl 2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate TFA salt (38.4 mg, 0.044 mmol), LiOH Example 2: (S)-2-((2R,3R)-3-((S)-1-((3R,4S,5S)-4-((S)-2-((1R,3S,4S)-2-(6-(2,5-Dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (C2)

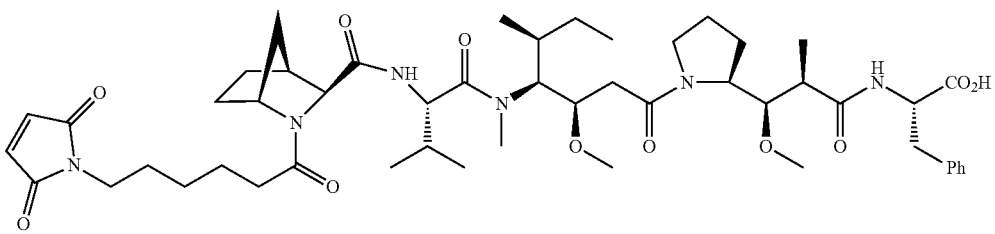

(C2)

monohydrate (50.0 mg, 1.19 mmol) and a solvent mixture of MeOH—H₂O (2:1, 4.0 mL). The mixture was stirred at room temperature for 60 hours. The LC-MS analysis indicated the reaction was complete. The reaction mixture was concentrated and purified by reverse phase HPLC, C18 column, eluted with acetonitrile-H₂O (10-70%) containing 0.05% TFA. The fractions containing the desired product were combined and concentrated to give (S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid as a TFA salt, MS m/z 742.5 (M+1). Retention time 1.15 minutes.

Step 6: To a solution of 3-(2-(maleimido)ethoxy)propanoic acid (2.2 mg, 0.010 mmol) in DMF (1 ml) were added HATU (3.7 mg, 0.0098 mmol) and DIEA (3.6 mg, 0.028 mmol). The reaction was stirred for 5 min, and then (S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (8 mg, 0.0093 mmol) in DMF (0.5 ml) was added. The reaction mixture was stirred at rt for 1 h and then concentrated and purified by preparative HPLC (10-60% acetonitrile-H₂O containing 0.05% TFA) to obtain (S)-2-((2R,3R)-3-((S)-1-((3R,4S,5S)-4-((S)-2-((1R,3S,4S)-2-(3-(2-(2,5-Dioxo-2,5-dihydro-1H-pyrrol-1-yl)ethoxy)propanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (C1). MS m/z 937.5 (M+H). Retention time 1.138 min.

(S)-2-((2R,3R)-3-((S)-1-((3R,4S,5S)-4-((S)-2-((1R,3S,4S)-2-(6-(2,5-Dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (2) was made according to the method in Example 1, except in step 6 6-(2,5-dioxo-2,5-dihydro-1H-pyrrol-1-yl)hexanoic acid (EMCA)(1.2 mg, 0.0058 mmol) in DMF (1.0 mL) was used in place of 3-(2-(maleimido)ethoxy)propanoic acid. (S)-2-((2R,3R)-3-((S)-1-((3R,4S,5S)-4-((S)-2-((1R,3S,4S)-2-(6-(2,5-Dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (2) MS m/z 935.6 (M+1). Retention time 1.17 minutes.

Example 3: (1R,3S,4S)—N—((S)-1-(((3R,4S,5S)-1-((S)-2-((1R,2R)-3-(((S)—N-1-(3-(4-((2,5-Dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (C3)

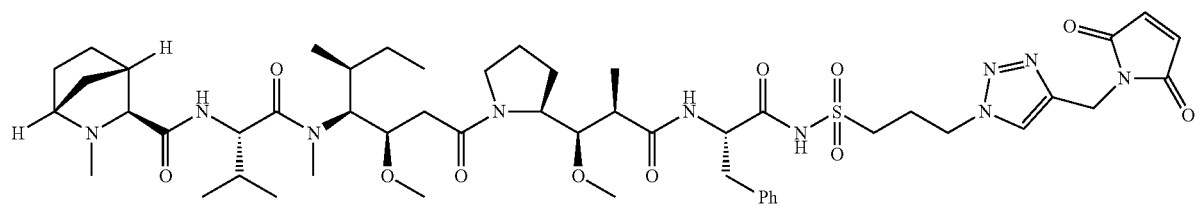

(C3)

Step 1: To a stirred solution of sodium azide (3.50 g, 53.8 mmol) in water (25 mL) was added a solution of 1,3-propane sulfone (6.10 g, 50.0 mmol) in acetone (25 mL). The reaction mixture was stirred at room temperature for 24 hours and concentrated to dryness. The resulting solid was suspended in diethyl ether (100 mL) and stirred at reflux for 1 hour. The suspension was cooled to room temperature and the solid was collected by filtration, washed with acetone and diethyl ether, and dried under vacuum, affording 3-azido-1-propanesulfonic acid. MS m/z 188.1 (M+1). ¹H NMR (400 MHz, CD₃OD): δ 3.47 (t, J=6.8 Hz, 2H), 2.87 (t, J=7.6 Hz, 2H), 2.07-2.00 (m, 2H).

Step 2: 3-Azido-1-propanesulfonic acid (2.07 g, 13.0 mmol) was suspended in toluene. PCl₅ (2.61 g, 13.0 mmol) was added. The mixture was heated at reflux for 3 hours. The reaction mixture was cooled to room temperature, and filtered to remove insolubles. The filter cake was washed with DCM. The combined filtrates were concentrated to give 3-azidopropane-1-sulfonyl chloride as a dark yellow oil, which was used in the next step without further purification.

Step 3: To NH₄OH (5 mIL) cooled at 0° C. was added 3-azidopropane-1-sulfonyl chloride (1.75 g, 9.53 mmol). After 10 minutes, the reaction mixture was warmed to room temperature and stirred at the same temperature for 3 hours. The oily mixture became clear. The reaction mixture was extracted with EtOAc three times. The organic phase was washed with brine, dried over anhydrous MgSO₄, and concentrated. The residual solvent was further removed under high vacuum for 18 hours to give 3-azidopropane-1-sulfonamide. MS m/z 187.1 (M+1). ¹H NMR (400 MHz, CDCl₃): δ 4.83 (s, 2H), 3.51 (t, J=6.4 Hz, 2H), 3.23 (t, J=7.6 Hz, 2H), 2.17-2.10 (m, 2H).

Step 4: (S)-2-((tert-Butoxycarbonyl)amino)-3-phenylpropanoic acid (100 mg, 0.38 mmol) was dissolved in DMF (4 mL), followed by addition of DIEA (0.395 mL, 2.26 mmol) and HATU (358 mg, 0.940 mmol). After 15 minutes, 3-azidopropane-1-sulfonamide (186 mg, 1.13 mmol) was added. The reaction mixture was stirred for 2 hours at which time LCMS analysis indicated the completion of the reaction. The resulting mixture was then purified by reverse phase HPLC using C18 column, eluted with 10-90% acetonitrile-H₂O containing 0.05% TFA. The fractions containing the desired product were pooled and lyophilized to obtain (S)-tert-butyl (1-(3-azidopropylsulfonamido)-1-oxo-3-phenylpropan-2-yl)carbamate. MS m/z 312.1 (M+1-Boc). Retention time 1.15 minutes. The product thus obtained (72.4 mg. 0.176 mmol) was dissolved in 3M methanolic HCl (5 mL). The solvent was removed under reduced pressure. The residue was taken up in acetonitrile and H₂O and lyophilized to give (S)-2-amino-N-((3-azidopropyl)sulfonyl)-3-phenylpropanamide as a pinkish yellowish solid. MS m/z 312.1 (M+1). ¹H NMR (400 MHz, CD₃OD): δ 7.42-7.31 (m, 5H), 4.16-4.13 (m, 1H), 3.51-3.47 (m, 4H), 3.32-3.26 (m, 1H), 3.13-3.08 (m, 1H), 2.00-1.94 (m, 2H).

Step 5: To Boc-Val-Dil-Dap-OH (195 mg, 0.34 mmol) dissolved in DMF (4 mL) were added DIEA (132 mg, 1.02 mmol) and HATU (108 mg, 0.28 mmol). The reaction mixture was stirred for 15 minutes at room temperature before (S)-2-amino-N-((3-azidopropyl)sulfonyl)-3-phenylpropanamide (59.2 mg, 0.17 mmol) was added. The reaction mixture was stirred for additional 2 hours at room temperature. And then purified by reverse-phase HPLC to afford the desired product (95 mg, 65% yield, MS m/z 865.4 (M+1), Retention time 1.43 minutes). The product was dissolved in 3M HCl in MeOH (3 mL). Solvents were removed under vacuum. Then acetonitrile and H₂O were added to the residue and the solution was lyophilized to obtain the desired product, (S)-1-(((3R,4S,5S)-1-((S)-2-((1R,2R)-3-(((S)—N-1-(3-azidopropylsulfonamido)-1-oxo-3-phenyl-propan-2-yl)amino)-1-methoxy-2-methyl-3-oxopropyl)pyrrolidin-1-yl)-3-methoxy-5-methyl-1-oxoheptan-4-yl)(methyl)amino)-2-amino-3-methyl-1-oxobutane. MS m/z 765.4 (M+1). Retention time 1.04 minutes.

Step 6: To (1R,3S,4S)-2-(tert-butoxycarbonyl)-2-azabicyclo[2.2.1]heptane-3-carboxylic acid (16.5 mg, 0.068 mmol) in DMF (2.0 mL) were added DIEA (17.6 mg, 0.137 mmol) and HATU (21.6 mg, 0.057 mmol). The reaction mixture was stirred at room temperature for 10 minutes before (S)-1-(((3R,4S,5S)-1-((S)-2-((1R,2R)-3-(((S)—N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-2-amino-3-methyl-1-oxobutane (20 mg, TFA salt, 0.023 mmol) was added. The reaction mixture was stirred for 2 hours at room temperature at which time LCMS analysis indicated the completion of the reaction. The resulting mixture was then purified by reverse phase HPLC using C18 column, eluted with 10-90% ACN-H₂O containing 0.05% TFA. The fractions containing the desired product were pooled and lyophilized to obtain (1R,3S,4S)—N—((S)-1-(((3R,4S,5S)-1-((S)-2-((1R,2R)-3-(((S)—N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-(tert-butoxycarbonyl)-2-azabicyclo[2.2.1]heptane-3-carboxamide. MS m/z 988.5 (M+1). Retention time 1.51 minutes. The product thus obtained (9.4 mg. 0.0095 mmol) was dissolved in methanolic HCl (3M, 2.0 mL). The solvent was removed slowly under reduced pressure. The residue was dissolved in acetonitrile and H₂O and lyophilized to give (1R,3S,4S)—N—((S)-1-(((3R,4S,5S)-1-((S)-2-((1R,2R)-3-(((S)—N-1-(3-Azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide as a HCl salt. MS m/z 888.5 (M+1). Retention time 1.10 minutes.

Step 7: (1R,3S,4S)—N—((S)-1-(((3R,4S,5S)-1-((S)-2-((1R,2R)-3-(((S)—N-1-(3-Azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (8.8 mg, 0.0099 mmol) was dissolved in MeOH (2.0 mL). Paraformaldehyde (10.1 mg, 0.337 mmol) and acetic acid (0.0102 mL) were added, followed by sodium cyanoborohydride (21.2 mg, 0.337 mmol). The reaction mixture was heated at 50° C. with stirring for 1 hour. Additional paraformaldehyde (10.1 mg, 0.337 mmol), acetic acid (0.0102 mL) and sodium cyanoborohydride (21.2 mg, 0.337 mmol) were added. After 1 hour at 50° C., LCMS analysis indicated the completion of the reaction. The resulting mixture was then purified by reverse phase HPLC using C18 column, eluted with 10-90% ACN-H₂O containing 0.05% TFA. The fractions containing the desired product were pooled and lyophilized to obtain (1R,3S,4S)—N—((S)-1-(((3R,4S,5S)-1-((S)-2-((1R,2R)-3-(((S)—N-1-(3-Azidopropylsulfonamido)-1-oxo-3-phenyl-propan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide. MS m/z 902.5 (M+1). Retention time 1.12 minutes.

Step 8: A solution of (1R,3S,4S)—N—((S)-1-(((3R,4S,5S)-1-((S)-2-((1R,2R)-3-(((S)—N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (5.2 mg, 0.0058 mmol), 1-(prop-2-yn-1-yl)-1H-pyrrole-2,5- dione (1.56 mg, 0.012 mmol) and CuSO$_4$ (0.7 mg, 0.004 mmol) in DMF (2.0 mL) and H$_2$O (0.5 mL) was treated with L-ascorbic acid sodium salt (2.5 mg, 0.014 mmol) and stirred at room temperature for 2 hours. Additional CuSO4 (0.7 mg, 0.004 mmol) and L-ascorbic acid sodium salt (2.5 mg, 0.014 mmol) were added. After additional 2 hours at room temperature, LCMS analysis indicated the completion of the reaction. The resulting mixture was then purified by reverse phase HPLC using C18 column, eluted with 10-90% acetonitrile-H$_2$O containing 0.05% TFA. The fractions containing the desired product were pooled and lyophilized to obtain (1R,3S,4S)—N—((S)-1-(((3R,4S,5S)-1-((S)-2-((1R, 2R)-3-(((S)—N-1-(3-(4-((2,5-Dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (C3). MS m/z 1037.4 (M+1). Retention time 1.00 minutes.

Example 4: Synthesis of (S)-2-((bis(dimethylamino)methylene)amino)-1-(((3R,4S,5S)-1-((S)-2-((1R,2R)-3-(((S)—N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (C4)

concentrated to give 3-azidopropane-1-sulfonyl chloride as a yellow-brown oil, which was used in the next step without further purification.

Step 3: NH$_4$OH (28%, 5 mL) was cooled to 0° C. 3-azidopropane-1-sulfonyl chloride (1.75 g, 9.53 mmol) was added. After 10 min, the reaction was warmed to rt, and then was stirred for 3 hours at rt. The two phases became homogeneous. The reaction mixture was extracted with EtOAc three times. The combined organic phases was washed with brine, dried over MgSO$_4$, and concentrated on a rotary evaporator followed by high vacuum for 18 h to give 3-azidopropane-1-sulfonamide. MS m/z 187.1 (M+23). $^1$H NMR (400 MHz, CDCl$_3$): δ 4.83 (s, 2H), 3.51 (t, J=6.4 Hz, 2H), 3.23 (t, J=7.6 Hz, 2H), 2.17-2.10 (m, 2H).

Step 4: (S)-2-((tert-Butoxycarbonyl)amino)-3-phenylpropanoic acid (100 mg, 0.38 mmol) was dissolved in DMF (4 mL). DIEA (0.395 mL, 2.26 mmol) and HATU (358 mg, 0.94 mmol) were added. After 15 min, 3-azidopropane-1-sulfonamide (186 mg, 1.13 mmol) was added. The reaction was stirred for 2 h. LCMS indicated a completion of the reaction. The reaction mixture was purified by preparative HPLC using a 10-90% gradient to obtain (S)-tert-butyl (1-(3-azidopropylsulfonamido)-1-oxo-3-phenylpropan-2-yl)carbamate. MS m/z 312.1 (M+1-Boc). Retention time 1.15 min. The product thus obtained (72.4 mg. 0.176 mmol) was dissolved in methanolic HCl (3 M, 5 mL). The solvent was removed by evaporation. The residue was lyophilized from acetonitrile and H$_2$O to give (S)-2-amino-N-((3-azidopropyl)sulfonyl)-3-phenylpropanamide as a pinkish yellowish solid. MS m/z 312.1 (M+1)$^1$H NMR (400 MHz, CD$_3$OD): δ 7.42-7.31 (m, 5H), 4.16-4.13 (m, 1H), 3.51-3.47 (m, 4H), 3.32-3.26 (m, 1H), 3.13-3.08 (m, 1H), 2.00-1.94 (m, 2H).

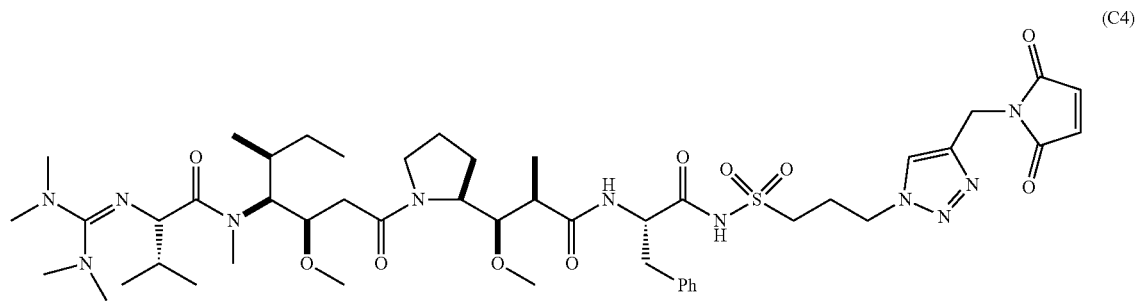

(C4)

Step 1: To a stirred solution of sodium azide (3.5 g, 54 mmol) in water (25 ml) was added a solution of 1,3-propane sulfone (6.1 g, 50 mmol) in acetone (25 ml). The reaction mixture was stirred at rt for 24 h, and concentrated. The resulting solid was suspended in diethyl ether (100 ml) and stirred at reflux for 1 h. The suspension was cooled to rt. The solid was collected by filtration, washed with acetone and diethyl ether, and dried under vacuum, affording of 3-azido-1-propanesulfonic acid. MS m/z 188.1 (M+23). $^1$H NMR (400 MHz, CD$_3$OD): δ 3.47 (t, J=6.8 Hz, 2H), 2.87 (t, J=7.6 Hz, 2H), 2.07-2.00 (m, 2H).

Step 2: 3-Azido-1-propanesulfonic acid (2.07 g, 13 mmol) was suspended in toluene. PCl$_5$ (2.61 g, 13 mmol) was added. The mixture was heated at reflux for 3 h. The reaction was cooled to rt. Insoluble matters were removed by filtration, and washed with DCM. The combined filtrate was Step 5: To Boc-Val-Dil-Dap-OH (195 mg, 0.3 4 mmol) in DMF (4 mL) were added DIEA (132 mg, 1.02 mmol) and HATU (108 mg, 0.28 mmol). It was stirred 15 min at rt. (S)-2-amino-N-((3-azidopropyl)sulfonyl)-3-phenylpropanamide (59.2 mg, 0.17 mmol) was added. The reaction was stirred for 2 h at rt. The crude material was purified by preparative HPLC to afford the desired product (95 mg, 65% yield, MS m/z 865.4 (M+1), Retention time 1.43 minutes). The product was dissolved in 3M HCl in MeOH (3 mL). Solvents were removed by evaporation. The residue was lyophilized from acetonitle-water to obtain (S)-1-(((3R,4S,5S)-1-((S)-2-((1R,2R)-3-(((S)—N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-2-amino-3-methyl-1-oxobutane,

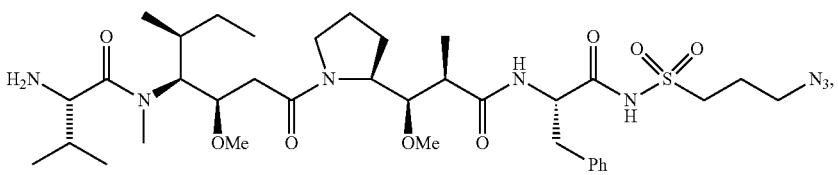 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)CCCN=[N+]=[N-])OC)N(C)C(=O)[C@@H](N)C(C)C]

as an HCl salt, MS m/z 765.4 (M+1), retention time 1.04 min.

Step 6: To (S)-1-(((3R,4S,5S)-1-((S)-2-((1R,2R)-3-(((S)—N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-2-amino-3-methyl-1-oxobutane HCl salt (20 mg, 0.025 mmol) in DMF (2 mL) were added DIEA (0.024 mL, 0.14 mmol) and HATU (21.6 mg, 0.057 mmol). The reaction was stirred at rt for 2 h. LCMS indicated completion of the reaction. The resulting mixture was then purified by preparative HPLC using a 10-90% gradient to obtain (S)-2-((bis(dimethylamino)methylene)amino)-1-(((3R,4S,5S)-1-((S)-2-((1R,2R)-3-(((S)—N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane as a TFA salt. MS m/z 863.5 (M+1). Retention time 1.169 min.

Step 7: (S)-2-((Bis(dimethylamino)methylene)amino)-1-(((3R,4S,5S)-1-((S)-2-((1R,2R)-3-(((S)—N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane TFA salt (87.4 mg, 0.089 mmol) and 1-(prop-2-yn-1-yl)-1H-pyrrole-2,5-dione (24.2 mg, 0.0179 mmol) were suspended in 3.0 mL each of t-BuOH and water. The reaction vessel was filled with $N_2$ by vacuum-fill cycle with $N_2$ five times. Degassed solutions of sodium L-ascorbate (17.7 mg, 0.089 mmol) in $H_2O$ (2.4 ml) and $CuSO_4$ (2.86 mg, 0.018 mmol) in $H_2O$ (0.6 ml) were added successively and the reaction was stirred at rt for 5 h. LCMS indicated completion of the reaction. The crude material was purified by preparative HPLC using a 20-45% gradient to obtain (S)-2-((bis(dimethylamino)methylene)amino)-1-(((3R,4S,5S)-1-((S)-2-((1R,2R)-3-(((S)—N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (C4) as a TFA salt. MS m/z 998.5 (M+1). Retention time 1.014 min.

Example 5: Synthesis of 6'O-methyl-7'C-((23-(4-((2,5-dioxo-2,5-dihydro-1H-pyrrol-1-yl)methyl)-1H-1,2,3-triazol-1-yl)-3,6,9,12,15,18,21-heptaoxatricosanthio)methyl)-α-Amanitin (C5), 7'C-((23-azido-3,6,9,12,15,18,21-heptaoxatricosanthio)methyl)-α-Amanitin (A-3) and 6'O-methyl-7'C-((23-azido-3,6,9,12,15,18,21-heptaoxatricosanthio)methyl)-α-Amanitin (A4)

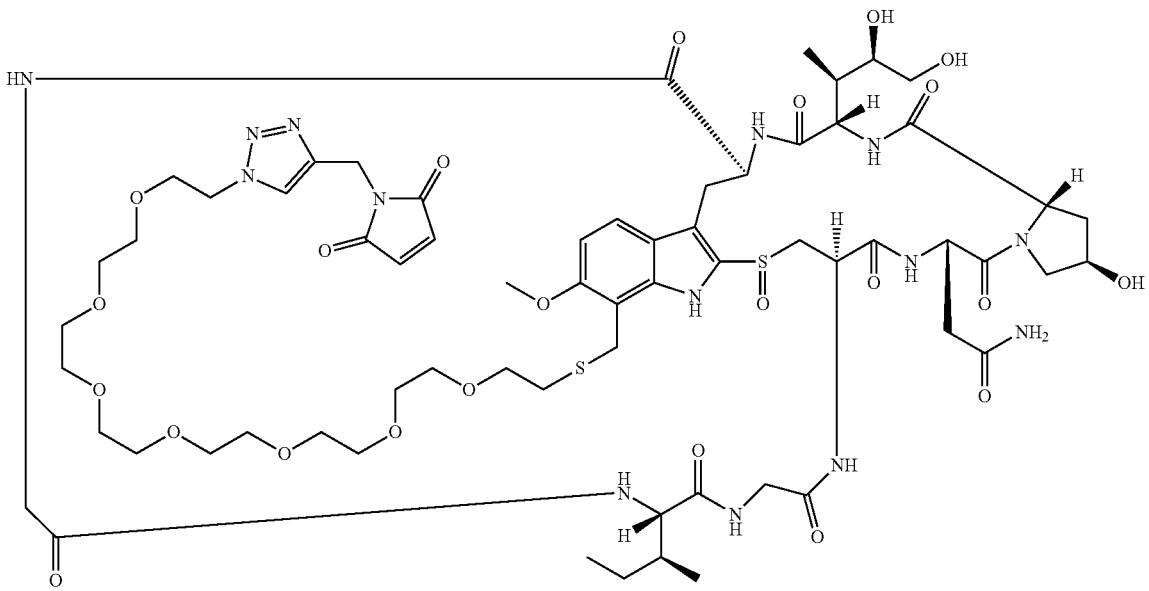

(C5)

Step 1: Formaldehyde (0.035 mL, 0.44 mmol) and 23-azido-3,6,9,12,15,18,21-heptaoxatricosane-1-thiol (35 mg, 0.11 mmol) were added to a solution of α-Amanitin (20 mg, 0.022 mmol) in MeOH (2 mL). Triethylamine (1.2 mL, 8.7 mmol) and acetic acid (0.25 mL, 4.4 mmol) were added to the reaction mixture and flushed with $N_2$ gas three times. The reaction mixture was stirred at 40° C. for 2 days. After concentration in vacuo, the residue was then purified by HPLC and lyophilized to give 7'C-((23-azido-3,6,9,12,15, 18,21-heptaoxatricosanthio)methyl)-α-Amanitin. MS (m+1)=1342.4, HPLC Peak RT=0.834 min, 1H-NMR (MeOD, 500 MHz) δ 10.65 (s, 1H), 8.81 (m, 1H), 8.59 (d, 1H, J=2.0 Hz), 8.45 (m, 2H), 8.33 (s, 1H), 8.14 (d, 1H, J=10.5 Hz), 8.00 (d, 1H, J=12.0 Hz), 7.90 (d, 1H, J=11.0 Hz), 7.67 (s, 1H), 7.48 (d, 1H, J=11.0 Hz), 6.69 (d, 1H, J=10.5 Hz), 5.25 (m, 1H), 5.12 (m, 1H), 4.74 (bs, 1H), 4.61 (dd, 1H, J=6.5 and 12.0 Hz), 4.51 (m, 2H), 4.29 (dd, 1H, J=10.5 and 23.0 Hz), 4.09 (m, 3H), 3.92 (m, 1H), 3.38-3.73 (m, 43H), 3.29 (m, 2H), 3.21 (m, 1H), 3.06 (m, 1H), 3.12 (m, 1H), 2.91 (m, 1H), 2.56 (m, 2H), 2.39 (m, 2H), 2.00 (m, 1H), 1.60 (m, 2H), 1.15 (m, 1H), 0.94 (d, 3H, J=9.0 Hz), 0.85 (m, 6H).

Step 2: 7'C-((23-azido-3,6,9,12,15,18,21-heptaoxatricosanthio)methyl)-α-Amanitin (14.0 mg, 0.011 mmol) and DMSO (1 mL) were treated with methyliodide (0.0007 mL) and K2CO3 (1.5 mg) at rt and stirred at rt for 1 h. Additional methyliodide (0.0007 mL) and K2CO3 (1.5 mg) were added at rt and stirred at rt for 2 h. Additional methyliodide (0.0007 mL) and K2CO3 (1.5 mg) at rt and stirred at rt for 2 h, again. The reaction mixture was then purified by RP-C18 ISCO and lyophilized to give 6'O-methyl-7'C-((23-azido-3,6,9,12,15,18,21-heptaoxatricosanthio)methyl)-α-Amanitin. MS (m+2/2)=679.0, HPLC Peak RT=0.887 min, 1H-NMR (MeOD, 500 MHz) δ 10.75 (s, 1H), 8.83 (m, 1H), 8.64 (d, 1H, J=2.0 Hz), 8.52 (d, 1H, J=10.0 Hz), 8.47 (d, 1H, J=3.5 Hz), 8.36 (s, 1H), 8.18 (d, 1H, J=8.5 Hz), 8.05 (d, 1H, J=9.5 Hz), 7.96 (d, 1H, J=9.0 Hz), 7.70 (d, 1H, J=9.0 Hz), 7.69 (s, 1H), 6.98 (d, 1H, J=9.0 Hz), 5.33 (m, 1H), 5.18 (m, 1H), 4.80 (bs, 1H), 4.68 (dd, 1H, J=5.5 and 9.5 Hz), 4.56 (m, 2H), 4.35 (dd, 1H, J=9.0 and 18.5 Hz), 4.10-4.21 (m, 3H), 3.97 (m, 1H), 3.92 (s, 3H), 3.45-3.79 (m, 42H), 3.35-3.44 (m, 3H), 3.11 (m, 1H), 2.96 (m, 1H), 2.61 (m, 2H), 2.44 (m, 2H), 2.06 (m, 1H), 1.65 (m, 2H), 1.21 (m, 1H), 0.99 (d, 3H, J=7.0 Hz), 0.90 (m, 6H).

Step 3: 6'O-methyl-7'C-((23-azido-3,6,9,12,15,18,21-heptaoxatricosanthio)methyl)-α-Amanitin (8 mg, 0.006 mmol) and 1-(prop-2-yn-1-yl)-1H-pyrrole-2,5-dione (2 mg, 0.012 mmol) were added to t-butanol (0.5 mL) and the reaction mixture was flushed with $N_2$ gas five times. L-Ascorbic acid sodium salt (1 mg, 0.006 mmol), $CuSO_4$ (0.2 mg, 0.0012 mmol) and 0.5 mL of $H_2O$ were then added. The reaction mixture was flushed with $N_2$ gas five times and stirred at rt for 4 h, and then purified by RP-C18 ISCO to give 6'O-methyl-7'C-((23-(4-((2,5-dioxo-2,5-dihydro-1H-pyrrol-1-yl)methyl)-1H-1,2,3-triazol-1-yl)-3,6,9,12,15,18,21-heptaoxatricosanthio)methyl)-α-Amanitin (C5). MS (m+2/2) =746.5, HPLC Peak RT=0.850 min, 1H-NMR (MeOD, 500 MHz) δ 10.74 (s, 1H), 8.83 (m, 1H), 8.63 (d, 1H, J=2.0 Hz), 8.51 (d, 1H, J=10.0 Hz), 8.47 (d, 1H, J=3.5 Hz), 8.36 (s, 1H), 8.17 (d, 1H, J=8.5 Hz), 8.04 (d, 1H, J=10.0 Hz), 7.96 (d, 1H, J=9.5 Hz), 7.94 (s, 1H), 7.69 (d, 1H, J=9.0 Hz), 6.97 (d, 1H, J=9.0 Hz), 6.83 (s, 2H), 5.34 (m, 1H), 5.17 (m, 1H), 4.79 (bs, 1H), 4.75 (s, 2H), 4.68 (dd, 1H, J=5.0 and 9.5 Hz), 4.56 (m, 2H), 4.52 (t, 1H, J=5.0 Hz), 4.34 (dd, 1H, J=9.0 and 18.5 Hz), 4.08-4.20 (m, 3H), 3.97 (m, 1H), 3.91 (s, 3H), 3.39-3.78 (m, 38H), 3.10 (m, 1H), 2.94 (dd, 1H, J=14.0 and 15.0 Hz), 2.61 (m, 2H), 2.41 (m, 2H), 2.05 (m, 1H), 1.57-1.68 (m, 2H), 1.20 (m, 1H), 0.99 (d, 3H, J=7.0 Hz), 0.91 (m, 6H).

Example 6: Synthesis of 6'O-methyl-7'C-((4-(3-(23-((4-maleimido)methyl-1H-1,2,3-triazol-1-yl)-3,6,9,12,15,18,21-heptaoxatricosyl)ureido)butylthio)methyl)-α-Amanitin (C6)

(C6)

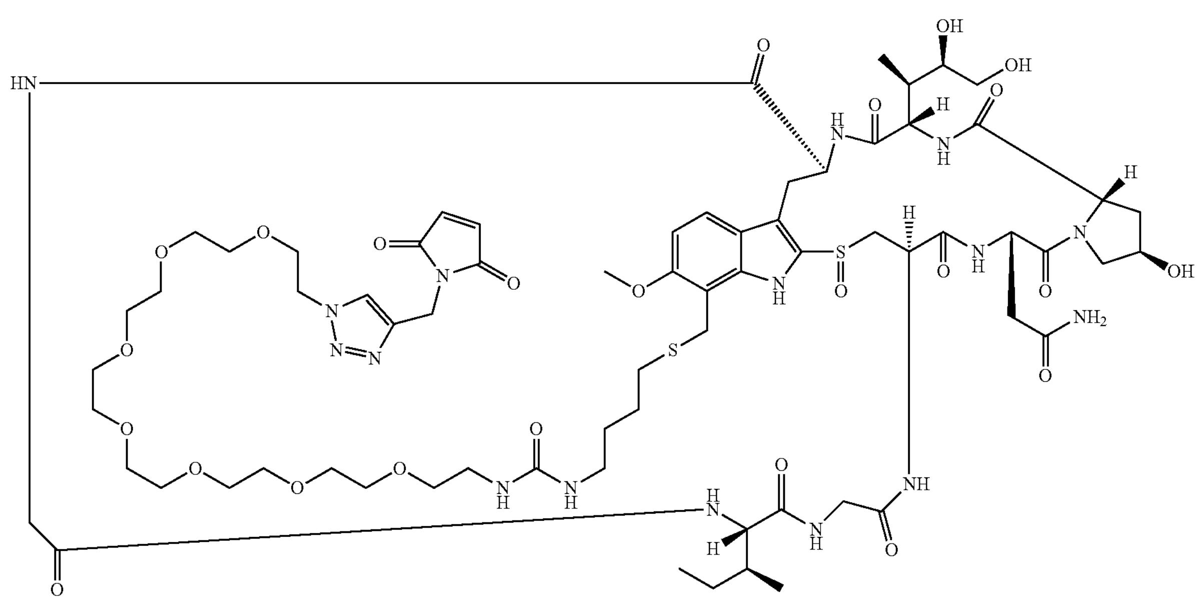

Step 1: Formaldehyde (0.027 mL, 0.33 mmol) and tert-butyl (4-mercaptobutyl)carbamate (i-7) (34 mg, 0.16 mmol) were added to a solution of α-Amanitin (A) (15 mg, 0.016 mmol) in MeOH (5 mL) and triethylamine (0.46 mL, 3.26 mmol) in a 40 mL vial, and the reaction mixture was stirred at 40° C. for 3 days. After concentration in vacuo, the residue was dissolved in 2 mL of MeOH and 408 μL of 2M of trimethylsilyl diazomethane in diethyl ether was added and the mixture was stirred for 2 h at rt. Then another 408 μL of 2M of trimethylsilyl diazomethane in diethyl ether was added and stirred at rt for 2 h. The reaction mixture was purified by HPLC and lyophilized to give 6'O-methyl-7'C-((4-t-butoxycarbonylaminobutylthio)methyl)-α-Amanitin (A-4),

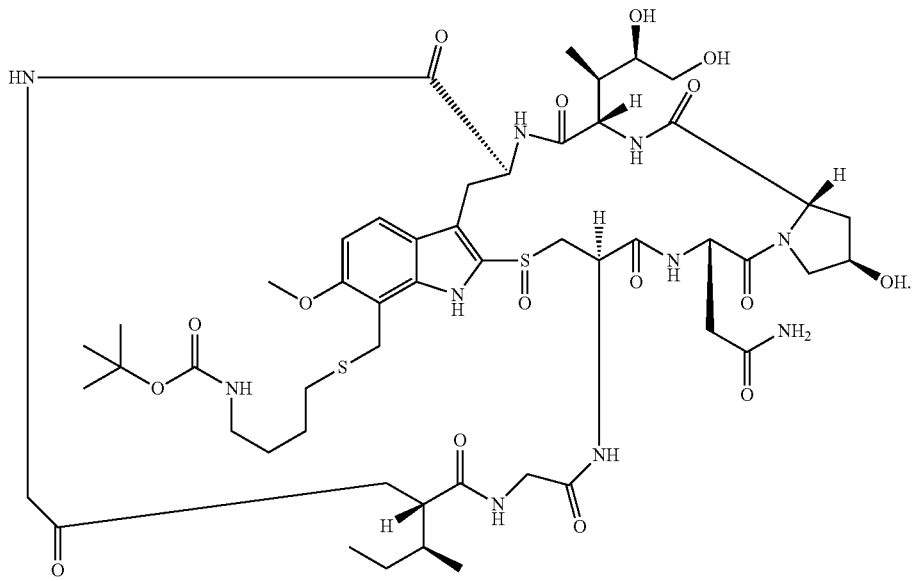

(A-4)

MS (m+2-boc/2)=525.8, HPLC Peak RT=0.936 min, 1H-NMR (MeOD-d4, 400 MHz) δ 10.78 (s, 1H), 8.84 (m, 1H), 8.59 (d, 1H, J=2.4 Hz), 8.48 (s, 1H), 8.46 (d, 1H, J=14.4 Hz), 8.35 (s, 1H), 8.15 (d, 1H, J=8.8 Hz), 8.01 (d, 1H, J=10.0 Hz), 7.92 (d, 1H, J=8.8 Hz), 7.69 (s, 1H), 7.63 (d, 1H, J=8.8 Hz), 6.92 (d, 1H, J=8.8 Hz), 5.28 (m, 1H), 5.13 (m, 1H), 4.73 (bs, 1H), 4.61 (dd, 1H, J=5.6 and 8.4 Hz), 4.51 (m, 2H), 4.30 (dd, 1H, J=8.8 and 18.4 Hz), 4.12 (m, 1H), 4.04 (d, 1H, J=13.2 Hz), 3.94 (d, 1H, J=13.2 Hz), 3.92 (m, 1H), 3.86 (s, 3H), 3.35-3.75 (m, 14H), 3.05 (m, 1H), 2.92 (m, 3H), 2.49 (m, 4H), 2.00 (m, 1H), 1.39-1.65 (m, 8H), 1.37 (s, 9H), 1.15 (m, 1H), 0.93 (d, 3H, J=7.2 Hz), 0.84 (m, 6H).

Step 2: TFA (1 mL) was added to 8 mg of compound (A-4) in a 40 mL vial and the resulting solution was allowed to stand at rt for 2 min and then concentrated under vacuum to give 6'O-methyl-7'C-((4-aminobutylthio)methyl)-α-Amanitin (A-5),

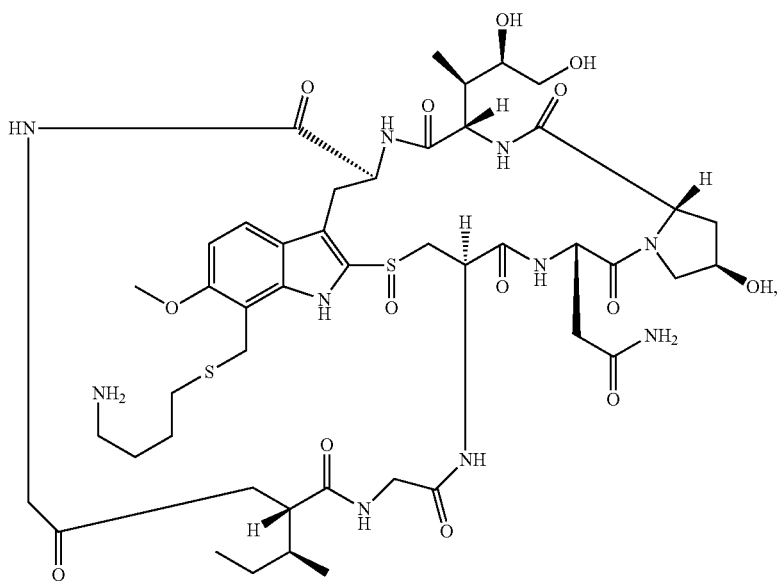

(A-5)

which was used without further purification. MS (m+1)=1050.4, HPLC Peak RT=0.635 min, 1H-NMR (MeOD-d4, 400 MHz) b 8.87 (m, 1H), 8.58 (d, 1H, J=2.4 Hz), 8.48 (d, 1H, J=10.4 Hz), 8.44 (d, 1H, J=1.6 Hz), 8.16 (d, 1H, J=8.4 Hz), 7.97 (d, 1H, J=9.6 Hz), 7.94 (d, 1H, J=9.2 Hz), 7.62 (d, 1H, J=8.8 Hz), 6.92 (d, 1H, J=9.2 Hz), 5.25 (m, 1H), 5.13 (m, 1H), 4.73 (m, 1H), 4.60 (dd, 1H, J=5.6 and 9.2 Hz), 4.49 (m, 2H), 4.28 (dd, 1H, J=8.8 and 18.4 Hz), 4.12 (m, 1H), 4.04 (d, 1H, J=13.2 Hz), 3.99 (s, 2H), 3.92 (m, 1H), 3.86 (s, 3H), 3.83 (s, 1H), 3.60-3.72 (m, 4H), 3.30-3.60 (m, 10H), 3.00-3.20 (m, 2H), 2.90 (m, 1H), 2.76 (m, 2H), 2.00 (m, 1H), 1.50-1.75 (m, 7H), 1.16 (d, 1H, J=5.6 Hz), 1.24 (m, 2H, J=7.6 Hz), 1.15 (m, 1H), 0.94 (d, 3H, J=6.8 Hz), 0.85 (m, 6H).

Step 3: Triethylamine (3 μL, 18 μmol) was added to a solution of compound (A-5) (7.5 mg, 7 mol) and 4-nitrophenyl (23-(4-((2,5-dioxo-2,5-dihydro-1H-pyrrol-1-yl)methyl)-1H-1,2,3-triazol-1-yl)-3,6,9,12,15,18,21-heptaoxatricosyl)carbamate (5.0 mg, 7 μmol) in DMF (1 mL) and the reaction mixture was stirred at rt for 2 h, purified by HPLC and lyophilized to give 6'O-methyl-7'C-((4-(3-(23-((4-maleimido)methyl-1H-1,2,3-triazol-1-yl)-3,6,9,12,15,18,21-heptaoxatricosyl)ureido)butylthio)methyl)-α-Amanitin (C6). MS (m+2/2)=803.5, HPLC Peak RT=0.834 min, 1H-NMR (MeOD-d4, 400 MHz) δ 10.76 (s, 1H), 8.84 (m, 1H), 8.59 (d, 1H, J=2.0 Hz), 8.49 (s, 1H), 8.47 (d, 1H, J=8.0 Hz), 8.15 (d, 1H, J=8.4 Hz), 8.01 (d, 1H, J=9.6 Hz), 7.92 (d, 1H, J=8.8 Hz), 7.90 (s, 1H), 7.63 (d, 1H, J=8.8 Hz), 6.92 (d, 1H, J=9.2 Hz), 6.79 (s, 2H), 5.28 (m, 1H), 5.13 (m, 1H), 4.74 (m, 1H), 4.71 (s, 2H), 4.62 (dd, 1H, J=5.2 and 9.6 Hz), 4.49 (m, 4H), 4.30 (dd, 1H, J=8.8 and 18.4 Hz), 4.14 (m, 1H), 4.04 (d, 1H, J=13.2 Hz), 3.94 (d, 1H, J=13.2 Hz), 3.92 (m, 1H), 3.85 (s, 3H), 3.80 (t, 2H, J=4.8 Hz), 3.35-3.75 (m, 38H), 2.90-3.10 (m, 4H), 2.92 (m, 1H), 2.40 (m, 4H), 2.01 (m, 1H), 1.38-1.65 (m, 6H), 1.15 (m, 1H), 0.94 (d, 3H, J=6.8 Hz), 0.85 (m, 6H).

Example 7: Synthesis of Tetrafluorophenyl ester of 6'O-methyl-7'C-((4-(3-(carboxy)propanecarboxamido)butylthio)methyl)-α-Amanitin (C7)

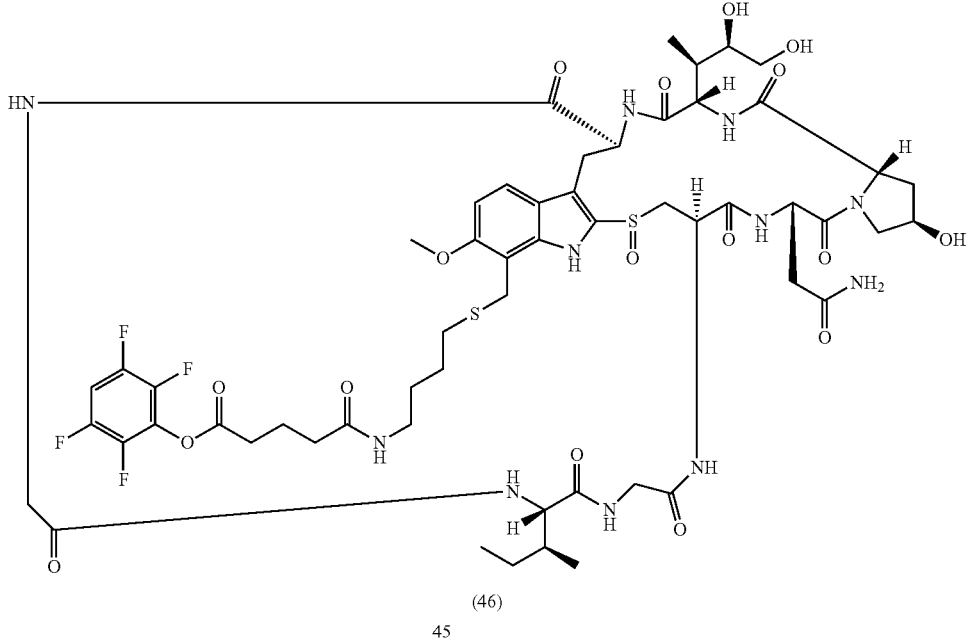

(C7)

(46)

(A-5) (5 mg, 5 μmol) and DMF (1 mL) were combined in a 40 mL vial to give a clear solution. bis(2,3,5,6-tetrafluorophenyl) glutarate (2 mg, 5 μmol) and DIEA (4 μL, 20 μmol) were added. After the reaction mixture was stirred at rt for 2 h, the reaction mixture was purified by HPLC to give Tetrafluorophenyl ester of 6'O-methyl-7'C-((4-(3-(carboxy)propanecarboxamido)butylthio)methyl)-α-Amanitin (C-7). MS (m+1)=1313.3, HPLC Peak RT=0.996 min, 1H-NMR (MeOD, 400 MHz) δ 10.78 (s, 1H), 8.85 (m, 1H), 8.59 (s, 1H), 8.49 (s, 1H), 8.47 (d, 1H, J=10.0 Hz), 8.35 (bs, 1H), 8.15 (d, 1H, J=8.0 Hz), 8.01 (d, 1H, J=9.6 Hz), 7.93 (d, 1H, J=8.8 Hz), 7.69 (bs, 1H), 7.63 (d, 1H, J=8.8 Hz), 7.36 (m, 1H), 6.92 (d, 1H, J=8.8 Hz), 5.27 (m, 1H), 5.14 (m, 1H), 4.75 (bs, 1H), 4.61 (dd, 1H, J=5.2 and 9.6 Hz), 4.51 (m, 2H), 4.30 (dd, 1H, J=8.4 and 18.0 Hz), 4.12 (m, 1H), 4.00 (d, 1H, J=13.2 Hz), 3.95 (d, 1H, J=13.2 Hz), 3.91 (m, 1H), 3.85 (s, 3H), 3.34-3.70 (m, 9H), 3.08 (m, 4H), 2.91 (m, 1H), 2.73 (t, 2H, J=14.4 Hz), 1.98 (t, 2H, J=7.6 Hz), 1.92-2.04 (m, 1H), 1.40-1.60 (m, 6H), 1.16 (m, 1H), 0.94 (d, 3H, J=6.8 Hz), 0.87 (m, 6H). Other compounds of Formula (A), Formula (B), Formula (A-1), Formula (A-2), Formula (A-3), Formula (B-1), Formula (A-1a), Formula (A-2a), Formula (A-3a) or Formula (B-1a) can be made using the methods of Examples 1-7 and appropriate starting materials.

Example 8: Preparation of the Linker Payload MPET.DM4

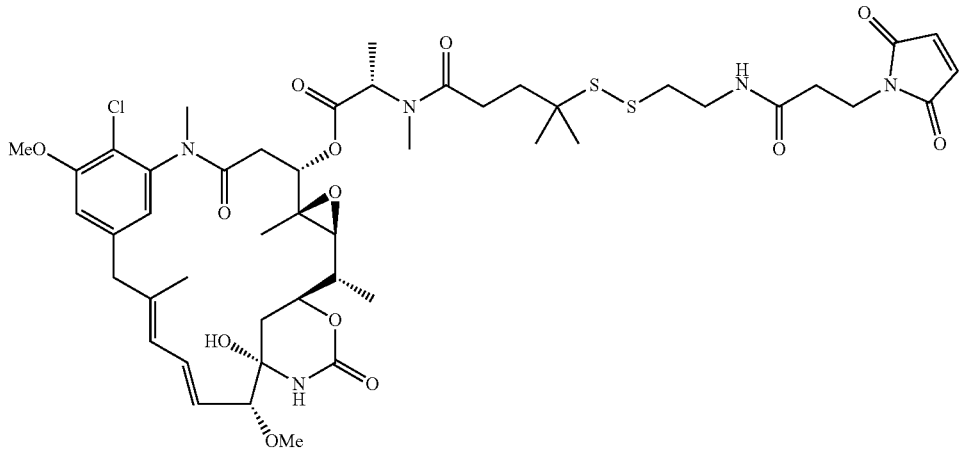 [SMILES: COc1cc2cc(c1Cl)N(C)C(=O)C[C@H](OC(=O)[C@H](C)N(C)C(=O)CCC(C)(C)SSCCNC(=O)CCN1C(=O)C=CC1=O)[C@]1(C)O[C@H]1[C@H](C)[C@@H]1C[C@@](O)(NC(=O)O1)[C@H](OC)/C=C/C=C(\C)C2]

Analytical Methods

Unless otherwise indicated, the following HPLC and HPLC/MS methods were used in the preparation of Intermediates and Examples.

LC/MS analysis was performed on an Agilent 1200 sl/6140 system.

Column: Waters Acquity HSS T3 C18, 50×2.0, 1.8 um

Mobile Phase: A) $H_2O$+0.05% TFA; B: acetonitrile+0.035% TFA

Pump Method:

| Time | A % | B % | Flow (mL/min) |
|---|---|---|---|
| 0 | 90 | 10 | 0.9 |
| 1.35 | 0 | 100 | 0.9 |
| 1.36 | 0 | 100 | 0.9 |
| 1.95 | 0 | 100 | 0.9 |
| 1.96 | 90 | 10 | 0.9 |
| 2.0 | 90 | 10 | 0.9 |

Detection: UV Diode Array at 190 nm-400 nm

MS Scan: 200-1350 amu

ELSD: 60° C.

MS Parameters:

| Polarity | Positive |
|---|---|
| Drying Gas | 12 |
| Nebulizer Pressure | 50 |
| Drying Gas Temperature | 350 |
| Capillary Voltage | 3000 |

(14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzena-cyclotetradecaphane-10,12-dien-4-yl N-(4-((2-(3-(2,5-dioxo-2,5-dihydro-1H-pyrrol-1-yl)propanamido)ethyl)disulfanyl)-4-methylpentanoyl)-N-methyl-L-alaninate

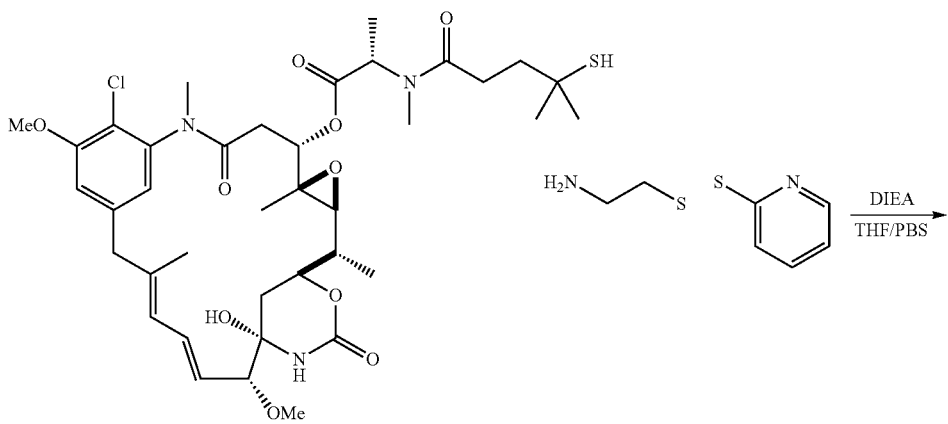

(DM4)

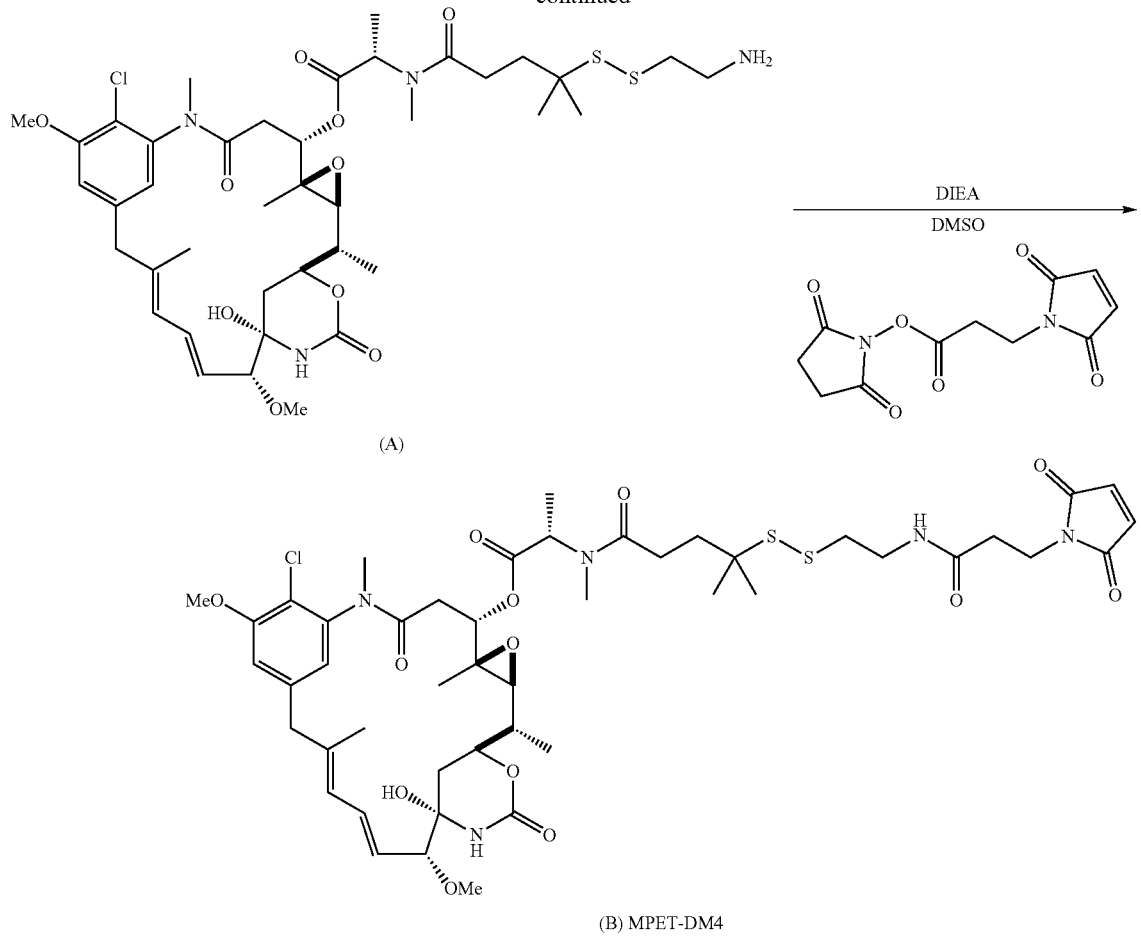

(B) MPET-DM4

Step 1: Preparation of (14S,16S,32S,33S,2R,4S, 10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-((2-aminoethyl)disulfanyl)-4-methylpentanoyl)-N-methyl-L-alaninate To DM4 (480 mg, 0.62 mmol) dissolved in PBS buffer (10.5 mL) and anhydrous THF (21 mL) were added 2-(pyridin-2-yldisulfanyl)ethan-1-amine (151 mg, 0.68 mmol) and DIEA (0.27 mL, 1.54 mmol) at room temperature. The reaction mixture was stirred at room temperature for 30 min and concentrated in vacuo. The aqueous residue was diluted with $CH_3CN$ (1 mL) and $H_2O$ (2 mL) and purified by reverse phase ISCO, eluted with 10-60% acetonitrile-$H_2O$ containing 0.05% TFA. Fractions containing desired product were lyophilized to obtain desired product (555 mg, 93% yield). $^1$H NMR (400 MHz, MeOD-$d_4$) δ ppm 0.83 (s, 3H) 1.21 (d, J=5.0 Hz, 3H) 1.25 (s, 3H) 1.28 (s, 3H) 1.30 (d, J=5.0 Hz, 3H) 1.45-1.55 (m, 3H) 1.67 (s, 3H) 1.84-1.88 (m, 1H) 1.95-2.01 (m, 1H) 2.14 (dd, J=5.0 and 15.0 Hz, 1H) 2.37-2.43 (m, 1H) 2.53-2.59 (m, 1H) 2.64 (dd, J=10.0 and 15.0 Hz, 1H) 2.82-2.89 (m, 5H) 2.91 (d, J=10.0 Hz, 1H) 3.16 (dd, J=5.0 and 10.0 Hz, 2H) 3.20 (s, 3H) 3.23 (d, J=10.0 Hz, 1H) 3.35 (s, 3H) 3.55 (d, J=5.0 Hz, 1H) 3.58 (d, J=10.0 Hz, 1H) 4.15-4.20 (m, 1H) 4.64 (dd, J=5.0 and 10.0 Hz, 1H) 5.43 (q, J=5.0 Hz, 2H) 5.66 (dd, J=10.0 and 15.0 Hz, 1H)) 6.58 (dd, J=10.0 and 15.0 Hz, 1H) 6.65 (d, J=10.0 Hz, 1H) 6.66 (s, 1H) 7.11 (bs, 1H) 7.28 (bs, 1H); MS m/z 855.3 (M+H), Retention time 0.988 minutes.

Step 2: Preparation of (14S,16S,32S,33S,2R,4S, 10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-((2-(3-(2,5-dioxo-2,5-dihydro-1H-pyrrol-1-yl)propanamido)ethyl)disulfanyl)-4-methylpentanoyl)-N-methyl-L-alaninate To (14S,16S,32S,33S,2R,4S,10E,12E,14R)-86-chloro-14-hydroxy-85,14-dimethoxy-33,2,7,10-tetramethyl-12,6-dioxo-7-aza-1(6,4)-oxazinana-3(2,3)-oxirana-8(1,3)-benzenacyclotetradecaphane-10,12-dien-4-yl N-(4-((2-aminoethyl)disulfanyl)-4-methylpentanoyl)-N-methyl-L-alaninate (555 mg, 0.57 mmol) dissolved in anhydrous DMSO (7 mL) were added 2,5-dioxopyrrolidin-1-yl 3-(2,5-dioxo-2,5-dihydro-1H-pyrrol-1-yl)propanoate (171 mg, 0.63 mmol) and DIEA (249 mL, 1.43 mmol) at room temperature. The reaction mixture was stirred at room temperature for 15 min and neutralized using TFA. The mixture was cooled to 0° C. with iced bath, followed by addition of $CH_3CN$ (2 mL) and $H_2O$ (7 mL), and then purified by reverse phase ISCO, eluting with 10-70% acetonitrile-$H_2O$ containing 0.05% TFA. Fractions containing desired product were lyophilized to obtain desired product (430 mg, 66% yield).). $^1$H NMR (400 MHz, CDCl$_3$) □□ppm 0.81 (s, 3H) 1.23 (s, 3H) 1.24 (s, 3H) 1.25 (s, 1H) 1.28 (d, J=5.0 Hz, 3H) 1.31 (d, J=5.0 Hz, 3H) 1.43-1.49 (m, 1H) 1.61 (d, J=15.0 Hz, 1H) 1.64 (s, 3H) 1.81-1.87 (m, 1H) 1.94-2.01 (m, 1H) 2.19 (dd, J=5.0 and 15.0 Hz, 1H) 2.30-2.36 (m, 1H) 2.54 (t, J=5.0 Hz, 2H) 2.61 (dd, J=10.0 and 15.0 Hz, 1H) 2.70 (t, J=5.0 Hz, 2H) 2.88 (s, 3H) 3.00 (d, J=10.0 Hz, 1H) 3.13 (d, J=10.0 Hz, 1H) 3.21 (s, 3H) 3.55 (s, 3H) 3.45 (q, J=5.0 Hz, 2H) 3.49 (d, J=5.0 Hz, 1H) 3.62 (d, J=10.0 Hz, 1H) 3.83 (t, J=5.0 Hz, 1H) 3.98 (s, 3H) 4.32 (m, 1H) 4.80 (dd, J=5.0 and 10.0 Hz, 1H) 5.28 (d, J=5.0 Hz, 1H) 5.66 (dd, J=10.0 and 15.0 Hz, 1H)) 6.22 (bs, 1H) 6.42 (dd, J=10.0 and 15.0 Hz, 1H) 6.50 (s, 1H) 6.63 (s, 1H) 6.66 (d, J=10.0 Hz, 1H) 6.70 (s, 2H) 6.83 (s, 1H); MS m/z 988.3 (M+H-H$_2$O), Retention time 1.145 minutes.

3. Conjugation and Preparation of ADCs

Processes for Making Antibody Conjugate of Formula (I)

A general reaction scheme for the formation of conjugates of Formula (I) is shown in Scheme 1 below:

Scheme 1

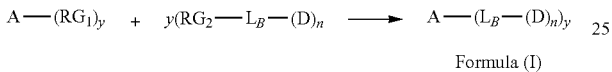

Formula (I)

where: $RG_1$ is a reactive group, by way of example only a thiol or amine or ketone, which reacts with a compatible reactive group, $RG_2$, attached to the linker-drug moiety thereby covalently linking antibody fragment, A, to one or more linker-drug moieties. A non-limiting examples of such reactions of $RG_1$ and $RG_2$ groups is a maleimide ($RG_2$) reacting with a thiol ($RG_1$) to give a succinimide ring, or a hydroxylamine ($RG_2$) reacting with a ketone ($RG_1$) to give an oxime.

A general reaction scheme for the formation of conjugates of Formula (II) is shown in Scheme 2 below:

Scheme 2

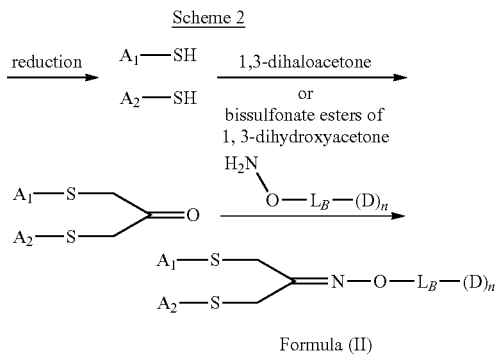

Formula (II)

where: $A_1$, $A_2$, $L_B$, D and n are as defined herein, the 1,3-dihaloacetone is selected from 1,3-dichloroacetone, 1,3-dibromoacetone, and 1,3-diiodoacetone, and the reduction step is accomplished using a reducing agent selected from dithiothreitol (DTT) and Tris(2-carboxyethyl)phosphine hydrochloride (TCEP-HCl).

A general reaction scheme for the formation of conjugates of Formula (C) is shown in Scheme 3 below:

Scheme 3

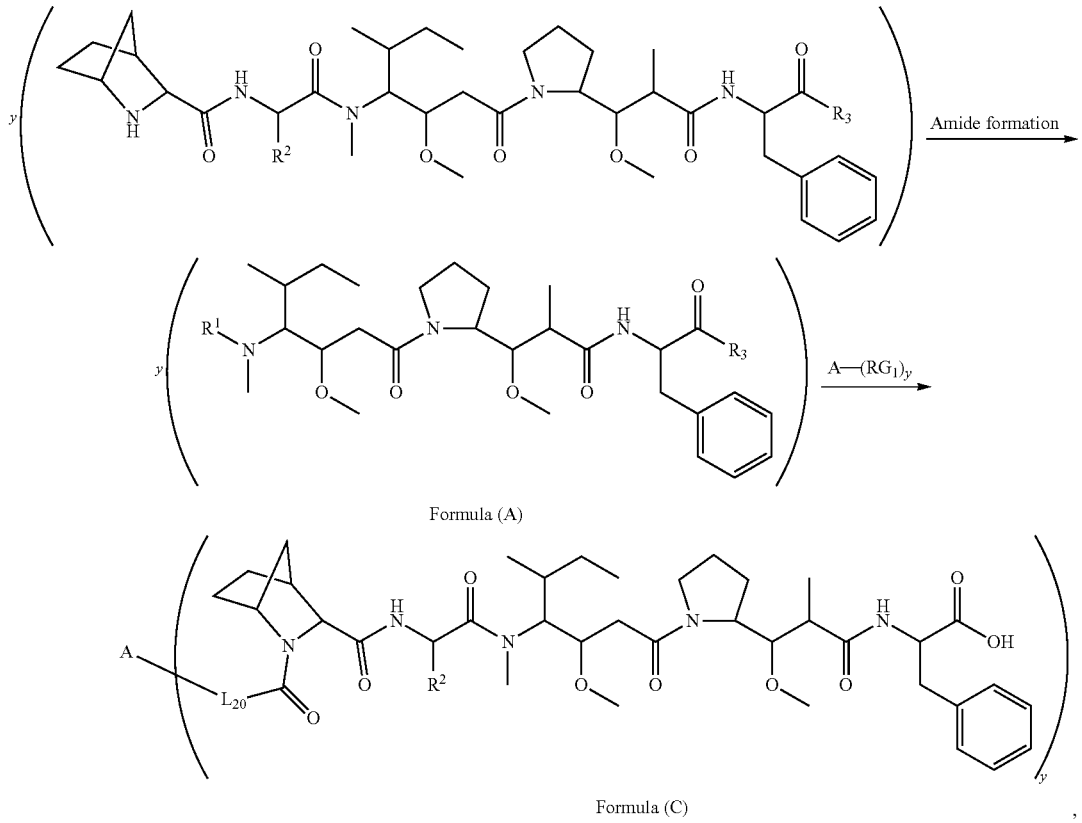

where: $R^1$ is

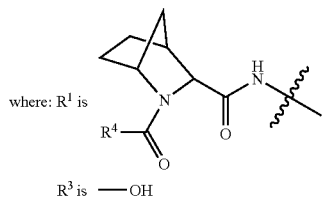

$R^3$ is —OH where: $L_{20}$ is $-L_1R^{40}$; $R^4$ is $-L_1R^{14}$, $-L_2R^{24}$ or $-L_2R^{34}$ and $RG_1$ is a reactive group, by way of example only a thiol or amine or ketone, which reacts with a compatible $R^{14}$, $R^{24}$ or $R^{34}$ group of a compound of Formula (A) to form a corresponding $R^{40}$ group. By way of example, a maleimide reacting with a thiol to give a succinimide ring, or a hydroxylamine reacting with a ketone to give an oxime. A, $R^2$, $L_1$, $L_2$, $R^{14}$, $R^{24}$, $R^{34}$ and $R^{40}$ are as defined herein.

A general reaction scheme for the formation of conjugates of Formula (C-1) is shown in Scheme 4 below:

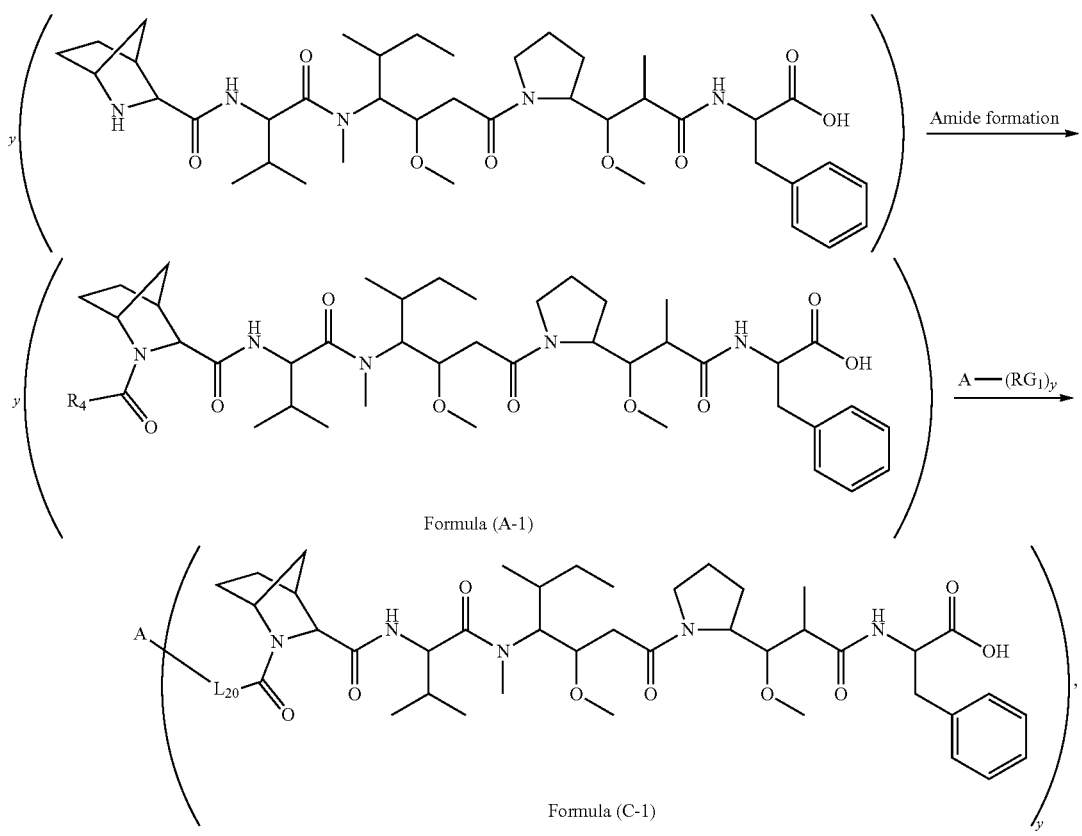

where: $L_{20}$ is $-L_1R^{40}$; $R^4$ is $-L_1R^{14}$, $-L_2R^{24}$ or $-L_2R^{34}$ and $RG_1$ is a reactive group which reacts with a compatible $R^{14}$, $R^{24}$ or $R^{34}$ group of a compound of Formula (A-1) to form a corresponding $R^{40}$ group. By way of example, a maleimide reacting with a thiol to give a succinimide ring, or a hydroxylamine reacting with a ketone to give an oxime. A, $L_1$, $L_2$, $R^{14}$, $R^{24}$, $R^{34}$ and $R^{40}$ are as defined herein.

A general reaction scheme for the formation of conjugates of Formula (C-1a) is shown in Scheme 5 below:

Scheme 5

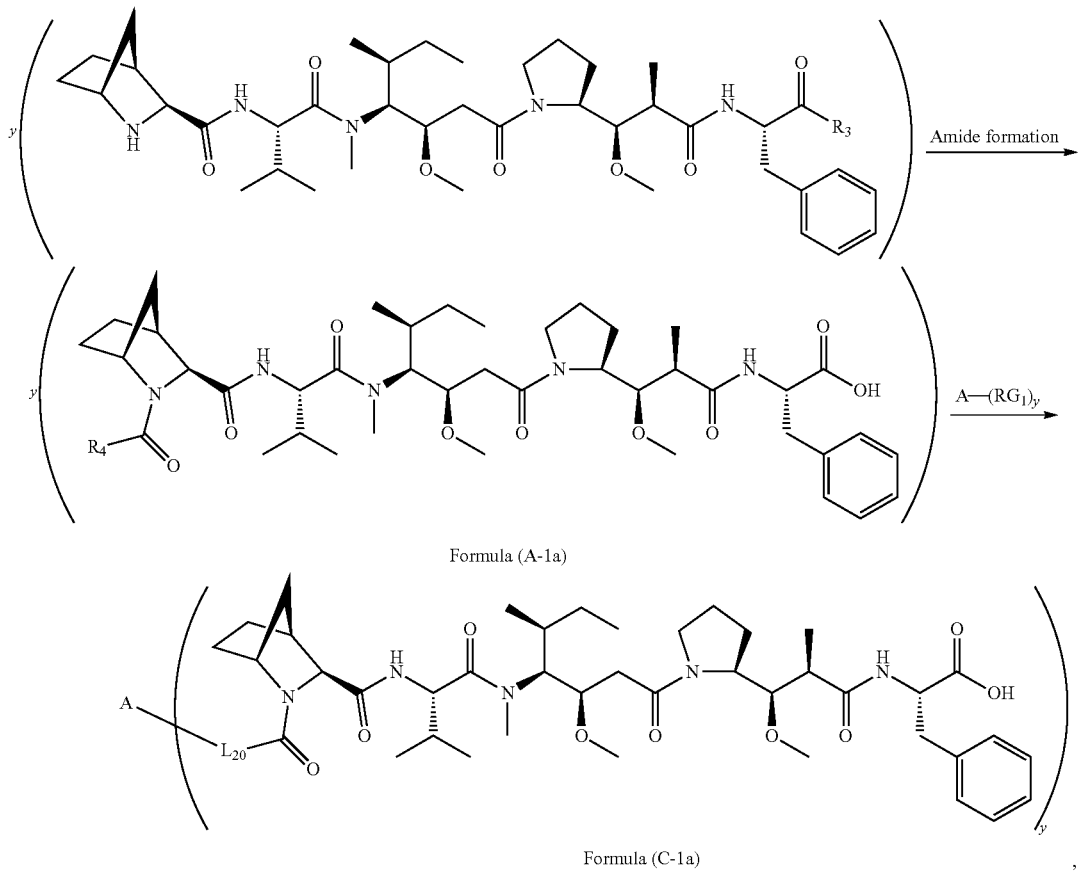

Formula (A-1a)

Formula (C-1a)

where: $L_{20}$ is $-L_1R^{40}$; $R^4$ is $-L_1R^{14}$, $-L_2R^{24}$ or $-L_2R^{34}$ and $RG_1$ is a reactive group, by way of example only a thiol or amine or ketone, which reacts with a compatible $R^{14}$, $R^{24}$ or $R^{34}$ group of a compound of Formula (A-1a) to form a corresponding $R^{40}$ group. By way of example, a maleimide reacting with a thiol to give a succinimide ring, or a hydroxylamine reacting with a ketone to give an oxime. A, $L_1$, $L_2$, $R^{14}$, $R^{24}$, $R^{34}$ and $R^{40}$ are as defined herein.

A general reaction scheme for the formation of conjugates of Formula (D) is shown in Scheme 6 below:

Scheme 6

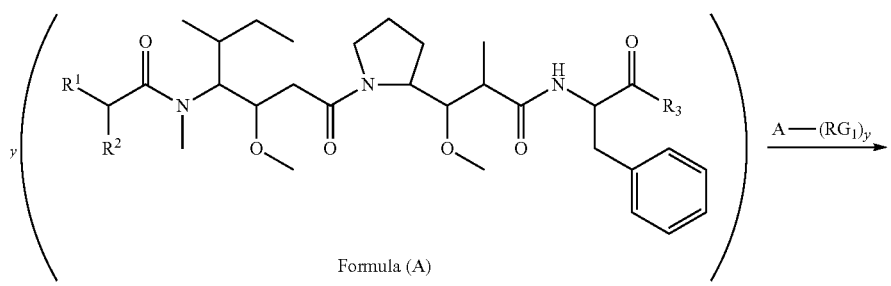

Formula (A)

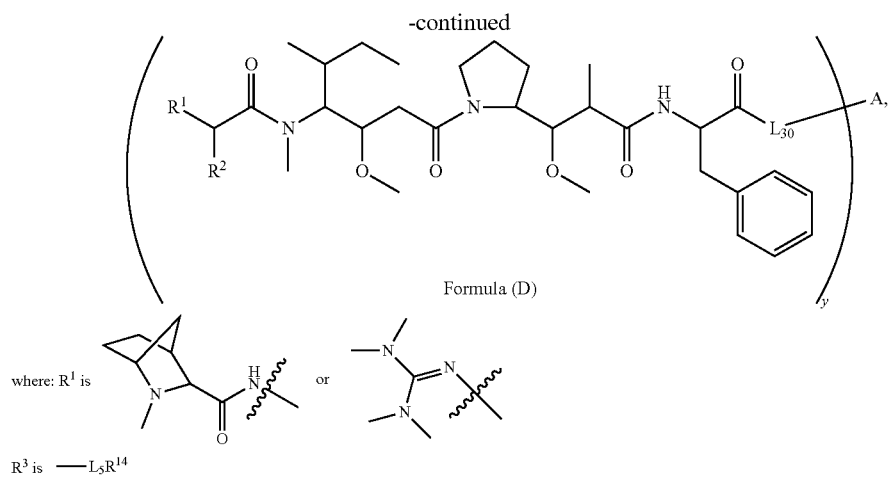

Formula (D)

where: $R^1$ is [structure] or [structure]

$R^3$ is —$L_5R^{14}$ where: $L_{30}$ is -$L_5R^{40}$; $R^3$ is -$L_5R^1$ and $RG_1$ is a reactive group which, by way of example only a thiol or amine or ketone, reacts with a compatible $R^{14}$ group of a compound of Formula (A) to form a corresponding $R^{40}$ group. By way of example, a maleimide reacting with a thiol to give a succinimide ring, or a hydroxylamine reacting with a ketone to give an oxime. A, $R^2$, $L_5$, $R^{14}$ and $R^{40}$ are as defined herein.

A general reaction scheme for the formation of conjugates of Formula (D-1) is shown in Scheme 7 below:

Scheme 7

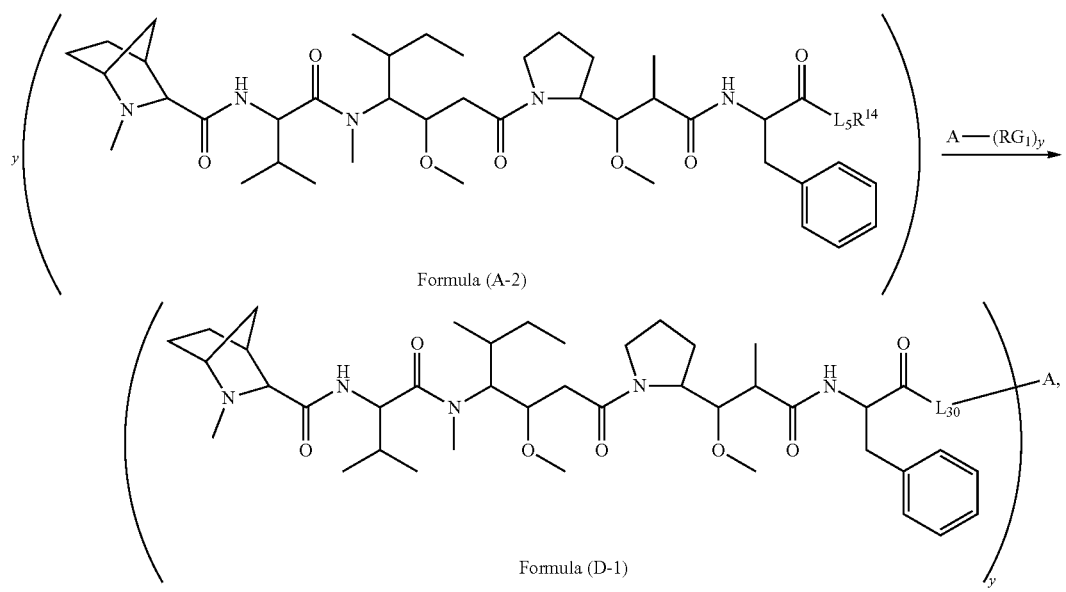

Formula (A-2)

Formula (D-1)

where: $L_{30}$ is -$L_5R^{40}$ and $RG_1$ is a reactive group, by way of example only a thiol or amine or ketone, which reacts with a compatible $R^{14}$ group of a compound of Formula (A-2) to form a corresponding $R^{40}$ group. By way of example, a maleimide reacting with a thiol to give a succinimide ring, or a hydroxylamine reacting with a ketone to give an oxime. A, $L_5$, $R^{14}$ and $R^{40}$ are as defined herein.

A general reaction scheme for the formation of conjugates of Formula (D-1a) is shown in Scheme 8 below:

Scheme 8

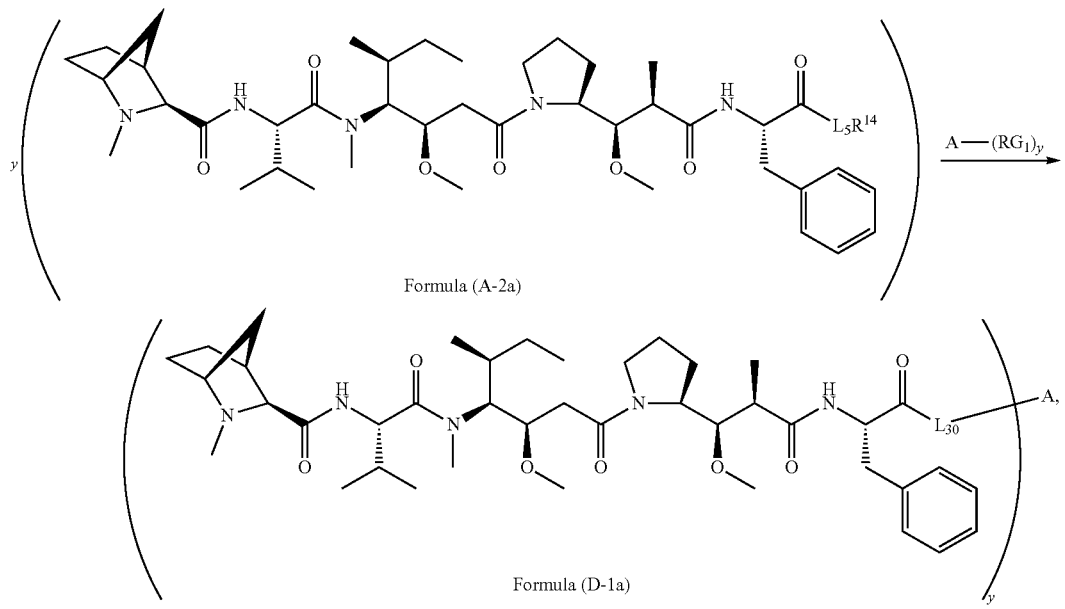

Formula (A-2a)

Formula (D-1a)

where: $L_{30}$ is $-L_5R^{40}$ and $RG_1$ is a reactive group, by way of example only a thiol or amine or ketone, which reacts with a compatible $R^{14}$ group of a compound of Formula (A-2) to form a corresponding $R^{40}$ group. By way of example, a maleimide reacting with a thiol to give a succinimide ring, or a hydroxylamine reacting with a ketone to give an oxime. A, $L_5$, $R^{14}$ and $R^{40}$ are as defined herein.

A general reaction scheme for the formation of conjugates of Formula (D-2) is shown in Scheme 9 below:

where: $L_{30}$ is $-L_5R^{40}$ and $RG_1$ is a reactive group, by way of example only a thiol or amine or ketone, which reacts with a compatible $R^{14}$ group of a compound of Formula (A-3) to form a corresponding $R^{40}$ group. By way of example, a maleimide reacting with a thiol to give a succinimide ring, or a hydroxylamine reacting with a ketone to give an oxime. A, $L_5$, $R^{14}$ and $R^{40}$ are as defined herein.

A general reaction scheme for the formation of conjugates of Formula (D-2a) is shown in Scheme 10 below:

Scheme 9

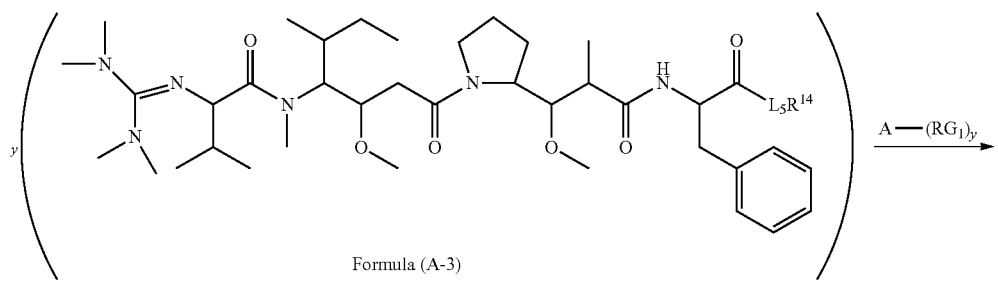

Formula (A-3)

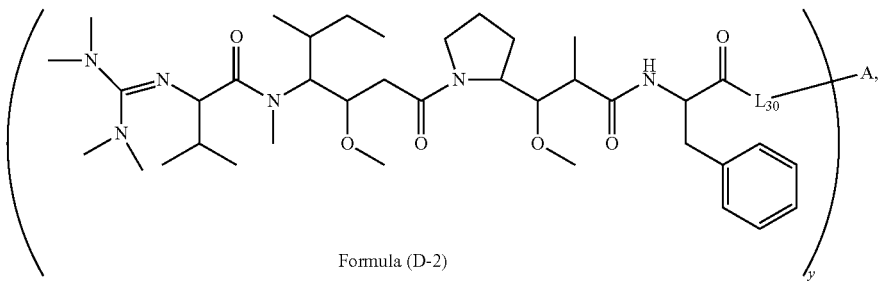

Formula (D-2)

Scheme 10

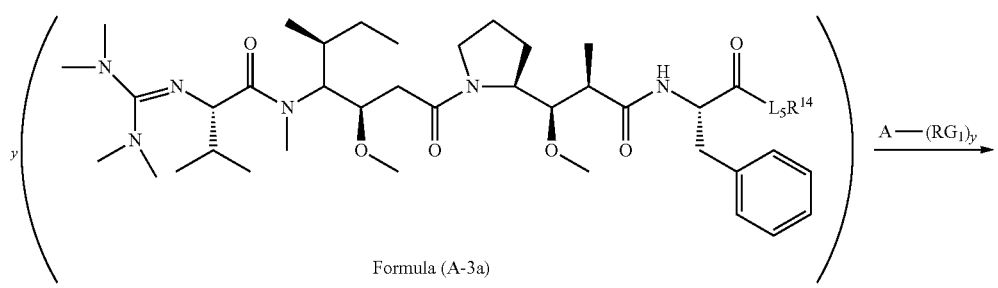

Formula (A-3a)

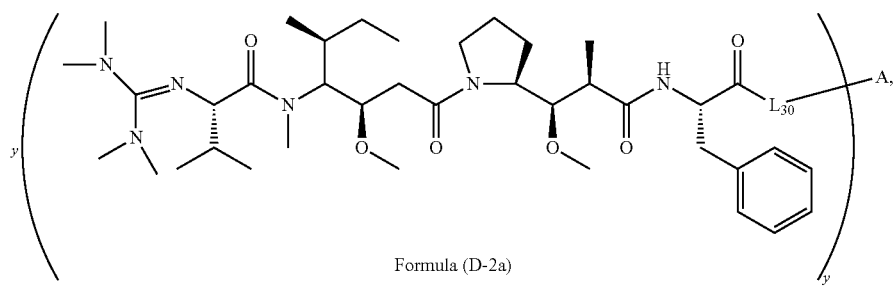

Formula (D-2a)

where: $L_{30}$ is -$L_5R^{40}$ and $RG_1$ is a reactive group, by way of example only a thiol or amine or ketone, which reacts with a compatible $R^{14}$ group of a compound of Formula (A-3a) to form a corresponding $R^{40}$ group. By way of example, a maleimide reacting with a thiol to give a succinimide ring, or a hydroxylamine reacting with a ketone to give an oxime. A, $L_5$, $R^{14}$ and $R^{40}$ are as defined herein.

A general reaction scheme for the formation of conjugates of Formula (E) is shown in Scheme 11 below:

Scheme 11

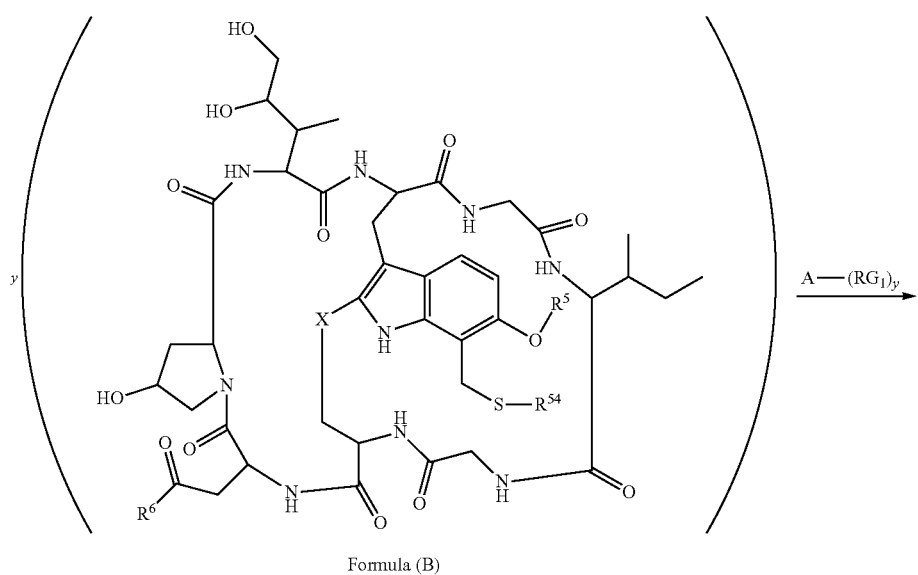

Formula (B)

-continued

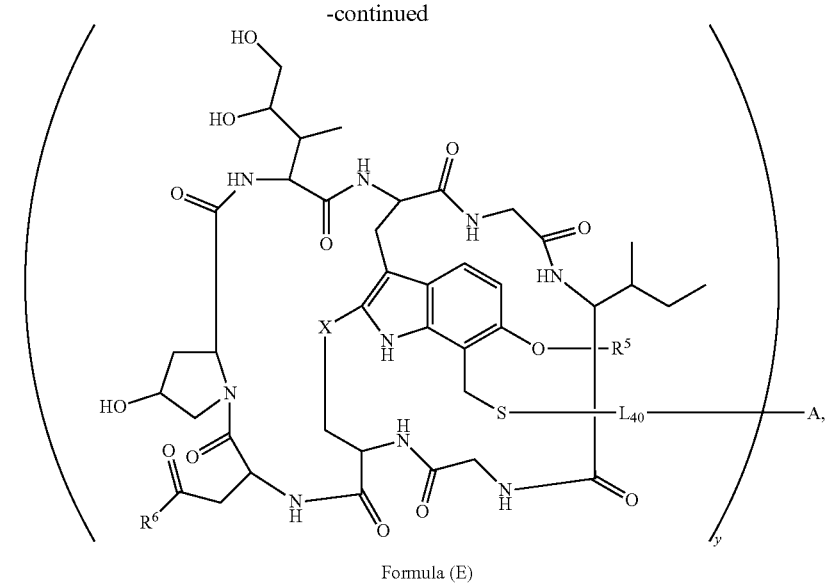

Formula (E)

where: $L_{40}$ is $-L_6R^{40}$; $R^{54}$ is $-L_6R^{14}$, $-L_7R^{24}$ or $-L_7R^{34}$ and $RG_1$ is a reactive group, by way of example only a thiol or amine or ketone, which reacts with a compatible $R^{14}$, $R^{24}$ or $R^{34}$ group of a compound of Formula (B) to form a corresponding $R^{40}$ group. By way of example, a maleimide reacting with a thiol to give a succinimide ring, or a hydroxylamine reacting with a ketone to give an oxime. A, X, $R^5$, $R^6$, $L_6$, $L_7$, $R^{14}$, $R^{24}$, $R^{34}$ and $R^{40}$ are as defined herein.

A general reaction scheme for the formation of conjugates of Formula (E-1) is shown in Scheme 12 below:

Scheme 12

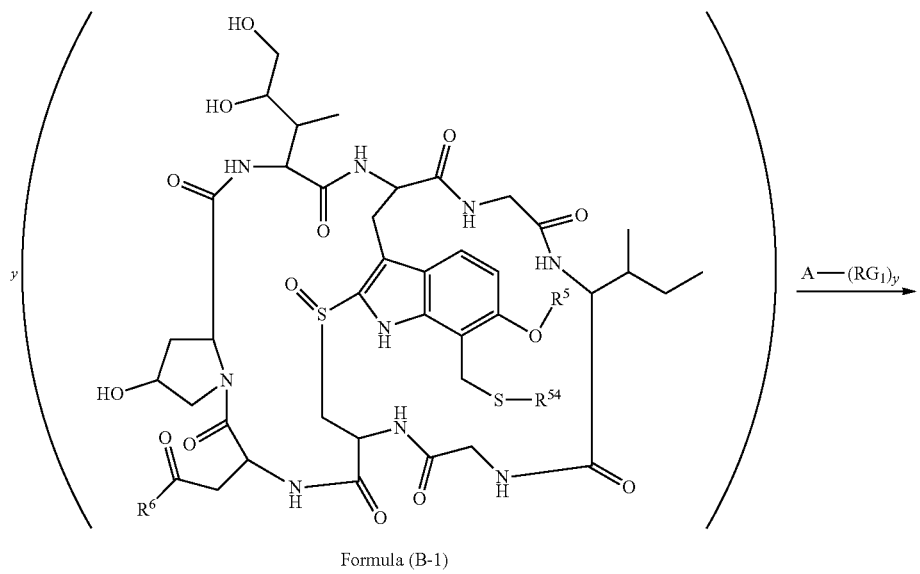

Formula (B-1)

-continued

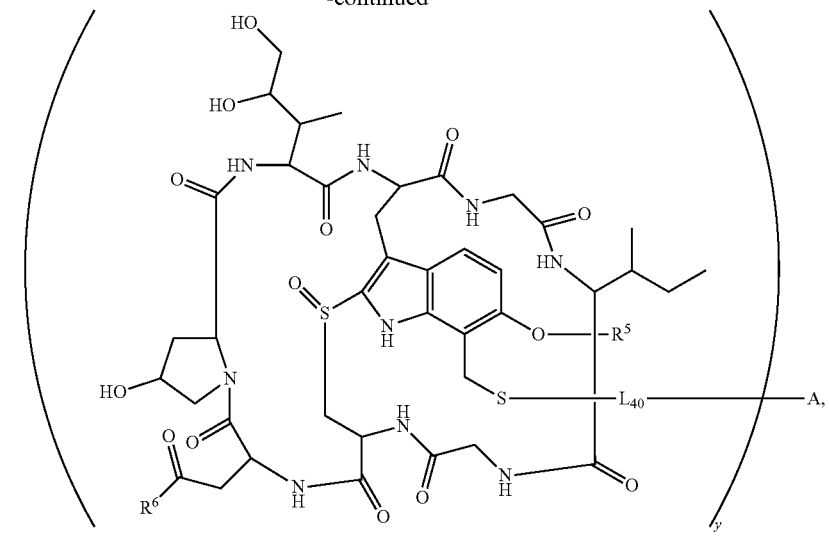

Formula (E-1)

where: $L_{40}$ is $-L_6R^{40}$; $R^{54}$ is $-L_6R^{14}$, $-L_7R^{24}$ or $-L_7R^{34}$ and $RG_1$ is a reactive group, by way of example only a thiol or amine or ketone, which reacts with a compatible $R^{14}$, $R^{24}$ or $R^{34}$ group of a compound of Formula (B-1) to form a corresponding $R^{40}$ group. By way of example, a maleimide reacting with a thiol to give a succinimide ring, or a hydroxylamine reacting with a ketone to give an oxime. A, y, $R^5$, $R^6$, $L_6$, $L_7$, $R^{14}$, $R^{24}$, $R^{34}$ and $R^{40}$ are as defined herein.

A general reaction scheme for the formation of conjugates of Formula (E-1a) is shown in Scheme 13 below:

Scheme 13

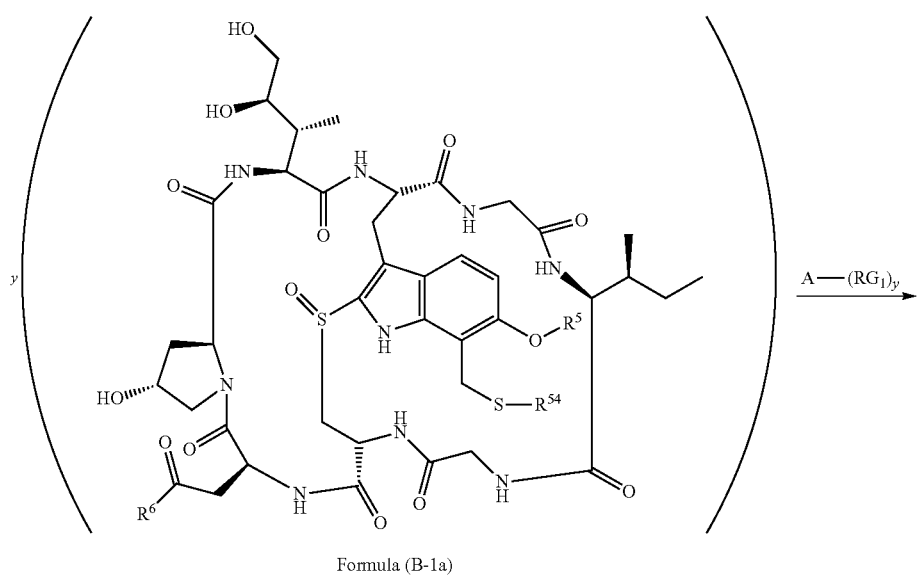

Formula (B-1a)

-continued

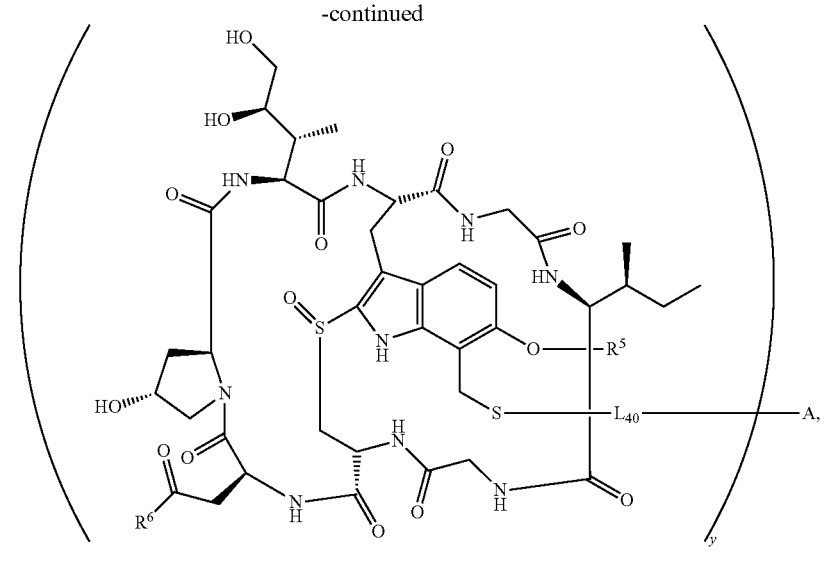

Formula (E-1a)

where: $L_{40}$ is $-L_6R^{40}$; $R^{54}$ is $-L_6R^{14}$, $-L_7R^{24}$ or $-L_7R^{34}$ and $RG_1$ is a reactive group, by way of example only a thiol or amine or ketone, which reacts with a compatible $R^{14}$, $R^{24}$ or $R^{34}$ group of a compound of Formula (B-1a) to form a corresponding $R^{40}$ group. By way of example, a maleimide reacting with a thiol to give a succinimide ring, or a hydroxylamine reacting with a ketone to give an oxime. A, y, $R^5$, $R^6$, $L_6$, $L_7$, $R^{14}$, $R^{24}$, $R^{34}$ and $R^{40}$ are as defined herein.

A general reaction scheme for the formation of conjugates comprising a maytansinoid moiety is shown in Scheme 14 below:

Scheme 14

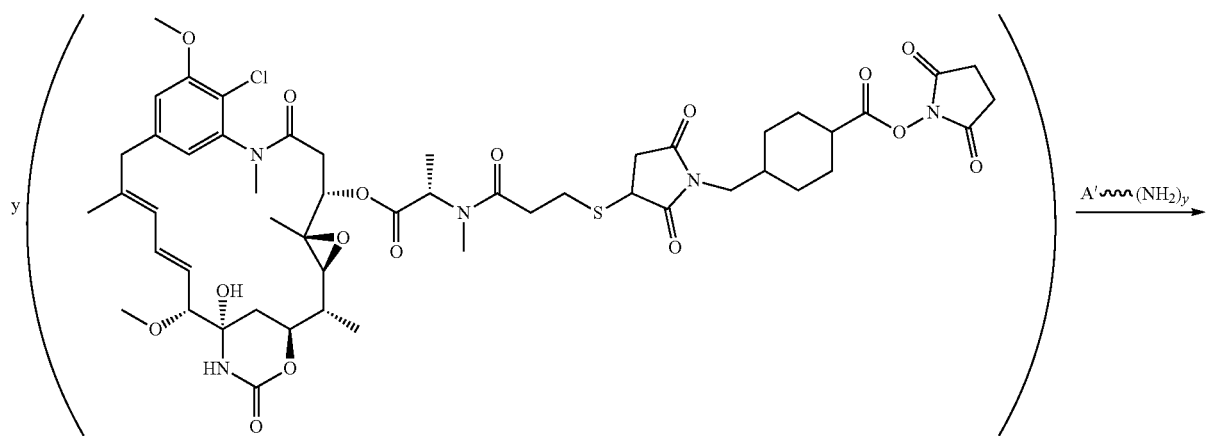

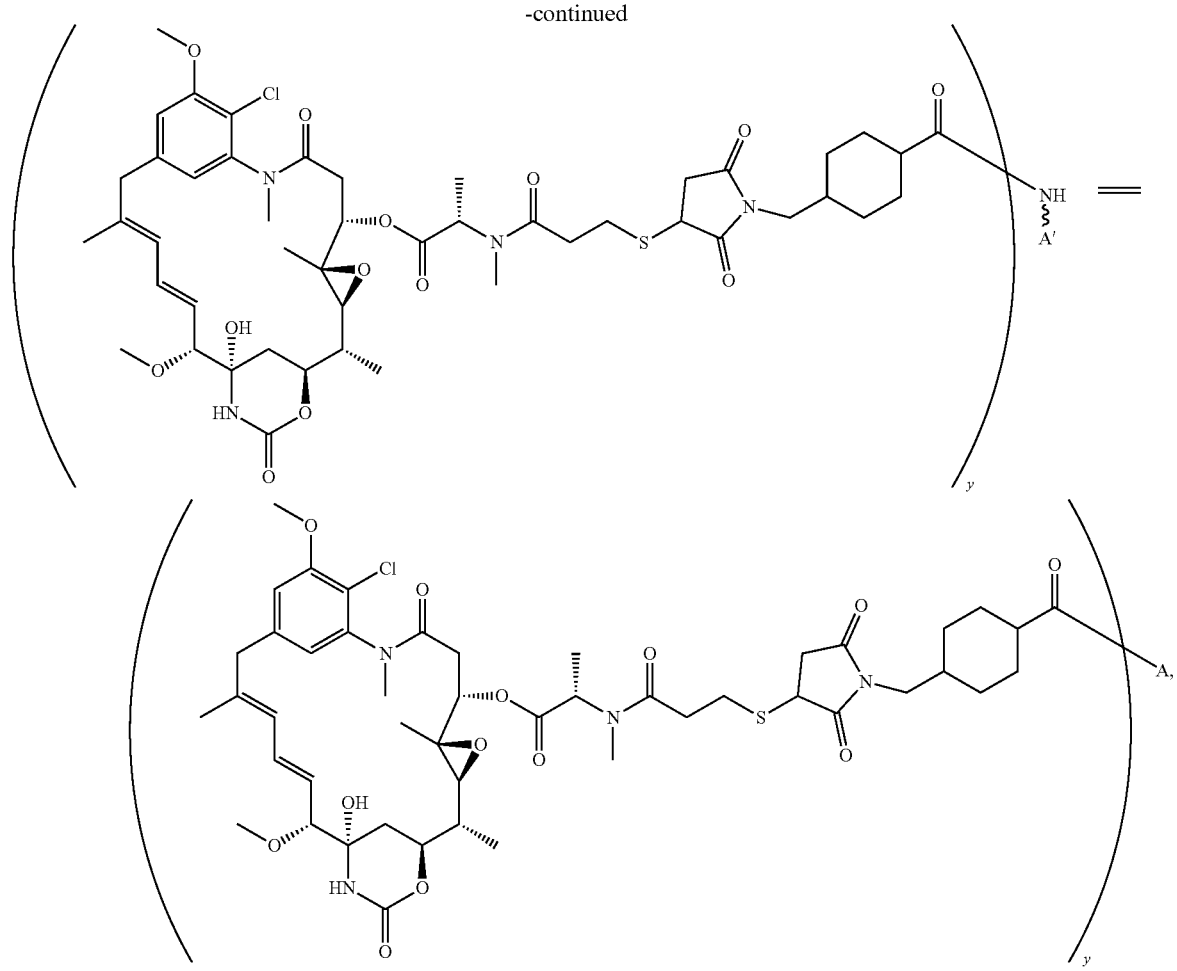
where one or more NHS esters of one or more linker-payloads reacts with one or more free amines on A (i.e. $(A'-(NH_2)_y)$, thereby forming a conjugate. A is as defined herein and A' is the portion of A which does not include the free amine moiety.
A general reaction scheme for the formation of conjugates comprising a maytansinoid moiety is shown in Scheme 15 below:
Scheme 15
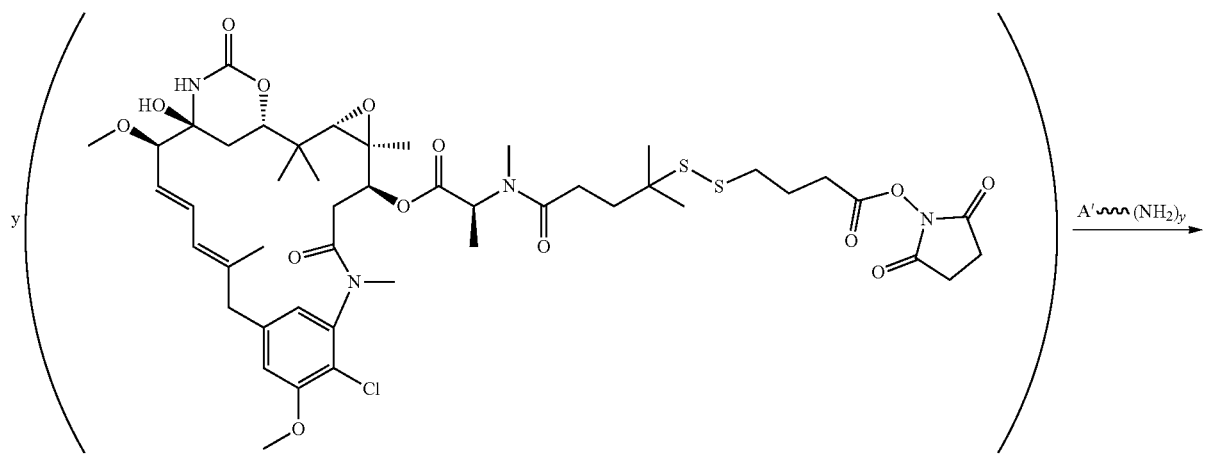

-continued

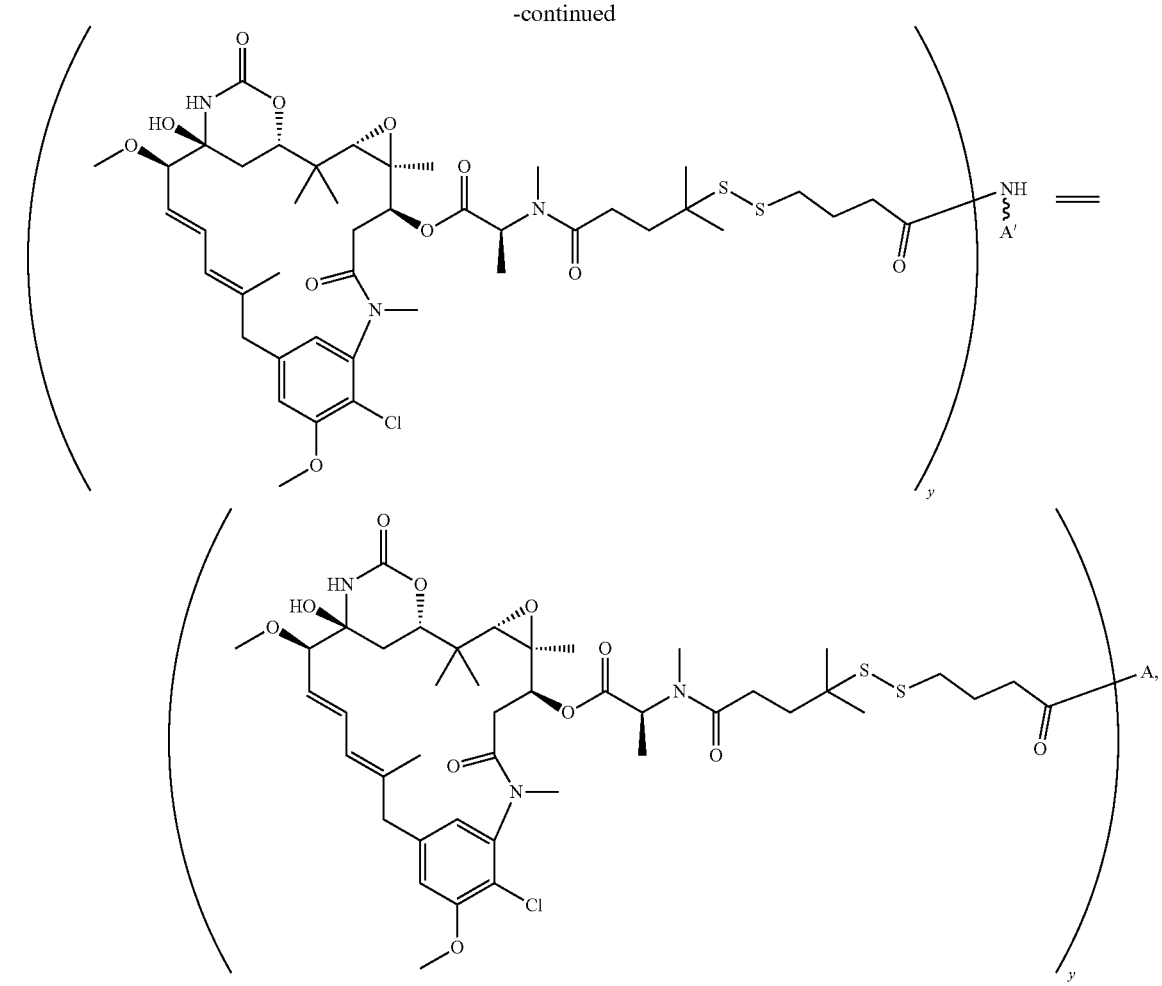

where one or more NHS esters of one or more linker-payloads reacts with one or more free amines on A (i.e. (A'-(NH$_2$)$_y$), thereby forming a conjugate. A is as defined herein and A' is the portion of A which does not include the free amine moiety.

A general reaction scheme for the formation of conjugates comprising a maytansinoid moiety is shown in Scheme 16 below:

Scheme 16

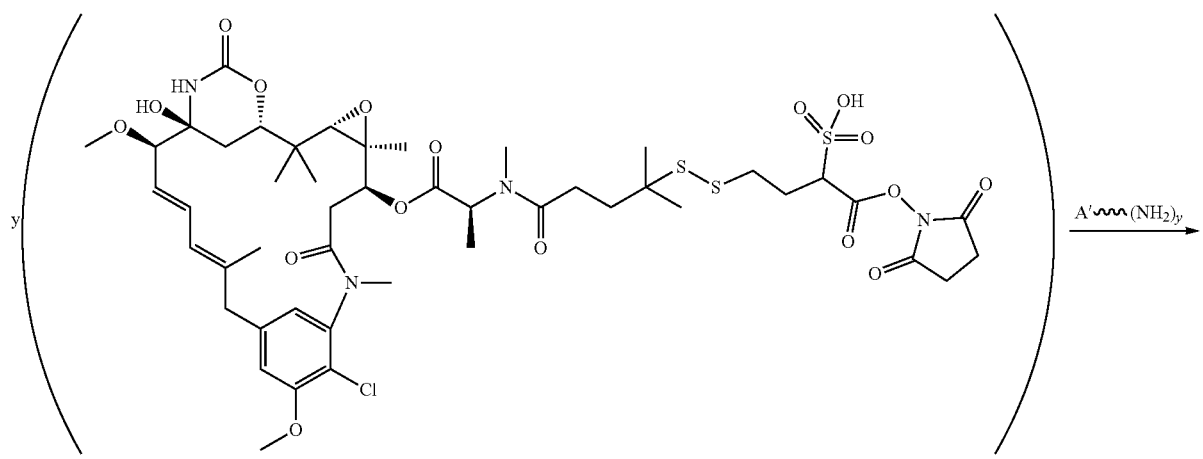

-continued

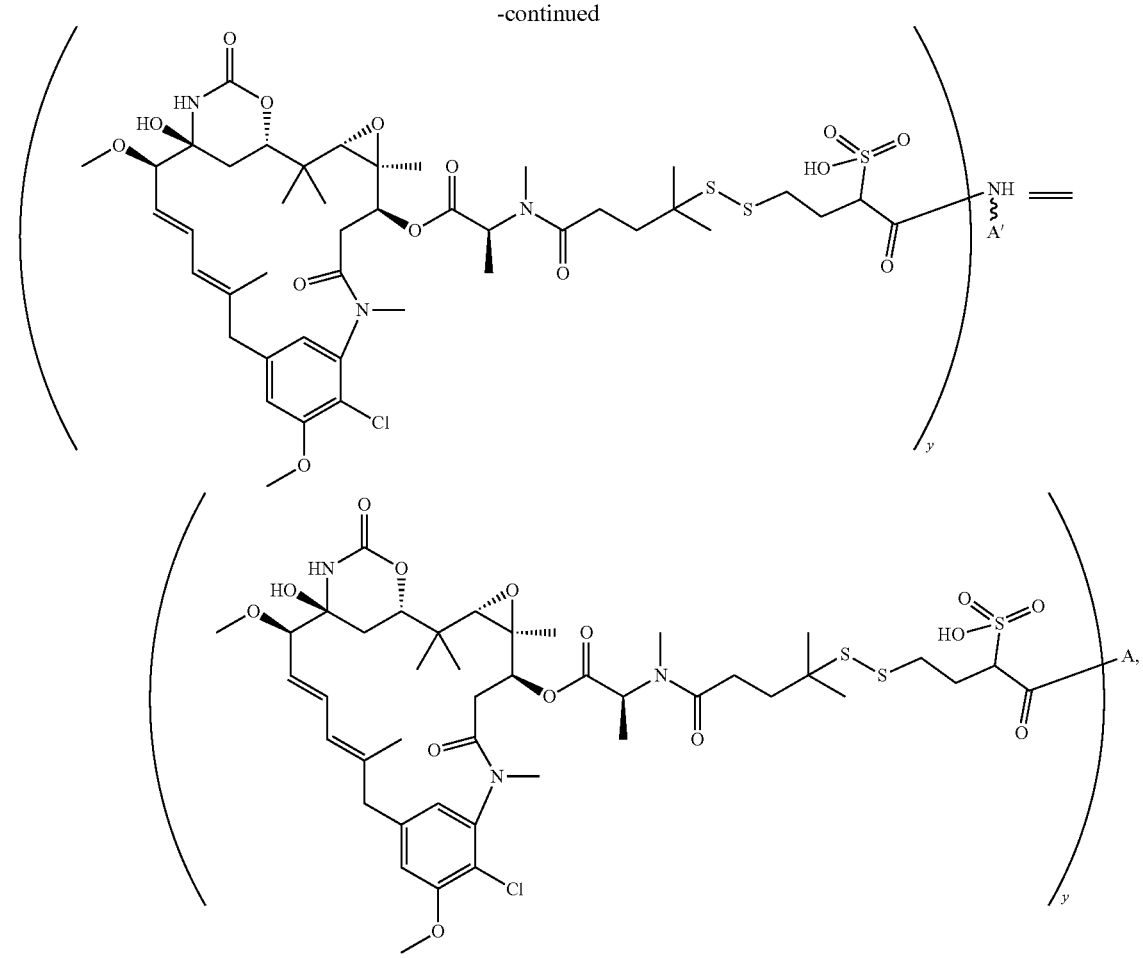

where one or more NHS esters of one or more linker-payloads reacts with one or more free amines on A (i.e. (A'-(NH$_2$)$_y$), thereby forming a conjugate. A is as defined herein and A' is the portion of A which does not include the free amine moiety.

A general reaction scheme for the formation of conjugates comprising a maytansinoid moiety is shown in Scheme 17 below:

Scheme 17

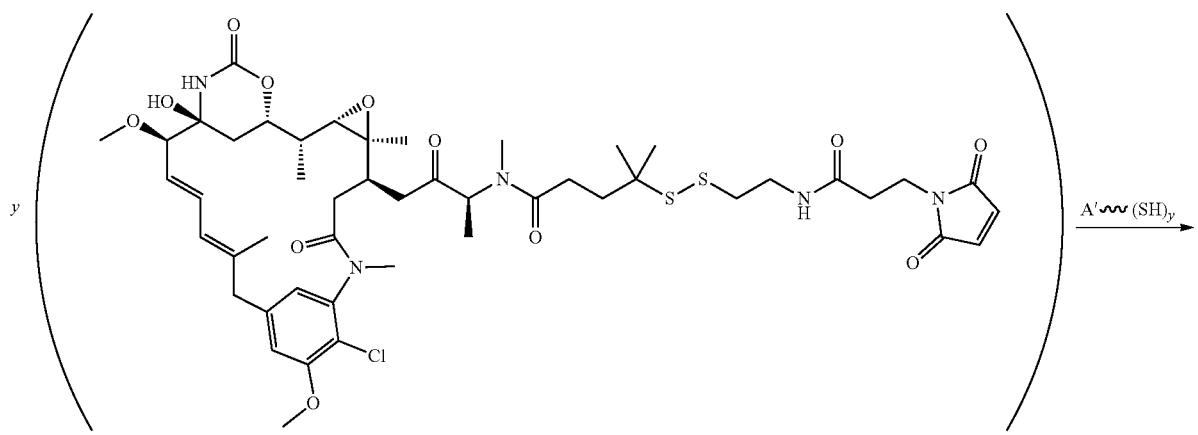

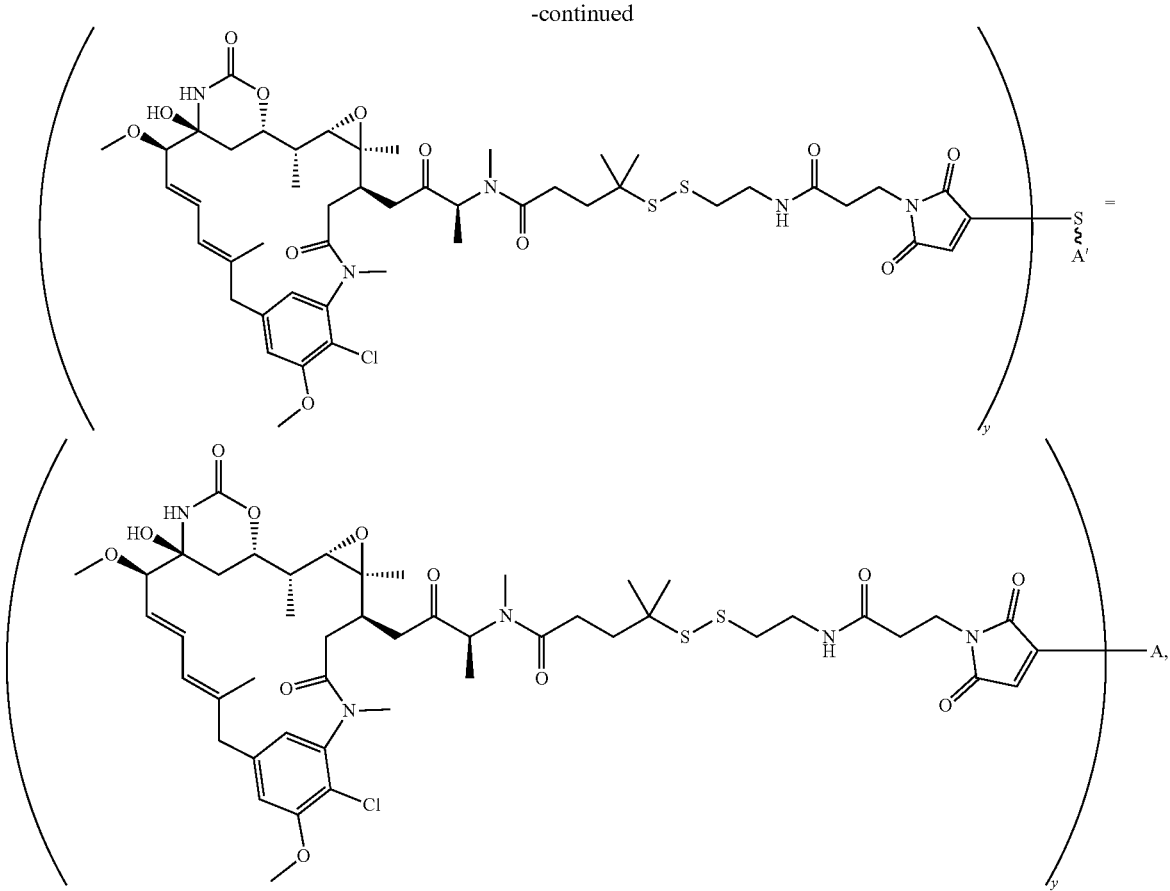

where one or more maleimides of one or more linker-payloads reacts with one or more free thiols on A (i.e. (A'-(SH)$_y$), thereby forming a conjugate. A is as defined herein and A' is the portion of A which does not include the free thiol moiety.

4. Characterization and Selection of Desirable Anti-cKIT ADCs

Determination of DAR and Aggregation of the ADCs

DAR value of the cKIT ADO was evaluated by liquid chromatography-mass spectrometry (LC-MS). A compound-to-antibody ratio was extrapolated from LC-MS data for reduced and deglycosylated (when appropriate, i.e. when Fc is included) samples. LC-MS allows quantitation of the average number of molecules of linker-payload (compound) attached to an antibody in a conjugate sample.

Antibody drug conjugates of the invention were evaluated using analytical methods. Such analytical methodology and results can demonstrate that the conjugates have favorable properties, for example properties that would make them easier to manufacture, easier to administer to patients, more efficacious, and/or potentially safer for patients. One example is the determination of molecular size by size exclusion chromatography (SEC) wherein the amount of desired antibody species in a sample is determined relative to the amount of high molecular weight contaminants (e.g., dimer, multimer, or aggregated antibody) or low molecular weight contaminants (e.g., antibody fragments, degradation products, or individual antibody chains) present in the sample. In general, it is desirable to have higher amounts of monomer and lower amounts of, for example, aggregated antibody due to the impact of, for example, aggregates on other properties of the antibody sample such as but not limited to clearance rate, immunogenicity, and toxicity. A further example is the determination of the hydrophobicity by hydrophobic interaction chromatography (HIC) wherein the hydrophobicity of a sample is assessed relative to a set of standard antibodies of known properties. In general, it is desirable to have low hydrophobicity due to the impact of hydrophobicity on other properties of the antibody sample such as but not limited to aggregation, aggregation overtime, adherence to surfaces, hepatotoxicity, clearance rates, and pharmacokinetic exposure. See Damle, N. K., Nat Biotechnol. 2008; 26(8):884-885; Singh, S. K., Pharm Res. 2015; 32(11):3541-71.

Selection of Anti-cKIT ADCs

To select anti-cKIT ADCs suitable for using in the methods described herein, an in vitro human hematopoietic stem cell killing assay can be used to screen the anti-cKIT ADCs for their efficacy and potency. For example, the methods described in Example 5 can be used to screen anti-cKIT ADCs. Suitable anti-cKIT ADCs can be selected based on EC50, e.g., anti-cKIT ADC with an EC50 less than 500 μg/ml, e.g., less than 100 μg/ml, less than 50 μg/ml, less than 10 μg/ml, or less than 5 μg/ml.

Furthermore, it has been reported that cKIT expresses on mast cells, and stem-cell factor (SCF), the ligand of cKIT, induces direct degranulation of rat peritoneal mast cells in vitro and in vivo (Taylor et al., Immunology. 1995 November; 86(3):427-33). SCF also induces human mast cell degranulation in vivo (Costa et al., J Exp Med. 1996; 183(6):

2681-6). To avoid potential detrimental effects caused by mast cell degranulation in transplant recipients, selected cKIT ADCs can be tested for their ability to induce mast cell degranulation in vitro. For example, experiments described in Example 6 can be used to screen cKIT ADCs, and suitable anti-cKIT ADCs can be selected based on minimal mast cell degranulation, e.g., a baseline corrected O.D. readout of less than 0.25, e.g., less than 0.2, less than 0.15, or less than 0.1, in a beta-hexosaminidase release assay.

cKIT Antibody and Antibody Fragments

The present disclosure provides for antibodies or antibody fragments (e.g., antigen binding fragments) that specifically bind to human cKIT. Antibodies or antibody fragments (e.g., antigen binding fragments) of the present disclosure include, but are not limited to, the human monoclonal antibodies or fragments thereof described below.

In some embodiments, the presently disclosed anti-cKIT antibodies or antibody fragments (e.g., antigen binding fragments) have a reduced ability for causing mast cell degranulation, even when cross-linked and/or multimerized into larger complexes, in comparison to a full-length anti-cKIT antibody. In some embodiments, the anti-cKIT antibodies or antibody fragments (e.g., antigen binding fragments) disclosed herein are modified to have reduced ability to induce mast cell degranulation, even when cross-linked and/or multimerized into larger complexes. For example, the anti-cKIT antibodies or antibody fragments (e.g., antigen binding fragments) disclosed herein are modified to have an reduced ability to induce mast cell degranulation that is, is about, or is at least 10%, 20%, 30%, 40%, 50%, 60%, 70%, 80%, 90% reduced in comparison to a full-length anti-cKIT antibody, or an F(ab')$_2$ or an F(ab)$_2$ fragment thereof, even when cross-linked and/or multimerized into larger complexes. In some embodiments, the anti-cKIT antibodies or antibody fragments (e.g., antigen binding fragments) disclosed herein may comprise an anti-cKIT Fab or Fab' fragment. In some embodiments, the anti-cKIT antibodies or antibody fragments (e.g., antigen binding fragments) disclosed herein may have minimal ability to induce mast cell degranulation, e.g., a baseline corrected O.D. readout of less than 0.25, e.g., less than 0.2, less than 0.15, or less than 0.1, in a beta-hexosaminidase release assay, even when cross-linked and/or multimerized into larger complexes.

The antibody drug conjugates provided herein include a human cKIT-binding antibody fragment (e.g., Fab or Fab'). In some embodiments, antibody drug conjugates provided herein include a human or humanized antibody fragment (e.g., Fab or Fab') that specifically binds to human cKIT. In some embodiments, antibody drug conjugates provided herein include a human or humanized Fab' that specifically binds to human cKIT. In some embodiments, antibody drug conjugates provided herein include a human or humanized Fab that specifically binds to human cKIT.

In some embodiments, the antibody or antibody fragment (e.g., Fab or Fab') that specifically binds to human cKIT comprises a VH domain having an amino acid sequence of any VH domain described in Table 1 (e.g., SEQ ID NO: 10, 36, 54, 69, 95). Other suitable antibody or antibody fragment (e.g., Fab or Fab') can include a VH domain that has at least 80, 85, 90, 95, 96, 97, 98, or 99 percent sequence identity to any of the VH domains described in Table 1.

In some embodiments, the antibody or antibody fragment (e.g., Fab or Fab') that specifically binds to human cKIT comprises a VH CDR (or HCDR) having an amino acid sequence of any one of the VH CDRs (or HCDR) listed in Table 1. In particular aspects, the present disclosure provides the antibody or antibody fragment (e.g., Fab or Fab') comprising (or alternatively, consisting of) one, two, three, four, five or more VH CDRs (or HCDR) having an amino acid sequence of any of the VH CDRs (or HCDR) listed in Table 1.

In some embodiments, the antibody or antibody fragment (e.g., Fab or Fab') that specifically binds to human cKIT comprises a VL domain having an amino acid sequence of any VL domain described in Table 1 (e.g., SEQ ID NO: 23, 47, 82, 108). Other suitable antibody or antibody fragment (e.g., Fab or Fab') can include a VL domain that has at least 80, 85, 90, 95, 96, 97, 98, or 99 percent sequence identity to any of the VL domains described in Table 1.

In some embodiments, the antibody or antibody fragment (e.g., Fab or Fab') that specifically binds to human cKIT comprises a VL CDR (or LCDR) having an amino acid sequence of any one of the VL CDRs (or LCDR) listed in Table 1. In particular aspects, the present disclosure provides the antibody or antibody fragment (e.g., Fab or Fab') comprising (or alternatively, consisting of) one, two, three, four, five or more VL CDRs (or LCDR) having an amino acid sequence of any of the VL CDRs (or LCDR) listed in Table 1.

Other anti-cKIT antibody or antibody fragment (e.g., Fab or Fab') disclosed herein include amino acids that have been mutated, yet have at least 60, 70, 80, 90 or 95 percent sequence identity in the CDR regions with the CDR regions depicted in the sequences described in Table 1. In some aspects, it includes mutant amino acid sequences wherein no more than 1, 2, 3, 4 or 5 amino acids have been mutated in the CDR regions when compared with the CDR regions depicted in the sequence described in Table 1.

The present disclosure also provides nucleic acid sequences that encode VH, VL, the heavy chain, and the light chain of the antibody or antibody fragment (e.g., Fab or Fab') that specifically binds to human cKIT. Such nucleic acid sequences can be optimized for expression in mammalian cells.

TABLE 1

Sequences of exemplary anti-cKIT antibodies and antibody fragments

| Anti-cKIT Ab1/Fab1/Fab'1 | | |
|---|---|---|
| SEQ ID NO: 1 | HCDR1 (Kabat) | SYAIS |
| SEQ ID NO: 2 | HCDR2 (Kabat) | VIFPAEGAPGYAQKFQG |
| SEQ ID NO: 3 | HCDR3 (Kabat) | GGYISDFDV |
| SEQ ID NO: 4 | HCDR1 (Chothia) | GGTFSSY |
| SEQ ID NO: 5 | HCDR2 (Chothia) | FPAEGA |
| SEQ ID NO: 3 | HCDR3 (Chothia) | GGYISDFDV |
| SEQ ID NO: 6 | HCDR1 (Combined) | GGTFSSYAIS |
| SEQ ID NO: 2 | HCDR2 (Combined) | VIFPAEGAPGYAQKFQG |
| SEQ ID NO: 3 | HCDR3 (Combined) | GGYISDFDV |
| SEQ ID NO: 7 | HCDR1 (IMGT) | GGTFSSYA |

TABLE 1-continued

Sequences of exemplary anti-cKIT antibodies and antibody fragments

| SEQ ID NO: 8 | HCDR2 (IMGT) | IFPAEGAP |
|---|---|---|
| SEQ ID NO: 9 | HCDR3 (IMGT) | ARGGYISDFDV |
| SEQ ID NO: 10 | VH | QVQLVQSGAEVKKPGSSVKVSCKASGGTFSSYAIS<br>WVRQAPGQGLEWMGVIFPAEGAPGYAQKFQGRVT<br>ITADESTSTAYMELSSLRSEDTAVYYCARGGYISDFD<br>VWGQGTLVTVSS |
| SEQ ID NO: 11 | VH DNA | CAGGTGCAATTGGTGCAGAGCGGTGCCGAAGTG<br>AAAAAACCGGGCAGCAGCGTGAAAGTTAGCTGCA<br>AAGCATCCGGAGGGACGTTTAGCAGCTATGCGAT<br>TAGCTGGGTGCGCCAGGCCCCGGGCCAGGGCCT<br>CGAGTGGATGGGCGTTATCTTCCCGGCTGAAGGC<br>GCTCCGGGTTACGCCCAGAAATTTCAGGGCCGG<br>GTGACCATTACCGCCGATGAAAGCACCAGCACCG<br>CCTATATGGAACTGAGCAGCCTGCGCAGCGAAGA<br>TACGGCCGTGTATTATTGCGCGCGTGGTGGTTAC<br>ATCTCTGACTTCGATGTTTGGGGCCAAGGCACCC<br>TGGTGACTGTTAGCTCA |
| SEQ ID NO: 12 | Ab HC | QVQLVQSGAEVKKPGSSVKVSCKASGGTFSSYAIS<br>WVRQAPGQGLEWMGVIFPAEGAPGYAQKFQGRVT<br>ITADESTSTAYMELSSLRSEDTAVYYCARGGYISDFD<br>VWGQGTLVTVSSASTKGPSVFPLAPSSKSTSGGTA<br>ALGCLVKDYFPEPVTVSWNSGALTSGVHTFPAVLQ<br>SSGLYSLSSVVTVPSSSLGTQTYICNVNHKPSNTKV<br>DKRVEPKSCDKTHTCPPCPAPELLGGPSVFLFPPKP<br>KDTLMISRTPEVTCVVVDVSHEDPEVKFNWYVDGV<br>EVHNAKTKPREEQYNSTYRVVSVLTVLHQDWLNGK<br>EYKCKVSNKALPAPIEKTISKAKGQPREPQVYTLPPS<br>REEMTKNQVSLTCLVKGFYPSDIAVEWESNGQPEN<br>NYKTTPPVLDSDGSFFLYSKLTVDKSRWQQGNVFS<br>CSVMHEALHNHYTQKSLSLSPGK |
| SEQ ID NO: 13 | Ab HC DNA | CAGGTGCAATTGGTGCAGAGCGGTGCCGAAGTG<br>AAAAAACCGGGCAGCAGCGTGAAAGTTAGCTGCA<br>AAGCATCCGGAGGGACGTTTAGCAGCTATGCGAT<br>TAGCTGGGTGCGCCAGGCCCCGGGCCAGGGCCT<br>CGAGTGGATGGGCGTTATCTTCCCGGCTGAAGGC<br>GCTCCGGGTTACGCCCAGAAATTTCAGGGCCGG<br>GTGACCATTACCGCCGATGAAAGCACCAGCACCG<br>CCTATATGGAACTGAGCAGCCTGCGCAGCGAAGA<br>TACGGCCGTGTATTATTGCGCGCGTGGTGGTTAC<br>ATCTCTGACTTCGATGTTTGGGGCCAAGGCACCC<br>TGGTGACTGTTAGCTCAGCTAGCACCAAGGGCCC<br>CAGCGTGTTCCCCCTGGCCCCCAGCAGCAAGTCT<br>ACTTCCGGCGGAACTGCTGCCCTGGGTTGCCTGG<br>TGAAGGACTACTTCCCCGAGCCCGTGACAGTGTC<br>CTGGAACTCTGGGGCTCTGACTTCCGGCGTGCAC<br>ACCTTCCCCGCCGTGCTGCAGAGCAGCGGCCTG<br>TACAGCCTGAGCAGCGTGGTGACAGTGCCCTCCA<br>GCTCTCTGGGAACCCAGACCTATATCTGCAACGT<br>GAACCACAAGCCCAGCAACACCAAGGTGGACAAG<br>AGAGTGGAGCCCAAGAGCTGCGACAAGACCCAC<br>ACCTGCCCCCCTGCCCAGCTCCAGAACTGCTGG<br>GAGGGCCTTCCGTGTTCCTGTTCCCCCCCAAGCC<br>CAAGGACACCCTGATGATCAGCAGGACCCCCGAG<br>GTGACCTGCGTGGTGGTGGACGTGTCCCACGAG<br>GACCCAGAGGTGAAGTTCAACTGGTACGTGGACG<br>GCGTGGAGGTGCACAACGCCAAGACCAAGCCCA<br>GAGAGGAGCAGTACAACAGCACCTACAGGGTGGT<br>GTCCGTGCTGACCGTGCTGCACCAGGACTGGCT<br>GAACGGCAAAGAATACAAGTGCAAAGTCTCCAAC<br>AAGGCCCTGCCAGCCCCAATCGAAAAGACAATCA<br>GCAAGGCCAAGGGCCAGCCACGGGAGCCCCAGG<br>TGTACACCCTGCCCCCCAGCCGGGAGGAGATGA<br>CCAAGAACCAGGTGTCCCTGACCTGTCTGGTGAA<br>GGGCTTCTACCCCAGCGATATCGCCGTGGAGTGG<br>GAGAGCAACGGCCAGCCCGAGAACAACTACAAGA<br>CCACCCCCCCAGTGCTGGACAGCGACGGCAGCT<br>TCTTCCTGTACAGCAAGCTGACCGTGGACAAGTC<br>CAGGTGGCAGCAGGGCAACGTGTTCAGCTGCAG<br>CGTGATGCACGAGGCCCTGCACAACCACTACACC<br>CAGAAGTCCCTGAGCCTGAGCCCCGGCAAG |
| SEQ ID NO: 14 | Fab' HC(EU236) | QVQLVQSGAEVKKPGSSVKVSCKASGGTFSSYAIS<br>WVRQAPGQGLEWMGVIFPAEGAPGYAQKFQGRVT<br>ITADESTSTAYMELSSLRSEDTAVYYCARGGYISDFD<br>VWGQGTLVTVSSASTKGPSVFPLAPSSKSTSGGTA<br>ALGCLVKDYFPEPVTVSWNSGALTSGVHTFPAVLQ<br>SSGLYSLSSVVTVPSSSLGTQTYICNVNHKPSNTKV<br>DKRVEPKSCDKTHTCPPCPAPELLG |

TABLE 1-continued

Sequences of exemplary anti-cKIT antibodies and antibody fragments

| | | |
|---|---|---|
| SEQ ID NO: 15 | Fab' HC DNA | CAGGTGCAATTGGTGCAGAGCGGTGCCGAAGTG<br>AAAAAACCGGGCAGCAGCGTGAAAGTTAGCTGCA<br>AAGCATCCGGAGGGACGTTTAGCAGCTATGCGAT<br>TAGCTGGGTGCGCCAGGCCCCGGGCCAGGGCCT<br>CGAGTGGATGGGCGTTATCTTCCCGGCTGAAGGC<br>GCTCCGGGTTACGCCCAGAAATTTCAGGGCCGG<br>GTGACCATTACCGCCGATGAAAGCACCAGCACCG<br>CCTATATGGAACTGAGCAGCCTGCGCAGCGAAGA<br>TACGGCCGTGTATTATTGCGCGCGTGGTGGTTAC<br>ATCTCTGACTTCGATGTTTGGGGCCAAGGCACCC<br>TGGTGACTGTTAGCTCAGCTAGCACCAAGGGCCC<br>CAGCGTGTTCCCCCTGGCCCCCAGCAGCAAGTCT<br>ACTTCCGGCGGAACTGCTGCCCTGGGTTGCCTGG<br>TGAAGGACTACTTCCCCGAGCCCGTGACAGTGTC<br>CTGGAACTCTGGGGCTCTGACTTCCGGCGTGCAC<br>ACCTTCCCCGCCGTGCTGCAGAGCAGCGGCCTG<br>TACAGCCTGAGCAGCGTGGTGACAGTGCCCTCCA<br>GCTCTCTGGGAACCCAGACCTATATCTGCAACGT<br>GAACCACAAGCCCAGCAACACCAAGGTGGACAAG<br>AGAGTGGAGCCCAAGAGCTGCGACAAGACCCAC<br>ACCTGCCCCCCCTGCCCAGCTCCAGAACTGCTGG<br>GA |
| SEQ ID NO: 118 | Cys Fab-<br>HC(EU221)-HC-<br>E152C (EU) | QVQLVQSGAEVKKPGSSVKVSCKASGGTFSSYAIS<br>WVRQAPGQGLEWMGVIFPAEGAPGYAQKFQGRVT<br>ITADESTSTAYMELSSLRSEDTAVYYCARGGYISDFD<br>VWGQGTLVTVSSASTKGPSVFPLAPSSKSTSGGTA<br>ALGCLVKDYFPCPVTVSWNSGALTSGVHTFPAVLQ<br>SSGLYSLSSVVTVPSSSLGTQTYICNVNHKPSNTKV<br>DKRVEPKSCD |
| SEQ ID NO: 119 | Fab' HC(EU230) | QVQLVQSGAEVKKPGSSVKVSCKASGGTFSSYAIS<br>WVRQAPGQGLEWMGVIFPAEGAPGYAQKFQGRVT<br>ITADESTSTAYMELSSLRSEDTAVYYCARGGYISDFD<br>VWGQGTLVTVSSASTKGPSVFPLAPSSKSTSGGTA<br>ALGCLVKDYFPEPVTVSWNSGALTSGVHTFPAVLQ<br>SSGLYSLSSVVTVPSSSLGTQTYICNVNHKPSNTKV<br>DKRVEPKSCDKTHTCPPCP |
| SEQ ID NO: 120 | Fab' HC(EU232) | QVQLVQSGAEVKKPGSSVKVSCKASGGTFSSYAIS<br>WVRQAPGQGLEWMGVIFPAEGAPGYAQKFQGRVT<br>ITADESTSTAYMELSSLRSEDTAVYYCARGGYISDFD<br>VWGQGTLVTVSSASTKGPSVFPLAPSSKSTSGGTA<br>ALGCLVKDYFPEPVTVSWNSGALTSGVHTFPAVLQ<br>SSGLYSLSSVVTVPSSSLGTQTYICNVNHKPSNTKV<br>DKRVEPKSCDKTHTCPPCPAP |
| SEQ ID NO: 121 | Fab' HC(EU236)-Pro | QVQLVQSGAEVKKPGSSVKVSCKASGGTFSSYAIS<br>WVRQAPGQGLEWMGVIFPAEGAPGYAQKFQGRVT<br>ITADESTSTAYMELSSLRSEDTAVYYCARGGYISDFD<br>VWGQGTLVTVSSASTKGPSVFPLAPSSKSTSGGTA<br>ALGCLVKDYFPEPVTVSWNSGALTSGVHTFPAVLQ<br>SSGLYSLSSVVTVPSSSLGTQTYICNVNHKPSNTKV<br>DKRVEPKSCDKTHTCPPCPAPELLGP |
| SEQ ID NO: 16 | LCDR1 (Kabat) | RASQSISNYLA |
| SEQ ID NO: 17 | LCDR2 (Kabat) | DASSLQS |
| SEQ ID NO: 18 | LCDR3 (Kabat) | QQYYYESIT |
| SEQ ID NO: 19 | LCDR1 (Chothia) | SQSISNY |
| SEQ ID NO: 20 | LCDR2 (Chothia) | DAS |
| SEQ ID NO: 21 | LCDR3 (Chothia) | YYYESI |
| SEQ ID NO: 16 | LCDR1 (Combined) | RASQSISNYLA |
| SEQ ID NO: 17 | LCDR2 (Combined) | DASSLQS |
| SEQ ID NO: 18 | LCDR3 (Combined) | QQYYYESIT |
| SEQ ID NO: 22 | LCDR1 (IMGT) | QSISNY |
| SEQ ID NO: 20 | LCDR2 (IMGT) | DAS |
| SEQ ID NO: 18 | LCDR3 (IMGT) | QQYYYESIT |
| SEQ ID NO: 23 | VL (kappa) | DIQMTQSPSSLSASVGDRVTITCRASQSISNYLAWY<br>QQKPGKAPKLLIYDASSLQSGVPSRFSGSGSGTDFT<br>LTISSLQPEDFATYYCQQYYYESITFGQGTKVEIK |
| SEQ ID NO: 24 | VL DNA | GATATCCAGATGACCCAGAGCCCGAGCAGCCTGA<br>GCGCCAGCGTGGGCGATCGCGTGACCATTACCT<br>GCAGAGCCAGCCAGTCTATTTCTAACTACCTGGC<br>TTGGTACCAGCAGAAACCGGGCAAAGCGCCGAAA<br>CTATTAATCTACGACGCTTCTTCTCTGCAAAGCGG<br>CGTGCCGAGCCGCTTTAGCGGCAGCGGATCCGG<br>CACCGATTTCACCCTGACCATTAGCTCTCTGCAAC<br>CGGAAGACTTTGCGACCTATTATTGCCAGCAGTA<br>CTACTACGAATCTATCACCTTTGGCCAGGGCACG<br>AAAGTTGAAATTAAA |
| SEQ ID NO: 25 | Ab/Fab' LC (kappa) | DIQMTQSPSSLSASVGDRVTITCRASQSISNYLAWY<br>QQKPGKAPKLLIYDASSLQSGVPSRFSGSGSGTDFT<br>LTISSLQPEDFATYYCQQYYYESITFGQGTKVEIKRT |

TABLE 1-continued

Sequences of exemplary anti-cKIT antibodies and antibody fragments

| | | |
|---|---|---|
| | | VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| SEQ ID NO: 26 | Ab/Fab' LC DNA | GATATCCAGATGACCCAGAGCCCGAGCAGCCTGA GCGCCAGCGTGGGCGATCGCGTGACCATTACCT GCAGAGCCAGCCAGTCTATTTCTAACTACCTGGC TTGGTACCAGCAGAAACCGGGCAAAGCGCCGAAA CTATTAATCTACGACGCTTCTTCTCTGCAAAGCGG CGTGCCGAGCCGCTTTAGCGGCAGCGGATCCGG CACCGATTTCACCCTGACCATTAGCTCTCTGCAAC CGGAAGACTTTGCGACCTATTATTGCCAGCAGTA CTACTACGAATCTATCACCTTTGGCCAGGGCACG AAAGTTGAAATTAAACGTACGGTGGCCGCTCCCA GCGTGTTCATCTTCCCCCCCAGCGACGAGCAGCT GAAGAGTGGCACCGCCAGCGTGGTGTGCCTGCT GAACAACTTCTACCCCCGGGAGGCCAAGGTGCAG TGGAAGGTGGACAACGCCCTGCAGAGCGGCAAC AGCCAGGAGAGCGTCACCGAGCAGGACAGCAAG GACTCCACCTACAGCCTGAGCAGCACCCTGACCC TGAGCAAGGCCGACTACGAGAAGCATAAGGTGTA CGCCTGCGAGGTGACCCACCAGGGCCTGTCCAG CCCCGTGACCAAGAGCTTCAACAGGGGCGAGTG C |
| SEQ ID NO: 122 | Cys Fab-LC-E165C (EU) | DIQMTQSPSSLSASVGDRVTITCRASQSISNYLAWY QQKPGKAPKLLIYDASSLQSGVPSRFSGSGSGTDFT LTISSLQPEDFATYYCQQYYYESITFGQGTKVEIKRT VAAPSVFIFPPSDEQLKSGTASVVCLLNNFYPREAK VQWKVDNALQSGNSQESVTCQDSKDSTYSLSSTLT LSKADYEKHKVYACEVTHQGLSSPVTKSFNRGEC |
| SEQ ID NO: 123 | Cys Fab-LC-S114C (EU) | DIQMTQSPSSLSASVGDRVTITCRASQSISNYLAWY QQKPGKAPKLLIYDASSLQSGVPSRFSGSGSGTDFT LTISSLQPEDFATYYCQQYYYESITFGQGTKVEIKRT VAAPCVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |

Anti-cKIT Ab2/Fab2/Fab'2

| | | |
|---|---|---|
| SEQ ID NO: 27 | HCDR1 (Kabat) | SHALS |
| SEQ ID NO: 28 | HCDR2 (Kabat) | GIIPSFGTADYAQKFQG |
| SEQ ID NO: 29 | HCDR3 (Kabat) | GLYDFDY |
| SEQ ID NO: 30 | HCDR1 (Chothia) | GGTFSSH |
| SEQ ID NO: 31 | HCDR2 (Chothia) | IPSFGT |
| SEQ ID NO: 29 | HCDR3 (Chothia) | GLYDFDY |
| SEQ ID NO: 32 | HCDR1 (Combined) | GGTFSSHALS |
| SEQ ID NO: 28 | HCDR2 (Combined) | GIIPSFGTADYAQKFQG |
| SEQ ID NO: 29 | HCDR3 (Combined) | GLYDFDY |
| SEQ ID NO: 33 | HCDR1 (IMGT) | GGTFSSHA |
| SEQ ID NO: 34 | HCDR2 (IMGT) | IIPSFGTA |
| SEQ ID NO: 35 | HCDR3 (IMGT) | ARGLYDFDY |
| SEQ ID NO: 36 | VH | QVQLVQSGAEVKKPGSSVKVSCKASGGTFSSHALS WVRQAPGQGLEWMGGIIPSFGTADYAQKFQGRVTI TADESTSTAYMELSSLRSEDTAVYYCARGLYDFDY WGQGTLVTVSS |
| SEQ ID NO: 37 | VH DNA | CAGGTGCAATTGGTGCAGAGCGGTGCCGAAGTG AAAAAACCGGGCAGCAGCGTGAAAGTTAGCTGCA AAGCATCCGGAGGGACGTTTTCTTCTCATGCTCT GTCTTGGGTGCGCCAGGCCCCGGGCCAGGGCCT CGAGTGGATGGGCGGTATCATCCCGTCTTTCGGC ACTGCGGACTACGCCCAGAAATTTCAGGGCCGGG TGACCATTACCGCCGATGAAAGCACCAGCACCGC CTATATGGAACTGAGCAGCCTGCGCAGCGAAGAT ACGGCCGTGTATTATTGCGCGCGTGGTCTGTACG ACTTCGACTACGGGGCCAAGGCACCCTGGTGAC TGTTAGCTCA |
| SEQ ID NO: 38 | Ab HC | QVQLVQSGAEVKKPGSSVKVSCKASGGTFSSHALS WVRQAPGQGLEWMGGIIPSFGTADYAQKFQGRVTI TADESTSTAYMELSSLRSEDTAVYYCARGLYDFDY WGQGTLVTVSSASTKGPSVFPLAPSSKSTSGGTAA LGCLVKDYFPEPVTVSWNSGALTSGVHTFPAVLQS SGLYSLSSVVTVPSSSLGTQTYICNVNHKPSNTKVD KRVEPKSCDKTHTCPPCPAPELLGGPSVFLFPPKPK DTLMISRTPEVTCVVVDVSHEDPEVKFNWYVDGVE VHNAKTKPREEQYNSTYRVVSVLTVLHQDWLNGKE YKCKVSNKALPAPIEKTISKAKGQPREPQVYTLPPSR EEMTKNQVSLTCLVKGFYPSDIAVEWESNGQPENN YKTTPPVLDSDGSFFLYSKLTVDKSRWQQGNVFSC SVMHEALHNHYTQKSLSLSPGK |

TABLE 1-continued

Sequences of exemplary anti-cKIT antibodies and antibody fragments

| | | |
|---|---|---|
| SEQ ID NO: 39 | Ab HC DNA | CAGGTGCAATTGGTGCAGAGCGGTGCCGAAGTG
AAAAAACCGGGCAGCAGCGTGAAAGTTAGCTGCA
AAGCATCCGGAGGGACGTTTTCTTCTCATGCTCT
GTCTTGGGTGCGCCAGGCCCCGGGCCAGGGCCT
CGAGTGGATGGGCGGTATCATCCCGTCTTTCGGC
ACTGCGGACTACGCCCAGAAATTTCAGGGCCGGG
TGACCATTACCGCCGATGAAAGCACCAGCACCGC
CTATATGGAACTGAGCAGCCTGCGCAGCGAAGAT
ACGGCCGTGTATTATTGCGCGCGTGGTCTGTACG
ACTTCGACTACTGGGGCCAAGGCACCCTGGTGAC
TGTTAGCTCAGCTAGCACCAAGGGCCCCAGCGTG
TTCCCCCTGGCCCCCAGCAGCAAGTCTACTTCCG
GCGGAACTGCTGCCCTGGGTTGCCTGGTGAAGG
ACTACTTCCCCGAGCCCGTGACAGTGTCCTGGAA
CTCTGGGGCTCTGACTTCCGGCGTGCACACCTTC
CCCGCCGTGCTGCAGAGCAGCGGCCTGTACAGC
CTGAGCAGCGTGGTGACAGTGCCCTCCAGCTCTC
TGGGAACCCAGACCTATATCTGCAACGTGAACCA
CAAGCCCAGCAACACCAAGGTGGACAAGAGAGTG
GAGCCCAAGAGCTGCGACAAGACCCACACCTGC
CCCCCCTGCCCAGCTCCAGAACTGCTGGGAGGG
CCTTCCGTGTTCCTGTTCCCCCCCAAGCCCAAGG
ACACCCTGATGATCAGCAGGACCCCCGAGGTGAC
CTGCGTGGTGGTGGACGTGTCCCACGAGGACCC
AGAGGTGAAGTTCAACTGGTACGTGGACGGCGTG
GAGGTGCACAACGCCAAGACCAAGCCCAGAGAG
GAGCAGTACAACAGCACCTACAGGGTGGTGTCCG
TGCTGACCGTGCTGCACCAGGACTGGCTGAACG
GCAAAGAATACAAGTGCAAAGTCTCCAACAAGGC
CCTGCCAGCCCCAATCGAAAAGACAATCAGCAAG
GCCAAGGGCCAGCCACGGGAGCCCCAGGTGTAC
ACCCTGCCCCCAGCCGGGAGGAGATGACCAAG
AACCAGGTGTCCCTGACCTGTCTGGTGAAGGGCT
TCTACCCCAGCGATATCGCCGTGGAGTGGGAGAG
CAACGGCCAGCCCGAGAACAACTACAAGACCACC
CCCCCAGTGCTGGACAGCGACGGCAGCTTCTTCC
TGTACAGCAAGCTGACCGTGGACAAGTCCAGGTG
GCAGCAGGGCAACGTGTTCAGCTGCAGCGTGAT
GCACGAGGCCCTGCACAACCACTACACCCAGAAG
TCCCTGAGCCTGAGCCCCGGCAAG |
| SEQ ID NO: 40 | Fab' HC(EU236) | QVQLVQSGAEVKKPGSSVKVSCKASGGTFSSHALS
WVRQAPGQGLEWMGGIIPSFGTADYAQKFQGRVTI
TADESTSTAYMELSSLRSEDTAVYYCARGLYDFDY
WGQGTLVTVSSASTKGPSVFPLAPSSKSTSGGTAA
LGCLVKDYFPEPVTVSWNSGALTSGVHTFPAVLQS
SGLYSLSSVVTVPSSSLGTQTYICNVNHKPSNTKVD
KRVEPKSCDKTHTCPPCPAPELLG |
| SEQ ID NO: 41 | Fab' HC DNA | CAGGTGCAATTGGTGCAGAGCGGTGCCGAAGTG
AAAAAACCGGGCAGCAGCGTGAAAGTTAGCTGCA
AAGCATCCGGAGGGACGTTTTCTTCTCATGCTCT
GTCTTGGGTGCGCCAGGCCCCGGGCCAGGGCCT
CGAGTGGATGGGCGGTATCATCCCGTCTTTCGGC
ACTGCGGACTACGCCCAGAAATTTCAGGGCCGGG
TGACCATTACCGCCGATGAAAGCACCAGCACCGC
CTATATGGAACTGAGCAGCCTGCGCAGCGAAGAT
ACGGCCGTGTATTATTGCGCGCGTGGTCTGTACG
ACTTCGACTACTGGGGCCAAGGCACCCTGGTGAC
TGTTAGCTCAGCTAGCACCAAGGGCCCCAGCGTG
TTCCCCCTGGCCCCCAGCAGCAAGTCTACTTCCG
GCGGAACTGCTGCCCTGGGTTGCCTGGTGAAGG
ACTACTTCCCCGAGCCCGTGACAGTGTCCTGGAA
CTCTGGGGCTCTGACTTCCGGCGTGCACACCTTC
CCCGCCGTGCTGCAGAGCAGCGGCCTGTACAGC
CTGAGCAGCGTGGTGACAGTGCCCTCCAGCTCTC
TGGGAACCCAGACCTATATCTGCAACGTGAACCA
CAAGCCCAGCAACACCAAGGTGGACAAGAGAGTG
GAGCCCAAGAGCTGCGACAAGACCCACACCTGC
CCCCCCTGCCCAGCTCCAGAACTGCTGGGA |
| SEQ ID NO: 124 | Cys Fab-
HC(EU221)-HC-
E152C (EU) | QVQLVQSGAEVKKPGSSVKVSCKASGGTFSSHALS
WVRQAPGQGLEWMGGIIPSFGTADYAQKFQGRVTI
TADESTSTAYMELSSLRSEDTAVYYCARGLYDFDY
WGQGTLVTVSSASTKGPSVFPLAPSSKSTSGGTAA
LGCLVKDYFPCPVTVSWNSGALTSGVHTFPAVLQS
SGLYSLSSVVT̄VPSSSLGTQTYICNVNHKPSNTKVD
KRVEPKSCD |
| SEQ ID NO: 125 | Fab' HC(EU230) | QVQLVQSGAEVKKPGSSVKVSCKASGGTFSSHALS
WVRQAPGQGLEWMGGIIPSFGTADYAQKFQGRVTI
TADESTSTAYMELSSLRSEDTAVYYCARGLYDFDY |

TABLE 1-continued

Sequences of exemplary anti-cKIT antibodies and antibody fragments

| | | |
|---|---|---|
| | | WGQGTLVTVSSASTKGPSVFPLAPSSKSTSGGTAA LGCLVKDYFPEPVTVSWNSGALTSGVHTFPAVLQS SGLYSLSSVVTVPSSSLGTQTYICNVNHKPSNTKVD KRVEPKSCDKTHTCPPCP |
| SEQ ID NO: 126 | Fab' HC(EU232) | QVQLVQSGAEVKKPGSSVKVSCKASGGTFSSHALS WVRQAPGQGLEWMGGIIPSFGTADYAQKFQGRVTI TADESTSTAYMELSSLRSEDTAVYYCARGLYDFDY WGQGTLVTVSSASTKGPSVFPLAPSSKSTSGGTAA LGCLVKDYFPEPVTVSWNSGALTSGVHTFPAVLQS SGLYSLSSVVTVPSSSLGTQTYICNVNHKPSNTKVD KRVEPKSCDKTHTCPPCPAP |
| SEQ ID NO: 127 | Fab' HC(EU236)-Pro | QVQLVQSGAEVKKPGSSVKVSCKASGGTFSSHALS WVRQAPGQGLEWMGGIIPSFGTADYAQKFQGRVTI TADESTSTAYMELSSLRSEDTAVYYCARGLYDFDY WGQGTLVTVSSASTKGPSVFPLAPSSKSTSGGTAA LGCLVKDYFPEPVTVSWNSGALTSGVHTFPAVLQS SGLYSLSSVVTVPSSSLGTQTYICNVNHKPSNTKVD KRVEPKSCDKTHTCPPCPAPELLGP |
| SEQ ID NO: 42 | LCDR1 (Kabat) | RASQDISQDLA |
| SEQ ID NO: 17 | LCDR2 (Kabat) | DASSLQS |
| SEQ ID NO: 43 | LCDR3 (Kabat) | QQYYYLPST |
| SEQ ID NO: 44 | LCDR1 (Chothia) | SQDISQD |
| SEQ ID NO: 20 | LCDR2 (Chothia) | DAS |
| SEQ ID NO: 45 | LCDR3 (Chothia) | YYYLPS |
| SEQ ID NO: 42 | LCDR1 (Combined) | RASQDISQDLA |
| SEQ ID NO: 17 | LCDR2 (Combined) | DASSLQS |
| SEQ ID NO: 43 | LCDR3 (Combined) | QQYYYLPST |
| SEQ ID NO: 46 | LCDR1 (IMGT) | QDISQD |
| SEQ ID NO: 20 | LCDR2 (IMGT) | DAS |
| SEQ ID NO: 43 | LCDR3 (IMGT) | QQYYYLPST |
| SEQ ID NO: 47 | VL (kappa) | DIQMTQSPSSLSASVGDRVTITCRASQDISQDLAWY QQKPGKAPKLLIYDASSLQSGVPSRFSGSGSGTDFT LTISSLQPEDFAVYYCQQYYYLPSTFGQGTKVEIK |
| SEQ ID NO: 48 | VL DNA | GATATCCAGATGACCCAGAGCCCGAGCAGCCTGA GCGCCAGCGTGGGCGATCGCGTGACCATTACCT GCAGAGCCAGCCAGGACATTTCTCAGGACCTGGC TTGGTACCAGCAGAAACCGGGCAAAGCGCCGAAA CTATTAATCTACGACGCTTCTTCTCTGCAAAGCGG CGTGCCGAGCCGCTTTAGCGGCAGCGGATCCGG CACCGATTTCACCCTGACCATTAGCTCTCTGCAAC CGGAAGACTTTGCGGTGTATTATTGCCAGCAGTA CTACTACCTGCCGTCTACCTTTGGCCAGGGCACG AAAGTTGAAATTAAA |
| SEQ ID NO: 49 | Ab/Fab' LC (kappa) | DIQMTQSPSSLSASVGDRVTITCRASQDISQDLAWY QQKPGKAPKLLIYDASSLQSGVPSRFSGSGSGTDFT LTISSLQPEDFAVYYCQQYYYLPSTFGQGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| SEQ ID NO: 50 | Ab/Fab' LC DNA | GATATCCAGATGACCCAGAGCCCGAGCAGCCTGA GCGCCAGCGTGGGCGATCGCGTGACCATTACCT GCAGAGCCAGCCAGGACATTTCTCAGGACCTGGC TTGGTACCAGCAGAAACCGGGCAAAGCGCCGAAA CTATTAATCTACGACGCTTCTTCTCTGCAAAGCGG CGTGCCGAGCCGCTTTAGCGGCAGCGGATCCGG CACCGATTTCACCCTGACCATTAGCTCTCTGCAAC CGGAAGACTTTGCGGTGTATTATTGCCAGCAGTA CTACTACCTGCCGTCTACCTTTGGCCAGGGCACG AAAGTTGAAATTAAACGTACGGTGGCCGCTCCCA GCGTGTTCATCTTCCCCCCCAGCGACGAGCAGCT GAAGAGTGGCACCGCCAGCGTGGTGTGCCTGCT GAACAACTTCTACCCCCGGGAGGCCAAGGTGCAG TGGAAGGTGGACAACGCCCTGCAGAGCGGCAAC AGCCAGGAGAGCGTCACCGAGCAGGACAGCAAG GACTCCACCTACAGCCTGAGCAGCACCCTGACCC TGAGCAAGGCCGACTACGAGAAGCATAAGGTGTA CGCCTGCGAGGTGACCCACCAGGGCCTGTCCAG CCCCGTGACCAAGAGCTTCAACAGGGGCGAGTG C |
| SEQ ID NO: 128 | Cys Fab-LC-E165C (EU) | DIQMTQSPSSLSASVGDRVTITCRASQDISQDLAWY QQKPGKAPKLLIYDASSLQSGVPSRFSGSGSGTDFT LTISSLQPEDFAVYYCQQYYYLPSTFGQGTKVEIKRT VAAPSVFIFPPSDEQLKSGTASVVCLLNNFYPREAK VQWKVDNALQSGNSQESVTCQDSKDSTYSLSSTLT LSKADYEKHKVYACEVTHQGLSSPVTKSFNRGEC |
| SEQ ID NO: 129 | Cys Fab-LC-S114C (EU) | DIQMTQSPSSLSASVGDRVTITCRASQDISQDLAWY QQKPGKAPKLLIYDASSLQSGVPSRFSGSGSGTDFT LTISSLQPEDFAVYYCQQYYYLPSTFGQGTKVEIKRT |

TABLE 1-continued

Sequences of exemplary anti-cKIT antibodies and antibody fragments

```
                                VAAPCVFIFPPSDEQLKSGTASVVCLLNNFYPREAK
                                VQWKVDNALQSGNSQESVTEQDSKDSTYSLSSTLT
                                LSKADYEKHKVYACEVTHQGLSSPVTKSFNRGEC
```

Anti-cKIT Ab3/Fab3/Fab'3

| SEQ ID NO: | | | |
|---|---|---|---|
| SEQ ID NO: 1 | HCDR1 | (Kabat) | SYAIS |
| SEQ ID NO: 51 | HCDR2 | (Kabat) | TIGPFEGQPRYAQKFQG |
| SEQ ID NO: 3 | HCDR3 | (Kabat) | GGYISDFDV |
| SEQ ID NO: 4 | HCDR1 | (Chothia) | GGTFSSY |
| SEQ ID NO: 52 | HCDR2 | (Chothia) | GPFEGQ |
| SEQ ID NO: 3 | HCDR3 | (Chothia) | GGYISDFDV |
| SEQ ID NO: 6 | HCDR1 | (Combined) | GGTFSSYAIS |
| SEQ ID NO: 51 | HCDR2 | (Combined) | TIGPFEGQPRYAQKFQG |
| SEQ ID NO: 3 | HCDR3 | (Combined) | GGYISDFDV |
| SEQ ID NO: 7 | HCDR1 | (IMGT) | GGTFSSYA |
| SEQ ID NO: 53 | HCDR2 | (IMGT) | IGPFEGQP |
| SEQ ID NO: 9 | HCDR3 | (IMGT) | ARGGYISDFDV |
| SEQ ID NO: 54 | VH | | QVQLVQSGAEVKKPGSSVKVSCKASGGTFSSYAIS WVRQAPGQGLEWMGTIGPFEGQPRYAQKFQGRVT ITADESTSTAYMELSSLRSEDTAVYYCARGGYISDFD VWGQGTLVTVSS |
| SEQ ID NO: 55 | VH DNA | | CAGGTGCAATTGGTGCAGAGCGGTGCCGAAGTG AAAAAACCGGGCAGCAGCGTGAAAGTTAGCTGCA AAGCATCCGGAGGGACGTTTAGCAGCTATGCGAT TAGCTGGGTGCGCCAGGCCCCGGGCCAGGGCCT CGAGTGGATGGGCACTATCGGTCCGTTCGAAGGC CAGCCGCGTTACGCCCAGAAATTTCAGGGCCGG GTGACCATTACCGCCGATGAAAGCACCAGCACCG CCTATATGGAACTGAGCAGCCTGCGCAGCGAAGA TACGGCCGTGTATTATTGCGCGCGTGGTGGTTAC ATCTCTGACTTCGATGTTTGGGGCCAAGGCACCC TGGTGACTGTTAGCTCA |
| SEQ ID NO: 56 | Ab HC | | QVQLVQSGAEVKKPGSSVKVSCKASGGTFSSYAIS WVRQAPGQGLEWMGTIGPFEGQPRYAQKFQGRVT ITADESTSTAYMELSSLRSEDTAVYYCARGGYISDFD VWGQGTLVTVSSASTKGPSVFPLAPSSKSTSGGTA ALGCLVKDYFPEPVTVSWNSGALTSGVHTFPAVLQ SSGLYSLSSVVTVPSSSLGTQTYICNVNHKPSNTKV DKRVEPKSCDKTHTCPPCPAPELLGGPSVFLFPPKP KDTLMISRTPEVTCVVVDVSHEDPEVKFNWYVDGV EVHNAKTKPREEQYNSTYRVVSVLTVLHQDWLNGK EYKCKVSNKALPAPIEKTISKAKGQPREPQVYTLPPS REEMTKNQVSLTCLVKGFYPSDIAVEWESNGQPEN NYKTTPPVLDSDGSFFLYSKLTVDKSRWQQGNVFS CSVMHEALHNHYTQKSLSLSPGK |
| SEQ ID NO: 57 | Ab HC DNA | | CAGGTGCAATTGGTGCAGAGCGGTGCCGAAGTG AAAAAACCGGGCAGCAGCGTGAAAGTTAGCTGCA AAGCATCCGGAGGGACGTTTAGCAGCTATGCGAT TAGCTGGGTGCGCCAGGCCCCGGGCCAGGGCCT CGAGTGGATGGGCACTATCGGTCCGTTCGAAGGC CAGCCGCGTTACGCCCAGAAATTTCAGGGCCGG GTGACCATTACCGCCGATGAAAGCACCAGCACCG CCTATATGGAACTGAGCAGCCTGCGCAGCGAAGA TACGGCCGTGTATTATTGCGCGCGTGGTGGTTAC ATCTCTGACTTCGATGTTTGGGGCCAAGGCACCC TGGTGACTGTTAGCTCAGCTAGCACCAAGGGCCC AAGTGTGTTTCCCCTGGCCCCCAGCAGCAAGTCT ACTTCCGGCGGAACTGCTGCCCTGGGTTGCCTGG TGAAGGACTACTTCCCCGAGCCCGTGACAGTGTC CTGGAACTCTGGGGCTCTGACTTCCGGCGTGCAC ACCTTCCCCGCCGTGCTGCAGAGCAGCGGCCTG TACAGCCTGAGCAGCGTGGTGACAGTGCCCTCCA GCTCTCTGGGAACCCAGACCTATATCTGCAACGT GAACCACAAGCCCAGCAACACCAAGGTGGACAAG AGAGTGGAGCCCAAGAGCTGCGACAAGACCCAC ACCTGCCCCCCCTGCCCAGCTCCAGAACTGCTGG GAGGGCCTTCCGTGTTCCTGTTCCCCCCCAAGCC CAAGGACACCCTGATGATCAGCAGGACCCCCGAG GTGACCTGCGTGGTGGTGGACGTGTCCCACGAG GACCCAGAGGTGAAGTTCAACTGGTACGTGGACG GCGTGGAGGTGCACAACGCCAAGACCAAGCCCA GAGAGGAGCAGTACAACAGCACCTACAGGGTGGT GTCCGTGCTGACCGTGCTGCACCAGGACTGGCT GAACGGCAAAGAATACAAGTGCAAAGTCTCCAAC AAGGCCCTGCCAGCCCCAATCGAAAAGACAATCA GCAAGGCCAAGGGCCAGCCACGGGAGCCCCAGG TGTACACCCTGCCCCCCAGCCGGGAGGAGATGA |

TABLE 1-continued

Sequences of exemplary anti-cKIT antibodies and antibody fragments

| | | |
|---|---|---|
| | | CCAAGAACCAGGTGTCCCTGACCTGTCTGGTGAA<br>GGGCTTCTACCCCAGCGATATCGCCGTGGAGTGG<br>GAGAGCAACGGCCAGCCCGAGAACAACTACAAGA<br>CCACCCCCCCAGTGCTGGACAGCGACGGCAGCT<br>TCTTCCTGTACAGCAAGCTGACCGTGGACAAGTC<br>CAGGTGGCAGCAGGGCAACGTGTTCAGCTGCAG<br>CGTGATGCACGAGGCCCTGCACAACCACTACACC<br>CAGAAGTCCCTGAGCCTGAGCCCCGGCAAG |
| SEQ ID NO: 58 | Fab' HC(EU236) | QVQLVQSGAEVKKPGSSVKVSCKASGGTFSSYAIS<br>WVRQAPGQGLEWMGTIGPFEGQPRYAQKFQGRVT<br>ITADESTSTAYMELSSLRSEDTAVYYCARGGYISDFD<br>VWGQGTLVTVSSASTKGPSVFPLAPSSKSTSGGTA<br>ALGCLVKDYFPEPVTVSWNSGALTSGVHTFPAVLQ<br>SSGLYSLSSVVTVPSSSLGTQTYICNVNHKPSNTKV<br>DKRVEPKSCDKTHTCPPCPAPELLG |
| SEQ ID NO: 59 | Fab' HC DNA | CAGGTGCAATTGGTGCAGAGCGGTGCCGAAGTG<br>AAAAAACCGGGCAGCAGCGTGAAAGTTAGCTGCA<br>AAGCATCCGGAGGGACGTTTAGCAGCTATGCGAT<br>TAGCTGGGTGCGCCAGGCCCCGGGCCAGGGCCT<br>CGAGTGGATGGGCACTATCGGTCCGTTCGAAGGC<br>CAGCCGCGTTACGCCCAGAAATTTCAGGGCCGG<br>GTGACCATTACCGCCGATGAAAGCACCAGCACCG<br>CCTATATGGAACTGAGCAGCCTGCGCAGCGAAGA<br>TACGGCCGTGTATTATTGCGCGCGTGGTGGTTAC<br>ATCTCTGACTTCGATGTTTGGGGCCAAGGCACCC<br>TGGTGACTGTTAGCTCAGCTAGCACCAAGGGCCC<br>AAGTGTGTTTCCCCTGGCCCCCAGCAGCAAGTCT<br>ACTTCCGGCGGAACTGCTGCCCTGGGTTGCCTGG<br>TGAAGGACTACTTCCCCGAGCCCGTGACAGTGTC<br>CTGGAACTCTGGGGCTCTGACTTCCGGCGTGCAC<br>ACCTTCCCCGCCGTGCTGCAGAGCAGCGGCCTG<br>TACAGCCTGAGCAGCGTGGTGACAGTGCCCTCCA<br>GCTCTCTGGGAACCCAGACCTATATCTGCAACGT<br>GAACCACAAGCCCAGCAACACCAAGGTGGACAAG<br>AGAGTGGAGCCCAAGAGCTGCGACAAGACCCAC<br>ACCTGCCCCCCCTGCCCAGCTCCAGAACTGCTGG<br>GA |
| SEQ ID NO: 130 | Cys Fab<br>HC(EU221)-HC-<br>E152C (EU) | QVQLVQSGAEVKKPGSSVKVSCKASGGTFSSYAIS<br>WVRQAPGQGLEWMGTIGPFEGQPRYAQKFQGRVT<br>ITADESTSTAYMELSSLRSEDTAVYYCARGGYISDFD<br>VWGQGTLVTVSSASTKGPSVFPLAPSSKSTSGGTA<br>ALGCLVKDYFPCPVTVSWNSGALTSGVHTFPAVLQ<br>SSGLYSLSSVVTVPSSSLGTQTYICNVNHKPSNTKV<br>DKKVEPKSCD |
| SEQ ID NO: 131 | Fab' HC(EU230) | QVQLVQSGAEVKKPGSSVKVSCKASGGTFSSYAIS<br>WVRQAPGQGLEWMGTIGPFEGQPRYAQKFQGRVT<br>ITADESTSTAYMELSSLRSEDTAVYYCARGGYISDFD<br>VWGQGTLVTVSSASTKGPSVFPLAPSSKSTSGGTA<br>ALGCLVKDYFPEPVTVSWNSGALTSGVHTFPAVLQ<br>SSGLYSLSSVVTVPSSSLGTQTYICNVNHKPSNTKV<br>DKRVEPKSCDKTHTCPPCP |
| SEQ ID NO: 132 | Fab' HC(EU232) | QVQLVQSGAEVKKPGSSVKVSCKASGGTFSSYAIS<br>WVRQAPGQGLEWMGTIGPFEGQPRYAQKFQGRVT<br>ITADESTSTAYMELSSLRSEDTAVYYCARGGYISDFD<br>VWGQGTLVTVSSASTKGPSVFPLAPSSKSTSGGTA<br>ALGCLVKDYFPEPVTVSWNSGALTSGVHTFPAVLQ<br>SSGLYSLSSVVTVPSSSLGTQTYICNVNHKPSNTKV<br>DKRVEPKSCDKTHTCPPCPAP |
| SEQ ID NO: 133 | Fab' HC(EU236)-Pro | QVQLVQSGAEVKKPGSSVKVSCKASGGTFSSYAIS<br>WVRQAPGQGLEWMGTIGPFEGQPRYAQKFQGRVT<br>ITADESTSTAYMELSSLRSEDTAVYYCARGGYISDFD<br>VWGQGTLVTVSSASTKGPSVFPLAPSSKSTSGGTA<br>ALGCLVKDYFPEPVTVSWNSGALTSGVHTFPAVLQ<br>SSGLYSLSSVVTVPSSSLGTQTYICNVNHKPSNTKV<br>DKRVEPKSCDKTHTCPPCPAPELLGP |
| SEQ ID NO: 16 | LCDR1 (Kabat) | RASQSISNYLA |
| SEQ ID NO: 17 | LCDR2 (Kabat) | DASSLQS |
| SEQ ID NO: 18 | LCDR3 (Kabat) | QQYYYESIT |
| SEQ ID NO: 19 | LCDR1 (Chothia) | SQSISNY |
| SEQ ID NO: 20 | LCDR2 (Chothia) | DAS |
| SEQ ID NO: 21 | LCDR3 (Chothia) | YYYESI |
| SEQ ID NO: 16 | LCDR1 (Combined) | RASQSISNYLA |
| SEQ ID NO: 17 | LCDR2 (Combined) | DASSLQS |

TABLE 1-continued

Sequences of exemplary anti-cKIT antibodies and antibody fragments

| SEQ ID NO: 18 | LCDR3 (Combined) | QQYYYESIT |
|---|---|---|
| SEQ ID NO: 22 | LCDR1 (IMGT) | QSISNY |
| SEQ ID NO: 20 | LCDR2 (IMGT) | DAS |
| SEQ ID NO: 18 | LCDR3 (IMGT) | QQYYYESIT |
| SEQ ID NO: 23 | VL (kappa) | DIQMTQSPSSLSASVGDRVTITCRASQSISNYLAWY QQKPGKAPKLLIYDASSLQSGVPSRFSGSGSGTDFT LTISSLQPEDFATYYCQQYYYESITFGQGTKVEIK |
| SEQ ID NO: 24 | VL DNA | GATATCCAGATGACCCAGAGCCCGAGCAGCCTGA GCGCCAGCGTGGGCGATCGCGTGACCATTACCT GCAGAGCCAGCCAGTCTATTTCTAACTACCTGGC TTGGTACCAGCAGAAACCGGGCAAAGCGCCGAAA CTATTAATCTACGACGCTTCTTCTCTGCAAAGCGG CGTGCCGAGCCGCTTTAGCGGCAGCGGATCCGG CACCGATTTCACCCTGACCATTAGCTCTCTGCAAC CGGAAGACTTTGCGACCTATTATTGCCAGCAGTA CTACTACGAATCTATCACCTTTGGCCAGGGCACG AAAGTTGAAATTAAA |
| SEQ ID NO: 25 | Ab/Fab' LC (kappa) | DIQMTQSPSSLSASVGDRVTITCRASQSISNYLAWY QQKPGKAPKLLIYDASSLQSGVPSRFSGSGSGTDFT LTISSLQPEDFATYYCQQYYYESITFGQGTKVEIKRT VAAPSVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |
| SEQ ID NO: 26 | Ab/Fab' LC DNA | GATATCCAGATGACCCAGAGCCCGAGCAGCCTGA GCGCCAGCGTGGGCGATCGCGTGACCATTACCT GCAGAGCCAGCCAGTCTATTTCTAACTACCTGGC TTGGTACCAGCAGAAACCGGGCAAAGCGCCGAAA CTATTAATCTACGACGCTTCTTCTCTGCAAAGCGG CGTGCCGAGCCGCTTTAGCGGCAGCGGATCCGG CACCGATTTCACCCTGACCATTAGCTCTCTGCAAC CGGAAGACTTTGCGACCTATTATTGCCAGCAGTA CTACTACGAATCTATCACCTTTGGCCAGGGCACG AAAGTTGAAATTAAACGTACGGTGGCCGCTCCCA GCGTGTTCATCTTCCCCCCCAGCGACGAGCAGCT GAAGAGTGGCACCGCCAGCGTGGTGTGCCTGCT GAACAACTTCTACCCCCGGGAGGCCAAGGTGCAG TGGAAGGTGGACAACGCCCTGCAGAGCGGCAAC AGCCAGGAGAGCGTCACCGAGCAGGACAGCAAG GACTCCACCTACAGCCTGAGCAGCACCCTGACCC TGAGCAAGGCCGACTACGAGAAGCATAAGGTGTA CGCCTGCGAGGTGACCCACCAGGGCCTGTCCAG CCCCGTGACCAAGAGCTTCAACAGGGGCGAGTG C |
| SEQ ID NO: 134 | Cys Fab-LC-E165C (EU) | DIQMTQSPSSLSASVGDRVTITCRASQSISNYLAWY QQKPGKAPKLLIYDASSLQSGVPSRFSGSGSGTDFT LTISSLQPEDFATYYCQQYYYESITFGQGTKVEIKRT VAAPSVFIFPPSDEQLKSGTASVVCLLNNFYPREAK VQWKVDNALQSGNSQESVTCQDSKDSTYSLSSTLT LSKADYEKHKVYACEVTHQGLSSPVTKSFNRGEC |
| SEQ ID NO: 135 | Cys Fab-LC-S114C (EU) | DIQMTQSPSSLSASVGDRVTITCRASQSISNYLAWY QQKPGKAPKLLIYDASSLQSGVPSRFSGSGSGTDFT LTISSLQPEDFATYYCQQYYYESITFGQGTKVEIKRT VAAPCVFIFPPSDEQLKSGTASVVCLLNNFYPREAK VQWKVDNALQSGNSQESVTEQDSKDSTYSLSSTLT LSKADYEKHKVYACEVTHQGLSSPVTKSFNRGEC |

Anti-cKIT Ab4/Fab4/Fab'4

| SEQ ID NO: 60 | HCDR1 (Kabat) | TNSAAWN |
|---|---|---|
| SEQ ID NO: 61 | HCDR2 (Kabat) | RIYYRSQWLNDYAVSVKS |
| SEQ ID NO: 62 | HCDR3 (Kabat) | QLTYPYTVYHKALDV |
| SEQ ID NO: 63 | HCDR1 (Chothia) | GDSVSTNSA |
| SEQ ID NO: 64 | HCDR2 (Chothia) | YYRSQWL |
| SEQ ID NO: 62 | HCDR3 (Chothia) | QLTYPYTVYHKALDV |
| SEQ ID NO: 65 | HCDR1 (Combined) | GDSVSTNSAAWN |
| SEQ ID NO: 61 | HCDR2 (Combined) | RIYYRSQWLNDYAVSVKS |
| SEQ ID NO: 62 | HCDR3 (Combined) | QLTYPYTVYHKALDV |
| SEQ ID NO: 66 | HCDR1 (IMGT) | GDSVSTNSAA |
| SEQ ID NO: 67 | HCDR2 (IMGT) | IYYRSQWLN |
| SEQ ID NO: 68 | HCDR3 (IMGT) | ARQLTYPYTVYHKALDV |
| SEQ ID NO: 69 | VH | QVQLQQSGPGLVKPSQTLSLTCAISGDSVSTNSAA WNWIRQSPSRGLEWLGRIYYRSQWLNDYAVSVKS RITINPDTSKNQFSLQLNSVTPEDTAVYYCARQLTYP YTVYHKALDVWGQGTLVTVSS |
| SEQ ID NO: 70 | VH DNA | CAGGTGCAATTGCAGCAGAGCGGTCCGGGCCTG GTGAAACCGAGCCAGACCCTGAGCCTGACCTGC GCGATTTCCGGAGATAGCGTGAGCACTAACTCTG CTGCTTGGAACTGGATTCGTCAGAGCCCGAGCCG |

TABLE 1-continued

Sequences of exemplary anti-cKIT antibodies and antibody fragments

|  |  |  |
|---|---|---|
|  |  | TGGCCTCGAGTGGCTGGGCCGTATCTACTACCGT<br>AGCCAGTGGCTGAACGACTATGCCGTGAGCGTGA<br>AAAGCCGCATTACCATTAACCCGGATACTTCGAAA<br>AACCAGTTTAGCCTGCAACTGAACAGCGTGACCC<br>CGGAAGATACGGCCGTGTATTATTGCGCGCGTCA<br>GCTGACTTACCCGTACACTGTTTACCATAAAGCTC<br>TGGATGTTTGGGGTCAAGGAACCCTGGTCACCGT<br>CTCCTCG |
| SEQ ID NO: 71 | Ab HC | QVQLQQSGPGLVKPSQTLSLTCAISGDSVSTNSAA<br>WNWIRQSPSRGLEWLGRIYYRSQWLNDYAVSVKS<br>RITINPDTSKNQFSLQLNSVTPEDTAVYYCARQLTYP<br>YTVYHKALDVWGQGTLVTVSSASTKGPSVFPLAPS<br>SKSTSGGTAALGCLVKDYFPEPVTVSWNSGALTSG<br>VHTFPAVLQSSGLYSLSSVVTVPSSSLGTQTYICNV<br>NHKPSNTKVDKRVEPKSCDKTHTCPPCPAPELLGG<br>PSVFLFPPKPKDTLMISRTPEVTCVVVDVSHEDPEV<br>KFNWYVDGVEVHNAKTKPREEQYNSTYRVVSVLTV<br>LHQDWLNGKEYKCKVSNKALPAPIEKTISKAKGQPR<br>EPQVYTLPPSREEMTKNQVSLTCLVKGFYPSDIAVE<br>WESNGQPENNYKTTPPVLDSDGSFFLYSKLTVDKS<br>RWQQGNVFSCSVMHEALHNHYTQKSLSLSPGK |
| SEQ ID NO: 72 | Ab HC DNA | CAGGTGCAATTGCAGCAGAGCGGTCCGGGCCTG<br>GTGAAACCGAGCCAGACCCTGAGCCTGACCTGC<br>GCGATTTCCGGAGATAGCGTGAGCACTAACTCTG<br>CTGCTTGGAACTGGATTCGTCAGAGCCCGAGCCG<br>TGGCCTCGAGTGGCTGGGCCGTATCTACTACCGT<br>AGCCAGTGGCTGAACGACTATGCCGTGAGCGTGA<br>AAAGCCGCATTACCATTAACCCGGATACTTCGAAA<br>AACCAGTTTAGCCTGCAACTGAACAGCGTGACCC<br>CGGAAGATACGGCCGTGTATTATTGCGCGCGTCA<br>GCTGACTTACCCGTACACTGTTTACCATAAAGCTC<br>TGGATGTTTGGGGTCAAGGAACCCTGGTCACCGT<br>CTCCTCGGCTAGCACCAAGGGCCCCAGCGTGTTC<br>CCCCTGGCCCCCAGCAGCAAGTCTACTTCCGGCG<br>GAACTGCTGCCCTGGGTTGCCTGGTGAAGGACTA<br>CTTCCCCGAGCCCGTGACAGTGTCCTGGAACTCT<br>GGGGCTCTGACTTCCGGCGTGCACACCTTCCCCG<br>CCGTGCTGCAGAGCAGCGGCCTGTACAGCCTGA<br>GCAGCGTGGTGACAGTGCCCTCCAGCTCTCTGG<br>GAACCCAGACCTATATCTGCAACGTGAACCACAA<br>GCCCAGCAACACCAAGGTGGACAAGAGAGTGGA<br>GCCCAAGAGCTGCGACAAGACCCACACCTGCCC<br>CCCCTGCCCAGCTCCAGAACTGCTGGGAGGGCC<br>TTCCGTGTTCCTGTTCCCCCCCAAGCCCAAGGAC<br>ACCCTGATGATCAGCAGGACCCCCGAGGTGACCT<br>GCGTGGTGGTGGACGTGTCCCACGAGGACCCAG<br>AGGTGAAGTTCAACTGGTACGTGGACGGCGTGGA<br>GGTGCACAACGCCAAGACCAAGCCCAGAGAGGA<br>GCAGTACAACAGCACCTACAGGGTGGTGTCCGTG<br>CTGACCGTGCTGCACCAGGACTGGCTGAACGGC<br>AAAGAATACAAGTGCAAAGTCTCCAACAAGGCCC<br>TGCCAGCCCCAATCGAAAAGACAATCAGCAAGGC<br>CAAGGGCCAGCCACGGGAGCCCCAGGTGTACAC<br>CCTGCCCCCCAGCCGGGAGGAGATGACCAAGAA<br>CCAGGTGTCCCTGACCTGTCTGGTGAAGGGCTTC<br>TACCCCAGCGATATCGCCGTGGAGTGGGAGAGC<br>AACGGCCAGCCCGAGAACAACTACAAGACCACCC<br>CCCCAGTGCTGGACAGCGACGGCAGCTTCTTCCT<br>GTACAGCAAGCTGACCGTGGACAAGTCCAGGTGG<br>CAGCAGGGCAACGTGTTCAGCTGCAGCGTGATGC<br>ACGAGGCCCTGCACAACCACTACACCCAGAAGTC<br>CCTGAGCCTGAGCCCCGGCAAG |
| SEQ ID NO: 73 | Fab' HC (EU236) | QVQLQQSGPGLVKPSQTLSLTCAISGDSVSTNSAA<br>WNWIRQSPSRGLEWLGRIYYRSQWLNDYAVSVKS<br>RITINPDTSKNQFSLQLNSVTPEDTAVYYCARQLTYP<br>YTVYHKALDVWGQGTLVTVSSASTKGPSVFPLAPS<br>SKSTSGGTAALGCLVKDYFPEPVTVSWNSGALTSG<br>VHTFPAVLQSSGLYSLSSVVTVPSSSLGTQTYICNV<br>NHKPSNTKVDKRVEPKSCDKTHTCPPCPAPELLG |
| SEQ ID NO: 74 | Fab' HC DNA | CAGGTGCAATTGCAGCAGAGCGGTCCGGGCCTG<br>GTGAAACCGAGCCAGACCCTGAGCCTGACCTGC<br>GCGATTTCCGGAGATAGCGTGAGCACTAACTCTG<br>CTGCTTGGAACTGGATTCGTCAGAGCCCGAGCCG<br>TGGCCTCGAGTGGCTGGGCCGTATCTACTACCGT<br>AGCCAGTGGCTGAACGACTATGCCGTGAGCGTGA<br>AAAGCCGCATTACCATTAACCCGGATACTTCGAAA<br>AACCAGTTTAGCCTGCAACTGAACAGCGTGACCC<br>CGGAAGATACGGCCGTGTATTATTGCGCGCGTCA |

TABLE 1-continued

Sequences of exemplary anti-cKIT antibodies and antibody fragments

| | | |
|---|---|---|
| | | GCTGACTTACCCGTACACTGTTTACCATAAAGCTC<br>TGGATGTTTGGGGTCAAGGAACCCTGGTCACCGT<br>CTCCTCGGCTAGCACCAAGGGCCCCAGCGTGTTC<br>CCCCTGGCCCCCAGCAGCAAGTCTACTTCCGGCG<br>GAACTGCTGCCCTGGGTTGCCTGGTGAAGGACTA<br>CTTCCCCGAGCCCGTGACAGTGTCCTGGAACTCT<br>GGGGCTCTGACTTCCGGCGTGCACACCTTCCCCG<br>CCGTGCTGCAGAGCAGCGGCCTGTACAGCCTGA<br>GCAGCGTGGTGACAGTGCCCTCCAGCTCTCTGG<br>GAACCCAGACCTATATCTGCAACGTGAACCACAA<br>GCCCAGCAACACCAAGGTGGACAAGAGAGTGGA<br>GCCCAAGAGCTGCGACAAGACCCACACCTGCCC<br>CCCCTGCCCAGCTCCAGAACTGCTGGGA |
| SEQ ID NO: 136 | Cys Fab HC(EU221)-HC-E152C (EU) | QVQLQQSGPGLVKPSQTLSLTCAISGDSVSTNSAA<br>WNWIRQSPSRGLEWLGRIYYRSQWLNDYAVSVKS<br>RITINPDTSKNQFSLQLNSVTPEDTAVYYCARQLTYP<br>YTVYHKALDVWGQGTLVTVSSASTKGPSVFPLAPS<br>SKSTSGGTAALGCLVKDYFPCPVTVSWNSGALTSG<br>VHTFPAVLQSSGLYSLSSVVTVPSSSLGTQTYICNV<br>NHKPSNTKVDKRVEPKSCD |
| SEQ ID NO: 137 | Fab' HC(EU230) | QVQLQQSGPGLVKPSQTLSLTCAISGDSVSTNSAA<br>WNWIRQSPSRGLEWLGRIYYRSQWLNDYAVSVKS<br>RITINPDTSKNQFSLQLNSVTPEDTAVYYCARQLTYP<br>YTVYHKALDVWGQGTLVTVSSASTKGPSVFPLAPS<br>SKSTSGGTAALGCLVKDYFPEPVTVSWNSGALTSG<br>VHTFPAVLQSSGLYSLSSVVTVPSSSLGTQTYICNV<br>NHKPSNTKVDKRVEPKSCDKTHTCPPCP |
| SEQ ID NO: 138 | Fab' HC(EU232) | QVQLQQSGPGLVKPSQTLSLTCAISGDSVSTNSAA<br>WNWIRQSPSRGLEWLGRIYYRSQWLNDYAVSVKS<br>RITINPDTSKNQFSLQLNSVTPEDTAVYYCARQLTYP<br>YTVYHKALDVWGQGTLVTVSSASTKGPSVFPLAPS<br>SKSTSGGTAALGCLVKDYFPEPVTVSWNSGALTSG<br>VHTFPAVLQSSGLYSLSSVVTVPSSSLGTQTYICNV<br>NHKPSNTKVDKRVEPKSCDKTHTCPPCPAP |
| SEQ ID NO: 139 | Fab' HC(EU236)-Pro | QVQLQQSGPGLVKPSQTLSLTCAISGDSVSTNSAA<br>WNWIRQSPSRGLEWLGRIYYRSQWLNDYAVSVKS<br>RITINPDTSKNQFSLQLNSVTPEDTAVYYCARQLTYP<br>YTVYHKALDVWGQGTLVTVSSASTKGPSVFPLAPS<br>SKSTSGGTAALGCLVKDYFPEPVTVSWNSGALTSG<br>VHTFPAVLQSSGLYSLSSVVTVPSSSLGTQTYICNV<br>NHKPSNTKVDKRVEPKSCDKTHTCPPCPAPELLGP |
| SEQ ID NO: 75 | LCDR1 (Kabat) | SGDNLGDQYVS |
| SEQ ID NO: 76 | LCDR2 (Kabat) | DDTDRPS |
| SEQ ID NO: 77 | LCDR3 (Kabat) | QSTDSKSVV |
| SEQ ID NO: 78 | LCDR1 (Chothia) | DNLGDQY |
| SEQ ID NO: 79 | LCDR2 (Chothia) | DDT |
| SEQ ID NO: 80 | LCDR3 (Chothia) | TDSKSV |
| SEQ ID NO: 75 | LCDR1 (Combined) | SGDNLGDQYVS |
| SEQ ID NO: 76 | LCDR2 (Combined) | DDTDRPS |
| SEQ ID NO: 77 | LCDR3 (Combined) | QSTDSKSVV |
| SEQ ID NO: 81 | LCDR1 (IMGT) | NLGDQY |
| SEQ ID NO: 79 | LCDR2 (IMGT) | DDT |
| SEQ ID NO: 77 | LCDR3 (IMGT) | QSTDSKSVV |
| SEQ ID NO: 82 | VL (lambda) | DIELTQPPSVSVSPGQTASITCSGDNLGDQYVSWYQ<br>QKPGQAPVLVIYDDTDRPSGIPERFSGSNSGNTATL<br>TISGTQAEDEADYYCQSTDSKSVVFGGGTKLTVL |
| SEQ ID NO: 83 | VL DNA | GATATCGAACTGACCCAGCCGCCGAGCGTGAGC<br>GTGAGCCCGGGCCAGACCGCGAGCATTACCTGT<br>AGCGGCGATAACCTGGGTGACCAATACGTTTCTT<br>GGTACCAGCAGAAACCGGGCCAGGCGCCGGTGC<br>TGGTGATCTACGACGACACTGACCGTCCGAGCGG<br>CATCCCGGAACGTTTTAGCGGATCCAACAGCGGC<br>AACACCGCGACCCTGACCATTAGCGGCACCCAGG<br>CGGAAGACGAAGCGGATTATTACTGCCAGTCTAC<br>TGACTCTAAATCTGTTGTTTGGCGGCGGCACG<br>AAGTTAACCGTCCTA |
| SEQ ID NO: 84 | Ab/Fab' LC (lambda) | DIELTQPPSVSVSPGQTASITCSGDNLGDQYVSWYQ<br>QKPGQAPVLVIYDDTDRPSGIPERFSGSNSGNTATL<br>TISGTQAEDEADYYCQSTDSKSVVFGGGTKLTVLGQ<br>PKAAPSVTLFPPSSEELQANKATLVCLISDFYPGAVT<br>VAWKADSSPVKAGVETTTPSKQSNNKYAASSYLSL<br>TPEQWKSHRSYSCQVTHEGSTVEKTVAPTECS |
| SEQ ID NO: 85 | Ab/Fab' LC DNA | GATATCGAACTGACCCAGCCGCCGAGCGTGAGC<br>GTGAGCCCGGGCCAGACCGCGAGCATTACCTGT<br>AGCGGCGATAACCTGGGTGACCAATACGTTTCTT<br>GGTACCAGCAGAAACCGGGCCAGGCGCCGGTGC<br>TGGTGATCTACGACGACACTGACCGTCCGAGCGG<br>CATCCCGGAACGTTTTAGCGGATCCAACAGCGGC |

TABLE 1-continued

Sequences of exemplary anti-cKIT antibodies and antibody fragments

|  |  |  |
|---|---|---|
|  |  | AACACCGCGACCCTGACCATTAGCGGCACCCAGG<br>CGGAAGACGAAGCGGATTATTACTGCCAGTCTAC<br>TGACTCTAAATCTGTTGTGTTTGGCGGCGGCACG<br>AAGTTAACCGTCCTAGGCCAGCCTAAGGCCGCTC<br>CCTCCGTGACCCTGTTCCCCCCCAGCTCCGAGGA<br>ACTGCAGGCCAACAAGGCCACCCTGGTGTGCCTG<br>ATCAGCGACTTCTACCCTGGCGCCGTGACCGTGG<br>CCTGGAAGGCCGACAGCAGCCCCGTGAAGGCCG<br>GCGTGGAGACAACCACCCCCAGCAAGCAGAGCA<br>ACAACAAGTACGCCGCCAGCAGCTACCTGAGCCT<br>GACCCCCGAGCAGTGGAAGAGCCACAGAAGCTA<br>CAGCTGCCAGGTCACCCACGAGGGCAGCACCGT<br>GGAGAAAACCGTGGCCCCCACCGAGTGCAGC |
| SEQ ID NO: 140 | Cys Fab-LC<br>(lambda)-A143C<br>(EU) | DIELTQPPSVSVSPGQTASITCSGDNLGDQYVSWYQ<br>QKPGQAPVLVIYDDTDRPSGIPERFSGSNSGNTATL<br>TISGTQAEDEADYYCQSTDSKSVVFGGGTKLTVLGQ<br>PKAAPSVTLFPPSSEELQANKATLVCLISDFYPGCVT<br>VAWKADSSPVKAGVETTTPSKQSNNKYAASSYLSL<br>TPEQWKSHRSYSCQVTHEGSTVEKTVAPTECS |

Anti-cKIT Ab5/Fab5/Fab'5

| SEQ ID NO: 86 | HCDR1 (Kabat) | NYWIA |
|---|---|---|
| SEQ ID NO: 87 | HCDR2 (Kabat) | IIYPSNSYTLYSPSFQG |
| SEQ ID NO: 88 | HCDR3 (Kabat) | VPPGGSISYPAFDH |
| SEQ ID NO: 89 | HCDR1 (Chothia) | GYSFTNY |
| SEQ ID NO: 90 | HCDR2 (Chothia) | YPSNSY |
| SEQ ID NO: 88 | HCDR3 (Chothia) | VPPGGSISYPAFDH |
| SEQ ID NO: 91 | HCDR1 (Combined) | GYSFTNYWIA |
| SEQ ID NO: 87 | HCDR2 (Combined) | IIYPSNSYTLYSPSFQG |
| SEQ ID NO: 88 | HCDR3 (Combined) | VPPGGSISYPAFDH |
| SEQ ID NO: 92 | HCDR1 (IMGT) | GYSFTNYW |
| SEQ ID NO: 93 | HCDR2 (IMGT) | IYPSNSYT |
| SEQ ID NO: 94 | HCDR3 (IMGT) | ARVPPGGSISYPAFDH |
| SEQ ID NO: 95 | VH | QVQLVQSGAEVKKPGESLKISCKGSGYSFTNYWIA<br>WVRQMPGKGLEWMGIIYPSNSYTLYSPSFQGQVTI<br>SADKSISTAYLQWSSLKASDTAMYYCARVPPGGSIS<br>YPAFDHWGQGTLVTVSS |
| SEQ ID NO: 96 | VH DNA | CAGGTGCAATTGGTGCAGAGCGGTGCGGAAGTG<br>AAAAAACCGGGCGAAAGCCTGAAAATTAGCTGCA<br>AAGGCTCCGGATATAGCTTCACTAACTACTGGATC<br>GCTTGGGTGCGCCAGATGCCGGGCAAAGGTCTC<br>GAGTGGATGGGCATCATCTACCCGTCTAACAGCT<br>ACACCCTGTATAGCCCGAGCTTTCAGGGCCAGGT<br>GACCATTAGCGCGGATAAAAGCATCAGCACCGCG<br>TATCTGCAATGGAGCAGCCTGAAAGCGAGCGATA<br>CCGCGATGTATTATTGCGCGCGTGTTCCGCCGGG<br>TGGTTCTATCTCTTACCCGGCTTTCGATCATTGGG<br>GCCAAGGCACCCTGGTGACTGTTAGCTCA |
| SEQ ID NO: 97 | Ab HC | QVQLVQSGAEVKKPGESLKISCKGSGYSFTNYWIA<br>WVRQMPGKGLEWMGIIYPSNSYTLYSPSFQGQVTI<br>SADKSISTAYLQWSSLKASDTAMYYCARVPPGGSIS<br>YPAFDHWGQGTLVTVSSASTKGPSVFPLAPSSKST<br>SGGTAALGCLVKDYFPEPVTVSWNSGALTSGVHTF<br>PAVLQSSGLYSLSSVVTVPSSSLGTQTYICNVNHKP<br>SNTKVDKRVEPKSCDKTHTCPPCPAPELLGGPSVFL<br>FPPKPKDTLMISRTPEVTCVVVDVSHEDPEVKFNWY<br>VDGVEVHNAKTKPREEQYNSTYRVVSVLTVLHQDW<br>LNGKEYKCKVSNKALPAPIEKTISKAKGQPREPQVY<br>TLPPSREEMTKNQVSLTCLVKGFYPSDIAVEWESNG<br>QPENNYKTTPPVLDSDGSFFLYSKLTVDKSRWQQG<br>NVFSCSVMHEALHNHYTQKSLSLSPGK |
| SEQ ID NO: 98 | Ab HC DNA | CAGGTGCAATTGGTGCAGAGCGGTGCGGAAGTG<br>AAAAAACCGGGCGAAAGCCTGAAAATTAGCTGCA<br>AAGGCTCCGGATATAGCTTCACTAACTACTGGATC<br>GCTTGGGTGCGCCAGATGCCGGGCAAAGGTCTC<br>GAGTGGATGGGCATCATCTACCCGTCTAACAGCT<br>ACACCCTGTATAGCCCGAGCTTTCAGGGCCAGGT<br>GACCATTAGCGCGGATAAAAGCATCAGCACCGCG<br>TATCTGCAATGGAGCAGCCTGAAAGCGAGCGATA<br>CCGCGATGTATTATTGCGCGCGTGTTCCGCCGGG<br>TGGTTCTATCTCTTACCCGGCTTTCGATCATTGGG<br>GCCAAGGCACCCTGGTGACTGTTAGCTCAGCTAG<br>CACCAAGGGCCCCAGCGTGTTCCCCCTGGCCCC<br>CAGCAGCAAGTCTACTTCCGGCGGAACTGCTGCC<br>CTGGGTTGCCTGGTGAAGGACTACTTCCCCGAGC<br>CCGTGACAGTGTCCTGGAACTCTGGGGCTCTGAC<br>TTCCGGCGTGCACACCTTCCCCGCCGTGCTGCAG |

TABLE 1-continued

Sequences of exemplary anti-cKIT antibodies and antibody fragments

| | | |
|---|---|---|
| | | AGCAGCGGCCTGTACAGCCTGAGCAGCGTGGTG<br>ACAGTGCCCTCCAGCTCTCTGGGAACCCAGACCT<br>ATATCTGCAACGTGAACCACAAGCCCAGCAACAC<br>CAAGGTGGACAAGAGAGTGGAGCCCAAGAGCTG<br>CGACAAGACCCACACCTGCCCCCCCTGCCCAGCT<br>CCAGAACTGCTGGGAGGGCCTTCCGTGTTCCTGT<br>TCCCCCCCAAGCCCAAGGACACCCTGATGATCAG<br>CAGGACCCCCGAGGTGACCTGCGTGGTGGTGGA<br>CGTGTCCCACGAGGACCCAGAGGTGAAGTTCAAC<br>TGGTACGTGGACGGCGTGGAGGTGCACAACGCC<br>AAGACCAAGCCCAGAGAGGAGCAGTACAACAGCA<br>CCTACAGGGTGGTGTCCGTGCTGACCGTGCTGCA<br>CCAGGACTGGCTGAACGGCAAAGAATACAAGTGC<br>AAAGTCTCCAACAAGGCCCTGCCAGCCCCAATCG<br>AAAAGACAATCAGCAAGGCCAAGGGCCAGCCACG<br>GGAGCCCCAGGTGTACACCCTGCCCCCCAGCCG<br>GGAGGAGATGACCAAGAACCAGGTGTCCCTGACC<br>TGTCTGGTGAAGGGCTTCTACCCCAGCGATATCG<br>CCGTGGAGTGGGAGAGCAACGGCCAGCCCGAGA<br>ACAACTACAAGACCACCCCCCCAGTGCTGGACAG<br>CGACGGCAGCTTCTTCCTGTACAGCAAGCTGACC<br>GTGGACAAGTCCAGGTGGCAGCAGGGCAACGTG<br>TTCAGCTGCAGCGTGATGCACGAGGCCCTGCACA<br>ACCACTACACCCAGAAGTCCCTGAGCCTGAGCCC<br>CGGCAAG |
| SEQ ID NO: 99 | Fab' HC (EU236) | QVQLVQSGAEVKKPGESLKISCKGSGYSFTNYWIA<br>WVRQMPGKGLEWMGIIYPSNSYTLYSPSFQGQVTI<br>SADKSISTAYLQWSSLKASDTAMYYCARVPPGGSIS<br>YPAFDHWGQGTLVTVSSASTKGPSVFPLAPSSKST<br>SGGTAALGCLVKDYFPEPVTVSWNSGALTSGVHTF<br>PAVLQSSGLYSLSSVVTVPSSSLGTQTYICNVNHKP<br>SNTKVDKRVEPKSCDKTHTCPPCPAPELLG |
| SEQ ID NO: 100 | Fab' HC DNA | CAGGTGCAATTGGTGCAGAGCGGTGCGGAAGTG<br>AAAAAACCGGGCGAAAGCCTGAAAATTAGCTGCA<br>AAGGCTCCGGATATAGCTTCACTAACTACTGGATC<br>GCTTGGGTGCGCCAGATGCCGGGCAAAGGTCTC<br>GAGTGGATGGGCATCATCTACCCGTCTAACAGCT<br>ACACCCTGTATAGCCCGAGCTTTCAGGGCCAGGT<br>GACCATTAGCGCGGATAAAAGCATCAGCACCGCG<br>TATCTGCAATGGAGCAGCCTGAAAGCGAGCGATA<br>CCGCGATGTATTATTGCGCGCGTGTTCCGCCGGG<br>TGGTTCTATCTCTTACCCGGCTTTCGATCATTGGG<br>GCCAAGGCACCCTGGTGACTGTTAGCTCAGCTAG<br>CACCAAGGGCCCCAGCGTGTTCCCCCTGGCCCC<br>CAGCAGCAAGTCTACTTCCGGCGGAACTGCTGCC<br>CTGGGTTGCCTGGTGAAGGACTACTTCCCCGAGC<br>CCGTGACAGTGTCCTGGAACTCTGGGGCTCTGAC<br>TTCCGGCGTGCACACCTTCCCCGCCGTGCTGCAG<br>AGCAGCGGCCTGTACAGCCTGAGCAGCGTGGTG<br>ACAGTGCCCTCCAGCTCTCTGGGAACCCAGACCT<br>ATATCTGCAACGTGAACCACAAGCCCAGCAACAC<br>CAAGGTGGACAAGAGAGTGGAGCCCAAGAGCTG<br>CGACAAGACCCACACCTGCCCCCCCTGCCCAGCT<br>CCAGAACTGCTGGGA |
| SEQ ID NO: 141 | Cys Fab<br>HC(EU221)-HC-<br>E152C (EU) | QVQLVQSGAEVKKPGESLKISCKGSGYSFTNYWIA<br>WVRQMPGKGLEWMGIIYPSNSYTLYSPSFQGQVTI<br>SADKSISTAYLQWSSLKASDTAMYYCARVPPGGSIS<br>YPAFDHWGQGTLVTVSSASTKGPSVFPLAPSSKST<br>SGGTAALGCLVKDYFPCPVTVSWNSGALTSGVHTF<br>PAVLQSSGLYSLSSVVTVPSSSLGTQTYICNVNHKP<br>SNTKVDKRVEPKSCD |
| SEQ ID NO: 142 | Fab' HC(EU230) | QVQLVQSGAEVKKPGESLKISCKGSGYSFTNYWIA<br>WVRQMPGKGLEWMGIIYPSNSYTLYSPSFQGQVTI<br>SADKSISTAYLQWSSLKASDTAMYYCARVPPGGSIS<br>YPAFDHWGQGTLVTVSSASTKGPSVFPLAPSSKST<br>SGGTAALGCLVKDYFPEPVTVSWNSGALTSGVHTF<br>PAVLQSSGLYSLSSVVTVPSSSLGTQTYICNVNHKP<br>SNTKVDKRVEPKSCDKTHTCPPCP |
| SEQ ID NO: 143 | Fab' HC(EU232) | QVQLVQSGAEVKKPGESLKISCKGSGYSFTNYWIA<br>WVRQMPGKGLEWMGIIYPSNSYTLYSPSFQGQVTI<br>SADKSISTAYLQWSSLKASDTAMYYCARVPPGGSIS<br>YPAFDHWGQGTLVTVSSASTKGPSVFPLAPSSKST<br>SGGTAALGCLVKDYFPEPVTVSWNSGALTSGVHTF<br>PAVLQSSGLYSLSSVVTVPSSSLGTQTYICNVNHKP<br>SNTKVDKRVEPKSCDKTHTCPPCPAP |
| SEQ ID NO: 144 | Fab' HC(EU236)-Pro | QVQLVQSGAEVKKPGESLKISCKGSGYSFTNYWIA<br>WVRQMPGKGLEWMGIIYPSNSYTLYSPSFQGQVTI<br>SADKSISTAYLQWSSLKASDTAMYYCARVPPGGSIS |

TABLE 1-continued

Sequences of exemplary anti-cKIT antibodies and antibody fragments

| | | |
|---|---|---|
| | | YPAFDHWGQGTLVTVSSASTKGPSVFPLAPSSKST |
| | | SGGTAALGCLVKDYFPEPVTVSWNSGALTSGVHTF |
| | | PAVLQSSGLYSLSSVVTVPSSSLGTQTYICNVNHKP |
| | | SNTKVDKRVEPKSCDKTHTCPPCPAPELLGP |
| SEQ ID NO: 101 | LCDR1 (Kabat) | SGDNIGSIYAS |
| SEQ ID NO: 102 | LCDR2 (Kabat) | RDNKRPS |
| SEQ ID NO: 103 | LCDR3 (Kabat) | SVTDMEQHSV |
| SEQ ID NO: 104 | LCDR1 (Chothia) | DNIGSIY |
| SEQ ID NO: 105 | LCDR2 (Chothia) | RDN |
| SEQ ID NO: 106 | LCDR3 (Chothia) | TDMEQHS |
| SEQ ID NO: 101 | LCDR1 (Combined) | SGDNIGSIYAS |
| SEQ ID NO: 102 | LCDR2 (Combined) | RDNKRPS |
| SEQ ID NO: 103 | LCDR3 (Combined) | SVTDMEQHSV |
| SEQ ID NO: 107 | LCDR1 (IMGT) | NIGSIY |
| SEQ ID NO: 105 | LCDR2 (IMGT) | RDN |
| SEQ ID NO: 103 | LCDR3 (IMGT) | SVTDMEQHSV |
| SEQ ID NO: 108 | VL (lambda) | DIELTQPPSVSVSPGQTASITCSGDNIGSIYASWYQQ |
| | | KPGQAPVLVIYRDNKRPSGIPERFSGSNSGNTATLTI |
| | | SGTQAEDEADYYCSVTDMEQHSVFGGGTKLTVL |
| SEQ ID NO: 109 | VL DNA | GATATCGAACTGACCCAGCCGCCGAGCGTGAGC |
| | | GTGAGCCCGGGCCAGACCGCGAGCATTACCTGT |
| | | AGCGGCGATAACATCGGTTCTATCTACGCTTCTTG |
| | | GTACCAGCAGAAACCGGGCCAGGCGCCGGTGCT |
| | | GGTGATCTACCGTGACAACAAACGTCCGAGCGGC |
| | | ATCCCGGAACGTTTTAGCGGATCCAACAGCGGCA |
| | | ACACCGCGACCCTGACCATTAGCGGCACCCAGG |
| | | CGGAAGACGAAGCGGATTATTACTGCTCCGTTAC |
| | | TGACATGGAACAGCATTCTGTGTTTGGCGGCGGC |
| | | ACGAAGTTAACCGTCCTA |
| SEQ ID NO: 110 | Ab/Fab' LC (lambda) | DIELTQPPSVSVSPGQTASITCSGDNIGSIYASWYQQ |
| | | KPGQAPVLVIYRDNKRPSGIPERFSGSNSGNTATLTI |
| | | SGTQAEDEADYYCSVTDMEQHSVFGGGTKLTVLGQ |
| | | PKAAPSVTLFPPSSEELQANKATLVCLISDFYPGAVT |
| | | VAWKADSSPVKAGVETTTPSKQSNNKYAASSYLSL |
| | | TPEQWKSHRSYSCQVTHEGSTVEKTVAPTECS |
| SEQ ID NO: 111 | Ab/Fab' LC DNA | GATATCGAACTGACCCAGCCGCCGAGCGTGAGC |
| | | GTGAGCCCGGGCCAGACCGCGAGCATTACCTGT |
| | | AGCGGCGATAACATCGGTTCTATCTACGCTTCTTG |
| | | GTACCAGCAGAAACCGGGCCAGGCGCCGGTGCT |
| | | GGTGATCTACCGTGACAACAAACGTCCGAGCGGC |
| | | ATCCCGGAACGTTTTAGCGGATCCAACAGCGGCA |
| | | ACACCGCGACCCTGACCATTAGCGGCACCCAGG |
| | | CGGAAGACGAAGCGGATTATTACTGCTCCGTTAC |
| | | TGACATGGAACAGCATTCTGTGTTTGGCGGCGGC |
| | | ACGAAGTTAACCGTCCTAGGCCAGCCTAAGGCCG |
| | | CTCCCTCCGTGACCCTGTTCCCCCCCAGCTCCGA |
| | | GGAACTGCAGGCCAACAAGGCCACCCTGGTGTG |
| | | CCTGATCAGCGACTTCTACCCTGGCGCCGTGACC |
| | | GTGGCCTGGAAGGCCGACAGCAGCCCCGTGAAG |
| | | GCCGGCGTGGAGACAACCACCCCCAGCAAGCAG |
| | | AGCAACAACAAGTACGCCGCCAGCAGCTACCTGA |
| | | GCCTGACCCCCGAGCAGTGGAAGAGCCACAGAA |
| | | GCTACAGCTGCCAGGTCACCCACGAGGGCAGCA |
| | | CCGTGGAGAAAACCGTGGCCCCCACCGAGTGCA |
| | | GC |
| SEQ ID NO: 145 | Cys Fab-LC (lambda)-A144C (EU) | DIELTQPPSVSVSPGQTASITCSGDNIGSIYASWYQQ |
| | | KPGQAPVLVIYRDNKRPSGIPERFSGSNSGNTATLTI |
| | | SGTQAEDEADYYCSVTDMEQHSVFGGGTKLTVLGQ |
| | | PKAAPSVTLFPPSSEELQANKATLVCLISDFYPGCVT |
| | | VAWKADSSPVKAGVETTTPSKQSNNKYAASSYLSL |
| | | TPEQWKSHRSYSCQVTHEGSTVEKTVAPTECS |

Other anti-cKIT antibody or antibody fragment (e.g., Fab or Fab') disclosed herein include those where the amino acids or nucleic acids encoding the amino acids have been mutated, yet have at least 60, 70, 80, 90 or 95 percent identity to the sequences described in Table 1. In some aspects, it includes mutant amino acid sequences wherein no more than 1, 2, 3, 4 or 5 amino acids have been mutated in the variable regions when compared with the variable regions depicted in the sequence described in Table 1, while retaining substantially the same therapeutic activity.

Since each of these antibody or antibody fragment (e.g., Fab or Fab') can bind to cKIT, the VH, VL, heavy chain, and light chain sequences (amino acid sequences and the nucleotide sequences encoding the amino acid sequences) can be "mixed and matched" to create other cKIT-binding antibody or antibody fragment (e.g., Fab or Fab'). Such "mixed and matched" cKIT-binding antibody or antibody fragment (e.g., Fab or Fab') can be tested using the binding assays known in the art (e.g., ELISAs, and other assays described in the Example section). When these chains are mixed and matched, a VH sequence from a particular VH/VL pairing should be replaced with a structurally similar VH sequence. Likewise a heavy chain sequence from a particular heavy chain/light chain pairing should be replaced with a structurally similar heavy chain sequence. Likewise, a VL sequence from a particular VH/VL pairing should be replaced with a structurally similar VL sequence. Likewise, a light chain sequence from a particular heavy chain/light chain pairing should be replaced with a structurally similar light chain sequence.

Accordingly, in one aspect, the disclosure provides for an isolated antibody or antibody fragment (e.g., Fab or Fab') having: a heavy chain variable region comprising an amino acid sequence selected from the group consisting of SEQ ID NOs: 10, 36, 54, 69, and 95 (Table 1); and a light chain variable region comprising an amino acid sequence selected from the group consisting of SEQ ID NOs: 23, 47, 82, and 108 (Table 1); wherein the antibody or antibody fragment (e.g., Fab or Fab') specifically binds to human cKIT.

In another aspect, the disclosure provides an isolated antibody having: a heavy chain comprising an amino acid sequence selected from the group consisting of SEQ ID NOs: 12, 38, 56, 71, and 97; and a light chain comprising an amino acid sequence selected from the group consisting of SEQ ID NOs: 25, 49, 84, and 110.

In another aspect, the disclosure provides an isolated antibody fragment (e.g., Fab') having: a heavy chain comprising an amino acid sequence selected from the group consisting of SEQ ID NOs: 14, 40, 58, 73, and 99; and a light chain comprising an amino acid sequence selected from the group consisting of SEQ ID NOs: 25, 49, 84, and 110.

In another aspect, the present disclosure provides cKIT-binding antibody or antibody fragment (e.g., Fab or Fab') that comprises the heavy chain and light chain CDR1s, CDR2s and CDR3s as described in Table 1, or combinations thereof. The amino acid sequences of the VH CDR1s (or HCDR1) of the antibodies or antibody fragments (e.g., Fab or Fab') are shown in SEQ ID NOs: 1, 4, 6, 7, 27, 30, 32, 33, 60, 63, 65, 66, 86, 89, 91, and 92. The amino acid sequences of the VH CDR2s (or HCDR2) of the antibodies or antibody fragments (e.g., Fab or Fab') and are shown in SEQ ID NOs: 2, 5, 8, 28, 31, 34, 51, 52, 53, 61, 64, 67, 87, 90, and 93. The amino acid sequences of the VH CDR3s (or HCDR3) of the antibodies or antibody fragments (e.g., Fab or Fab') are shown in SEQ ID NOs: 3, 9, 29, 35, 62, 68, 88, and 94. The amino acid sequences of the VL CDR1s (or LCDR1) of the antibodies or antibody fragments (e.g., Fab or Fab') are shown in SEQ ID NOs: 16, 19, 22, 42, 44, 46, 75, 78, 81, 101, 104, and 107. The amino acid sequences of the VL CDR2s (or LCDR2) of the antibodies or antibody fragments (e.g., Fab or Fab') are shown in SEQ ID NOs: 17, 20, 76, 79, 102, and 105. The amino acid sequences of the VL CDR3s (or LCDR3) of the antibodies or antibody fragments (e.g., Fab or Fab') are shown in SEQ ID NOs: 18, 21, 43, 45, 77, 80, 103, and 106.

Given that each of these antibodies or antibody fragments (e.g., Fab or Fab') can bind to human cKIT and that antigen-binding specificity is provided primarily by the CDR1, 2 and 3 regions, the VH CDR1, 2 and 3 sequences (or HCDR1, 2, 3) and VL CDR1, 2 and 3 sequences (or LCDR1, 2, 3) can be "mixed and matched" (i.e., CDRs from different antibodies can be mixed and match, although each antibody must contain a VH CDR1, 2 and 3 and a VL CDR1, 2 and 3 to create a cKIT-binding antibody or antibody fragment (e.g., Fab or Fab'). Such "mixed and matched" cKIT-binding antibody or antibody fragment (e.g., Fab or Fab') can be tested using the binding assays known in the art. When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein.

Accordingly, the present disclosure provides an isolated antibody or antibody fragment (e.g., Fab or Fab') comprising a heavy chain CDR1 (HCDR1) comprising an amino acid sequence selected from the group consisting of SEQ ID NOs: 1, 4, 6, 7, 27, 30, 32, 33, 60, 63, 65, 66, 86, 89, 91, and 92; a heavy chain CDR2 (HCDR2) comprising an amino acid sequence selected from the group consisting of SEQ ID NOs: 2, 5, 8, 28, 31, 34, 51, 52, 53, 61, 64, 67, 87, 90, and 93; a heavy chain CDR3 (HCDR3) comprising an amino acid sequence selected from the group consisting of SEQ ID NOs: 3, 9, 29, 35, 62, 68, 88, and 94; a light chain CDR1 (LCDR1) comprising an amino acid sequence selected from the group consisting of SEQ ID NOs: 16, 19, 22, 42, 44, 46, 75, 78, 81, 101, 104, and 107; a light chain CDR2 (LCDR2) comprising an amino acid sequence selected from the group consisting of SEQ ID NOs: 17, 20, 76, 79, 102, and 105; and a light chain CDR3 (LCDR3) comprising an amino acid sequence selected from the group consisting of SEQ ID NOs: 18, 21, 43, 45, 77, 80, 103, and 106; wherein the antibody specifically binds cKIT.

In some embodiments, the antibody or antibody fragment (e.g., Fab or Fab') that specifically binds to human cKIT comprises a HCDR1 of SEQ ID NO: 1, a HCDR2 of SEQ ID NO: 2; a HCDR3 of SEQ ID NO: 3; a LCDR1 of SEQ ID NO:16; a LCDR2 of SEQ ID NO: 17; and a LCDR3 of SEQ ID NO: 18.

In some embodiments, the antibody or antibody fragment (e.g., Fab or Fab') that specifically binds to human cKIT comprises a HCDR1 of SEQ ID NO: 4, a HCDR2 of SEQ ID NO: 5; a HCDR3 of SEQ ID NO: 3; a LCDR1 of SEQ ID NO:19; a LCDR2 of SEQ ID NO: 20; and a LCDR3 of SEQ ID NO: 21.

In some embodiments, the antibody or antibody fragment (e.g., Fab or Fab') that specifically binds to human cKIT comprises a HCDR1 of SEQ ID NO: 6, a HCDR2 of SEQ ID NO: 2; a HCDR3 of SEQ ID NO: 3; a LCDR1 of SEQ ID NO:16; a LCDR2 of SEQ ID NO: 17; and a LCDR3 of SEQ ID NO: 18.

In some embodiments, the antibody or antibody fragment (e.g., Fab or Fab') that specifically binds to human cKIT comprises a HCDR1 of SEQ ID NO: 7, a HCDR2 of SEQ ID NO: 8; a HCDR3 of SEQ ID NO: 9; a LCDR1 of SEQ ID NO: 22; a LCDR2 of SEQ ID NO: 20; and a LCDR3 of SEQ ID NO: 18.

In some embodiments, the antibody or antibody fragment (e.g., Fab or Fab') that specifically binds to human cKIT comprises a HCDR1 of SEQ ID NO: 27, a HCDR2 of SEQ ID NO: 28; a HCDR3 of SEQ ID NO: 29; a LCDR1 of SEQ ID NO: 42; a LCDR2 of SEQ ID NO: 17; and a LCDR3 of SEQ ID NO: 43.

In some embodiments, the antibody or antibody fragment (e.g., Fab or Fab') that specifically binds to human cKIT comprises a HCDR1 of SEQ ID NO: 30, a HCDR2 of SEQ ID NO: 31; a HCDR3 of SEQ ID NO: 29; a LCDR1 of SEQ ID NO: 44; a LCDR2 of SEQ ID NO: 20; and a LCDR3 of SEQ ID NO: 45.

In some embodiments, the antibody or antibody fragment (e.g., Fab or Fab') that specifically binds to human cKIT comprises a HCDR1 of SEQ ID NO: 32, a HCDR2 of SEQ ID NO: 28; a HCDR3 of SEQ ID NO: 29; a LCDR1 of SEQ ID NO: 42; a LCDR2 of SEQ ID NO: 17; and a LCDR3 of SEQ ID NO: 43.

In some embodiments, the antibody or antibody fragment (e.g., Fab or Fab') that specifically binds to human cKIT comprises a HCDR1 of SEQ ID NO: 33, a HCDR2 of SEQ ID NO: 34; a HCDR3 of SEQ ID NO: 35; a LCDR1 of SEQ ID NO: 46; a LCDR2 of SEQ ID NO: 20; and a LCDR3 of SEQ ID NO: 43.

In some embodiments, the antibody or antibody fragment (e.g., Fab or Fab') that specifically binds to human cKIT comprises a HCDR1 of SEQ ID NO: 1, a HCDR2 of SEQ ID NO: 51; a HCDR3 of SEQ ID NO: 3; a LCDR1 of SEQ ID NO:16; a LCDR2 of SEQ ID NO: 17; and a LCDR3 of SEQ ID NO: 18.

In some embodiments, the antibody or antibody fragment (e.g., Fab or Fab') that specifically binds to human cKIT comprises a HCDR1 of SEQ ID NO: 4, a HCDR2 of SEQ ID NO: 52; a HCDR3 of SEQ ID NO: 3; a LCDR1 of SEQ ID NO:19; a LCDR2 of SEQ ID NO: 20; and a LCDR3 of SEQ ID NO: 21.

In some embodiments, the antibody or antibody fragment (e.g., Fab or Fab') that specifically binds to human cKIT comprises a HCDR1 of SEQ ID NO: 6, a HCDR2 of SEQ ID NO: 51; a HCDR3 of SEQ ID NO: 3; a LCDR1 of SEQ ID NO:16; a LCDR2 of SEQ ID NO: 17; and a LCDR3 of SEQ ID NO: 18.

In some embodiments, the antibody or antibody fragment (e.g., Fab or Fab') that specifically binds to human cKIT comprises a HCDR1 of SEQ ID NO: 7, a HCDR2 of SEQ ID NO: 53; a HCDR3 of SEQ ID NO: 9; a LCDR1 of SEQ ID NO: 22; a LCDR2 of SEQ ID NO: 20; and a LCDR3 of SEQ ID NO: 18.

In some embodiments, the antibody or antibody fragment (e.g., Fab or Fab') that specifically binds to human cKIT comprises a HCDR1 of SEQ ID NO: 60, a HCDR2 of SEQ ID NO: 61; a HCDR3 of SEQ ID NO: 62; a LCDR1 of SEQ ID NO: 75; a LCDR2 of SEQ ID NO: 76; and a LCDR3 of SEQ ID NO: 77.

In some embodiments, the antibody or antibody fragment (e.g., Fab or Fab') that specifically binds to human cKIT comprises a HCDR1 of SEQ ID NO: 63, a HCDR2 of SEQ ID NO: 64; a HCDR3 of SEQ ID NO: 62; a LCDR1 of SEQ ID NO: 78; a LCDR2 of SEQ ID NO: 79; and a LCDR3 of SEQ ID NO: 80.

In some embodiments, the antibody or antibody fragment (e.g., Fab or Fab') that specifically binds to human cKIT comprises a HCDR1 of SEQ ID NO: 65, a HCDR2 of SEQ ID NO: 61; a HCDR3 of SEQ ID NO: 62; a LCDR1 of SEQ ID NO:75; a LCDR2 of SEQ ID NO: 76; and a LCDR3 of SEQ ID NO: 77.

In some embodiments, the antibody or antibody fragment (e.g., Fab or Fab') that specifically binds to human cKIT comprises a HCDR1 of SEQ ID NO: 66, a HCDR2 of SEQ ID NO: 67; a HCDR3 of SEQ ID NO: 68; a LCDR1 of SEQ ID NO: 81; a LCDR2 of SEQ ID NO: 79; and a LCDR3 of SEQ ID NO: 77.

In some embodiments, the antibody or antibody fragment (e.g., Fab or Fab') that specifically binds to human cKIT comprises a HCDR1 of SEQ ID NO: 86, a HCDR2 of SEQ ID NO: 87; a HCDR3 of SEQ ID NO: 88; a LCDR1 of SEQ ID NO: 101; a LCDR2 of SEQ ID NO: 102; and a LCDR3 of SEQ ID NO: 103.

In some embodiments, the antibody or antibody fragment (e.g., Fab or Fab') that specifically binds to human cKIT comprises a HCDR1 of SEQ ID NO: 89, a HCDR2 of SEQ ID NO: 90; a HCDR3 of SEQ ID NO: 88; a LCDR1 of SEQ ID NO: 104; a LCDR2 of SEQ ID NO: 105; and a LCDR3 of SEQ ID NO: 106.

In some embodiments, the antibody or antibody fragment (e.g., Fab or Fab') that specifically binds to human cKIT comprises a HCDR1 of SEQ ID NO: 91, a HCDR2 of SEQ ID NO: 87; a HCDR3 of SEQ ID NO: 88; a LCDR1 of SEQ ID NO: 101; a LCDR2 of SEQ ID NO: 102; and a LCDR3 of SEQ ID NO: 103.

In some embodiments, the antibody or antibody fragment (e.g., Fab or Fab') that specifically binds to human cKIT comprises a HCDR1 of SEQ ID NO: 92, a HCDR2 of SEQ ID NO: 93; a HCDR3 of SEQ ID NO: 94; a LCDR1 of SEQ ID NO: 107; a LCDR2 of SEQ ID NO: 105; and a LCDR3 of SEQ ID NO: 103.

In some embodiments, the antibody or antibody fragment (e.g., Fab or Fab') that specifically binds to human cKIT comprises a heavy chain variable region (VH) comprising the amino acid sequence of SEQ ID NO: 10, and a light chain variable region (VL) comprising the amino acid sequence of SEQ ID NO: 23.

In some embodiments, the antibody or antibody fragment (e.g., Fab or Fab') that specifically binds to human cKIT comprises a VH comprising the amino acid sequence of SEQ ID NO: 36, and a VL comprising the amino acid sequence of SEQ ID NO: 47.

In some embodiments, the antibody or antibody fragment (e.g., Fab or Fab') that specifically binds to human cKIT comprises a VH comprising the amino acid sequence of SEQ ID NO: 54, and a VL comprising the amino acid sequence of SEQ ID NO: 23.

In some embodiments, the antibody or antibody fragment (e.g., Fab or Fab') that specifically binds to human cKIT comprises a VH comprising the amino acid sequence of SEQ ID NO: 69, and a VL comprising the amino acid sequence of SEQ ID NO: 82.

In some embodiments, the antibody or antibody fragment (e.g., Fab or Fab') that specifically binds to human cKIT comprises a VH comprising the amino acid sequence of SEQ ID NO: 95, and a VL comprising the amino acid sequence of SEQ ID NO: 108.

In some embodiments, the antibody fragment (e.g., Fab') that specifically binds to human cKIT comprises a heavy chain comprising the amino acid sequence of SEQ ID NO: 14, and a light chain comprising the amino acid sequence of SEQ ID NO: 25.

In some embodiments, the antibody fragment (e.g., Fab') that specifically binds to human cKIT comprises a heavy chain comprising the amino acid sequence of SEQ ID NO: 40, and a light chain comprising the amino acid sequence of SEQ ID NO: 49.

In some embodiments, the antibody fragment (e.g., Fab') that specifically binds to human cKIT comprises a heavy chain comprising the amino acid sequence of SEQ ID NO: 58, and a light chain comprising the amino acid sequence of SEQ ID NO: 25.

In some embodiments, the antibody fragment (e.g., Fab') that specifically binds to human cKIT comprises a heavy chain comprising the amino acid sequence of SEQ ID NO: 73, and a light chain comprising the amino acid sequence of SEQ ID NO: 84.

In some embodiments, the antibody fragment (e.g., Fab') that specifically binds to human cKIT comprises a heavy chain comprising the amino acid sequence of SEQ ID NO: 99, and a light chain comprising the amino acid sequence of SEQ ID NO: 110.

In some embodiments, the antibody fragment (e.g., Fab') that specifically binds to human cKIT comprises a heavy chain comprising an amino acid sequence selected from SEQ ID NO: 119, 120 or 121, and a light chain comprising the amino acid sequence of SEQ ID NO: 25.

In some embodiments, the antibody fragment (e.g., Fab') that specifically binds to human cKIT comprises a heavy chain comprising an amino acid sequence selected from SEQ ID NO: 125, 126, or 127, and a light chain comprising the amino acid sequence of SEQ ID NO: 49.

In some embodiments, the antibody fragment (e.g., Fab') that specifically binds to human cKIT comprises a heavy chain comprising an amino acid sequence selected from SEQ ID NO: 131, 132, or 133, and a light chain comprising the amino acid sequence of SEQ ID NO: 25.

In some embodiments, the antibody fragment (e.g., Fab') that specifically binds to human cKIT comprises a heavy chain comprising an amino acid sequence selected from SEQ ID NO: 137, 138, or 139, and a light chain comprising the amino acid sequence of SEQ ID NO: 84.

In some embodiments, the antibody fragment (e.g., Fab') that specifically binds to human cKIT comprises a heavy chain comprising an amino acid sequence selected from SEQ ID NO: 142, 143, or 144, and a light chain comprising the amino acid sequence of SEQ ID NO: 110.

In some embodiments, the antibody that specifically binds to human cKIT comprises a heavy chain comprising the amino acid sequence of SEQ ID NO: 12, and a light chain comprising the amino acid sequence of SEQ ID NO: 25.

In some embodiments, the antibody that specifically binds to human cKIT comprises a heavy chain comprising the amino acid sequence of SEQ ID NO: 38, and a light chain comprising the amino acid sequence of SEQ ID NO: 49.

In some embodiments, the antibody that specifically binds to human cKIT comprises a heavy chain comprising the amino acid sequence of SEQ ID NO: 56, and a light chain comprising the amino acid sequence of SEQ ID NO: 25.

In some embodiments, the antibody that specifically binds to human cKIT comprises a heavy chain comprising the amino acid sequence of SEQ ID NO: 71, and a light chain comprising the amino acid sequence of SEQ ID NO: 84.

In some embodiments, the antibody that specifically binds to human cKIT comprises a heavy chain comprising the amino acid sequence of SEQ ID NO: 97, and a light chain comprising the amino acid sequence of SEQ ID NO: 110.

In certain aspects, the antibody or antibody fragment (e.g., Fab or Fab') that specifically binds to human cKIT is an antibody or antibody fragment (e.g., Fab or Fab') described in Table 1.

1. Antibodies that Bind to the Same Epitope

The present disclosure provides the antibody or antibody fragment (e.g., Fab or Fab') that specifically binds to an epitope within the extracellular domain of the human cKIT receptor. In certain aspects the antibody or antibody fragment (e.g., Fab or Fab') can bind to an epitope within domains 1-3 of the human cKIT extracellular domain.

The present disclosure also provides antibody or antibody fragment (e.g., Fab or Fab') that binds to the same epitope as the anti-cKIT antibody or antibody fragment (e.g., Fab or Fab') described in Table 1. Additional antibody or antibody fragment (e.g., Fab or Fab') can therefore be identified based on their ability to cross-compete (e.g., to competitively inhibit the binding of, in a statistically significant manner) with other antibody or antibody fragment (e.g., Fab or Fab') in cKIT binding assays. A high throughput process for "binning" antibodies based upon their cross-competition is described in International Patent Application No. WO 2003/ 48731. The ability of a test antibody or antibody fragment (e.g., Fab or Fab') to inhibit the binding of antibody or antibody fragment (e.g., Fab or Fab') disclosed herein to a cKIT protein (e.g., human cKIT) demonstrates that the test antibody or antibody fragment (e.g., Fab or Fab') can compete with that antibody or antibody fragment (e.g., Fab or Fab') for binding to cKIT; such an antibody or antibody fragment (e.g., Fab or Fab') may, according to non-limiting theory, bind to the same or a related (e.g., a structurally similar or spatially proximal) epitope on the cKIT protein as the antibody or antibody fragment (e.g., Fab or Fab') with which it competes. In a certain aspect, the antibody or antibody fragment (e.g., Fab or Fab') that binds to the same epitope on cKIT as the antibody or antibody fragment (e.g., Fab or Fab') disclosed herein is a human or humanized antibody or antibody fragment (e.g., Fab or Fab'). Such human or humanized antibody or antibody fragment (e.g., Fab or Fab') can be prepared and isolated as described herein.

2. Modification of the Framework

Antibody drug conjugates disclosed herein may comprise modified cKIT-binding antibody or antibody fragment (e.g., Fab or Fab') that comprises modifications to framework residues within VH and/or VL, e.g. to improve the properties of the antibody drug conjugate.

In some embodiments, framework modifications are made to decrease immunogenicity of an antibody or antibody drug conjugate. For example, one approach is to "back-mutate" one or more framework residues to a corresponding germline sequence. Such residues can be identified by comparing antibody framework sequences to germline sequences from which the antibody is derived. To "match" framework region sequences to desired germline configuration, residues can be "back-mutated" to a corresponding germline sequence by, for example, site-directed mutagenesis. Such "back-mutated" antibodies or antibody drug conjugates are also intended to be encompassed by the invention.

Another type of framework modification involves mutating one or more residues within the framework region, or even within one or more CDR regions, to remove T-cell epitopes to thereby reduce the potential immunogenicity of the antibody or antibody drug conjugate. This approach is also referred to as "deimmunization" and is described in further detail in U.S. Patent Publication No. 2003/0153043 by Carr et al.

In addition or alternative to modifications made within the framework or CDR regions, antibodies can be engineered to alter one or more functional properties of the antibody, such as serum half-life, complement fixation. Furthermore, an antibody can be chemically modified (e.g., one or more chemical moieties can be attached to the antibody) or be modified to alter its glycosylation, again to alter one or more functional properties of the antibody. Each of these aspects is described in further detail below.

In one aspect, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains, to increase or decrease the stability of the antibody, or to allow conjugation to another molecule.

In some embodiments, the antibody or antibody fragment (e.g., Fab or Fab') disclosed herein include modified or engineered amino acid residues, e.g., one or more cysteine residues, as sites for conjugation to a drug moiety (Junutula J R, et al.: Nat Biotechnol 2008, 26:925-932). In one embodiment, the invention provides a modified antibody or antibody fragment (e.g., Fab or Fab') comprising a substitution of one or more amino acids with cysteine at the positions described herein. Sites for cysteine substitution are in the constant regions of the antibody or antibody fragment (e.g., Fab or Fab') and are thus applicable to a variety of antibody or antibody fragment (e.g., Fab or Fab'), and the sites are selected to provide stable and homogeneous conjugates. A modified antibody or fragment can have one, two or more cysteine substitutions, and these substitutions can be used in combination with other modification and conjugation methods as described herein. Methods for inserting cysteine at specific locations of an antibody are known in the art, see, e.g., Lyons et al, (1990) Protein Eng., 3:703-708, WO 2011/005481, WO2014/124316, WO 2015/138615. In certain embodiments, a modified antibody comprises a substitution of one or more amino acids with cysteine on its constant region selected from positions 117, 119, 121, 124, 139, 152, 153, 155, 157, 164, 169, 171, 174, 189, 191, 195, 197, 205, 207, 246, 258, 269, 274, 286, 288, 290, 292, 293, 320, 322, 326, 333, 334, 335, 337, 344, 355, 360, 375, 382, 390, 392, 398, 400 and 422 of a heavy chain of the antibody, and wherein the positions are numbered according to the EU system. In certain embodiments, a modified antibody fragment (e.g., Fab or Fab') comprises a substitution of one or more amino acids with cysteine on its constant region selected from positions 121, 124, 152, 153, 155, 157, 164, 169, 171, 174, 189, and 207 of a heavy chain of the antibody fragment (e.g., Fab or Fab'), and wherein the positions are numbered according to the EU system. In certain embodiments, a modified antibody fragment (e.g., Fab or Fab') comprises a substitution of one or more amino acids with cysteine on its constant region selected from positions 124, 152, 153, 155, 157, 164, 174, 189, and 207 of a heavy chain of the antibody fragment (e.g., Fab or Fab'), and wherein the positions are numbered according to the EU system.

In some embodiments, a modified antibody or antibody fragment (e.g., Fab or Fab') comprises a substitution of one or more amino acids with cysteine on its constant region selected from positions 107, 108, 109, 114, 126, 127, 129, 142, 143, 145, 152, 154, 156, 157, 159, 161, 165, 168, 169, 170, 182, 183, 188, 197, 199, and 203 of a light chain of the antibody or antibody fragment (e.g., Fab or Fab'), wherein the positions are numbered according to the EU system, and wherein the light chain is a human kappa light chain. In some embodiments, a modified antibody or antibody fragment (e.g., Fab or Fab') comprises a substitution of one or more amino acids with cysteine on its constant region selected from positions 107, 108, 114, 126, 127, 129, 142, 159, 161, 165, 183, and 203 of a light chain of the antibody or antibody fragment (e.g., Fab or Fab'), wherein the positions are numbered according to the EU system, and wherein the light chain is a human kappa light chain. In some embodiments, a modified antibody or antibody fragment (e.g., Fab or Fab') comprises a substitution of one or more amino acids with cysteine on its constant region selected from positions 114, 129, 142, 145, 152, 159, 161, 165, and 197 of a light chain of the antibody or antibody fragment (e.g., Fab or Fab'), wherein the positions are numbered according to the EU system, and wherein the light chain is a human kappa light chain. In some embodiments, a modified antibody or antibody fragment (e.g., Fab or Fab') comprises a substitution of one or more amino acids with cysteine on its constant region selected from positions 107, 108, 109, 126, 143, 145, 152, 154, 156, 157, 159, 182, 183, 188, 197, 199, and 203 of a light chain of the antibody or antibody fragment (e.g., Fab or Fab'), wherein the positions are numbered according to the EU system, and wherein the light chain is a human kappa light chain. In some embodiments, a modified antibody or antibody fragment (e.g., Fab or Fab') comprises a substitution of one or more amino acids with cysteine on its constant region selected from positions 145, 152, and 197 of a light chain of the antibody or antibody fragment (e.g., Fab or Fab'), wherein the positions are numbered according to the EU system, and wherein the light chain is a human kappa light chain. In some embodiments, a modified antibody or antibody fragment (e.g., Fab or Fab') comprises a substitution of one or more amino acids with cysteine on its constant region selected from positions 114 and 165 of a light chain of the antibody or antibody fragment (e.g., Fab or Fab'), wherein the positions are numbered according to the EU system, and wherein the light chain is a human kappa light chain.

In some embodiments, a modified antibody or antibody fragment (e.g., Fab or Fab') comprises a substitution of one or more amino acids with cysteine on its constant region selected from positions 143, 145, 147, 156, 159, 163, 168 of a light chain of the antibody or antibody fragment (e.g., Fab or Fab'), wherein the positions are numbered according to the EU system, and wherein the light chain is a human lambda light chain. In some embodiments, a modified antibody or antibody fragment (e.g., Fab or Fab') comprises cysteine at position 143 (by EU numbering) of a light chain of the antibody or antibody fragment (e.g., Fab or Fab'), wherein the light chain is a human lambda light chain.

In certain embodiments, a modified antibody or antibody fragment (e.g., Fab or Fab') comprises a combination of substitution of two or more amino acids with cysteine on its constant regions and the combination of positions can be selected from any of the positions listed above.

In some embodiments, a modified antibody or antibody fragment (e.g., Fab or Fab') comprises cysteine at one or more of the following positions: position 124 of the heavy chain, position 152 of the heavy chain, position 153 of the heavy chain, position 155 of the heavy chain, position 157 of the heavy chain, position 164 of the heavy chain, position 174 of the heavy chain, position 114 of the light chain, position 129 of the light chain, position 142 of the light chain, position 159 of the light chain, position 161 of the light chain, or position 165 of the light chain, and wherein the positions are numbered according to the EU system, and wherein the light chain is a kappa chain. In some embodiments, a modified antibody or antibody fragment (e.g., Fab or Fab') comprises cysteine at four of the following positions: position 124 of the heavy chain, position 152 of the heavy chain, position 153 of the heavy chain, position 155 of the heavy chain, position 157 of the heavy chain, position 164 of the heavy chain, position 174 of the heavy chain, position 114 of the light chain, position 129 of the light chain, position 142 of the light chain, position 159 of the light chain, position 161 of the light chain, or position 165 of the light chain, and wherein the positions are numbered according to the EU system, and wherein the light chain is a kappa chain.

In some embodiments, a modified antibody or antibody fragment (e.g., Fab or Fab') comprises cysteine at position 152 of the heavy chain, wherein the position is numbered according to the EU system. In some embodiments, a modified antibody or antibody fragment (e.g., Fab or Fab') comprises cysteine at position 124 of the heavy chain, wherein the position is numbered according to the EU system. In some embodiments, a modified antibody or antibody fragment (e.g., Fab or Fab') comprises cysteine at position 165 of the light chain, wherein the position is numbered according to the EU system and wherein the light chain is a kappa chain. In some embodiments, a modified antibody or antibody fragment (e.g., Fab or Fab') comprises cysteine at position 114 of the light chain, wherein the position is numbered according to the EU system and wherein the light chain is a kappa chain. In some embodiments, a modified antibody or antibody fragment (e.g., Fab or Fab') comprises cysteine at position 143 of the light chain, wherein the position is numbered according to the EU system and wherein the light chain is a lambda chain.

In some embodiments, a modified antibody or antibody fragment (e.g., Fab or Fab') comprises cysteines at position 152 of the heavy chain and position 165 of the light chain and wherein the positions are numbered according to the EU system, and wherein the light chain is a kappa chain. In some embodiments, a modified antibody or antibody fragment (e.g., Fab or Fab') comprises cysteines at position 152 of the heavy chain and position 114 of the light chain and wherein the positions are numbered according to the EU system, and wherein the light chain is a kappa chain. In some embodiments, a modified antibody or antibody fragment (e.g., Fab or Fab') comprises cysteines at position 152 of the heavy chain and position 143 of the light chain and wherein the positions are numbered according to the EU system, and wherein the light chain is a lambda chain. In some embodiments, a modified antibody or antibody fragment (e.g., Fab or Fab') comprises cysteines at position 124 and position 152 of the heavy chain and wherein the positions are numbered according to the EU system.

In some embodiments, a modified antibody or antibody fragment (e.g., Fab or Fab') comprises cysteine at one or more of the following positions: position 155 of the heavy chain, position 189 of the heavy chain, position 207 of the heavy chain, position 145 of the light chain, position 152 of the light chain, or position 197 of the light chain, and wherein the positions are numbered according to the EU system, and wherein the light chain is a kappa chain. In some embodiments, a modified antibody or antibody fragment (e.g., Fab or Fab') comprises cysteine at two or more (e.g., 2, 3, 4) of the following positions: position 155 of the heavy chain, position 189 of the heavy chain, position 207 of the heavy chain, position 145 of the light chain, position 152 of the light chain, or position 197 of the light chain, and wherein the positions are numbered according to the EU system, and wherein the light chain is a kappa chain.

In some embodiments, a modified antibody or antibody fragment (e.g., Fab or Fab') comprises cysteine at one or more of the following positions: position 124 of the heavy chain, position 152 of the heavy chain, position 153 of the heavy chain, position 155 of the heavy chain, position 157 of the heavy chain, position 164 of the heavy chain, position 174 of the heavy chain, position 114 of the light chain, position 129 of the light chain, position 142 of the light chain, position 159 of the light chain, position 161 of the light chain, or position 165 of the light chain, and wherein the positions are numbered according to the EU system, and wherein the light chain is a kappa chain. In some embodiments, a modified antibody or antibody fragment (e.g., Fab or Fab') comprises cysteine at two or more (e.g., 2, 3, 4) of the following positions: position 124 of the heavy chain, position 152 of the heavy chain, position 153 of the heavy chain, position 155 of the heavy chain, position 157 of the heavy chain, position 164 of the heavy chain, position 174 of the heavy chain, position 114 of the light chain, position 129 of the light chain, position 142 of the light chain, position 159 of the light chain, position 161 of the light chain, or position 165 of the light chain, and wherein the positions are numbered according to the EU system, and wherein the light chain is a kappa chain.

In some embodiments, a modified antibody fragment (e.g., Fab) that specifically binds to human cKIT comprises a heavy chain comprising the amino acid sequence of SEQ ID NO: 118, and a light chain comprising the amino acid sequence of SEQ ID NO: 122.

In some embodiments, a modified antibody fragment (e.g., Fab) that specifically binds to human cKIT comprises a heavy chain comprising the amino acid sequence of SEQ ID NO: 118, and a light chain comprising the amino acid sequence of SEQ ID NO: 123.

In some embodiments, a modified antibody fragment (e.g., Fab) that specifically binds to human cKIT comprises a heavy chain comprising the amino acid sequence of SEQ ID NO: 124, and a light chain comprising the amino acid sequence of SEQ ID NO: 128.

In some embodiments, a modified antibody fragment (e.g., Fab) that specifically binds to human cKIT comprises a heavy chain comprising the amino acid sequence of SEQ ID NO: 124, and a light chain comprising the amino acid sequence of SEQ ID NO: 129.

In some embodiments, a modified antibody fragment (e.g., Fab) that specifically binds to human cKIT comprises a heavy chain comprising the amino acid sequence of SEQ ID NO: 130, and a light chain comprising the amino acid sequence of SEQ ID NO: 134.

In some embodiments, a modified antibody fragment (e.g., Fab) that specifically binds to human cKIT comprises a heavy chain comprising the amino acid sequence of SEQ ID NO: 130, and a light chain comprising the amino acid sequence of SEQ ID NO: 135.

In some embodiments, a modified antibody fragment (e.g., Fab) that specifically binds to human cKIT comprises a heavy chain comprising the amino acid sequence of SEQ ID NO: 136, and a light chain comprising the amino acid sequence of SEQ ID NO: 140.

In some embodiments, a modified antibody fragment (e.g., Fab) that specifically binds to human cKIT comprises a heavy chain comprising the amino acid sequence of SEQ ID NO: 141, and a light chain comprising the amino acid sequence of SEQ ID NO: 145.

3. Production of the cKIT Antibodies or Antibody Fragments

Anti-cKIT antibody or antibody fragment (e.g., Fab or Fab') can be produced by any means known in the art, including but not limited to, recombinant expression, chemical synthesis, or enzymatic digestion of full-length monoclonal antibodies, which can be obtained by, e.g., hybridoma or recombinant production. Recombinant expression can be from any appropriate host cells known in the art, for example, mammalian host cells, bacterial host cells, yeast host cells, insect host cells, or made by a cell-free system (e.g., Sutro's Xpress CF™ Platform, http://www.sutrobio.com/technology/).

The disclosure further provides polynucleotides encoding the antibody or antibody fragment (e.g., Fab or Fab') described herein, e.g., polynucleotides encoding heavy or light chain variable regions or segments comprising the complementarity determining regions as described herein. In some aspects, the polynucleotide encoding the heavy chain variable regions (VH) has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 11, 37, 55, 70, and 96. In some aspects, the polynucleotide encoding the light chain variable regions (VL) has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 24, 48, 83, and 109.

In some aspects, the polynucleotide encoding the antibody heavy chain has at least 85%, 89%, 90%, 91%, 92%, 93%, 94%, 95%, 96%, 97%, 98%, 99%, or 100% nucleic acid sequence identity with a polynucleotide of SEQ ID NOs: 13, 39, 57, 72, and 98. In some aspects, the polynucleotide encoding the antibody light chain has at least 85%, 89%, 90%, 91%, 92%, 93%, 94%, 95%, 96%, 97%, 98%, 99%, or 100% nucleic acid sequence identity with a polynucleotide of SEQ ID NOs: 26, 50, 85, and 111.

In some aspects, the polynucleotide encoding the Fab' heavy chain has at least 85%, 89%, 90%, 91%, 92%, 93%, 94%, 95%, 96%, 97%, 98%, 99%, or 100% nucleic acid sequence identity with a polynucleotide of SEQ ID NOs: 15, 41, 59, 74, and 100. In some aspects, the polynucleotide encoding the Fab' light chain has at least 85%, 89%, 90%, 91%, 92%, 93%, 94%, 95%, 96%, 97%, 98%, 99%, or 100% nucleic acid sequence identity with a polynucleotide of SEQ ID NOs: 26, 50, 85, and 111.

The polynucleotides of the present disclosure can encode only the variable region sequence of an anti-cKIT antibody or antibody fragment (e.g., Fab or Fab'). They can also encode both a variable region and a constant region of the antibody or antibody fragment (e.g., Fab or Fab'). Some of the polynucleotide sequences encode a polypeptide that comprises variable regions of both the heavy chain and the light chain of one of an exemplified anti-cKIT antibody or antibody fragment (e.g., Fab or Fab').

The polynucleotide sequences can be produced by de novo solid-phase DNA synthesis or by PCR mutagenesis of an existing sequence (e.g., sequences as described in the Examples below) encoding an anti-cKIT antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, CA, 1990; Mattila et al., Nucleic Acids Res. 19:967, 1991; and Eckert et al., PCR Methods and Applications 1:17, 1991.

Also provided in the present disclosure are expression vectors and host cells for producing the anti-cKIT antibody or antibody fragment (e.g., Fab or Fab') described above. Various expression vectors can be employed to express the polynucleotides encoding the anti-cKIT antibody or antibody fragment (e.g., Fab or Fab'). Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the anti-cKIT polynucleotides and polypeptides in mammalian (e.g., human) cells include pThioHis A, B & C, pcDNA3.1/His, pEBVHis A, B & C (Invitrogen, San Diego, CA), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-cKIT antibody or antibody fragment (e.g., Fab or Fab'). In some aspects, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-cKIT antibody or antibody fragment (e.g., Fab or Fab'). These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-cKIT antibody or antibody fragment (e.g., Fab or Fab') sequences. More often, the inserted anti-cKIT antibody or antibody fragment (e.g., Fab or Fab') sequences are linked to a signal sequences before inclusion in the vector. Vectors to be used to receive sequences encoding anti-cKIT antibody or antibody fragment (e.g., Fab or Fab') light and heavy chain variable domains sometimes also encode constant regions or parts thereof. Such vectors allow expression of the variable regions as fusion proteins with the constant regions thereby leading to production of intact antibodies or fragments thereof.

The host cells for harboring and expressing the anti-cKIT antibody or antibody fragment (e.g., Fab or Fab') chains can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-cKIT antibody or antibody fragment (e.g., Fab or Fab') polypeptides. Insect cells in combination with baculovirus vectors can also be used.

In other aspects, mammalian host cells are used to express and produce the anti-cKIT antibody or antibody fragment (e.g., Fab or Fab') polypeptides of the present disclosure. For example, they can be either a hybridoma cell line expressing endogenous immunoglobulin genes (e.g., the myeloma hybridoma clones as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed, including the CHO cell lines, various COS cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-cKIT antibody or antibody fragment (e.g., Fab or Fab') chains can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Antibody fragments, such as Fab or Fab' may be produced by proteolytic cleavage of immunoglobulin molecules, using enzymes such as papain (to produce Fab fragments), or pepsin (to produce Fab' fragments), etc. Compared to Fab fragments, Fab' fragments also contain the hinge region which includes the two natural cysteines that form disulfide bonds between two heavy chains of an immunoglobulin molecule.

Therapeutic Uses

The conjugates of the present disclosure are useful in a variety of applications including, but not limited to, for ablating hematopoietic stem cells in a patient in need thereof, e.g., a hematopoietic stem cell transplantation recipient. Accordingly, provided herein are methods of ablating hematopoietic stem cells in a patient in need thereof by administering to the patient an effective amount of any of the conjugates described herein. Provided herein are also methods of conditioning a hematopoietic stem cell transplantation patient (e.g., a transplant recipient) by administering to the patient an effective amount of any of the conjugates described herein, and allowing a sufficient period of time for the conjugates to clear from the patient's circulation before performing hematopoietic stem cell transplantation to the patient. The conjugates can be administered to the patient intravenously. Also provided are use of any of the conjugates or pharmaceutical compositions described herein for ablating hematopoietic stem cells in a patient in need thereof. Further provided are use of any of the conjugates or pharmaceutical compositions described herein in the manufacture of a medicament for ablating hematopoietic stem cells in a patient in need thereof.

Endogenous hematopoietic stem cells usually reside within bone marrow sinusoids. This physical environment in which stem cells reside is referred to as the stem cell microenvironment, or stem cell niche. The stromal and other cells involved in this niche provide soluble and bound factors, which have a multitude of effects. Various models have been proposed for the interaction between hematopoietic stem cells and their niche. For example, a model has been suggested where, when a stem cell divides, only one daughter remains in the niche and the other daughter cell leaves the niche to differentiate. It has been proposed that the efficiency of engraftment can be enhanced by selective depletion of endogenous hematopoietic stem cells, thereby opening the stem cell niches for the engraftment of donor stem cells (see e.g., WO 2008/067115).

Hematopoietic stem cell (HSC) transplantation, or bone marrow transplantation (as called earlier), is an established treatment for a wide range of diseases that affect the body's blood stem cells such as leukemia, severe anemia, immune defects, and some enzyme deficiency diseases. These illnesses often lead to the patient needing to have his bone marrow replaced by new, healthy blood cells.

HSC transplantation is often allogeneic, which means that the patient receives stem cells from another individual of the same species, either a sibling, matched related, haploidentical related or unrelated, volunteer donor. It is estimated that about 30% of patients in need of hematopoietic stem cell transplantation have access to a sibling whose tissue type is suitable. The other 70% of patients must rely on the matching of an unrelated, volunteer donor or the availability of a haploidentical, related donor. It is important that the characteristics of donor and patient cells are comparable. The hematopoietic stem cell transplantation could also be autologous, in which the transplanted cells are originating from the subject itself, i.e., the donor and the recipient are the same individual. Further, the transplantations could be syngeneic, i.e., from a genetically identical individual such as a twin. In an additional aspect the transplantations could be xenogeneic, i.e., originating from a different species, which is of interest when there are not sufficient donors of the same species, such as for organ transplantations.

Before the HSC transplantation, patients usually undergo a pre-treatment or conditioning method. The purpose of this pre-treatment or conditioning is to remove as many undesired cells (e.g., malignant/cancer cells) in the body as possible, to minimize rejection, and/or to open up stem cell niches by depletion of endogenous HSCs for efficient engraftment of donor stem cells into those niches. Donor's healthy HSCs are then given to the patient intravenously, or in some cases intraosseously. Many risks, however, are associated with HSC transplantation, including poor engraftment, immunological rejection, graft-versus-host disease (GVHD), or infection. Although the donor and the patient's cells appear to be equal in terms of tissue type, e.g., the MHC molecules are matched (or haploidentical); there are still minor differences between these individuals that immune cells can perceive as dangerous. This means that the new immune system (white blood cells from the new stem cells) perceive the new body as "foreign", which provokes an immune attack. This reaction, called graft-versus-host disease (GVHD), can become life-threatening to the patient. Patients after HSC transplantation also have an increased risk of infections due to absence of white blood cells before the new marrow begins to function. This period can in some cases last for many months until the new immune system have matured. Some of these opportunistic infections may be life-threatening.

Thus, there is a need for improving the conditioning and transplantation methods and decreasing the risks associated with HSC transplantation and increasing its effectiveness for various disorders. Provided herein are new antibody drug conjugates that, by specifically killing the recipient's endogenous HSCs prior to transplantation but not all other immune cells, keep a partially active immune defense to combat infections right after transplantation, but at the same time provide an indirect immunosuppressive effect due to the subject's inability to form new immune cells from its own HSCs. Since the pre-treatment can be milder than chemotherapy or radiation, and with less serious side effects, it might induce less GVHD in transplant patients.

The antibody drug conjugates described herein could be used to ablate endogenous hematopoietic stem cell, e.g., in a pre-treatment/conditioning method before hematopoietic stem cell transplantation. For example, the conjugates of the invention could be used to treat any non-malignant condition/disorder wherein stem cell transplantation could be beneficial, such as Severe aplastic anemia (SAA), Wiskott Aldrich Syndrome, Hurlers Syndrome, familial haemophagocytic lymphohistiocytosis (FHL), Chronic granulomatous disease (CGD), Kostmanns syndrome, Severe immunodeficiency syndrome (SCID), other autoimmune disorders such as SLE, Multiple sclerosis, IBD, Crohns Disease, Ulcerative colitis, Sjogrens syndrome, vasculitis, Lupus, Myasthenia Gravis, Wegeners disease, inborn errors of metabolism and/or other immunodeficiencies.

Further, the conjugates of the invention could be used to treat any malignant condition/disorder wherein stem cell transplantation could be beneficial, such as hematologic diseases, hematological malignancies or solid tumors (e.g., renal cancer, hepatic cancer, pancreatic cancer). Common types of hematological diseases/malignancies that could be treated with the claimed methods and antibodies are leukemias, lymphomas and myelodysplastic syndromes. Leukemia is a type of cancer of the blood or bone marrow characterized by an abnormal increase of immature white blood cells called blast cells, and the term leukemia includes: acute lymphoblastic leukemia (ALL), acute myelogenous leukemia (AML), acute monocytic leukemia (AMoL), chronic lymphocytic leukemia (CLL), chronic myelogenous leukemia (CML) and other leukemias such as hairy cell leukemia (HCL), T-cell prolymphocytic leukemia (T-PLL), large granular lymphocytic leukemia and adult T-cell leukemia. In one aspect of the invention, the leukemia treated is acute leukemia. In a further aspect, the leukemia is ALL, AML or AMoL. Lymphomas include precursor T-cell leukemia/lymphoma, Burkitt lymphoma, follicular lymphoma, diffuse large B cell lymphoma, mantle cell lymphoma, B-cell chronic lymphocytic leukemia/lymphoma, MALT lymphoma, Mycosis fungoides, Peripheral T-cell lymphoma not otherwise specified, Nodular sclerosis form of Hodgkin lymphoma Mixed-cellularity subtype of Hodgkin lymphoma. Myelodysplastic syndrome (MDS) is the name of a group of conditions that occur when the blood-forming cells in the bone marrow are damaged. This damage leads to low numbers of one or more type of blood cells. MDS is subdivided into 7 categories; Refractory cytopenia with unilineage dysplasia (RCUD), Refractory anemia with ringed sideroblasts (RARS), Refractory cytopenia with multilineage dysplasia (RCMD), Refractory anemia with excess blasts-1 (RAEB-1), Refractory anemia with excess blasts-2 (RAEB-2), Myelodysplastic syndrome, unclassified (MDS-U), and Myelodysplastic syndrome associated with isolated del (5q).

In some embodiments, a patient in need of ablating hematopoietic stem cells (e.g., a hematopoietic stem cell transplantation recipient) may have an inherited immunodeficient disease, an autoimmune disorder, a hematopoietic disorder, or inborn errors of metabolism.

In some embodiments, the hematopoietic disorder can be selected from any of the following: Acute myeloid leukemia (AML), Acute lymphoblastic leukemia (ALL), acute monocytic leukemia (AMoL), Chronic myeloid leukemia (CML), Chronic lymphocytic leukemia (CLL), Myeloproliferative disorders, Myelodysplastic syndromes, Multiple myeloma, Non-Hodgkin lymphoma, Hodgkin disease, Aplastic anemia, Pure red cell aplasia, Paroxysmal nocturnal hemoglobinuria, Fanconi anemi, Thalassemia major, Sickle cell anemia, Severe combined immunodeficiency, Wiskott-Aldrich syndrome, Hemophagocytic lymphohistiocytosis.

Inborn errors of metabolism are also known as inherited metabolic diseases (IMB) or congenital metabolic diseases, which are a class of genetic diseases that include congenital disorders of carbohydrate metabolism, amino acid metabolism, organic acid metabolism, or lysosomal storage diseases. In some embodiments, inborn errors of metabolism are selected from mucopolysaccharidosis, Gaucher disease, metachromatic leukodystrophies, or adrenoleukodystrophies.

Further, the conjugates of the invention could be used to treat a gastrointestinal stromal tumor (GIST), such as GIST that is cKIT positive. In some embodiments, the conjugates of the invention could be used to treat GIST that expresses wild-type cKIT. In some embodiments, the conjugates of the invention could be used to treat GIST that is resistant to a treatment, e.g., imatinib (Glivec®/Gleevec®).

Combination Therapy

In certain instances, an antibody drug conjugate of the present disclosure can be used in combination with another conditioning regiment such as radiation therapy or chemotherapy.

In certain instances, an antibody drug conjugate of the present disclosure can be used in combination with another therapeutic agent, such as an anti-cancer agent, anti-nausea agent (or anti-emetic), pain reliever, mobilizing agent, or combinations thereof.

General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclosporine (Sandimmune®, Neoral® or Restasis®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In some embodiments, the antibody drug conjugate of the present disclosure can be used in combination with a CD47 blocker, e.g., an anti-CD47 antibody or fragment thereof. It was reported that an anti-CD47 microbody that blocks the interaction between CD47 and signal regulatory protein alpha (SIRPα) can enhance depletion of endogenous HSCs by a naked anti-c-Kit antibody (Chhabra et al., *Science Translational Medicine* 8 (351), 351ra105).

In some embodiments, the antibody drug conjugate of the present disclosure can be used in combination with another antibody or fragment thereof that specifically binds to hematopoietic stem cells or hematopoietic progenitor cells, e.g., anti-CD45 antibody or fragment thereof, anti-CD34 antibody or fragment thereof, anti-CD133 antibody or fragment thereof, anti-CD59 antibody or fragment thereof, or anti-CD90 antibody or fragment thereof. In some embodiments, the antibody drug conjugates of the present disclosure can be used in combination with a Dyrk1a inhibitor, such as Harmine, INDY, ML 315 hydrochloride, ProINDY, Tocris™ TC-S 7044, Tocris™ TG 003, FINDY, TBB, DMAT, CaNDY, etc.

In some embodiments, the antibody drug conjugate of the present disclosure can be used in combination with one or more immune suppressors, such as glucocorticoids, e.g., prednisone, dexamethasone, and hydrocortisone; cytostatics, e.g., alkylating agents, antimetabolites, methotrexate, azathioprine, mercaptopurine, dactinomycin, etc.; drugs acting on immunophilins, e.g., tacrolimus (Prograf®, Astograf XL® or Envarsus XR®), sirolimus (rapamycin or Rapamune®) and everolimus; interferons; opioids; TNF binding proteins; mycophenolate; fingolimod; myriocin; etc. In some embodiments, the antibody drug conjugate of the present disclosure can be used in combination with one or more agents that specifically deplete T cells, such as Fludarabine, Ciclosporin, anti-CD52 antibody, e.g., Alemtuzumab, Anti-thymocyte globulin (ATG), anti-CD3 antibody or fragment thereof, anti-CD4 antibody or fragment thereof, anti-$CD_8$ antibody or fragment thereof, or anti-human TCR α/β antibody or fragment thereof. T cell depletion therapies can reduce host versus graft reaction, which could lead to rejection of a transplant.

In some embodiments, the antibody drug conjugate of the present disclosure can be used in combination with one or more agents selected from plerixafor (also known as AMD3100, Mozobil®), granulocyte-macrophage colony stimulating factor (GM-CSF), e.g., sargramostim (Leukine®), or granulocyte-colony stimulating factor (G-CSF), e.g., filgrastim or pegfilgrastim (Zarzio®, Zarxio®, Neupogen®, Neulasta®, Nufil®, Religrast®, Emgrast®, Neukine®, Grafeel®, Imumax®, Filcad®).

In one aspect, an antibody drug conjugate of the present disclosure is combined in a pharmaceutical combination formulation, or dosing regimen as combination therapy, with a second compound having anti-cancer properties. The second compound of the pharmaceutical combination formulation or dosing regimen can have complementary activities to the conjugate of the combination such that they do not adversely affect each other.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

Pharmaceutical Compositions

To prepare pharmaceutical or sterile compositions including one or more antibody drug conjugates described herein, the provided conjugate(s) can be mixed with a pharmaceutically acceptable carrier or excipient.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, N Y, 1993; Lieberman, et al. (eds.), Pharmaceutical Dosage Forms: Tablets, Marcel Dekker, N Y, 1990; Lieberman, et al. (eds.) Pharmaceutical Dosage Forms: Disperse Systems, Marcel Dekker, N Y, 1990; Weiner and Kotkoskie, Excipient Toxicity and Safety, Marcel Dekker, Inc., New York, N.Y., 2000).

In some embodiments, the pharmaceutical composition comprising the antibody conjugate of the present invention is a lyophilisate preparation. In certain embodiments a pharmaceutical composition comprising the antibody conjugate is a lyophilisate in a vial containing an antibody conjugate, histidine, sucrose, and polysorbate 20. In certain embodiments the pharmaceutical composition comprising the antibody conjugate is a lyophilisate in a vial containing an antibody conjugate, sodium succinate, and polysorbate 20. In certain embodiments the pharmaceutical composition comprising the antibody conjugate is a lyophilisate in a vial containing an antibody conjugate, trehalose, citrate, and polysorbate 8. The lyophilisate can be reconstituted, e.g., with water, saline, for injection. In a specific embodiment, the solution comprises the antibody conjugate, histidine, sucrose, and polysorbate 20 at a pH of about 5.0. In another specific embodiment the solution comprises the antibody conjugate, sodium succinate, and polysorbate 20. In another specific embodiment, the solution comprises the antibody conjugate, trehalose dehydrate, citrate dehydrate, citric acid, and polysorbate 8 at a pH of about 6.6. For intravenous administration, the obtained solution will usually be further diluted into a carrier solution.

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising the antibody conjugate of the invention can be provided by continuous infusion, or by doses at intervals of, e.g., one day, one week, or 1-7 times per week, once every other week, once every three weeks, once every four weeks, once every five weeks, once every six weeks, once every seven weeks, or once every eight weeks. Doses may be provided intravenously, subcutaneously, or intraosseously. A specific dose protocol is one involving the maximal dose or dose frequency that avoids significant undesirable side effects.

For the antibody conjugates of the invention, the dosage administered to a patient may be 0.0001 mg/kg to 100 mg/kg of the patient's body weight. The dosage may be between 0.001 mg/kg and 50 mg/kg, 0.005 mg/kg and 20 mg/kg, 0.01 mg/kg and 20 mg/kg, 0.02 mg/kg and 10 mg/kg, 0.05 and 5 mg/kg, 0.1 mg/kg and 10 mg/kg, 0.1 mg/kg and 8 mg/kg, 0.1 mg/kg and 5 mg/kg, 0.1 mg/kg and 2 mg/kg, 0.1 mg/kg and 1 mg/kg of the patient's body weight. The dosage of the antibody conjugate may be calculated using the patient's weight in kilograms (kg) multiplied by the dose to be administered in mg/kg.

Doses of the antibody conjugates the invention may be repeated and the administrations may be separated by less than 1 day, at least 1 day, 2 days, 3 days, 5 days, 10 days, 15 days, 30 days, 45 days, 2 months, 75 days, 3 months, 4 months, 5 months, or at least 6 months. In some embodiments, an antibody conjugate of the invention is administered twice weekly, once weekly, once every two weeks, once every three weeks, once every four weeks, or less frequently.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by subcutaneous, intravenous, intraperitoneal, intracerebral, intramuscular, intraocular, intraarterial, intracerebrospinal, intralesional administration, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874, 064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

Methods for co-administration or treatment with a second therapeutic agent, e.g., a cytokine, steroid, chemotherapeutic agent, antibiotic, or radiation (such as total body irradiation (TBI)), are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice:A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies, which can be administered in combination with the antibody conjugates of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibody conjugates of the invention. The two or more therapies may be administered within one same patient visit.

The invention provides protocols for the administration of pharmaceutical composition comprising antibody conjugates of the invention alone or in combination with other therapies to a subject in need thereof. The therapies of the combination therapies of the present invention can be administered concomitantly or sequentially to a subject. The therapy of the combination therapies of the present invention can also be cyclically administered. Cycling therapy involves the administration of a first therapy for a period of time, followed by the administration of a second therapy for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies of the combination therapies of the invention can be administered to a subject concurrently.

The term "concurrently" is not limited to the administration of therapies at exactly the same time, but rather it is meant that a pharmaceutical composition comprising antibodies or fragments thereof the invention are administered to a subject in a sequence and within a time interval such that the antibodies or antibody conjugates of the invention can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic effect. Each therapy can be administered to a subject separately, in any appropriate form and by any suitable route. In various embodiments, the therapies are administered to a subject less than 5 minutes apart, less than 15 minutes apart, less than 30 minutes apart, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies are administered within the same patient visit.

The combination therapies can be administered to a subject in the same pharmaceutical composition. Alternatively, the therapeutic agents of the combination therapies can be administered concurrently to a subject in separate pharmaceutical compositions. The therapeutic agents may be administered to a subject by the same or different routes of administration.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1: Generation of Anti-cKIT ADC

Preparation of Anti-cKit Antibodies and Antibody Fragments with or without Site-Specific Cysteine Mutations Human anti-cKIT antibodies and antibody fragments were generated as described previously in WO2014150937 and WO2016020791.

DNA encoding variable regions of the heavy and light chains of an anti-cKit antibody were amplified from a vector isolated in a phage display based screen and cloned into mammalian expression vectors that contain the constant regions of human IgG1 heavy chain and human kappa light chain or lambda light chain. Vectors contain a CMV promoter and a signal peptide (MPLLLLLPLLWAGALA (SEQ ID NO: 151) for heavy chain and MSVLTQVLALLLL-WLTGTRC (SEQ ID NO: 152) for light chain, and appropriate signal and selection sequences for amplification of DNA in a bacterial host, e.g. *E. coli* DH5alpha cells, transient expression in mammalian cells, e.g. HEK293 cells, or stable transfection into mammalian cells, e.g. CHO cells. To introduce Cys mutations, site-directed mutagenesis PCR was conducted with oligos designed to substitute single Cys residues at certain site in the constant regions of the heavy chain or light chain coding sequences. Examples of Cys substitution mutations are E152C or S375C of heavy chain; E165C or S114C of kappa light chain; or A143C of the lambda light chain (all EU numbering). In some cases, two or more Cys mutations were combined to make an antibody with multiple Cys substitutions, for example HC-E152C-S375C, lambda LC-A143C-HC-E152C, kappa LC-E165C-HC-E152C, or kappa LC-S114C-HC-E152C (all EU numbering). To generate plasmids encoding antibody fragments, mutagenesis PCR was conducted with oligos designed to remove or modify a portion of the heavy chain constant region. For example, a PCR was performed to remove residues 222-447 (EU numbering) of the heavy chain constant region such that a stop codon was encoded directly after residue 221 (EU number) in order to make an expression construct for a Fab fragment. For example, a PCR was performed to remove residues 233-447 (EU numbering) of the heavy chain constant region such that a stop codon was encoded directly after residue 232 (EU number) in order to make an expression construct for a Fab' fragment including the two Cys residues of the IgG1 hinge.

Anti-cKit antibodies, antibody fragments, and Cys mutant antibodies or antibody fragments were expressed in 293 Freestyle™ cells by co-transfecting heavy chain and light chain plasmids using transient transfection methods as described previously (Meissner, et al., *Biotechnol Bioeng.* 75:197-203 (2001)). The expressed antibodies were purified from the cell supernatants by standard affinity chromatography methods using an appropriate resin such as Protein A, Protein G, Capto-L or LambdaFabSelect resins. Alternatively, anti-cKit antibodies, antibody fragments, and Cys mutant antibodies or antibody fragments were expressed in a CHO by co-transfecting a heavy chain vector and a light chain vector into CHO cells. Cells underwent selection, and stably transfected cells were then cultured under conditions optimized for antibody production. Antibodies were purified from the cell supernatants as above.

Reduction, Re-Oxidation and Conjugation of Anti-cKit Antibodies and Antibody Fragments to Toxins Compounds comprised of a reactive moiety, e.g. a maleimide group, for reaction to a thiol group (Cys side chain) on the antibody or antibody fragment, a linker as described, and a functional moiety, such as an auristatin or other toxin, were conjugated to Cys residues, native or engineered into the antibody using methods described previously (e.g., in WO2014124316, WO2015138615, Junutula J R, et al., Nature Biotechnology 26:925-932 (2008)).

Because engineered Cys residues in antibodies expressed in mammalian cells are modified by adducts (disulfides) such as glutathione (GSH) and/or cysteine during biosynthesis (Chen et al. 2009), the modified Cys as initially expressed is unreactive to thiol reactive reagents such as maleimido or bromo-acetamide or iodo-acetamide groups. To conjugate engineered Cys residues, glutathione or cysteine adducts need to be removed by reducing disulfides, which generally entails reducing all disulfides in the expressed antibody. Because native Cys residues in antibodies and antibody fragments generally form disulfide bonds to other Cys residues in the antibody or antibody fragment, these are also unreactive to thiol reactive reagents until the disulfides are reduced. Reduction of disulfides can be accomplished by first exposing antibody to a reducing agent such as dithiothreitol (DTT), cysteine, or Tris(2-carboxyethyl)phosphine hydrochloride (TCEP-HCl). Optionally, the reducing agent can be removed to allow re-oxidation of all native disulfide bonds of the antibody or antibody fragment to restore and/or stabilize the functional antibody structure.

In cases where an antibody or antibody fragment was conjugated only at engineered Cys residues, in order to reduce native disulfide bonds and disulfide bond between the cysteine or GSH adducts of engineered Cys residue(s), freshly prepared DTT was added to purified Cys mutant antibodies, to a final concentration of 10 mM or 20 mM. After antibody incubation with DTT at 37° C. for 1 hour, mixtures were dialyzed against PBS for three days with daily buffer exchange to remove DTT and re-oxidize native disulfide bonds. The re-oxidation process was monitored by reverse-phase HPLC, which is able to separate antibody tetramer from individual heavy and light chain molecules. Reactions were analyzed on a PRLP-S 4000A column (50 mm×2.1 mm, Agilent) heated to 80° C. and column elution was carried out by a linear gradient of 30-60% acetonitrile in water containing 0.1% TFA at a flow rate of 1.5 ml/min. The elution of proteins from the column was monitored at 280 nm. Dialysis was allowed to continue until reoxidation was complete. Reoxidation restores intra-chain and inter-chain disulfides, while dialysis allows cysteines and glutathiones connected to the newly-introduced Cys residue(s) to dialyze away. After re-oxidation, maleimide-containing compounds were added to re-oxidized antibodies or antibody fragments in PBS buffer (pH 7.2) at ratios of typically 1.5:1, 2:1, or 5:1 to engineered Cys, and incubations were carried out for 1 hour. Typically, excess free compound was removed by purification over Protein A or other appropriate resin by standard methods followed by buffer exchange into PBS.

Alternatively, antibodies or antibody fragments with engineered Cys sites were reduced and re-oxidized using an on-resin method. Protein A Sepharose beads (1 ml per 10 mg antibody) were equilibrated in PBS (no calcium or magnesium salts) and then added to an antibody sample in batch mode. A stock of 0.5 M cysteine was prepared by dissolving 850 mg of cysteine HCl in 10 ml of a solution prepared by adding 3.4 g of NaOH to 250 ml of 0.5 M sodium phosphate pH 8.0 and then 20 mM cysteine was added to the antibody/bead slurry, and mixed gently at room temperature for 30-60 minutes. Beads were loaded to a gravity column and washed with 50 bed volumes of PBS in less than 30 minutes. Then the column was capped with beads resuspended in one bed volume of PBS. To modulate the rate of re-oxidation, 50 nM to 1 μM copper chloride was optionally added. The re-oxidation progress was monitored by removing a small test sample of the resin, eluting in IgG Elution buffer (Thermo), and analyzing by RP-HPLC as described above. Once re-oxidation progressed to desired completeness, conjugation could be initiated immediately by addition of 2-3 molar excess of compound over engineered cysteines, and allowing the mixture to react for 5-10 minutes at room temperature before the column was washed with at least 20 column volumes of PBS. Antibody conjugates were eluted with IgG elution buffer and neutralized with 0.1 volumes 0.5 M sodium phosphate pH 8.0 and buffer exchanged to PBS. In some instances, instead of initiating conjugation with antibody on the resin, the column was washed with at least 20 column volumes of PBS, and antibody was eluted with IgG elution buffer and neutralized with buffer pH 8.0. Antibodies were then either used for conjugation reactions or flash frozen for future use.

In some instances, it is desired to conjugate to native Cys residues, such as those that usually form the heavy chain to light chain interchain disulfide bond and the Cys residues in the hinge region of the antibody that usually form heavy chain to heavy chain interchain disulfide bonds, in the absence of engineered Cys residues or at the same time as conjugation was also directed to engineered Cys residues. In these cases, the antibody or antibody fragment was reduced by adding 5-fold excess of TCEP to disulfide bonds and incubated the sample at 37° C. for 1 hour. The samples were then immediately conjugated or frozen at <−60° C. for future conjugation. Maleimide-containing compounds were added to antibodies or antibody fragments in PBS buffer (pH 7.2) at ratios of typically 2:1 to Cys residues used for conjugation, and incubations were carried out for 1 hour. Typically, excess free compound was removed by desalting column followed by more extensive buffer exchange to PBS.

Conjugation to lysine residues can be prepared by reacting antibodies or antibody fragments with a linker-drug compound which comprises an amine reactive group, such as an NHS ester or a tetrafluorophenyl ester, (e.g., compound (7), SMCC-DM1, Sulfo-SPDB-DM4 or SPDB-DM4). By way of example, Compound (7) was conjugated to lysine residues on anti-HER2 Fab-HC-E152C. Specifically, anti-HER2 Fab-HC-E152C was expressed by transient transfection in HEK293 cells. Fab was captured from the media by capto-L (GE Healthcare) affinity purification, eluted in IgG Elution Buffer (Pierce) and buffer exchanged to PBS by ultraconcentrator (Amicon). To the Fab solution (5.8 mg/ml) was added a 2-fold molar excess of Compound (7). The mixture was incubated at room temperature for 30 minutes and then the mixture was quenched with 50 mM Tris pH 8. The resulting conjugate was then purified by preparative SEC in PBS.

Generation of Antibody Fragments from Full-Length Antibodies

In some instances, antibody fragments were generated by genetic manipulation of the antibody heavy chain coding sequence, as described above, such that the product of expression was a fragment of an antibody. In other instances, antibodies were generated by enzymatic digest of full-length antibodies.

To generate Fab fragments comprising residues 1-222 (EU numbering) of a starting antibody, the full antibody was treated with immobilized papain resin (ThermoFisher Scientific) according to manufacturer's protocol. Briefly, the immobilized papain resin is prepared by equilibrating in a digestion buffer of freshly dissolved 20 mM cysteine-HCl adjusted to pH 7.0. The antibody is adjusted to approximately 10 mg/ml and buffer exchanged into the digestion buffer and added to resin at a ratio of 4 mg IgG per ml resin and incubated at 37° C. for 5-7 hours. The resin is then removed, and the antibody fragment is purified by either an appropriate affinity resin, for example the intact IgG and Fc fragment are separated from the Fab fragment by binding to Protein A resin, or the separation is conducted by size exclusion chromatography.

To generate F(ab')$_2$ fragments comprising residues 1-236 (EU numbering) of the starting antibody, the full antibody was treated with a proteolytic enzyme. Briefly, the antibody is prepared in PBS at approximately 10 mg/ml. The enzyme is added at a 1:100 weight/weight ratio and incubated for 2 hours at 37° C. The antibody fragment is purified by either an appropriate affinity resin, for example the intact IgG and Fc fragment are separated from the Fab' fragment by binding to Protein A resin, or the separation is conducted by size exclusion chromatography.

Properties of Anti-cKit-Toxin Antibody and Antibody Fragment Conjugates

Antibody and antibody fragment conjugates were analyzed to determine extent of conjugation. A compound-to-antibody ratio was extrapolated from LC-MS data for reduced and deglycosylated (where appropriate) samples. LC/MS allows quantitation of the average number of molecules of linker-payload (compound) attached to an antibody in a conjugate sample. High pressure liquid chromatography (HPLC) separates antibody into light and heavy chains, and under reducing conditions, separates heavy chain (HC) and light chain (LC) according to the number of linker-payload groups per chain. Mass spectral data enables identification of the component species in the mixture, e.g., LC, LC+1, LC+2, HC, HC+1, HC+2, etc. From the average loading on the LC and HC chains, the average compound to antibody ratio can be calculated for an antibody conjugate. A compound-to-antibody ratio for a given conjugate sample represents the average number of compound (linker-payload) molecules attached to a tetrameric antibody containing two light chains and two heavy chains.

Conjugates were profiled using analytical size-exclusion chromatography (AnSEC) on Superdex 200 10/300 GL (GE Healthcare) and/or Protein KW-803 5 μm 300×8 mm (Shodex) columns; aggregation was analyzed based on analytical size exclusion chromatography.

Preparation of Exemplary Anti-cKIT Fab-Toxin Conjugates

To generate anti-cKIT Fab'-toxin DAR4 conjugates or anti-Her2 Fab-toxin DAR4 control conjugate, 50 mg full IgG (WT, without introduced cysteines) was digested with a proteolytic enzyme. The F(ab')$_2$ fragment was purified by SEC on a Superdex-S200 (GE Healthcare) column. Alternatively, to generate anti-HER2 control conjugates or anti-cKit Fab'-toxin DAR4 conjugates, a vector encoding the Fab' HC was co-transfected with a vector encoding the Fab' LC in CHO. The expressed Fab' was purified by capture on Protein G resin. The F(ab')$_2$ or Fab' was reduced by addition of TCEP (5× excess to interchain disulfides) and immediately reacted with a compound of the invention (2.5× excess to free Cys residues). Reaction was monitored by RP-HPLC, and additional 1× equivalents of compound were added until reaction was completed. Free compound was removed by PD10 desalting column (GE Healthcare). DAR were experimentally determined to be ≥3.9. Specific conjugates studied further in the provided examples are listed in Table 2.

To generate anti-cKIT Fab-toxin DAR2 conjugates, a vector encoding the Fab HC with an introduced Cys residue (HC 1-221 with E152C by EU numbering) was co-transfected with a vector encoding the Fab LC with an introduced Cys residue (kappa LC K107C, kappa LC S114C, or kappa LC E165C by EU numbering) in HEK293. To generate anti-Her2 Fab-toxin DAR2 control conjugates, a vector encoding the Fab HC with an introduced Cys residue (HC 1-222 with E152C by EU numbering, and a C-terminal His$_6$ tag (SEQ ID NO: 162)) was co-transfected with a vector encoding the Fab LC with an introduced Cys residue (kappa LC K107C, kappa LC S114C, or kappa LC E165C by EU numbering) in HEK293. The expressed Fabs were purified by capture on Capto-L resin (GE Healthcare) and elution with standard IgG Elution Buffer (Thermo). Fabs were buffer exchanged to PBS using Amicon ultra devices. Fabs were reduced with DTT and allowed to reoxidize at room temperature. After reformation of the interchain disulfide bond, the Fabs were conjugated to Compound 6 (3× excess to free Cys residues). Reaction was allowed to proceed for 30 min at room temperature and monitored by RP-HPLC with detection at 310 nm. Conjugated Fabs were purified over protein A (anti-her2) or capto-L (anti-cKit) resins and were washed with PBS+1% Triton X-100 and washed with extensive PBS before elution in IgG Elution Buffer. Fabs were then buffer exchanged to PBS using Amicon Ultra devices. Specific conjugates studied further in the provided examples are listed in Table 2 below with experimentally determined DAR values.

To generate anti-cKIT F(ab')$_2$-toxin DAR2 conjugates, a vector encoding the HC with introduced Cys residues (E152C and S375C by EU numbering) was co-transfected with a vector encoding the Fab LC in CHO. To generate anti-Her2 F(ab')₂-toxin DAR2 control conjugates, a vector encoding the HC with introduced Cys residues (E152C and S375C by EU numbering) was co-transfected with a vector encoding the Fab LC in HEK293. The expressed IgGs were purified by capture on protein A or mabselectsure resin (GE Healthcare) and elution with standard IgG Elution Buffer (Thermo). Full IgGs were reduced with DTT at room temperature and reoxidized following removal of DTT as monitored by RP-HPLC. The reoxidized IgGs were then digested with a proteolytic enzyme to generate F(ab')₂ fragments. For anti-cKIT fragments, F(ab')₂'s were buffer exchanged to PBS using Amicon ultra devices. For anti-HER2 fragment, F(ab')₂ fraction was enriched by preparative HIC and then buffer exchanged to PBS using Amicon ultra devices. The F(ab')₂'s were conjugated to Compound 4 or Compound 5 (4× excess to free Cys residues). Reaction was allowed to proceed for 30 min at room temperature and monitored by RP-HPLC with detection at 310 nm. Conjugated F(ab')₂'s were purified over capto-L (anti-cKit Ab3) resins and were washed with PBS+1% Triton X-100 and washed with extensive PBS before elution in IgG Elution Buffer or by preparative SEC (anti-her2 and anti-cKIT Ab4). F(ab')₂'s were then concentrated and buffer exchanged to PBS using Amicon Ultra devices. Specific conjugates studied further in the provided examples are listed in Table 2 below with experimentally determined DAR values.

To generate anti-cKIT Fab-toxin DAR1 conjugates, a vector encoding the HC with introduced Cys residues (E152C by EU numbering) was co-transfected with a vector encoding the Fab LC in HEK293. The expressed IgG was purified by capture on protein A resin (GE Healthcare) and elution with standard IgG Elution Buffer (Thermo). Full IgGs were reduced with DTT at room temperature and reoxidized following removal of DTT as monitored by RP-HPLC. IgG was digested with immobilized papain (Thermo) to generate Fab fragment. Fabs were buffer exchanged to PBS using Amicon ultra devices. Fabs were conjugated to Compound 4 (4× excess to free Cys residues). Reaction was allowed to proceed for 30 min at room temperature and monitored by RP-HPLC with detection at 310 nm. Conjugated Fab was purified by preparative SEC in PBS.

To generate anti-Her2 Fab-toxin DAR1 control conjugates, a vector encoding the Fab HC with introduced Cys residues (E152C by EU numbering) was co-transfected with a vector encoding the Fab LC in HEK293. The expressed Fabs were purified by capture on Capto-L resin (GE Healthcare) and elution with standard IgG Elution Buffer (Thermo). Fabs were buffer exchanged to PBS using Amicon ultra devices. The Fab was conjugated to Compound 7 (2× molar excess to Fab). Reaction was allowed to proceed for 30 m at room temperature and monitored by RP-HPLC with detection at 310 nm. Conjugation was quenched with 50 mM Tris pH 8.0. Conjugated Fab was purified by preparative SEC in PBS.

TABLE 2

Exemplary anti-cKIT or control conjugates

| Conjug. No. | Antibody fragment | Conjugation Method | Antibody fragment HC sequence | Antibody fragment LC sequence | Payload | DAR |
|---|---|---|---|---|---|---|
| J1 | Anti-cKIT Fab'1 | Native Cysteine conjugation* | SEQ ID NO: 14 | SEQ ID NO: 25 | Compound (1) | 4 |
| J2 | Anti-cKIT Fab'2 | Native Cysteine conjugation | SEQ ID NO: 40 | SEQ ID NO: 49 | Compound (1) | 4 |
| J3 | Anti-cKIT Fab'3 | Native Cysteine conjugation | SEQ ID NO: 58 | SEQ ID NO: 25 | Compound (1) | 4 |
| J4 | Anti-cKIT Fab'4 | Native Cysteine conjugation | SEQ ID NO: 73 | SEQ ID NO: 84 | Compound (1) | 4 |
| J5 | Anti-cKIT Fab'5 | Native Cysteine conjugation | SEQ ID NO: 99 | SEQ ID NO: 110 | Compound (1) | 4 |
| J6 | Anti-Her2 Fab' | Native Cysteine conjugation | EVQLVESGGGLVQ PGGSLRLSCAASG FNIKDTYIHWVRQA PGKGLEWVARIYP TNGYTRYADSVKG RFTISADTSKNTAY LQMNSLRAEDTAV YYCSRWGGDGFY AMDYWGQGTLVT VSSASTKGPSVFPL APSSKSTSGGTAA LGCLVKDYFPEPVT VSWNSGALTSGVH TFPAVLQSSGLYSL SSVVTVPSSSLGT QTYICNVNHKPSNT KVDKKVEPKSCDK THTCPPCPAPELL G (SEQ ID NO: 146) | DIQMTQSPSSLSAS VGDRVTITCRASQ DVNTAVAWYQQKP GKAPKLLIYSASFL YSGVPSRFSGSRS GTDFTLTISSLQPE DFATYYCQQHYTT PPTFGQGTKVEIKR TVAAPSVFIFPPSD EQLKSGTASVVCLL NNFYPREAKVQWK VDNALQSGNSQES VTEQDSKDSTYSL SSTLTLSKADYEKH KVYACEVTHQGLS SPVTKSFNRGEC (SEQ ID NO: 147) | Compound (1) | 4 |

TABLE 2-continued

Exemplary anti-cKIT or control conjugates

| Conjug. No. | Antibody fragment | Conjugation Method | Antibody fragment HC sequence | Antibody fragment LC sequence | Payload | DAR |
|---|---|---|---|---|---|---|
| J7 | Anti-cKIT Fab3 | Engineered Cysteines at HC-E152C and LC-E165C (EU) | SEQ ID NO: 130 | SEQ ID NO: 134 | Compound (6) | 1.7 |
| J8 | Anti-Her2 Fab | Engineered Cysteines at HC-E152C and LC-K107C (EU) | EVQLVESGGGLVQ PGGSLRLSCAASG FNIKDTYIHWVRQA PGKGLEWVARIYP TNGYTRYADSVKG RFTISADTSKNTAY LQMNSLRAEDTAV YYCSRWGGDGFY AMDYWGQGTLVT VSSASTKGPSVFPL APSSKSTSGGTAA LGCLVKDYFPCPV TVSWNSGALTSGV HTFPAVLQSSGLY SLSSVVTVPSSSLG TQTYICNVNHKPSN TKVDKKVEPKSCD KHHHHHH (SEQ ID NO: 148) | DIQMTQSPSSLSAS VGDRVTITCRASQ DVNTAVAWYQQKP GKAPKLLIYSASFL YSGVPSRFSGSRS GTDFTLTISSLQPE DFATYYCQQHYTT PPTFGQGTKVEICR TVAAPSVFIFPPSD EQLKSGTASVVCLL NNFYPREAKVQWK VDNALQSGNSQES VTEQDSKDSTYSL SSTLTLSKADYEKH KVYACEVTHQGLS SPVTKSFNRGEC (SEQ ID NO: 149) | Compound (6) | 1.8 |
| J9 | Anti-cKIT F(ab'4)$_2$ | Engineered Cysteines at HC-E152C (EU) | QVQLQQSGPGLVK PSQTLSLTCAISGD SVSTNSAAWNWIR QSPSRGLEWLGRI YYRSQWLNDYAVS VKSRITINPDTSKN QFSLQLNSVTPED TAVYYCARQLTYP YTVYHKALDVWGQ GTLVTVSSastkgpsv fplapssskstsggtaalgcl vkdyfpCpvtvswnsgal tsgvhtfpavlqssglysls svvtvpssslgtqtyicnvn hkpsntkvdkrvepkscd kthtcppcpapellg (SEQ ID NO: 153) | SEQ ID NO: 84 | Compound (4) | 1.9 |
| J10 | Anti-cKIT F(ab'3)$_2$ | Engineered Cysteines at HC-E152C (EU) | QVQLVQSGAEVKK PGSSVKVSCKASG GTFSSYAISWVRQ APGQGLEWMGTIG PFEGQPRYAQKFQ GRVTITADESTSTA YMELSSLRSEDTA VYYCARGGYISDF DVWGQGTLVTVSS astkgpsvfplapssksts ggtaalgclvkdyfpCpvt vswnsgaltsgvhtfpavl gssglyslssvvtvpssslg tqtyicnvnhkpsntkvdk rvepkscdkthtcppcpa pellg (SEQ ID NO: 154) | SEQ ID NO: 25 | Compound (5) | 2 |
| J11 | Anti-cKIT Fab3 | Engineered Cysteines at HC-E152C (EU) | QVQLVQSGAEVKK PGSSVKVSCKASG GTFSSYAISWVRQ APGQGLEWMGTIG PFEGQPRYAQKFQ GRVTITADESTSTA YMELSSLRSEDTA VYYCARGGYISDF DVWGQGTLVTVSS ASTKGPSVFPLAPS SKSTSGGTAALGC LVKDYFPcPVTVS | SEQ ID NO: 25 | Compound (4) | 0.9 |

TABLE 2-continued

Exemplary anti-cKIT or control conjugates

| Conjug. No. | Antibody fragment | Conjugation Method | Antibody fragment HC sequence | Antibody fragment LC sequence | Payload | DAR |
|---|---|---|---|---|---|---|
| | | | WNSGALTSGVHTF PAVLQSSGLYSLSS VVTVPSSSLGTQT YICNVNHKPSNTKV DKKVEPKSCDKTH (SEQ ID NO: 155) | | | |
| J12 | Anti-Her2 F(ab')₂ | Engineered Cysteines at HC-E152C (EU) | EVQLVESGGGLVQ PGGSLRLSCAASG FNIKDTYIHWVRQA PGKGLEWVARIYP TNGYTRYADSVKG RFTISADTSKNTAY LQMNSLRAEDTAV YYCSRWGGDGFY AMDYWGQGTLVT VSSASTKGPSVFPL APSSKSTSGGTAA LGCLVKDYFPCPV TVSWNSGALTSGV HTFPAVLQSSGLY SLSSVVTVPSSSLG TQTYICNVNHKPSN TKVDKKVEPKSCD KTHTCPPCPAPELL G (SEQ ID NO: 156) | SEQ ID NO: 147 | Compound (4) | 1.7 |
| J13 | Anti-Her2 Fab | Engineered Cysteines at HC-E152C (EU) | EVQLVESGGGLVQ PGGSLRLSCAASG FNIKDTYIHWVRQA PGKGLEWVARIYP TNGYTRYADSVKG RFTISADTSKNTAY LQMNSLRAEDTAV YYCSRWGGDGFY AMDYWGQGTLVT VSSASTKGPSVFPL APSSKSTSGGTAA LGCLVKDYFPCPV TVSWNSGALTSGV HTFPAVLQSSGLY SLSSVVTVPSSSLG TQTYICNVNHKPSN TKVDKKVEPKSCD K (SEQ ID NO: 157) | SEQ ID NO: 147 | Compound (7) | 0.9 |
| J14 | Anti-cKIT Fab'1 | Native Cysteine conjugation | SEQ ID NO: 14 | SEQ ID NO: 25 | mc-MMAF | 4 |
| J15 | Anti-cKIT Fab'1 | Native Cysteine conjugation | SEQ ID NO: 14 | SEQ ID NO: 25 | Compound (5) | 4 |
| J16 | Anti-cKIT Fab'1 | Native Cysteine conjugation | SEQ ID NO: 14 | SEQ ID NO: 25 | Compound (2) | 4 |
| J17 | Anti-cKIT Fab'2 | Native Cysteine conjugation | SEQ ID NO: 40 | SEQ ID NO: 49 | mc-MMAF | 4 |
| J18 | Anti-cKIT Fab'2 | Native Cysteine conjugation | SEQ ID NO: 40 | SEQ ID NO: 49 | Compound (5) | 4 |
| J19 | Anti-cKIT Fab'2 | Native Cysteine conjugation | SEQ ID NO: 40 | SEQ ID NO: 49 | Compound (2) | 4 |
| J20 | Anti-cKIT Fab'3 | Native Cysteine conjugation | SEQ ID NO: 132 | SEQ ID NO: 25 | mc-MMAF | 4 |

TABLE 2-continued

Exemplary anti-cKIT or control conjugates

| Conjug. No. | Antibody fragment | Conjugation Method | Antibody fragment HC sequence | Antibody fragment LC sequence | Payload | DAR |
|---|---|---|---|---|---|---|
| J21 | Anti-cKIT Fab'3 | Native Cysteine conjugation | SEQ ID NO: 58 | SEQ ID NO: 25 | Compound (5) | 4 |
| J22 | Anti-cKIT Fab'3 | Native Cysteine conjugation | SEQ ID NO: 132 | SEQ ID NO: 25 | Compound (2) | 4 |
| | Anti-cKIT Fab4 | HC-E152C (EU) | QVQLQQSGPGLVK PSQTLSLTCAISGD SVSTNSAAWNWIR QSPSRGLEWLGRI YYRSQWLNDYAVS VKSRITINPDTSKN QFSLQLNSVTPED TAVYYCARQLTYP YTVYHKALDVWGQ GTLVTVSSastkgpsv fplapssksts ggtaalgcl vkdyfpCpvtvswnsgal tsgvhtfpavlgssglysls svvtvpssslgtqtyicnvn hkpsntkvdkrvepkscd k (SEQ ID NO: 158) | SEQ ID NO: 84 | none | |
| | Anti-cKIT Fab1 | HC-E152C (EU) | QVQLVQSGAEVK KPGSSVKVSCKA SGGTFSSYAISW VRQAPGQGLEW MGVIFPAEGAPG YAQKFQGRVTIT ADESTSTAYMEL SSLRSEDTAVYY CARGGYISDFDV WGQGTLVTVSSa stkgpsvfplapssksts ggtaalgclvkdyfpCp vtvswnsgaltsgvhtfp avlqssglyslssvvtvp ssslgtqtyicnvnhkps ntkvdkrvepkscdk (SEQ ID NO: 159) | SEQ ID NO: 25 | none | |
| | Anti-cKIT Fab2 | HC-E152C (EU) | QVQLVQSGAEVK KPGSSVKVSCKA SGGTFSSHALSW VRQAPGQGLEW MGGIIPSFGTADY AQKFQGRVTITA DESTSTAYMELS SLRSEDTAVYYC ARGLYDFDYWG QGTLVTVSSastkg psvfplapssksts ggt aalgclvkdyfpCpvtv swnsgaltsgvhtfpavl qssglyslssvvtvpsss lgtqtyicnvnhkpsntk vdkrvepkscdk (SEQ ID NO: 160) | SEQ ID NO: 49 | none | |
| | Anti-cKIT Fab3 | HC-E152C (EU) | QVQLVQSGAEVK KPGSSVKVSCKA SGGTFSSYAISW VRQAPGQGLEW MGTIGPFEGQPR YAQKFQGRVTIT ADESTSTAYMEL SSLRSEDTAVYY CARGGYISDFDV WGQGTLVTVSSA STKGPSVFPLAP SSKSTSGGTAAL GCLVKDYFPCPV | SEQ ID NO: 25 | none | |

TABLE 2-continued

Exemplary anti-cKIT or control conjugates

| Conjug. No. | Antibody fragment | Conjugation Method | Antibody fragment HC sequence | Antibody fragment LC sequence | Payload | DAR |
|---|---|---|---|---|---|---|
| | | | TVSWNSGALTSG VHTFPAVLQSSG LYSLSSVVTVPSS SLGTQTYICNVN HKPSNTKVDKKV EPKSCDK (SEQ ID NO: 161) | | | |
| | Anti-Her2 Fab | HC-E152C (EU) | SEQ ID NO: 157 | SEQ ID NO: 147 | none | |
| | Anti-cKIT Fab'5 | Native Cysteine conjugation | SEQ ID NO: 143 | SEQ ID NO: 110 | Compound (1) | 3.9 |
| | Anti-cKIT Fab'5 | Native Cysteine conjugation | SEQ ID NO: 143 | SEQ ID NO: 110 | Compound (1) | 3.7 |
| | Anti-cKIT Fab'5 | Native Cysteine conjugation | SEQ ID NO: 143 | SEQ ID NO: 110 | mc-MMAF | 4 |
| JW | Anti-cKIT Fab'2 | Native Cysteine conjugation | SEQ ID NO: 126 | SEQ ID NO: 49 | Compound (1) | 3.9 |
| JX | Anti-cKIT Fab'2 | Native Cysteine conjugation | SEQ ID NO: 126 | SEQ ID NO: 49 | mc-MMAF | 3.9 |
| JY | Anti-cKIT Fab'3 | Native Cysteine conjugation | SEQ ID NO: 132 | SEQ ID NO: 25 | Compound (1) | 3.9 |
| JZ | Anti-cKIT Fab'3 | Native Cysteine conjugation | SEQ ID NO: 132 | SEQ ID NO: 25 | mc-MMAF | 3.9 |

*native Cys conjugation means the drug is attached to the antibody fragment at one or more of the native cysteine residues selected from LC-214C and HC-220C-226C-229C (all positions by EU numbering).

Example 2: Generation of Human, Cyno, Mouse and Rat cKIT Extracellular Domain Proteins, and of cKIT Subdomains 1-3, and 4-5 for Binding Assays Human, mouse and rat cKIT extracellular domains (ECD) were gene synthesized based on amino acid sequences from the GenBank or Uniprot databases (see Table 3 below). Cynomolgus cKIT and 1 ECD cDNA template were gene synthesized based on amino acid sequences information generated using mRNA from various cyno tissues (e.g. Zyagen Laboratories; Table 4 below). All synthesized DNA fragments were cloned into appropriate expression vectors e.g. hEF1-HTLV based vector (pFUSE-mIgG2A-Fc2) with C-terminal tags to allow for purification.

TABLE 3

Sequences of human, mouse, rat cKIT constructs

| Name | Description | Accession Number | SEQ ID NO: |
|---|---|---|---|
| Human cKIT D1-5 (extracellular domain) | Human cKIT tr. variant 2, residues 26-520-TAG QPSVSPGEPSPPSIHPGKSDLIVRVGDEI RLLCTDPGFVKWTFEILDETNENKQNEW ITEKAEATNTGKYTCTNKHGLSNSIYVFV RDPAKLFLVDRSLYGKEDNDTLVRCPLT DPEVTNYSLKGCQGKPLPKDLRFIPDPK AGIMIKSVKRAYHRLCLHCSVDQEGKSV LSEKFILKVRPAFKAVPVVSVSKASYLLR EGEEFTVTCTIKDVSSSVYSTWKRENSQ TKLQEKYNSWHHGDFNYERQATLTISSA RVNDSGVFMCYANNTFGSANVTTTLEVV DKGFINIFPMINTTVFVNDGENVDLIVEYE AFPKPEHQQWIYMNRTFTDKWEDYPKS ENESNIRYVSELHLTRLKGTEGGTYTFLV | NM_001093772 | 112 |

TABLE 3-continued

Sequences of human, mouse, rat cKIT constructs

| Name | Description | Accession Number | SEQ ID NO: |
|---|---|---|---|
| | SNSDVNAAIAFNVYVNTKPEILTYDRLVN GMLQCVAAGFPEPTIDWYFCPGTEQRC SASVLPVDVQTLNSSGPPFGKLVVQSSI DSSAFKHNGTVECKAYNDVGKTSAYFNF AFKEQIHPHTLFTPRSHHHHHH | | |
| Human cKIT D1-3 | Human cKIT tr. Variant 1, residues 26-311-TAG QPSVSPGEPSPPSIHPGKSDLIVRVGDEI RLLCTDPGFVKWTFEILDETNENKQNEW ITEKAEATNTGKYTCTNKHGLSNSIYVFV RDDPAKLFLVDRSLYGKEDNDTLVRCPLT DPEVTNYSLKGCQGKPLPKDLRFIPDPK AGIMIKSVKRAYHRLCLHCSVDQEGKSV LSEKFILKVRPAFKAVPVVSVSKASYLLR EGEEFTVTCTIKDVSSSVYSTWKRENSQ TKLQEKYNSWHHGDFNYERQATLTISSA RVNDSGVFMCYANNTFGSANVTTTLEVV DKGRSHHHHHH | NM_000222 | 113 |
| Human cKIT D4-5 | Human cKIT tr. variant 1, residues 311-524-TAG GFINIFPMINTTVFVNDGENVDLIVEYEAF PKPEHQQWIYMNRTFTDKWEDYPKSEN ESNIRYVSELHLTRLKGTEGGTYTFLVSN SDVNAAIAFNVYVNTKPEILTYDRLVNGM LQCVAAGFPEPTIDWYFCPGTEQRCSAS VLPVDVQTLNSSGPPFGKLVVQSSIDSS AFKHNGTVECKAYNDVGKTSAYFNFAFK GNNKEQIHPHTLFTPRSHHHHHH | NM_000222 | 114 |
| Mouse cKIT D1-5 | Mouse cKIT tr. variant 1, residues 26-527-TAG SQPSASPGEPSPPSIHPAQSELIVEAGDT LSLTCIDPDFVRWTFKTYFNEMVENKKN EWIQEKAEATRTGTYTCSNSNGLTSSIYV FVRDPAKLFLVGLPLFGKEDSDALVRCPL TDPQVSNYSLIECDGKSLPTDLTFVPNPK AGITIKNVKRAYHRLCVRCAAQRDGTWL HSDKFTLKVRAAIKAIPVVSVPETSHLLKK GDTFTVVCTIKDVSTSVNSMWLKMNPQP QHIAQVKHNSWHRGDFNYERQETLTISS ARVDDSGVFMCYANNTFGSANVTTTLKV VEKGFINISPVKNTTVFVTDGENVDLVVE YEAYPKPEHQQWIYMNRTSANKGKDYV KSDNKSNIRYVNQLRLTRLKGTEGGTYT FLVSNSDASASVTFNVYVNTKPEILTYDR LINGMLQCVAEGFPEPTIDWYFCTGAEQ RCTTPVSPVDVQVQNVSVSPFGKLVVQS SIDSSVFRHNGTVECKASNDVGKSSAFF NFAFKEQIQAHTLFTPLEVLFQGPRSPRG PTIKPCPPCKCPAPNLLGGPSVFIFPPKIK DVLMISLSPIVTCVVVDVSEDDPDVQISW FVNNVEVHTAQTQTHREDYNSTLRVVSA LPIQHQDWMSGKEFKCKVNNKDLPAPIE RTISKPKGSVRAPQVYVLPPPEEEMTKK QVTLTCMVTDFMPEDIYVEWTNNGKTEL NYKNTEPVLDSDGSYFMYSKLRVEKKN WVERNSYSCSVVHEGLHNHHTTKSFSR TPGK | NM_001122733 | 115 |
| Rat cKIT D1-5 | Rat cKIT, residues 25-526-TAG SQPSASPGEPSPPSIQPAQSELIVEAGDT IRLTCTDPAFVKWTFEILDVRIENKQSEWI REKAEATHTGKYTCVSGSGLRSSIYVFV RDPAVLFLVGLPLFGKEDNDALVRCPLT DPQVSNYSLIECDGKSLPTDLKFVPNPKA GITIKNVKRAYHRLCIRCAAQREGKWMR SDKFTLKVRAAIKAIPVVSVPETSHLLKEG DTFTVICTIKDVSTSVDSMWIKLNPQPQS KAQVKRNSWHQGDFNYERQETLTISSA RVNDSGVFMCYANNTFGSANVTTTLKVV EKGFINIFPVKNTTVFVTDGENVDLVVEF EAYPKPEHQQWIYMNRTPTNRGEDYVK SDNQSNIRYVNELRLTRLKGTEGGTYTFL | NM_022264 | 116 |

TABLE 3-continued

Sequences of human, mouse, rat cKIT constructs

| Name | Description | Accession Number | SEQ ID NO: |
|---|---|---|---|
| | VSNSDVSASVTFDVYVNTKPEILTYDRLM NGRLQCVAAGFPEPTIDWYFCTGAEQR CTVPVPPVDVQIQNASVSPFGKLVVQSSI DSSVFRHNGTVECKASNAVGKSSAFFNF AFKGNSKEQIQPHTLFTPRSLEVLFQGP GSPPLKECPPCAAPDLLGGPSVFIFPPKI KDVLMISLSPMVTCVVVDVSEDDPDVQIS WFVNNVEVHTAQTQTHREDYNSTLRVV SALPIQHQDWMSGKEFKCKVNNRALPS PIEKTISKPRGPVRAPQVYVLPPPAEEMT KKEFSLTCMITGFLPAEIAVDWTSNGRTE QNYKNTATVLDSDGSYFMYSKLRVQKST WERGSLFACSVVHEGLHNHLTTKTISRS LGK | | |

TABLE 4

Sequences of cynomolgus cKIT protein

| Construct | Cynomolgus monkey cKIT, residues 25-520-TAG | SEQ ID NO |
|---|---|---|
| Cynomolgus monkey cKIT D1-5 | MYRMQLLSCIALSLALVTNSQPSVSPGEPSPPS IHPAKSELIVRVGNEIRLLCIDPGFVKWTFEIL DETNENKQNEWITEKAEATNTGKYTCTNKHGLS SSIYVFVRDPAKLFLVDRSLYGKEDNDTLVRCP LTDPEVTSYSLKGCQGKPLPKDLRFVPDPKAGI TIKSVKRAYHRLCLHCSADQEGKSVLSDKFILK VRPAFKAVPVVSVSKASYLLREGEEFTVTCTIK DVSSSVYSTWKRENSQTKLQEKYNSWHHGDFNY ERQATLTISSARVNDSGVFMCYANNTFGSANVT TTLEVVDKGFINIFPMINTTVFVNDGENVDLIV EYEAFPKPEHQQWIYMNRTFTDKWEDYPKSENE SNIRYVSELHLTRLKGTEGGTYTFLVSNSDVNA SIAFNVYVNTKPEILTYDRLVNGMLQCVAAGFP EPTIDWYFCPGTEQRCSASVLPVDVQTLNASGP PFGKLVVQSSIDSSAFKHNGTVECKAYNDVGKT SAYFNFAFKGNNKEQIHPHTLFTPRSHHHHHH | 117 |

Amino acid sequence in one letter code, signal peptide underlined

Expression of Recombinant cKIT ECD Proteins

The desired cKIT recombinant proteins were expressed in HEK293 derived cell lines (293FS) previously adapted to suspension culture and grown in serum-free medium Free-Style-293 (Gibco, catalogue #12338018). Both small scale and large scale protein production were via transient transfection and was performed in multiple shaker flasks (Nalgene), up to 1 L each, with 293Fectin® (Life Technologies, catalogue #12347019) as a plasmid carrier. Total DNA and 293Fectin was used at a ratio of 1:1.5 (w:v). DNA to culture ratio was 1 mg/L. The cell culture supernatants were harvested 3-4 days post transfection, centrifuged and sterile filtered prior to purification.

Tagged ECD Protein Purification

Recombinant Fc-tagged cKIT extracellular domain proteins (e.g., human cKIT ECD-Fc, human cKIT (ECD subdomains 1-3, 4-5)-Fc, cyno cKIT-mFc, rat cKIT-mFc, mouse cKIT-mFc) were purified from the cell culture supernatant. The clarified supernatant was passed over a Protein A Sepharose® column which had been equilibrated with PBS. After washing to baseline, the bound material was eluted with Pierce Immunopure® low pH Elution Buffer, or 100 mM glycine (pH 2.7) and immediately neutralized with ⅛ the elution volume of 1 M Tris pH 9.0. The pooled protein was concentrated if necessary using Amicon® Ultra 15 mL centrifugal concentrators with 10 kD or 30 kD nominal molecular weight cut-offs. The pools were then purified by SEC using a Superdex® 200 26/60 column to remove aggregates. The purified protein was then characterized by SDS-PAGE and SEC-MALLS (Multi-angle laser light scattering). Concentration was determined by absorbance at 280 nm, using the theoretical absorption coefficients calculated from the sequence by Vector NTI.

Example 3: Binding of cKIT Fabs to cKIT ECD Subdomains

To help define the binding sites of the cKIT Abs, the human cKIT ECD was divided into subdomains 1-3 (ligand binding domain) and subdomains 4-5 (dimerization domain). To determine which subdomains were bound, a sandwich ELISA assay was employed. 1 µg/ml of ECD diluted in 1×Phosphate buffered saline corresponding to cKIT subdomains 1-3, subdomains 4-5 or full-length cKIT ECD were coated on 96 well Immulon® 4-HBX plates (Thermo Scientific Cat #3855, Rockford, Ill.) and incubated overnight at 4° C. Plates were washed three times with wash buffer (1×Phosphate buffered saline (PBS) with 0.01% Tween-20 (Bio-Rad 101-0781)). Plates were blocked with 280 µl/well 3% Bovine Serum Albumin diluted in 1×PBS for 2 hrs at room temperature. Plates were washed three times with wash buffer. Antibodies were prepared at 2 µg/ml in wash buffer with 5-fold dilutions for 8 points and added to ELISA plates at 100 µl/well in triplicate. Plates were incubated on an orbital shaker shaking at 200 rpm for 1 hr at room temperature. Assay plates were washed three times with wash buffer. Secondary antibody F(ab')$_2$ Fragment Goat anti-human IgG (H+L) (Jackson Immunoresearch Cat #109-036-088, West Grove, Pa.) was prepared 1:10,000 in wash buffer and added to ELISA plates at 100 µl/well. Plates were incubated with secondary antibody for 1 hr at room temperature shaking at 200 rpm on an orbital shaker. Assay plates were washed three times with wash buffer. To develop the ELISA signal, 100 µl/well of Sure Blue® TMB substrate (KPL Cat #52-00-03, Gaithersburg, Md.) was added to plates and allowed to incubate for 10 mins at room temperature. To stop the reaction 50 µl of 1N Hydrochloric Acid was added to each well. Absorbance was measured at 450 nm using a Molecular Devices SpectraMax® M5 plate reader. To determine the binding response of each antibody the optical density measurements were averaged, standard deviation values generated and graphed using Excel. The binding characteristics of individual anti-cKIT antibody to cKIT can be found in Table 5.

Example 4: Affinity Measurements of cKIT Antibodies

Affinity of the antibodies to cKIT species orthologues and also to human cKIT was determined using SPR technology using a Biacore® 2000 instrument (GE Healthcare, Pittsburgh, Pa.) and with CM5 sensor chips.

Briefly, HBS-P (0.01 M HEPES, pH 7.4, 0.15 M NaCl, 0.005% Surfactant P20) supplemented with 2% Odyssey® blocking buffer (Li-Cor Biosciences, Lincoln, Nebr.) was used as the running buffer for all the experiments. The immobilization level and analyte interactions were measured by response unit (RU). Pilot experiments were performed to test and confirm the feasibility of the immobilization of the anti-human Fc antibody (Catalog number BR100839, GE Healthcare, Pittsburgh, Pa.) and the capture of the test antibodies.

For kinetic measurements, the experiments were performed in which the antibodies were captured to the sensor chip surface via the immobilized anti-human Fc antibody and the ability of the cKIT proteins to bind in free solution was determined. Briefly, g/ml of anti-human Fc antibody at pH 5 was immobilized on a CM5 sensor chip through amine coupling at flow rate of 5 µl/min on both flow cells to reach 10,500 RUs. 0.1-1 µg/ml of test antibodies were then injected at 10 µl/min for 1 minute. Captured levels of the antibodies were generally kept below 200 RUs. Subsequently, 3.125-50 nM of cKIT receptor extracellular domains (ECD) were diluted in a 2-fold series and injected at a flow rate of 40 µl/min for 3 min over both reference and test flow cells. A table of tested ECDs is listed below (Table 5). Dissociation of ECD binding was followed for 10 min. After each injection cycle, the chip surface was regenerated with 3 M MgCl$_2$ at 10 µl/min for 30 seconds. All experiments were performed at 25° C. and the response data were globally fitted with a simple 1:1 interaction model (using Scrubber 2 @ software version 2.0b (BioLogic Software) to obtain estimates of on rate ($k_a$), off-rate ($k_d$) and affinity ($K_D$). Table 6 lists the domain binding and affinity of selected anti-cKIT antibodies.

TABLE 5 cKIT ECD isotype and source

| ECD Isotype | Tag | Source |
|---|---|---|
| Human | C-terminal 6× His (SEQ ID NO: 162) | Novartis construct |
| Cyno | C-terminal 6× His (SEQ ID NO: 162) | Novartis construct |
| Mouse | C-terminal 6× His (SEQ ID NO: 162) | Sino Biological Inc (Catalog number: 50530-M08H) |
| Rat | C-terminal mFc | Novartis construct |

TABLE 6

Antibody affinity and cross reactivity

| Ab | cKIT domain binding | KD (pM) to human cKIT ECD in SET | KD (pM) to cyno cKIT ECD in SET | Reactivity to mouse cKIT | Reactivity to rat cKIT |
|---|---|---|---|---|---|
| Anti-cKIT Ab1 | D1-3 | 94 | 170 | Not reactive | Not reactive |
| Anti-cKIT Ab2 | D1-3 | 7 | 10 | Not reactive | Not reactive |
| Anti-cKIT Ab3 | D1-3 | 160 | 52 | Not reactive | Not reactive |
| Anti-cKIT Ab4 | D4-5 | 2400 | 140 | Yes | Yes |
| Anti-cKIT Ab5 | D1-3 | 110 | 180 | Yes | Yes |

Example 5 In Vitro Human and Mouse HSC Cell Killing Assays by cKIT ADCs

In Vitro HSC Viability Assays

Human mobilized peripheral blood hematopoietic stem cells (HSCs) were obtained from HemaCare (catalog number M001F-GCSF-3). Each vial of ~1 million cells was thawed and diluted into 10 ml of 1×HBSS and centrifuged for 7 minutes at 1200 rpm. The cell pellet was resuspended in 18 ml of growth medium containing three growth factors (StemSpan SFEM (StemCell Technologies, catalog number 09650) with 50 ng/ml each of TPO (R&D Systems, catalog number 288-TP) Flt3 ligand (Life Technologies, catalog number PHC9413), and IL-6 (Life Technologies, catalog number PHC0063), supplemented with amino acids (Gibco, catalog number 10378-016)).

Bone marrow cells from C57BL/6J mice were harvested from the femurs and tibiae, resuspended in IMDM (HyClone, catalog number SH30228.01) and pooled. Cells were centrifuged for 10 minutes at 300 g. The cell pellet was resuspended in AutoMACS buffer (1×PBS+0.5% BSA+2 mM EDTA) at a concentration of 100 million cells in 40 µl. The lineage antibody cocktail (Miltenyi, catalog number 130-090-858) was added at a concentration of 10 µl per 100 million cells. Cells were incubated for 10 minutes in the cold room before addition of 30 µl of AutoMACS buffer and 20 µl of biotinylated magnetic beads per 100 million cells. This new suspension was incubated in the cold room for 15 minutes. Cells were centrifuged for 10 minutes at 300 g. The pellet was resuspended in 2 ml of AutoMACS buffer and passed through a cell strainer. Cells were selected on the AutoMACS using the "deplete" protocol. The negative fraction from the sort was centrifuged for 10 minutes at 300 g and resuspended in 1 ml of HBSS. The resuspended cells were stained with anti-CD45-PerCP-Cy5.5 (Becton Dickinson, catalog number 550994), anti-CD48-FITC (eBioscience, catalog number 11-0481-82), anti-CD150-PE (BioLegend, catalog number 115904), and anti-Sca-1 (Becton Dickinson, catalog number 560653). Cells were incubated at room temperature for 30 minutes, centrifuged for 5 minutes at 300 g, and resuspended in 700 µl of FACS buffer for sorting. Sca-1+ cells were positively sorted on a FACS Aria. After sort, cells were placed into growth media containing three growth factors (StemSpan SFEM with 50 ng/ml TPO (R&D Systems, catalog number 288-TP), Flt3 ligand (Life Technologies, catalog number PHC9413), and IL-6 (Life Technologies, catalog number PHC0063) supplemented with amino acids (Gibco, catalog number 10378-016)).

Test agents were diluted in duplicate into a 384-well black assay plate at a final volume of 5 µl, starting at 10 µg/ml and with 1:3 serial dilutions. Cells from above were added to each well at a final volume of 45 µl. Cells were incubated at 37° C. and 5% oxygen for 7 days. At the end of culture, cells were harvested for staining by centrifuging the assay plate for 4 minutes at 1200 rpm. Supernatants were then aspirated and the cells were washed and transferred to a different 384-well plate (Greiner Bio-One TC-treated, black clear flat, catalog number 781092).

For human cell assays, each well was stained with anti-CD34-PerCP (Becton Dickinson, catalog number 340666) and anti-CD90-APC (Becton Dickinson, catalog number 559869), washed, and resuspended in FACS buffer to a final volume of 50 µl. For mouse cell assays, each well was stained with anti-CD45-PerCP-Cy5.5 (Becton Dickinson, catalog number 550994), anti-CD48-FITC (eBioscience, catalog number 11-0481-82), anti-CD150-PE (BioLegend, catalog number 115904), anti-cKIT-APC (Becton Dickinson, catalog number 553356), and anti-Sca-1 (Becton Dickinson, catalog number 560653), washed, and resuspended in FACS buffer to a final volume of 50 µl. Cells were then analyzed on a Becton Dickinson Fortessa flow cytometer and quantified for analysis.

Figure 2:
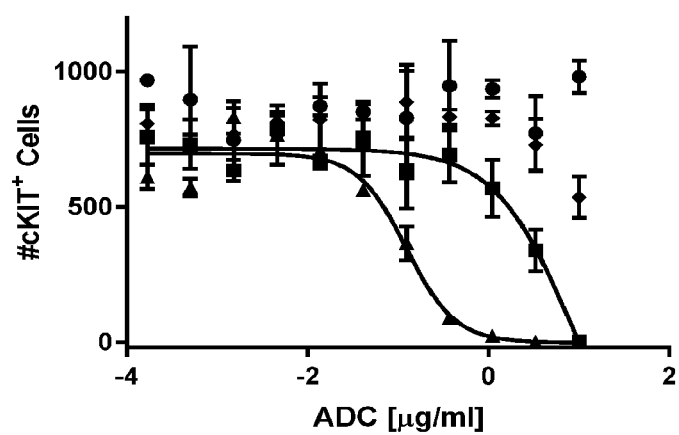
FIG. 2 is a line graph showing both J4 (squares) and J5 (triangles) anti-cKIT conjugates killed mouse long term HSCs (cKIT$^+$ cells). J5 (triangles) was more potent than J4 (squares) in this mouse HSC killing assay. A control ADC, J6 (diamonds) did not kill mouse HSCs as compared to PBS control (circles).
Figure 9A:
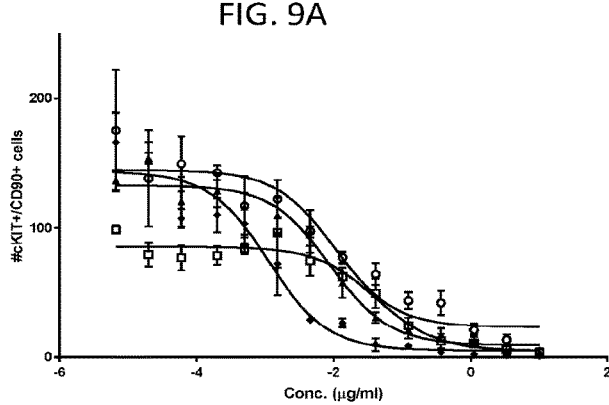
FIGS. 9A-9C represent in vitro killing assay results using human cells. Mobilized peripheral blood HSCs were cultured with growth factors and the stated test agent for 7 days and viability was measured by flow cytometry and cell count. Anti-cKit Fab' DAR4 test agents were prepared with different Fabs: anti-cKIT Fab'1 (FIG. 9A), Fab'2 (FIG. 9B), or Fab'3 (FIG. 9C). Payloads tested were C1 (open square), mc-MMAF (open circle), C5 (diamond) or C2 (triangle). Data represent mean with standard deviation and 3-parameter response curve fits for triplicates measured in the same experiment.
Figure 9B:
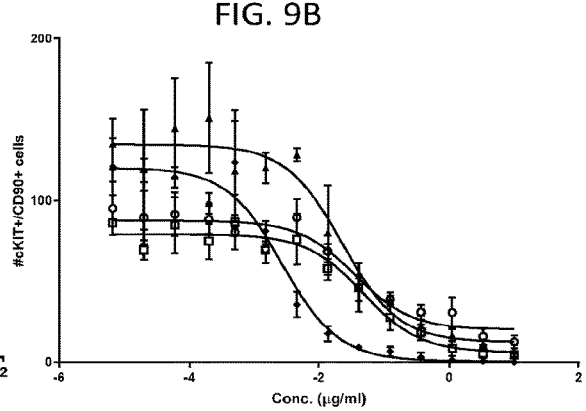
Figure 9C:
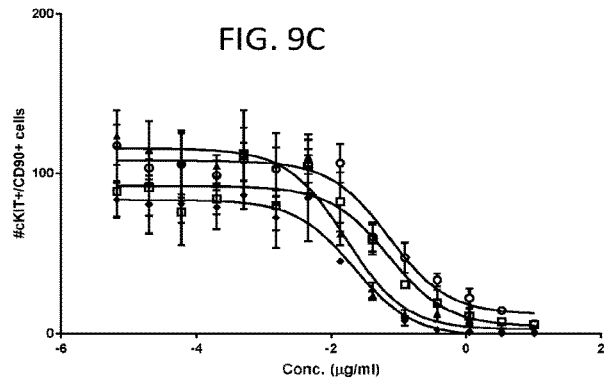
Figure 10A:
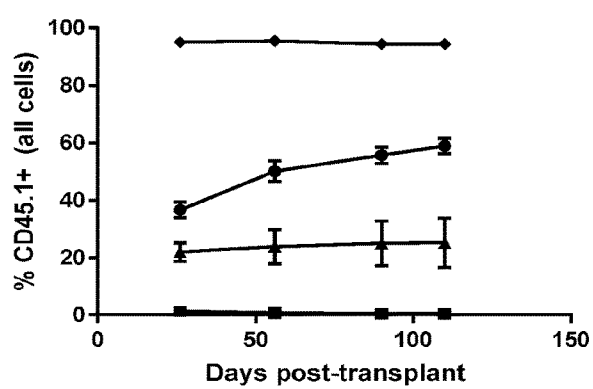
FIGS. 10A-10D are line graphs showing timecourse of establishment of donor cell chimerism in blood samples taken from transplanted mice. C57BL/6J mice (n=5 for anti-cKit-treated group or n=2 for PBS-treated group) were dosed with 10 mg/kg anti-cKit-Fab'5-DAR4-C1 (triangles), 20 mg/kg anti-cKit-Fab'5-DAR4-C1 (circles), or PBS (squares) infused over seven days and then transplanted two days later with CD45.1+ donor cells. Two control animals were irradiated with 1100 RADS (diamonds) one day prior to transplant. The line graphs show the percent donor cells (CD45.1+) measured in the population of all cells (FIG. 10A), myeloid cells (FIG. 10B), B-cells (FIG. 10C) or T-cells (FIG. 10D) by FACS analysis of blood samples taken at each timepoint. Data represent mean with standard error.
Figure 10B:
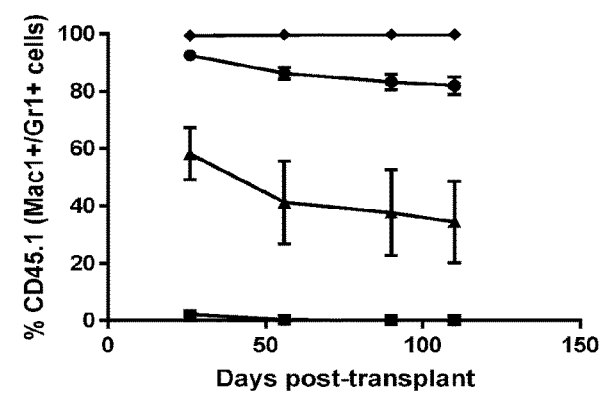
Figure 10C:
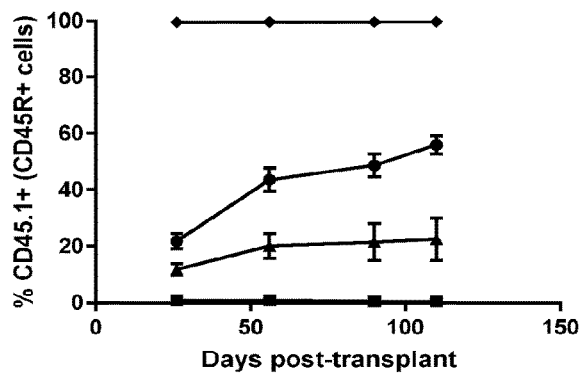
Figure 10D:
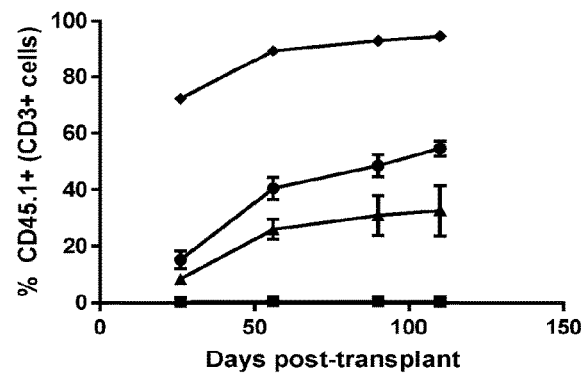

Toxin conjugates of antibodies and antibody fragments recognizing cKIT killed HSCs as determined in this assay. Quantitation of cells by FACS showed fewer viable cells in wells treated with anti-cKIT-toxin conjugates than in control wells treated with PBS or with isotype control toxin conjugates of antibody or antibody fragment. Data are shown in FIG. 1, FIG. 2 and FIG. 9 and summarized in Table 7. The naming convention used herein is J #, correspond to the specific Conjugate No. described in Table 2.

TABLE 7

Cell viability after treatment of anti-cKIT Fab-toxin conjugates

| Conjugate tested | Cell population | EC50 (ng/ml) |
| --- | --- | --- |
| J3 | Human total nucleated cells | 45 |
|  | Human CD34+ cells | 8 |
|  | Human CD90+ cells | 12 |
| J2 | Human total nucleated cells | 58 |
|  | Human CD34+ cells | 11 |
|  | Human CD90+ cells | 16 |
| J1 | Human total nucleated cells | 48 |
|  | Human CD34+ cells | 11 |
|  | Human CD90+ cells | 13 |
| J4 | Mouse total nucleated cells | 3800 |
|  | Mouse CD45+ cells | 3800 |
|  | Mouse cKIT+ cells | 8 |
| J5 | Mouse total nucleated cells | 210 |
|  | Mouse CD45+ cells | 210 |
|  | Mouse cKIT+ cells | 120 |
| J14 | Human total nucleated cells | 7 |
|  | Human CD34+ cells | 10 |
|  | Human CD90+ cells | 11 |
| J15 | Human total nucleated cells | 6 |
|  | Human CD34+ cells | 5 |
|  | Human CD90+ cells | 1 |
| J16 | Human total nucleated cells | 6 |
|  | Human CD34+ cells | 7 |
|  | Human CD90+ cells | 9 |
| J17 | Human total nucleated cells | 12 |
|  | Human CD34+ cells | 16 |
|  | Human CD90+ cells | 37 |
| J18 | Human total nucleated cells | 15 |
|  | Human CD34+ cells | 11 |
|  | Human CD90+ cells | 3 |
| J19 | Human total nucleated cells | 14 |
|  | Human CD34+ cells | 16 |
|  | Human CD90+ cells | 23 |
| J20 | Human total nucleated cells | 20 |
|  | Human CD34+ cells | 25 |
|  | Human CD90+ cells | 72 |

TABLE 7-continued

Cell viability after treatment of anti-cKIT Fab-toxin conjugates

| Conjugate tested | Cell population | EC50 (ng/ml) |
| --- | --- | --- |
| J21 | Human total nucleated cells | 154 |
|  | Human CD34+ cells | 88 |
|  | Human CD90+ cells | 22 |
| J22 | Human total nucleated cells | 8 |
|  | Human CD34+ cells | 10 |
|  | Human CD90+ cells | 17 |

Example 6 In Vitro Assay of Human Mast Cell Degranulation

Mature mast cells were generated using CD34+ progenitors from mobilized peripheral blood. CD34+ cells were cultured in StemSpan SFEM (StemCell Technologies) supplemented with recombinant human stem cell factor (rhSCF, 50 ng/ml, Gibco), recombinant human interleukin 6 (rhIL-6, 50 ng/ml, Gibco), recombinant human IL-3 (30 ng/ml, Peprotech), GlutaMAX (2 nM, Gibco), penicillin (100 U/ml, Hyclone) and streptomycin (100 µg/ml, Hyclone). Recombinant hIl-3 was added only during the first week of the culture. After the third week, half of the medium was replaced weekly with fresh medium containing rhIL-6 (50 ng/ml) and rhSCF (50 ng/ml). Mature mast cell purity was evaluated by surface staining of high-affinity IgE receptor (FCεRI, eBioscience) and CD117 (BD). Cells were used between week 8 and 12 of the culture.

The derived mast cells were washed once to remove SCF, and the required amount of cells was incubated overnight in mast cell medium containing rhIL-6 (50 ng/ml) with or without rhSCF (50 ng/ml). As positive control for mast cell degranulation, a portion of the cells were sensitized with human myeloma IgE (100 ng/ml, EMD Millipore). The following day, anti-cKIT antibody or antibody fragments or toxin conjugates thereof, mouse monoclonal anti-human IgG1 (Fab specific, Sigma), goat anti-human IgE (Abcam) and compound 48/80 (Sigma) dilutions were prepared in HEPES degranulation buffer (10 mM HEPES, 137 mM NaCl, 2.7 mM KCl, 0.4 mM sodium phosphate dibasic, 5.6 mM glucose, pH adjusted at 7.4 and mixed with 1.8 mM calcium chloride and 1.3 mM magnesium sulfate) supplemented with 0.04% bovine serum albumin (BSA, Sigma). Test agents and anti-IgG1 were mixed together in a V-bottom 384-well assay plate while anti-IgE and compound 48/80 were tested alone. The assay plate was incubated 30 min at 37° C. During the incubation, cells were washed 3 times with HEPES degranulation buffer+0.04% BSA to remove medium and unbound IgE. Cells were resuspended in HEPES degranulation buffer+0.04% BSA and seeded at 3000 cells per well in the assay plate for a final reaction volume of 50 µl. Cells that were sensitized with IgE were used only with anti-IgE as a positive control for degranulation. The assay plate was incubated 30 min at 37° C. for degranulation to occur. During this incubation, ρ-nitro-N-acetyl-β-D-glucosamine (pNAG, Sigma) buffer was prepared by sonicating 3.5 mg/ml of pNAG in citrate buffer (40 mM citric acid, 20 mM sodium phosphate dibasic, pH 4.5). β-hexosaminidase release was measured by mixing 20 µl of cell supernatant with 40 µl of pNAG solution in a flat-bottom 384-well plate. This plate was incubated for 1.5 hour at 37° C., and the reaction was stopped by the addition of 40 µl of stop solution (400 mM glycine, pH 10.7). Absorbance was read using a plate reader at $\lambda=405$ nm with reference filter at $\lambda=620$ nm.

Full-length IgG controls used in the mast cell degranulation assays are described in Table 8.

TABLE 8

Full-length IgG controls used in the mast cell degranulation assays

| | Name | HC sequence | LC sequence |
|---|---|---|---|
| IgG control for J1 | Anti-cKIT Ab1 | SEQ ID NO: 12 | SEQ ID NO: 25 |
| IgG control for J2 | Anti-cKIT Ab2 | SEQ ID NO: 38 | SEQ ID NO: 49 |
| IgG control for J3 | Anti-cKIT Ab3 | SEQ ID NO: 56 | SEQ ID NO: 25 |
| IgG control for J4 | Anti-cKIT Ab4 | SEQ ID NO: 71 | SEQ ID NO: 84 |
| IgG control for J6 | Anti-Her2 | EVQLVESGGGLVQPGGSLRLSCAASGF NIKDTYIHWVRQAPGKGLEWVARIYPTN GYTRYADSVKGRFTISADTSKNTAYLQM NSLRAEDTAVYYCSRWGGDGFYAMDY WGQGTLVTVSSASTKGPSVFPLAPSSKS TSGGTAALGCLVKDYFPEPVTVSWNSG ALTSGVHTFPAVLQSSGLYSLSSVVTVP SSSLGTQTYICNVNHKPSNTKVDKKVEP KSCDKTHTCPPCPAPELLGGPSVFLFPP KPKDTLMISRTPEVTCVVVDVSHEDPEV KFNWYVDGVEVHNAKTKPREEQYNSTY RVVSVLTVLHQDWLNGKEYKCKVSNKA LPAPIEKTISKAKGQPREPQVYTLPPSRE EMTKNQVSLTCLVKGFYPSDIAVEWESN GQPENNYKTTPPVLDSDGSFFLYSKLTV DKSRWQQGNVFSCSVMHEALHNHYTQ KSLSLSPGK (SEQ ID NO: 150) | SEQ ID NO: 147 |

Figure 3A:
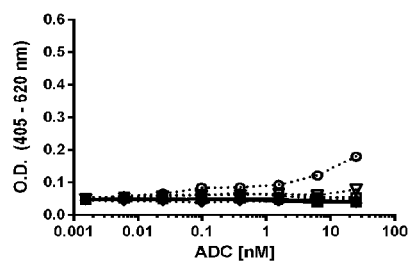
FIGS. 3A-3L are line graphs showing representative results of in vitro human mast cell degranulation assays, which used human peripheral blood HSC-derived mast cells and beta-hexosaminidase release as the readout (assessed by absorbance at 405 nm with baseline subtraction based on reference absorbance at 620 nm). Data shown here were collected in the absence of SCF.
Figure 3B:
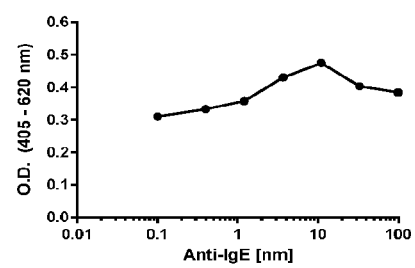
Figure 3C:
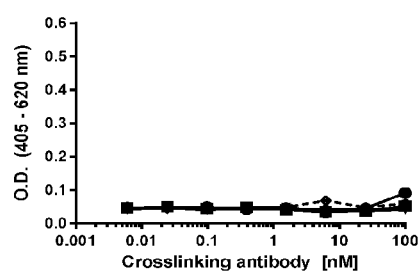
Figure 3D:
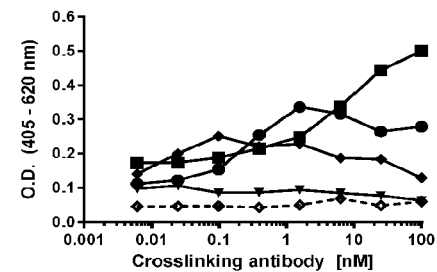
Figure 3E:
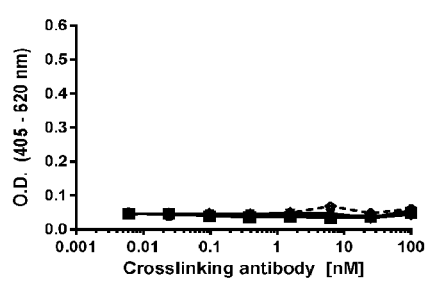
Figure 3F:
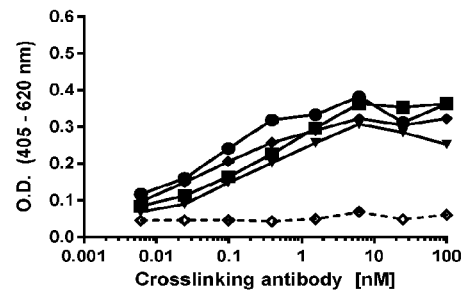
Figure 3G:
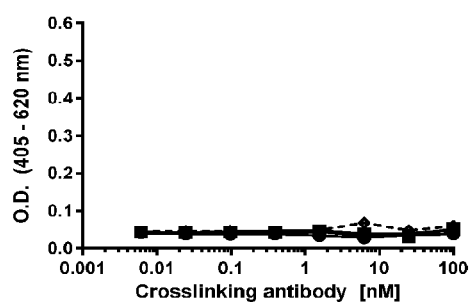
Figure 3H:
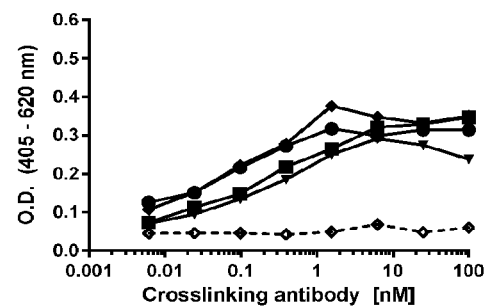
Figure 3I:
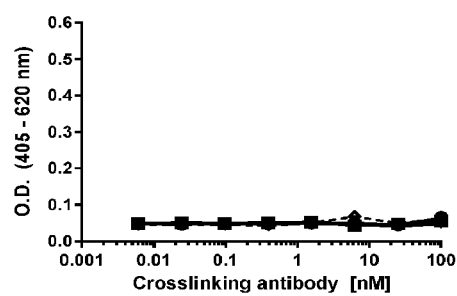
Figure 3J:
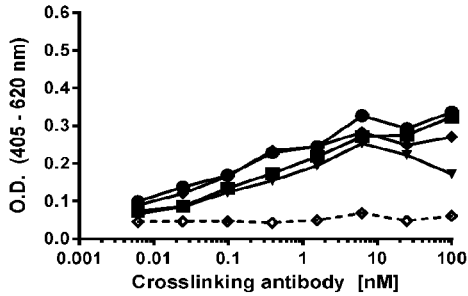
Figure 3K:
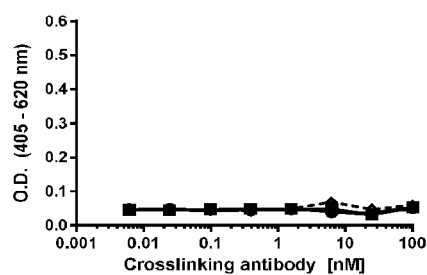
Figure 3L:
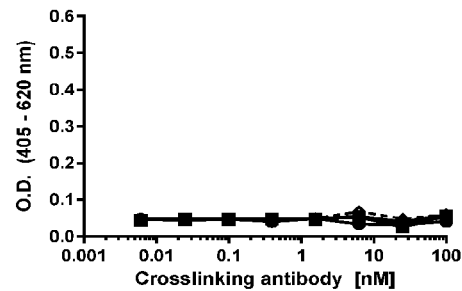

As shown in FIG. 3A, certain clones of the antagonist anti-cKIT antibody class are less likely to cause mast cell degranulation. It further suggests that the Fab or Fab' fragment is not able to cause mast cell degranulation. Upon crosslinking with a Fab-specific antibody (FIG. 3C-3J), the full length IgG but not the anti-cKIT Fab'-toxin DAR4 format shows increased degranulation. This suggests that the Fab' fragment does not cause mast cell degranulation even when bound and multimerized into larger complexes as could be observed if a patient developed or had pre-existing anti-drug antibodies recognizing Fab or Fab' fragments.

Example 7 In Vivo Ablation of Human HSCs from Mouse Host

To assess test agents for in vivo efficacy against human HSCs, mice that are severely immune deficient (NOD.Cg-Prkdc$^{scid}$ IL2rg$^{tm1Wjl}$/SzJ, Jackson Laboratory, stock number 005557, a.k.a. NSG) were transplanted with human HSCs after sublethal irradiation (250 RADS in a $^{137}$Cs gamma irradiator). CDs34+ hematopoietic stem cells (HSCs) were obtained from AllCells (catalog numberCB008F-S). Each vial of ~1 million cells was thawed, diluted into 10 ml 1×HBSS and centrifuged for 7 minutes at 1200 rpm. The cell pellet was resuspended in HBSS at 100,000 cells/ml. A total of 20,000 cells were transplanted per mouse via retro orbital injection 24 hours after irradiation. Human HSCs were allowed to engraft in the NSG mice for at least 4 weeks. Percent human chimerism was determined by flow cytometry of blood samples. For this, blood was stained with the following antibodies: anti-human CD45-e450 (eBioscience, catalog #48-0459-42), anti-mouse CD$_{45}$-APC (Becton Dickinson, catalog #559864anti-human CD33-Pe (Becton Dickinson, catalog #347787), anti-human CD19-FITC (Becton Dickinson, catalog #555422), and anti-human CD3-PeCy7 (Becton Dickinson, catalog #557851). Once human chimerism was confirmed, humanized NSG mice were dosed with a test agent intraperitoneally b.i.d. The degree of human chimerism was re-assessed after dosing. To assess presence or absence of human HSCs, mice were euthanized and bone marrow was isolated and stained with the following antibodies: anti-human CD45-e450 (eBioscience, catalog #48-0459-42), anti-mouse CD45-APC (Becton Dickinson, catalog #559864), anti-human CD34-PE (Becton Dickinson, catalog #348057), anti-human CD38-FITC (Becton Dickinson, catalog #340926), anti-human CD11b-PE (Becton Dickinson, catalog #555388), anti-human CD33-PeCy7 (Becton Dickinson, catalog #333946), anti-human CD19-FITC (Becton Dickinson, catalog #555412), and anti-human CD3-PeCy7 (Becton Dickinson, catalog #557851). Cell populations were assessed via flow cytometry and analyzed with FlowJo.

Figure 4:
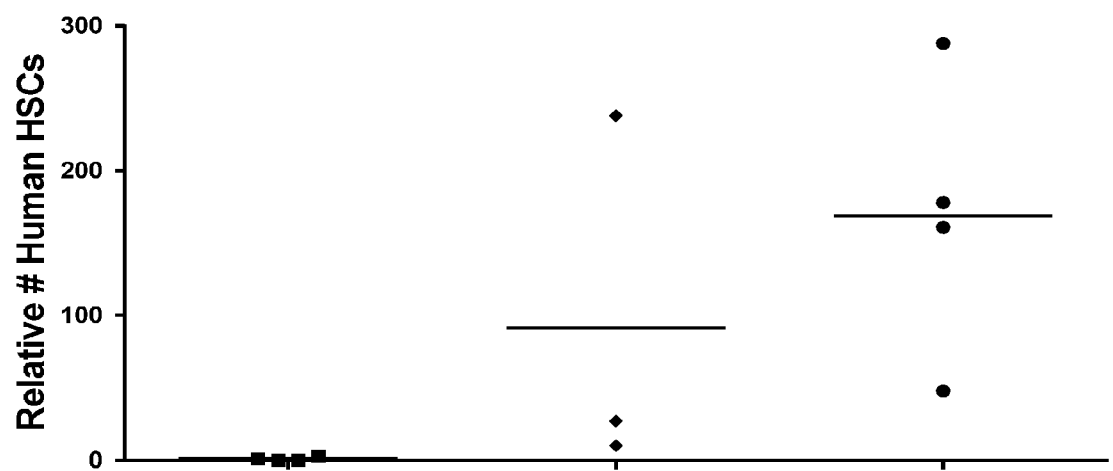
FIG. 4 is a dot plot showing relative numbers of human HSCs present in bone marrow of humanized NSG mice following treatment with various agents. J7 conjugate depleted human HSCs (squares) relative to PBS control (circles), whereas the control J8 conjugate (diamonds) did not deplete human HSCs in the bone marrow.

In one particular experiment, mice were dosed with 10 mg/kg of conjugate J7 (described in Table 2) twice a day for 1 2, or 4 days or isotype control conjugate J8 twice a day for 4 days. Mice were euthanized on day 21 and their bone marrow was analyzed. As shown in FIG. 4, mice treated with conjugate J7 for even 1 day showed depletion of human HSCs (human CD45+, human CD34+, human CD38−), while mice treated with isotype control conjugate J8 showed variable chimerism likely due to variation of the humanization prior to treatment, based on comparison to the vehicle (PBS) treated group.

Figure 5:
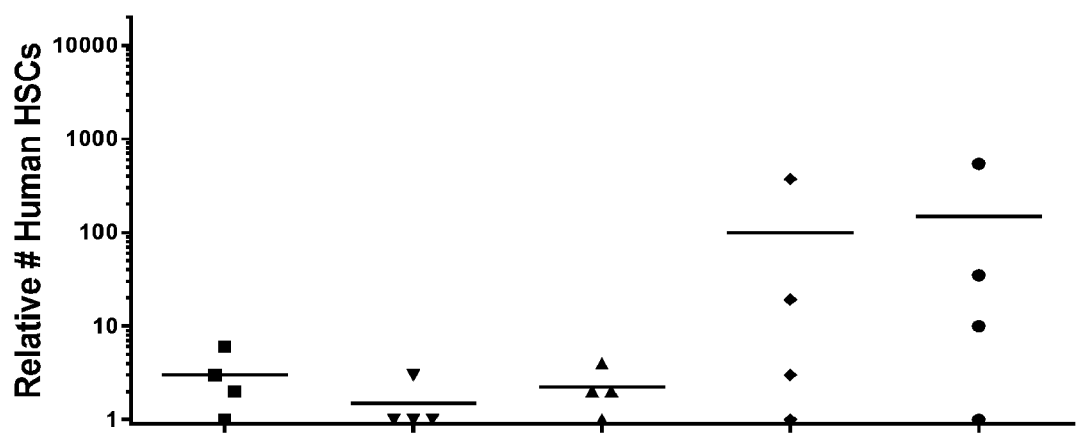
FIG. 5 is a dot plot showing relative numbers of human HSCs present in bone marrow of humanized NSG mice following treatment with various agents. Anti-cKIT Fab'-(1) DAR4 conjugates depleted human HSCs relative to PBS control (circles). The tested anti-cKIT conjugates (described in Table 2) were: J3 (squares); J2 (up triangles); J1 (down triangles). The control mice treated with J6 (diamonds) were not depleted of human HSCs in the bone marrow.

In one particular experiment, mice were dosed with 10 mg/kg of anti-cKIT conjugate J1, J2, or J3, or isotype control conjugate J6 for 2 days. Mice were euthanized on day 21 and their bone marrow was analyzed. As shown in FIG. 5, mice treated with an anti-cKIT conjugate J1, J2, or J3 showed reduced human HSCs (human CD45+, human CD34+, human CD38−), while mice treated with isotype control conjugate J6 showed variable chimerism.

Figure 13:
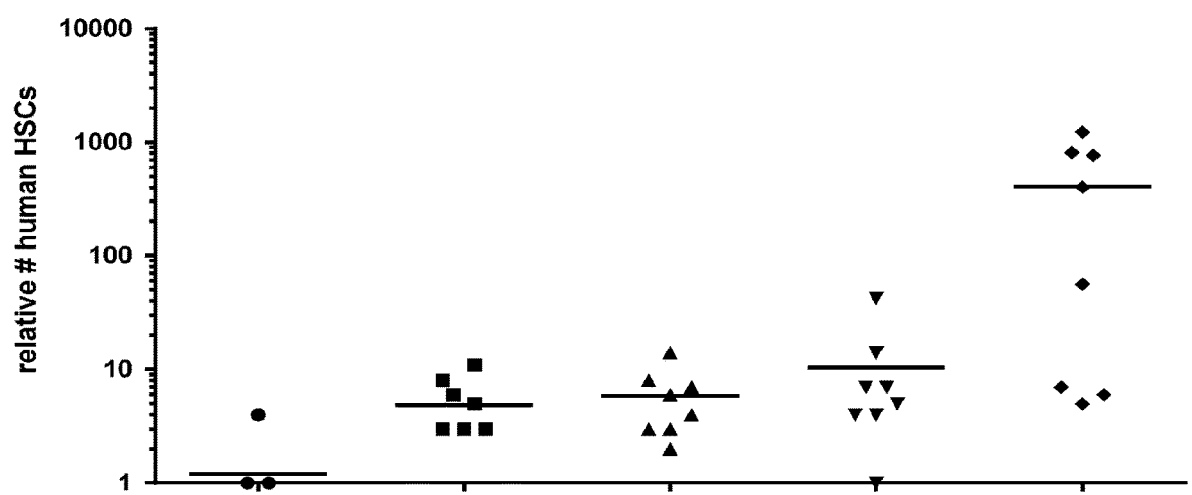
FIG. 13 is a dot plot showing relative numbers of human HSCs present in bone marrow of humanized NSG mice following treatment with various agents. Anti-cKIT Fab'-DAR4 conjugates depleted human HSCs relative to PBS control (diamonds). The tested anti-cKIT conjugates (described in Table 2) were: JW (circles); JX (squares); JY (up triangles); JZ (down triangles).

In one particular experiment, mice were dosed with 10 mg/kg of anti-cKIT conjugate JW, JX, JY, or JZ for 2 days. Mice were euthanized on day 21 and their bone marrow was analyzed. As shown in FIG. 13, mice treated with an anti-cKIT conjugate JW, JX, JY, or JZ showed reduced human HSCs (human CD45+, human CD34+, human CD38−).

These three experiments together show that anti-cKIT Fab-toxin or anti-cKit Fab'-toxin conjugates were able to deplete HSCs from bone marrow. Both the anti-cKIT Fab-amanitin conjugates (e.g., J7) and the anti-cKIT Fab'-auristatin conjugates (e.g., J1, J2, J3, JW, JX, JY) were able to ablate human HSCs in vivo.

Example 8 In Vivo Ablation of Mouse HSCs in Immune-Competent Mice

To assess test agents for in vivo efficacy against mouse HSCs, C57BL/6J mice (males, 10 weeks of age, Jackson Laboratory, stock #000664) were dosed with a test agent intraperitoneally b.i.d. Hematology profile was assessed as early as one day after last dose or up to 21 days after last dose by standard methods. To assess presence or absence of mouse HSCs, mice were euthanized and bone marrow was isolated and stained with the following antibodies: anti-mouse CD45-PerCP-Cy5.5 (Becton Dickinson, catalog #550994), anti-mouse cKIT-APC (Becton Dickinson, catalog #553356), anti-mouse CD48-FITC (eBioscience, catalog #11-0481-82), anti-mouse CD150-PE (BioLegend, catalog #115904), anti-mouse Sca-V450 (Becton Dickinson, catalog #560653), anti-mouse Lin-biotin (Miltenyi, catalog #120-001-547), and Pe-Cy7-streptavidin (Becton Dickinson, catalog #557598). Cell populations were assessed via flow cytometry and analyzed with FlowJo.

Figure 6:
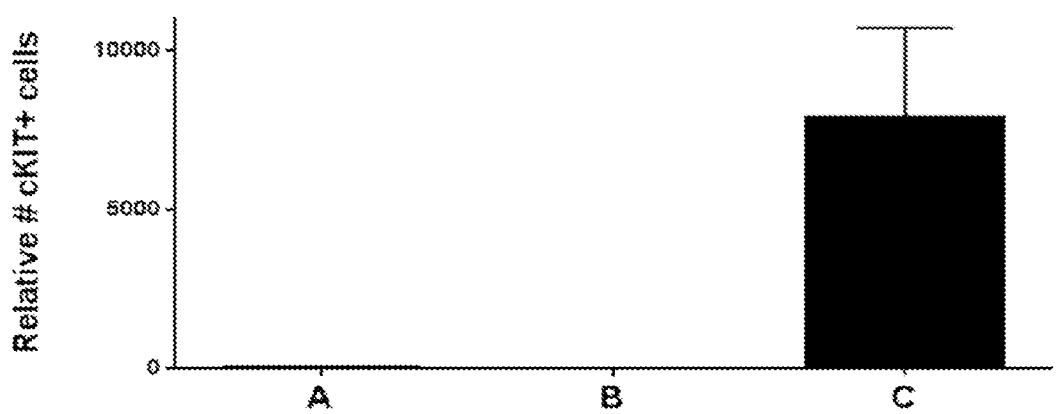
FIG. 6 is a bar graph showing relative numbers of HSCs present in bone marrow of C57Bl/6 mice following treatment with various agents. Bar A=J4 conjugate treated mice, Bar B=J5 conjugate treated mice, Bar C=PBS treated mice.

In one particular experiment, mice were dosed twice daily with 10 mg/kg of anti-cKIT conjugate J4 or J5 (described in Table 2), or PBS for 4 days. Mice were euthanized on day 13 for bone marrow analysis. Groups treated with anti-cKIT conjugate J4 or J5 showed significantly reduced levels of stem and progenitor (cKIT+) cells in bone marrow compared to PBS treated control group (FIG. 6), demonstrating that treatment with anti-cKIT Fab'-auristatin conjugates such as J4 or J5 were able to ablate HSCs in vivo in normal mice.

In order to determine if ablation by anti-cKIT antibody or antibody fragment conjugates of the invention is sufficient to enable transplant, mice treated as above can be subsequently given HSC transplant. For example, CD45.2 mice treated with anti-cKIT Fab'-toxin conjugate can be transplanted with donor HSCs that are from CD45.1 mice approximately one week after dosing. In another example, mice treated with anti-cKIT Fab'-toxin conjugate can be treated with an immune-suppressing agent, such as an agent causing T-cell depletion approximately one week after dosing and approximately 1-2 days prior to being transplanted with donor HSCs that are from CD45.1 mice. One method for T-cell depletion is to dose mice with 0.5 mg per mouse of anti-mouse TCR β chain antibody (clone H57-597; Biolegend) q.i.d. for two days. T-cell depletion can be confirmed by taking a blood sample for hematology profiling following dosing. In such examples, the progress of the transplant would be monitored by looking for CD45.1 chimerism in blood samples. In such examples, the success of transplant can be determined by euthanizing the mice approximately 3-4 months or 5-6 months after transplant for bone marrow analysis looking for populations of CD45.1 and CD45.2 HSCs. Alternatively, successful transplant can be determined by euthanizing the mice at least 4 or 6 months after primary transplant and performing secondary transplant into a fully irradiated host mice and looking for CD45.1 chimerism in blood samples following the secondary transplant.

Figure 7A:
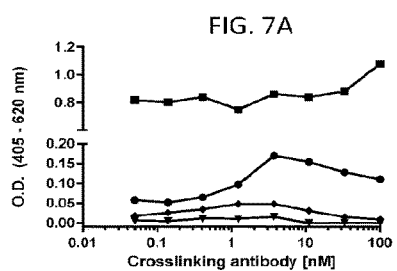
FIGS. 7A-7I are line graphs showing representative results of in vitro human mast cell degranulation assays, which used human peripheral blood HSC-derived mast cells and beta-hexosaminidase release as the readout (assessed by absorbance at 405 nm with baseline subtraction based on reference absorbance at 620 nm). Data shown here were collected in the absence of SCF. The line graphs show mast cell degranulation level triggered by antibodies or antibody fragments at various concentrations: 0.006 nM (triangles); 0.098 nM (diamonds); 1.6 nM (circles); and 25 nM (squares), when the test agents were cross-linked using an antibody specific for the Fab portion on the antibody test agents (titrated on x-axis).
Figure 7B:
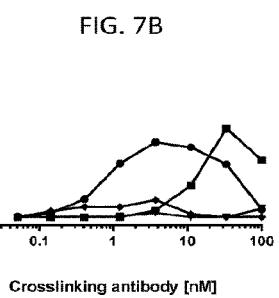
Figure 7C:
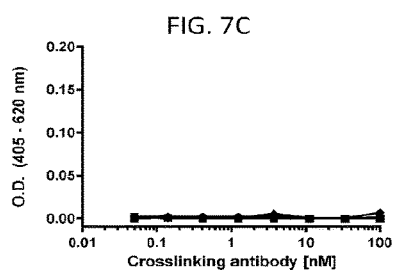
Figure 7D:
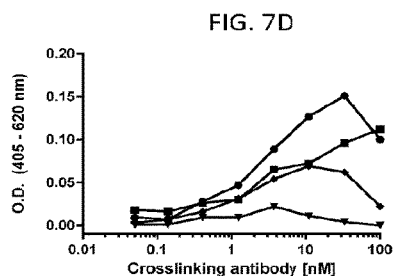
Figure 7E:
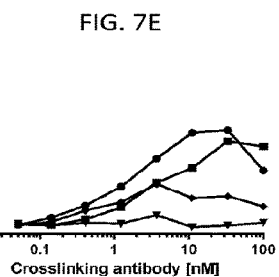
Figure 7F:
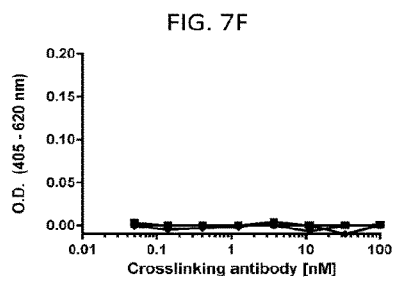
Figure 7G:
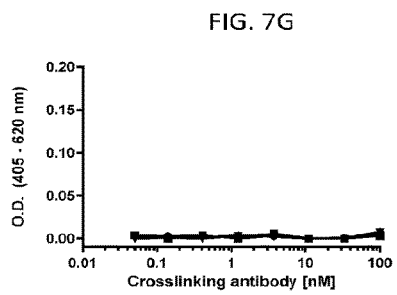
Figure 7H:
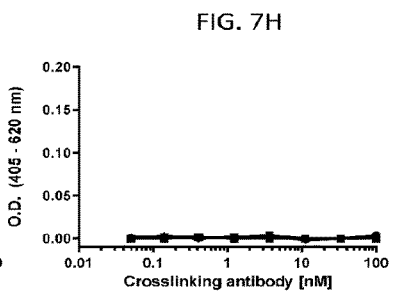
Figure 7I:
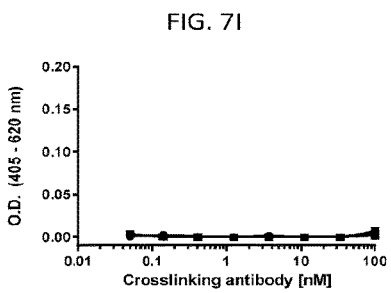

Example 9 In Vitro Assay of Human Mast Cell Degranulation by Full-Length Anti-cKIT Antibody, F(Ab') and Fab Fragments Thereof, and Conjugates Thereof Mature mast cells were generated and tested with anti-cKIT antibody and F(ab')$_2$ and Fab fragments or toxin conjugates thereof as described in Example 6. As shown in FIGS. 7A-7C, full length anti-cKIT Ab4 (HC-E152C-S375C) and F(ab'4)$_2$ (HC-E152C) fragment conjugated with compound (4) caused mast cell degranulation when cross-linked, while no mast cell degranulation was triggered by Fab4 (HC-E152C) fragment at all tested concentrations. FIGS. 7D-7F show that full length anti-cKIT Ab3 (HC-E152C-S375C) and F(ab'3)$_2$ (HC-E152C) fragment conjugated with compound (3) caused mast cell degranulation when cross-linked, while no mast cell degranulation was triggered by Fab3 (E152C) fragment conjugated with compound (4) at all tested concentrations. This suggests that the Fab fragment or conjugates thereof do not cause mast cell degranulation even when bound and multimerized into larger complexes as could be observed if a patient developed or had pre-existing anti-drug antibodies recognizing Fab fragments. On the other hand, F(ab')$_2$ fragments and conjugates do cause mast cell degranulation at a level similar to the full-length anti-cKIT antibody when bound and multimerized into larger complexes.

Example 10 In Vitro Assay of Human Mast Cell Degranulation by Full-Length Anti-cKIT Antibody and F(Ab') and Fab Fragments Thereof Mature mast cells were generated and tested with anti-cKIT antibody and F(ab')$_2$ and Fab fragments as described in Example 6.

As shown in FIGS. 8A-8C, full length anti-cKIT Ab4 and F(ab'4)$_2$ fragment caused mast cell degranulation when cross-linked, while no mast cell degranulation was triggered by Fab4 (HC-E152C) fragment at all tested concentrations. FIGS. 8D-8F show that full length anti-cKIT Ab1 and F(ab'1)$_2$ fragment caused mast cell degranulation when cross-linked, while no mast cell degranulation was triggered by Fab1 (HC-E152C) fragment at all tested concentrations. FIGS. 8G-8I show that full length anti-cKIT Ab2 and F(ab'2)$_2$ fragment caused mast cell degranulation when cross-linked, while no mast cell degranulation was triggered by Fab2 (HC-E152C) fragment at all tested concentrations. FIGS. 8J-8L show that full length anti-cKIT Ab3 and F(ab'3)$_2$ fragment caused mast cell degranulation when cross-linked, while no mast cell degranulation was triggered by Fab3 (HC-E152C) fragment at all tested concentrations. This suggests that the Fab fragments do not cause mast cell degranulation even when bound and multimerized into larger complexes as could be observed if a patient developed or had pre-existing anti-drug antibodies recognizing Fab fragments. On the other hand, F(ab')$_2$ fragments do cause mast cell degranulation at a level similar to the full-length anti-cKIT antibody when bound and multimerized into larger complexes.

Example 11 Syngeneic Bone Marrow Transplant in Immune-Competent Mice

In a particular experiment, C57BL/6J (CD45.2, males, 10 weeks of age, Jackson Laboratory, stock #000664) mice were dosed with 2.5, 5, or 10 mg/ml anti-c-KIT Fab'5-(1) (Fab'-DAR4) in a mini-pump (Alzet, catalog #2001) placed subcutaneously in the back. The mini-pump held a volume of 200 µl and infused at a constant rate of 1 µl/hour, over the course of 7 days. Seven days after the mini-pump was implanted, it was then removed to halt any further administration of drug. Forty-eight hours after mini-pump removal, the mice were transplanted with bone marrow from donor mice which were congenically marked at CD45 (CD45.1, B6.SJL-Ptprc$^a$ Pepc$^b$/BoyJ, males, 10 weeks of age, Jackson Laboratory, stock #002014). The progress of the transplant was monitored in the peripheral blood by looking for CD45.1 chimerism at one month intervals. In this experiment, the blood chimerism has been monitored for 4 months as shown in FIG. 10. Chimerism in peripheral blood was assessed by flow cytometry. Blood samples were stained with anti-mCD45.1-PerCP-Cy5.5 (1:100, BD #560580), anti-mCD45.2-BUV395 (1:100, BD #564616), anti-Mac-PE (1:500, BD #553331), anti-GR1-FITC (1:100, BD #553127), anti-B220-APC (1:400, BD #553092), and anti-CD3-V450 (1:100, BD #560801) acquired on a Fortessa flow cytometer (Becton Dickinson), and analyzed with FlowJo software (TreeStar). The level of chimerism was determined by comparing populations that were positive for either CD45.2 (host) or CD45.1 (donor). Total donor chimerism represented the overall white blood cell population. In addition, subpopulations of T cells, B cells, and myeloid cells were further assessed for donor chimerism. T cell donor chimerism was based on looking at CD45.2 (host) vs. CD45.1 (donor) in CD3+ cells. B cell donor chimerism was based on looking at CD45.2 (host) vs. CD45.1 (donor) in CD45R+ cells. Myeloid chimerism was based on looking at CD45.2 (host) vs. CD45.2 (donor) in Mac-1+/Gr-1+ cells. This experiment shows that mice conditioned with an anti-cKit-Fab' conjugate can be engrafted with donor cells that reconstitute the myeloid, B-cell, and T-cell lineages which is indicative of successful HSC engraftment.

Figure 11A:
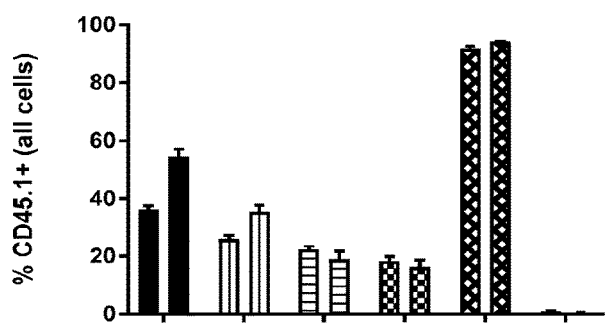
FIGS. 11A-11B are bar graphs showing donor cell chimerism in blood samples taken from transplanted mice. C57BL/6J mice (n=5 for anti-cKit-treated group or n=2 for PBS-treated group) were dosed with 10 mg/kg anti-cKit-Fab'5-DAR4-C1 (horizontal stripes), 20 mg/kg anti-cKit Fab'5-DAR4-C1 (vertical stripes), 40 mg/kg anti-cKit-Fab'5-DAR4-C1 (solid), 40 mg/kg anti-cKit-Fab'5'-DAR4-mc-MMAF (checkered), or PBS (open, black border) infused over five days and then transplanted one day later with CD45.1+ donor cells. Two control animals were irradiated with 1100 RADS (hatched) one day prior to transplant. The graphs show the percent donor cells (CD45.1+) measured in the population of all cells (FIG. 11A) or myeloid cells (FIG. 11B) by FACS analysis of blood samples taken at day 28 (left bar for each group) or day 56 (right bar for each group) post-transplant. Data represent mean with standard error.
Figure 11B:
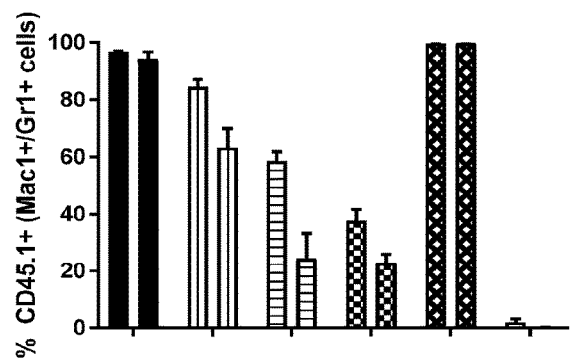

In another experiment, C57BL/6J (CD45.2, males, 10 weeks of age, Jackson Laboratory, stock #000664) mice were dosed with 2.5, 5, or 10 mg/ml anti-c-KIT Fab'5-(1) (Fab'-DAR4) or 10 mg/ml anti-c-KIT Fab'5-mc-MMAF (Fab'-DAR4) in a mini-pump (Alzet, catalog #2001) placed subcutaneously in the back. The mini-pump held a volume of 200 µl and infused at a constant rate of 1 µl/hour, over the course of 7 days. Five days after the mini-pump was implanted, it was then removed to halt any further administration of drug. Within 24 hours after mini-pump removal, the mice were then transplanted with bone marrow from donor mice which were congenically marked at CD45 (CD45.1, B6.SJL-Ptprc$^a$ Pepc$^b$/BoyJ, males 10 weeks of age, Jackson Laboratory, stock #002014). The progress of the transplant was monitored in the peripheral blood by looking for CD45.1 chimerism at one month intervals. In this experiment, the blood chimerism has been monitored for 2 months as shown in FIG. 11. Chimerism in peripheral blood was assessed by flow cytometry. Blood samples were stained with (anti-mCD45.1-PerCP-Cy5.5 (1:100, BD #560580), anti-mCD45.2-BUV395 (1:100, BD #564616), anti-Mac-PE (1:500, BD #553331), anti-GR1-FITC (1:100, BD #553127), anti-B220-APC (1:400, BD #553092), and anti-CD3-V450 (1:100, BD #560801)), acquired on a Fortessa flow cytometer (Becton Dickinson), and analyzed with FlowJo software (TreeStar). The level of chimerism was determined by comparing populations that were positive for either CD45.2 (host) or CD45.1 (donor). Total donor chimerism represented the overall white blood cell population. In addition, myeloid cells in the peripheral blood were further assessed for donor chimerism. Myeloid chimerism was based on looking at CD45.2 (host) vs. CD45.2 (donor) in Mac-1+/Gr-1+ cells. This experiment shows that mice conditioned with an anti-cKit-Fab' conjugate can be successfully engrafted with donor cells that reconstitute the myeloid compartment to an extent similar to mice conditioned with lethal irradiation (FIG. 11B). Lower levels of total donor chimerism in anti-cKit conditioned mice relative to irradiated mice (FIG. 11A) are likely due to the more targeted nature of the anti-cKit conditioning agent that does not remove long-lived CD45.2+ B-cells and T-cells from circulation.

Figure 12A:
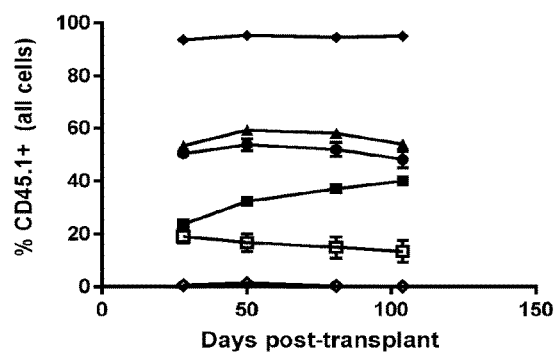
FIGS. 12A-12B are line graphs showing timecourse of establishment of donor cell chimerism in blood samples taken from transplanted mice. C57BL/6J mice (n=5 for anti-cKit-treated group or n=2 for PBS-treated group) were irradiated with 300 RADS and three days later were either not dosed (squares) or were dosed with 10 mg/kg anti-cKit-Fab'5-DAR4-C1 (triangles) or 20 mg/kg anti-cKit-Fab'5-DAR4-C1 (circles) infused over three days and then transplanted two days later with CD45.1+ donor cells. An additional group of 5 animals were only dosed with 10 mg/kg anti-cKit-Fab'5-DAR4-C1 (open squares) infused over three days and then transplanted two days later. Two control animals were irradiated with 1100 RADS (diamonds) one day prior to transplant and two control animals were untreated (open diamonds) prior to transplant. The line graphs show the percent donor cells (CD45.1+) measured in the population of all cells (FIG. 12A) or myeloid cells (FIG. 12B) by FACS analysis of blood samples taken at each timepoint. Data represent mean with standard error.
Figure 12B:
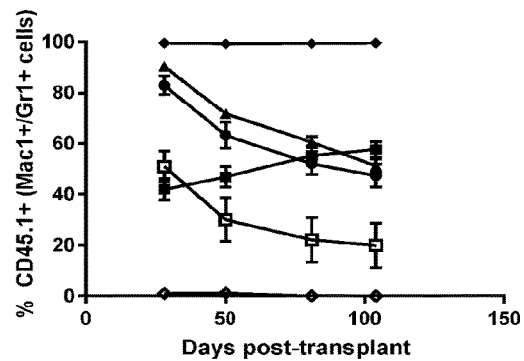

In another experiment, C57BL/6J (CD45.2, males, 10 weeks of age, Jackson Laboratory, stock #000664) mice were irradiated with 300 RADS. After three days they were dosed with 2.5 or 5 mg/ml anti-c-KIT Fab'5-(1) (Fab'-DAR4) in a mini-pump (Alzet, catalog #2001) placed subcutaneously in the back. One group was treated only with irradiation and one group was treated only with 2.5 mg/ml anti-c-KIT Fab'5-(1) (Fab'-DAR4). The mini-pump held a volume of 200 µl and infused at a constant rate of 1 µl/hour, over the course of 7 days. Three days after the mini-pump was implanted, it was then removed to halt any further administration of drug. Within 48 hours after mini-pump removal, the mice were then transplanted with bone marrow from donor mice which were congenically marked at CD45 (CD45.1, B6.SJL-Ptprc$^a$ Pepc$^b$/BoyJ, males 10 weeks of age, Jackson Laboratory, stock #002014). The progress of the transplant was monitored in the peripheral blood by looking for CD45.1 chimerism at one month intervals. In this experiment, the blood chimerism has been monitored for 4 months as shown in FIG. 12. Chimerism in peripheral blood was assessed by flow cytometry. Blood samples were stained with (anti-mCD45.1-PerCP-Cy5.5 (1:100, BD #560580), anti-mCD45.2-BUV395 (1:100, BD #564616), anti-Mac-PE (1:500, BD #553331), anti-GR1-FITC (1:100, BD #553127), anti-B220-APC (1:400, BD #553092), and anti-CD3-V450 (1:100, BD #560801)), acquired on a Fortessa flow cytometer (Becton Dickinson), and analyzed with FlowJo software (TreeStar). The level of chimerism was determined by comparing populations that were positive for either CD45.2 (host) or CD45.1 (donor). Total donor chimerism represented the overall white blood cell population. In addition, myeloid cells in the peripheral blood were further assessed for donor chimerism. Myeloid chimerism was based on looking at CD45.2 (host) vs. CD45.2 (donor) in Mac-1+/Gr-1+ cells. This experiment shows that the anti-cKit-Fab' conjugate can be used as a conditioning agent in combination with other agents such as low dose irradiation and that mice conditioned in this way can be successfully engrafted with donor cells.

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims to the invention are non-limiting and are provided below.

Although particular aspects and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the aspects described herein. Other aspects, advantages, and modifications considered to be within the scope of the following claims. Those skilled in the art will recognize or be able to ascertain, using no more than routine experimentation, many equivalents of the specific aspects of the invention described herein. Such equivalents are intended to be encompassed by the following claims. Redrafting of claim scope in later filed corresponding applications may be due to limitations by the patent laws of various countries and should not be interpreted as giving up subject matter of the claims.

What is claimed is:

1. A conjugate having the structure of Formula (C):

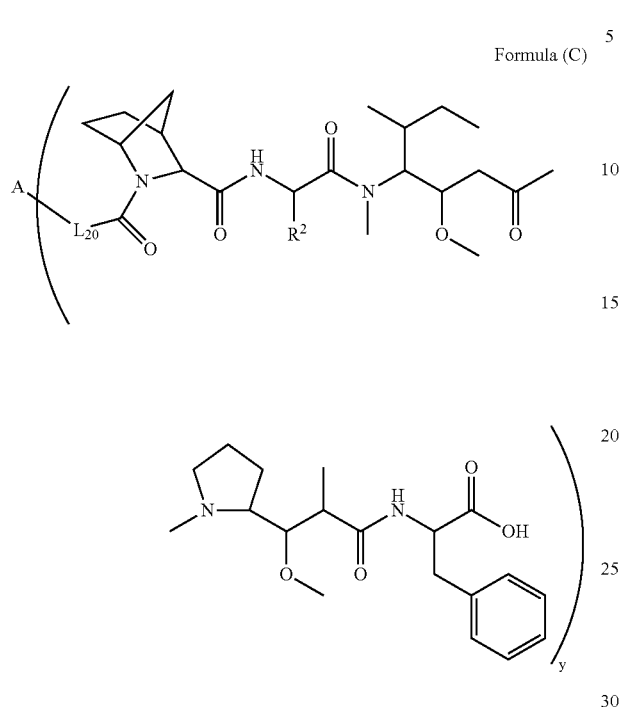

Formula (C)

wherein:

A is an antibody fragment that specifically binds to human cKIT;

y is an integer from 1 to 10;

$R^2$ is $C_1$-$C_6$alkyl;

$L_{20}$ is -$L_1R^{40}$;

Li is -$((CH_2)_mO)_p(CH_2)_mX_1L_4$-, —$((CH_2)_mO)_p(CH_2)_mX_2L_4$-, —$((CH_2)_mO)_p(CH_2)_m$—, —$(CH_2)_m$—, —$(CH_2)_mX_1(CH_2)_m$—, —$(CH_2)_mNHC(=O)(CH_2)_m$—, —$(CH_2)_mNHC(=O)(CH_2)_mC(=O)NH(CH_2)_m$—, —$((CH_2)_mO)_p(CH_2)_mNHC(=O)(CH_2)_m$, —$((CH_2)_mO)_pCH_2)_mC(=O)NH(CH_2)_m$—, $X_3X_4C(=O)((CH_2)_mO)_p(CH_2)_m$—, —$X_3X_4C(=O)(CH_2)_m$—, —$X_3C(=O)(CH_2)_mNHC(=O)(CH_2)_m$, —$X_3C(=O)(CH_2)_mNHC(=O)((CH_2)_mO)_p(CH_2)_m$—, —$(CH_2)_mC(R_7)_2$—, —$(CH_2)_mC(R_7)_2SS(CH_2)_mNHC(=O)(CH_2)_m$ or —$(CH_2)_mX_3C(=O)(CH_2)_mNHC(=O)((CH_2)_mO)_p(CH_2)_m$—;

$L_4$ is —$((CH_2)_m$;

$X_1$ is

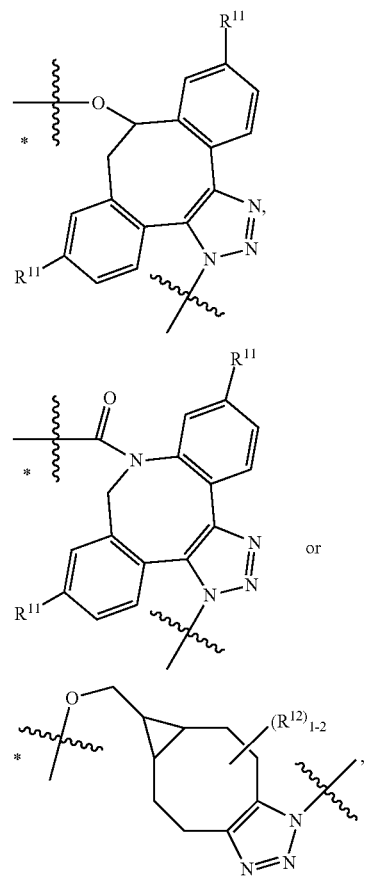

where the * indicates attachment point to $L_4$;

$X_2$ is

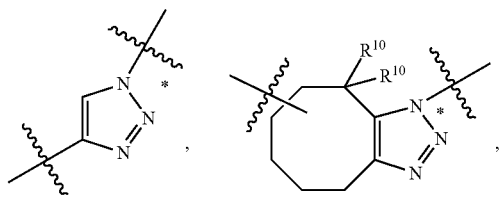

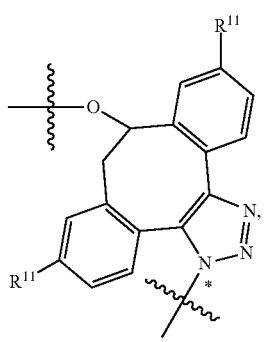

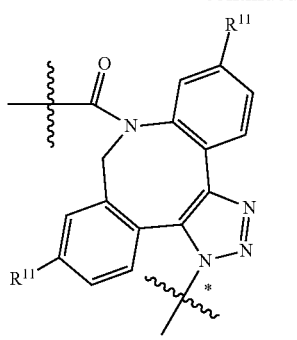
or
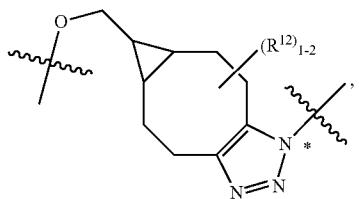
where the * indicates attachment point to $L_4$;
$X_3$ is
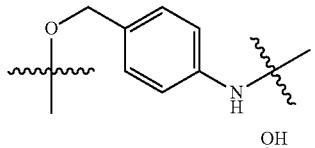
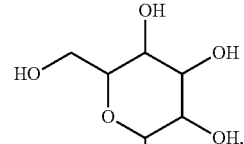
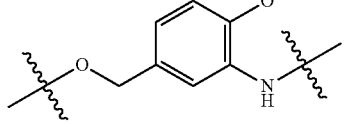
or
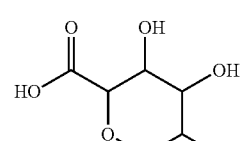
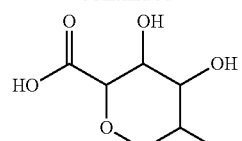
$X_4$ is
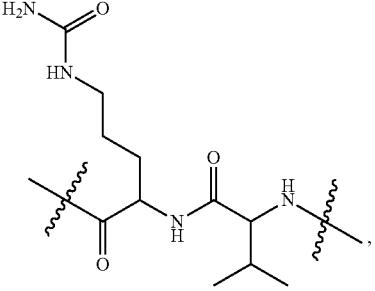
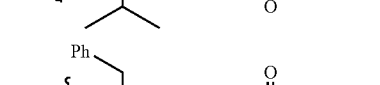
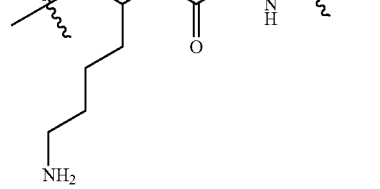

445
-continued
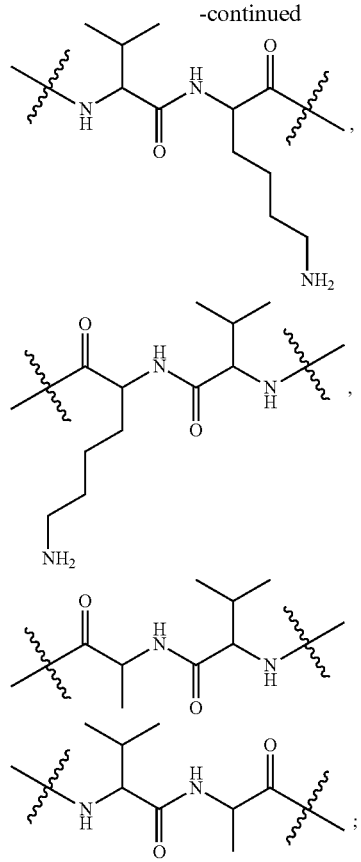
R⁴⁰ is
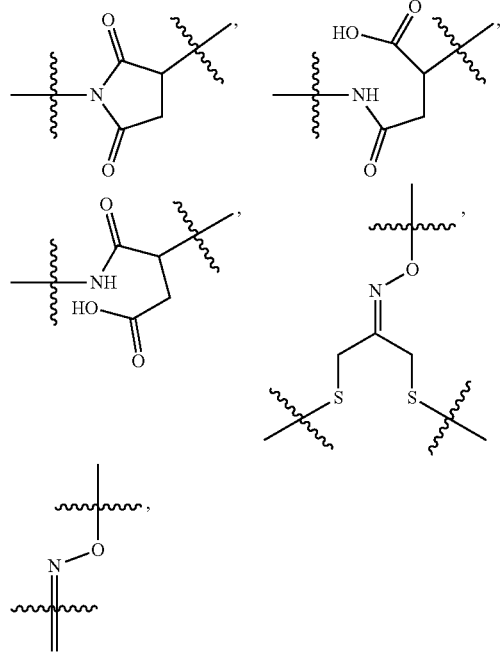
—NR⁷C(=O)CH₂—, —NHC(=O)CH₂—,
—S(=O)₂CH₂CH₂—, —(CH₂)₂S(=O)₂CH₂CH₂—,
—NR⁷S(=O)₂CH₂CH₂, —NR⁷C(=O)CH₂CH₂—,
446
—NH—, —C(=O)—, —NHC(=O)—,
—CH₂NHCH₂CH₂—, —NHCH₂CH₂—, —S—,
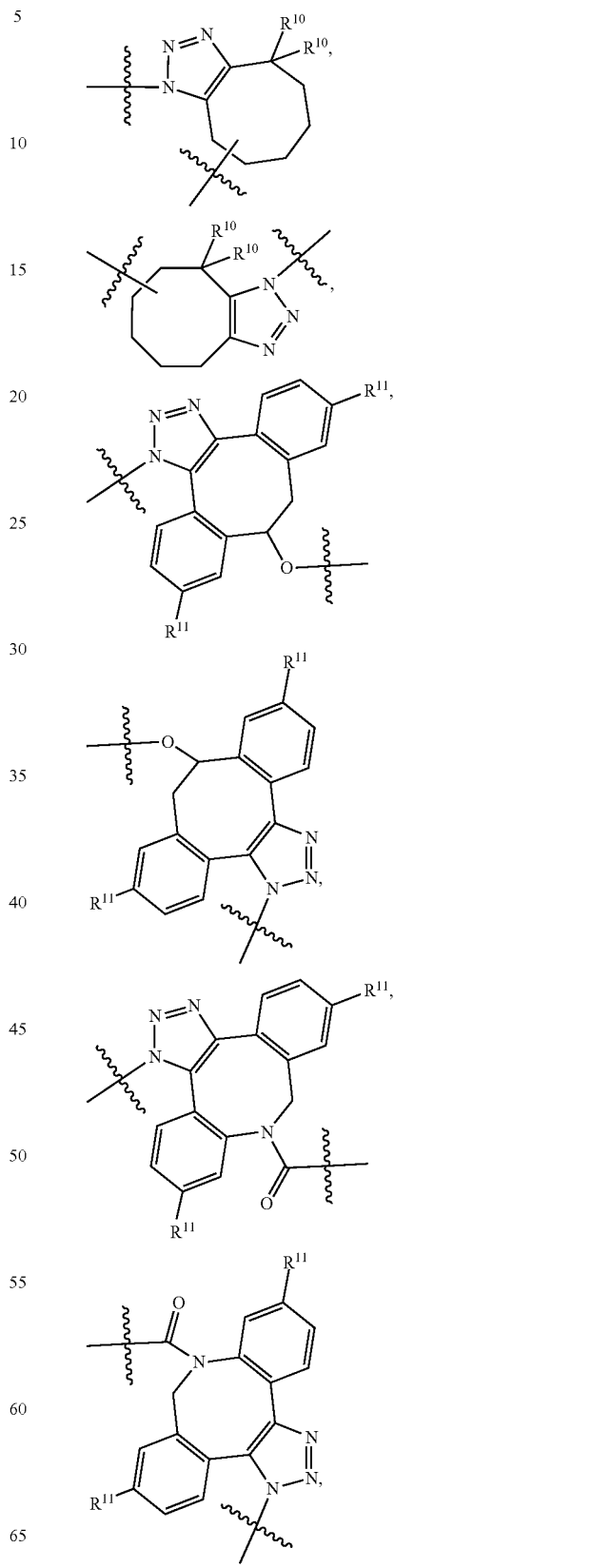

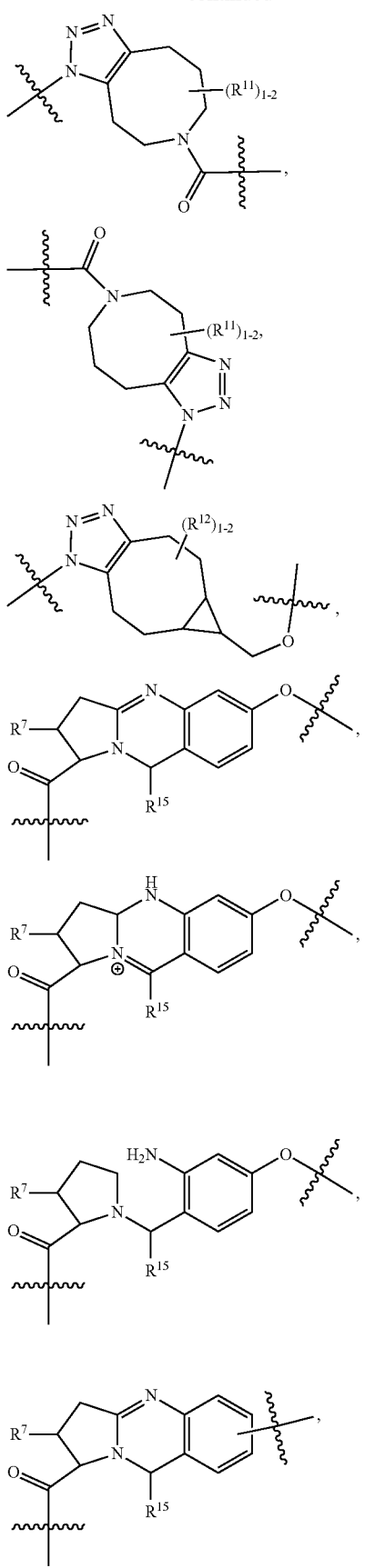
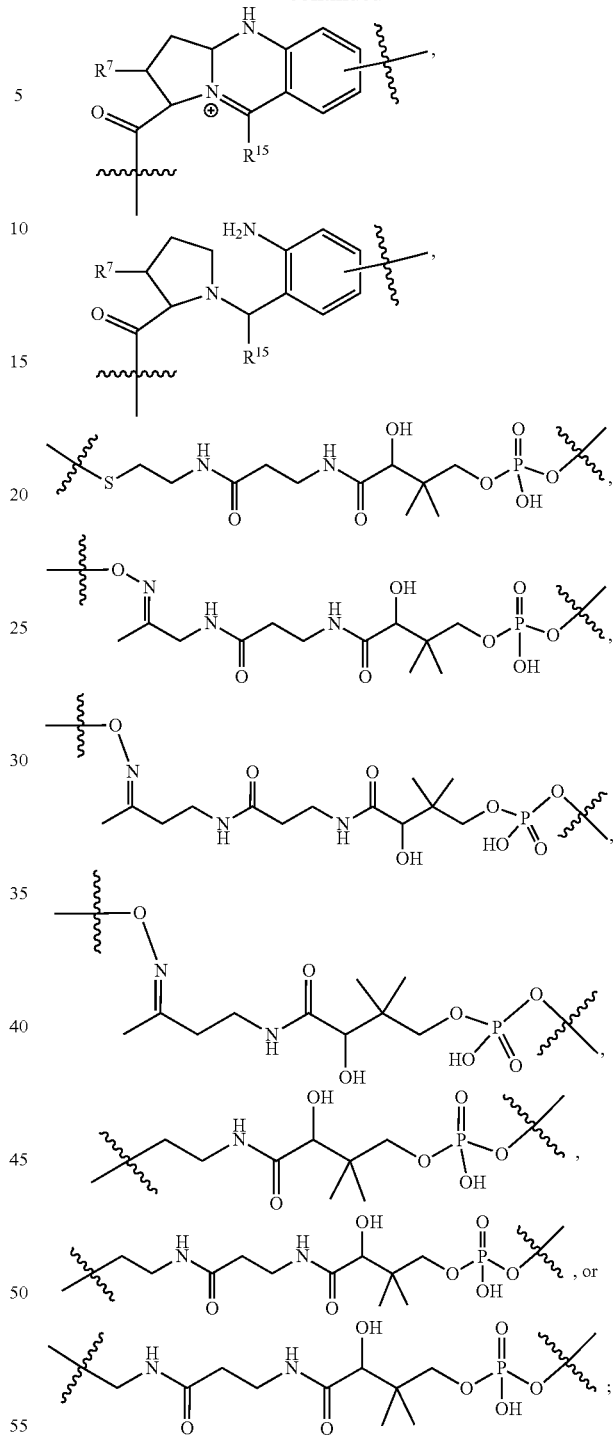
each R⁷ is independently selected from H and $C_1$-$C_6$alkyl;
each R¹⁰ is independently selected from H, $C_1$-$C_6$alkyl, F, Cl, and —OH;
each R¹¹ is independently selected from H, $C_1$-$C_6$alkyl, F, Cl, —NH₂, —OCH₃, —OCH₂CH₃, —N(CH₃)₂, —CN, —NO₂ and —OH;
each R¹² is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH;

each $R^{15}$ is independently selected from H, —CH$_3$ and phenyl;

each m is independently selected from 1, 2, 3, 4, 5, 6, 7, 8, 9 and 10; and each p is independently selected from 1, 2, 3, 4, 5, 6, 7, 8, 9, 10, 11, 12, 13 and 14; and wherein the antibody fragment that specifically binds to human cKIT is selected from any of the following:

(1) a Fab or Fab' comprising (i) a heavy chain variable region that comprises (a) a HCDR1 (Heavy Chain Complementarity Determining Region 1) comprising the amino acid sequence of SEQ ID NO: 1, (b) a HCDR2 (Heavy Chain Complementarity Determining Region 2) comprising the amino acid sequence of SEQ ID NO: 2, and (c) a HCDR3 (Heavy Chain Complementarity Determining Region 3) comprising the amino acid sequence of SEQ ID NO: 3; and (ii) a light chain variable region that comprises: (d) a LCDR1 (Light Chain Complementarity Determining Region 1) comprising the amino acid sequence of SEQ ID NO: 16, (e) a LCDR2 (Light Chain Complementarity Determining Region 2) comprising the amino acid sequence of SEQ ID NO: 17, and (f) a LCDR3 (Light Chain Complementarity Determining Region 3) comprising the amino acid sequence of SEQ ID NO: 18;

(2) a Fab or Fab' comprising (i) a heavy chain variable region that comprises (a) a HCDR1 comprising the amino acid sequence of SEQ ID NO: 4, (b) a HCDR2 comprising the amino acid sequence of SEQ ID NO: 5, and (c) a HCDR3 comprising the amino acid sequence of SEQ ID NO: 3; and (ii) a light chain variable region that comprises: (d) a LCDR1 comprising the amino acid sequence of SEQ ID NO: 19, (e) a LCDR2 comprising the amino acid sequence of SEQ ID NO: 20, and (f) a LCDR3 comprising the amino acid sequence of SEQ ID NO: 21;

(3) a Fab or Fab' comprising (i) a heavy chain variable region that comprises (a) a HCDR1 comprising the amino acid sequence of SEQ ID NO: 6, (b) a HCDR2 comprising the amino acid sequence of SEQ ID NO: 2, and (c) a HCDR3 comprising the amino acid sequence of SEQ ID NO: 3; and (ii) a light chain variable region that comprises: (d) a LCDR1 comprising the amino acid sequence of SEQ ID NO: 16, (e) a LCDR2 comprising the amino acid sequence of SEQ ID NO: 17, and (f) a LCDR3 comprising the amino acid sequence of SEQ ID NO: 18;

(4) a Fab or Fab' comprising (i) a heavy chain variable region that comprises (a) a HCDR1 comprising the amino acid sequence of SEQ ID NO: 7, (b) a HCDR2 comprising the amino acid sequence of SEQ ID NO: 8, and (c) a HCDR3 comprising the amino acid sequence of SEQ ID NO: 9; and (ii) a light chain variable region that comprises: (d) a LCDR1 comprising the amino acid sequence of SEQ ID NO: 22, (e) a LCDR2 comprising the amino acid sequence of SEQ ID NO: 20, and (f) a LCDR3 comprising the amino acid sequence of SEQ ID NO: 18;

(5) a Fab or Fab' comprising (i) a heavy chain variable region that comprises (a) a HCDR1 comprising the amino acid sequence of SEQ ID NO: 27, (b) a HCDR2 comprising the amino acid sequence of SEQ ID NO: 28, and (c) a HCDR3 comprising the amino acid sequence of SEQ ID NO: 29; and (ii) a light chain variable region that comprises: (d) a LCDR1 comprising the amino acid sequence of SEQ ID NO: 42, (e) a LCDR2 comprising the amino acid sequence of SEQ ID NO: 17, and (f) a LCDR3 comprising the amino acid sequence of SEQ ID NO: 43;

(6) a Fab or Fab' comprising (i) a heavy chain variable region that comprises (a) a HCDR1 comprising the amino acid sequence of SEQ ID NO: 30, (b) a HCDR2 comprising the amino acid sequence of SEQ ID NO: 31, and (c) a HCDR3 comprising the amino acid sequence of SEQ ID NO: 29; and (ii) a light chain variable region that comprises: (d) a LCDR1 comprising the amino acid sequence of SEQ ID NO: 44, (e) a LCDR2 comprising the amino acid sequence of SEQ ID NO: 20, and (f) a LCDR3 comprising the amino acid sequence of SEQ ID NO: 45;

(7) a Fab or Fab' comprising (i) a heavy chain variable region that comprises (a) a HCDR1 comprising the amino acid sequence of SEQ ID NO: 32, (b) a HCDR2 comprising the amino acid sequence of SEQ ID NO: 28, and (c) a HCDR3 comprising the amino acid sequence of SEQ ID NO: 29; and (ii) a light chain variable region that comprises: (d) a LCDR1 comprising the amino acid sequence of SEQ ID NO: 42, (e) a LCDR2 comprising the amino acid sequence of SEQ ID NO: 17, and (f) a LCDR3 comprising the amino acid sequence of SEQ ID NO: 43;

(8) a Fab or Fab' comprising (i) a heavy chain variable region that comprises (a) a HCDR1 comprising the amino acid sequence of SEQ ID NO: 33, (b) a HCDR2 comprising the amino acid sequence of SEQ ID NO: 34, and (c) a HCDR3 comprising the amino acid sequence of SEQ ID NO: 35; and (ii) a light chain variable region that comprises: (d) a LCDR1 comprising the amino acid sequence of SEQ ID NO: 46, (e) a LCDR2 comprising the amino acid sequence of SEQ ID NO: 20, and (f) a LCDR3 comprising the amino acid sequence of SEQ ID NO: 43;

(9) a Fab or Fab' comprising (i) a heavy chain variable region that comprises (a) a HCDR1 comprising the amino acid sequence of SEQ ID NO: 60, (b) a HCDR2 comprising the amino acid sequence of SEQ ID NO: 61, and (c) a HCDR3 comprising the amino acid sequence of SEQ ID NO: 62; and (ii) a light chain variable region that comprises: (d) a LCDR1 comprising the amino acid sequence of SEQ ID NO: 75, (e) a LCDR2 comprising the amino acid sequence of SEQ ID NO: 76, and (f) a LCDR3 comprising the amino acid sequence of SEQ ID NO: 77;

(10) a Fab or Fab' comprising (i) a heavy chain variable region that comprises (a) a HCDR1 comprising the amino acid sequence of SEQ ID NO: 63, (b) a HCDR2 comprising the amino acid sequence of SEQ ID NO: 64, and (c) a HCDR3 comprising the amino acid sequence of SEQ ID NO: 62; and (ii) a light chain variable region that comprises: (d) a LCDR1 comprising the amino acid sequence of SEQ ID NO: 78, (e) a LCDR2 comprising the amino acid sequence of SEQ ID NO: 79, and (f) a LCDR3 comprising the amino acid sequence of SEQ ID NO: 80;

(11) a Fab or Fab' comprising (i) a heavy chain variable region that comprises (a) a HCDR1 comprising the amino acid sequence of SEQ ID NO: 65, (b) a HCDR2 comprising the amino acid sequence of SEQ ID NO: 61, and (c) a HCDR3 comprising the amino acid sequence of SEQ ID NO: 62; and (ii) a light chain variable region that comprises: (d) a LCDR1 comprising the amino acid sequence of SEQ ID NO: 75, (e) a LCDR2 comprising the amino acid sequence of SEQ ID NO: 76, and (f) a LCDR3 comprising the amino acid sequence of SEQ ID NO: 77;

(12) a Fab or Fab' comprising (i) a heavy chain variable region that comprises (a) a HCDR1 comprising the amino acid sequence of SEQ ID NO: 66, (b) a HCDR2 comprising the amino acid sequence of SEQ ID NO: 67, and (c) a HCDR3 comprising the amino acid sequence of SEQ ID NO: 68; and (ii) a light chain variable region that comprises: (d) a LCDR1 comprising the amino acid sequence of SEQ ID NO: 81, (e) a LCDR2 comprising the amino acid sequence of SEQ ID NO: 79, and (f) a LCDR3 comprising the amino acid sequence of SEQ ID NO: 77;

(13) a Fab or Fab' comprising (i) a heavy chain variable region that comprises (a) a HCDR1 comprising the amino acid sequence of SEQ ID NO: 86, (b) a HCDR2 comprising the amino acid sequence of SEQ ID NO: 87, and (c) a HCDR3 comprising the amino acid sequence of SEQ ID NO: 88; and (ii) a light chain variable region that comprises: (d) a LCDR1 comprising the amino acid sequence of SEQ ID NO: 101, (e) a LCDR2 comprising the amino acid sequence of SEQ ID NO: 102, and (f) a LCDR3 comprising the amino acid sequence of SEQ ID NO: 103;

(14) a Fab or Fab' comprising (i) a heavy chain variable region that comprises (a) a HCDR1 comprising the amino acid sequence of SEQ ID NO: 89, (b) a HCDR2 comprising the amino acid sequence of SEQ ID NO: 90, and (c) a HCDR3 comprising the amino acid sequence of SEQ ID NO: 88; and (ii) a light chain variable region that comprises: (d) a LCDR1 comprising the amino acid sequence of SEQ ID NO: 104, (e) a LCDR2 comprising the amino acid sequence of SEQ ID NO: 105, and (f) a LCDR3 comprising the amino acid sequence of SEQ ID NO: 106;

(15) a Fab or Fab' comprising (i) a heavy chain variable region that comprises (a) a HCDR1 comprising the amino acid sequence of SEQ ID NO: 91, (b) a HCDR2 comprising the amino acid sequence of SEQ ID NO: 87, and (c) a HCDR3 comprising the amino acid sequence of SEQ ID NO: 88; and (ii) a light chain variable region that comprises: (d) a LCDR1 comprising the amino acid sequence of SEQ ID NO: 101, (e) a LCDR2 comprising the amino acid sequence of SEQ ID NO: 102, and (f) a LCDR3 comprising the amino acid sequence of SEQ ID NO: 103;

(16) a Fab or Fab' comprising (i) a heavy chain variable region that comprises (a) a HCDR1 comprising the amino acid sequence of SEQ ID NO: 92, (b) a HCDR2 comprising the amino acid sequence of SEQ ID NO: 93, and (c) a HCDR3 comprising the amino acid sequence of SEQ ID NO: 94; and (ii) a light chain variable region that comprises: (d) a LCDR1 comprising the amino acid sequence of SEQ ID NO: 107, (e) a LCDR2 comprising the amino acid sequence of SEQ ID NO: 105, and (f) a LCDR3 comprising the amino acid sequence of SEQ ID NO: 103;

(17) a Fab or Fab' comprising a heavy chain variable region (VH) that comprises SEQ ID NO: 10, and a light chain variable region (VL) that comprises SEQ ID NO: 23;

(18) a Fab or Fab' comprising a VH that comprises SEQ ID NO: 36, and a VL that comprises SEQ ID NO: 47;

(19) a Fab or Fab' comprising a VH that comprises SEQ ID NO: 69, and a VL that comprises SEQ ID NO: 82;

(20) a Fab or Fab' comprising a VH that comprises SEQ ID NO: 95, and a VL that comprises SEQ ID NO: 108;

(21) a Fab' comprising a heavy chain that comprises SEQ ID NO: 14, and a light chain that comprises SEQ ID NO: 25;

(22) a Fab' comprising a heavy chain that comprises SEQ ID NO: 40, and a light chain that comprises SEQ ID NO: 49;

(23) a Fab' comprising a heavy chain that comprises SEQ ID NO: 73, and a light chain that comprises SEQ ID NO: 84;

(24) a Fab' comprising a heavy chain that comprises SEQ ID NO: 99, and a light chain that comprises SEQ ID NO:110;

(25) a Fab comprising a heavy chain that comprises SEQ ID NO: 118, and a light chain that comprises SEQ ID NO: 122;

(26) a Fab comprising a heavy chain that comprises SEQ ID NO: 118, and a light chain that comprises SEQ ID NO: 123;

(27) a Fab comprising a heavy chain that comprises SEQ ID NO: 124, and a light chain that comprises SEQ ID NO: 128;

(28) a Fab comprising a heavy chain that comprises SEQ ID NO: 124, and a light chain that comprises SEQ ID NO: 129;

(29) a Fab comprising a heavy chain that comprises SEQ ID NO: 130, and a light chain that comprises SEQ ID NO: 134;

(30) a Fab comprising a heavy chain that comprises SEQ ID NO: 130, and a light chain that comprises SEQ ID NO: 135;

(31) a Fab comprising a heavy chain that comprises SEQ ID NO: 136, and a light chain that comprises SEQ ID NO: 140;

(32) a Fab comprising a heavy chain that comprises SEQ ID NO: 141, and a light chain that comprises SEQ ID NO: 145;

(33) a Fab comprising a heavy chain that comprises an amino acid sequence selected from SEQ ID NO: 119, 120 or 121, and a light chain comprising the amino acid sequence of SEQ ID NO: 25;

(34) a Fab comprising a heavy chain that comprises an amino acid sequence selected from SEQ ID NO: 125, 126, or 127, and a light chain comprising the amino acid sequence of SEQ ID NO: 49;

(35) a Fab comprising a heavy chain that comprises an amino acid sequence selected from SEQ ID NO: 137, 138, or 139, and a light chain comprising the amino acid sequence of SEQ ID NO: 84; or

(36) a Fab comprising a heavy chain that comprises an amino acid sequence selected from SEQ ID NO: 142, 143, or 144, and a light chain comprising the amino acid sequence of SEQ ID NO: 110.

2. The conjugate of claim 1, selected from
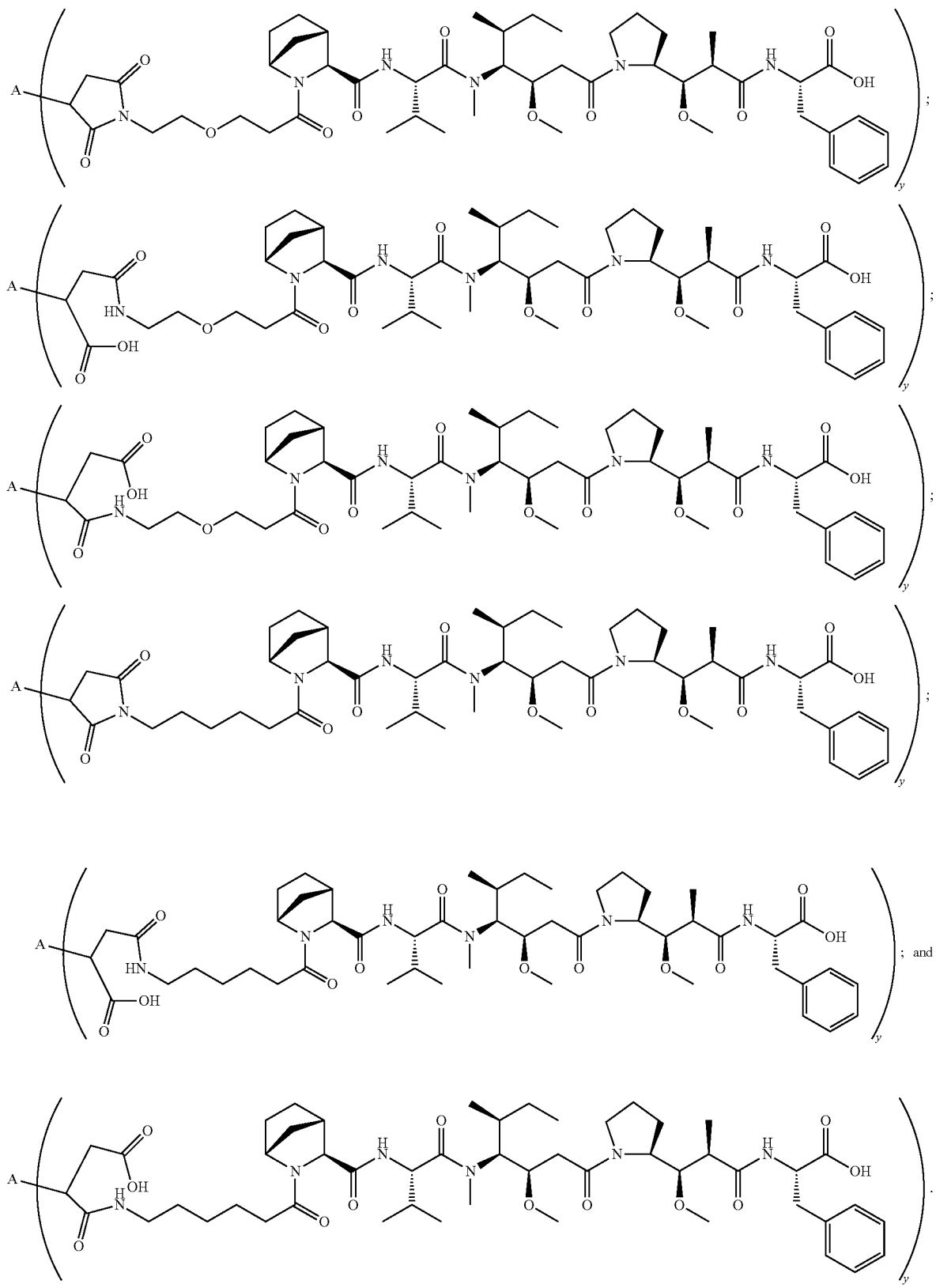

3. The conjugate of claim 1, wherein y is 1, 2, 3 or 4.

4. The conjugate of claim 1, wherein the antibody fragment specifically binds to
   (a) the extracellular domain of human cKIT (SEQ ID NO: 112); or
   (b) an epitope in domains 1-3 of human cKIT (SEQ ID NO: 113).

5. The conjugate of claim 1, wherein the antibody fragment is a human or humanized Fab or Fab'.

6. The conjugate of claim 1, wherein the antibody fragment is a Fab' and $L_{20}$ is attached to a native cysteine residue in the hinge region of the Fab'.

7. The conjugate of claim 1, wherein the antibody fragment comprises at least one non-native cysteine introduced into a constant region, and $L_{20}$ is attached to the non-native cysteine.

8. The conjugate of claim 1, wherein the antibody fragment comprises cysteine at one or more of the following positions (all positions by EU numbering):
   (a) position 152 of the heavy chain,
   (b) position 114 or 165 of the kappa light chain, or
   (c) position 143 of the lambda light chain.

9. The conjugate of claim 1, wherein the conjugate has a half-life less than about 24-48 hours.

10. The conjugate of claim 1, wherein the conjugate does not induce mast cell degranulation.

11. A pharmaceutical composition comprising the conjugate of claim 1 and a pharmaceutically acceptable carrier.

\* \* \* \* \*

SEQUENCE LISTING

```
<160> NUMBER OF SEQ ID NOS: 162

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ser Tyr Ala Ile Ser
1               5

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Val Ile Phe Pro Ala Glu Gly Ala Pro Gly Tyr Ala Gln Lys Phe Gln
1               5                   10                  15

Gly

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Gly Tyr Ile Ser Asp Phe Asp Val
1               5

<210> SEQ ID NO 4
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4
```

Gly Gly Thr Phe Ser Ser Tyr
1               5

<210> SEQ ID NO 5
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Phe Pro Ala Glu Gly Ala
1               5

<210> SEQ ID NO 6
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Thr Phe Ser Ser Tyr Ala Ile Ser
1               5                   10

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Gly Thr Phe Ser Ser Tyr Ala
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ile Phe Pro Ala Glu Gly Ala Pro
1               5

<210> SEQ ID NO 9
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ala Arg Gly Gly Tyr Ile Ser Asp Phe Asp Val
1               5                   10

-continued

```
<210> SEQ ID NO 10
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Phe Pro Ala Glu Gly Ala Pro Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
            100                 105                 110

Leu Val Thr Val Ser Ser
        115

```
<210> SEQ ID NO 11
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11
```
caggtgcaat tggtgcagag cggtgccgaa gtgaaaaaac cgggcagcag cgtgaaagtt      60
agctgcaaag catccggagg gacgtttagc agctatgcga ttagctgggt gcgccaggcc     120
ccgggccagg gcctcgagtg gatgggcgtt atcttcccgg ctgaaggcgc tccgggttac     180
gcccagaaat tcagggccgg ggtgaccatt accgccgatg aaagcaccag caccgcctat     240
atggaactga gcagcctgcg cagcgaagat acggccgtgt attattgcgc gcgtggtggt     300
tacatctctg acttcgatgt ttggggccaa ggcaccctgg tgactgttag ctca          354

```
<210> SEQ ID NO 12
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

```
Gly Val Ile Phe Pro Ala Gly Ala Pro Gly Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Tyr Ile Ser Asp Phe Asp Val Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
435                 440                 445

<210> SEQ ID NO 13
<211> LENGTH: 1344
```

| | | | |
|---|---|---|---|
| <212> TYPE: DNA | | | |
| <213> ORGANISM: Artificial Sequence | | | |
| <220> FEATURE: | | | |
| <221> NAME/KEY: source | | | |
| <223> OTHER INFORMATION: /note="Description of Artificial Sequence: Synthetic polynucleotide" | | | |

<400> SEQUENCE: 13

```
caggtgcaat tggtgcagag cggtgccgaa gtgaaaaaac cgggcagcag cgtgaaagtt      60
agctgcaaag catccggagg gacgtttagc agctatgcga ttagctgggt gcgccaggcc     120
ccgggccagg gcctcgagtg gatgggcgtt atcttcccgg ctgaaggcgc tccgggttac     180
gcccagaaat tcagggccg ggtgaccatt accgccgatg aaagcaccag caccgccctat     240
atggaactga gcagcctgcg cagcgaagat acggccgtgt attattgcgc gcgtggtggt     300
tacatctctg acttcgatgt ttggggccaa ggcacccctgg tgactgttag ctcagctagc    360
accaagggcc ccagcgtgtt cccccctggcc cccagcagca gtctacttc cggcggaact     420
gctgccctgg gttgcctggt gaaggactac ttccccgagc ccgtgacagt gtcctggaac     480
tctggggctc tgacttccgg cgtgcacacc ttccccgccg tgctgcagag cagcggcctg     540
tacagcctga gcagcgtggt gacagtgccc tccagctctc tgggaaccca gacctatatc     600
tgcaacgtga accacaagcc cagcaacacc aaggtggaca agagagtgga gcccaagagc     660
tgcgacaaga cccacacctg cccccccctgc ccagctccag aactgctggg agggccttcc     720
gtgttcctgt tccccccaa gcccaaggac accctgatga tcagcaggac ccccgaggtg     780
acctgcgtgg tggtggacgt gtcccacgag gacccagagg tgaagttcaa ctggtacgtg     840
gacggcgtgg aggtgcacaa cgccaagacc aagcccagag aggagcagta caacagcacc     900
tacagggtgt gtccgtgct gaccgtgctg caccaggact ggctgaacgg caaagaatac     960
aagtgcaaag tctccaacaa ggccctgcca gccccaatcg aaaagacaat cagcaaggcc    1020
aagggccagc cacgggagcc ccaggtgtac accctgcccc cagccgggga ggagatgacc    1080
aagaaccagg tgtccctgac ctgtctggtg aagggcttct accccagcga tatcgccgtg    1140
gagtgggaga gcaacggcca gcccgagaac aactacaaga ccaccccccc agtgctggac    1200
agcgacggca gcttcttcct gtacagcaag ctgaccgtgg acaagtccag gtggcagcag    1260
ggcaacgtgt tcagctgcag cgtgatgcac gaggccctgc acaaccacta cacccagaag    1320
tccctgagcc tgagccccgg caag                                           1344
```

<210> SEQ ID NO 14
<211> LENGTH: 237
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Phe Pro Ala Glu Gly Ala Pro Gly Tyr Ala Gln Lys Phe
    50                  55                  60
```

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly
225                 230                 235

<210> SEQ ID NO 15
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
caggtgcaat tggtgcagag cggtgccgaa gtgaaaaaac cgggcagcag cgtgaaagtt      60
agctgcaaag catccggagg gacgtttagc agctatgcga ttagctgggt gcgccaggcc     120
ccgggccagg gcctcgagtg gatgggcgtt atcttcccgg ctgaaggcgc tccgggttac     180
gcccagaaat ttcagggccg ggtgaccatt accgccgatg aaagcaccag caccgcctat     240
atggaactga gcagcctgcg cagcgaagat acggccgtgt attattgcgc gcgtggtggt     300
tacatctctg acttcgatgt ttggggccaa ggcaccctgg tgactgttag ctcagctagc     360
accaagggcc cagcgtgtt ccccctggcc cccagcagca agtctacttc cggcggaact     420
gctgccctgg gttgcctggt gaaggactac ttccccgagc ccgtgacagt gtcctggaac     480
tctggggctc tgacttccgg cgtgcacacc ttccccgccg tgctgcagag cagcggcctg     540
tacagcctga gcagcgtggt gacagtgccc tccagctctc tgggaaccca gacctatatc     600
tgcaacgtga accacaagcc cagcaacacc aaggtggaca gagagtgga gcccaagagc     660 tgcgacaaga cccacacctg ccccccctgc ccagctccag aactgctggg a              711

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 16

Arg Ala Ser Gln Ser Ile Ser Asn Tyr Leu Ala
1               5                   10

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Asp Ala Ser Ser Leu Gln Ser
1               5

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gln Gln Tyr Tyr Tyr Glu Ser Ile Thr
1               5

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ser Gln Ser Ile Ser Asn Tyr
1               5

<210> SEQ ID NO 20
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Asp Ala Ser
1

<210> SEQ ID NO 21
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Tyr Tyr Tyr Glu Ser Ile
1               5
```

<210> SEQ ID NO 22
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gln Ser Ile Ser Asn Tyr
1               5

<210> SEQ ID NO 23
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr Glu Ser Ile
                85                  90                  95

Thr Phe Gly Gln Gly Thr Lys Val Glu Ile Lys
            100                 105

<210> SEQ ID NO 24
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
gatatccaga tgacccagag cccgagcagc ctgagcgcca gcgtgggcga tcgcgtgacc        60
attacctgca gagccagcca gtctatttct aactacctgg cttggtacca gcagaaaccg       120
ggcaaagcgc cgaaactatt aatctacgac gcttcttctc tgcaaagcgg cgtgccgagc       180
cgctttagcg gcagcggatc cggcaccgat ttcaccctga ccattagctc tctgcaaccg       240
gaagactttg cgacctatta ttgccagcag tactactacg aatctatcac ctttggccag       300
ggcacgaaag ttgaaattaa a                                                 321

<210> SEQ ID NO 25
<211> LENGTH: 214
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Tyr Glu Ser Ile
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
gatatccaga tgacccagag cccgagcagc ctgagcgcca gcgtgggcga tcgcgtgacc      60
attacctgca gagccagcca gtctatttct aactacctgg cttggtacca gcagaaaccg     120
ggcaaagcgc cgaaactatt aatctacgac gcttcttctc tgcaaagcgg cgtgccgagc     180
cgctttagcg gcagcggatc cggcaccgat ttcaccctga ccattagctc tctgcaaccg     240
gaagactttg cgacctatta ttgccagcag tactactacg aatctatcac ctttggccag     300
ggcacgaaag ttgaaattaa acgtacggtg gccgctccca gcgtgttcat cttcccccca     360
agcgacgagc agctgaagag tggcaccgcc agcgtggtgt gcctgctgaa caacttctac     420
ccccgggagg ccaaggtgca gtggaaggtg gacaacgccc tgcagagcgg caacagccag     480
gagagcgtca ccgagcagga cagcaaggac tccacctaca gcctgagcag caccctgacc     540
ctgagcaagg ccgactacga gaagcataag gtgtacgcct gcgaggtgac ccaccagggc     600
```
ctgtccagcc ccgtgaccaa gagcttcaac aggggcgagt gc     642

<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ser His Ala Leu Ser
1               5

<210> SEQ ID NO 28
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Ile Ile Pro Ser Phe Gly Thr Ala Asp Tyr Ala Gln Lys Phe Gln
1               5                   10                  15

Gly

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Leu Tyr Asp Phe Asp Tyr
1               5

<210> SEQ ID NO 30
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gly Gly Thr Phe Ser Ser His
1               5

<210> SEQ ID NO 31
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ile Pro Ser Phe Gly Thr
1               5

```
<210> SEQ ID NO 32
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Gly Thr Phe Ser Ser His Ala Leu Ser
1               5                   10

<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gly Gly Thr Phe Ser Ser His Ala
1               5

<210> SEQ ID NO 34
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ile Ile Pro Ser Phe Gly Thr Ala
1               5

<210> SEQ ID NO 35
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Ala Arg Gly Leu Tyr Asp Phe Asp Tyr
1               5

<210> SEQ ID NO 36
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
            20                  25                  30
```

```
Ala Leu Ser Trp Val Arg Gln Ala Pro Gly Gln Gly Leu Glu Trp Met
            35                  40                  45

Gly Gly Ile Ile Pro Ser Phe Gly Thr Ala Asp Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Leu Tyr Asp Phe Asp Tyr Trp Gly Gln Gly Thr Leu Val
            100                 105                 110

Thr Val Ser Ser
        115
```

<210> SEQ ID NO 37
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 37

```
caggtgcaat tggtgcagag cggtgccgaa gtgaaaaaac cgggcagcag cgtgaaagtt    60
agctgcaaag catccggagg gacgttttct tctcatgctc tgtcttgggt gcgccaggcc   120
ccgggccagg gcctcgagtg gatgggcggt atcatcccgt ctttcggcac tgcggactac   180
gcccagaaat tcagggccgg ggtgaccatt accgccgatg aaagcaccag caccgcctat   240
atggaactga gcagcctgcg cagcgaagat acggccgtgt attattgcgc gcgtggtctg   300
tacgacttcg actactgggg ccaaggcacc ctggtgactg ttagctca              348
```

<210> SEQ ID NO 38
<211> LENGTH: 446
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser His
            20                  25                  30

Ala Leu Ser Trp Val Arg Gln Ala Pro Gly Gln Gly Leu Glu Trp Met
            35                  40                  45

Gly Gly Ile Ile Pro Ser Phe Gly Thr Ala Asp Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Leu Tyr Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
```

```
                Val Lys Asp Tyr Phe Pro Glu Pro Val Thr Val Ser Trp Asn Ser Gly
                145                 150                 155                 160

Ala Leu Thr Ser Gly Val His Thr Phe Pro Ala Val Leu Gln Ser Ser
                                165                 170                 175

Gly Leu Tyr Ser Leu Ser Ser Val Val Thr Val Pro Ser Ser Ser Leu
                            180                 185                 190

Gly Thr Gln Thr Tyr Ile Cys Asn Val Asn His Lys Pro Ser Asn Thr
                        195                 200                 205

Lys Val Asp Lys Arg Val Glu Pro Lys Ser Cys Asp Lys Thr His Thr
                    210                 215                 220

Cys Pro Pro Cys Pro Ala Pro Glu Leu Leu Gly Gly Pro Ser Val Phe
                225                 230                 235                 240

Leu Phe Pro Pro Lys Pro Lys Asp Thr Leu Met Ile Ser Arg Thr Pro
                                245                 250                 255

Glu Val Thr Cys Val Val Val Asp Val Ser His Glu Asp Pro Glu Val
                            260                 265                 270

Lys Phe Asn Trp Tyr Val Asp Gly Val Glu Val His Asn Ala Lys Thr
                        275                 280                 285

Lys Pro Arg Glu Glu Gln Tyr Asn Ser Thr Tyr Arg Val Val Ser Val
                    290                 295                 300

Leu Thr Val Leu His Gln Asp Trp Leu Asn Gly Lys Glu Tyr Lys Cys
                305                 310                 315                 320

Lys Val Ser Asn Lys Ala Leu Pro Ala Pro Ile Glu Lys Thr Ile Ser
                                325                 330                 335

Lys Ala Lys Gly Gln Pro Arg Glu Pro Gln Val Tyr Thr Leu Pro Pro
                            340                 345                 350

Ser Arg Glu Glu Met Thr Lys Asn Gln Val Ser Leu Thr Cys Leu Val
                        355                 360                 365

Lys Gly Phe Tyr Pro Ser Asp Ile Ala Val Glu Trp Glu Ser Asn Gly
                    370                 375                 380

Gln Pro Glu Asn Asn Tyr Lys Thr Thr Pro Pro Val Leu Asp Ser Asp
                385                 390                 395                 400

Gly Ser Phe Phe Leu Tyr Ser Lys Leu Thr Val Asp Lys Ser Arg Trp
                                405                 410                 415

Gln Gln Gly Asn Val Phe Ser Cys Ser Val Met His Glu Ala Leu His
                            420                 425                 430

Asn His Tyr Thr Gln Lys Ser Leu Ser Leu Ser Pro Gly Lys
                        435                 440                 445

<210> SEQ ID NO 39
<211> LENGTH: 1338
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39
caggtgcaat tggtgcagag cggtgccgaa gtgaaaaaac cgggcagcag cgtgaaagtt      60
agctgcaaag catccggagg acgtttttct tctcatgctc tgtcttgggt gcgccaggcc     120
ccgggccagg gcctcgagtg gatgggcggt atcatcccgt ctttcggcac tgcggactac     180
gcccagaaat ttcagggccg ggtgaccatt accgccgatg aaagcaccag caccgcctat     240
```

```
atggaactga gcagcctgcg cagcgaagat acggccgtgt attattgcgc gcgtggtctg      300
tacgacttcg actactgggg ccaaggcacc ctggtgactg ttagctcagc tagcaccaag      360
ggccccagcg tgttccccct ggcccccagc agcaagtcta cttccggcgg aactgctgcc      420
ctgggttgcc tggtgaagga ctacttcccc gagcccgtga cagtgtcctg gaactctggg      480
gctctgactt ccggcgtgca caccttcccc gccgtgctgc agagcagcgg cctgtacagc      540
ctgagcagcg tggtgacagt gccctccagc tctctgggaa cccagaccta tatctgcaac      600
gtgaaccaca agcccagcaa caccaaggtg acaagagag tggagcccaa gagctgcgac       660
aagacccaca cctgcccccc ctgcccagct ccagaactgc tgggagggcc ttccgtgttc      720
ctgttccccc ccaagcccaa ggacaccctg atgatcagca ggaccccga ggtgacctgc       780
gtggtggtgg acgtgtccca cgaggaccca gaggtgaagt tcaactggta cgtggacggc      840
gtggaggtgc acaacgccaa gaccaagccc agagaggagc agtacaacag cacctacagg      900
gtggtgtccg tgctgaccgt gctgcaccag gactggctga acggcaaaga atacaagtgc      960
aaagtctcca acaaggccct gccagcccca atcgaaaaga caatcagcaa ggccaagggc     1020
cagccacggg agccccaggt gtacaccctg cccccagcc gggaggagat gaccaagaac      1080
caggtgtccc tgacctgtct ggtgaagggc ttctacccca gcgatatcgc cgtggagtgg     1140
gagagcaacg gccagcccga gaacaactac aagaccaccc ccccagtgct ggacagcgac     1200
ggcagcttct tcctgtacag caagctgacc gtggacaagt ccaggtggca gcagggcaac     1260
gtgttcagct gcagcgtgat gcacgaggcc ctgcacaacc actacaccca gaagtccctg     1320
agcctgagcc ccggcaag                                                   1338
```

<210> SEQ ID NO 40
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
            20                  25                  30

Ala Leu Ser Trp Val Arg Gln Ala Pro Gly Gln Gly Leu Glu Trp Met
        35                  40                  45

Gly Gly Ile Ile Pro Ser Phe Gly Thr Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Tyr Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Arg Val Glu Pro Lys Ser Cys Asp Lys Thr His Thr
210                 215                 220

Cys Pro Pro Cys Pro Ala Pro Glu Leu Leu Gly
225                 230                 235
```

<210> SEQ ID NO 41
<211> LENGTH: 705
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 41

```
caggtgcaat tggtgcagag cggtgccgaa gtgaaaaaac cgggcagcag cgtgaaagtt      60
agctgcaaag catccggagg gacgttttct tctcatgctc tgtcttgggt gcgccaggcc     120
ccgggccagg gcctcgagtg gatgggcggt atcatcccgt ctttcggcac tgcggactac     180
gcccagaaat tcagggccg gtgaccatt accgccgatg aaagcaccag caccgcctat      240
atggaactga gcagcctgcg cagcgaagat acggccgtgt attattgcgc gcgtggtctg     300
tacgacttcg actactgggg ccaaggcacc ctggtgactg ttagctcagc tagcaccaag     360
ggccccagcg tgttccccct ggccccagc agcaagtcta cttccggcgg aactgctgcc     420
ctgggttgcc tggtgaagga ctacttcccc gagcccgtga cagtgtcctg gaactctggg     480
gctctgactt ccggcgtgca caccttcccc gccgtgctgc agagcagcgg cctgtacagc     540
ctgagcagcg tggtgacagt gccctccagc tctctgggaa cccagaccta tatctgcaac     600
gtgaaccaca gcccagcaa caccaaggtg gacaagagag tggagcccaa gagctgcgac     660
aagacccaca cctgcccccc ctgcccagct ccagaactgc tggga                    705
```

<210> SEQ ID NO 42
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 42

```
Arg Ala Ser Gln Asp Ile Ser Gln Asp Leu Ala
1               5                   10
```

<210> SEQ ID NO 43
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 43

```
Gln Gln Tyr Tyr Tyr Leu Pro Ser Thr
1               5
```

```
<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ser Gln Asp Ile Ser Gln Asp
1               5
```

```
<210> SEQ ID NO 45
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Tyr Tyr Tyr Leu Pro Ser
1               5
```

```
<210> SEQ ID NO 46
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gln Asp Ile Ser Gln Asp
1               5
```

```
<210> SEQ ID NO 47
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Gln Asp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Tyr Tyr Leu Pro Ser
                85                  90                  95

Thr Phe Gly Gln Gly Thr Lys Val Glu Ile Lys
```

<210> SEQ ID NO 48
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 48

```
gatatccaga tgacccagag cccgagcagc ctgagcgcca gcgtgggcga tcgcgtgacc      60
attacctgca gagccagcca ggacatttct caggacctgg cttggtacca gcagaaaccg     120
ggcaaagcgc cgaaactatt aatctacgac gcttcttctc tgcaaagcgg cgtgccgagc     180
cgctttagcg gcagcggatc cggcaccgat ttcaccctga ccattagctc tctgcaaccg     240
gaagactttg cggtgtatta ttgccagcag tactactacc tgccgtctac ctttggccag     300
ggcacgaaag ttgaaattaa a                                               321
```

<210> SEQ ID NO 49
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Gln Asp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Tyr Tyr Leu Pro Ser
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 50
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50

```
gatatccaga tgacccagag cccgagcagc ctgagcgcca gcgtgggcga tcgcgtgacc      60
attacctgca gagccagcca ggacatttct caggacctgg cttggtacca gcagaaaccg     120
ggcaaagcgc cgaaactatt aatctacgac gcttcttctc tgcaaagcgg cgtgccgagc     180
cgctttagcg gcagcggatc cggcaccgat ttcaccctga ccattagctc tctgcaaccg     240
gaagactttg cggtgtatta ttgccagcag tactactacc tgccgtctac ctttggccag     300
ggcacgaaag ttgaaattaa acgtacggtg gccgctccca gcgtgttcat cttcccccc      360 agcgacgagc agctgaagag tggcaccgcc agcgtggtgt gcctgctgaa caacttctac     420
ccccgggagg ccaaggtgca gtggaaggtg acaacgcccc tgcagagcgg caacagccag     480
gagagcgtca ccgagcagga cagcaaggac tccacctaca gcctgagcag caccctgacc     540
ctgagcaagg ccgactacga aagcataag gtgtacgcct gcgaggtgac ccaccagggc      600
ctgtccagcc ccgtgaccaa gagcttcaac aggggcgagt gc                         642
```

<210> SEQ ID NO 51
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Thr Ile Gly Pro Phe Glu Gly Gln Pro Arg Tyr Ala Gln Lys Phe Gln
1               5                   10                  15

Gly

<210> SEQ ID NO 52
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Gly Pro Phe Glu Gly Gln
1               5

<210> SEQ ID NO 53
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

```
Ile Gly Pro Phe Glu Gly Gln Pro
1               5
```

```
<210> SEQ ID NO 54
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Thr Ile Gly Pro Phe Glu Gly Gln Pro Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
            100                 105                 110

Leu Val Thr Val Ser Ser
        115
```

```
<210> SEQ ID NO 55
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55
```

```
caggtgcaat tggtgcagag cggtgccgaa gtgaaaaaac cgggcagcag cgtgaaagtt        60
agctgcaaag catccggagg gacgtttagc agctatgcga ttagctgggt gcgccaggcc       120
ccgggccagg gcctcgagtg gatgggcact atcggtccgt tcgaaggcca gccgcgttac       180
gcccagaaat tcagggccgg ggtgaccatt accgccgatg aaagcaccag caccgcctat       240
atggaactga gcagcctgcg cagcgaagat acggccgtgt attattgcgc gcgtggtggt       300
tacatctctg acttcgatgt ttggggccaa ggcaccctgg tgactgttag ctca             354
```

```
<210> SEQ ID NO 56
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

-continued

```
                    20                  25                  30
Ala Ile Ser Trp Val Arg Gln Ala Pro Gly Gln Gly Leu Glu Trp Met
                35                  40                  45
Gly Thr Ile Gly Pro Phe Glu Gly Gln Pro Arg Tyr Ala Gln Lys Phe
            50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Gly Gly Tyr Ile Ser Asp Phe Asp Val Trp Gly Gln Gly Thr
                100                 105                 110
Leu Val Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
                130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Arg Val Glu Pro Lys Ser Cys Asp Lys Thr
                210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Asn Ser Thr Tyr Arg Val Val
                290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445
```

<210> SEQ ID NO 57
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57

```
caggtgcaat tggtgcagag cggtgccgaa gtgaaaaaac cgggcagcag cgtgaaagtt      60
agctgcaaag catccggagg gacgtttagc agctatgcga ttagctgggt gcgccaggcc     120
ccgggccagg gcctcgagtg gatgggcact atcggtccgt tcgaaggcca gccgcgttac     180
gcccagaaat ttcagggccg ggtgaccatt accgccgatg aaagcaccag caccgcctat     240
atggaactga gcagcctgcg cagcgaagat acggccgtgt attattgcgc gcgtggtggt     300
tacatctctg acttcgatgt ttggggccaa ggcaccctgg tgactgttag ctcagctagc     360
accaagggcc caagtgtgtt tcccctggcc cccagcagca gtctacttc cggcggaact      420
gctgccctgg gttgcctggt gaaggactac ttccccgagc ccgtgacagt gtcctggaac     480
tctggggctc tgacttccgg cgtgcacacc ttccccgccg tgctgcagag cagcggcctg     540
tacagcctga gcagcgtggt gacagtgccc tccagctctc tgggaaccca gacctatatc     600
tgcaacgtga accacaagcc cagcaacacc aaggtggaca agagagtgga gcccaagagc     660
tgcgacaaga cccacacctg ccccccctgc ccagctccag aactgctggg agggccttcc     720
gtgttcctgt tccccccaa gcccaaggac accctgatga tcagcaggac ccccgaggtg      780
acctgcgtgg tggtggacgt gtcccacgag gacccagagg tgaagttcaa ctggtacgtg     840
gacggcgtgg aggtgcacaa cgccaagacc aagcccagag aggagcagta caacagcacc     900
tacagggtgg tgtccgtgct gaccgtgctg caccaggact ggctgaacgg caaagaatac     960
aagtgcaaag tctccaacaa ggccctgcca gccccaatcg aaaagacaat cagcaaggcc    1020
aagggccagc cacgggagcc ccaggtgtac accctgcccc cagccgggga ggagatgacc    1080
aagaaccagg tgtccctgac ctgtctggtg aagggcttct accccagcga tatcgccgtg    1140
gagtgggaga gcaacggcca gcccgagaac aactacaaga ccaccccccc agtgctggac    1200
agcgacggca gcttcttcct gtacagcaag ctgaccgtgg acaagtccag gtggcagcag    1260
ggcaacgtgt tcagctgcag cgtgatgcac gaggccctgc acaaccacta cacccagaag    1320
tccctgagcc tgagccccgg caag                                           1344
```

<210> SEQ ID NO 58
<211> LENGTH: 237
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 58

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

```
Gly Thr Ile Gly Pro Phe Glu Gly Gln Pro Arg Tyr Ala Gln Lys Phe
                50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly
225                 230                 235
```

<210> SEQ ID NO 59
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 59

```
caggtgcaat tggtgcagag cggtgccgaa gtgaaaaaac cgggcagcag cgtgaaagtt     60
agctgcaaag catccggagg gacgtttagc agctatgcga ttagctgggt gcgccaggcc    120
ccgggccagg gcctcgagtg gatgggcact atcggtccgt tcgaaggcca gccgcgttac    180
gcccagaaat tcagggccgg ggtgaccatt accgccgatg aaagcaccag caccgcctat    240
atggaactga gcagcctgcg cagcgaagat acggccgtgt attattgcgc gcgtggtggt    300
tacatctctg acttcgatgt ttggggccaa ggcaccctgg tgactgttag ctcagctagc    360
accaagggcc caagtgtgtt tcccctggcc ccagcagca agtctacttc cggcggaact    420
gctgccctgg gttgcctggt gaaggactac ttccccgagc ccgtgacagt gtcctggaac    480
tctggggctc tgacttccgg cgtgcacacc ttccccgccg tgctgcagag cagcggcctg    540
tacagcctga gcagcgtggt gacagtgccc tccagctctc tgggaaccca gacctatatc    600
tgcaacgtga accacaagcc cagcaacacc aaggtggaca agagagtgga gcccaagagc    660
tgcgacaaga cccacacctg cccccccctgc ccagctccag aactgctggg a    711
```

<210> SEQ ID NO 60
<211> LENGTH: 7
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 60

Thr Asn Ser Ala Ala Trp Asn
1               5

<210> SEQ ID NO 61
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Arg Ile Tyr Tyr Arg Ser Gln Trp Leu Asn Asp Tyr Ala Val Ser Val
1               5                   10                  15

Lys Ser

<210> SEQ ID NO 62
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gln Leu Thr Tyr Pro Tyr Thr Val Tyr His Lys Ala Leu Asp Val
1               5                   10                  15

<210> SEQ ID NO 63
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Asp Ser Val Ser Thr Asn Ser Ala
1               5

<210> SEQ ID NO 64
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Tyr Tyr Arg Ser Gln Trp Leu
1               5

<210> SEQ ID NO 65
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 65

Gly Asp Ser Val Ser Thr Asn Ser Ala Ala Trp Asn
1               5                   10

<210> SEQ ID NO 66
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Gly Asp Ser Val Ser Thr Asn Ser Ala Ala
1               5                   10

<210> SEQ ID NO 67
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Ile Tyr Tyr Arg Ser Gln Trp Leu Asn
1               5

<210> SEQ ID NO 68
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ala Arg Gln Leu Thr Tyr Pro Tyr Thr Val Tyr His Lys Ala Leu Asp
1               5                   10                  15
Val

<210> SEQ ID NO 69
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Gln Trp Leu Asn Asp Tyr Ala
    50                  55                  60

Val Ser Val Lys Ser Arg Ile Thr Ile Asn Pro Asp Thr Ser Lys Asn

```
                65                  70                  75                  80
Gln Phe Ser Leu Gln Leu Asn Ser Val Thr Pro Glu Asp Thr Ala Val
                    85                  90                  95

Tyr Tyr Cys Ala Arg Gln Leu Thr Tyr Pro Tyr Thr Val Tyr His Lys
                100                 105                 110

Ala Leu Asp Val Trp Gly Gln Gly Thr Leu Val Thr Val Ser Ser
                115                 120                 125
```

<210> SEQ ID NO 70
<211> LENGTH: 381
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70

```
caggtgcaat tgcagcagag cggtccgggc ctggtgaaac cgagccagac cctgagcctg      60
acctgcgcga tttccggaga tagcgtgagc actaactctg ctgcttggaa ctggattcgt     120
cagagcccga gccgtggcct cgagtggctg ggccgtatct actaccgtag ccagtggctg     180
aacgactatg ccgtgagcgt gaaaagccgc attaccatta acccggatac ttcgaaaaac     240
cagtttagcc tgcaactgaa cagcgtgacc ccggaagata cggccgtgta ttattgcgcg     300
cgtcagctga cttacccgta cactgtttac cataaagctc tggatgtttg gggtcaagga     360
accctggtca ccgtctcctc g                                               381
```

<210> SEQ ID NO 71
<211> LENGTH: 457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
                20                  25                  30

Ser Ala Ala Trp Asn Trp Ile Arg Gln Ser Pro Ser Arg Gly Leu Glu
            35                  40                  45

Trp Leu Gly Arg Ile Tyr Tyr Arg Ser Gln Trp Leu Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Leu Thr Tyr Pro Tyr Thr Val Tyr His Lys
                100                 105                 110

Ala Leu Asp Val Trp Gly Gln Gly Thr Leu Val Thr Val Ser Ser Ala
                115                 120                 125

Ser Thr Lys Gly Pro Ser Val Phe Pro Leu Ala Pro Ser Ser Lys Ser
            130                 135                 140

Thr Ser Gly Gly Thr Ala Ala Leu Gly Cys Leu Val Lys Asp Tyr Phe
145                 150                 155                 160
```

```
Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
        180                 185                 190

Ser Ser Val Val Thr Val Pro Ser Ser Ser Leu Gly Thr Gln Thr Tyr
            195                 200                 205

Ile Cys Asn Val Asn His Lys Pro Ser Asn Thr Lys Val Asp Lys Arg
        210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
        290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 72
<211> LENGTH: 1371
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 72
caggtgcaat tgcagcagag cggtccgggc ctggtgaaac cgagccagac cctgagcctg      60
acctgcgcga tttccggaga tagcgtgagc actaactctg ctgcttggaa ctggattcgt     120
cagagcccga gccgtggcct cgagtggctg ggccgtatct actaccgtag ccagtggctg     180
aacgactatg ccgtgagcgt gaaaagccgc attaccatta acccggatac ttcgaaaaac     240
cagtttagcc tgcaactgaa cagcgtgacc ccggaagata cggccgtgta ttattgcgcg     300
```

```
cgtcagctga cttacccgta cactgtttac cataaagctc tggatgtttg gggtcaagga    360
accctggtca ccgtctcctc ggctagcacc aagggcccca gcgtgttccc cctggccccc    420
agcagcaagt ctacttccgg cggaactgct gccctgggtt gcctggtgaa ggactacttc    480
cccgagcccg tgacagtgtc ctggaactct ggggctctga cttccggcgt gcacaccttc    540
cccgccgtgc tgcagagcag cggcctgtac agcctgagca gcgtggtgac agtgccctcc    600
agctctctgg gaacccagac ctatatctgc aacgtgaacc acaagcccag caacaccaag    660
gtggacaaga gagtggagcc caagagctgc gacaagaccc acacctgccc ccctgccca    720
gctccagaac tgctggggag gccttccgtg ttcctgttcc cccccaagcc caaggacacc    780
ctgatgatca gcaggacccc cgaggtgacc tgcgtggtgg tggacgtgtc ccacgaggac    840
ccagaggtga agttcaactg gtacgtggac ggcgtggagg tgcacaacgc caagaccaag    900
cccagagagg agcagtacaa cagcacctac agggtggtgt ccgtgctgac cgtgctgcac    960
caggactggc tgaacggcaa agaatacaag tgcaaagtct ccaacaaggc cctgccagcc   1020
ccaatcgaaa agacaatcag caaggccaag ggccagccac gggagcccca ggtgtacacc   1080
ctgccccccca gccgggagga gatgaccaag aaccaggtgt ccctgacctg tctggtgaag   1140
ggcttctacc ccagcgatat cgccgtggag tgggagagca acggccagcc cgagaacaac   1200
tacaagacca cccccccagt gctggacagc gacggcagct tcttcctgta cagcaagctg   1260
accgtggaca gtccaggtg cagcagggc aacgtgttca gctgcagcgt gatgcacgag   1320
gccctgcaca accactacac ccagaagtcc ctgagcctga gccccggcaa g           1371
```

<210> SEQ ID NO 73
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 73

```
Gln Val Gln Leu Gln Gln Ser Gly Pro Gly Leu Val Lys Pro Ser Gln
1               5                  10                  15

Thr Leu Ser Leu Thr Cys Ala Ile Ser Gly Asp Ser Val Ser Thr Asn
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Gln Trp Leu Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Leu Thr Tyr Pro Tyr Thr Val Tyr His Lys
            100                 105                 110

Ala Leu Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
```

165                 170                 175
Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly
                245

<210> SEQ ID NO 74
<211> LENGTH: 738
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
caggtgcaat tgcagcagag cggtccgggc ctggtgaaac cgagccagac cctgagcctg        60
acctgcgcga tttccggaga tagcgtgagc actaactctg ctgcttggaa ctggattcgt       120
cagagcccga gccgtggcct cgagtggctg ggccgtatct actaccgtag ccagtggctg       180
aacgactatg ccgtgagcgt gaaaagccgc attaccatta cccggatact tcgaaaaac        240 cagtttagcc tgcaactgaa cagcgtgacc ccggaagata cggccgtgta ttattgcgcg       300
cgtcagctga cttacccgta cactgtttac cataaagctc tggatgtttg ggtcaagga       360 accctggtca ccgtctcctc ggctagcacc aagggcccca gcgtgttccc cctggccccc       420
agcagcaagt ctacttccgg cggaactgct gccctgggtt gcctggtgaa ggactacttc       480
cccgagcccg tgacagtgtc ctggaactct ggggctctga cttccggcgt gcacaccttc       540
cccgccgtgc tgcagagcag cggcctgtac agcctgagca gcgtggtgac agtgccctcc       600
agctctctgg gaacccagac ctatatctgc aacgtgaacc acaagcccag caacaccaag       660
gtggacaaga gagtggagcc caagagctgc gacaagaccc acacctgccc ccctgccca        720 gctccagaac tgctggga                                                     738

<210> SEQ ID NO 75
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Ser Gly Asp Asn Leu Gly Asp Gln Tyr Val Ser
1               5                   10

<210> SEQ ID NO 76
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 76

Asp Asp Thr Asp Arg Pro Ser
1               5

<210> SEQ ID NO 77
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Gln Ser Thr Asp Ser Lys Ser Val Val
1               5

<210> SEQ ID NO 78
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Asp Asn Leu Gly Asp Gln Tyr
1               5

<210> SEQ ID NO 79
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Asp Asp Thr
1

<210> SEQ ID NO 80
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Thr Asp Ser Lys Ser Val
1               5

<210> SEQ ID NO 81
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Asn Leu Gly Asp Gln Tyr
```

<210> SEQ ID NO 82
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 82

```
Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Asp Gln Tyr Val
            20                  25                  30

Ser Trp Tyr Gln Gln Lys Pro Gly Gln Ala Pro Val Leu Val Ile Tyr
        35                  40                  45

Asp Asp Thr Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Thr Asp Ser Lys Ser Val Val
                85                  90                  95

Phe Gly Gly Gly Thr Lys Leu Thr Val Leu
            100                 105
```

<210> SEQ ID NO 83
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 83

```
gatatcgaac tgacccagcc gccgagcgtg agcgtgagcc cgggccagac cgcgagcatt      60
acctgtagcg gcgataacct gggtgaccaa tacgtttctt ggtaccagca gaaaccgggc     120
caggcgccgg tgctggtgat ctacgacgac actgaccgtc cgagcggcat cccggaacgt     180
tttagcggat ccaacagcgg caacaccgcg accctgacca ttagcggcac ccaggcggaa     240
gacgaagcgg attattactg ccagtctact gactctaaat ctgttgtgtt tggcggcggc     300
acgaagttaa ccgtccta                                                  318
```

<210> SEQ ID NO 84
<211> LENGTH: 212
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 84

```
Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Asp Gln Tyr Val
            20                  25                  30

Ser Trp Tyr Gln Gln Lys Pro Gly Gln Ala Pro Val Leu Val Ile Tyr
        35                  40                  45
```

Asp Asp Thr Asp Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Thr Asp Ser Lys Ser Val Val
             85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
            130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
            165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
            195                 200                 205

Thr Glu Cys Ser
    210

<210> SEQ ID NO 85
<211> LENGTH: 636
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
gatatcgaac tgacccagcc gccgagcgtg agcgtgagcc cgggccagac cgcgagcatt      60
acctgtagcg gcgataacct gggtgaccaa tacgtttctt ggtaccagca gaaaccgggc     120
caggcgccgg tgctggtgat ctacgacgac actgaccgtc cgagcggcat cccggaacgt     180
tttagcggat ccaacagcgg caacaccgcg accctgacca ttagcggcac ccaggcggaa     240
gacgaagcgg attattactg ccagtctact gactctaaat ctgttgtgtt tggcggcggc     300
acgaagttaa ccgtcctagg ccagcctaag gccgctccct ccgtgaccct gttccccccc     360
agctccgagg aactgcaggc caacaaggcc accctggtgt gcctgatcag cgacttctac     420
cctggcgccg tgaccgtggc ctggaaggcc gacagcagcc ccgtgaaggc cggcgtggag     480
acaaccaccc ccagcaagca gagcaacaac aagtacgccg ccagcagcta cctgagcctg     540 accccccgagc agtggaagag ccacagaagc tacagctgcc aggtcaccca cgagggcagc     600
accgtggaga aaaccgtggc ccccaccgag tgcagc                              636

<210> SEQ ID NO 86
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

```
Asn Tyr Trp Ile Ala
1               5
```

<210> SEQ ID NO 87
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

```
Ile Ile Tyr Pro Ser Asn Ser Tyr Thr Leu Tyr Ser Pro Ser Phe Gln
1               5                   10                  15
Gly
```

<210> SEQ ID NO 88
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

```
Val Pro Pro Gly Gly Ser Ile Ser Tyr Pro Ala Phe Asp His
1               5                   10
```

<210> SEQ ID NO 89
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

```
Gly Tyr Ser Phe Thr Asn Tyr
1               5
```

<210> SEQ ID NO 90
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

```
Tyr Pro Ser Asn Ser Tyr
1               5
```

<210> SEQ ID NO 91
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

```
Gly Tyr Ser Phe Thr Asn Tyr Trp Ile Ala
```

```
<210> SEQ ID NO 92
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Gly Tyr Ser Phe Thr Asn Tyr Trp
1               5

<210> SEQ ID NO 93
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Ile Tyr Pro Ser Asn Ser Tyr Thr
1               5

<210> SEQ ID NO 94
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Ala Arg Val Pro Pro Gly Gly Ser Ile Ser Tyr Pro Ala Phe Asp His
1               5                   10                  15

<210> SEQ ID NO 95
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Ser Asn Ser Tyr Thr Leu Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Pro Pro Gly Gly Ser Ile Ser Tyr Pro Ala Phe Asp His
            100                 105                 110
```

Trp Gly Gln Gly Thr Leu Val Thr Val Ser Ser
        115                 120

<210> SEQ ID NO 96
<211> LENGTH: 369
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96
caggtgcaat tggtgcagag cggtgcggaa gtgaaaaaac cgggcgaaag cctgaaaatt      60
agctgcaaag ctccggata  tagcttcact aactactgga tcgcttgggt gcgccagatg     120
ccgggcaaag gtctcgagtg gatgggcatc atctacccgt ctaacagcta caccctgtat     180
agcccgagct ttcagggcca ggtgaccatt agcgcggata aaagcatcag caccgcgtat     240
ctgcaatgga gcagcctgaa agcgagcgat accgcgatgt attattgcgc gcgtgttccg     300
ccgggtggtt ctatctctta cccggctttc gatcattggg gccaaggcac cctggtgact     360
gttagctca                                                              369

<210> SEQ ID NO 97
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Ser Asn Ser Tyr Thr Leu Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Pro Pro Gly Gly Ser Ile Ser Tyr Pro Ala Phe Asp His
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val

```
                    195                 200                 205
Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 98
<211> LENGTH: 1359
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 98
caggtgcaat tggtgcagag cggtgcggaa gtgaaaaaac cgggcgaaag cctgaaaatt      60
agctgcaaag ctccggata tagcttcact aactactgga tcgcttgggt gcgccagatg     120
ccgggcaaag gtctcgagtg gatgggcatc atctacccgt ctaacagcta cccctgtat     180 agcccgagct ttcagggcca ggtgaccatt agcgcggata aaagcatcag caccgcgtat     240
ctgcaatgga gcagcctgaa agcgagcgat accgcgatgt attattgcgc gcgtgttccg     300
ccgggtggtt ctatctctta cccggctttc gatcattggg gccaaggcac cctggtgact     360
gttagctcag ctagcaccaa gggcccagc gtgttccccc tggcccccag cagcaagtct     420
acttccggcg gaactgctgc cctgggttgc ctggtgaagg actacttccc cgagcccgtg     480
acagtgtcct ggaactctgg ggctctgact tccggcgtgc acaccttccc cgccgtgctg     540
```

```
cagagcagcg gcctgtacag cctgagcagc gtggtgacag tgccctccag ctctctggga      600
acccagacct atatctgcaa cgtgaaccac aagcccagca acaccaaggt ggacaagaga      660
gtggagccca agagctgcga caagacccac acctgccccc cctgcccagc tccagaactg      720
ctgggagggc cttccgtgtt cctgttcccc cccaagccca aggacaccct gatgatcagc      780 aggaccccg aggtgacctg cgtggtggtg gacgtgtccc acgaggaccc agaggtgaag       840
ttcaactggt acgtggacgg cgtggaggtg cacaacgcca agaccaagcc agagaggag       900 cagtacaaca gcacctacag ggtggtgtcc gtgctgaccg tgctgcacca ggactggctg      960
aacggcaaag aatacaagtg caaagtctcc aacaaggccc tgccagcccc aatcgaaaag    1020
acaatcagca aggccaaggg ccagccacgg gagccccagg tgtacaccct gccccccagc    1080
cgggaggaga tgaccaagaa ccaggtgtcc ctgacctgtc tggtgaaggg cttctacccc    1140
agcgatatcg ccgtggagtg ggagagcaac ggccagcccg agaacaacta caagaccacc    1200
cccccagtgc tggacagcga cggcagcttc ttcctgtaca gcaagctgac cgtggacaag    1260
tccaggtggc agcagggcaa cgtgttcagc tgcagcgtga tgcacgaggc cctgcacaac    1320
cactacaccc agaagtccct gagcctgagc cccggcaag                            1359
```

<210> SEQ ID NO 99
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Ser Asn Ser Tyr Thr Leu Tyr Ser Pro Ser Phe
    50                  55                  60

Gln Gly Gln Val Thr Ile Ser Ala Asp Lys Ser Ile Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Pro Pro Gly Gly Ser Ile Ser Tyr Pro Ala Phe Asp His
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

```
Asn His Lys Pro Ser Asn Thr Lys Val Asp Lys Arg Val Glu Pro Lys
        210                 215                 220

Ser Cys Asp Lys Thr His Thr Cys Pro Pro Cys Pro Ala Pro Glu Leu
225                 230                 235                 240

Leu Gly

<210> SEQ ID NO 100
<211> LENGTH: 726
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 100
caggtgcaat tggtgcagag cggtgcggaa gtgaaaaaac cgggcgaaag cctgaaaatt      60
agctgcaaag ctccggata  tagcttcact aactactgga tcgcttgggt gcgccagatg    120
ccgggcaaag gtctcgagtg gatgggcatc atctaccgt  ctaacagcta caccctgtat    180
agcccgagct tcagggcca  ggtgaccatt agcgcggata aaagcatcag caccgcgtat    240
ctgcaatgga gcagcctgaa agcgagcgat accgcgatgt attattgcgc gcgtgttccg    300
ccgggtggtt ctatctctta cccggctttc gatcattggg gccaaggcac cctggtgact    360
gttagctcag ctagcaccaa gggcccagc gtgttccccc tggcccccag cagcaagtct    420
acttccggcg gaactgctgc cctggttgc ctggtgaagg actacttccc cgagcccgtg    480
acagtgtcct ggaactctgg ggctctgact tccggcgtgc acaccttccc cgccgtgctg    540
cagagcagcg gcctgtacag cctgagcagc gtggtgacag tgccctccag ctctctggga    600
acccagacct atatctgcaa cgtgaaccac aagcccagca caccaaggt ggacaagaga    660 gtggagccca gagctgcga  caagacccac acctgccccc cctgccagc tccagaactg    720 ctggga                                                              726

<210> SEQ ID NO 101
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Ser Gly Asp Asn Ile Gly Ser Ile Tyr Ala Ser
1               5                   10

<210> SEQ ID NO 102
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Arg Asp Asn Lys Arg Pro Ser
1               5

<210> SEQ ID NO 103
```

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Ser Val Thr Asp Met Glu Gln His Ser Val
1               5                   10

<210> SEQ ID NO 104
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Asp Asn Ile Gly Ser Ile Tyr
1               5

<210> SEQ ID NO 105
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Arg Asp Asn
1

<210> SEQ ID NO 106
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Thr Asp Met Glu Gln His Ser
1               5

<210> SEQ ID NO 107
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Asn Ile Gly Ser Ile Tyr
1               5

<210> SEQ ID NO 108
<211> LENGTH: 107
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 108

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Gly Ser Ile Tyr Ala
            20                  25                  30

Ser Trp Tyr Gln Gln Lys Pro Gly Gln Ala Pro Val Leu Val Ile Tyr
        35                  40                  45

Arg Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Val Thr Asp Met Glu Gln His Ser
                85                  90                  95

Val Phe Gly Gly Gly Thr Lys Leu Thr Val Leu
            100                 105

<210> SEQ ID NO 109
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 109
gatatcgaac tgacccagcc gccgagcgtg agcgtgagcc cgggccagac cgcgagcatt      60
acctgtagcg gcgataacat cggttctatc tacgcttctt ggtaccagca gaaaccgggc     120
caggcgccgg tgctggtgat ctaccgtgac aacaaacgtc cgagcggcat cccggaacgt     180
tttagcggat ccaacagcgg caacaccgcg accctgacca ttagcggcac ccaggcggaa     240
gacgaagcgg attattactg ctccgttact gacatggaac agcattctgt gtttggcggc     300
ggcacgaagt taaccgtcct a                                               321

<210> SEQ ID NO 110
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Gly Ser Ile Tyr Ala
            20                  25                  30

Ser Trp Tyr Gln Gln Lys Pro Gly Gln Ala Pro Val Leu Val Ile Tyr
        35                  40                  45

Arg Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Val Thr Asp Met Glu Gln His Ser
```

```
            85                  90                  95
Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
                115                 120                 125

Asn Lys Ala Thr Leu Val Cys Leu Ile Ser Asp Phe Tyr Pro Gly Ala
            130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
                180                 185                 190

Ser Cys Gln Val Thr His Glu Gly Ser Thr Val Glu Lys Thr Val Ala
            195                 200                 205

Pro Thr Glu Cys Ser
    210
```

<210> SEQ ID NO 111
<211> LENGTH: 639
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 111

```
gatatcgaac tgacccagcc gccgagcgtg agcgtgagcc cgggccagac cgcgagcatt      60
acctgtagcg gcgataacat cggttctatc tacgcttctt ggtaccagca gaaaccgggc     120
caggcgccgg tgctggtgat ctaccgtgac aacaaacgtc cgagcggcat cccggaacgt     180
tttagcggat ccaacagcgg caacaccgcg accctgacca ttagcggcac ccaggcggaa     240
gacgaagcgg attattactg ctccgttact gacatggaac agcattctgt gtttggcggc     300
ggcacgaagt taaccgtcct aggccagcct aaggccgctc cctccgtgac cctgttcccc     360
cccagctccg aggaactgca ggccaacaag gccaccctgg tgtgcctgat cagcgacttc     420
taccctggcg ccgtgaccgt ggcctggaag gccgacagca gccccgtgaa ggccggcgtg     480
gagacaacca cccccagcaa gcagagcaac aacaagtacg ccgccagcag ctacctgagc     540 ctgaccccg agcagtggaa gagccacaga agctacagct gccaggtcac ccacgagggc      600
agcaccgtgg agaaaaccgt ggccccccacc gagtgcagc                            639
```

<210> SEQ ID NO 112
<211> LENGTH: 503
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 112

```
Gln Pro Ser Val Ser Pro Gly Glu Pro Ser Pro Ser Ile His Pro
1               5                   10                  15

Gly Lys Ser Asp Leu Ile Val Arg Val Gly Asp Glu Ile Arg Leu Leu
                20                  25                  30

Cys Thr Asp Pro Gly Phe Val Lys Trp Thr Phe Glu Ile Leu Asp Glu
```

```
                 35                  40                  45
Thr Asn Glu Asn Lys Gln Asn Glu Trp Ile Thr Glu Lys Ala Glu Ala
 50                  55                  60
Thr Asn Thr Gly Lys Tyr Thr Cys Thr Asn Lys His Gly Leu Ser Asn
 65                  70                  75                  80
Ser Ile Tyr Val Phe Val Arg Asp Pro Ala Lys Leu Phe Leu Val Asp
                 85                  90                  95
Arg Ser Leu Tyr Gly Lys Glu Asp Asn Asp Thr Leu Val Arg Cys Pro
                100                 105                 110
Leu Thr Asp Pro Glu Val Thr Asn Tyr Ser Leu Lys Gly Cys Gln Gly
                115                 120                 125
Lys Pro Leu Pro Lys Asp Leu Arg Phe Ile Pro Asp Pro Lys Ala Gly
                130                 135                 140
Ile Met Ile Lys Ser Val Lys Arg Ala Tyr His Arg Leu Cys Leu His
145                 150                 155                 160
Cys Ser Val Asp Gln Glu Gly Lys Ser Val Leu Ser Glu Lys Phe Ile
                165                 170                 175
Leu Lys Val Arg Pro Ala Phe Lys Ala Val Pro Val Val Ser Val Ser
                180                 185                 190
Lys Ala Ser Tyr Leu Leu Arg Glu Gly Glu Glu Phe Thr Val Thr Cys
                195                 200                 205
Thr Ile Lys Asp Val Ser Ser Ser Val Tyr Ser Thr Trp Lys Arg Glu
                210                 215                 220
Asn Ser Gln Thr Lys Leu Gln Glu Lys Tyr Asn Ser Trp His His Gly
225                 230                 235                 240
Asp Phe Asn Tyr Glu Arg Gln Ala Thr Leu Thr Ile Ser Ser Ala Arg
                245                 250                 255
Val Asn Asp Ser Gly Val Phe Met Cys Tyr Ala Asn Asn Thr Phe Gly
                260                 265                 270
Ser Ala Asn Val Thr Thr Thr Leu Glu Val Val Asp Lys Gly Phe Ile
                275                 280                 285
Asn Ile Phe Pro Met Ile Asn Thr Thr Val Phe Val Asn Asp Gly Glu
                290                 295                 300
Asn Val Asp Leu Ile Val Glu Tyr Glu Ala Phe Pro Lys Pro Glu His
305                 310                 315                 320
Gln Gln Trp Ile Tyr Met Asn Arg Thr Phe Thr Asp Lys Trp Glu Asp
                325                 330                 335
Tyr Pro Lys Ser Glu Asn Glu Ser Asn Ile Arg Tyr Val Ser Glu Leu
                340                 345                 350
His Leu Thr Arg Leu Lys Gly Thr Glu Gly Gly Thr Tyr Thr Phe Leu
                355                 360                 365
Val Ser Asn Ser Asp Val Asn Ala Ala Ile Ala Phe Asn Val Tyr Val
                370                 375                 380
Asn Thr Lys Pro Glu Ile Leu Thr Tyr Asp Arg Leu Val Asn Gly Met
385                 390                 395                 400
Leu Gln Cys Val Ala Ala Gly Phe Pro Glu Pro Thr Ile Asp Trp Tyr
                405                 410                 415
Phe Cys Pro Gly Thr Glu Gln Arg Cys Ser Ala Ser Val Leu Pro Val
                420                 425                 430
Asp Val Gln Thr Leu Asn Ser Ser Gly Pro Pro Phe Gly Lys Leu Val
                435                 440                 445
Val Gln Ser Ser Ile Asp Ser Ser Ala Phe Lys His Asn Gly Thr Val
                450                 455                 460
```

```
Glu Cys Lys Ala Tyr Asn Asp Val Gly Lys Thr Ser Ala Tyr Phe Asn
465                 470                 475                 480

Phe Ala Phe Lys Glu Gln Ile His Pro His Thr Leu Phe Thr Pro Arg
                485                 490                 495

Ser His His His His His His
            500
```

<210> SEQ ID NO 113
<211> LENGTH: 294
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 113

```
Gln Pro Ser Val Ser Pro Gly Glu Pro Ser Pro Pro Ser Ile His Pro
1               5                   10                  15

Gly Lys Ser Asp Leu Ile Val Arg Val Gly Asp Glu Ile Arg Leu Leu
            20                  25                  30

Cys Thr Asp Pro Gly Phe Val Lys Trp Thr Phe Glu Ile Leu Asp Glu
        35                  40                  45

Thr Asn Glu Asn Lys Gln Asn Glu Trp Ile Thr Glu Lys Ala Glu Ala
    50                  55                  60

Thr Asn Thr Gly Lys Tyr Thr Cys Thr Asn Lys His Gly Leu Ser Asn
65                  70                  75                  80

Ser Ile Tyr Val Phe Val Arg Asp Pro Ala Lys Leu Phe Leu Val Asp
                85                  90                  95

Arg Ser Leu Tyr Gly Lys Glu Asp Asn Asp Thr Leu Val Arg Cys Pro
            100                 105                 110

Leu Thr Asp Pro Glu Val Thr Asn Tyr Ser Leu Lys Gly Cys Gln Gly
        115                 120                 125

Lys Pro Leu Pro Lys Asp Leu Arg Phe Ile Pro Asp Pro Lys Ala Gly
    130                 135                 140

Ile Met Ile Lys Ser Val Lys Arg Ala Tyr His Arg Leu Cys Leu His
145                 150                 155                 160

Cys Ser Val Asp Gln Glu Gly Lys Ser Val Leu Ser Glu Lys Phe Ile
                165                 170                 175

Leu Lys Val Arg Pro Ala Phe Lys Ala Val Pro Val Val Ser Val Ser
            180                 185                 190

Lys Ala Ser Tyr Leu Leu Arg Glu Gly Glu Glu Phe Thr Val Thr Cys
        195                 200                 205

Thr Ile Lys Asp Val Ser Ser Ser Val Tyr Ser Thr Trp Lys Arg Glu
    210                 215                 220

Asn Ser Gln Thr Lys Leu Gln Glu Lys Tyr Asn Ser Trp His His Gly
225                 230                 235                 240

Asp Phe Asn Tyr Glu Arg Gln Ala Thr Leu Thr Ile Ser Ser Ala Arg
                245                 250                 255

Val Asn Asp Ser Gly Val Phe Met Cys Tyr Ala Asn Asn Thr Phe Gly
            260                 265                 270

Ser Ala Asn Val Thr Thr Thr Leu Glu Val Val Asp Lys Gly Arg Ser
        275                 280                 285

His His His His His His
    290
```

```
<210> SEQ ID NO 114
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Gly Phe Ile Asn Ile Phe Pro Met Ile Asn Thr Thr Val Phe Val Asn
1               5                   10                  15

Asp Gly Glu Asn Val Asp Leu Ile Val Glu Tyr Glu Ala Phe Pro Lys
            20                  25                  30

Pro Glu His Gln Gln Trp Ile Tyr Met Asn Arg Thr Phe Thr Asp Lys
        35                  40                  45

Trp Glu Asp Tyr Pro Lys Ser Glu Asn Glu Ser Asn Ile Arg Tyr Val
    50                  55                  60

Ser Glu Leu His Leu Thr Arg Leu Lys Gly Thr Glu Gly Gly Thr Tyr
65                  70                  75                  80

Thr Phe Leu Val Ser Asn Ser Asp Val Asn Ala Ala Ile Ala Phe Asn
                85                  90                  95

Val Tyr Val Asn Thr Lys Pro Glu Ile Leu Thr Tyr Asp Arg Leu Val
            100                 105                 110

Asn Gly Met Leu Gln Cys Val Ala Ala Gly Phe Pro Glu Pro Thr Ile
        115                 120                 125

Asp Trp Tyr Phe Cys Pro Gly Thr Glu Gln Arg Cys Ser Ala Ser Val
    130                 135                 140

Leu Pro Val Asp Val Gln Thr Leu Asn Ser Ser Gly Pro Pro Phe Gly
145                 150                 155                 160

Lys Leu Val Val Gln Ser Ser Ile Asp Ser Ser Ala Phe Lys His Asn
                165                 170                 175

Gly Thr Val Glu Cys Lys Ala Tyr Asn Asp Val Gly Lys Thr Ser Ala
            180                 185                 190

Tyr Phe Asn Phe Ala Phe Lys Gly Asn Asn Lys Glu Gln Ile His Pro
        195                 200                 205

His Thr Leu Phe Thr Pro Arg Ser His His His His His
    210                 215                 220

<210> SEQ ID NO 115
<211> LENGTH: 741
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Ser Gln Pro Ser Ala Ser Pro Gly Glu Pro Ser Pro Pro Ser Ile His
1               5                   10                  15

Pro Ala Gln Ser Glu Leu Ile Val Glu Ala Gly Asp Thr Leu Ser Leu
            20                  25                  30

Thr Cys Ile Asp Pro Asp Phe Val Arg Trp Thr Phe Lys Thr Tyr Phe
        35                  40                  45

Asn Glu Met Val Glu Asn Lys Lys Asn Glu Trp Ile Gln Glu Lys Ala
    50                  55                  60

Glu Ala Thr Arg Thr Gly Thr Tyr Thr Cys Ser Asn Ser Asn Gly Leu
```

-continued

```
                65                  70                  75                  80
        Thr Ser Ser Ile Tyr Val Phe Val Arg Asp Pro Ala Lys Leu Phe Leu
                            85                  90                  95
        Val Gly Leu Pro Leu Phe Gly Lys Glu Asp Ser Asp Ala Leu Val Arg
                       100                 105                 110
        Cys Pro Leu Thr Asp Pro Gln Val Ser Asn Tyr Ser Leu Ile Glu Cys
                       115                 120                 125
        Asp Gly Lys Ser Leu Pro Thr Asp Leu Thr Phe Val Pro Asn Pro Lys
                       130                 135                 140
        Ala Gly Ile Thr Ile Lys Asn Val Lys Arg Ala Tyr His Arg Leu Cys
        145                 150                 155                 160
        Val Arg Cys Ala Ala Gln Arg Asp Gly Thr Trp Leu His Ser Asp Lys
                            165                 170                 175
        Phe Thr Leu Lys Val Arg Ala Ala Ile Lys Ala Ile Pro Val Val Ser
                            180                 185                 190
        Val Pro Glu Thr Ser His Leu Leu Lys Lys Gly Asp Thr Phe Thr Val
                       195                 200                 205
        Val Cys Thr Ile Lys Asp Val Ser Thr Ser Val Asn Ser Met Trp Leu
                       210                 215                 220
        Lys Met Asn Pro Gln Pro Gln His Ile Ala Gln Val Lys His Asn Ser
        225                 230                 235                 240
        Trp His Arg Gly Asp Phe Asn Tyr Glu Arg Gln Glu Thr Leu Thr Ile
                            245                 250                 255
        Ser Ser Ala Arg Val Asp Asp Ser Gly Val Phe Met Cys Tyr Ala Asn
                            260                 265                 270
        Asn Thr Phe Gly Ser Ala Asn Val Thr Thr Leu Lys Val Val Glu
                       275                 280                 285
        Lys Gly Phe Ile Asn Ile Ser Pro Val Lys Asn Thr Thr Val Phe Val
                       290                 295                 300
        Thr Asp Gly Glu Asn Val Asp Leu Val Val Glu Tyr Glu Ala Tyr Pro
        305                 310                 315                 320
        Lys Pro Glu His Gln Gln Trp Ile Tyr Met Asn Arg Thr Ser Ala Asn
                            325                 330                 335
        Lys Gly Lys Asp Tyr Val Lys Ser Asp Asn Lys Ser Asn Ile Arg Tyr
                            340                 345                 350
        Val Asn Gln Leu Arg Leu Thr Arg Leu Lys Gly Thr Glu Gly Gly Thr
                       355                 360                 365
        Tyr Thr Phe Leu Val Ser Asn Ser Asp Ala Ser Ala Ser Val Thr Phe
                       370                 375                 380
        Asn Val Tyr Val Asn Thr Lys Pro Glu Ile Leu Thr Tyr Asp Arg Leu
        385                 390                 395                 400
        Ile Asn Gly Met Leu Gln Cys Val Ala Glu Gly Phe Pro Glu Pro Thr
                            405                 410                 415
        Ile Asp Trp Tyr Phe Cys Thr Gly Ala Glu Gln Arg Cys Thr Thr Pro
                            420                 425                 430
        Val Ser Pro Val Asp Val Gln Val Gln Asn Val Ser Val Ser Pro Phe
                       435                 440                 445
        Gly Lys Leu Val Val Gln Ser Ser Ile Asp Ser Ser Val Phe Arg His
                       450                 455                 460
        Asn Gly Thr Val Glu Cys Lys Ala Ser Asn Asp Val Gly Lys Ser Ser
        465                 470                 475                 480
        Ala Phe Phe Asn Phe Ala Phe Lys Glu Gln Ile Gln Ala His Thr Leu
                            485                 490                 495
```

Phe Thr Pro Leu Glu Val Leu Phe Gln Gly Pro Arg Ser Pro Arg Gly
            500                 505                 510

Pro Thr Ile Lys Pro Cys Pro Cys Lys Cys Pro Ala Pro Asn Leu
            515                 520                 525

Leu Gly Gly Pro Ser Val Phe Ile Phe Pro Pro Lys Ile Lys Asp Val
            530                 535                 540

Leu Met Ile Ser Leu Ser Pro Ile Val Thr Cys Val Val Asp Val
545                 550                 555                 560

Ser Glu Asp Asp Pro Asp Val Gln Ile Ser Trp Phe Val Asn Asn Val
            565                 570                 575

Glu Val His Thr Ala Gln Thr Gln Thr His Arg Glu Asp Tyr Asn Ser
            580                 585                 590

Thr Leu Arg Val Val Ser Ala Leu Pro Ile Gln His Gln Asp Trp Met
            595                 600                 605

Ser Gly Lys Glu Phe Lys Cys Lys Val Asn Asn Lys Asp Leu Pro Ala
            610                 615                 620

Pro Ile Glu Arg Thr Ile Ser Lys Pro Lys Gly Ser Val Arg Ala Pro
625                 630                 635                 640

Gln Val Tyr Val Leu Pro Pro Glu Glu Glu Met Thr Lys Lys Gln
            645                 650                 655

Val Thr Leu Thr Cys Met Val Thr Asp Phe Met Pro Glu Asp Ile Tyr
            660                 665                 670

Val Glu Trp Thr Asn Asn Gly Lys Thr Glu Leu Asn Tyr Lys Asn Thr
            675                 680                 685

Glu Pro Val Leu Asp Ser Asp Gly Ser Tyr Phe Met Tyr Ser Lys Leu
            690                 695                 700

Arg Val Glu Lys Lys Asn Trp Val Glu Arg Asn Ser Tyr Ser Cys Ser
705                 710                 715                 720

Val Val His Glu Gly Leu His Asn His His Thr Thr Lys Ser Phe Ser
            725                 730                 735

Arg Thr Pro Gly Lys
            740

<210> SEQ ID NO 116
<211> LENGTH: 741
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Ser Gln Pro Ser Ala Ser Pro Gly Glu Pro Ser Pro Pro Ser Ile Gln
1               5                   10                  15

Pro Ala Gln Ser Glu Leu Ile Val Glu Ala Gly Asp Thr Ile Arg Leu
            20                  25                  30

Thr Cys Thr Asp Pro Ala Phe Val Lys Trp Thr Phe Glu Ile Leu Asp
            35                  40                  45

Val Arg Ile Glu Asn Lys Gln Ser Glu Trp Ile Arg Glu Lys Ala Glu
    50                  55                  60

Ala Thr His Thr Gly Lys Tyr Thr Cys Val Ser Gly Ser Gly Leu Arg
65                  70                  75                  80

Ser Ser Ile Tyr Val Phe Val Arg Asp Pro Ala Val Leu Phe Leu Val
                85                  90                  95

```
Gly Leu Pro Leu Phe Gly Lys Glu Asp Asn Asp Ala Leu Val Arg Cys
            100                 105                 110

Pro Leu Thr Asp Pro Gln Val Ser Asn Tyr Ser Leu Ile Glu Cys Asp
        115                 120                 125

Gly Lys Ser Leu Pro Thr Asp Leu Lys Phe Val Pro Asn Pro Lys Ala
    130                 135                 140

Gly Ile Thr Ile Lys Asn Val Lys Arg Ala Tyr His Arg Leu Cys Ile
145                 150                 155                 160

Arg Cys Ala Ala Gln Arg Glu Gly Lys Trp Met Arg Ser Asp Lys Phe
                165                 170                 175

Thr Leu Lys Val Arg Ala Ala Ile Lys Ala Ile Pro Val Val Ser Val
            180                 185                 190

Pro Glu Thr Ser His Leu Leu Lys Glu Gly Asp Thr Phe Thr Val Ile
        195                 200                 205

Cys Thr Ile Lys Asp Val Ser Thr Val Asp Ser Met Trp Ile Lys
    210                 215                 220

Leu Asn Pro Gln Pro Gln Ser Lys Ala Gln Val Lys Arg Asn Ser Trp
225                 230                 235                 240

His Gln Gly Asp Phe Asn Tyr Glu Arg Gln Glu Thr Leu Thr Ile Ser
                245                 250                 255

Ser Ala Arg Val Asn Asp Ser Gly Val Phe Met Cys Tyr Ala Asn Asn
            260                 265                 270

Thr Phe Gly Ser Ala Asn Val Thr Thr Thr Leu Lys Val Val Glu Lys
        275                 280                 285

Gly Phe Ile Asn Ile Phe Pro Val Lys Asn Thr Thr Val Phe Val Thr
    290                 295                 300

Asp Gly Glu Asn Val Asp Leu Val Val Glu Phe Glu Ala Tyr Pro Lys
305                 310                 315                 320

Pro Glu His Gln Gln Trp Ile Tyr Met Asn Arg Thr Pro Thr Asn Arg
                325                 330                 335

Gly Glu Asp Tyr Val Lys Ser Asp Asn Gln Ser Asn Ile Arg Tyr Val
            340                 345                 350

Asn Glu Leu Arg Leu Thr Arg Leu Lys Gly Thr Glu Gly Thr Tyr
        355                 360                 365

Thr Phe Leu Val Ser Asn Ser Asp Val Ser Ala Ser Val Thr Phe Asp
    370                 375                 380

Val Tyr Val Asn Thr Lys Pro Glu Ile Leu Thr Tyr Asp Arg Leu Met
385                 390                 395                 400

Asn Gly Arg Leu Gln Cys Val Ala Ala Gly Phe Pro Glu Pro Thr Ile
                405                 410                 415

Asp Trp Tyr Phe Cys Thr Gly Ala Glu Gln Arg Cys Thr Val Pro Val
            420                 425                 430

Pro Pro Val Asp Val Gln Ile Gln Asn Ala Ser Val Ser Pro Phe Gly
        435                 440                 445

Lys Leu Val Val Gln Ser Ser Ile Asp Ser Ser Val Phe Arg His Asn
    450                 455                 460

Gly Thr Val Glu Cys Lys Ala Ser Asn Ala Val Gly Lys Ser Ser Ala
465                 470                 475                 480

Phe Phe Asn Phe Ala Phe Lys Gly Asn Ser Lys Glu Gln Ile Gln Pro
                485                 490                 495

His Thr Leu Phe Thr Pro Arg Ser Leu Glu Val Leu Phe Gln Gly Pro
            500                 505                 510

Gly Ser Pro Pro Leu Lys Glu Cys Pro Pro Cys Ala Ala Pro Asp Leu
```

```
                515                 520                 525
Leu Gly Gly Pro Ser Val Phe Ile Phe Pro Lys Ile Lys Asp Val
    530                 535                 540
Leu Met Ile Ser Leu Ser Pro Met Val Thr Cys Val Val Asp Val
545                 550                 555                 560
Ser Glu Asp Asp Pro Asp Val Gln Ile Ser Trp Phe Val Asn Asn Val
                565                 570                 575
Glu Val His Thr Ala Gln Thr Gln Thr His Arg Glu Asp Tyr Asn Ser
            580                 585                 590
Thr Leu Arg Val Val Ser Ala Leu Pro Ile Gln His Gln Asp Trp Met
        595                 600                 605
Ser Gly Lys Glu Phe Lys Cys Lys Val Asn Asn Arg Ala Leu Pro Ser
    610                 615                 620
Pro Ile Glu Lys Thr Ile Ser Lys Pro Arg Gly Pro Val Arg Ala Pro
625                 630                 635                 640
Gln Val Tyr Val Leu Pro Pro Ala Glu Glu Met Thr Lys Lys Glu
                645                 650                 655
Phe Ser Leu Thr Cys Met Ile Thr Gly Phe Leu Pro Ala Glu Ile Ala
            660                 665                 670
Val Asp Trp Thr Ser Asn Gly Arg Thr Glu Gln Asn Tyr Lys Asn Thr
        675                 680                 685
Ala Thr Val Leu Asp Ser Asp Gly Ser Tyr Phe Met Tyr Ser Lys Leu
    690                 695                 700
Arg Val Gln Lys Ser Thr Trp Glu Arg Gly Ser Leu Phe Ala Cys Ser
705                 710                 715                 720
Val Val His Glu Gly Leu His Asn His Leu Thr Thr Lys Thr Ile Ser
                725                 730                 735
Arg Ser Leu Gly Lys
            740

<210> SEQ ID NO 117
<211> LENGTH: 527
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Met Tyr Arg Met Gln Leu Leu Ser Cys Ile Ala Leu Ser Leu Ala Leu
1               5                  10                  15
Val Thr Asn Ser Gln Pro Ser Val Ser Pro Gly Glu Pro Ser Pro Pro
                20                  25                  30
Ser Ile His Pro Ala Lys Ser Glu Leu Ile Val Arg Val Gly Asn Glu
            35                  40                  45
Ile Arg Leu Leu Cys Ile Asp Pro Gly Phe Val Lys Trp Thr Phe Glu
        50                  55                  60
Ile Leu Asp Glu Thr Asn Glu Asn Lys Gln Asn Glu Trp Ile Thr Glu
65                  70                  75                  80
Lys Ala Glu Ala Thr Asn Thr Gly Lys Tyr Thr Cys Thr Asn Lys His
                85                  90                  95
Gly Leu Ser Ser Ser Ile Tyr Val Phe Val Arg Asp Pro Ala Lys Leu
            100                 105                 110
Phe Leu Val Asp Arg Ser Leu Tyr Gly Lys Glu Asp Asn Asp Thr Leu
        115                 120                 125
```

```
Val Arg Cys Pro Leu Thr Asp Pro Glu Val Thr Ser Tyr Ser Leu Lys
    130                 135                 140

Gly Cys Gln Gly Lys Pro Leu Pro Lys Asp Leu Arg Phe Val Pro Asp
145                 150                 155                 160

Pro Lys Ala Gly Ile Thr Ile Lys Ser Val Lys Arg Ala Tyr His Arg
                165                 170                 175

Leu Cys Leu His Cys Ser Ala Asp Gln Glu Gly Lys Ser Val Leu Ser
            180                 185                 190

Asp Lys Phe Ile Leu Lys Val Arg Pro Ala Phe Lys Ala Val Pro Val
        195                 200                 205

Val Ser Val Ser Lys Ala Ser Tyr Leu Leu Arg Glu Gly Glu Glu Phe
    210                 215                 220

Thr Val Thr Cys Thr Ile Lys Asp Val Ser Ser Val Tyr Ser Thr
225                 230                 235                 240

Trp Lys Arg Glu Asn Ser Gln Thr Lys Leu Gln Glu Lys Tyr Asn Ser
                245                 250                 255

Trp His His Gly Asp Phe Asn Tyr Glu Arg Gln Ala Thr Leu Thr Ile
            260                 265                 270

Ser Ser Ala Arg Val Asn Asp Ser Gly Val Phe Met Cys Tyr Ala Asn
        275                 280                 285

Asn Thr Phe Gly Ser Ala Asn Val Thr Thr Leu Glu Val Val Asp
290                 295                 300

Lys Gly Phe Ile Asn Ile Phe Pro Met Ile Asn Thr Thr Val Phe Val
305                 310                 315                 320

Asn Asp Gly Glu Asn Val Asp Leu Ile Val Glu Tyr Glu Ala Phe Pro
                325                 330                 335

Lys Pro Glu His Gln Gln Trp Ile Tyr Met Asn Arg Thr Phe Thr Asp
            340                 345                 350

Lys Trp Glu Asp Tyr Pro Lys Ser Glu Asn Glu Ser Asn Ile Arg Tyr
        355                 360                 365

Val Ser Glu Leu His Leu Thr Arg Leu Lys Gly Thr Glu Gly Gly Thr
    370                 375                 380

Tyr Thr Phe Leu Val Ser Asn Ser Asp Val Asn Ala Ser Ile Ala Phe
385                 390                 395                 400

Asn Val Tyr Val Asn Thr Lys Pro Glu Ile Leu Thr Tyr Asp Arg Leu
                405                 410                 415

Val Asn Gly Met Leu Gln Cys Val Ala Ala Gly Phe Pro Glu Pro Thr
            420                 425                 430

Ile Asp Trp Tyr Phe Cys Pro Gly Thr Glu Gln Arg Cys Ser Ala Ser
        435                 440                 445

Val Leu Pro Val Asp Val Gln Thr Leu Asn Ala Ser Gly Pro Pro Phe
    450                 455                 460

Gly Lys Leu Val Val Gln Ser Ser Ile Asp Ser Ser Ala Phe Lys His
465                 470                 475                 480

Asn Gly Thr Val Glu Cys Lys Ala Tyr Asn Asp Val Gly Lys Thr Ser
                485                 490                 495

Ala Tyr Phe Asn Phe Ala Phe Lys Gly Asn Asn Lys Glu Gln Ile His
            500                 505                 510

Pro His Thr Leu Phe Thr Pro Arg Ser His His His His His His
        515                 520                 525

<210> SEQ ID NO 118
<211> LENGTH: 222
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Val Ile Phe Pro Ala Glu Gly Ala Pro Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Cys Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp
    210                 215                 220

<210> SEQ ID NO 119
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Val Ile Phe Pro Ala Glu Gly Ala Pro Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

Ala Arg Gly Gly Tyr Ile Ser Asp Phe Asp Val Trp Gly Gln Gly Thr
            85                  90                  95
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
                210                 215                 220

His Thr Cys Pro Pro Cys Pro
225                 230

<210> SEQ ID NO 120
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Val Ile Phe Pro Ala Glu Gly Ala Pro Gly Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

```
Asn Thr Lys Val Asp Lys Arg Val Glu Pro Lys Ser Cys Asp Lys Thr
    210                 215                 220

His Thr Cys Pro Pro Cys Pro Ala Pro
225                 230
```

<210> SEQ ID NO 121
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Phe Pro Ala Glu Gly Ala Pro Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Pro
225                 230                 235
```

<210> SEQ ID NO 122
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Glu Ser Ile
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Cys Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 123
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Glu Ser Ile
                85                  90                  95

Thr Phe Gly Gln Gly Thr Lys Val Glu Ile Lys Arg Thr Val Ala Ala
                100                 105                 110

Pro Cys Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln

```
145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 124
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
                20                  25                  30

Ala Leu Ser Trp Val Arg Gln Ala Pro Gly Gln Gly Leu Glu Trp Met
            35                  40                  45

Gly Gly Ile Ile Pro Ser Phe Gly Thr Ala Asp Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Tyr Asp Phe Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Cys Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Arg Val Glu Pro Lys Ser Cys Asp
            210                 215                 220

<210> SEQ ID NO 125
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
                20                  25                  30

Ala Leu Ser Trp Val Arg Gln Ala Pro Gly Gln Gly Leu Glu Trp Met
            35                  40                  45

Gly Gly Ile Ile Pro Ser Phe Gly Thr Ala Asp Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Tyr Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
210                 215                 220

Cys Pro Pro Cys Pro
225

<210> SEQ ID NO 126
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
                20                  25                  30

Ala Leu Ser Trp Val Arg Gln Ala Pro Gly Gln Gly Leu Glu Trp Met
            35                  40                  45

Gly Gly Ile Ile Pro Ser Phe Gly Thr Ala Asp Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Tyr Asp Phe Asp Tyr Trp Gly Gln Gly Thr Leu Val
            100                 105                 110

-continued

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
    210                 215                 220

Cys Pro Pro Cys Pro Ala Pro
225                 230

<210> SEQ ID NO 127
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 127

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
            20                  25                  30

Ala Leu Ser Trp Val Arg Gln Ala Pro Gly Gln Gly Leu Glu Trp Met
        35                  40                  45

Gly Gly Ile Ile Pro Ser Phe Gly Thr Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Tyr Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Pro

```
                225                 230                 235

<210> SEQ ID NO 128
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Gln Asp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Tyr Tyr Leu Pro Ser
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Cys Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 129
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Gln Asp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60
```

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Tyr Tyr Tyr Leu Pro Ser
                 85                  90                  95

Thr Phe Gly Gln Gly Thr Lys Val Glu Ile Lys Arg Thr Val Ala Ala
            100                 105                 110

Pro Cys Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 130
<211> LENGTH: 222
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 130

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Thr Ile Gly Pro Phe Glu Gly Gln Pro Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Cys Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205
Asn Thr Lys Val Asp Lys Val Glu Pro Lys Ser Cys Asp
        210                 215                 220

<210> SEQ ID NO 131
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Thr Ile Gly Pro Phe Glu Gly Gln Pro Arg Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Gly Tyr Ile Ser Asp Phe Asp Val Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Lys Thr
    210                 215                 220
His Thr Cys Pro Pro Cys Pro
225                 230

<210> SEQ ID NO 132
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr

```
                 20                  25                  30
Ala Ile Ser Trp Val Arg Gln Ala Pro Gly Gln Gly Leu Glu Trp Met
             35                  40                  45
Gly Thr Ile Gly Pro Phe Glu Gly Gln Pro Arg Tyr Ala Gln Lys Phe
         50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Gly Tyr Ile Ser Asp Phe Asp Val Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Lys Thr
    210                 215                 220
His Thr Cys Pro Pro Cys Pro Ala Pro
225                 230

<210> SEQ ID NO 133
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Gln Val Gln Leu Val Gln Ser Gly Ala Glu Val Lys Lys Pro Gly Ser
 1               5                  10                  15
Ser Val Lys Val Ser Cys Lys Ala Ser Gly Gly Thr Phe Ser Ser Tyr
             20                  25                  30
Ala Ile Ser Trp Val Arg Gln Ala Pro Gly Gln Gly Leu Glu Trp Met
         35                  40                  45
Gly Thr Ile Gly Pro Phe Glu Gly Gln Pro Arg Tyr Ala Gln Lys Phe
     50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Gly Tyr Ile Ser Asp Phe Asp Val Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
            210                 215                 220

His Thr Cys Pro Pro Cys Pro Ala Pro Glu Leu Leu Gly Pro
225                 230                 235

<210> SEQ ID NO 134
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Glu Ser Ile
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Cys Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 135
<211> LENGTH: 214
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Glu Ser Ile
                85                  90                  95

Thr Phe Gly Gln Gly Thr Lys Val Glu Ile Lys Arg Thr Val Ala Ala
                100                 105                 110

Pro Cys Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 136
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 136

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Gln Trp Leu Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Leu Thr Tyr Pro Tyr Thr Val Tyr His Lys
```

```
                    100                 105                 110
Ala Leu Asp Val Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160

Pro Cys Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp
225                 230

<210> SEQ ID NO 137
<211> LENGTH: 240
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 137

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Gln Trp Leu Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Leu Thr Tyr Pro Tyr Thr Tyr His Lys
            100                 105                 110

Ala Leu Asp Val Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
        130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220
```

```
Val Glu Pro Lys Ser Cys Asp Lys Thr His Thr Cys Pro Pro Cys Pro
225                 230                 235                 240
```

<210> SEQ ID NO 138
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 138

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Gln Trp Leu Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Leu Thr Tyr Pro Tyr Thr Val Tyr His Lys
            100                 105                 110

Ala Leu Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro
```

<210> SEQ ID NO 139
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 139

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
```

```
            20                  25                  30
Ser Ala Ala Trp Asn Trp Ile Arg Gln Ser Pro Ser Arg Gly Leu Glu
            35                  40                  45

Trp Leu Gly Arg Ile Tyr Tyr Arg Ser Gln Trp Leu Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Leu Thr Tyr Pro Tyr Thr Val Tyr His Lys
            100                 105                 110

Ala Leu Asp Val Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
            130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
            195                 200                 205

Ile Cys Asn Val Asn His Lys Pro Ser Asn Thr Lys Val Asp Lys Arg
        210                 215                 220

Val Glu Pro Lys Ser Cys Asp Lys Thr His Thr Cys Pro Pro Cys Pro
225                 230                 235                 240

Ala Pro Glu Leu Leu Gly Pro
                245

<210> SEQ ID NO 140
<211> LENGTH: 212
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 140

Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Asp Gln Tyr Val
            20                  25                  30

Ser Trp Tyr Gln Gln Lys Pro Gly Gln Ala Pro Val Leu Val Ile Tyr
        35                  40                  45

Asp Asp Thr Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Thr Asp Ser Lys Ser Val Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
            115                 120                 125
```

```
Lys Ala Thr Leu Val Cys Leu Ile Ser Asp Phe Tyr Pro Gly Cys Val
            130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
                195                 200                 205

Thr Glu Cys Ser
      210

<210> SEQ ID NO 141
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ala Trp Val Arg Gln Met Pro Gly Lys Gly Leu Glu Trp Met
        35                  40                  45

Gly Ile Ile Tyr Pro Ser Asn Ser Tyr Thr Leu Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Pro Pro Gly Gly Ser Ile Ser Tyr Pro Ala Phe Asp His
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Cys Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp
225

<210> SEQ ID NO 142
<211> LENGTH: 236
```

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Ala Trp Val Arg Gln Met Pro Gly Lys Gly Leu Glu Trp Met
            35                  40                  45

Gly Ile Ile Tyr Pro Ser Asn Ser Tyr Thr Leu Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Pro Pro Gly Gly Ser Ile Ser Tyr Pro Ala Phe Asp His
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro
225                 230                 235

<210> SEQ ID NO 143
<211> LENGTH: 238
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 143

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Ala Trp Val Arg Gln Met Pro Gly Lys Gly Leu Glu Trp Met
            35                  40                  45

Gly Ile Ile Tyr Pro Ser Asn Ser Tyr Thr Leu Tyr Ser Pro Ser Phe
50                  55                  60

Gln Gly Gln Val Thr Ile Ser Ala Asp Lys Ser Ile Ser Thr Ala Tyr

```
                65                  70                  75                  80
Leu Gln Trp Ser Ser Leu Lys Ala Ser Asp Thr Ala Met Tyr Tyr Cys
                    85                  90                  95

Ala Arg Val Pro Pro Gly Gly Ser Ile Ser Tyr Pro Ala Phe Asp His
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                    165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro
225                 230                 235
```

<210> SEQ ID NO 144
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 144

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Ala Trp Val Arg Gln Met Pro Gly Lys Gly Leu Glu Trp Met
            35                  40                  45

Gly Ile Ile Tyr Pro Ser Asn Ser Tyr Thr Leu Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                    85                  90                  95

Ala Arg Val Pro Pro Gly Gly Ser Ile Ser Tyr Pro Ala Phe Asp His
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                    165                 170                 175

Pro Ala Val Leu Gln Ser Ser Gly Leu Tyr Ser Leu Ser Ser Val Val
                180                 185                 190
```

```
Thr Val Pro Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
        210                 215                 220

Ser Cys Asp Lys Thr His Thr Cys Pro Pro Cys Pro Ala Pro Glu Leu
225                 230                 235                 240

Leu Gly Pro

<210> SEQ ID NO 145
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Gly Ser Ile Tyr Ala
            20                  25                  30

Ser Trp Tyr Gln Gln Lys Pro Gly Gln Ala Pro Val Leu Val Ile Tyr
        35                  40                  45

Arg Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Val Thr Asp Met Glu Gln His Ser
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Cys
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 146
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 146

Glu Val Gln Leu Val Glu Ser Gly Gly Gly Leu Val Gln Pro Gly Gly
```

```
            1               5                   10                  15
        Ser Leu Arg Leu Ser Cys Ala Ala Ser Gly Phe Asn Ile Lys Asp Thr
                        20                  25                  30

Tyr Ile His Trp Val Arg Gln Ala Pro Gly Lys Gly Leu Glu Trp Val
                        35                  40                  45

Ala Arg Ile Tyr Pro Thr Asn Gly Tyr Thr Arg Tyr Ala Asp Ser Val
                        50                  55                  60

Lys Gly Arg Phe Thr Ile Ser Ala Asp Thr Ser Lys Asn Thr Ala Tyr
        65                      70                  75                  80

Leu Gln Met Asn Ser Leu Arg Ala Glu Asp Thr Ala Val Tyr Tyr Cys
                        85                  90                  95

Ser Arg Trp Gly Gly Asp Gly Phe Tyr Ala Met Asp Tyr Trp Gly Gln
                        100                 105                 110

Gly Thr Leu Val Thr Val Ser Ser Ala Ser Thr Lys Gly Pro Ser Val
                        115                 120                 125

Phe Pro Leu Ala Pro Ser Ser Lys Ser Thr Ser Gly Gly Thr Ala Ala
                        130                 135                 140

Leu Gly Cys Leu Val Lys Asp Tyr Phe Pro Glu Pro Val Thr Val Ser
        145                     150                 155                 160

Trp Asn Ser Gly Ala Leu Thr Ser Gly Val His Thr Phe Pro Ala Val
                        165                 170                 175

Leu Gln Ser Ser Gly Leu Tyr Ser Leu Ser Ser Val Val Thr Val Pro
                        180                 185                 190

Ser Ser Ser Leu Gly Thr Gln Thr Tyr Ile Cys Asn Val Asn His Lys
                        195                 200                 205

Pro Ser Asn Thr Lys Val Asp Lys Lys Val Glu Pro Lys Ser Cys Asp
                        210                 215                 220

Lys Thr His Thr Cys Pro Pro Cys Pro Ala Pro Glu Leu Leu Gly
        225                     230                 235

<210> SEQ ID NO 147
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 147

Asp Ile Gln Met Thr Gln Ser Pro Ser Ser Leu Ser Ala Ser Val Gly
        1               5                   10                  15

Asp Arg Val Thr Ile Thr Cys Arg Ala Ser Gln Asp Val Asn Thr Ala
                        20                  25                  30

Val Ala Trp Tyr Gln Gln Lys Pro Gly Lys Ala Pro Lys Leu Leu Ile
                        35                  40                  45

Tyr Ser Ala Ser Phe Leu Tyr Ser Gly Val Pro Ser Arg Phe Ser Gly
                        50                  55                  60

Ser Arg Ser Gly Thr Asp Phe Thr Leu Thr Ile Ser Ser Leu Gln Pro
        65                      70                  75                  80

Glu Asp Phe Ala Thr Tyr Tyr Cys Gln Gln His Tyr Thr Thr Pro Pro
                        85                  90                  95

Thr Phe Gly Gln Gly Thr Lys Val Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 148
<211> LENGTH: 231
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 148

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Cys Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys His His His His His His
225                 230
```

<210> SEQ ID NO 149
<211> LENGTH: 214

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Cys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 150
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

85                  90                  95
Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 151
<211> LENGTH: 16
<212> TYPE: PRT
<213> ORGANISM: Human cytomegalovirus

<400> SEQUENCE: 151

```
Met Pro Leu Leu Leu Leu Pro Leu Leu Trp Ala Gly Ala Leu Ala
1               5                   10                  15
```

<210> SEQ ID NO 152
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

```
Met Ser Val Leu Thr Gln Val Leu Ala Leu Leu Leu Trp Leu Thr
1               5                   10                  15

Gly Thr Arg Cys
            20
```

<210> SEQ ID NO 153
<211> LENGTH: 246
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 153

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Gln Trp Leu Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Gln Leu Thr Tyr Pro Tyr Thr Val Tyr His Lys
        100                 105                 110

Ala Leu Asp Val Trp Gly Gln Gly Thr Leu Val Thr Val Ser Ser Ala
    115                 120                 125

Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Cys Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
        180                 185                 190

Ser Ser Val Val Thr Val Pro Ser Ser Ser Leu Gly Thr Gln Thr Tyr
    195                 200                 205

Ile Cys Asn Val Asn His Lys Pro Ser Asn Thr Lys Val Asp Lys Arg
210                 215                 220

Val Glu Pro Lys Ser Cys Asp Lys Thr His Thr Cys Pro Pro Cys Pro
225                 230                 235                 240

Ala Pro Glu Leu Leu Gly
```

```
<210> SEQ ID NO 154
<211> LENGTH: 237
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 154

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Thr Ile Gly Pro Phe Glu Gly Gln Pro Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Cys Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly
225                 230                 235

<210> SEQ ID NO 155
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 155

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

Gly Thr Ile Gly Pro Phe Glu Gly Gln Pro Arg Tyr Ala Gln Lys Phe
            50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Cys Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His
225

<210> SEQ ID NO 156
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Cys Pro Val Thr Val Ser
145                 150                 155                 160

```
Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly
225                 230                 235

<210> SEQ ID NO 157
<211> LENGTH: 225
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 157

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Cys Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys
225

<210> SEQ ID NO 158
<211> LENGTH: 232
<212> TYPE: PRT
<213> ORGANISM: Artificial Sequence
<220> FEATURE:
<221> NAME/KEY: source
```

-continued

<223> OTHER INFORMATION: /note="Description of Artificial Sequence:
Synthetic polypeptide"

<400> SEQUENCE: 158

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Thr Asn
            20                  25                  30

Ser Ala Ala Trp Asn Trp Ile Arg Gln Ser Pro Ser Arg Gly Leu Glu
        35                  40                  45

Trp Leu Gly Arg Ile Tyr Tyr Arg Ser Gln Trp Leu Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Leu Thr Tyr Pro Tyr Thr Val Tyr His Lys
            100                 105                 110

Ala Leu Asp Val Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Cys Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys
225                 230

<210> SEQ ID NO 159
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 159

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Phe Pro Ala Glu Gly Ala Pro Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Gly Gly Tyr Ile Ser Asp Phe Asp Val Trp Gly Gln Gly Thr
                100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Cys Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys
    210                 215                 220

<210> SEQ ID NO 160
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 160

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
            20                  25                  30

Ala Leu Ser Trp Val Arg Gln Ala Pro Gly Gln Gly Leu Glu Trp Met
        35                  40                  45

Gly Gly Ile Ile Pro Ser Phe Gly Thr Ala Asp Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Tyr Asp Phe Asp Tyr Trp Gly Gln Gly Thr Leu Val
                100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Cys Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys
    210                 215                 220
```

<210> SEQ ID NO 161
<211> LENGTH: 223
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 161

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Thr Ile Gly Pro Phe Glu Gly Gln Pro Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Cys Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys
    210                 215                 220

<210> SEQ ID NO 162
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 6xHis tag"

<400> SEQUENCE: 162

His His His His His His
1               5